US012545636B2

(12) United States Patent
Jayaraman et al.

(10) Patent No.: US 12,545,636 B2
(45) Date of Patent: Feb. 10, 2026

(54) ACYCLIC LIPIDS AND METHODS OF USE THEREOF

(71) Applicant: Renagade Therapeutics Management Inc., Cambridge, MA (US)

(72) Inventors: Muthusamy Jayaraman, Walpole, MA (US); Stephen Scully, Concord, MA (US)

(73) Assignee: Renagade Therapeutics Management Inc., Watertown, MA (US)

( * ) Notice: Subject to any disclaimer, the term of this patent is extended or adjusted under 35 U.S.C. 154(b) by 76 days.

(21) Appl. No.: 17/972,395

(22) Filed: Oct. 24, 2022

(65) Prior Publication Data

US 2023/0202966 A1 Jun. 29, 2023

Related U.S. Application Data

(63) Continuation of application No. PCT/US2022/076430, filed on Sep. 14, 2022.

(60) Provisional application No. 63/293,284, filed on Dec. 23, 2021, provisional application No. 63/336,018, filed on Apr. 28, 2022, provisional application No. 63/244,152, filed on Sep. 14, 2021.

(51) Int. Cl.

| | |
|---|---|
| ***C07C 219/06*** | (2006.01) |
| ***C07C 219/08*** | (2006.01) |
| ***C07C 219/10*** | (2006.01) |

(52) U.S. Cl.

CPC .......... *C07C 219/06* (2013.01); *C07C 219/08* (2013.01); *C07C 219/10* (2013.01)

(58) Field of Classification Search

CPC .. A61K 9/5123; C07C 219/06; C07C 219/08; C07C 219/10

See application file for complete search history.

(56) References Cited

U.S. PATENT DOCUMENTS

| | | | |
|---|---|---|---|
| 9,408,914 | B2 | 8/2016 | Kuboyama et al. |
| 9,682,922 | B2 | 6/2017 | Manoharan et al. |
| 10,059,655 | B2 | 8/2018 | Brito et al. |
| 10,166,298 | B2 | 1/2019 | Ansell et al. |
| 10,906,867 | B2 | 2/2021 | Brito et al. |
| 2014/0045913 | A1 | 2/2014 | Kuboyama et al. |
| 2020/0368173 | A1 | 11/2020 | Hatanaka et al. |
| 2022/0402862 | A1 | 12/2022 | Scully et al. |
| 2023/0331657 | A1 * | 10/2023 | Patwardhan ......... C07D 213/55 |

FOREIGN PATENT DOCUMENTS

| | | | |
|---|---|---|---|
| WO | WO-2015095340 | A1 | 6/2015 |
| WO | WO-2017075531 | A1 | 5/2017 |
| WO | WO-2018081480 | A1 | 5/2018 |
| WO | WO-2018144775 | A1 | 8/2018 |
| WO | WO-2018191719 | A1 | 10/2018 |
| WO | WO-2018225873 | A1 | 12/2018 |
| WO | WO-2018232120 | A1 | 12/2018 |
| WO | WO-2019036000 | A1 | 2/2019 |
| WO | WO-2019036008 | A1 | 2/2019 |
| WO | WO-2020012180 | A2 | 1/2020 |
| WO | WO-2020061367 | A1 | 3/2020 |
| WO | WO-2020072605 | A1 | 4/2020 |
| WO | WO-2021000041 | A1 | 1/2021 |
| WO | WO-2021055833 | A1 | 3/2021 |
| WO | WO-2021204179 | A1 | 10/2021 |
| WO | WO-2021226597 | A2 | 11/2021 |
| WO | WO-2022140252 | A1 | 6/2022 |
| WO | WO-2022251665 | A1 | 12/2022 |
| WO | WO-2023081526 | A1 * | 5/2023 |

OTHER PUBLICATIONS

Zhou et al. "Circular RNA: metabolism, functions and interactions with proteins," Mol. Cancer (2020) 19:172, pp. 1-19 (Year: 2020).*

* cited by examiner

*Primary Examiner* — Adam C Milligan
*Assistant Examiner* — William Y Lee
(74) *Attorney, Agent, or Firm* — Christopher K. Haley; Carl A. Morales; Goodwin Procter LLP

(57) ABSTRACT

The present disclosure details various lipids, compositions, and/or methods of optimized systems and delivery vehicles for the delivery of nucleic acid sequences, polypeptides or peptides for use in vaccinating against infectious agents.

17 Claims, 14 Drawing Sheets

Specification includes a Sequence Listing.

FIG. 3A, continued
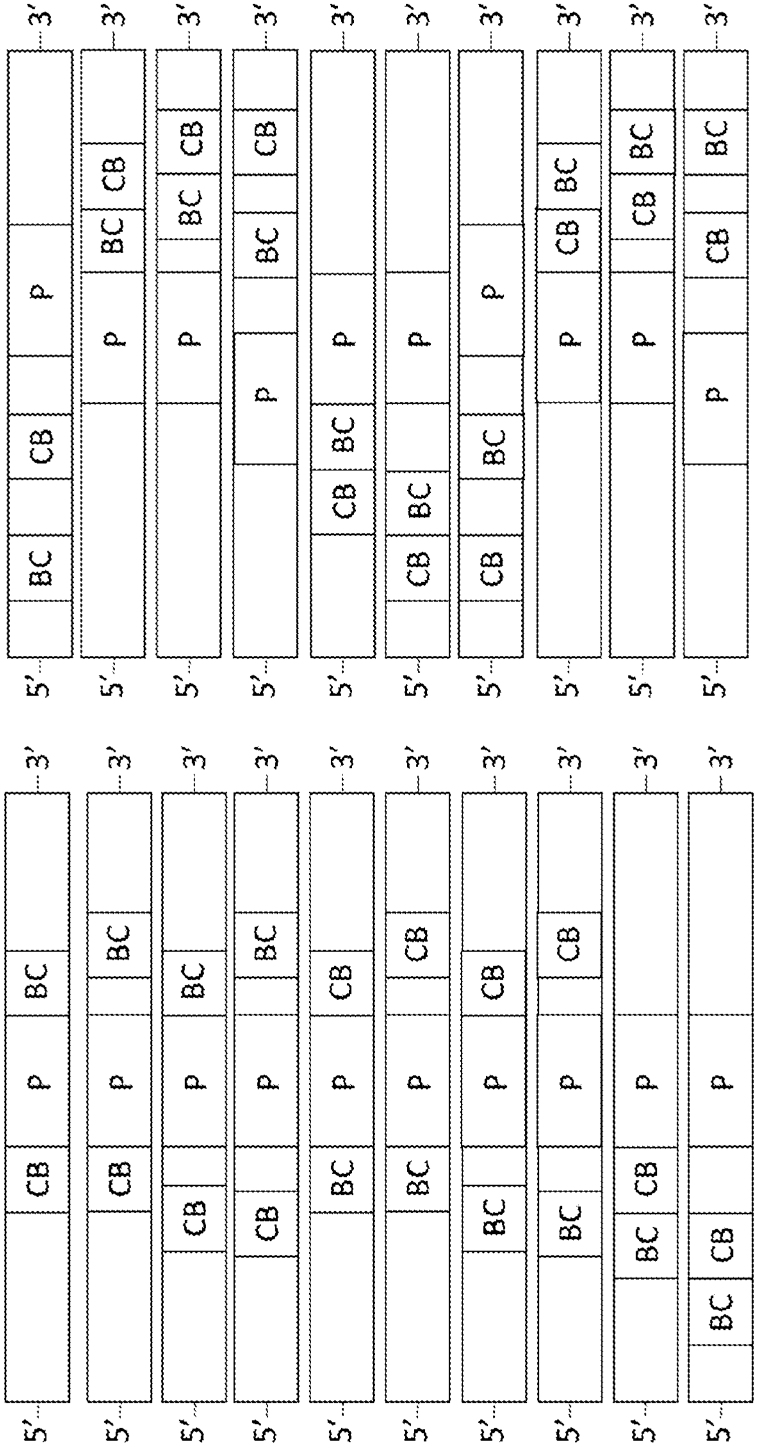

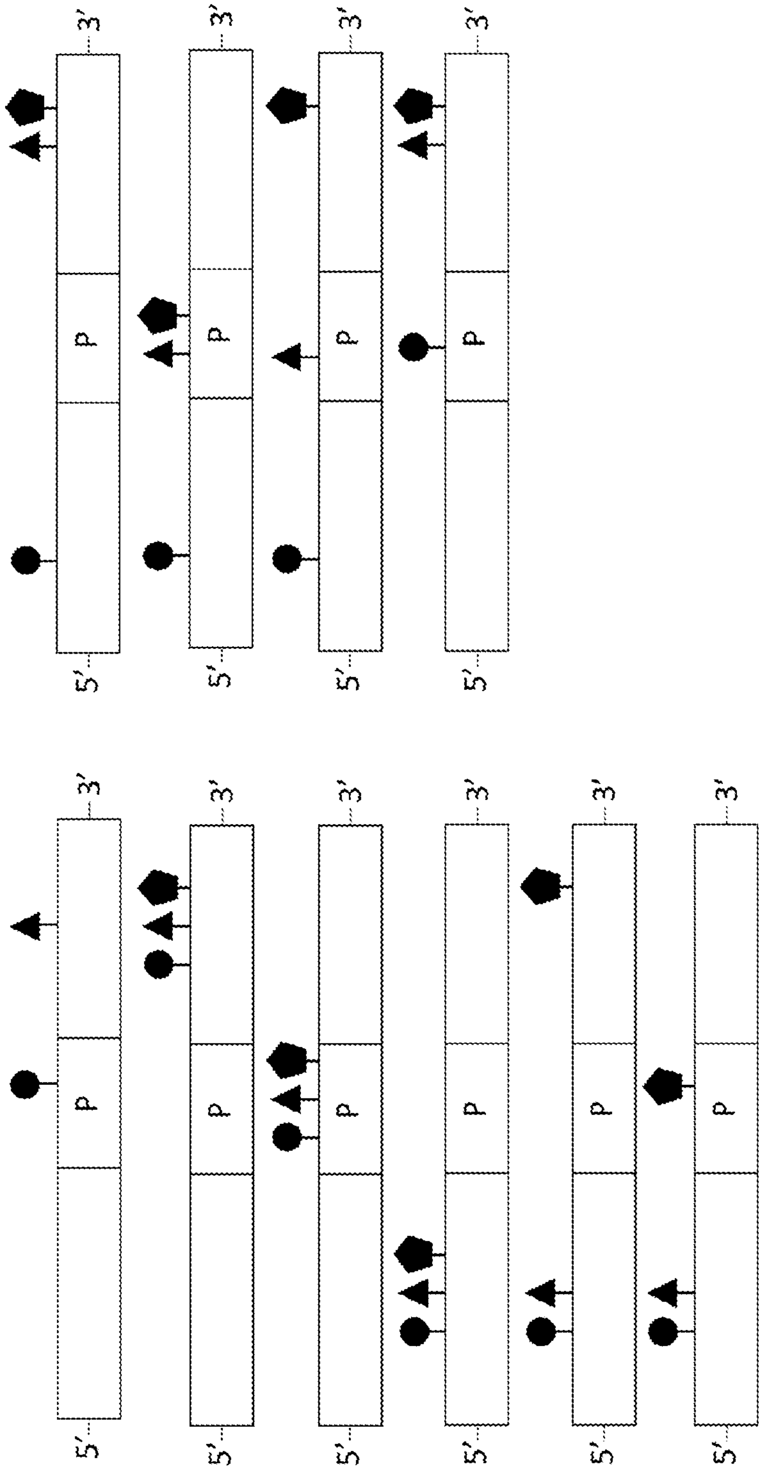
FIG. 3C, continued

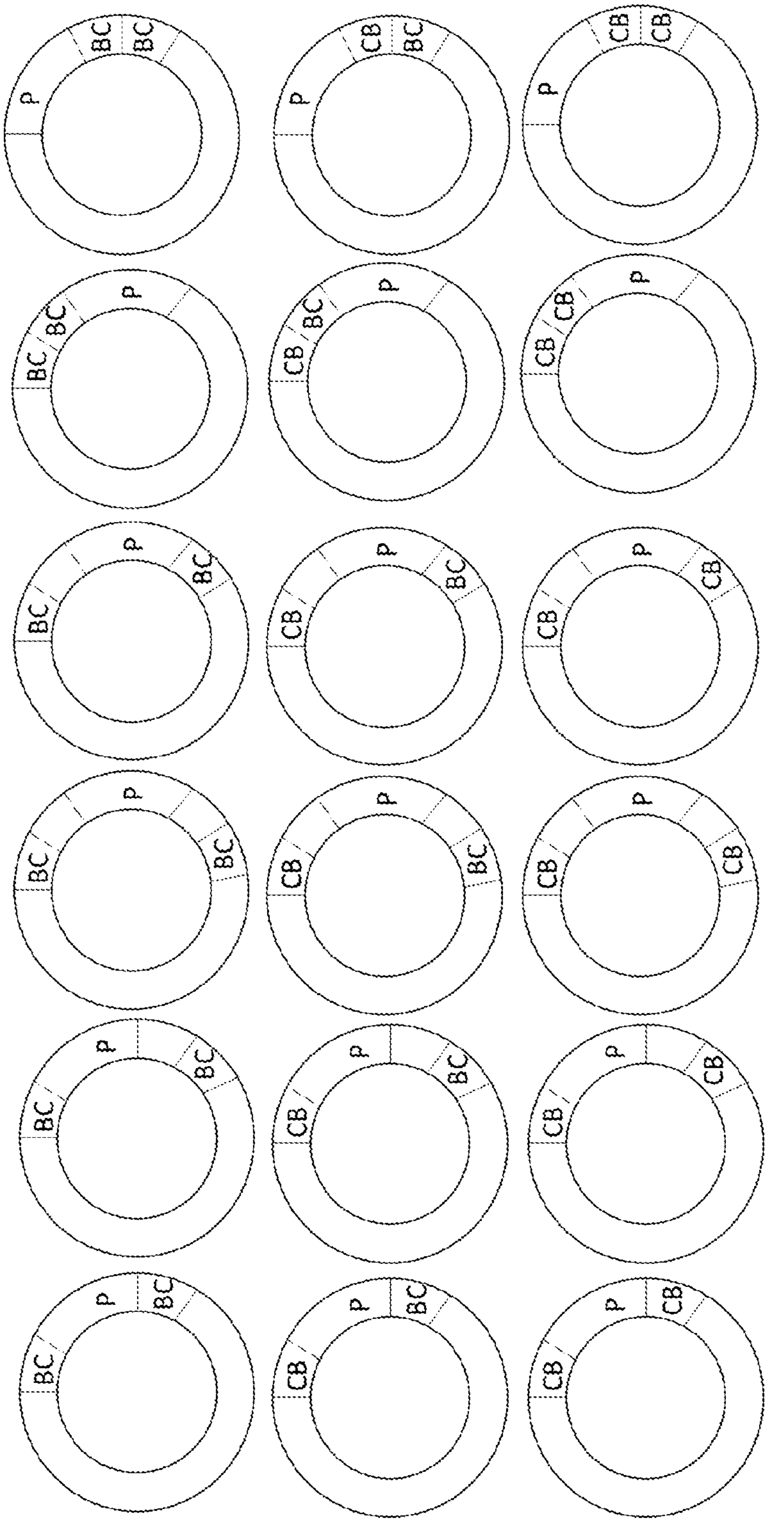
FIG. 4A, continued

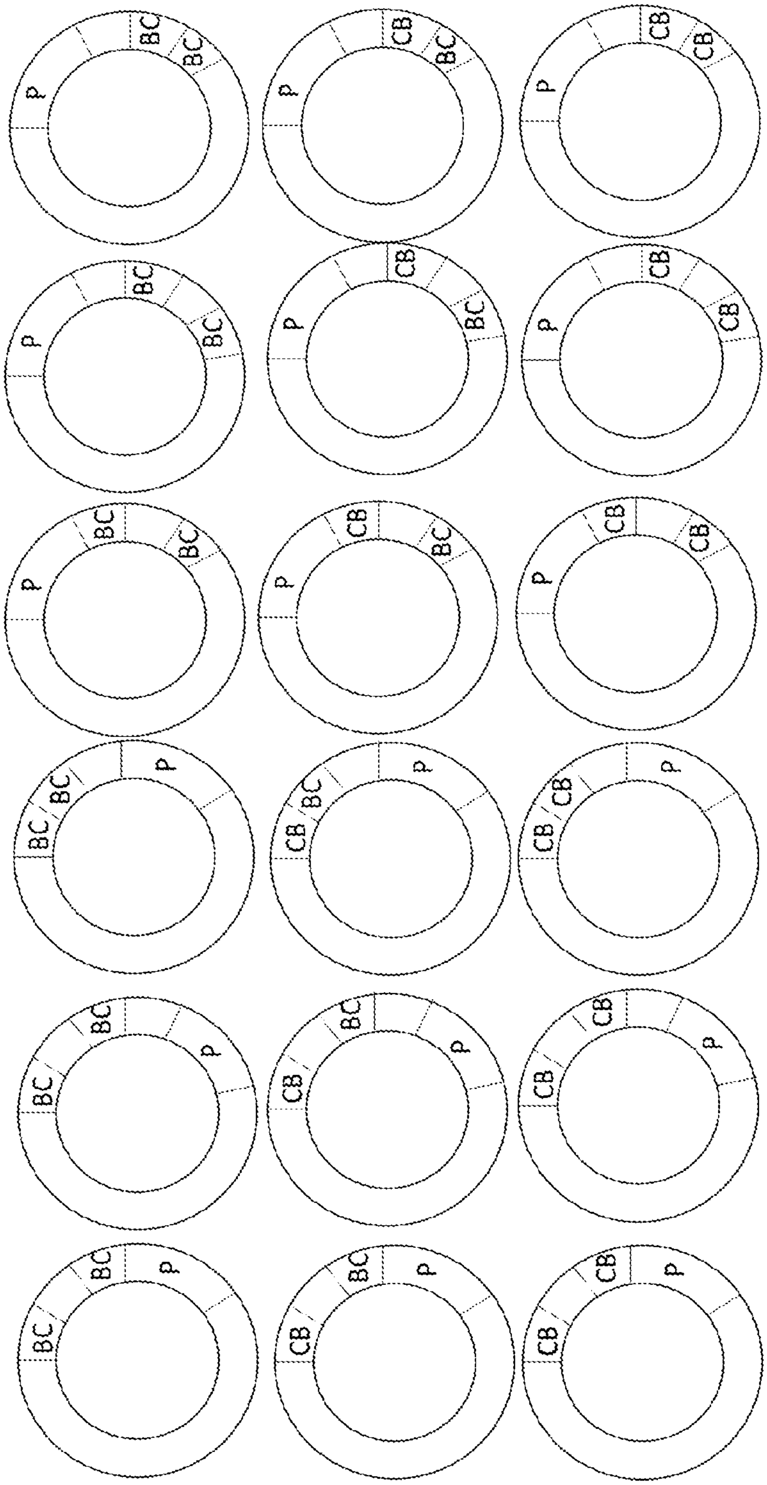
FIG. 4A, continued

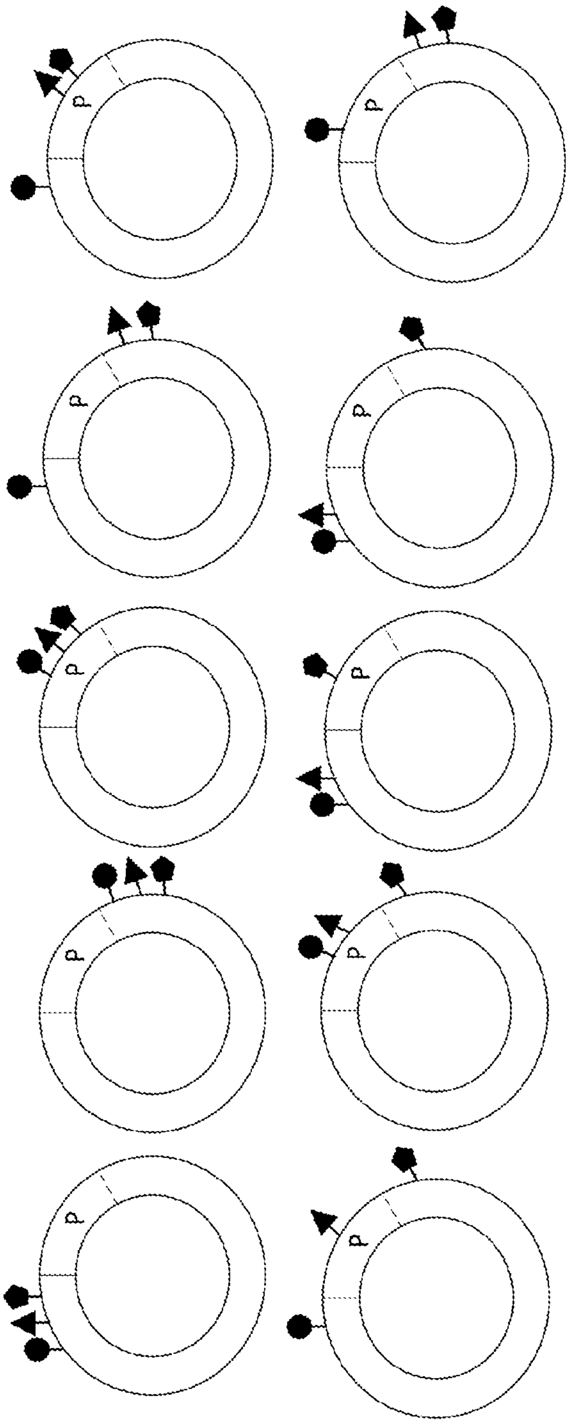
FIG. 4C, continued

ACYCLIC LIPIDS AND METHODS OF USE THEREOF

CROSS REFERENCE TO RELATED APPLICATIONS

This application is a continuation of International Application No. PCT/US2022/076430, filed Sep. 14, 2022, which claims priority to U.S. Provisional Patent Application Nos. 63/244,152, filed Sep. 14, 2021; 63/293,284, filed Dec. 23, 2021; and 63/336,018, filed Apr. 28, 2022; the contents of each of which are hereby incorporated by reference herein in their entirety.

SEQUENCE LISTING

The instant application contains a Sequence Listing which has been submitted electronically in xml format and is hereby incorporated by reference in its entirety. The xml copy, created on Feb. 2, 2023, is named REG-005WOC1.xml and is 98,780 bytes in size.

FIELD OF THE DISCLOSURE

The present disclosure relates to optimized systems for delivery of nucleic acid sequences, polypeptides or peptides and methods of use of these optimized systems for the treatment of diseases, disorders and/or conditions.

BACKGROUND OF THE DISCLOSURE

Proteins have been the standard for therapeutics but the use of nucleic acids as therapeutic modalities for a variety of diseases and therapeutic indications has gained in prominence over the past few years. Various companies have shown that nucleic acids (e.g., siRNA, mRNA, circular RNA, DNA, ASO, etc.) can be more effective when compared to protein based therapies, but there is a need for targeted delivery systems for both nucleic acid and protein therapeutics in order to ensure the therapeutic is localized to a targeted cell, tissue or organ.

Current delivery systems, including lipid based delivery systems such as lipid nanoparticles, focus on protecting the cargo being delivered, but do not focus on the lipids being used for the delivery system and often do not focus on the localized delivery of the cargo or delivery system. There exists a need in the art for improved lipid based delivery systems.

SUMMARY OF THE DISCLOSURE

The present disclosure provides new lipids which can be used in the delivery vehicles of the delivery systems and a tropism discovery platform for screening and developing targeting systems for localized delivery, e.g., to immune cells, of nucleic acid and protein therapeutics.

In an aspect of the disclosure, provided herein is a lipid having a structure of any of Formulae (VII-A), (VII-B), (VII-C), (I-A), (II), (III-B), (III-C), (III-D), (III-E), (III-F), (VIII-B), (IV), (VI), and (X), or a pharmaceutically acceptable salt thereof, or any lipid in Table (I), or a salt or solvate thereof, see below, collectively referred to as "Lipids of the Disclosure" and each individually referred to as a "Lipid of the Disclosure.".

In an aspect of the disclosure, provided herein is a pharmaceutical composition comprising:

a) a polynucleotide encoding at least one protein of interest, and b) a delivery vehicle comprising at least one lipid wherein the composition elicits an immune response in a subject.

In an aspect, the polynucleotides are DNA.

In an aspect, the polynucleotides are RNA.

In an aspect, the RNA are short interfering RNA (siRNA).

In an aspect, the siRNA inhibits or suppresses the expression of a target of interest in a cell.

In an aspect, the inhibition or suppression is about 30%, 40%, 50%, 60%, 70%, 80%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100%.

In an aspect, the polynucleotides are substantially circular.

In an aspect, polynucleotide comprises an internal ribosome entry site (IRES) sequence that is operably linked to the payload sequence region.

In an aspect, the IRES sequence comprises a sequence derived from picornavirus complementary DNA, encephalomyocarditis virus (EMCV) complementary DNA, poliovirus complementary DNA, or an Antennapedia gene from *Drosophila melanogaster.*

In an aspect, the polynucleotide comprises a termination element, wherein the termination element comprises at least one stop codon.

In an aspect, the polynucleotide comprises a regulatory element.

In an aspect, the polynucleotide comprises at least one masking agent.

In an aspect, the substantially circular polynucleotide is produced using in vitro transcription.

In an aspect, the payload sequence region comprises a non-coding nucleic acid sequence.

In an aspect, the payload sequence region comprises a coding nucleic acid sequence.

In an aspect, the coding nucleic acid sequence encodes a protein of interest for *Campylobacter jejuni*. In an aspect, the coding nucleic acid sequence encodes a protein of interest for *Clostridium difficile*. In an aspect, the coding nucleic acid sequence encodes a protein of interest for *Entamoeba histolytica*. In an aspect, the coding nucleic acid sequence encodes a protein of interest for enterotoxin B. In an aspect, the coding nucleic acid sequence encodes a protein of interest for Norwalk virus or norovirus. In an aspect, the coding nucleic acid sequence encodes a protein of interest for *Helicobacter pylori*. In an aspect, the coding nucleic acid sequence encodes a protein of interest for rotavirus. In an aspect, the coding nucleic acid sequence encodes a protein of interest for *Candida* yeast. In an aspect, the coding nucleic acid sequence encodes a protein of interest for coronavirus. In an aspect, the coding nucleic acid sequence encodes a protein of interest for SARS-CoV. In an aspect, the coding nucleic acid sequence encodes a protein of interest for SARS-CoV-2. In an aspect, the coding nucleic acid sequence encodes a protein of interest for MERS-CoV. In an aspect, the coding nucleic acid sequence encodes a protein of interest for Enterovirus 71. In an aspect, the coding nucleic acid sequence encodes a protein of interest for Epstein-Barr virus. In an aspect, the coding nucleic acid sequence encodes a protein of interest for Gram-Negative Bacteria. In an aspect, the Gram-Negative Bacteria is *Bordetella*. In an aspect, the coding nucleic acid sequence encodes a protein of interest for Gram-Positive Bacteria. In an aspect, the Gram-Positive Bacteria is *Clostridium tetani*. In an aspect, the Gram-Positive Bacteria is *Francisella tularensis*. In an aspect, the Gram-Positive Bacteria is *Streptococcus* bacteria. In an aspect, the Gram-Positive Bacteria is *Staphylococcus* bacteria. In an aspect, the coding nucleic acid sequence encodes a protein of interest for Hepatitis. In an aspect, the coding nucleic acid sequence encodes a protein of interest for Human Cytomegalovirus. In an aspect, the coding nucleic acid sequence encodes a protein of interest for Human Immunodeficiency Virus. In an aspect, the coding nucleic acid sequence encodes a protein of interest for Human Papilloma Virus. In an aspect, the coding nucleic acid sequence encodes a protein of interest for Influenza. In an aspect, the coding nucleic acid sequence encodes a protein of interest for John Cunningham Virus. In an aspect, the coding nucleic acid sequence encodes a protein of interest for *Mycobacterium*. In an aspect, the coding nucleic acid sequence encodes a protein of interest for Poxviruses. In an aspect, the coding nucleic acid sequence encodes a protein of interest for *Pseudomonas aeruginosa*. In an aspect, the coding nucleic acid sequence encodes a protein of interest for Respiratory Syncytial Virus. In an aspect, the coding nucleic acid sequence encodes a protein of interest for Rubella virus. In an aspect, the coding nucleic acid sequence encodes a protein of interest for Varicella zoster virus. In an aspect, the coding nucleic acid sequence encodes a protein of interest for Chikungunya virus. In an aspect, the coding nucleic acid sequence encodes a protein of interest for Dengue virus. In an aspect, the coding nucleic acid sequence encodes a protein of interest for Rabies virus. In an aspect, the coding nucleic acid sequence encodes a protein of interest for *Trypanosoma cruzi* and/or Chagas disease. In an aspect, the coding nucleic acid sequence encodes a protein of interest for Ebola virus. In an aspect, the coding nucleic acid sequence encodes a protein of interest for *Plasmodium falciparum*. In an aspect, the coding nucleic acid sequence encodes a protein of interest for Marburg virus. In an aspect, the coding nucleic acid sequence encodes a protein of interest for Japanese encephalitis virus. In an aspect, the coding nucleic acid sequence encodes a protein of interest for St. Louis encephalitis virus. In an aspect, the coding nucleic acid sequence encodes a protein of interest for West Nile Virus. In an aspect, the coding nucleic acid sequence encodes a protein of interest for Yellow Fever virus. In an aspect, the coding nucleic acid sequence encodes a protein of interest for *Bacillus anthracis*. In an aspect, the coding nucleic acid sequence encodes a protein of interest for Botulinum toxin. In an aspect, the coding nucleic acid sequence encodes a protein of interest for Ricin. In an aspect, the coding nucleic acid sequence encodes a protein of interest for Shiga toxin and/or Shiga-like toxin. In an aspect, the polynucleotide comprises at least one modification.

In an aspect, at least 20% of the bases are modified. In an aspect, at least 30% of the bases are modified. In an aspect, at least 40% of the bases are modified. In an aspect, at least 50% of the bases are modified. In an aspect, at least 60% of the bases are modified. In an aspect, at least 70% of the bases are modified. In an aspect, at least 80% of the bases are modified. In an aspect, wherein at least 90% of the bases are modified. In an aspect, at least 100% of the bases are modified. In an aspect, a specific base comprises at least one modification.

In an aspect, the base is adenine. In an aspect, at least 20% of the adenine bases are modified. In an aspect, at least 30% of the adenine bases are modified. In an aspect, at least 40% of the adenine bases are modified. In an aspect, at least 50% of the adenine bases are modified. In an aspect, at least 60% of the adenine bases are modified. In an aspect, at least 70% of the adenine bases are modified. In an aspect, at least 80% of the adenine bases are modified. In an aspect, at least 90% of the adenine bases are modified. In an aspect, at least 100% of the adenine bases are modified.

In an aspect, the base is guanine. In an aspect, at least 20% of the guanine bases are modified. In an aspect, at least 30% of the guanine bases are modified. In an aspect, at least 40% of the guanine bases are modified. In an aspect, at least 50% of the guanine bases are modified. In an aspect, at least 60% of the guanine bases are modified. In an aspect, at least 70% of the guanine bases are modified. In an aspect, at least 80% of the guanine bases are modified. In an aspect, at least 90% of the guanine bases are modified. In an aspect, at least 100% of the guanine bases are modified.

In an aspect, the base is cytosine. In an aspect, at least 20% of the cytosine bases are modified. In an aspect, at least 30% of the cytosine bases are modified. In an aspect, at least 40% of the cytosine bases are modified. In an aspect, at least 50% of the cytosine bases are modified. In an aspect, at least 60% of the cytosine bases are modified. In an aspect, at least 70% of the cytosine bases are modified. In an aspect, at least 80% of the cytosine bases are modified. In an aspect, at least 90% of the cytosine bases are modified. In an aspect, at least 100% of the cytosine bases are modified.

In an aspect, the base is uracil. In an aspect, at least 20% of the uracil bases are modified. In an aspect, at least 30% of the uracil bases are modified. In an aspect, at least 40% of the uracil bases are modified. In an aspect, at least 50% of the uracil bases are modified. In an aspect, at least 60% of the uracil bases are modified. In an aspect, at least 70% of the uracil bases are modified. In an aspect, at least 80% of the uracil bases are modified. In an aspect, at least 90% of the uracil bases are modified. In an aspect, at least 100% of the uracil bases are modified.

In an aspect, the at least one modification is pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, and 4-methoxy-2-thio-pseudouridine, 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, and 4-methoxy-1-methyl-pseudoisocytidine, 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, and 2-methoxy-adenine, inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, or N2,N2-dimethyl-6-thio-guanosine.

In an aspect, the pharmaceutical composition comprises at least one cationic lipid selected from selected from the group consisting of any lipid in Table (I); any lipid having a structure of Formula (VII-A), (VIII-A), (IX-A), (VII-B), (VII-C), (I-A), (II), (III-B), (III-C), (III-D), (III-E), (III-F), (VIII-B), (IV), (VI), (X), or (X-A); and combinations thereof.

In an aspect, the pharmaceutical composition comprises an additional cationic lipid.

In an aspect, the pharmaceutical composition comprises a neutral lipid.

In an aspect, the pharmaceutical composition comprises an anionic lipid.

In an aspect, the pharmaceutical composition comprises a helper lipid.

In an aspect, the pharmaceutical composition comprises a stealth lipid.

In an aspect, the weight ratio of the lipids and the polynucleotide is from about 100:1 to about 1:1.

In an aspect, the pharmaceutical composition delivers the cargo or payload to immune cells in a subject in need thereof. The immune cells can be T cells, e.g., CD8+ T cells, CD4+ T cells, or T regulatory cells. The immune cells can also be, e.g., macrophages or dendritic cells.

In an aspect, a vaccine formulation comprises the pharmaceutical composition.

In an aspect, provided herein is a method of vaccinating a subject against an infectious agent comprising contacting a subject with the vaccine formulation or preparation and eliciting an immune response.

In an aspect, the infectious agent is *Campylobacter jejuni, Clostridium difficile, Entamoeba histolytica*, enterotoxin B, Norwalk virus or norovirus, *Helicobacter pylori*, rotavirus, *Candida* yeast, coronavirus including SARS-CoV, SARS-CoV-2 and MERS-CoV, Enterovirus 71, Epstein-Barr virus, Gram-Negative Bacteria including *Bordetella*, Gram-Positive Bacteria including *Clostridium tetani, Francisella tularensis, Streptococcus* bacteria and *Staphylococcus* bacteria, and Hepatitis, Human Cytomegalovirus, Human Immunodeficiency Virus, Human Papilloma Virus, Influenza, John Cunningham Virus, *Mycobacterium*, Poxviruses, *Pseudomonas aeruginosa*, Respiratory Syncytial Virus, Rubella virus, Varicella zoster virus, Chikungunya virus, Dengue virus, Rabies virus, *Trypanosoma cruzi* and/or Chagas disease, Ebola virus, *Plasmodium falciparum*, Marburg virus, Japanese encephalitis virus, St. Louis encephalitis virus, West Nile Virus, Yellow Fever virus, *Bacillus anthracis*, Botulinum toxin, Ricin, or Shiga toxin and/or Shiga-like toxin.

In an aspect, the contacting is enteral (into the intestine), gastroenteral, epidural (into the dura mater), oral (by way of the mouth), transdermal, intracerebral (into the cerebrum), intracerebroventricular (into the cerebral ventricles), epicutaneous (application onto the skin), intradermal (into the skin itself), subcutaneous (under the skin), nasal administration (through the nose), intravenous (into a vein), intravenous bolus, intravenous drip, intra-arterial (into an artery), intramuscular (into a muscle), intracardiac (into the heart), intraosseous infusion (into the bone marrow), intrathecal (into the spinal canal), intraparenchymal (into brain tissue), intraperitoneal (infusion or injection into the peritoneum), intravesical infusion, intravitreal (through the eye), intracavernous injection (into a pathologic cavity) intracavitary (into the base of the penis), intravaginal administration, intrauterine, extra-amniotic administration, transdermal (diffusion through the intact skin for systemic distribution), transmucosal (diffusion through a mucous membrane), transvaginal, insufflation (snorting), sublingual, sublabial, enema, eye drops (onto the conjunctiva), ear drops, auricular (in or by way of the ear), buccal (directed toward the cheek), conjunctival, cutaneous, dental (to a tooth or teeth), electro-osmosis, endocervical, endosinusial, endotracheal, extracorporeal, hemodialysis, infiltration, interstitial, intra-abdominal, intra-amniotic, intra-articular, intrabiliary, intrabronchial, intrabursal, intracartilaginous (within a cartilage), intracaudal (within the cauda equine), intracisternal (within the cisterna magna cerebellomedularis), intracorneal (within the cornea), dental intracoronal, intracoronary (within the coronary arteries), intracorporus cavernosum (within the dilatable spaces of the corporus cavernosa of the penis), intradiscal (within a disc), intraductal (within a duct of a gland), intraduodenal (within the duodenum), intradural (within or beneath the dura), intraepidermal (to the epidermis), intraesophageal (to the esophagus), intragastric (within the stomach), intragingival (within the gingivae), intraileal (within the distal portion of the small intestine), intralesional (within or introduced directly to a localized lesion), intraluminal (within a lumen of a tube), intralymphatic (within the lymph), intramedullary (within the marrow cavity of a bone), intrameningeal (within the meninges), intramyocardial (within the myocardium), intraocular (within the eye), intraovarian (within the ovary), intrapericardial (within the pericardium), intrapleural (within the pleura), intraprostatic (within the prostate gland), intrapulmonary (within the lungs or its bronchi), intrasinal (within the nasal or periorbital sinuses), intraspinal (within the vertebral column), intrasynovial (within the synovial cavity of a joint), intratendinous (within a tendon), intratesticular (within the testicle), intrathecal (within the cerebrospinal fluid at any level of the cerebrospinal axis), intrathoracic (within the thorax), intratubular (within the tubules of an organ), intratumor (within a tumor), intratympanic (within the aurus media), intravascular (within a vessel or vessels), intraventricular (within a ventricle), iontophoresis (by means of electric current where ions of soluble salts migrate into the tissues of the body), irrigation (to bathe or flush open wounds or body cavities), laryngeal (directly upon the larynx), nasogastric (through the nose and into the stomach), occlusive dressing technique (topical route administration which is then covered by a dressing which occludes the area), ophthalmic (to the external eye), oropharyngeal (directly to the mouth and pharynx), parenteral, percutaneous, periarticular, peridural, perineural, periodontal, rectal, respiratory (within the respiratory tract by inhaling orally or nasally for local or systemic effect), retrobulbar (behind the pons or behind the eyeball), soft tissue, subarachnoid, subconjunctival, submucosal, topical, transplacental (through or across the placenta), transtracheal (through the wall of the trachea), transtympanic (across or through the tympanic cavity), ureteral (to the ureter), urethral (to the urethra), vaginal, caudal block, diagnostic, nerve block, biliary perfusion, cardiac perfusion, photopheresis, or spinal.

DETAILED DESCRIPTION OF THE DISCLOSURE

I. Introduction to Tropism Delivery Systems

Nucleic acid therapy has emerged as the dominant method of treating various diseases and therapeutic indications given the versatility, lower immune response and higher potency as compared to traditional therapies. For example, nucleic acid therapy includes the use of small interfering (siRNA) to reduce the translation of messenger RNA (mRNA), mRNA as a way to produce a target of interest, circular RNA (oRNA) which can provide continuous production of a polypeptide or peptide or can be a sponge to compete with other RNA molecules, and viral vectors to provide a continuous production of a target of interest. However, some nucleic acids are unstable and easily degraded so they need to be formulated to prevent the degradation and to aid in the intracellular delivery of the nucleic acids.

Current delivery vehicles, including lipid based delivery vehicles such as lipid nanoparticles and liposomes, focus on protecting the cargo but do not concentrate on localizing the delivery of the cargo or delivery vehicle to a specific area in vivo.

Figure 1:
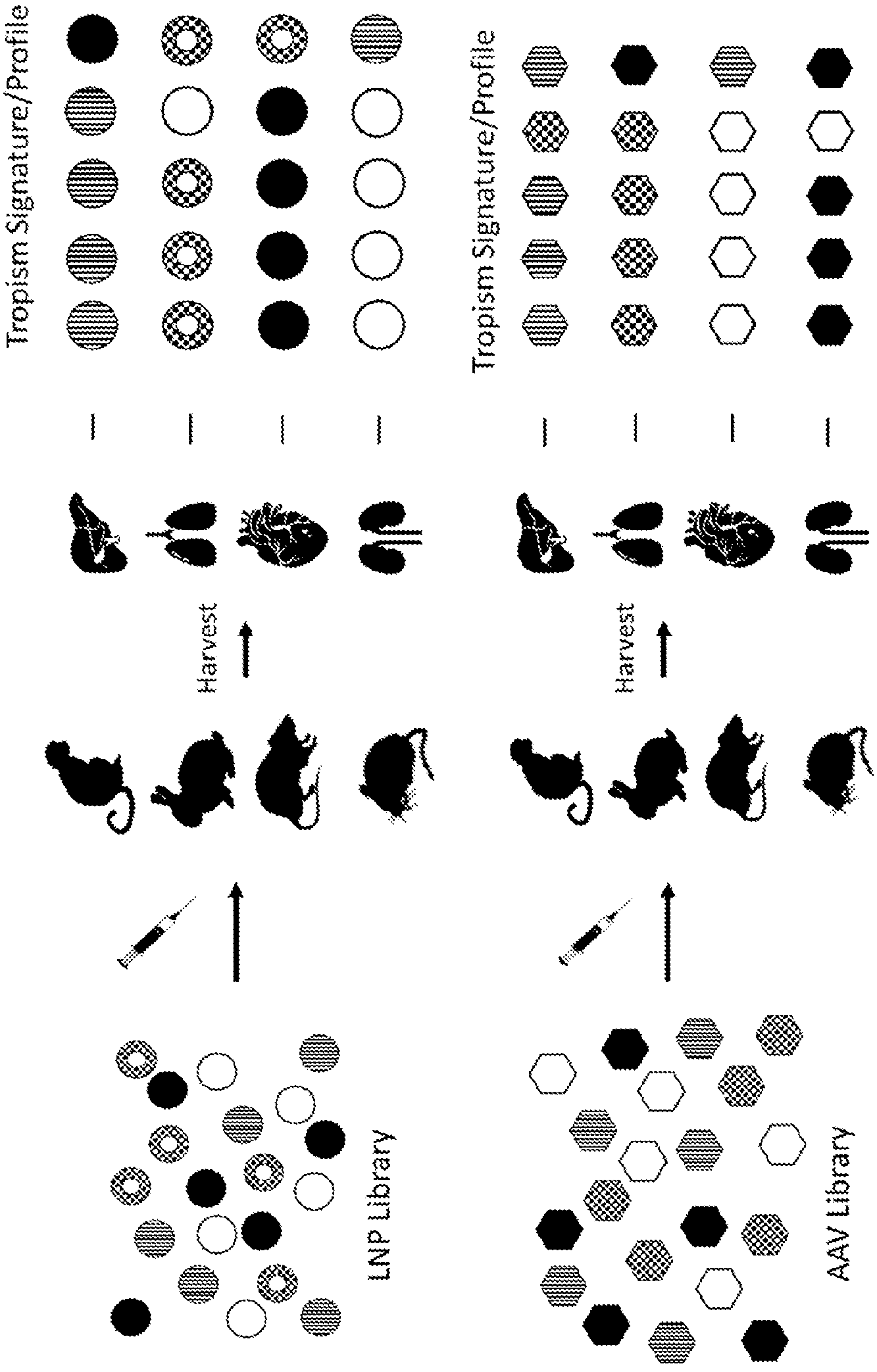
FIG. 1 is a diagram illustrating one embodiment of the tropism discovery platform of the present disclosure.

Provided herein is a tropism discovery platform for evaluating targeting systems for localized delivery to a specific target area, cell or tissue. As shown in FIG. 1, the tropism discovery platform can be used to evaluate a lipid nanoparticle (LNP) library and/or a library of AAVs in order to determine the tropism or signature profile of the targeting systems in the library. The library can be administered to a subject (e.g., non-human primate, rabbit, mouse, rat or another mammal) and the organs and tissues of the subject are scanned and/or harvested and analyzed to determine the location of the identifiers (e.g., barcodes, labels, signals and/or tags) contained in or associated with the LNPs or the AAVs in the library. This analysis provides the tropism signature or profile of each LNP and AAV in the library.

Originator Construct Architecture

Figure 2:
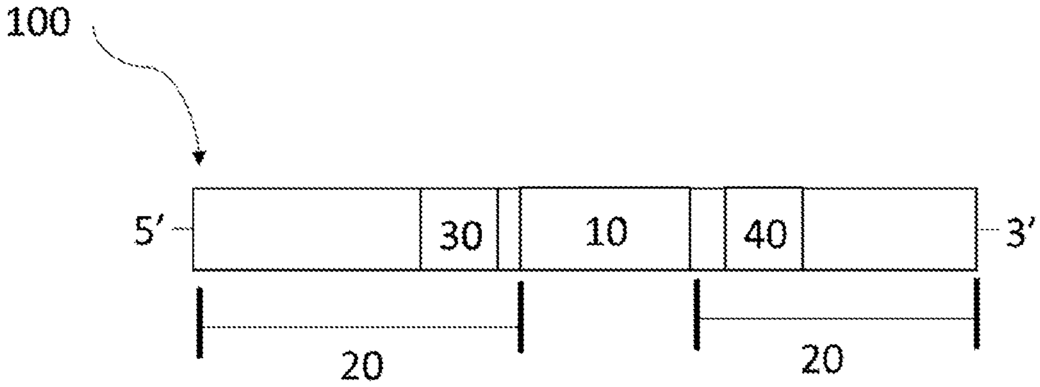
FIG. 2 is a diagram illustrating an originator polynucleotide construct of the present disclosure which may be linear or circular.

The targeting systems of the tropism discovery platform may include originator constructs which encode or include a cargo or payload. An example of an originator polynucleotide construct 100, which may be linear or circular, is provided in FIG. 2. The originator polynucleotide construct 100 may include at least one payload region 10 which is or encodes a payload or cargo of interest. The originator polynucleotide construct 100 may contain 1 or 2 flanking regions 20 and the flanking regions 20 may be located 5' to the payload region 10 or 3' to the payload region 10. In some instances the originator polynucleotide construct 100 does not contain a flanking region 20. The flanking region 20 of the originator polynucleotide construct 100 may include at least one regulatory region 30. At least one flanking region 20 of the originator polynucleotide construct 100 may include at least one identifier region 40. The identifier region 40 may be, but is not limited to, a barcode, label, signal and/or tag. Additionally, the identifier region 40 may be located within the payload region 10 or may be located in the payload region 10 and at least one flanking region 20.

In some embodiments, the originator construct comprises from about 5 to about 10,000 residues. As a non-limiting examples, the length of the originator construct may be from 5 to 30, from 5 to 50, from 5 to 100, from 5 to 250, from 5 to 500, from 5 to 1,000, from 5 to 1,500, from 5 to 3,000 from 5 to 5,000, from 5 to 7,000, from 5 to 10,000 from 30 to 50, from 30 to 100, from 30 to 250, from 30 to 500, from 30 to 1,000, from 30 to 1,500, from 30 to 3,000, from 30 to 5,000, from 30 to 7,000, from 30 to 10,000, from 100 to 250, from 100 to 500, from 100 to 1,000, from 100 to 1,500, from 100 to 3,000, from 100 to 5,000, from 100 to 7,000, from 100 to 10,000, from 500 to 1,000, from 500 to 1,500, from 500 to 2,000, from 500 to 3,000, from 500 to 5,000, from 500 to 7,000, from 500 to 10,000, from 1,000 to 1,500, from 1,000 to 2,000, from 1,000 to 3,000, from 1,000 to 5,000, from 1,000 to 7,000, from 1,000 to 10,000, from 1,500 to 3,000, from 1,500 to 5,000, from 1,500 to 7,000, from 1,500 to 10,000, from 2,000 to 3,000, from 2,000 to 5,000, from 2,000 to 7,000, from 2,000 to 10,000, from 3,000 to 5,000, from 3,000 to 7,000, from 3,000 to 10,000, from 5,000 to 7,000, from 5,000 to 10,000, and from 7,000 to 10,000.

In some embodiments, the length of the payload region is greater than about 5 residues in length such as, but not limited to, at least or greater than about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 40, 45, 50, 55, 60, 70, 80, 90, 100, 120, 140, 160, 180, 200, 250, 300, 350, 400, 450, 500, 600, 700, 800, 900, 1,000, 1,100, 1,200, 1,300, 1,400, 1,500, 1,600, 1,700, 1,800, 1,900, 2,000, 2,500, 3,000, 4,000, 5,000, 6,000, 7,000, 8,000, 9,000, 10,000 or more than 10,000 residues.

In some embodiments, the flanking region may range independently from 0 to 10,000 residues in length such as, but not limited to, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 40, 45, 50, 55, 60, 70, 80, 90, 100, 120, 140, 160, 180, 200, 250, 300, 350, 400, 450, 500, 600, 700, 800, 900, 1,000, 1,100, 1,200, 1,300, 1,400, 1,500, 1,600, 1,700, 1,800, 1,900, 2,000, 2,500, 3,000, 4,000, 5,000, 6,000, 7,000, 8,000, 9,000, and 10,000.

In some embodiments, the regulatory region may range independently from 0 to 3,000 residues in length such as, but not limited to, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 40, 45, 50, 55, 60, 70, 80, 90, 100, 120, 140, 160, 180, 200, 250, 300, 350, 400, 450, 500, 600, 700, 800, 900, 1,000, 1,100, 1,200, 1,300, 1,400, 1,500, 1,600, 1,700, 1,800, 1,900, 2,000, 2,500, and 3,000.

In some embodiments, the originator construct may be cyclized, or concatemerized, to generate a molecule to assist interactions between 3' and 5' ends of the originator construct Benchmark Construct Architecture Originator constructs which include at least one identifier (e.g., barcodes, labels, signals and/or tags) are referred to as benchmark constructs. The benchmark polynucleotide construct may comprise 1, 2, 3, 4, 5, 6, 7, 8, 9, or 10 or more identifiers which may be the same or different throughout the benchmark polynucleotide construct.

In some embodiments, the identifier region may range independently from 1 to 3,000 residues in length such as, but not limited to, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 40, 45, 50, 55, 60, 70, 80, 90, 100, 120, 140, 160, 180, 200, 250, 300, 350, 400, 450, 500, 600, 700, 800, 900, 1,000, 1,100, 1,200, 1,300, 1,400, 1,500, 1,600, 1,700, 1,800, 1,900, 2,000, 2,500, and 3,000. As a non-limiting example the identifier region may be 1-5 residues, 2-5 residues, 3-5 residues, 2-7 residues, 3-7 residues, 1-10 residues, 2-10 residues, 3-10 residues, 5-10 residues, 7-10 residues, 1-15 residues, 2-15 residues, 3-15 residues, 5-15 residues, 7-15 residues, 10-15 residues, 12-15 residues, 1-20 residues, 2-20 residues, 3-20 residues, 5-20 residues, 7-20 residues, 10-20 residues, 12-20 residues, 15-20 residues, 17-20 residues, 1-25 residues, 2-25 residues, 3-25 residues, 5-25 residues, 7-25 residues, 10-25 residues, 12-25 residues, 15-25 residues, 17-25 residues, 20-25 residues, 1-30 residues, 2-30 residues, 3-30 residues, 5-30 residues, 7-30 residues, 10-30 residues, 12-30 residues, 15-30 residues, 17-30 residues, 20-30 residues, 25-30 residues, 1-35 residues, 2-35 residues, 3-35 residues, 5-35 residues, 7-35 residues, 10-35 residues, 12-35 residues, 15-35 residues, 17-35 residues, 20-35 residues, 25-35 residues, 30-35 residues, 1-35 residues, 2-35 residues, 3-35 residues, 5-35 residues, 7-35 residues, 10-35 residues, 12-35 residues, 15-35 residues, 17-35 residues, 20-35 residues, 25-35 residues, 30-35 residues, 1-40 residues, 2-40 residues, 3-40 residues, 5-40 residues, 7-40 residues, 10-40 residues, 12-40 residues, 15-40 residues, 17-40 residues, 20-40 residues, 25-40 residues, 30-40 residues, 35-40 residues, 1-45 residues, 2-45 residues, 3-45 residues, 5-45 residues, 7-45 residues, 10-45 residues, 12-45 residues, 15-45 residues, 17-45 residues, 20-45 residues, 25-45 residues, 30-45 residues, 35-45 residues, 40-45 residues, 1-50 residues, 2-50 residues, 3-50 residues, 5-50 residues, 7-50 residues, 10-50 residues, 12-50 residues, 15-50 residues, 17-50 residues, 20-50 residues, 25-50 residues, 30-50 residues, 35-50 residues, 40-50 residues, or 45-50 residues in length.

Figure 3A:
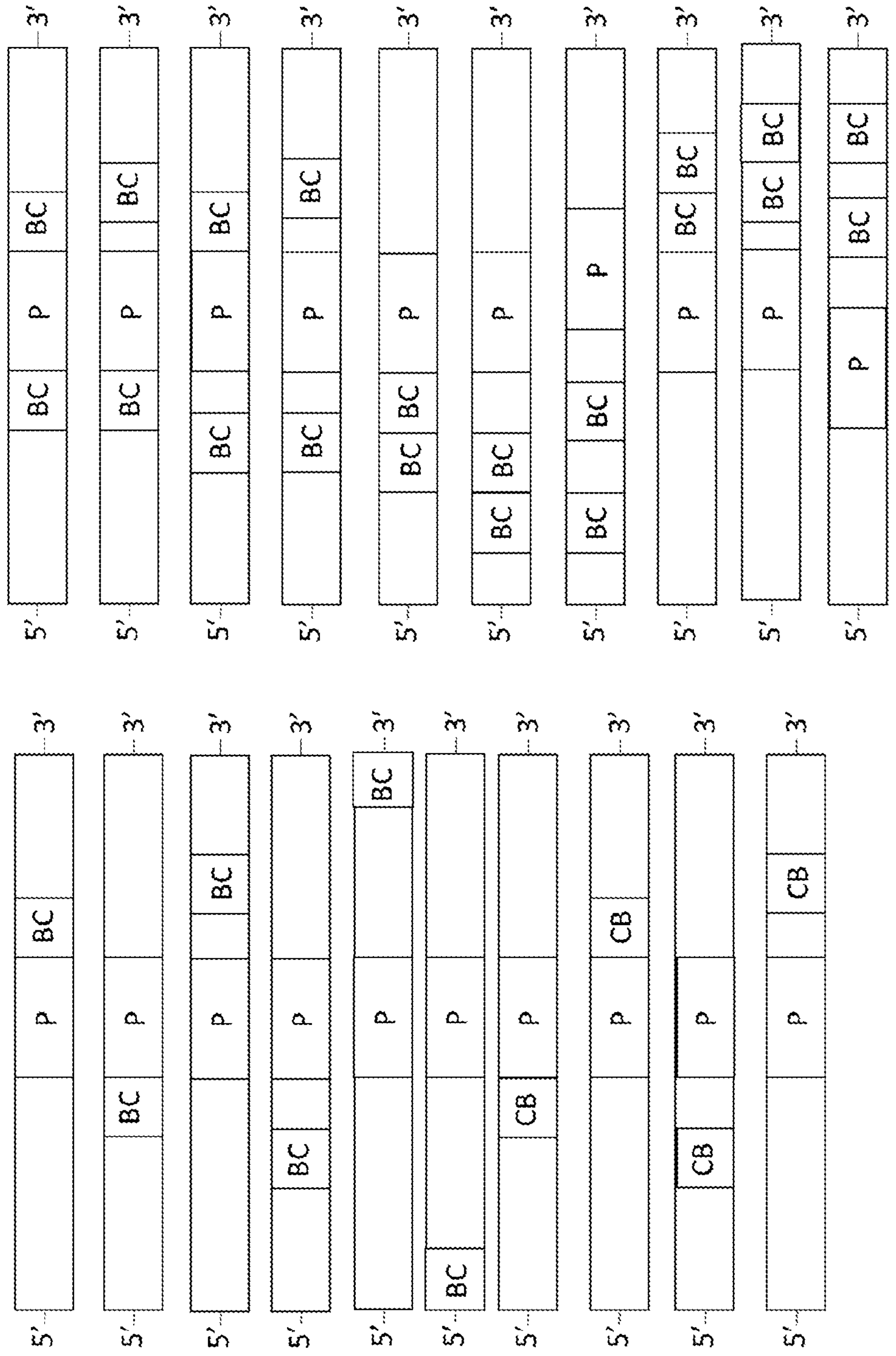
FIG. 3A is a diagram illustrating a series of benchmark polynucleotide constructs of the present disclosure which may include at least one barcode region (BC) and/or an inverted barcode region (CB) and a payload region (P).
Figure 3B:
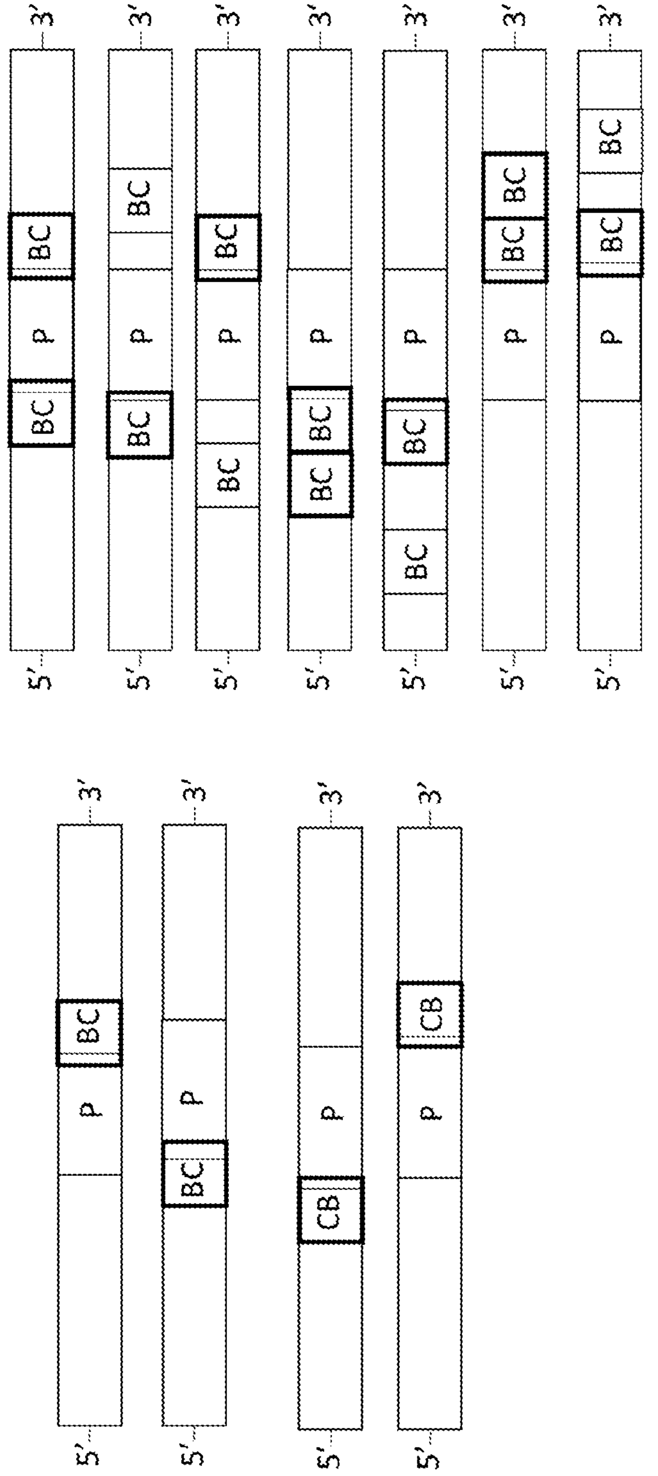
FIG. 3B is a diagram illustrating a series of benchmark polynucleotide constructs of the present disclosure where the barcode region (BC) or inverted barcode region (CB) may overlap the payload region (P).
Figure 3C:
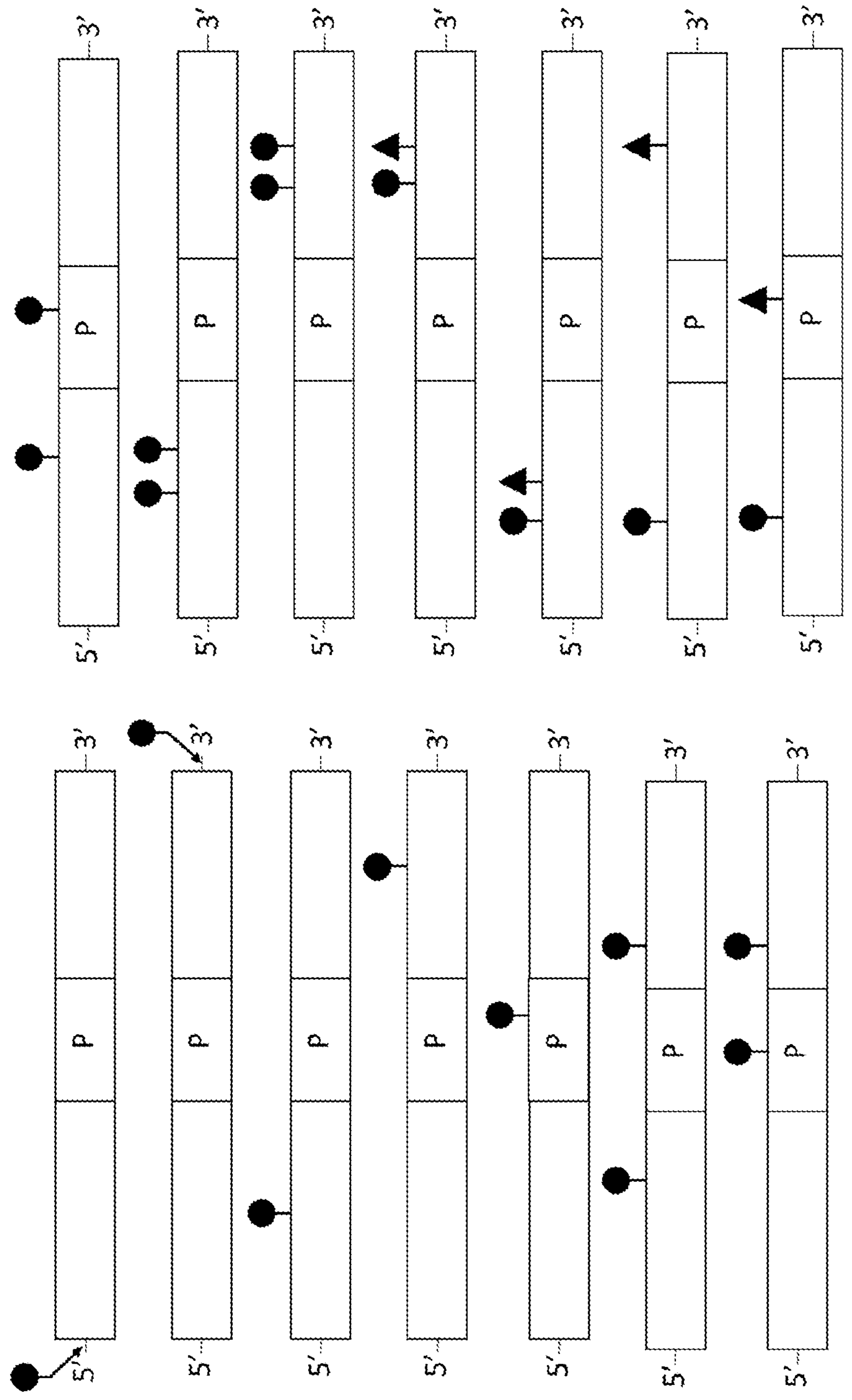
FIG. 3C is a diagram illustrating a series of benchmark polynucleotide constructs of the present disclosure which may include at least one tag and/or label.
Figure 4A:
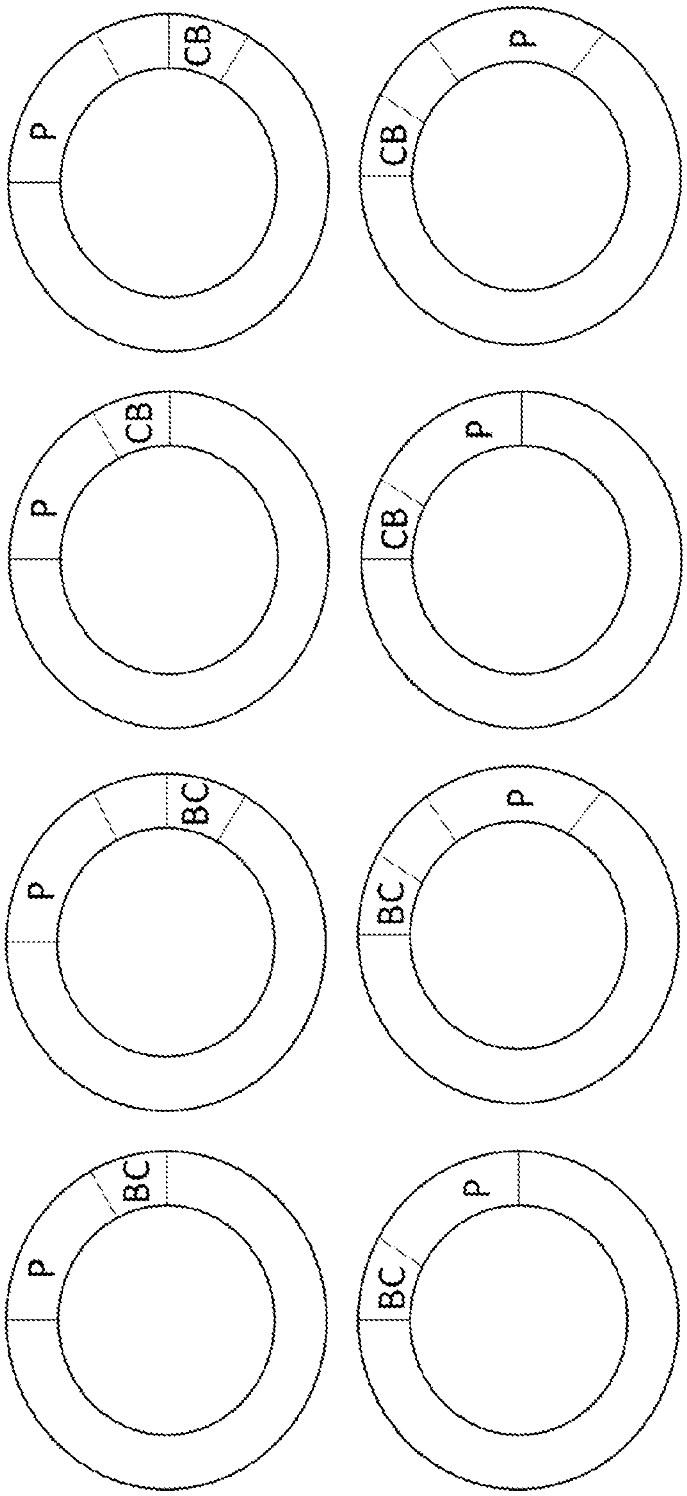
FIG. 4A is a diagram illustrating a series of circular benchmark polynucleotide constructs of the present disclosure which may include at least one barcode region (BC) and/or an inverted barcode region (CB) and a payload region (P).
Figure 4B:
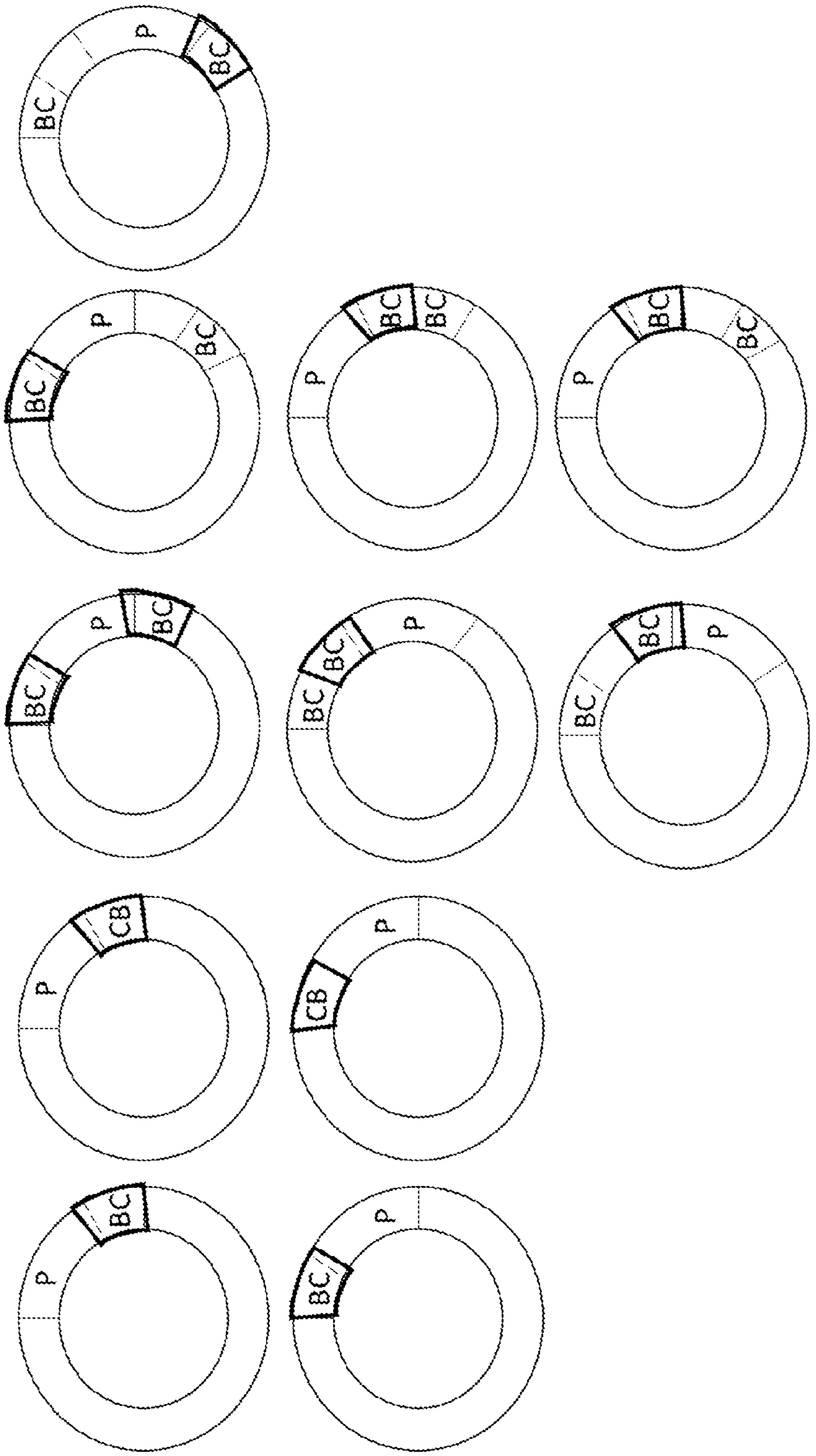
FIG. 4B is a diagram illustrating a series of circular benchmark polynucleotide constructs of the present disclosure where the barcode region (BC) or inverted barcode region (CB) may overlap the payload region (P).
Figure 4C:
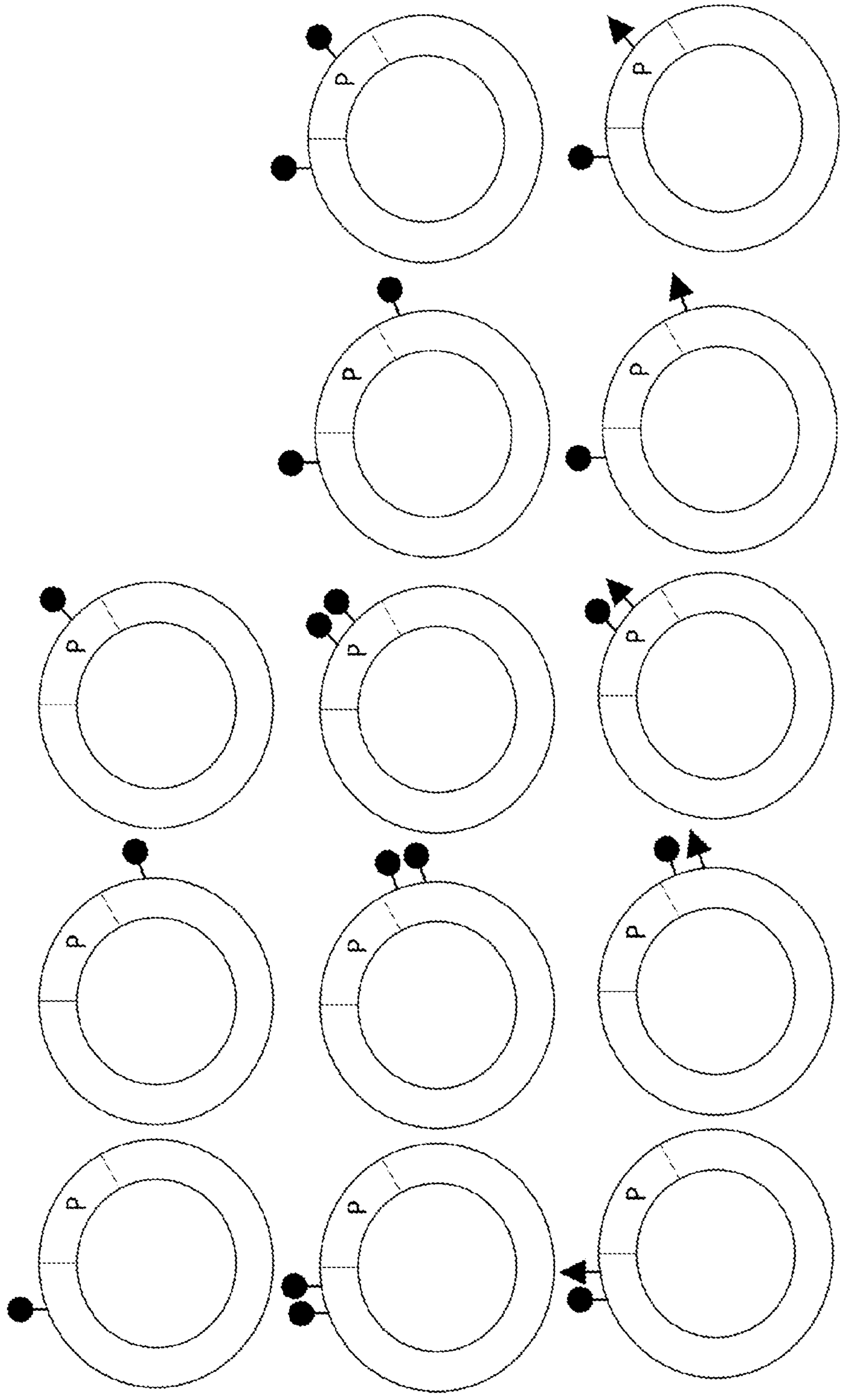
FIG. 4C is a diagram illustrating a series of circular benchmark polynucleotide constructs of the present disclosure which may include at least one tag and/or label.

Non-limiting examples of benchmark polynucleotide constructs with at least one identifier, which may be linear or circular, are provided in FIG. 3A, FIG. 3B and FIG. 3C. Non-limiting examples of circular benchmark polynucleotide constructs with at least one identifier are provided in FIG. 4A, FIG. 4B and FIG. 4C. In FIG. 3A, FIG. 3B, FIG. 4A and FIG. 4B the benchmark polynucleotide constructs include a payload region (referred to as "P" in the figure) and at least one identifier region (referred to as "BC" in the figure) and/or an inverted identifier region (referred to as "CB" in the figure). In FIG. 3C and FIG. 4C the benchmark polynucleotide constructs include a payload region (referred to as "P" in the figure) and at least one identifier moiety associated with the benchmark polynucleotide construct.

In some embodiments, the identifier region in the benchmark construct overlaps with the payload region. As used herein, "overlap" means that at least one nucleotide of the identifier region extends into the payload region. In some aspects the identifier region overlaps with the payload region by 1 nucleotide, 2 nucleotides, 3 nucleotides, 4 nucleotides, 5 nucleotides, 6 nucleotides, 7 nucleotides, 8 nucleotides, 9 nucleotides, 10 nucleotides, 11 nucleotides, 12 nucleotides, 13 nucleotides, 14 nucleotides, 15 nucleotides, 16 nucleotides, 17 nucleotides, 18 nucleotides, 19 nucleotides, 20 nucleotides, 21 nucleotides, 22 nucleotides, 23 nucleotides, 24 nucleotides, 25 nucleotides, 26 nucleotides, 27 nucleotides, 28 nucleotides, 29 nucleotides, 30 nucleotides, 31 nucleotides, 32 nucleotides, 33 nucleotides, 34 nucleotides, 35 nucleotides, 36 nucleotides, 37 nucleotides, 38 nucleotides, 39 nucleotides, 40 nucleotides 41 nucleotides, 42 nucleotides, 43 nucleotides, 44 nucleotides, 45 nucleotides, 46 nucleotides, 47 nucleotides, 48 nucleotides, 49 nucleotides, 50 nucleotides or more than 50 nucleotides. In some aspects the identifier region overlaps with the payload region by 1-5 nucleotides, 2-5 nucleotides, 3-5 nucleotides, 2-7 nucleotides, 3-7 nucleotides, 1-10 nucleotides, 2-10 nucleotides, 3-10 nucleotides, 5-10 nucleotides, 7-10 nucleotides, 1-15 nucleotides, 2-15 nucleotides, 3-15 nucleotides, 5-15 nucleotides, 7-15 nucleotides, 10-15 nucleotides, 12-15 nucleotides, 1-20 nucleotides, 2-20 nucleotides, 3-20 nucleotides, 5-20 nucleotides, 7-20 nucleotides, 10-20 nucleotides, 12-20 nucleotides, 15-20 nucleotides, 17-20 nucleotides, 1-25 nucleotides, 2-25 nucleotides, 3-25 nucleotides, 5-25 nucleotides, 7-25 nucleotides, 10-25 nucleotides, 12-25 nucleotides, 15-25 nucleotides, 17-25 nucleotides, 20-25 nucleotides, 1-30 nucleotides, 2-30 nucleotides, 3-30 nucleotides, 5-30 nucleotides, 7-30 nucleotides, 10-30 nucleotides, 12-30 nucleotides, 15-30 nucleotides, 17-30 nucleotides, 20-30 nucleotides, 25-30 nucleotides, 1-35 nucleotides, 2-35 nucleotides, 3-35 nucleotides, 5-35 nucleotides, 7-35 nucleotides, 10-35 nucleotides, 12-35 nucleotides, 15-35 nucleotides, 17-35 nucleotides, 20-35 nucleotides, 25-35 nucleotides, 30-35 nucleotides, 1-35 nucleotides, 2-35 nucleotides, 3-35 nucleotides, 5-35 nucleotides, 7-35 nucleotides, 10-35 nucleotides, 12-35 nucleotides, 15-35 nucleotides, 17-35 nucleotides, 20-35 nucleotides, 25-35 nucleotides, 30-35 nucleotides, 1-40 nucleotides, 2-40 nucleotides, 3-40 nucleotides, 5-40 nucleotides, 7-40 nucleotides, 10-40 nucleotides, 12-40 nucleotides, 15-40 nucleotides, 17-40 nucleotides, 20-40 nucleotides, 25-40 nucleotides, 30-40 nucleotides, 35-40 nucleotides, 1-45 nucleotides, 2-45 nucleotides, 3-45 nucleotides, 5-45 nucleotides, 7-45 nucleotides, 10-45 nucleotides, 12-45 nucleotides, 15-45 nucleotides, 17-45 nucleotides, 20-45 nucleotides, 25-45 nucleotides, 30-45 nucleotides, 35-45 nucleotides, 40-45 nucleotides, 1-50 nucleotides, 2-50 nucleotides, 3-50 nucleotides, 5-50 nucleotides, 7-50 nucleotides, 10-50 nucleotides, 12-50 nucleotides, 15-50 nucleotides, 17-50 nucleotides, 20-50 nucleotides, 25-50 nucleotides, 30-50 nucleotides, 35-50 nucleotides, 40-50 nucleotides, or 45-50 nucleotides.

In some embodiments, the benchmark polynucleotide construct comprises a payload region and an identifier region. The identifier region may be located 5' to the payload region, 3' to the payload region, or the identifier region may overlap with the 5' end or the 3' end of the payload region.

In some embodiments, the benchmark polynucleotide construct comprises a payload region and two identifier regions. Each identifier region may independently be located 5' to the payload region, 3' to the payload region, or the identifier region may overlap with the 5' end or the 3' end of the payload region.

As a non-limiting example, the first identifier region is located 5' to the payload region and the second identifier region is located 3' to the payload region. As a non-limiting example, the first and second identifier regions are located 5' to the payload region. As a non-limiting example, the first and second identifier regions are located 3' to the payload region.

As a non-limiting example, the first identifier region is inverted and is located 5' to the payload region and the second identifier region is located 3' to the payload region. As a non-limiting example, the first identifier region is inverted and is located 5' to the payload region and the second identifier region is inverted and is located 3' to the payload region. As a non-limiting example, the first identifier region is located 5' to the payload region and the second identifier region is inverted and is located 3' to the payload region. As a non-limiting example, the first and second identifier regions are both inverted and are located 5' to the payload region. As a non-limiting example, the first and second identifier regions are located 5' to the payload region and the first identifier region is inverted. As a non-limiting example, the first and second identifier regions are located 5' to the payload region and the second identifier region is inverted. As a non-limiting example, the first and second identifier region are both inverted and located 3' to the payload region. As a non-limiting example, the first and second identifier regions are located 3' to the payload region and the first identifier region is inverted. As a non-limiting example, the first and second identifier regions are located 3' to the payload region and the second identifier region is inverted.

As a non-limiting example, the first identifier region is located 5' to the payload region and overlaps with the payload region and the second identifier region is located 3' to the payload region. As a non-limiting example, the first identifier region is located 5' to the payload region and the second identifier region is located 3' to the payload region and overlaps with the payload region.

As a non-limiting example, the first and second identifier regions are located 5' to the payload region and the second identifier region overlaps with the payload region. As a non-limiting example, the first and second identifier regions are located 3' to the payload region and the first identifier region overlaps with the payload region.

As a non-limiting example, the first identifier region is inverted, is located 5' to the payload region and overlaps with the payload region, and the second identifier region is located 3' to the payload region. As a non-limiting example, the first identifier region is inverted and is located 5' to the payload region and the second identifier region is located 3' to the payload region and overlaps with the payload region. As a non-limiting example, the first identifier region is inverted, is located 5' to the payload region, the second identifier region is located 3' to the payload region, and both of the first and second identifier regions overlap with the payload region.

As a non-limiting example, the first identifier region is inverted, is located 5' to the payload region and overlaps with the payload region, and the second identifier region is inverted and is located 3' to the payload region. As a non-limiting example, the first identifier region is inverted and is located 5' to the payload region and the second identifier region is inverted, is located 3' to the payload region and overlaps with the payload region. As a non-limiting example, the first identifier region is inverted and is located 5' to the payload region, and the second identifier region is inverted and is located 3' to the payload region, and both of the first and second identifier regions overlap with the payload region.

As a non-limiting example, the first identifier region is located 5' to the payload region and overlaps with the payload region, and the second identifier region is inverted and is located 3' to the payload region. As a non-limiting example, the first identifier region is located 5' to the payload region and the second identifier region is inverted, is located 3' to the payload region and overlaps with the payload region. As a non-limiting example, the first identifier region is located 5' to the payload region and the second identifier region is inverted and is located 3' to the payload region, and both of the first and second identifier regions overlap with the payload region.

As a non-limiting example, the first and second identifier regions are both inverted and are located 5' to the payload region, and the second identifier region overlaps with the payload region. As a non-limiting example, the first and second identifier regions are located 5' to the payload region and the first identifier region is inverted, and the second identifier region overlaps with the payload region. As a non-limiting example, the first and second identifier regions are located 5' to the payload region and the second identifier region is inverted and overlaps with the payload region. As a non-limiting example, the first and second identifier region are both inverted and located 3' to the payload region, and the first identifier region overlap with the payload region. As a non-limiting example, the first and second identifier regions are located 3' to the payload region and the first identifier region is inverted and overlaps with the payload region. As a non-limiting example, the first and second identifier regions are located 3' to the payload region and the second identifier region is inverted, and the first payload region overlap with the payload region.

In some embodiments, at least one identifier moiety may be associated with the benchmark polynucleotide construct. The benchmark polynucleotide construct may have 1, 2, 3, 4, 5, 6, 7, 8, 9, or 10 or more identifier moieties associated with the benchmark polynucleotide construct which may be the same moiety or different moieties associated with the benchmark polynucleotide construct. Each identifier moiety may independently be located on the flanking region 5' to the payload region, on the flanking region 3' to the payload region, or the location of the identifier moiety may span the 5' end or the 3'end of the payload region and a flanking region. In some aspects the location of the identifier moiety may include one or more nucleotides of the payload region such as, but not limited to, 1 nucleotide, 2 nucleotides, 3 nucleotides, 4 nucleotides, 5 nucleotides, 6 nucleotides, 7 nucleotides, 8 nucleotides, 9 nucleotides, 10 nucleotides, 11 nucleotides, 12 nucleotides, 13 nucleotides, 14 nucleotides, 15 nucleotides, 16 nucleotides, 17 nucleotides, 18 nucleotides, 19 nucleotides, 20 nucleotides, 21 nucleotides, 22 nucleotides, 23 nucleotides, 24 nucleotides, 25 nucleotides, 26 nucleotides, 27 nucleotides, 28 nucleotides, 29 nucleotides, 30 nucleotides, 31 nucleotides, 32 nucleotides, 33 nucleotides, 34 nucleotides, 35 nucleotides, 36 nucleotides, 37 nucleotides, 38 nucleotides, 39 nucleotides, 40 nucleotides 41 nucleotides, 42 nucleotides, 43 nucleotides, 44 nucleotides, 45 nucleotides, 46 nucleotides, 47 nucleotides, 48 nucleotides, 49 nucleotides, 50 nucleotides or more than 50 nucleotides. In some aspects the location of the identifier moiety may include one or more nucleotides of the payload region such as, but not limited to, 1-5 nucleotides, 2-5 nucleotides, 3-5 nucleotides, 2-7 nucleotides, 3-7 nucleotides, 1-10 nucleotides, 2-10 nucleotides, 3-10 nucleotides, 5-10 nucleotides, 7-10 nucleotides, 1-15 nucleotides, 2-15 nucleotides, 3-15 nucleotides, 5-15 nucleotides, 7-15 nucleotides, 10-15 nucleotides, 12-15 nucleotides, 1-20 nucleotides, 2-20 nucleotides, 3-20 nucleotides, 5-20 nucleotides, 7-20 nucleotides, 10-20 nucleotides, 12-20 nucleotides, 15-20 nucleotides, 17-20 nucleotides, 1-25 nucleotides, 2-25 nucleotides, 3-25 nucleotides, 5-25 nucleotides, 7-25 nucleotides, 10-25 nucleotides, 12-25 nucleotides, 15-25 nucleotides, 17-25 nucleotides, 20-25 nucleotides, 1-30 nucleotides, 2-30 nucleotides, 3-30 nucleotides, 5-30 nucleotides, 7-30 nucleotides, 10-30 nucleotides, 12-30 nucleotides, 15-30 nucleotides, 17-30 nucleotides, 20-30 nucleotides, 25-30 nucleotides, 1-35 nucleotides, 2-35 nucleotides, 3-35 nucleotides, 5-35 nucleotides, 7-35 nucleotides, 10-35 nucleotides, 12-35 nucleotides, 15-35 nucleotides, 17-35 nucleotides, 20-35 nucleotides, 25-35 nucleotides, 30-35 nucleotides, 1-35 nucleotides, 2-35 nucleotides, 3-35 nucleotides, 5-35 nucleotides, 7-35 nucleotides, 10-35 nucleotides, 12-35 nucleotides, 15-35 nucleotides, 17-35 nucleotides, 20-35 nucleotides, 25-35 nucleotides, 30-35 nucleotides, 1-40 nucleotides, 2-40 nucleotides, 3-40 nucleotides, 5-40 nucleotides, 7-40 nucleotides, 10-40 nucleotides, 12-40 nucleotides, 15-40 nucleotides, 17-40 nucleotides, 20-40 nucleotides, 25-40 nucleotides, 30-40 nucleotides, 35-40 nucleotides, 1-45 nucleotides, 2-45 nucleotides, 3-45 nucleotides, 5-45 nucleotides, 7-45 nucleotides, 10-45 nucleotides, 12-45 nucleotides, 15-45 nucleotides, 17-45 nucleotides, 20-45 nucleotides, 25-45 nucleotides, 30-45 nucleotides, 35-45 nucleotides, 40-45 nucleotides, 1-50 nucleotides, 2-50 nucleotides, 3-50 nucleotides, 5-50 nucleotides, 7-50 nucleotides, 10-50 nucleotides, 12-50 nucleotides, 15-50 nucleotides, 17-50 nucleotides, 20-50 nucleotides, 25-50 nucleotides, 30-50 nucleotides, 35-50 nucleotides, 40-50 nucleotides, or 45-50 nucleotides.

In some embodiments, one identifier moiety may be associated with the benchmark polynucleotide construct. As a non-limiting example, the identifier moiety may be associated with the benchmark polynucleotide construct on the 5' end of the benchmark polynucleotide construct. As a non-limiting example, the identifier moiety may be associated with the benchmark polynucleotide construct on the 5' flanking region. As a non-limiting example, the identifier moiety may be associated with the benchmark polynucleotide construct on the 3' flanking region. As a non-limiting example, the identifier moiety may be associated with the benchmark polynucleotide construct on the 3' end of the benchmark polynucleotide construct. As a non-limiting example, the identifier moiety may be associated with the benchmark polynucleotide construct on the payload region. As a non-limiting example, the benchmark polynucleotide construct comprises an identifier moiety and the location of the identifier moiety spans the 5' end of the payload region and the 5' flanking region. As a non-limiting example, the benchmark polynucleotide construct comprises an identifier moiety and the location of the identifier moiety spans the 3' end of the payload region and the 3' flanking region.

In some embodiments, two identifier moieties are associated with the benchmark polynucleotide construct. As a non-limiting example, the first identifier moiety and the second identifier moiety are located on the 5' flanking region. As a non-limiting example, the first identifier moiety and the second identifier moiety are located on the payload region. As a non-limiting example, the first identifier moiety and the second identifier moiety are located on the 3' flanking region. As a non-limiting example, the first identifier moiety and the second identifier moiety are located on the 5' end of the benchmark polynucleotide construct. As a non-limiting example, the first identifier moiety and the second identifier moiety are located on the 3' end of the benchmark polynucleotide construct.

As a non-limiting example, the first identifier moiety is located on the 5' end of the benchmark polynucleotide construct and the second identifier moiety is located on the 5' flanking region. As a non-limiting example, the first identifier moiety is located on the 5' end of the benchmark polynucleotide construct and the second identifier moiety is located on the payload region. As a non-limiting example, the first identifier moiety is located on the 5' end of the benchmark polynucleotide construct and the second identifier moiety is located on the 3' flanking region. As a non-limiting example, the first identifier moiety is located on the 5' end of the benchmark polynucleotide construct and the location of the second identifier moiety spans the 5' flanking region and the payload region. As a non-limiting example, the first identifier moiety is located on the 5' end of the benchmark polynucleotide construct and the location of the second identifier moiety spans the 3' flanking region and the payload region. As a non-limiting example, the first identifier moiety is located on the 5' end of the benchmark polynucleotide construct and the second identifier moiety is located on the 3' end of the benchmark polynucleotide construct.

As a non-limiting example, the first identifier moiety is located on the 5' flanking region and the second identifier moiety is located on the payload region. As a non-limiting example, the first identifier moiety is located on the 5' flanking region and the second identifier moiety is located on the 3' flanking region. As a non-limiting example, the first identifier moiety is located on the 5' flanking region and the location of the second identifier moiety spans the 5' flanking region and the payload region. As a non-limiting example, the first identifier moiety is located on the 5' flanking region and the location of the second identifier moiety spans the 3' flanking region and the payload region. As a non-limiting example, the first identifier moiety is located on the 5' flanking region and the second identifier moiety is located on the 5' end of the benchmark polynucleotide construct. As a non-limiting example, the first identifier moiety is located on the 5' flanking region and the second identifier moiety is located on the 3' end of the benchmark polynucleotide construct.

As a non-limiting example, the location of the first identifier moiety spans the 5' flanking region and the payload region and the second identifier moiety is located on the 5' end of the benchmark polynucleotide construct. As a non-limiting example, the location of the first identifier moiety spans the 5' flanking region and the payload region and the second identifier moiety is located on the 5' flanking region. As a non-limiting example, the location of the first identifier moiety spans the 5' flanking region and the payload region and the second identifier moiety is located on the payload region. As a non-limiting example, the location of the first identifier moiety spans the 5' flanking region and the payload region and the location of the second identifier moiety spans the 3' flanking region and the payload region. As a non-limiting example, the location of the first identifier moiety spans the 5' flanking region and the payload region and the second identifier moiety is located on the 3' flanking region. As a non-limiting example, the location of the first identifier moiety spans the 5' flanking region and the payload region and the second identifier moiety is located on the 3' end of the benchmark polynucleotide construct.

As a non-limiting example, the first identifier moiety is located on the payload region and the second identifier moiety is located on the 5' end of the benchmark polynucleotide construct. As a non-limiting example, the first identifier moiety is located on the payload region and the second identifier moiety is located on the 5' flanking region. As a non-limiting example, the first identifier moiety is located on the payload region and the location of the second identifier moiety spans the 5' flanking region and the payload region. As a non-limiting example, the first identifier moiety is located on the payload region and the location of the second identifier moiety spans the 3' flanking region and the payload region. As a non-limiting example, the first identifier moiety is located on the payload region and the second identifier moiety is located on the 3' flanking region. As a non-limiting example, the first identifier moiety is located on the payload region and the second identifier moiety is located on the 3' end of the benchmark polynucleotide construct.

As a non-limiting example, the location of the first identifier moiety spans the 3' flanking region and the payload region and the second identifier moiety is located on the 5' end of the benchmark polynucleotide construct. As a non-limiting example, the location of the first identifier moiety spans the 3' flanking region and the payload region and the second identifier moiety is located on the 5' flanking region. As a non-limiting example, the location of the first identifier moiety spans the 3' flanking region and the payload region and the location of the second identifier moiety spans the 5' flanking region and the payload region. As a non-limiting example, the location of the first identifier moiety spans the 3' flanking region and the payload region and the second identifier moiety is located on the payload region. As a non-limiting example, the location of the first identifier moiety spans the 3' flanking region and the payload region and the second identifier moiety is located on the 3' flanking region. As a non-limiting example, the location of the first identifier moiety spans the 3' flanking region and the payload region and the second identifier moiety is located on the 3'end of the benchmark polynucleotide construct.

As a non-limiting example, the location of the first identifier moiety spans the 3' flanking region and the payload region and the second identifier moiety is located on the 5' flanking region. As a non-limiting example, the location of the first identifier moiety spans the 5' flanking region and the payload region and the second identifier moiety is located on the payload region. As a non-limiting example, the location of the first identifier moiety spans the 5' flanking region and the payload region and the location of the second identifier moiety spans the 3' flanking region and the payload region. As a non-limiting example, the location of the first identifier moiety spans the 5' flanking region and the payload region and the second identifier moiety is located on the 3' flanking region. As a non-limiting example, the location of the first identifier moiety spans the 5' flanking region and the payload region and the second identifier moiety is located on the 3' end of the benchmark polynucleotide construct.

As a non-limiting example, the first identifier moiety is located on the 3' flanking region and the second identifier moiety is located on the 5' end of the benchmark polynucleotide construct. As a non-limiting example, the first identifier moiety is located on the 3' flanking region and the second identifier moiety is located on the 5' flanking region. As a non-limiting example, the first identifier moiety is located on the 3' flanking region and the location of the second identifier moiety spans the 5' flanking region and the payload region. As a non-limiting example, the first identifier moiety is located on the 3' flanking region and the second identifier moiety is located on the payload region. As a non-limiting example, the first identifier moiety is located on the 3' flanking region and the location of the second identifier moiety spans the 3' flanking region and the payload region. As a non-limiting example, the first identifier moiety is located on the 3' flanking region and the second identifier moiety is located on the 3' end of the benchmark polynucleotide construct.

As a non-limiting example, the first identifier moiety is located on the 3' end of the benchmark polynucleotide construct and the second identifier moiety is located on the 5' end of the benchmark polynucleotide construct. As a non-limiting example, the first identifier moiety is located on the 3' end of the benchmark polynucleotide construct and the second identifier moiety is located on the 5' flanking region. As a non-limiting example, the first identifier moiety is located on the 5' end of the benchmark polynucleotide construct and the location of the second identifier moiety spans the 5' flanking region and the payload region. As a non-limiting example, the first identifier moiety is located on the 3' end of the benchmark polynucleotide construct and the second identifier moiety is located on the payload region. As a non-limiting example, the first identifier moiety is located on the 5' end of the benchmark polynucleotide construct and the location of the second identifier moiety spans the 3' flanking region and the payload region. As a non-limiting example, the first identifier moiety is located on the 3' end of the benchmark polynucleotide construct and the second identifier moiety is located on the 3' flanking region.

In some embodiments, three identifier moieties are associated with the benchmark polynucleotide construct.

In some embodiments, four identifier moieties are associated with the benchmark polynucleotide construct.

In some embodiments, five identifier moieties are associated with the benchmark polynucleotide construct.

In some embodiments, six identifier moieties are associated with the benchmark polynucleotide construct.

In some embodiments, seven identifier moieties are associated with the benchmark polynucleotide construct.

In some embodiments, eight identifier moieties are associated with the benchmark polynucleotide construct.

In some embodiments, nine identifier moieties are associated with the benchmark polynucleotide construct.

In some embodiments, ten identifier moieties are associated with the benchmark polynucleotide construct.

II. Cargo and Payloads

The originator constructs and benchmark constructs of the present disclosure may comprise, encode or be conjugated to a cargo or payload. As used herein, the term “cargo” or “payload” can refer to one or more molecules or structures encompassed in a delivery vehicle for delivery to or into a cell or tissue. Non-limiting examples of cargo can include a nucleic acid, a polypeptide, peptide, protein, a liposome, a label, a tag, a small chemical molecule, a large biological molecule, and any combinations or fragments thereof. In the originator constructs and benchmark constructs, the region of the construct which comprises or encodes the cargo or payload is referred to as the "cargo region" or the "payload region."

In some embodiments, the cargo or payload is or encodes a biologically active molecule such as, but not limited to a therapeutic protein. As used herein, the term "biologically active" refers to a characteristic of any agent that has activity in a biological system, and particularly in an organism. For instance, an agent that, when administered to an organism, has a biological effect on that organism, is considered to be biologically active. In some embodiments, the cargo or payload is or encodes one or more prophylactically- or therapeutically-active proteins, polypeptides, or other factors. As a non-limiting example, the cargo or payload may be or encode an agent that enhances tumor killing activity such as, but not limited to, TRAIL or tumor necrosis factor (TNF), in a cancer. As another non-limiting example, the cargo or payload may be or encode an agent suitable for the treatment of conditions such as muscular dystrophy (e.g., cargo or payload is or encodes Dystrophin), cardiovascular disease (e.g., cargo or payload is or encodes SERCA2a, GATA4, Tbx5, Mef2C, Hand2, Myocd, etc.), neurodegenerative disease (e.g., cargo or payload is or encodes NGF, BDNF, GDNF, NT-3, etc.), chronic pain (e.g., cargo or payload is or encodes GlyRal), an enkephalin, or a glutamate decarboxylase (e.g., cargo or payload is or encodes GAD65, GAD67, or another isoform), lung disease (e.g., cargo or payload is or encodes CFTR), hemophilia (e.g., cargo or payload is or encodes Factor VIII or Factor IX), neoplasia (e.g., cargo or payload is or encodes PTEN, ATM, ATR, EGFR, ERBB2, ERBB3, ERBB4, Notch1, Notch2, Notch3, Notch4, AKT, AKT2, AKT3, HIF, HI Fla, HIF3a, Met, HRG, Bcl2, PPARalpha, PPAR gamma, WT1 (Wilms Tumor), FGF Receptor Family members (5 members: 1, 2, 3, 4, 5), CDKN2a, APC, RB (retinoblastoma), MEN1, VHL, BRCA1, BRCA2, AR (Androgen Receptor), TSG101, IGF, IGF Receptor, Igfl (4 variants), Igf2 (3 variants), Igfl Receptor, Igf2 Receptor, Bax, Bcl2, caspases family (9 members: 1, 2, 3, 4, 6, 7, 8, 9, 12), Kras, Ape), age-related macular degeneration (e.g., cargo or payload is or encodes Aber, Cc12, Cc2, cp (ceruloplasmin), Timp3, cathepsin D, Vldlr), schizophrenia (e.g. Neuregulin (Nrgl), Erb4 (receptor for Neuregulin), Complexin-1 (Cplx1), Tphl Tryptophan hydroxylase, Tph2 Tryptophan hydroxylase 2, Neurexin 1, GSK3, GSK3a, GSK3b, 5-HIT (Slc6a4), COMT, DRD (Drdla), SLC6A3, DAOA, DTNBPI, Dao (Dao1)), trinucleotide repeat disorders (e.g., HTT (Huntington's Dx), SBMA/SMAXI/AR (Kennedy's Dx), FXN/X25 (Friedrich's Ataxia), ATX3 (Machado-Joseph's Dx), ATXNI and ATXN2 (spinocerebellar ataxias), DMPK (myotonic dystrophy), Atrophin-1 and Atnl(DRPLA Dx), CBP (Creb-BP-global instability), VLDLR (Alzheimer's), Atxn7, Atxn10), fragile X syndrome (e.g., cargo or payload is or encodes FMR2, FXRI, FXR2, mGLUR5), secretase related disorders (e.g., cargo or payload is or encodes APH-1 (alpha and beta), Presenilin (Psenl), nicastrin (Ncstn), PEN-2), ALS (e.g., cargo or payload is or encodes SOD1, ALS2, STEX, FUS, TARD BP, VEGF (VEGF-a, VEGF-b, VEGF-c)), autism (e.g., cargo or payload is or encodes Mecp2, BZRAP1, MDGA2, Sema5A, Neurexin 1), Alzheimer's disease (e.g., cargo or payload is or encodes E1, CHIP, UCH, UBB, Tau, LRP, PICALM, Clusterin, PS1, SORL1, CR1, Vldlr, Uba1, Uba3, CHIP28 (Aqp1, Aquaporin 1), Uchl1, Uchl3, APP), inflammation (e.g., cargo or payload is or encodes IL-10, IL-1 (IL-Ia, IL-Ib), IL-13, IL-17 (IL-17a (CTLA8), IL-17b, IL-17c, IL-17d, IL-171), 11-23, Cx3crl, ptpn22, TNFa, NOD2/CARD15 for IBD, IL-6, IL-12 (IL-12a, IL-12b), CTLA4, Cx3cll), Parkinson's Disease (e.g., x-Synuclein, DJ-1, LRRK2, Parkin, PINK1), blood and coagulation disorders, such as, e.g., anemia, bare lymphocyte syndrome, bleeding disorders, hemophagocytic lymphohistiocytosis disorders, hemophilia A, hemophilia B, hemorrhagic disorders, leukocyte deficiencies and disorders, sickle cell anemia, and thalassemia (e.g., cargo or payload is or encodes CRAN1, CDA1, RPS19, DBA, PKLR, PK1, NT5C3, UMPH1, PSNI, RHAG, RH50A, NRAMP2, SPTB, ALAS2, ANH1, ASB, ABCB7, ABC7, ASAT, TAPBP, TPSN, TAP2, ABCB3, PSF2, RING11, MHC2TA, C2TA, RFX5, RFXAP, RFX5, TBXA2R, P2RX1, P2X1, HF1, CFH, HUS, MCFD2, FANCA, FAC A, FA1, FA, FA A, FAAP95, FAAP90, FLJ34064, FANCB, FANCC, FACC, BRCA2, FANCDI, FANCD2, FANCD, FACD, FAD, FANCE, FACE, FANCF, XRCC9, FANCG, BR1PI, BACH1, FANCJ, PHF9, FANCL, FANCM, KIAA1596, PRF1, HPLH2, UNC13D, MUNC13-4, HPLH3, HLH3, FHL3, F8, FSC, PI, ATT, F5, ITGB2, CD18, LCAMB, LAD, EIF2B1, EIF2BA, EIF2B2, EIF2B3, EIF2B5, LVWM, CACH, CLE, EIF2B4, HBB, HBA2, HBB, HBD, LCRB, HBA1), B-cell non-Hodgkin lymphoma or leukemia (e.g., cargo or payload is or encodes BCL7A, BCL7, ALI, TCL5, SCL, TAL2, FLT3, NBS1, NBS, ZNFN1AI, 1KI, LYF1, HOXD4, HOX4B, BCR, CML, PHL, ALL, ARNT, KRAS2, RASK2, GMPS, AFIO, ARHGEF12, LARG, KIAA0382, CALM, CLTH, CEBPA, CEBP, CHIC2, BTL, FLT3, KIT, PBT, LPP, NPMI, NUP214, D9S46E, CAN, CAIN, RUNXI, CBFA2, AML1, WHSC1LI, NSD3, FLT3, AF1Q, NPMI, NUMA1, ZNF145, PLZF, PML, MYL, STAT5B, AF1Q, CALM, CLTH, ARL11, ARLTS1, P2RX7, P2X7, BCR, CML, PHL, ALL, GRAF, NF1, VRNF, WSS, NFNS, PTPNII, PTP2C, SHP2, NS1, BCL2, CCND1, PRAD1, BCL1, TCRA, GATA1, GF1, ERYF1, NFE1, ABLI, NQO1, DIA4, NMOR1, NUP214, D9S46E, CAN, CAIN), inflammation and immune related diseases and disorders (e.g., cargo or payload is or encodes KIR3DL1, NKAT3, NKB1, AMB11, K1R3DS1, IFNG, CXCL12, TNFRSF6, APT1, FAS, CD95, ALPS1A, IL2RG, SCIDX1, SCIDX, IMD4, CCL5, SCYA5, D17S136E, TCP228, IL10, CSIF, CMKBR2, CCR2, CMKBR5, CCCKR5 (CCR5), CD3E, CD3G, AICDA, AID, HIGM2, TNFRSF5, CD40, UNG, DGU, HIGM4, TNFSFS, CD40LG, HIGM1, IGM, FOXP3, IPEX, AIID, XPID, PIDX, TNFRSF14B, TACI), inflammation (e.g., cargo or payload is or encodes IL-10, IL-1 (IL-IA, IL-IB), IL-13, IL-17 (IL-17a (CTLA8), IL-17b, IL-17c, IL-17d, IL-171), 11-23, Cx3crl, ptpn22, TNFa, NOD2/CARD15 for IBD, IL-6, IL-12 (IL-12a, IL-12b), CTLA4, Cx3cII), JAK3, JAKL, DCLREIC, ARTEMIS, SCIDA, RAG1, RAG2, ADA, PTPRC, CD45, LCA, IL7R, CD3D, T3D, IL2RG, SCIDXI, SCIDX, IMD4), metabolic, liver, kidney and protein diseases and disorders (e.g., cargo or payload is or encodes TTR, PALB, APOA1, APP, AAA, CVAP, ADI, GSN, FGA, LYZ, TTR, PALB, KRT18, KRT8, CIRHIA, NAIC, TEX292, KIAA1988, CFTR, ABCC7, CF, MRP7, SLC2A2, GLUT2, G6PC, G6PT, G6PT1, GAA, LAMP2, LAMPB, AGL, GDE, GBE1, GYS2, PYGL, PFKM, TCF1, HNF1A, MODY3, SCOD1, SCO1, CTNNB1, PDGFRL, PDGRL, PRLTS, AX1NI, AXIN, CTNNB1, TP53, P53, LFS1, IGF2R, MPRI, MET, CASP8, MCH5, UMOD, HNFJ, FJHN, MCKD2, ADMCKD2, PAH, PKU1, QDPR, DHPR, PTS, FCYT, PKHD1, ARPKD, PKD1, PKD2, PKD4, PKDTS, PRKCSH, G19P1, PCLD, SEC63), muscular/skeletal diseases and disorders (e.g., cargo or payload is or encodes DMD, BMD, MYF6, LMNA, LMN1, EMD2, FPLD, CMDIA, HGPS, LGMDIB, LMNA, LMNI, EMD2, FPLD, CMDIA, FSHMD1A, FSHD1A, FKRP, MDC1C, LGMD2I, LAMA2, LAMM, LARGE, KIAA0609, MDC1D, FCMD, TTID, MYOT, CAPN3, CANP3, DYSF, LGMD2B, SGCG, LGMD2C, DMDA1, SCG3, SGCA, ADL, DAG2, LGMD2D, DMDA2, SGCB, LGMD2E, SGCD, SGD, LGMD2F, CMD1L, TCAP, LGMD2G, CMD1N, TRIM32, HT2A, LGMD2H, FKRP, MDCIC, LGMD21, TTN, CMD1G, TMD, LGMD2J, POMT1, CAV3, LGMD1C, SEPN1, SELN, RSMD1, PLEC1, PLTN, EBS1, LRP5, BMND1, LRP7, LR3, OPPG, VBCH2, CLCN7, CLC7, OPTA2, OSTMI, GL, TCIRG1, TIRC7, OC116, OPTB1, VAPB, VAPC, ALS8, SMN1, SMA1, SMA2, SMA3, SMA4, BSCL2, SPG17, GARS, SMAD1, CMT2D, HEXB, IGHMBP2, SMUBP2, CATF1, SMARD1), neurological and neuronal diseases and disorders (e.g., cargo or payload is or encodes SOD1, ALS2, STEX, FUS, TARDBP, VEGF (VEGF-a, VEGF-b, VEGF-c), APP, AAA, CVAP, ADI, APOE, AD2, PSEN2, AD4, STM2, APBB2, FE65LI, NOS3, PLAU, URK, ACE, DCPI, ACEI, MPO, PAC1PI, PAXIPIL, PTIP, A2M, BLMH, BMH, PSEN1, AD3, Mecp2, BZRAP1, MDGA2, Sema5A, Neurexin 1, GLO1, MECP2, RTT, PPMX, MRX16, MRX79, NLGN3, NLGN4, KIAA1260, AUTSX2, FMR2, FXR1, FXR2, mGLUR5, HD, IT15, PRNP, PRIP, JPH3, JP3, HDL2, TBP, SCA17, NR4A2, NURR1, NOT, TINUR, SNCAIP, TBP, SCA17, SNCA, NACP, PARK1, PARK4, DJI, PARK7, LRRK2, PARK8, PINK1, PARK6, UCHL1, PARK5, SNCA, NACP, PARK1, PARK4, PRKN, PARK2, PDJ, DBH, NDUFV2, MECP2, RTT, PPMX, MRX16, MRX79, CDKL5, STK9, MECP2, RTT, PPMX, MRX16, MRX79, x-Synuclein, DJ-1, Neuregulin-1 (Nrgl), Erb4 (receptor for Neuregulin), Complexin-1 (Cplx1), Tphl Tryptophan hydroxylase, Tph2, Tryptophan hydroxylase 2, Neurexin 1, GSK3, GSK3a, GSK3b, 5-HTT (Slc6a4), CONT, DRD (Drdla), SLC6A, DAOA, DTNBP1, Dao (Dao1), APH-1 (alpha and beta), Presenilin (Psenl), Nicastrin, (Ncstn), PEN-2, Nos1, Parp1, Nat1, Nat2, HTT, SBMA/SMAX1/AR, FXN/X25, ATX3, TXN, ATXN2, DMPK, Atrophin-1, Atnl, CBP, VLDLR, Atxn7, and Atxn1O), and ocular diseases and disorders (e.g., Aber, Cc12, Cc2, cp (ceruloplasmin), Timp3, cathepsin-D, Vldlr, Ccr2, CRYAA, CRYA1, CRYBB2, CRYB2, PITX3, BFSP2, CP49, CP47, CRYAA, CRYAI, PAX6, AN2, MGDA, CRYBA1, CRYB1, CRYGC, CRYG3, CCL, LIM2, MP19, CRYGD, CRYG4, BFSP2, CP49, CP47, HSF4, CTM, HSF4, CTM, MIP, AQPO, CRYAB, CRYA2, CTPP2, CRYBB1, CRYGD, CRYG4, CRYBB2, CRYB2, CRYGC, CRYG3, CCL, CRYAA, CRYAI, GJA8, CX50, CAE1, GJA3, CX46, CZP3, CAE3, CCM1, CAM, KRIT1, APOA1, TGFBI, CSD2, CDGG1, CSD, BIGH3, CDG2, TACSTD2, TROP2, M1SI, VSX1, RINX, PPCD, PPD, KTCN, COL8A2, FECD, PPCD2, PIP5K3, CFD, KERA, CNA2, MYOC, TIGR, GLCIA, JO AG, GPOA, OPTN, GLC1E, FIP2, HYPL, NRP, CYP1BI, GLC3A, OPA1, NTG, NPG, CYP1BI, GLC3A, CRB1, RP12, CRX, CORD2, CRD, RPGRIPI, LCA6, CORD9, RPE65, RP20, AIPL1, LCA4, GUCY2D, GUC2D, LCA1, CORD6, RDH12, LCA3, ELOVL4, ADMD, STGD2, STGD3, RDS, RP7, PRPH2, PRPH, AVMD, AOFMD, and VMD2).

In some embodiments, the cargo or payload is or encodes a factor that can affect the differentiation of a cell. As a non-limiting example, the expression of one or more of Oct4, Klf4, Sox2, c-Myc, L-Myc, dominant-negative p53, Nanog, Glis1, Lin28, TFIID, mir-302/367, or other miRNAs can cause the cell to become an induced pluripotent stem (iPS) cell.

In some embodiments, the cargo or payload is or encodes a factor for transdifferentiating cells. Non-limiting examples of factors include: one or more of GATA4, Tbx5, Mef2C, Myocd, Hand2, SRF, Mesp1, SMARCD3 for cardiomyocytes; Ascii, Nurr1, Lmx1A, Bm2, Myt11, NeuroD1, FoxA2 for neural cells; and Hnf4a, Foxa1, Foxa2 or Foxa3 for hepatic cells.

Polypeptides, Proteins and Peptides

The originator constructs and benchmark constructs of the present disclosure may comprise, encode or be conjugated to a cargo or payload which is a polypeptide, protein or peptide. As used herein, the term "polypeptide" generally refers to polymers of amino acids linked by peptide bonds and embraces "protein and "peptides." Polypeptides for the present disclosure include all polypeptides, proteins and/or peptides known in the art. Non-limiting categories of polypeptides include antigens, antibodies, antibody fragments, cytokines, peptides, hormones, enzymes, oxidants, antioxidants, synthetic polypeptides, and chimeric polypeptides.

As used herein, the term "peptide" generally refers to shorter polypeptides of about 50 amino acids or less. Peptides with only two amino acids may be referred to as "dipeptides." Peptides with only three amino acids may be referred to as "tripeptides." Polypeptides generally refer to polypeptides with from about 4 to about 50 amino acids. Peptides may be obtained via any method known to those skilled in the art. In some embodiments, peptides may be expressed in culture. In some embodiments, peptides may be obtained via chemical synthesis (e.g. solid phase peptide synthesis).

In some embodiments, the originator constructs and benchmark constructs of the present disclosure may comprise, encode or be conjugated to a cargo or payload which is a simple protein which upon hydrolysis yields the amino acids and occasionally small carbohydrate compounds. Non-limiting examples of simple proteins include albumins, albuminoids, globulins, glutelins, histones and protamines.

In some embodiments, the originator constructs and benchmark constructs of the present disclosure may comprise, encode or be conjugated to a cargo or payload which is a conjugated protein which may be a simple protein associated with a non-protein. Non-limiting examples of conjugated proteins include glycoproteins, hemoglobins, lecithoproteins, nucleoproteins, and phosphoproteins.

In some embodiments, the originator constructs and benchmark constructs of the present disclosure may comprise, encode or be conjugated to a cargo or payload which is a derived protein which is a protein that is derived from a simple or conjugated protein by chemical or physical means. Non-limiting examples of derived proteins include denatured proteins and peptides.

In some embodiments, the polypeptide, protein or peptide may be unmodified.

In some embodiments, the polypeptide, protein or peptide may be modified. Types of modifications include, but are not limited to, Phosphorylation, Glycosylation, Acetylation, Ubiquitylation/Sumoylation, Methylation, Palmitoylation, Quinone, Amidation, Myristoylation, Pyrrolidone carboxylic acid, Hydroxylation, Phosphopantetheine, Prenylation, GPI anchoring, Oxidation, ADP-ribosylation, Sulfation, S-nitrosylation, Citrullination, Nitration, Gamma-carboxyglutamic acid, Formylation, Hypusine, Topaquinone (TPQ), Bromination, Lysine topaquinone (LTQ), Tryptophan tryptophylquinone (TTQ), Iodination, and Cysteine tryptophylquinone (CTQ). In some aspects, the polypeptide, protein or peptide may be modified by a post-transcriptional modification which can affect its structure, subcellular localization, and/or function.

In some embodiments, the polypeptide, protein or peptide may be modified using phosphorylation. Phosphorylation, or the addition of a phosphate group to serine, threonine, or tyrosine residues, is one of most common forms of protein modification. Protein phosphorylation plays an important role in fine tuning the signal in the intracellular signaling cascades.

In some embodiments, the polypeptide, protein or peptide may be modified using ubiquitination which is the covalent attachment of ubiquitin to target proteins. Ubiquitination-mediated protein turnover has been shown to play a role in driving the cell cycle as well as in protein-degradation-independent intracellular signaling pathways.

In some embodiments, the polypeptide, protein or peptide may be modified using acetylation and methylation which can play a role in regulating gene expression. As a non-limiting example, the acetylation and methylation could mediate the formation of chromatin domains (e.g., euchromatin and heterochromatin) which could have an impact on mediating gene silencing.

In some embodiments, the polypeptide, protein or peptide may be modified using glycosylation. Glycosylation is the attachment of one of a large number of glycan groups and is a modification that occurs in about half of all proteins and plays a role in biological processes including, but not limited to, embryonic development, cell division, and regulation of protein structure. The two main types of protein glycosylation are N-glycosylation and O-glycosylation. For N-glycosylation the glycan is attached to an asparagine and for O-glycosylation the glycan is attached to a serine or threonine.

In some embodiments, the polypeptide, protein or peptide may be modified using Sumoylation. Sumoylation is the addition of SUMOs (small ubiquitin-like modifiers) to proteins and is a post-translational modification similar to ubiquitination.

Antibodies

As used herein, the term "antibody" is referred to in the broadest sense and specifically covers various embodiments including, but not limited to monoclonal antibodies, polyclonal antibodies, multispecific antibodies (e.g. bispecific antibodies formed from at least two intact antibodies), and antibody fragments (e.g., diabodies) so long as they exhibit a desired biological activity (e.g., "functional"). Antibodies are primarily amino acid based molecules which are monomeric or multimeric polypeptides which comprise at least one amino acid region derived from a known or parental antibody sequence and at least one amino acid region derived from a non-antibody sequence. The antibodies may comprise one or more modifications (including, but not limited to the addition of sugar moieties, fluorescent moieties, chemical tags, etc.). For the purposes herein, an "antibody" may comprise a heavy and light variable domain as well as an Fc region.

The cargo or payload may comprise or may encode polypeptides that form one or more functional antibodies.

In some embodiments, the cargo or payload may comprise or may encode polypeptides that form or function as any antibody including, but not limited to, antibodies that are known in the art and/or antibodies that are commercially available which may be therapeutic, diagnostic, or for research purposes. Additionally, the cargo or payload may comprise or may encode fragments of such antibodies or antibodies such as, but not limited to, variable domains or complementarity determining regions (CDRs).

As used herein, the term "native antibody" refers to an usually heterotetrameric glycoprotein of about 150,000 Daltons, composed of two identical light (L) chains and two identical heavy (H) chains. Genes encoding antibody heavy and light chains are known and segments making up each have been well characterized and described (Matsuda, F. et al., 1998. The Journal of Experimental Medicine. 188(11); 2151-62 and Li, A. et al., 2004. Blood. 103(12): 4602-9, the content of each of which are herein incorporated by reference in their entirety). Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. As used herein, the term "light chain" refers to a component of an antibody from any vertebrate species assigned to one of two clearly distinct types, called kappa and lambda based on amino acid sequences of constant domains. Depending on the amino acid sequence of the constant domain of their heavy chains, antibodies can be assigned to different classes. There are five major classes of intact antibodies: IgA, IgD, IgE, IgG, and IgM, and several of these may be further divided into subclasses (isotypes), e.g., IgG1, IgG2, IgG3, IgG4, IgA, and IgA2.

As used herein, the term "variable domain" refers to specific antibody domains found on both the antibody heavy and light chains that differ extensively in sequence among antibodies and are used in the binding and specificity of each particular antibody for its particular antigen. Variable domains comprise hypervariable regions. As used herein, the term "hypervariable region" refers to a region within a variable domain comprising amino acid residues responsible for antigen binding. The amino acids present within the hypervariable regions determine the structure of the complementarity determining regions (CDRs) that become part of the antigen-binding site of the antibody. As used herein, the term "CDR" refers to a region of an antibody comprising a structure that is complimentary to its target antigen or epitope. Other portions of the variable domain, not interacting with the antigen, are referred to as framework (FW) regions. The antigen-binding site (also known as the antigen combining site or paratope) comprises the amino acid residues necessary to interact with a particular antigen. The exact residues making up the antigen-binding site are typically elucidated by co-crystallography with bound antigen, however computational assessments can also be used based on comparisons with other antibodies (Strohl, W. R. Therapeutic Antibody Engineering. Woodhead Publishing, Philadelphia PA. 2012. Ch. 3, p. 47-54, the contents of which is herein incorporated by reference in its entirety). Determining residues making up CDRs may include the use of numbering schemes including, but not limited to, those taught by Kabat [Wu, T. T. et al., 1970, JEM, 132(2):211-50 and Johnson, G. et al., 2000, Nucleic Acids Res. 28(1): 214-8, the contents of each of which are herein incorporated by reference in their entirety], Chothia [Chothia and Lesk, J. Mol. Biol. 196, 901 (1987), Chothia et al., Nature 342, 877 (1989) and A1-Lazikani, B. et al., 1997, J. Mol. Biol.

273(4):927-48, the contents of each of which are herein incorporated by reference in their entirety], Lefranc (Lefranc, M. P. et al., 2005, Immunome Res. 1:3) and Honegger (Honegger, A. and Pluckthun, A. 2001. J. Mol. Biol. 309(3):657-70, the contents of which are herein incorporated by reference in their entirety).

$V_H$ and $V_L$ domains each have three CDRs. $V_L$ CDRs are referred to herein as CDR-L1, CDR-L2 and CDR-L3, in order of occurrence when moving from N- to C-terminus along the variable domain polypeptide. $V_H$ CDRs are referred to herein as CDR-H1, CDR-H2, and CDR-H3, in order of occurrence when moving from N- to C-terminus along the variable domain polypeptide. Each of CDRs have favored canonical structures with the exception of the CDR-H3, which comprises amino acid sequences that may be highly variable in sequence and length between antibodies resulting in a variety of three-dimensional structures in antigen-binding domains. In some cases, CDR-H3s may be analyzed among a panel of related antibodies to assess antibody diversity.

Various methods of determining CDR sequences are known in the art and may be applied to known antibody sequences. The system described by Kabat, also referred to as "numbered according to Kabat," "Kabat numbering," "Kabat definitions," and "Kabat labeling," provides an unambiguous residue numbering system applicable to any variable domain of an antibody, and provides precise residue boundaries defining the three CDRs of each chain. (Kabat et al., Sequences of Proteins of Immunological Interest, National Institutes of Health, Bethesda, Md. (1987) and (1991), the contents of which are incorporated by reference in their entirety). Kabat CDRs and comprise about residues 24-34 (CDR1), 50-56 (CDR2) and 89-97 (CDR3) in the light chain variable domain, and 31-35 (CDR1), 50-65 (CDR2) and 95-102 (CDR3) in the heavy chain variable domain. Chothia and coworkers found that certain sub-portions within Kabat CDRs adopt nearly identical peptide backbone conformations, despite having great diversity at the level of amino acid sequence. (Chothia et al. (1987) J. Mol. Biol. 196: 901-917; and Chothia et al. (1989) Nature 342: 877-883, the contents of each of which is herein incorporated by reference in its entirety). These CDRs can be referred to as "Chothia CDRs," "Chothia numbering," or "numbered according to Chothia," and comprise about residues 24-34 (CDR1), 50-56 (CDR2) and 89-97 (CDR3) in the light chain variable domain, and 26-32 (CDR1), 52-56 (CDR2) and 95-102 (CDR3) in the heavy chain variable domain. Mol. Biol. 196:901-917 (1987). The system described by MacCallum, also referred to as "numbered according to MacCallum," or "MacCallum numbering" comprises about residues 30-36 (CDR1), 46-55 (CDR2) and 89-96 (CDR3) in the light chain variable domain, and 30-35 (CDR1), 47-58 (CDR2) and 93-101 (CDR3) in the heavy chain variable domain. (MacCallum et al. ((1996) J. Mol. Biol. 262(5): 732-745), the contents of which is herein incorporated by reference in its entirety). The system described by AbM, also referred to as "numbering according to AbM," or "AbM numbering" comprises about residues 24-34 (CDR1), 50-56 (CDR2) and 89-97 (CDR3) in the light chain variable domain, and 26-35 (CDR1), 50-58 (CDR2) and 95-102 (CDR3) in the heavy chain variable domain. The IMGT (INTERNATIONAL IMMUNOGENETICS INFORMATION SYSTEM) numbering of variable regions can also be used, which is the numbering of the residues in an immunoglobulin variable heavy or light chain according to the methods of the IIMGT (Lefranc, M.-P., "The IMGT unique numbering for immunoglobulins, T cell Receptors and Ig-like domains", The Immunologist, 7, 132-136 (1999), and is herein incorporated by reference in its entirety by reference). As used herein, "IMGT sequence numbering" or "numbered according to IMTG," refers to numbering of the sequence encoding a variable region according to the IMGT. For the heavy chain variable domain, when numbered according to IMGT, the hypervariable region ranges from amino acid positions 27 to 38 for CDR1, amino acid positions 56 to 65 for CDR2, and amino acid positions 105 to 117 for CDR3. For the light chain variable domain, when numbered according to IMGT, the hypervariable region ranges from amino acid positions 27 to 38 for CDR1, amino acid positions 56 to 65 for CDR2, and amino acid positions 105 to 117 for CDR3.

In some embodiments, the cargo or payload may comprise or may encode antibodies which have been produced using methods known in the art such as, but are not limited to immunization and display technologies (e.g., phage display, yeast display, and ribosomal display), hybridoma technology, heavy and light chain variable region cDNA sequences selected from hybridomas or from other sources, In some embodiments, the cargo or payload may comprise or may encode antibodies which were developed using any naturally occurring or synthetic antigen. As used herein, an "antigen" is an entity which induces or evokes an immune response in an organism. An immune response is characterized by the reaction of the cells, tissues and/or organs of an organism to the presence of a foreign entity. Such an immune response typically leads to the production by the organism of one or more antibodies against the foreign entity, e.g., antigen or a portion of the antigen. As used herein, "antigens" also refer to binding partners for specific antibodies or binding agents in a display library.

As used herein, the term "monoclonal antibody" refers to an antibody obtained from a population of substantially homogeneous cells (or clones), i.e., the individual antibodies comprising the population are identical and/or bind the same epitope, except for possible variants that may arise during production of the monoclonal antibodies, such variants generally being present in minor amounts. In contrast to polyclonal antibody preparations that typically include different antibodies directed against different determinants (epitopes), each monoclonal antibody is directed against a single determinant on the antigen The modifier "monoclonal" indicates the character of the antibody as being obtained from a substantially homogeneous population of antibodies, and is not to be construed as requiring production of the antibody by any particular method. The monoclonal antibodies herein include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies.

As used herein, the term "humanized antibody" refers to a chimeric antibody comprising a minimal portion from one or more non-human (e.g., murine) antibody source(s) with the remainder derived from one or more human immunoglobulin sources. For the most part, humanized antibodies are human immunoglobulins (recipient antibody) in which residues from the hypervariable region from an antibody of the recipient are replaced by residues from the hypervariable region from an antibody of a non-human species (donor antibody) such as mouse, rat, rabbit or nonhuman primate having the desired specificity, affinity, and/or capacity.

In some embodiments, the cargo or payload may comprise or may encode antibody mimetics. As used herein, the term "antibody mimetic" refers to any molecule which mimics the function or effect of an antibody and which binds specifically and with high affinity to their molecular targets. In some embodiments, antibody mimetics may be monobodies, designed to incorporate the fibronectin type III domain (Fn3) as a protein scaffold. In some embodiments, antibody mimetics may be those known in the art including, but are not limited to affibody molecules, affilins, affitins, anticalins, avimers, Centyrins, DARPINS™, fynomers, Kunitz domains, and domain peptides. In other embodiments, antibody mimetics may include one or more non-peptide regions.

Antibody Fragments and Variants

In some embodiments, the cargo or payload may comprise or may encode antibody fragments which comprise antigen binding regions from full-length antibodies. Non-limiting examples of antibody fragments include Fab, Fab', $F(ab')_2$, and Fv fragments, diabodies, linear antibodies, single-chain antibody molecules, and multispecific antibodies formed from antibody fragments. Papain digestion of antibodies produces two identical antigen-binding fragments, called "Fab" fragments, each with a single antigen-binding site. Also produced is a residual "Fc" fragment, whose name reflects its ability to crystallize readily. Pepsin treatment yields an $F(ab')_2$ fragment that has two antigen-binding sites and is still capable of cross-linking antigen. Compounds and/or compositions of the present disclosure may comprise one or more of these fragments.

In some embodiments, the Fc region may be a modified Fc region wherein the Fc region may have a single amino acid substitution as compared to the corresponding sequence for the wild-type Fc region, wherein the single amino acid substitution yields an Fc region with preferred properties to those of the wild-type Fc region. Non-limiting examples of Fc properties that may be altered by the single amino acid substitution include bind properties or response to pH conditions As used herein, the term "Fv" refers to an antibody fragment comprising the minimum fragment on an antibody needed to form a complete antigen binding site. These regions consist of a dimer of one heavy chain and one light chain variable domain in tight, non-covalent association. Fv fragments can be generated by proteolytic cleavage, but are largely unstable. Recombinant methods are known in the art for generating stable Fv fragments, typically through insertion of a flexible linker between the light chain variable domain and the heavy chain variable domain to form a single chain Fv (scFv) or through the introduction of a disulfide bridge between heavy and light chain variable domains.

As used herein, the term "single chain Fv" or "scFv" refers to a fusion protein of $V_H$ and $V_L$ antibody domains, wherein these domains are linked together into a single polypeptide chain by a flexible peptide linker. In some embodiments, the Fv polypeptide linker enables the scFv to form the desired structure for antigen binding. In some embodiments, scFvs are utilized in conjunction with phage display, yeast display or other display methods where they may be expressed in association with a surface member (e.g. phage coat protein) and used in the identification of high affinity peptides for a given antigen.

As used herein, the term "antibody variant" refers to a modified antibody (in relation to a native or starting antibody) or a biomolecule resembling a native or starting antibody in structure and/or function (e.g., an antibody mimetic). Antibody variants may be altered in their amino acid sequence, composition, or structure as compared to a native antibody. Antibody variants may include, but are not limited to, antibodies with altered isotypes (e.g., IgA, IgD, IgE, $IgG_1$, $IgG_2$, $IgG_3$, $IgG_4$, or IgM), humanized variants, optimized variants, multispecific antibody variants (e.g., bispecific variants), and antibody fragments.

Multispecific Antibodies

In some embodiments, the cargo or payload may be or may encode antibodies that bind more than one epitope. As used herein, the terms "multibody" or "multispecific antibody" refer to an antibody wherein two or more variable regions bind to different epitopes. The epitopes may be on the same or different targets. In certain embodiments, a multispecific antibody is a "bispecific antibody," which recognizes two different epitopes on the same or different antigens.

In some embodiments, multi-specific antibodies may be prepared by the methods used by BIOATLA® and described in International Patent publication WO201109726, the contents of which are herein incorporated by reference in their entirety. First a library of homologous, naturally occurring antibodies is generated by any method known in the art (i.e., mammalian cell surface display), then screened by FACSAria or another screening method, for multi-specific antibodies that specifically bind to two or more target antigens. In some embodiments, the identified multi-specific antibodies are further evolved by any method known in the art, to produce a set of modified multi-specific antibodies. These modified multi-specific antibodies are screened for binding to the target antigens. In some embodiments, the multi-specific antibody may be further optimized by screening the evolved modified multi-specific antibodies for optimized or desired characteristics.

In some embodiments, multi-specific antibodies may be prepared by the methods used by BIOATLA® and described in Unites States Publication No. US20150252119, the contents of which are herein incorporated by reference in their entirety. In one approach, the variable domains of two parent antibodies, wherein the parent antibodies are monoclonal antibodies are evolved using any method known in the art in a manner that allows a single light chain to functionally complement heavy chains of two different parent antibodies. Another approach requires evolving the heavy chain of a single parent antibody to recognize a second target antigen. A third approach involves evolving the light chain of a parent antibody so as to recognize a second target antigen. Methods for polypeptide evolution are described in International Publication WO2012009026, the contents of which are herein incorporated by reference in their entirety, and include as non-limiting examples, Comprehensive Positional Evolution (CPE), Combinatorial Protein Synthesis (CPS), Comprehensive Positional Insertion (CPI), Comprehensive Positional Deletion (CPD), or any combination thereof. The Fc region of the multi-specific antibodies described in United States Publication No. US20150252119 may be created using a knob-in-hole approach, or any other method that allows the Fc domain to form heterodimers. The resultant multi-specific antibodies may be further evolved for improved characteristics or properties such as binding affinity for the target antigen.

Bispecific Antibodies

In some embodiments, the cargo or payload may be or may encode bispecific antibodies. As used herein, the term "bispecific antibody" refers to an antibody capable of binding two different antigens. Such antibodies typically comprise regions from at least two different antibodies. Such antibodies typically comprise antigen-binding regions from at least two different antibodies. For example, a bispecific monoclonal antibody (BsMAb, BsAb) is an artificial protein composed of fragments of two different monoclonal antibodies, thus allowing the BsAb to bind to two different types of antigen.

In some cases, the cargo or payload may be or may encode bispecific antibodies comprising antigen-binding regions from two different anti-tau antibodies. For example, such bispecific antibodies may comprise binding regions from two different antibodies Bispecific antibody frameworks may include any of those described in Riethmuller, G., 2012. *Cancer Immunity.* 12:12-18; Marvin, J. S. et al., 2005. *Acta Pharmacologica Sinica.* 26(6):649-58; and Schaefer, W. et al., 2011. *PNAS.* 108(27): 11187-92, the contents of each of which are herein incorporated by reference in their entirety.

New generations of BsMAb, called "trifunctional bispecific" antibodies, have been developed. These consist of two heavy and two light chains, one each from two different antibodies, where the two Fab regions (the arms) are directed against two antigens, and the Fc region (the foot) comprises the two heavy chains and forms the third binding site.

Of the two paratopes that form the tops of the variable domains of a bispecific antibody, one can be directed against a target antigen and the other against a T-lymphocyte antigen like CD3. In the case of trifunctional antibodies, the Fc region may additionally bind to a cell that expresses Fc receptors, like a macrophage, a natural killer (NK) cell or a dendritic cell. In sum, the targeted cell is connected to one or two cells of the immune system, which subsequently destroy it.

Other types of bispecific antibodies have been designed to overcome certain problems, such as short half-life, immunogenicity and side-effects caused by cytokine liberation. They include chemically linked Fabs, consisting only of the Fab regions, and various types of bivalent and trivalent single-chain variable fragments (scFvs), fusion proteins mimicking the variable domains of two antibodies. The furthest developed of these newer formats are the bispecific T-cell engagers (BiTEs) and mAb2's, antibodies engineered to contain an Fcab antigen-binding fragment instead of the Fc constant region.

Using molecular genetics, two scFvs can be engineered in tandem into a single polypeptide, separated by a linker domain, called a "tandem scFv" (tascFv). TascFvs have been found to be poorly soluble and require refolding when produced in bacteria, or they may be manufactured in mammalian cell culture systems, which avoids refolding requirements but may result in poor yields. Construction of a tascFv with genes for two different scFvs yields a "bispecific single-chain variable fragments" (bis-scFvs). Only two tascFvs have been developed clinically by commercial firms; both are bispecific agents in active early phase development by Micromet for oncologic indications, and are described as "Bispecific T-cell Engagers (BiTE)." Blinatumomab is an anti-CD19/anti-CD3 bispecific tascFv that potentiates T-cell responses to B-cell non-Hodgkin lymphoma in Phase 2. MT110 is an anti-EP-CAM/anti-CD3 bispecific tascFv that potentiates T-cell responses to solid tumors in Phase 1. Bispecific, tetravalent "TandAbs" are also being researched by Affimed.

In some embodiments, the cargo or payload may be or may encode antibodies comprising a single antigen-binding domain. These molecules are extremely small, with molecular weights approximately one-tenth of those observed for full-sized mAbs. Further antibodies may include "nanobodies" derived from the antigen-binding variable heavy chain regions ($V_{HHS}$) of heavy chain antibodies found in camels and llamas, which lack light chains.

Disclosed and claimed in PCT Publication WO2014144573 (the contents of which are herein incorporated by reference in its entirety) to Memorial Sloan-Kettering Cancer Center are multimerization technologies for making dimeric multispecific binding agents (e.g., fusion proteins comprising antibody components) with improved properties over multispecific binding agents without the capability of dimerization.

In some cases, the cargo or payload may be or may encode tetravalent bispecific antibodies (TetBiAbs as disclosed and claimed in PCT Publication WO2014144357, the contents of which are herein incorporated in its entirety). TetBiAbs feature a second pair of Fab fragments with a second antigen specificity attached to the C-terminus of an antibody, thus providing a molecule that is bivalent for each of the two antigen specificities. The tetravalent antibody is produced by genetic engineering methods, by linking an antibody heavy chain covalently to a Fab light chain, which associates with its cognate, co-expressed Fab heavy chain.

In some aspects, the cargo or payload may be or may encode biosynthetic antibodies as described in U.S. Pat. No. 5,091,513 (the contents of which are herein incorporated by reference in their entirety). Such antibody may include one or more sequences of amino acids constituting a region which behaves as a biosynthetic antibody binding site (BABS). The sites comprise 1) non-covalently associated or disulfide bonded synthetic $V_H$ and $V_L$ dimers, 2) $V_H$-$V_L$ or $V_L$-$V_H$ single chains wherein the $V_H$ and $V_L$ are attached by a polypeptide linker, or 3) individuals $V_H$ or $V_L$ domains. The binding domains comprise linked CDR and FR regions, which may be derived from separate immunoglobulins. The biosynthetic antibodies may also include other polypeptide sequences which function, e.g., as an enzyme, toxin, binding site, or site of attachment to an immobilization media or radioactive atom. Methods are disclosed for producing the biosynthetic antibodies, for designing BABS having any specificity that can be elicited by in vivo generation of antibody, and for producing analogs thereof.

In some embodiments, the cargo or payload may be or may encode antibodies with antibody acceptor frameworks taught in U.S. Pat. No. 8,399,625. Such antibody acceptor frameworks may be particularly well suited accepting CDRs from an antibody of interest. In some cases, CDRs from anti-tau antibodies known in the art or developed according to the methods presented herein may be used.

Miniaturized Antibody

In some embodiments, the cargo or payload may be or may encode a "miniaturized" antibody. Among the best examples of mAb miniaturization are the small modular immunopharmaceuticals (SMIPs) from Trubion Pharmaceuticals. These molecules, which can be monovalent or bivalent, are recombinant single-chain molecules containing one $V_L$, one $V_H$ antigen-binding domain, and one or two constant "effector" domains, all connected by linker domains. Presumably, such a molecule might offer the advantages of increased tissue or tumor penetration claimed by fragments while retaining the immune effector functions conferred by constant domains. At least three "miniaturized" SMIPs have entered clinical development. TRU-015, an anti-CD20 SMIP developed in collaboration with Wyeth, is the most advanced project, having progressed to Phase 2 for rheumatoid arthritis (RA). Earlier attempts in systemic lupus erythrematosus (SLE) and B cell lymphomas were ultimately discontinued. Trubion and Facet Biotechnology are collaborating in the development of TRU-016, an anti-CD37 SMIP, for the treatment of CLL and other lymphoid neoplasias, a project that has reached Phase 2. Wyeth has licensed the anti-CD20 SMIP SBI-087 for the treatment of autoimmune diseases, including RA, SLE, and possibly multiple sclerosis, although these projects remain in the earliest stages of clinical testing.

Diabodies

In some embodiments, the cargo or payload may be or may encode diabodies. As used herein, the term "diabody" refers to a small antibody fragment with two antigen-binding sites. Diabodies comprise a heavy chain variable domain $V_H$ connected to a light chain variable domain $V_L$ in the same polypeptide chain. By using a linker that is too short to allow pairing between the two domains on the same chain, the domains are forced to pair with the complementary domains of another chain and create two antigen-binding sites.

Diabodies are functional bispecific single-chain antibodies (bscAb). These bivalent antigen-binding molecules are composed of non-covalent dimers of scFvs, and can be produced in mammalian cells using recombinant methods. (See, e.g., Mack et al., *Proc. Natl. Acad. Sci.,* 92: 7021-7025, 1995). Few diabodies have entered clinical development. An iodine-123-labeled diabody version of the anti-CEA chimeric antibody cT84.66 has been evaluated for pre-surgical immunoscintigraphic detection of colorectal cancer in a study sponsored by the Beckman Research Institute of the City of Hope (Clinicaltrials.gov NCT00647153).

Unibody

In some embodiments, the cargo or payload may be or may encode a "unibody," in which the hinge region has been removed from IgG4 molecules. While IgG4 molecules are unstable and can exchange light-heavy chain heterodimers with one another, deletion of the hinge region prevents heavy chain-heavy chain pairing entirely, leaving highly specific monovalent light/heavy heterodimers, while retaining the Fe region to ensure stability and half-life in vivo. This configuration may minimize the risk of immune activation or oncogenic growth, as IgG4 interacts poorly with FcRs and monovalent unibodies fail to promote intracellular signaling complex formation. These contentions are, however, largely supported by laboratory, rather than clinical, evidence. Other antibodies may be "miniaturized" antibodies, which are compacted 100 kDa antibodies.

Intrabodies

In some embodiments, the cargo or payload may be or may encode intrabodies. The term "intrabody" refers to a form of antibody that is not secreted from a cell in which it is produced, but instead targets one or more intracellular proteins. Intrabodies may be used to affect a multitude of cellular processes including, but not limited to intracellular trafficking, transcription, translation, metabolic processes, proliferative signaling, and cell division. In some embodiments, methods of the present disclosure may include intrabody-based therapies. In some such embodiments, variable domain sequences and/or CDR sequences disclosed herein may be incorporated into one or more constructs for intrabody-based therapy. For example, intrabodies may target one or more glycated intracellular proteins or may modulate the interaction between one or more glycated intracellular proteins and an alternative protein.

More than two decades ago, intracellular antibodies against intracellular targets were first described (Biocca, Neuberger and Cattaneo *EMBO J.* 9: 101-108, 1990, the contents of which are herein incorporated by reference in their entirety). The intracellular expression of intrabodies in different compartments of mammalian cells allows blocking or modulation of the function of endogenous molecules (Biocca, et al., *EMBO J.* 9: 101-108, 1990; Colby et al., Proc. Natl. Acad. Sci. U.S.A. 101: 17616-21, 2004, the contents of which are herein incorporated by reference in their entirety). Intrabodies can alter protein folding, protein-protein, protein-DNA, protein-RNA interactions and protein modification. They can induce a phenotypic knockout and work as neutralizing agents by direct binding to the target antigen, by diverting its intracellular trafficking or by inhibiting its association with binding partners. They have been largely employed as research tools and are emerging as therapeutic molecules for the treatment of human diseases such as viral pathologies, cancer and misfolding diseases. The fast-growing bio-market of recombinant antibodies provides intrabodies with enhanced binding specificity, stability, and solubility, together with lower immunogenicity, for their use in therapy.

In some embodiments, intrabodies have advantages over interfering RNA (iRNA); for example, iRNA has been shown to exert multiple non-specific effects, whereas intrabodies have been shown to have high specificity and affinity to target antigens. Furthermore, as proteins, intrabodies possess a much longer active half-life than iRNA. Thus, when the active half-life of the intracellular target molecule is long, gene silencing through iRNA may be slow to yield an effect, whereas the effects of intrabody expression can be almost instantaneous. Lastly, it is possible to design intrabodies to block certain binding interactions of a particular target molecule, while sparing others.

Intrabodies are often single chain variable fragments (scFvs) expressed from a recombinant nucleic acid molecule and engineered to be retained intracellularly (e.g., retained in the cytoplasm, endoplasmic reticulum, or periplasm). Intrabodies may be used, for example, to ablate the function of a protein to which the intrabody binds. The expression of intrabodies may also be regulated through the use of inducible promoters in the nucleic acid expression vector comprising the intrabody. Intrabodies may be produced for use in the viral genomes of the disclosure using methods known in the art, such as those disclosed and reviewed in: Marasco et al., 1993 *Proc. Natl. Acad. Sci. USA,* 90: 7889-7893; Chen et al., 1994, *Hum. Gene Ther.* 5:595-601; Chen et al., 1994, *Proc. Natl. Acad. Sci. USA,* 91: 5932-5936; Maciejewski et al., 1995, *Nature Med.,* 1: 667-673; Marasco, 1995, *Immunotech,* 1: 1-19; Mhashilkar, et al., 1995, *EMBO J.* 14: 1542-51; Chen et al., 1996, *Hum. Gene Therap.,* 7: 1515-1525; Marasco, *Gene Ther.* 4:11-15, 1997; Rondon and Marasco, 1997, *Annu. Rev. Microbiol.* 51:257-283; Cohen, et al., 1998, *Oncogene* 17:2445-56; Proba et al., 1998, *J. Mol. Biol.* 275:245-253; Cohen et al., 1998, *Oncogene* 17:2445-2456; Hassanzadeh, et al., 1998, *FEBS Lett.* 437: 81-6; Richardson et al., 1998, *Gene Ther.* 5:635-44; Ohage and Steipe, 1999, *J. Mol. Biol.* 291:1119-1128; Ohage et al., 1999, *J. Mol. Biol.* 291:1129-1134; Wirtz and Steipe, 1999, *Protein Sci.* 8:2245-2250; Zhu et al., 1999, *J. Immunol. Methods* 231:207-222; Arafat et al., 2000, *Cancer Gene Ther.* 7:1250-6; der Maur et al., 2002, *J. Biol. Chem.* 277:45075-85; Mhashilkar et al., 2002, *Gene Ther.* 9:307-19; and Wheeler et al., 2003, *FASEB J.* 17: 1733-5; and references cited therein). In particular, a CCR5 intrabody has been produced by Steinberger et al., 2000, *Proc. Natl. Acad. Sci. USA* 97:805-810). See generally Marasco, W A, 1998, "Intrabodies: Basic Research and Clinical Gene Therapy Applications" Springer: New York; and for a review of scFvs, see Pluckthun in "The Pharmacology of Monoclonal Antibodies," 1994, vol. 113, Rosenburg and Moore eds. Springer-Verlag, New York, pp. 269-315; the contents of each of which are each incorporated by reference in their entireties.

Sequences from donor antibodies may be used to develop intrabodies. Intrabodies are often recombinantly expressed as single domain fragments such as isolated $V_H$ and $V_L$ domains or as a single chain variable fragment (scFv) antibody within the cell. For example, intrabodies are often expressed as a single polypeptide to form a single chain antibody comprising the variable domains of the heavy and light chains joined by a flexible linker polypeptide. Intrabodies typically lack disulfide bonds and are capable of modulating the expression or activity of target genes through their specific binding activity. Single chain antibodies can also be expressed as a single chain variable region fragment joined to the light chain constant region.

As is known in the art, an intrabody can be engineered into recombinant polynucleotide vectors to encode sub-cellular trafficking signals at its N or C terminus to allow expression at high concentrations in the sub-cellular compartments where a target protein is located. For example, intrabodies targeted to the endoplasmic reticulum (ER) are engineered to incorporate a leader peptide and, optionally, a C-terminal ER retention signal. Intrabodies intended to exert activity in the nucleus are engineered to include a nuclear localization signal. Lipid moieties are joined to intrabodies in order to tether the intrabody to the cytosolic side of the plasma membrane. Intrabodies can also be targeted to exert function in the cytosol. For example, cytosolic intrabodies are used to sequester factors within the cytosol, thereby preventing them from being transported to their natural cellular destination.

There are certain technical challenges with intrabody expression. In particular, protein conformational folding and structural stability of the newly-synthesized intrabody within the cell is affected by reducing conditions of the intracellular environment.

Intrabodies of the disclosure may be promising therapeutic agents for the treatment of misfolding diseases, including Tauopathies, prion diseases, Alzheimer's, Parkinson's, and Huntington's, because of their virtually infinite ability to specifically recognize the different conformations of a protein, including pathological isoforms, and because they can be targeted to the potential sites of aggregation (both intra- and extracellular sites). These molecules can work as neutralizing agents against amyloidogenic proteins by preventing their aggregation, and/or as molecular shunters of intracellular traffic by rerouting the protein from its potential aggregation site.

Maxibodies

In some embodiments, the cargo or payload may be or may encode a maxibody (bivalent scFV fused to the amino terminus of the Fc (CH2-CH3 domains) of IgG.

Chimeric Antigen Receptors (CARs)

In some embodiments, the cargo or payload may be or may encode a chimeric antigen receptors (CARs) which when transduced into immune cells (e.g., T cells and NK cells), can re-direct the immune cells against the target (e.g., a tumor cell) which expresses a molecule recognized by the extracellular target moiety of the CAR.

As used herein, the term "chimeric antigen receptor (CAR)" refers to a synthetic receptor that mimics TCR on the surface of T cells. In general, a CAR is composed of an extracellular targeting domain, a transmembrane domain/region and an intracellular signaling/activation domain. In a standard CAR receptor, the components: the extracellular targeting domain, transmembrane domain and intracellular signaling/activation domain, are linearly constructed as a single fusion protein. The extracellular region comprises a targeting domain/moiety (e.g., a scFv) that recognizes a specific tumor antigen or other tumor cell-surface molecules. The intracellular region may contain a signaling domain of TCR complex (e.g., the signal region of CD3ζ), and/or one or more costimulatory signaling domains, such as those from CD28, 4-1BB (CD137) and OX-40 (CD134). For example, a "first-generation CAR" only has the CD3ζ signaling domain, whereas in an effort to augment T-cell persistence and proliferation, costimulatory intracellular domains are added, giving rise to second generation CARs having a CD3ζ signal domain plus one costimulatory signaling domain, and third generation CARs having CD3ζ signal domain plus two or more costimulatory signaling domains. A CAR, when expressed by a T cell, endows the T cell with antigen specificity determined by the extracellular targeting moiety of the CAR. In some aspects, one or more elements such as homing and suicide genes could be added to develop a more competent and safer architecture of CAR (so called the fourth generation CAR).

In some embodiments, the extracellular targeting domain is joined through the hinge (also called space domain or spacer) and transmembrane regions to an intracellular signaling domain. The hinge connects the extracellular targeting domain to the transmembrane domain which transverses the cell membrane and connects to the intracellular signaling domain. The hinge may need to be varied to optimize the potency of CAR transformed cells toward cancer cells due to the size of the target protein where the targeting moiety binds, and the size and affinity of the targeting domain itself. Upon recognition and binding of the targeting moiety to the target cell, the intracellular signaling domain leads to an activation signal to the CAR T cell, which is further amplified by the "second signal" from one or more intracellular costimulatory domains. The CAR T cell, once activated, can destroy the target cell.

In some embodiments, the CAR may be split into two parts, each part is linked a dimerizing domain, such that an input that triggers the dimerization promotes assembly of the intact functional receptor. Wu and Lim reported a split CAR in which the extracellular CD19 binding domain and the intracellular signaling element are separated and linked to the FKBP domain and the FRB* (T2089L mutant of FKBP-rapamycin binding) domain that heterodimerize in the presence of the rapamycin analog AP21967. The split receptor is assembled in the presence of AP21967 and together with the specific antigen binding, activates T cells (Wu et al., Science, 2015, 625(6258): aab4077, the contents of which are herein incorporated by reference in its entirety).

In some embodiments, the CAR may be designed as an inducible CAR which has an incorporation of a Tet-On inducible system to a CD19 CAR construct. The CD19 CAR is activated only in the presence of doxycycline (Dox). Sakemura reported that Tet-CD19CAR T cells in the presence of Dox were equivalently cytotoxic against CD19+ cell lines and had equivalent cytokine production and proliferation upon CD19 stimulation, compared with conventional CD19CAR T cells (Sakemura et al., Cancer Immuno. Res., 2016 Jun. 21, Epub; the contents of which is herein incorporated by reference in its entirety). The dual systems provide more flexibility to turn-on and off of the CAR expression in transduced T cells.

In some embodiments, the cargo or payload may be or may encode a first generation CAR, or a second generation CAR, or a third generation CAR, or a fourth generation CAR. In some embodiments, the cargo or payload may be or may encode a full CAR construct composed of the extracellular domain, the hinge and transmembrane domain and the intracellular signaling region. In other embodiments, the cargo or payload may be or may encode a component of the full CAR construct including an extracellular targeting moiety, a hinge region, a transmembrane domain, an intracellular signaling domain, one or more co-stimulatory domain, and other additional elements that improve CAR architecture and functionality including but not limited to a leader sequence, a homing element and a safety switch, or the combination of such components.

In some embodiments, the cargo or payload may be or may encode a tunable CARs. The reversible on-off switch mechanism allows management of acute toxicity caused by excessive CAR-T cell expansion. The ligand conferred regulation of the CAR may be effective in offsetting tumor escape induced by antigen loss, avoiding functional exhaustion caused by tonic signaling due to chronic antigen exposure and improving the persistence of CAR expressing cells in vivo. The tunable CAR may be utilized to down regulate CAR expression to limit on target on tissue toxicity caused by tumor lysis syndrome. Down regulating the expression of the CARs following anti-tumor efficacy may prevent (1) on target off tumor toxicity caused by antigen expression in normal tissue; (2) antigen independent activation in vivo.

Extracellular Targeting Domain/Moiety

In some embodiments, the extracellular target moiety of a CAR may be any agent that recognizes and binds to a given target molecule, for example, a neoantigen on tumor cells, with high specificity and affinity. The target moiety may be an antibody and variants thereof that specifically binds to a target molecule on tumor cells, or a peptide aptamer selected from a random sequence pool based on its ability to bind to the target molecule on tumor cells, or a variant or fragment thereof that can bind to the target molecule on tumor cells, or an antigen recognition domain from native T-cell receptor (TCR) (e.g. CD4 extracellular domain to recognize HIV infected cells), or exotic recognition components such as a linked cytokine that leads to recognition of target cells bearing the cytokine receptor, or a natural ligand of a receptor.

In some embodiments, the targeting domain of a CAR may be a Ig NAR, a Fab fragment, a Fab' fragment, a F(ab)'2 fragment, a F(ab)'3 fragment, Fv, a single chain variable fragment (scFv), a bis-scFv, a (scFv)2, a minibody, a diabody, a triabody, a tetrabody, a disulfide stabilized Fv protein (dsFv), a unibody, a nanobody, or an antigen binding region derived from an antibody that specifically recognizes a target molecule, for example a tumor specific antigen (TSA). In one embodiment, the targeting moiety is a scFv antibody. The scFv domain, when it is expressed on the surface of a CAR T cell and subsequently binds to a target protein on a cancer cell, is able to maintain the CAR T cell in proximity to the cancer cell and to trigger the activation of the T cell. A scFv can be generated using routine recombinant DNA technology techniques and is discussed in the present disclosure.

In some embodiments, the targeting moiety of a CAR construct may be an aptamer such as a peptide aptamer that specifically binds to a target molecule of interest. The peptide aptamer may be selected from a random sequence pool based on its ability to bind to the target molecule of interest.

In some embodiments, the targeting moiety of a CAR construct may be a natural ligand of the target molecule, or a variant and/or fragment thereof capable of binding the target molecule. In some aspects, the targeting moiety of a CAR may be a receptor of the target molecule, for example, a full length human CD27, as a CD70 receptor, may be fused in frame to the signaling domain of CD3 ζ forming a CD27 chimeric receptor as an immunotherapeutic agent for CD70-positive malignancies.

In some embodiments, the targeting moiety of a CAR may recognize a tumor specific antigen (TSA), for example a cancer neoantigen which is restrictedly expressed on tumor cells.

As non-limiting examples, the CAR of the present disclosure may comprise the extracellular targeting domain capable of binding to a tumor specific antigen selected from 5T4, 707-AP, A33, AFP (α-fetoprotein), AKAP-4 (A kinase anchor protein 4), ALK, α5β1-integrin, androgen receptor, annexin II, alpha-actinin-4, ART-4, B1, B7H3, B7H4, BAGE (B melanoma antigen), BCMA, BCR-ABL fusion protein, beta-catenin, BKT-antigen, BTAA, CA-I (carbonic anhydrase I), CA50 (cancer antigen 50), CA125, CA15-3, CA195, CA242, calretinin, CAIX (carbonic anhydrase), CAMEL (cytotoxic T-lymphocyte recognized antigen on melanoma), CAM43, CAP-1, Caspase-8/m, CD4, CD5, CD7, CD19, CD20, CD22, CD23, CD25, CD27/m, CD28, CD30, CD33, CD34, CD36, CD38, CD40/CD154, CD41, CD44v6, CD44v7/8, CD45, CD49f, CD56, CD68KP1, CD74, CD79a/CD79b, CD103, CD123, CD133, CD138, CD171, cdc27/m, CDK4 (cyclin dependent kinase 4), CDKN2A, CDS, CEA (carcinoembryonic antigen), CEACAM5, CEACAM6, chromogranin, c-Met, c-Myc, coa-1, CSAp, CT7, CT10, cyclophilin B, cyclin B1, cytoplasmic tyrosine kinases, cytokeratin, DAM-10, DAM-6, dek-can fusion protein, desmin, DEPDC1 (DEP domain containing 1), E2A-PRL, EBNA, EGF-R (epidermal growth factor receptor), EGP-1 (epithelial glycoprotein-1) (TROP-2), EGP-2, EGP-40, EGFR (epidermal growth factor receptor), EGFRvIII, EF-2, ELF2M, EMMPRIN, EpCAM (epithelial cell adhesion molecule), EphA2, Epstein Barr virus antigens, Erb (ErbB1; ErbB3; ErbB4), ETA (epithelial tumor antigen), ETV6-AML1 fusion protein, FAP (fibroblast activation protein), FBP (folate-binding protein), FGF-5, folate receptor, FOS related antigen 1, fucosyl GM1, G250, GAGE (GAGE-1; GAGE-2), galectin, GD2 (ganglioside), GD3, GFAP (glial fibrillary acidic protein), GM2 (oncofetal antigen-immunogenic-1; OFA-I-1), GnT-V, Gp100, H4-RET, HAGE (helicase antigen), HER-2/neu, HIFs (hypoxia inducible factors), HIF-1, HIF-2, HLA-A2, HLA-A*0201-R170I, HLA-A1 1, HMWMAA, Hom/Mel-40, HSP70-2M (Heat shock protein 70), HST-2, HTgp-175, hTERT (or hTRT), human papillomavirus-E6/human papillomavirus-E7 and E6, iCE (immune-capture EIA), IGF-1R, IGH-IGK, IL-2R, IL-5, ILK (integrin-linked kinase), IMP3 (insulin-like growth factor II mRNA-binding protein 3), IRF4 (interferon regulatory factor 4), KDR (kinase insert domain receptor), KIAA0205, KRAB-zinc finger protein (KID)-3; KID31, KSA (17-1A), Kras, LAGE, LCK, LDLR/FUT (LDLR-fucosyltransferaseAS fusion protein), LeY (Lewis Y), MAD-CT-1, MAGE (tyrosinase, melanoma-associated antigen) (MAGE-1; MAGE-3), melan-A tumor antigen (MART), MART-2/Ski, MC1R (melanocortin 1 receptor), MDM2, mesothelin, MPHOSPH1, MSA (muscle-specific actin), mTOR (mammalian targets of rapamycin), MUC-1, MUC-2, MUM-1 (melanoma associated antigen (mutated) 1), MUM-2, MUM-3, Myosin/m, MYL-RAR, NA88-A, N-acetylglucosaminyltransferase, neo-PAP, NF-KB (nuclear factor-kappa B), neurofilament, NSE (neuron-specific enolase), Notch receptors, NuMa, N-Ras, NY-BR-1, NY-CO-1, NY-ESO-1, Oncostatin M, OS-9, OY-TES1, p53 mutants, p190 minor bcr-abl, p15(58), pl85erbB2, pl80erbB-3, PAGE (prostate associated gene), PAP (prostatic acid phosphatase), PAX3, PAX5, PDGFR (platelet derived growth factor receptor), cytochrome P450 involved in piperidine and pyrrolidine utilization (PIPA), Pml-RAR alpha fusion protein, PR-3 (proteinase 3), PSA (prostate specific antigen), PSM, PSMA (Prostate stem cell antigen), PRAME (preferentially expressed antigen of melanoma), PTPRK, RAGE (renal tumor antigen), Raf (A-Raf, B-Raf and C-Raf), Ras, receptor tyrosine kinases, RCAS1, RGSS, ROR1 (receptor tyrosine kinase-like orphan receptor 1), RU1, RU2, SAGE, SART-1, SART-3, SCP-1, SDCCAG16, SP-17 (sperm protein 17), src-family, SSX (synovial sarcoma X breakpoint)-1, SSX-2(HOM-MEL-40), SSX-3, SSX-4, SSX-5, STAT-3, STAT-5, STAT-6, STEAD, STn, survivin, syk-ZAP70, TA-90 (Mac-2 binding protein\cyclophilin C-associated protein), TAAL6, TACSTD1 (tumor associated calcium signal transducer 1), TACSTD2, TAG-72-4, TAGE, TARP (T cell receptor gamma alternate reading frame protein), TEL/AML1 fusion protein, TEM1, TEM8 (endosialin or CD248), TGFβ, TIE2, TLP, TMPRSS2 ETS fusion gene, TNF-receptor (TNF-α receptor, TNF-β receptor; or TNF-γ receptor), transferrin receptor, TPS, TRP-1 (tyrosine related protein 1), TRP-2, TRP-2/INT2, TSP-180, VEGF receptor, WNT, WT-1 (Wilm's tumor antigen) and XAGE.

In some embodiments, the cargo or payload may be or may encode a CAR which comprises a universal immune receptor which has a targeting moiety capable of binding to a labelled antigen.

In some embodiments, the cargo or payload may be or may encode a CAR which comprises a targeting moiety capable of binding to a pathogen antigen.

In some embodiments, the cargo or payload may be or may encode a CAR which comprises a targeting moiety capable of binding to non-protein molecules such as tumor-associated glycolipids and carbohydrates.

In some embodiments, the cargo or payload may be or may encode a CAR which comprises a targeting moiety capable of binding to a component within the tumor microenvironment including proteins expressed in various tumor stroma cells including tumor associated macrophages (TAMs), immature monocytes, immature dendritic cells, immunosuppressive CD4+CD25+ regulatory T cells (Treg) and MDSCs.

In some embodiments, the cargo or payload may be or may encode a CAR which comprises a targeting moiety capable of binding to a cell surface adhesion molecule, a surface molecule of an inflammatory cell that appears in an autoimmune disease, or a TCR causing autoimmunity. As non-limiting examples, the targeting moiety of the present disclosure may be a scFv antibody that recognizes a tumor specific antigen (TSA), for example scFvs of antibodies SS, SS1 and HN1 that specifically recognize and bind to human mesothelin, scFv of antibody of GD2, a CD19 antigen binding domain, a NKG2D ligand binding domain, human anti-mesothelin scFvs, an anti-CS1 binding agent, an anti-BCMA binding domain, anti-CD19 scFv antibody, GFR alpha 4 antigen binding fragments, anti-CLL-1 (C-type lectin-like molecule 1) binding domains, CD33 binding domains, a GPC3 (glypican-3) binding domain, a GFR alpha4 (Glycosyl-phosphatidylinositol (GPI)-linked GDNF family α-receptor 4 cell-surface receptor) binding domain, CD123 binding domains, an anti-ROR1 antibody or fragments thereof, scFvs specific to GPC-3, scFv for CSPG4, and scFv for folate receptor alpha.

Intracellular Signaling Domains

The intracellular domain of a CAR fusion polypeptide, after binding to its target molecule, transmits a signal to the immune effector cell, activating at least one of the normal effector functions of immune effector cells, including cytolytic activity (e.g., cytokine secretion) or helper activity. Therefore, the intracellular domain comprises an "intracellular signaling domain" of a T cell receptor (TCR).

In some aspects, the entire intracellular signaling domain can be employed. In other aspects, a truncated portion of the intracellular signaling domain may be used in place of the intact chain as long as it transduces the effector function signal.

In some embodiments, the intracellular signaling domain may contain signaling motifs which are known as immunoreceptor tyrosine-based activation motifs (ITAMs). Examples of ITAM containing cytoplasmic signaling sequences include those derived from TCR CD3zeta, FcR gamma, FcR beta, CD3 gamma, CD3 delta, CD3 epsilon, CD5, CD22, CD79a, CD79b, and CD66d. In one example, the intracellular signaling domain is a CD3 zeta (CD3ζ) signaling domain.

In some embodiments, the intracellular region further comprises one or more costimulatory signaling domains which provide additional signals to the immune effector cells. These costimulatory signaling domains, in combination with the signaling domain can further improve expansion, activation, memory, persistence, and tumor-eradicating efficiency of CAR engineered immune cells (e.g., CAR T cells). In some cases, the costimulatory signaling region contains 1, 2, 3, or 4 cytoplasmic domains of one or more intracellular signaling and/or costimulatory molecules. The costimulatory signaling domain may be the intracellular/cytoplasmic domain of a costimulatory molecule, including but not limited to CD2, CD7, CD27, CD28, 4-1BB (CD137), OX40 (CD134), CD30, CD40, ICOS (CD278), GITR (glucocorticoid-induced tumor necrosis factor receptor), LFA-1 (lymphocyte function-associated antigen-1), LIGHT, NKG2C, B7-H3. In one example, the costimulatory signaling domain is derived from the cytoplasmic domain of CD28. In another example, the costimulatory signaling domain is derived from the cytoplasmic domain of 4-1BB (CD137). In another example, the co-stimulatory signaling domain may be an intracellular domain of GITR as taught in U.S. Pat. No. 9,175,308; the contents of which are incorporated herein by reference in its entirety.

In some embodiments, the intracellular region may comprise a functional signaling domain from a protein selected from the group consisting of an MHC class I molecule, a TNF receptor protein, an immunoglobulin-like protein, a cytokine receptor, an integrin, a signaling lymphocytic activation protein (SLAM) such as CD48, CD229, 2B4, CD84, NTB-A, CRACC, BLAME, CD2F-10, SLAMF6, SLAMF7, an activating NK cell receptor, BTLA, a Toll ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), SLAMF7, NKp80 (KLRF1), NKp44, NKp30, NKp46, CD19, CD4, CD8alpha, CD8beta, IL2R beta, IL2R gamma, IL7R alpha, IL-15Ra, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, NKD2C SLP76, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, CD270 (HVEM), GADS, SLP-76, PAG/Cbp, CD19a, a ligand that specifically binds with CD83, DAP 10, TRIM, ZAP70, Killer immunoglobulin receptors (KIRs) such as KIR2DL1, KIR2DL2/L3, KIR2DL4, KIR2DL5A, KIR2DL5B, KIR2DS1, KIR2DS2, KIR2DS3, KIR2DS4, KIR2DS5, KIR3DL1/S1, KIR3DL2, KIR3DL3, and KIR2DP1; lectin related NK cell receptors such as Ly49, Ly49A, and Ly49C.

In some embodiments, the intracellular signaling domain of the present disclosure may contain signaling domains derived from JAK-STAT. In other embodiments, the intracellular signaling domain of the present disclosure may contain signaling domains derived from DAP-12 (Death associated protein 12) (Topfer et al., Immunol., 2015, 194: 3201-3212; and Wang et al., Cancer Immunol., 2015, 3: 815-826). DAP-12 is a key signal transduction receptor in NK cells. The activating signals mediated by DAP-12 play important roles in triggering NK cell cytotoxicity responses toward certain tumor cells and virally infected cells. The cytoplasmic domain of DAP12 contains an Immunoreceptor Tyrosine-based Activation Motif (ITAM). Accordingly, a CAR containing a DAP12-derived signaling domain may be used for adoptive transfer of NK cells.

Transmembrane Domains

In some embodiments, the CAR may comprise a transmembrane domain. As used herein, the term "Transmembrane domain (TM)" refers broadly to an amino acid sequence of about 15 residues in length which spans the plasma membrane. The transmembrane domain may include at least 20, 21, 22, 23, 24, 25, 26, 27, 28, 29, 30, 31, 32, 33, 34, 35, 36, 37, 38, 39, 40, 41, 42, 43, 44, or 45 amino acid residues and spans the plasma membrane. In some embodiments, the transmembrane domain may be derived either from a natural or from a synthetic source. The transmembrane domain of a CAR may be derived from any naturally membrane-bound or transmembrane protein. For example, the transmembrane region may be derived from (i.e. comprise at least the transmembrane region(s) of) the alpha, beta or zeta chain of the T-cell receptor, CD3 epsilon, CD4, CD5, CD8, CD8α, CD9, CD16, CD22, CD33, CD28, CD37, CD45, CD64, CD80, CD86, CD134, CD137, CD152, or CD154.

Alternatively, the transmembrane domain of the present disclosure may be synthetic. In some aspects, the synthetic sequence may comprise predominantly hydrophobic residues such as leucine and valine.

In some embodiments, the transmembrane domain may be selected from the group consisting of a CD8α transmembrane domain, a CD4 transmembrane domain, a CD 28 transmembrane domain, a CTLA-4 transmembrane domain, a PD-1 transmembrane domain, and a human IgG4 Fc region.

In some embodiments, the CAR may comprise an optional hinge region (also called spacer). A hinge sequence is a short sequence of amino acids that facilitates flexibility of the extracellular targeting domain that moves the target binding domain away from the effector cell surface to enable proper cell/cell contact, target binding and effector cell activation. The hinge sequence may be positioned between the targeting moiety and the transmembrane domain. The hinge sequence can be any suitable sequence derived or obtained from any suitable molecule. The hinge sequence may be derived from all or part of an immunoglobulin (e.g., IgG1, IgG2, IgG3, IgG4) hinge region, i.e., the sequence that falls between the CHI and CH2 domains of an immunoglobulin, e.g., an IgG4 Fc hinge, the extracellular regions of type 1 membrane proteins such as CD8α CD4, CD28 and CD7, which may be a wild-type sequence or a derivative. Some hinge regions include an immunoglobulin CH3 domain or both a CH3 domain and a CH2 domain. In certain embodiments, the hinge region may be modified from an IgG1, IgG2, IgG3, or IgG4 that includes one or more amino acid residues, for example, 1, 2, 3, 4 or 5 residues, substituted with an amino acid residue different from that present in an unmodified hinge.

In some embodiments, the CAR may comprise one or more linkers between any of the domains of the CAR. The linker may be between 1-30 amino acids long. In this regard, the linker may be 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 amino acids in length. In other embodiments, the linker may be flexible.

In some embodiments, the components including the targeting moiety, transmembrane domain and intracellular signaling domains may be constructed in a single fusion polypeptide. The fusion polypeptide may be the payload of an effector module of the disclosure.

In some embodiments, the cargo or payload may be or may encode a CD19 specific CAR targeting different B cell malignancies and HER2-specific CAR targeting sarcoma, glioblastoma, and advanced Her2-positive lung malignancy.

Tandem CAR (TanCAR)

In some embodiments, the CAR may be a tandem chimeric antigen receptor (TanCAR) which is able to target two, three, four, or more tumor specific antigens. In some aspects, The CAR is a bispecific TanCAR including two targeting domains which recognize two different TSAs on tumor cells. The bispecific TanCAR may be further defined as comprising an extracellular region comprising a targeting domain (e.g., an antigen recognition domain) specific for a first tumor antigen and a targeting domain (e.g., an antigen recognition domain) specific for a second tumor antigen. In other aspects, the CAR is a multispecific TanCAR that includes three or more targeting domains configured in a tandem arrangement. The space between the targeting domains in the TanCAR may be between about 5 and about 30 amino acids in length, for example, 6, 7, 8, 9, 10, 11, 12, 13, 14, 15, 16, 17, 18, 19, 20, 21, 22, 23, 24, 25, 26, 27, 28, 29 and 30 amino acids.

Split CAR

In some embodiments, the CAR components including the targeting moiety, transmembrane domain and intracellular signaling domains may be split into two or more parts such that it is dependent on multiple inputs that promote assembly of the intact functional receptor. As a non-limiting example, the split CAR consists of two parts that assemble in a small molecule-dependent manner; one part of the receptor features an extracellular antigen binding domain (e.g. scFv) and the other part has the intracellular signaling domains, such as the CD3ζ intracellular domain.

In other aspects, the split parts of the CAR system can be further modified to increase signal. As a non-limiting example, the second part of cytoplasmic fragment may be anchored to the plasma membrane by incorporating a transmembrane domain (e.g., CD8α transmembrane domain) to the construct. An additional extracellular domain may also be added to the second part of the CAR system, for instance an extracellular domain that mediates homo-dimerization. These modifications may increase receptor output activity, i.e., T cell activation.

In some embodiments, the two parts of the split CAR system contain heterodimerization domains that conditionally interact upon binding of a heterodimerizing small molecule. As such, the receptor components are assembled in the presence of the small molecule, to form an intact system which can then be activated by antigen engagement. Any known heterodimerizing components can be incorporated into a split CAR system. Other small molecule dependent heterodimerization domains may also be used, including, but not limited to, gibberellin-induced dimerization system (GID1-GAI), trimethoprim-SLF induced ecDHFR and FKBP dimerization and ABA (abscisic acid) induced dimerization of PP2C and PYL domains. The dual regulation using inducible assembly (e.g., ligand dependent dimerization) and degradation (e.g., destabilizing domain induced CAR degradation) of the split CAR system may provide more flexibility to control the activity of the CAR modified T cells.

Switchable CAR

In some embodiments, the CAR may be a switchable CAR which is a controllable CARs that can be transiently switched on in response to a stimulus (e.g. a small molecule). In this CAR design, a system is directly integrated in the hinge domain that separate the scFv domain from the cell membrane domain in the CAR. Such system is possible to split or combine different key functions of a CAR such as activation and costimulation within different chains of a receptor complex, mimicking the complexity of the TCR native architecture. This integrated system can switch the scFv and antigen interaction between on/off states controlled by the absence/presence of the stimulus.

Reversible CAR

In some embodiments, the CAR may be a reversible CAR system. In this CAR architecture, a LID domain (ligand-induced degradation) is incorporated into the CAR system. The CAR can be temporarily down-regulated by adding a ligand of the LID domain.

Inhibitory CAR (iCAR)

In some embodiments, the CAR may be inhibitory CARs. Inhibitory CAR (iCAR) refers to a bispecific CAR design wherein a negative signal is used to enhance the tumor specificity and limit normal tissue toxicity. This design incorporates a second CAR having a surface antigen recognition domain combined with an inhibitory signal domain to limit T cell responsiveness even with concurrent engagement of an activating receptor. This antigen recognition domain is directed towards a normal tissue specific antigen such that the T cell can be activated in the presence of first target protein, but if the second protein that binds to the iCAR is present, the T cell activation is inhibited.

As a non-limiting example, iCARs against Prostate specific membrane antigen (PMSA) based on CTLA4 and PD1 inhibitory domains demonstrated the ability to selectively limit cytokine secretion, cytotoxicity and proliferation induced by T cell activation.

Chimeric Switch Receptor

In some embodiments, the cargo or payload may be or may encode a chimeric switch receptors which can switch a negative signal to a positive signal. As used herein, the term "chimeric switch receptor" refers to a fusion protein comprising a first extracellular domain and a second transmembrane and intracellular domain, wherein the first domain includes a negative signal region and the second domain includes a positive intracellular signaling region. In some aspects, the fusion protein is a chimeric switch receptor that contains the extracellular domain of an inhibitory receptor on T cell fused to the transmembrane and cytoplasmic domain of a co-stimulatory receptor. This chimeric switch receptor may convert a T cell inhibitory signal into a T cell stimulatory signal.

As a non-limiting example, the chimeric switch receptor may comprise the extracellular domain of PD-1 fused to the transmembrane and cytoplasmic domain of CD28. In some aspects, Extracellular domains of other inhibitory receptors such as CTLA-4, LAG-3, TIM-3, KIRs and BTLA may also be fused to the transmembrane and cytoplasmic domain derived from costimulatory receptors such as CD28, 4-1BB, CD27, OX40, CD40, GTIR and ICOS.

In some embodiments, chimeric switch receptors may include recombinant receptors comprising the extracellular cytokine-binding domain of an inhibitory cytokine receptor (e.g., IL-13 receptor α (IL-13Rα1), IL-10R, and IL-4Ruα) fused to an intracellular signaling domain of a stimulatory cytokine receptor such as IL-2R (IL-2R□, IL-2Rβ and IL-2Rgamma) and IL-7Rα. One example of such chimeric cytokine receptor is a recombinant receptor containing the cytokine-binding extracellular domain of IL-4Rα linked to the intracellular signaling domain of IL-7Rα.

In some embodiments, the chimeric switch receptor may be a chimeric TGFβ receptor. The chimeric TGFβ receptor may comprise an extracellular domain derived from a TGFβ receptor such as TGFβ receptor 1, TGFβ receptor 2, TGFβ receptor 3, or any other TGFβ receptor or variant thereof; and a non-TGFβ receptor intracellular domain. The non-TGFβ receptor intracellular domain may be the intracellular domain or fragment thereof derived from TLR1, TLR2, TLR3, TLR4, TLR5, TLR6, TLR7, TLR8, TLR9, TLR10, CD28, 4-1BB (CD137), OX40 (CD134), CD3zeta, CD40, CD27, or a combination thereof.

Activation-Conditional CAR

In some embodiments, the cargo or payload may be or may encode an activation-conditional chimeric antigen receptor, which is only expressed in an activated immune cell. The expression of the CAR may be coupled to activation conditional control region which refers to one or more nucleic acid sequences that induce the transcription and/or expression of a sequence e.g., a CAR under its control. Such activation conditional control regions may be promoters of genes that are upregulated during the activation of the immune effector cell e.g. IL2 promoter or NFAT binding sites.

CAR Targeting to Tumor Cells with Specific Proteoglycan Markers

In some embodiments, the cargo or payload may be or may encode a CAR that targets specific types of cancer cells. Human cancer cells and metastasis may express unique and otherwise abnormal proteoglycans, such as polysaccharide chains (e.g., chondroitin sulfate (CS), dermatan sulfate (DS or CSB), heparan sulfate (HS) and heparin). Accordingly, the CAR may be fused with a binding moiety that recognizes cancer associated proteoglycans. In one example, a CAR may be fused with VAR2CSA polypeptide (VAR2-CAR) that binds with high affinity to a specific type of chondroitin sulfate A (CSA) attached to proteoglycans. The extracellular ScFv portion of the CAR may be substituted with VAR2CSA variants comprising at least the minimal CSA binding domain, generating CARs specific to chondroitin sulfate A (CSA) modifications. Alternatively, the CAR may be fused with a split-protein binding system to generate a spy-CAR, in which the scFv portion of the CAR is substituted with one portion of a split-protein binding system such as SpyTag and Spy-catcher and the cancer-recognition molecules (e.g. scFv and or VAR2-CSA) are attached to the CAR through the split-protein binding system.

Nucleic Acids

The originator constructs and benchmark constructs of the present disclosure may comprise a payload region (which may also be referred to as a cargo region) which is a nucleic acid. The term "nucleic acid," in its broadest sense, includes any compound and/or substance that comprise a polymer of nucleotides which may be referred to as polynucleotides. Exemplary nucleic acids or polynucleotides include, but are not limited to, ribonucleic acids (RNAs), deoxyribonucleic acids (DNAs), threose nucleic acids (TNAs), glycol nucleic acids (GNAs), peptide nucleic acids (PNAs), locked nucleic acids (LNAs) or hybrids thereof.

In some embodiments, the payload region comprises nucleic acid sequences encoding more than one cargo or payload.

In some embodiments, the payload region may be or encode a coding nucleic acid sequence.

In some embodiments, the payload region may be or encode a non-coding nucleic acid sequence.

In some embodiments, the payload region may be or encode both a coding and a non-coding nucleic acid sequence.

DNA

Deoxyribonucleic acid (DNA) is a molecule that carries genetic information for all living things and consists of two strands that wind around one another to form a shape known as a double helix. Each strand has a backbone made of alternating sugar (deoxyribose) and phosphate groups. Attached to each sugar is one of four bases: adenine (A), cytosine (C), guanine (G), and thymine (T). The two strands are held together by bonds between adenine and thymine or cytosine and guanine. The sequence of the bases along the backbones serves as instructions for assembling protein and RNA molecules.

In some embodiments, the payload region may be or encode a coding DNA.

In some embodiments, the payload region may be or encode a non-coding DNA.

In some embodiments, the payload region may be or encode both a coding and a non-coding DNA.

In some embodiments, the DNA may be modified. Types of modifications include, but are not limited to, methylation, acetylation, phosphorylation, ubiquitination, and sumoylation.

Vectors

In some embodiments, the originator constructs and/or benchmark constructs described herein can be or be encoded by vectors such as plasmids or viral vectors. In some embodiments, the originator constructs and/or benchmark constructs are or are encoded by viral vectors. Viral vectors may be, but are not limited to, Herpesvirus (HSV) vectors, retroviral vectors, adenoviral vectors, adeno-associated viral (AAV) vectors, lentiviral vectors, and the like. In some embodiments, the viral vectors are AAV vectors. In some embodiments, the viral vectors are lentiviral vectors. In some embodiments, the viral vectors are retroviral vectors. In some embodiments, the viral vectors are adenoviral vectors.

Adeno-Associated Viral (AAVs) Vectors

Viruses of the Parvoviridae family are small non-enveloped icosahedral capsid viruses characterized by a single stranded DNA genome. Parvoviridae family viruses consist of two subfamilies: Parvovirinae, which infect vertebrates, and Densovirinae, which infect invertebrates. Due to its relatively simple structure, easily manipulated using standard molecular biology techniques, this virus family is useful as a biological tool. The genome of the virus may be modified to contain a minimum of components for the assembly of a functional recombinant virus, or viral particle, which is loaded with or engineered to express or deliver a desired payload, which may be delivered to a target cell, tissue, organ, or organism.

The Parvoviridae family comprises the Dependovirus genus which includes adeno-associated viruses (AAV) capable of replication in vertebrate hosts including, but not limited to, human, primate, bovine, canine, equine, and ovine species.

The AAV vector genome is a linear, single-stranded DNA (ssDNA) molecule approximately 5,000 nucleotides (nts) in length. The AAV vector genome can comprise a payload region and at least one inverted terminal repeat (ITR) or ITR region. ITRs traditionally flank the coding nucleotide sequences for the non-structural proteins (encoded by Rep genes) and the structural proteins (encoded by capsid genes or Cap genes). While not wishing to be bound by theory, an AAV vector genome typically comprises two ITR sequences. The AAV vector genome comprises a characteristic T-shaped hairpin structure defined by the self-complementary terminal 145 nucleotides of the 5' and 3' ends of the ssDNA which form an energetically stable double stranded region. The double stranded hairpin structures comprise multiple functions including, but not limited to, acting as an origin for DNA replication by functioning as primers for the endogenous DNA polymerase complex of the host viral replication cell.

In addition to the encoded heterologous payload, AAV vector genomes may comprise, in whole or in part, of any naturally occurring and/or recombinant AAV serotype nucleotide sequence or variant. AAV variants may have sequences of significant homology at the nucleic acid (genome or capsid) and amino acid levels (capsids), to produce constructs which are generally physical and functional equivalents, replicate by similar mechanisms, and assemble by similar mechanisms. Chiorini et al., J. Vir. 71: 6823-33 (1997); Srivastava et al., J. Vir. 45:555-64 (1983); Chiorini et al., J. Vir. 73:1309-1319 (1999); Rutledge et al., J. Vir. 72:309-319 (1998); and Wu et al., J. Vir. 74: 8635-47 (2000), the contents of each of which are incorporated herein by reference in their entirety.

In some embodiments, the AAV vector genome comprises at least one control element which provides for the replication, transcription, and translation of a coding sequence encoded therein. Not all of the control elements need always be present as long as the coding sequence is capable of being replicated, transcribed, and/or translated in an appropriate host cell. Non-limiting examples of expression control elements include sequences for transcription initiation and/or termination, promoter and/or enhancer sequences, efficient RNA processing signals such as splicing and polyadenylation signals, sequences that stabilize cytoplasmic mRNA, sequences that enhance translation efficacy (e.g., Kozak consensus sequence), sequences that enhance protein stability, and/or sequences that enhance protein processing and/or secretion.

AAV vector genomes of the present disclosure may be produced recombinantly and may be based on adeno-associated virus (AAV) parent or reference sequences. As used herein, a "vector genome" is any molecule or moiety which transports, transduces, or otherwise acts as a carrier of a heterologous molecule such as the nucleic acids described herein.

In addition to single stranded AAV vector genomes (e.g., ssAAVs), the present disclosure also provides for self-complementary AAV (scAAVs) vector genomes. scAAV vector genomes contain DNA strands which anneal together to form double stranded DNA. By skipping second strand synthesis, scAAVs allow for rapid expression in the cell.

In some embodiments, the AAV vector genome is an scAAV.

In some embodiments, the AAV vector genome is an ssAAV.

In some embodiments, the AAV vector genome may be part of an AAV particles where the serotype of the capsid may be, but is not limited to, AAV1, AAV2, AAV2G9, AAV3, AAV3a, AAV3b, AAV3-3, AAV4, AAV4-4, AAV5, AAV6, AAV6.1, AAV6.2, AAV6.1.2, AAV7, AAV7.2, AAV8, AAV9, AAV9.11, AAV9.13, AAV9.16, AAV9.24, AAV9.45, AAV9.47, AAV9.61, AAV9.68, AAV9.84, AAV9.9, AAV10, AAV11, AAV12, AAV16.3, AAV24.1, AAV27.3, AAV42.12, AAV42-1b, AAV42-2, AAV42-3a, AAV42-3b, AAV42-4, AAV42-5a, AAV42-5b, AAV42-6b, AAV42-8, AAV42-10, AAV42-11, AAV42-12, AAV42-13, AAV42-15, AAV42-aa, AAV43-1, AAV43-12, AAV43-20, AAV43-21, AAV43-23, AAV43-25, AAV43-5, AAV44.1, AAV44.2, AAV44.5, AAV223.1, AAV223.2, AAV223.4, AAV223.5, AAV223.6, AAV223.7, AAV1-7/rh.48, AAV1-8/rh.49, AAV2-15/rh.62, AAV2-3/rh.61, AAV2-4/rh.50, AAV2-5/rh.51, AAV3.1/hu.6, AAV3.1/hu.9, AAV3-9/rh.52, AAV3-11/rh.53, AAV4-8/r11.64, AAV4-9/rh.54, AAV4-19/rh.55, AAV5-3/rh.57, AAV5-22/rh.58, AAV7.3/hu.7, AAV16.8/hu.10, AAV16.12/hu.11, AAV29.3/bb.1, AAV29.5/bb.2, AAV106.1/hu.37, AAV114.3/hu.40, AAV127.2/hu.41, AAV127.5/hu.42, AAV128.3/hu.44, AAV130.4/hu.48, AAV145.1/hu.53, AAV145.5/hu.54, AAV145.6/hu.55, AAV161.10/hu.60, AAV161.6/hu.61, AAV33.12/hu.17, AAV33.4/hu.15, AAV33.8/hu.16, AAV52/hu.19, AAV52.1/hu.20, AAV58.2/hu.25, AAVA3.3, AAVA3.4, AAVA3.5, AAVA3.7, AAVC1, AAVC2, AAVC5, AAV-DJ, AAV-DJ8, AAVF3, AAVF5, AAVH2, AAVrh.72, AAVhu.8, AAVrh.68, AAVrh.70, AAVpi.1, AAVpi.3, AAVpi.2, AAVrh.60, AAVrh.44, AAVrh.65, AAVrh.55, AAVrh.47, AAVrh.69, AAVrh.45, AAVrh.59, AAVhu.12, AAVH6, AAVLK03, AAVH-1/hu.1, AAVH-5/hu.3, AAVLG-10/rh.40, AAVLG-4/rh.38, AAVLG-9/hu.39, AAVN721-8/rh.43, AAVCh.5, AAVCh.5R1, AAVcy.2, AAVcy.3, AAVcy.4, AAVcy.5, AAVCy.5R1, AAVCy.5R2, AAVCy.5R3, AAVCy.5R4, AAVcy.6, AAVhu.1, AAVhu.2, AAVhu.3, AAVhu.4, AAVhu.5, AAVhu.6, AAVhu.7, AAVhu.9, AAVhu.10, AAVhu.11, AAVhu.13, AAVhu.15, AAVhu.16, AAVhu.17, AAVhu.18, AAVhu.20, AAVhu.21, AAVhu.22, AAVhu.23.2, AAVhu.24, AAVhu.25, AAVhu.27, AAVhu.28, AAVhu.29, AAVhu.29R, AAVhu.31, AAVhu.32, AAVhu.34, AAVhu.35, AAVhu.37, AAVhu.39, AAVhu.40, AAVhu.41, AAVhu.42, AAVhu.43, AAVhu.44, AAVhu.44R1, AAVhu.44R2, AAVhu.44R3, AAVhu.45, AAVhu.46, AAVhu.47, AAVhu.48, AAVhu.48R1, AAVhu.48R2, AAVhu.48R3, AAVhu.49, AAVhu.51, AAVhu.52, AAVhu.54, AAVhu.55, AAVhu.56, AAVhu.57, AAVhu.58, AAVhu.60, AAVhu.61, AAVhu.63, AAVhu.64, AAVhu.66, AAVhu.67, AAVhu.14/9, AAVhu.t 19, AAVrh.2, AAVrh.2R, AAVrh.8, AAVrh.8R, AAVrh.10, AAVrh.12, AAVrh.13, AAVrh.13R, AAVrh.14, AAVrh.17, AAVrh.18, AAVrh.19, AAVrh.20, AAVrh.21, AAVrh.22, AAVrh.23, AAVrh.24, AAVrh.25, AAVrh.31, AAVrh.32, AAVrh.33, AAVrh.34, AAVrh.35, AAVrh.36, AAVrh.37, AAVrh.37R2, AAVrh.38, AAVrh.39, AAVrh.40, AAVrh.46, AAVrh.48, AAVrh.48.1, AAVrh.48.1.2, AAVrh.48.2, AAVrh.49, AAVrh.51, AAVrh.52, AAVrh.53, AAVrh.54, AAVrh.56, AAVrh.57, AAVrh.58, AAVrh.61, AAVrh.64, AAVrh.64R1, AAVrh.64R2, AAVrh.67, AAVrh.73, AAVrh.74, AAVrh8R, AAVrh8R A586R mutant, AAVrh8R R533A mutant, AAAV, BAAV, caprine AAV, bovine AAV, AAVhE1.1, AAVhEr1.5, AAVhER1.14, AAVhEr1.8, AAVhEr1.16, AAVhEr1.18, AAVhEr1.35, AAVhEr1.7, AAVhEr1.36, AAVhEr2.29, AAVhEr2.4, AAVhEr2.16, AAVhEr2.30, AAVhEr2.31, AAVhEr2.36, AAVhER1.23, AAVhEr3.1, AAV2.5T, AAV-PAEC, AAV-LK01, AAV-LK02, AAV-LK03, AAV-LK04, AAV-LK05, AAV-LK06, AAV-LK07, AAV-LK08, AAV-LK09, AAV-LK10, AAV-LK11, AAV-LK12, AAV-LK13, AAV-LK14, AAV-LK15, AAV-LK16, AAV-LK17, AAV-LK18, AAV-LK19, AAV-PAEC2, AAV-PAEC4, AAV-PAEC6, AAV-PAEC7, AAV-PAEC8, AAV-PAEC11, AAV-PAEC12, AAV-2-pre-miRNA-101, AAV-8h, AAV-8b, AAV-h, AAV-b, AAV SM 10-2, AAV Shuffle 100-1, AAV Shuffle 100-3, AAV Shuffle 100-7, AAV Shuffle 10-2, AAV Shuffle 10-6, AAV Shuffle 10-8, AAV Shuffle 100-2, AAV SM 10-1, AAV SM 10-8, AAV SM 100-3, AAV SM 100-10, BNP61 AAV, BNP62 AAV, BNP63 AAV, AAVrh.50, AAVrh.43, AAVrh.62, AAVrh.48, AAVhu.19, AAVhu.11, AAVhu.53, AAV4-8/rh.64, AAVLG-9/hu.39, AAV54.5/hu.23, AAV54.2/hu.22, AAV54.7/hu.24, AAV54.1/hu.21, AAV54.4R/hu.27, AAV46.2/hu.28, AAV46.6/hu.29, AAV128.1/hu.43, true type AAV (ttAAV), UPENN AAV 10, Japanese AAV 10 serotypes, AAV CBr-7.1, AAV CBr-7.10, AAV CBr-7.2, AAV CBr-7.3, AAV CBr-7.4, AAV CBr-7.5, AAV CBr-7.7, AAV CBr-7.8, AAV CBr-B7.3, AAV CBr-B7.4, AAV CBr-E1, AAV CBr-E2, AAV CBr-E3, AAV CBr-E4, AAV CBr-E5, AAV CBr-e5, AAV CBr-E6, AAV CBr-E7, AAV CBr-E8, AAV CHt-1, AAV CHt-2, AAV CHt-3, AAV CHt-6.1, AAV CHt-6.10, AAV CHt-6.5, AAV CHt-6.6, AAV CHt-6.7, AAV CHt-6.8, AAV CHt-P1, AAV CHt-P2, AAV CHt-P5, AAV CHt-P6, AAV CHt-P8, AAV CHt-P9, AAV CKd-1, AAV CKd-10, AAV CKd-2, AAV CKd-3, AAV CKd-4, AAV CKd-6, AAV CKd-7, AAV CKd-8, AAV CKd-B1, AAV CKd-B2, AAV CKd-B3, AAV CKd-B4, AAV CKd-B5, AAV CKd-B6, AAV CKd-B7, AAV CKd-B8, AAV CKd-H1, AAV CKd-H2, AAV CKd-H3, AAV CKd-H4, AAV CKd-H5, AAV CKd-H6, AAV CKd-N3, AAV CKd-N4, AAV CKd-N9, AAV CLg-F1, AAV CLg-F2, AAV CLg-F3, AAV CLg-F4, AAV CLg-F5, AAV CLg-F6, AAV CLg-F7, AAV CLg-F8, AAV CLv-1, AAV CLv1-1, AAV Clv1-10, AAV CLv1-2, AAV CLv-12, AAV CLv1-3, AAV CLv-13, AAV CLv1-4, AAV Clv1-7, AAV Clv1-8, AAV Clv1-9, AAV CLv-2, AAV CLv-3, AAV CLv-4, AAV CLv-6, AAV CLv-8, AAV CLv-D1, AAV CLv-D2, AAV CLv-D3, AAV CLv-D4, AAV CLv-D5, AAV CLv-D6, AAV CLv-D7, AAV CLv-D8, AAV CLv-E1, AAV CLv-K1, AAV CLv-K3, AAV CLv-K6, AAV CLv-L4, AAV CLv-L5, AAV CLv-L6, AAV CLv-M1, AAV CLv-M11, AAV CLv-M2, AAV CLv-M5, AAV CLv-M6, AAV CLv-M7, AAV CLv-M8, AAV CLv-M9, AAV CLv-R1, AAV CLv-R2, AAV CLv-R3, AAV CLv-R4, AAV CLv-R5, AAV CLv-R6, AAV CLv-R7, AAV CLv-R8, AAV CLv-R9, AAV CSp-1, AAV CSp-10, AAV CSp-11, AAV CSp-2, AAV CSp-3, AAV CSp-4, AAV CSp-6, AAV CSp-7, AAV CSp-8, AAV CSp-8.10, AAV CSp-8.2, AAV CSp-8.4, AAV CSp-8.5, AAV CSp-8.6, AAV CSp-8.7, AAV CSp-8.8, AAV CSp-8.9, AAV CSp-9, AAV.hu.48R3, AAV.VR-355, AAV3B, AAV4, AAV5, AAVF1/HSC1, AAVF11/HSC11, AAVF12/HSC12, AAVF13/HSC13, AAVF14/HSC14, AAVF15/HSC15, AAVF16/HSC16, AAVF17/HSC17, AAVF2/HSC2, AAVF3/HSC3, AAVF4/HSC4, AAVF5/HSC5, AAVF6/HSC6, AAVF7/HSC7, AAVF8/HSC8, AAVF9/HSC9, PHP.B, PHP.A, G2B-26, G2B-13, TH1.1-32, and/or TH1.1-35 and variants thereof.

Inverted Terminal Repeats (ITRs)

In some embodiments, the AAV vector genomes may comprise at least one ITR region and a payload region. In some embodiments, the vector genome has two ITRs. These two ITRs flank the payload region at the 5' and 3' ends. The ITRs function as origins of replication comprising recognition sites for replication. ITRs comprise sequence regions which can be complementary and symmetrically arranged. ITRs incorporated into vector genomes of the disclosure may be comprised of naturally occurring polynucleotide sequences or recombinantly derived polynucleotide sequences.

The ITRs may be derived from the same serotype as the capsid or a derivative thereof. The ITR may be of a different serotype than the capsid. In some embodiments, the AAV particle has more than one ITR. In a non-limiting example, the AAV particle has a vector genome comprising two ITRs. In some embodiments, the ITRs are of the same serotype as one another. In another embodiment, the ITRs are of different serotypes. Non-limiting examples include zero, one or both of the ITRs having the same serotype as the capsid. In some embodiments both ITRs of the vector genome of the AAV particle are AAV2 ITRs.

Independently, each ITR may be about 100 to about 150 nucleotides in length. An ITR may be about 100-105 nucleotides in length, 106-110 nucleotides in length, 111-115 nucleotides in length, 116-120 nucleotides in length, 121-125 nucleotides in length, 126-130 nucleotides in length, 131-135 nucleotides in length, 136-140 nucleotides in length, 141-145 nucleotides in length or 146-150 nucleotides in length. In some embodiments, the ITRs are 140-142 nucleotides in length. Non-limiting examples of ITR length are 102, 140, 141, 142, 145 nucleotides in length, and those having at least 95% identity thereto.

Promoters

In some embodiments, the payload region of the vector genome comprises at least one element to enhance the transgene target specificity and expression (See e.g., Powell et al. Viral Expression Cassette Elements to Enhance Transgene Target Specificity and Expression in Gene Therapy, 2015; the contents of which are herein incorporated by reference in its entirety). Non-limiting examples of elements to enhance the transgene target specificity and expression include promoters, endogenous miRNAs, post-transcriptional regulatory elements (PREs), polyadenylation (PolyA) signal sequences and upstream enhancers (USEs), CMV enhancers and introns.

In some embodiments, the promoter is efficient when it drives expression of the polypeptide(s) encoded in the payload region of the vector genome of the AAV particle.

In some embodiments, the promoter is deemed to be efficient when it drives expression in the cell being targeted.

In some embodiments, the promoter drives expression of the payload for a period of time in targeted tissues. Expression driven by a promoter may be for a period of 1 hour, 2, hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 2 days, 3 days, 4 days, 5 days, 6 days, 1 week, 8 days, 9 days, 10 days, 11 days, 12 days, 13 days, 2 weeks, 15 days, 16 days, 17 days, 18 days, 19 days, 20 days, 3 weeks, 22 days, 23 days, 24 days, 25 days, 26 days, 27 days, 28 days, 29 days, 30 days, 31 days, 1 month, 2 months, 3 months, 4 months, 5 months, 6 months, 7 months, 8 months, 9 months, 10 months, 11 months, 1 year, 13 months, 14 months, 15 months, 16 months, 17 months, 18 months, 19 months, 20 months, 21 months, 22 months, 23 months, 2 years, 3 years, 4 years, 5 years, 6 years, 7 years, 8 years, 9 years, 10 years or more than 10 years. Expression may be for 1-5 hours, 1-12 hours, 1-2 days, 1-5 days, 1-2 weeks, 1-3 weeks, 1-4 weeks, 1-2 months, 1-4 months, 1-6 months, 2-6 months, 3-6 months, 3-9 months, 4-8 months, 6-12 months, 1-2 years, 1-5 years, 2-5 years, 3-6 years, 3-8 years, 4-8 years, or 5-10 years.

In some embodiments, the promoter drives expression of the payload for at least 1 month, 2 months, 3 months, 4 months, 5 months, 6 months, 7 months, 8 months, 9 months, 10 months, 11 months, 1 year, 2 years, 3 years 4 years, 5 years, 6 years, 7 years, 8 years, 9 years, 10 years, 11 years, 12 years, 13 years, 14 years, 15 years, 16 years, 17 years, 18 years, 19 years, 20 years, 21 years, 22 years, 23 years, 24 years, 25 years, 26 years, 27 years, 28 years, 29 years, 30 years, 31 years, 32 years, 33 years, 34 years, 35 years, 36 years, 37 years, 38 years, 39 years, 40 years, 41 years, 42 years, 43 years, 44 years, 45 years, 46 years, 47 years, 48 years, 49 years, 50 years, 55 years, 60 years, 65 years, or more than 65 years.

Promoters may be naturally occurring or non-naturally occurring. Non-limiting examples of promoters include viral promoters, plant promoters and mammalian promoters. In some embodiments, the promoters may be human promoters. In some embodiments, the promoter may be truncated.

Promoters which drive or promote expression in most tissues include, but are not limited to, human elongation factor 1α-subunit (EF1α), cytomegalovirus (CMV) immediate-early enhancer and/or promoter, chicken β-actin (CBA) and its derivative CAG, R glucuronidase (GUSB), or ubiquitin C (UBC). Tissue-specific expression elements can be used to restrict expression to certain cell types such as, but not limited to, muscle specific promoters, B cell promoters, monocyte promoters, leukocyte promoters, macrophage promoters, pancreatic acinar cell promoters, endothelial cell promoters, lung tissue promoters, astrocyte promoters, or nervous system promoters which can be used to restrict expression to neurons, astrocytes, or oligodendrocytes.

Non-limiting examples of muscle-specific promoters include mammalian muscle creatine kinase (MCK) promoter, mammalian desmin (DES) promoter, mammalian troponin I (TNNI2) promoter, and mammalian skeletal alpha-actin (ASKA) promoter (see, e.g. U.S. Patent Publication US20110212529, the contents of which are herein incorporated by reference in their entirety)

Non-limiting examples of tissue-specific expression elements for neurons include neuron-specific enolase (NSE), platelet-derived growth factor (PDGF), platelet-derived growth factor B-chain (PDGF-β), synapsin (Syn), methyl-CpG binding protein 2 (MeCP2), $Ca^{2+}$/calmodulin-dependent protein kinase II (CaMKII), metabotropic glutamate receptor 2 (mGluR2), neurofilament light (NFL) or heavy (NFH), β-globin minigene nβ2, preproenkephalin (PPE), enkephalin (Enk) and excitatory amino acid transporter 2 (EAAT2) promoters. Non-limiting examples of tissue-specific expression elements for astrocytes include glial fibrillary acidic protein (GFAP) and EAAT2 promoters. A non-limiting example of a tissue-specific expression element for oligodendrocytes includes the myelin basic protein (MBP) promoter.

In some embodiments, the promoter may be less than 1 kb. The promoter may have a length of 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, or more than 800 nucleotides. The promoter may have a length between 200-300, 200-400, 200-500, 200-600, 200-700, 200-800, 300-400, 300-500, 300-600, 300-700, 300-800, 400-500, 400-600, 400-700, 400-800, 500-600, 500-700, 500-800, 600-700, 600-800, or 700-800.

In some embodiments, the promoter may be a combination of two or more components of the same or different starting or parental promoters such as, but not limited to, CMV and CBA. Each component may have a length of 200, 210, 220, 230, 240, 250, 260, 270, 280, 290, 300, 310, 320, 330, 340, 350, 360, 370, 380, 381, 382, 383, 384, 385, 386, 387, 388, 389, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, or more than 800. Each component may have a length between 200-300, 200-400, 200-500, 200-600, 200-700, 200-800, 300-400, 300-500, 300-600, 300-700, 300-800, 400-500, 400-600, 400-700, 400-800, 500-600, 500-700, 500-800, 600-700, 600-800 or 700-800. In some embodiments, the promoter is a combination of a 382 nucleotide CMV-enhancer sequence and a 260 nucleotide CBA-promoter sequence.

In some embodiments, the vector genome comprises a ubiquitous promoter. Non-limiting examples of ubiquitous promoters include CMV, CBA (including derivatives CAG, CBh, etc.), EF-1$\alpha$, PGK, UBC, GUSB (hGBp), and UCOE (promoter of HNRPA2B1-CBX3).

In some embodiments, the promoter is not cell specific.

In some embodiments, the vector genome comprises an engineered promoter.

In some embodiments, the vector genome comprises a promoter from a naturally expressed protein.

Untranslated Regions (UTRs)

By definition, wild type untranslated regions (UTRs) of a gene are transcribed but not translated. Generally, the 5' UTR starts at the transcription start site and ends at the start codon and the 3' UTR starts immediately following the stop codon and continues until the termination signal for transcription.

Features typically found in abundantly expressed genes of specific target organs may be engineered into UTRs to enhance the stability and protein production. As a non-limiting example, a 5' UTR from mRNA normally expressed in the liver (e.g., albumin, serum amyloid A, Apolipoprotein A/B/E, transferrin, alpha fetoprotein, erythropoietin, or Factor VIII) may be used in the vector genomes of the AAV particles of the disclosure to enhance expression in hepatic cell lines or liver.

While not wishing to be bound by theory, wild-type 5' untranslated regions (UTRs) include features which play roles in translation initiation. Kozak sequences, which are commonly known to be involved in the process by which the ribosome initiates translation of many genes, are usually included in 5' UTRs. Kozak sequences have the consensus CCR(A/G)CCAUGG, where R is a purine (adenine or guanine) three bases upstream of the start codon (ATG), which is followed by another 'G'.

In some embodiments, the 5'UTR in the vector genome includes a Kozak sequence.

In some embodiments, the 5'UTR in the vector genome does not include a Kozak sequence.

While not wishing to be bound by theory, wild-type 3' UTRs are known to have stretches of Adenosines and Uridines embedded therein. These AU rich signatures are particularly prevalent in genes with high rates of turnover. Based on their sequence features and functional properties, the AU rich elements (AREs) can be separated into three classes (Chen et al., 1995, the contents of which are herein incorporated by reference in its entirety): Class I AREs, such as, but not limited to, c-Myc and MyoD, contain several dispersed copies of an AUUUA motif within U-rich regions. Class II AREs, such as, but not limited to, GM-CSF and TNF-a, possess two or more overlapping UUAUUUA(U/A)(U/A) nonamers. Class III ARES, such as, but not limited to, c-Jun and Myogenin, are less well defined. These U rich regions do not contain an AUUUA motif. Most proteins binding to the AREs are known to destabilize the messenger, whereas members of the ELAV family, most notably HuR, have been documented to increase the stability of mRNA. HuR binds to AREs of all the three classes. Engineering the HuR specific binding sites into the 3' UTR of nucleic acid molecules will lead to HuR binding and thus, stabilization of the message in vivo.

Introduction, removal or modification of 3' UTR AU rich elements (AREs) can be used to modulate the stability of polynucleotides. When engineering specific polynucleotides, e.g., payload regions of vector genomes, one or more copies of an ARE can be introduced to make polynucleotides less stable and thereby curtail translation and decrease production of the resultant protein. Likewise, AREs can be identified and removed or mutated to increase the intracellular stability and thus increase translation and production of the resultant protein.

In some embodiments, the 3' UTR of the vector genome may include an oligo(dT) sequence for templated addition of a poly-A tail.

In some embodiments, the vector genome may include at least one miRNA seed, binding site or full sequence. microRNAs (or miRNA or miR) are 19-25 nucleotide non-coding RNAs that bind to the sites of nucleic acid targets and down-regulate gene expression either by reducing nucleic acid molecule stability or by inhibiting translation. A microRNA sequence comprises a "seed" region, i.e., a sequence in the region of positions 2-8 of the mature microRNA, which sequence has perfect Watson-Crick complementarity to the miRNA target sequence of the nucleic acid.

In some embodiments, the vector genome may be engineered to include, alter or remove at least one miRNA binding site, sequence, or seed region.

Any UTR from any gene known in the art may be incorporated into the vector genome of the AAV particle. These UTRs, or portions thereof, may be placed in the same orientation as in the gene from which they were selected or they may be altered in orientation or location. In some embodiments, the UTR used in the vector genome of the AAV particle may be inverted, shortened, lengthened, made with one or more other 5' UTRs or 3' UTRs known in the art. As used herein, the term "altered" as it relates to a UTR, means that the UTR has been changed in some way in relation to a reference sequence. For example, a 3' or 5' UTR may be altered relative to a wild type or native UTR by the change in orientation or location as taught above or may be altered by the inclusion of additional nucleotides, deletion of nucleotides, swapping or transposition of nucleotides.

In some embodiments, the vector genome of the AAV particle comprises at least one artificial UTRs which is not a variant of a wild-type UTR.

In some embodiments, the vector genome of the AAV particle comprises UTRs which have been selected from a family of transcripts whose proteins share a common function, structure, feature or property.

Polyadenylation Sequence

In some embodiments, the vector genome comprises at least one polyadenylation sequence between the 3' end of the payload coding sequence and the 5' end of the 3'ITR.

In some embodiments, the polyadenylation (poly-A) sequence may range from absent to about 500 nucleotides in length. The polyadenylation sequence may be, but is not limited to, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, and 500 nucleotides in length.

In some embodiments, the polyadenylation sequence is 50-100 nucleotides in length. In some embodiments, the polyadenylation sequence is 50-150 nucleotides in length. In some embodiments, the polyadenylation sequence is 50-160 nucleotides in length. In some embodiments, the polyadenylation sequence is 50-200 nucleotides in length. In some embodiments, the polyadenylation sequence is 60-100 nucleotides in length. In some embodiments, the polyadenylation sequence is 60-150 nucleotides in length. In some embodiments, the polyadenylation sequence is 60-160 nucleotides in length. In some embodiments, the polyadenylation sequence is 60-200 nucleotides in length. In some embodiments, the polyadenylation sequence is 70-100 nucleotides in length. In some embodiments, the polyadenylation sequence is 70-150 nucleotides in length. In some embodiments, the polyadenylation sequence is 70-160 nucleotides in length. In some embodiments, the polyadenylation sequence is 70-200 nucleotides in length. In some embodiments, the polyadenylation sequence is 80-100 nucleotides in length. In some embodiments, the polyadenylation sequence is 80-150 nucleotides in length. In some embodiments, the polyadenylation sequence is 80-160 nucleotides in length. In some embodiments, the polyadenylation sequence is 80-200 nucleotides in length. In some embodiments, the polyadenylation sequence is 90-100 nucleotides in length. In some embodiments, the polyadenylation sequence is 90-150 nucleotides in length. In some embodiments, the polyadenylation sequence is 90-160 nucleotides in length. In some embodiments, the polyadenylation sequence is 90-200 nucleotides in length.

Linkers

Vector genomes may be engineered with one or more spacer or linker regions to separate coding or non-coding regions.

In some embodiments, the payload region of the vector genome may optionally encode one or more linker sequences. In some cases, the linker may be a peptide linker that may be used to connect the polypeptides encoded by the payload region (i.e., light and heavy antibody chains during expression). Some peptide linkers may be cleaved after expression to separate heavy and light chain domains, allowing assembly of mature antibodies or antibody fragments. Linker cleavage may be enzymatic. In some cases, linkers comprise an enzymatic cleavage site to facilitate intracellular or extracellular cleavage. Some payload regions encode linkers that interrupt polypeptide synthesis during translation of the linker sequence from an mRNA transcript. Such linkers may facilitate the translation of separate protein domains from a single transcript. In some cases, two or more linkers are encoded by a payload region of the vector genome.

Internal ribosomal entry site (IRES) is a nucleotide sequence (>500 nucleotides) that allows for initiation of translation in the middle of an mRNA sequence (Kim, J. H. et al., 2011. PLoS One 6(4): e18556; the contents of which are herein incorporated by reference in its entirety). Use of an IRES sequence ensures co-expression of genes before and after the IRES, though the sequence following the IRES may be transcribed and translated at lower levels than the sequence preceding the IRES sequence.

A peptides are small “self-cleaving” peptides (18-22 amino acids) derived from viruses such as foot-and-mouth disease virus (F2A), porcine teschovirus-1 (P2A), Thoseaasigna virus (T2A), or equine rhinitis A virus (E2A). The 2A designation refers specifically to a region of picornavirus polyproteins that lead to a ribosomal skip at the glycyl-prolyl bond in the C-terminus of the 2A peptide (Kim, J. H. et al., 2011. PLoS One 6(4): e18556; the contents of which are herein incorporated by reference in its entirety). This skip results in a cleavage between the 2A peptide and its immediate downstream peptide. As opposed to IRES linkers, 2A peptides generate stoichiometric expression of proteins flanking the 2A peptide and their shorter length can be advantageous in generating viral expression vectors.

Some payload regions encode linkers comprising furin cleavage sites. Furin is a calcium dependent serine endoprotease that cleaves proteins just downstream of a basic amino acid target sequence (Arg-X-(Arg/Lys)-Arg) (Thomas, G., 2002. Nature Reviews Molecular Cell Biology 3(10): 753-66; the contents of which are herein incorporated by reference in its entirety). Furin is enriched in the trans-golgi network where it is involved in processing cellular precursor proteins. Furin also plays a role in activating a number of pathogens. This activity can be taken advantage of for expression of polypeptides of the disclosure.

In some embodiments, the payload region may encode one or more linkers comprising cathepsin, matrix metalloproteinases or legumain cleavage sites. Such linkers are described e.g. by Cizeau and Macdonald in International Publication No. WO2008052322, the contents of which are herein incorporated in their entirety. Cathepsins are a family of proteases with unique mechanisms to cleave specific proteins. Cathepsin B is a cysteine protease and cathepsin D is an aspartyl protease. Matrix metalloproteinases are a family of calcium-dependent and zinc-containing endopeptidases. Legumain is an enzyme catalyzing the hydrolysis of (-Asn-Xaa-) bonds of proteins and small molecule substrates.

In some embodiments, payload regions may encode linkers that are not cleaved. Such linkers may include a simple amino acid sequence, such as a glycine rich sequence. In some cases, linkers may comprise flexible peptide linkers comprising glycine and serine residues. The linker may comprise flexible peptide linkers of different lengths, e.g. nxG4S, where n=1-10 and the length of the encoded linker varies between 5 and 50 amino acids. In a non-limiting example, the linker may be 5xG4S. These flexible linkers are small and without side chains so they tend not to influence secondary protein structure while providing a flexible linker between antibody segments (George, R. A., et al., 2002. Protein Engineering 15(11): 871-9; Huston, J. S. et al., 1988. PNAS 85:5879-83; and Shan, D. et al., 1999. Journal of Immunology. 162(11):6589-95; the contents of each of which are herein incorporated by reference in their entirety). Furthermore, the polarity of the serine residues improves solubility and prevents aggregation problems.

In some embodiments, payload regions of the disclosure may encode small and unbranched serine-rich peptide linkers, such as those described by Huston et al. in U.S. Pat. No. 5,525,491, the contents of which are herein incorporated in their entirety. Polypeptides encoded by the payload region of the disclosure, linked by serine-rich linkers, have increased solubility.

In some embodiments, payload regions of the disclosure may encode artificial linkers, such as those described by Whitlow and Filpula in U.S. Pat. No. 5,856,456 and Ladner et al. in U.S. Pat. No. 4,946,778, the contents of each of which are herein incorporated by their entirety.

Introns

In some embodiments, the payload region comprises at least one element to enhance the expression such as one or more introns or portions thereof. Non-limiting examples of introns include, MVM (67-97 bps), F.IX truncated intron 1 (300 bps), β-globin SD/immunoglobulin heavy chain splice acceptor (250 bps), adenovirus splice donor/immunoglobin splice acceptor (500 bps), SV40 late splice donor/splice acceptor (19S/16S) (180 bps) and hybrid adenovirus splice donor/IgG splice acceptor (230 bps).

In some embodiments, the intron or intron portion may be 100-500 nucleotides in length. The intron may have a length of 80, 90, 100, 110, 120, 130, 140, 150, 160, 170, 171, 172, 173, 174, 175, 176, 177, 178, 179, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490 or 500. The intron may have a length between 80-100, 80-120, 80-140, 80-160, 80-180, 80-200, 80-250, 80-300, 80-350, 80-400, 80-450, 80-500, 200-300, 200-400, 200-500, 300-400, 300-500, or 400-500.

Lentiviral Vectors

Lentiviral vectors are a type of retrovirus that can infect both dividing and nondividing cells because their viral shell can pass through the intact membrane of the nucleus of the target cell. Lentiviral vectors have the ability to deliver transgenes in tissues that had long appeared irremediably refractory to stable genetic manipulation. Lentivectors have also opened fresh perspectives for the genetic treatment of a wide array of hereditary as well as acquired disorders, and a real proposal for their clinical use seems imminent.

RNA

Ribonucleic acid (RNA) is a molecule that is made up of nucleotides, which are ribose sugars attached to nitrogenous bases and phosphate groups. The nitrogenous bases include adenine (A), guanine (G), uracil (U), and cytosine (C). Generally, RNA mostly exists in the single-stranded form but can also exists double-stranded in certain circumstances. The length, form and structure of RNA is diverse depending on the purpose of the RNA. For example, the length of an RNA can vary from a short sequence (e.g., siRNA) to a long sequences (e.g., lncRNA), can be linear (e.g., mRNA) or circular (e.g., oRNA), and can either be a coding (e.g., mRNA) or a non-coding (e.g., lncRNA) sequence.

In some embodiments, the payload region may be or encode a coding RNA.

In some embodiments, the payload region may be or encode a non-coding RNA.

In some embodiments, the payload region may be or encode both a coding and a non-coding RNA.

In some embodiments, the payload region comprises nucleic acid sequences encoding more than one cargo or payload.

In some embodiments, the payload region comprises a nucleic acid sequence to enhance the expression of a gene. As a non-limiting example, the nucleic acid sequence is a messenger RNA (mRNA). As another non-limiting example, the nucleic acid sequence is a circular RNA (oRNA).

In some embodiments, the payload region comprises a nucleic acid sequence to reduce or inhibit the expression of a gene. As a non-limiting example, the nucleic acid sequence is a small interfering RNA (siRNA) or a microRNA (miRNA)

Messenger RNA (mRNA)

In some embodiments, the originator constructs and/or benchmark constructs may be mRNA. As used herein, the term "messenger RNA" (mRNA) refers to any polynucleotide which encodes a target of interest and which is capable of being translated to produce the encoded target of interest in vitro, in vivo, in situ or ex vivo.

Generally, an mRNA molecule comprises at least a coding region, a 5' untranslated region (UTR), a 3' UTR, a 5' cap and a poly-A tail. In some aspects, one or more structural and/or chemical modifications or alterations may be included in the RNA which can reduce the innate immune response of a cell in which the mRNA is introduced. As used herein, a "structural" feature or modification is one in which two or more linked nucleotides are inserted, deleted, duplicated, inverted or randomized in a nucleic acid without significant chemical modification to the nucleotides themselves. Because chemical bonds will necessarily be broken and reformed to effect a structural modification, structural modifications are of a chemical nature and hence are chemical modifications. However, structural modifications will result in a different sequence of nucleotides. For example, the polynucleotide "ATCG" may be chemically modified to "AT-5meC-G".

Generally, the shortest length of a region of the originator constructs and/or benchmark constructs can be the length of a nucleic acid sequence that is sufficient to encode for a dipeptide, a tripeptide, a tetrapeptide, a pentapeptide, a hexapeptide, a heptapeptide, an octapeptide, a nonapeptide, or a decapeptide. In another embodiment, the length may be sufficient to encode a peptide of 2-30 amino acids, e.g. 5-30, 10-30, 2-25, 5-25, 10-25, or 10-20 amino acids. The length may be sufficient to encode for a peptide of at least 11, 12, 13, 14, 15, 17, 20, 25 or 30 amino acids, or a peptide that is no longer than 40 amino acids, e.g. no longer than 35, 30, 25, 20, 17, 15, 14, 13, 12, 11 or 10 amino acids.

Generally, the length of the region of the mRNA encoding a target of interest is greater than about 30 nucleotides in length (e.g., at least or greater than about 35, 40, 45, 50, 55, 60, 70, 80, 90, 100, 120, 140, 160, 180, 200, 250, 300, 350, 400, 450, 500, 600, 700, 800, 900, 1,000, 1,100, 1,200, 1,300, 1,400, 1,500, 1,600, 1,700, 1,800, 1,900, 2,000, 2,500, and 3,000, 4,000, 5,000, 6,000, 7,000, 8,000, 9,000, 10,000, 20,000, 30,000, 40,000, 50,000, 60,000, 70,000, 80,000, 90,000 or up to and including 100,000 nucleotides).

In some embodiments, the mRNA includes from about 30 to about 100,000 nucleotides (e.g., from 30 to 50, from 30 to 100, from 30 to 250, from 30 to 500, from 30 to 1,000, from 30 to 1,500, from 30 to 3,000, from 30 to 5,000, from 30 to 7,000, from 30 to 10,000, from 30 to 25,000, from 30 to 50,000, from 30 to 70,000, from 100 to 250, from 100 to 500, from 100 to 1,000, from 100 to 1,500, from 100 to 3,000, from 100 to 5,000, from 100 to 7,000, from 100 to 10,000, from 100 to 25,000, from 100 to 50,000, from 100 to 70,000, from 100 to 100,000, from 500 to 1,000, from 500 to 1,500, from 500 to 2,000, from 500 to 3,000, from 500 to 5,000, from 500 to 7,000, from 500 to 10,000, from 500 to 25,000, from 500 to 50,000, from 500 to 70,000, from 500 to 100,000, from 1,000 to 1,500, from 1,000 to 2,000, from 1,000 to 3,000, from 1,000 to 5,000, from 1,000 to 7,000, from 1,000 to 10,000, from 1,000 to 25,000, from 1,000 to 50,000, from 1,000 to 70,000, from 1,000 to 100,000, from 1,500 to 3,000, from 1,500 to 5,000, from 1,500 to 7,000, from 1,500 to 10,000, from 1,500 to 25,000, from 1,500 to 50,000, from 1,500 to 70,000, from 1,500 to 100,000, from 2,000 to 3,000, from 2,000 to 5,000, from 2,000 to 7,000, from 2,000 to 10,000, from 2,000 to 25,000, from 2,000 to 50,000, from 2,000 to 70,000, and from 2,000 to 100,000).

In some embodiments, the region or regions flanking the region encoding the target of interest may range independently from 15-1,000 nucleotides in length (e.g., greater than 30, 40, 45, 50, 55, 60, 70, 80, 90, 100, 120, 140, 160, 180, 200, 250, 300, 350, 400, 450, 500, 600, 700, 800, and 900 nucleotides or at least 30, 40, 45, 50, 55, 60, 70, 80, 90, 100, 120, 140, 160, 180, 200, 250, 300, 350, 400, 450, 500, 600, 700, 800, 900, and 1,000 nucleotides).

In some embodiments, the mRNA comprises a tailing sequence which can range from absent to 500 nucleotides in length (e.g., at least 60, 70, 80, 90, 120, 140, 160, 180, 200, 250, 300, 350, 400, 450, or 500 nucleotides). Where the tailing region is a polyA tail, the length may be determined in units of or as a function of polyA Binding Protein binding. In this embodiment, the polyA tail is long enough to bind at least 4 monomers of PolyA Binding Protein. PolyA Binding Protein monomers bind to stretches of approximately 38 nucleotides. As such, it has been observed that polyA tails of about 80 nucleotides and 160 nucleotides are functional.

In some embodiments, the mRNA comprises a capping sequence which comprises a single cap or a series of nucleotides forming the cap. The capping sequence may be from 1 to 10, e.g. 2-9, 3-8, 4-7, 1-5, 5-10, or at least 2, or 10 or fewer nucleotides in length. In some embodiments, the caping sequence is absent.

In some embodiments, the mRNA comprises a region comprising a start codon. The region comprising the start codon may range from 3 to 40, e.g., 5-30, 10-20, 15, or at least 4, or 30 or fewer nucleotides in length.

In some embodiments, the mRNA comprises a region comprising a stop codon. The region comprising the stop codon may range from 3 to 40, e.g., 5-30, 10-20, 15, or at least 4, or 30 or fewer nucleotides in length.

In some embodiments, the mRNA comprises a region comprising a restriction sequence. The region comprising the restriction sequence may range from 3 to 40, e.g., 5-30, 10-20, 15, or at least 4, or 30 or fewer nucleotides in length.

Untranslated Regions (UTRs)

In some embodiments, the mRNA comprises at least one untranslated region (UTR) which flanks the region encoding the target of interest. UTRs are transcribed by not translated.

The 5' UTR starts at the transcription start site and continues to the start codon but does not include the start codon; whereas, the 3'UTR starts immediately following the stop codon and continues until the transcriptional termination signal. While not wishing to be bound by theory, the UTRs may have a regulatory role in terms of translation and stability of the nucleic acid.

Natural 5' UTRs usually include features which have a role in translation initiation as they tend to include Kozak sequences which are commonly known to be involved in the process by which the ribosome initiates translation of many genes. Kozak sequences have the consensus CCR(A/G)CCAUGG, where R is a purine (adenine or guanine) three bases upstream of the start codon (AUG), which is followed by another 'G'. 5'UTR also have been known to form secondary structures which are involved in elongation factor binding.

3' UTRs are known to have stretches of Adenosines and Uridines embedded in them. These AU rich signatures are particularly prevalent in genes with high rates of turnover. Based on their sequence features and functional properties, the AU rich elements (AREs) can be separated into three classes (Chen et al., 1995): Class I AREs contain several dispersed copies of an AUUUA motif within U-rich regions. C-Myc and MyoD contain class I AREs. Class II AREs possess two or more overlapping UUAUUUA(U/A)(U/A) nonamers. Molecules containing this type of AREs include GM-CSF and TNF-α. Class III ARES are less well defined. These U rich regions do not contain an AUUUA motif. c-Jun and Myogenin are two well-studied examples of this class. Most proteins binding to the AREs are known to destabilize the messenger, whereas members of the ELAV family, most notably HuR, have been documented to increase the stability of mRNA. HuR binds to AREs of all the three classes. Engineering the HuR specific binding sites into the 3' UTR of nucleic acid molecules will lead to HuR binding and thus, stabilization of the message in vivo. Introduction, removal or modification of 3' UTR AU rich elements (AREs) can be used to modulate the stability of mRNA. For example, one or more copies of an ARE can be introduced to make mRNA less stable and thereby curtail translation and decrease production of the resultant protein. Alternatively, AREs can be identified and removed or mutated to increase the intracellular stability and thus increase translation and production of the resultant protein.

In some embodiments, the introduction of features often expressed in genes of target organs the stability and protein production of the mRNA can be enhanced in a specific organ and/or tissue. As a non-limiting example, the feature can be a UTR. As another example, the feature can be introns or portions of introns sequences.

5' Capping

The 5' cap structure of an mRNA is involved in nuclear export, increasing mRNA stability and binds the mRNA Cap Binding Protein (CBP), which is responsible for mRNA stability in the cell and translation competency through the association of CBP with poly(A) binding protein to form the mature cyclic mRNA species. The cap further assists the removal of 5' proximal introns removal during mRNA splicing.

Endogenous mRNA molecules may be 5'-end capped generating a 5'-ppp-5'-triphosphate linkage between a terminal guanosine cap residue and the 5'-terminal transcribed sense nucleotide of the mRNA molecule. This 5'-guanylate cap may then be methylated to generate an N7-methyl-guanylate residue. The ribose sugars of the terminal and/or anteterminal transcribed nucleotides of the 5' end of the mRNA may optionally also be 2'-0-methylated. 5'-decapping through hydrolysis and cleavage of the guanylate cap structure may target a nucleic acid molecule, such as an mRNA molecule, for degradation.

Modifications to mRNA may generate a non-hydrolyzable cap structure preventing decapping and thus increasing mRNA half-life. Because cap structure hydrolysis requires cleavage of 5'-ppp-5' phosphorodiester linkages, modified nucleotides may be used during the capping reaction. For example, a Vaccinia Capping Enzyme from New England Biolabs (Ipswich, MA) may be used with a-thio-guanosine nucleotides according to the manufacturer's instructions to create a phosphorothioate linkage in the 5'-ppp-5' cap.

Additional modified guanosine nucleotides may be used such as a-methyl-phosphonate and seleno-phosphate nucleotides.

Additional modifications include, but are not limited to, 2'-0-methylation of the ribose sugars of 5'-terminal and/or 5'-anteterminal nucleotides of the mRNA (as mentioned above) on the 2'-hydroxyl group of the sugar ring. Multiple distinct 5'-cap structures can be used to generate the 5'-cap of a nucleic acid molecule, such as an mRNA molecule.

Cap analogs, which herein are also referred to as synthetic cap analogs, chemical caps, chemical cap analogs, or structural or functional cap analogs, differ from natural (i.e. endogenous, wild-type or physiological) 5'-caps in their chemical structure, while retaining cap function. Cap analogs may be chemically (i.e. non-enzymatically) or enzymatically synthesized and/or linked to a nucleic acid molecule.

For example, the Anti-Reverse Cap Analog (ARCA) cap contains two guanines linked by a 5'-5'-triphosphate group, wherein one guanine contains an N7 methyl group as well as a 3'-0-methyl group (i.e., N7,3'-0-dimethyl-guanosine-5'-triphosphate-5'-guanosine ($m^7$G-3'mppp-G; which may equivalently be designated 3' O-Me-m7G(5')ppp(5')G). The 3'-0 atom of the other, unmodified, guanine becomes linked to the 5'-terminal nucleotide of the capped nucleic acid molecule (e.g. an mRNA). The N7- and 3'-0-methylated guanine provides the terminal moiety of the capped nucleic acid molecule (e.g. mRNA).

Another exemplary cap is mCAP, which is similar to ARCA but has a 2'-0-methyl group on guanosine (i.e., N7,2'-0-dimethyl-guanosine-5'-triphosphate-5'-guanosine, $m^7$Gm-ppp-G).

While cap analogs allow for the concomitant capping of a nucleic acid molecule in an in vitro transcription reaction, up to 20% of transcripts can remain uncapped. This, as well as the structural differences of a cap analog from an endogenous 5'-cap structures of nucleic acids produced by the endogenous, cellular transcription machinery, may lead to reduced translational competency and reduced cellular stability.

mRNA may also be capped post-transcriptionally, using enzymes, in order to generate more authentic 5'-cap structures. As used herein, the phrase "more authentic" refers to a feature that closely mirrors or mimics, either structurally or functionally, an endogenous or wild type feature. That is, a "more authentic" feature is better representative of an endogenous, wild-type, natural or physiological cellular function and/or structure as compared to synthetic features or analogs, etc., of the prior art, or which outperforms the corresponding endogenous, wild-type, natural or physiological feature in one or more respects. Non-limiting examples of more authentic 5'cap structures are those which, among other things, have enhanced binding of cap binding proteins, increased half-life, reduced susceptibility to 5' endonucleases and/or reduced 5'decapping, as compared to synthetic 5'cap structures known in the art (or to a wild-type, natural or physiological 5'cap structure). For example, recombinant Vaccinia Virus Capping Enzyme and recombinant 2'-0-methyltransferase enzyme can create a canonical 5'-5'-triphosphate linkage between the 5'-terminal nucleotide of an mRNA and a guanine cap nucleotide wherein the cap guanine contains an N7 methylation and the 5'-terminal nucleotide of the mRNA contains a 2'-0-methyl. Such a structure is termed the Cap1 structure. This cap results in a higher translational-competency and cellular stability and a reduced activation of cellular pro-inflammatory cytokines, as compared, e.g., to other 5'cap analog structures known in the art. Cap structures include, but are not limited to, 7mG(5*)ppp(5*)N,pN2p (cap 0), 7mG(5*)ppp(5*)NlmpNp (cap 1), and 7mG(5*)-ppp(5')NlmpN2mp (cap 2).

In some embodiments, the 5' terminal caps may include endogenous caps or cap analogs.

In some embodiments, a 5' terminal cap may comprise a guanine analog. Useful guanine analogs include, but are not limited to, inosine, N1-methyl-guanosine, 2'fluoro-guanosine, 7-deaza-guanosine, 8-oxo-guanosine, 2-amino-guanosine, LNA-guanosine, and 2-azido-guanosine.

IRES Sequences

In some embodiments, the mRNA may contain an internal ribosome entry site (IRES). First identified as a feature Picorna virus RNA, IRES plays an important role in initiating protein synthesis in absence of the 5' cap structure. An IRES may act as the sole ribosome binding site, or may serve as one of multiple ribosome binding sites of an mRNA. An mRNA that contains more than one functional ribosome binding site may encode several peptides or polypeptides that are translated independently by the ribosomes. Non-limiting examples of IRES sequences that can be used include without limitation, those from picornaviruses (e.g. FMDV), pest viruses (CFFV), polio viruses (PV), encephalomyocarditis viruses (ECMV), foot-and-mouth disease viruses (FMDV), hepatitis C viruses (HCV), classical swine fever viruses (CSFV), murine leukemia virus (MLV), simian immune deficiency viruses (SIV) or cricket paralysis viruses (CrPV).

Poly-A Tails

During RNA processing, a long chain of adenine nucleotides (poly-A tail) may be added to a polynucleotide such as an mRNA molecules in order to increase stability. Immediately after transcription, the 3' end of the transcript may be cleaved to free a 3' hydroxyl. Then poly-A polymerase adds a chain of adenine nucleotides to the R A. The process, called polyadenylation, adds a poly-A tail of a certain length.

In some embodiments, the length of a poly-A tail is greater than 30 nucleotides in length. In another embodiment, the poly-A tail is greater than 35 nucleotides in length (e.g., at least or greater than about 35, 40, 45, 50, 55, 60, 70, 80, 90, 100, 120, 140, 160, 180, 200, 250, 300, 350, 400, 450, 500, 600, 700, 800, 900, 1,000, 1,100, 1,200, 1,300, 1,400, 1,500, 1,600, 1,700, 1,800, 1,900, 2,000, 2,500, and 3,000 nucleotides). In some embodiments, the mRNA includes a poly-A tail from about 30 to about 3,000 nucleotides (e.g., from 30 to 50, from 30 to 100, from 30 to 250, from 30 to 500, from 30 to 750, from 30 to 1,000, from 30 to 1,500, from 30 to 2,000, from 30 to 2,500, from 50 to 100, from 50 to 250, from 50 to 500, from 50 to 750, from 50 to 1,000, from 50 to 1,500, from 50 to 2,000, from 50 to 2,500, from 50 to 3,000, from 100 to 500, from 100 to 750, from 100 to 1,000, from 100 to 1,500, from 100 to 2,000, from 100 to 2,500, from 100 to 3,000, from 500 to 750, from 500 to 1,000, from 500 to 1,500, from 500 to 2,000, from 500 to 2,500, from 500 to 3,000, from 1,000 to 1,500, from 1,000 to 2,000, from 1,000 to 2,500, from 1,000 to 3,000, from 1,500 to 2,000, from 1,500 to 2,500, from 1,500 to 3,000, from 2,000 to 3,000, from 2,000 to 2,500, and from 2,500 to 3,000).

In some embodiments, the poly-A tail is designed relative to the length of the overall mRNA. This design may be based on the length of the region coding for a target of interest, the length of a particular feature or region (such as a flanking region), or based on the length of the ultimate product expressed from the mRNA.

In this context the poly-A tail may be 10, 20, 30, 40, 50, 60, 70, 80, 90, or 100% greater in length than the mRNA or feature thereof. The poly-A tail may also be designed as a fraction of mRNA to which it belongs. In this context, the poly-A tail may be 10, 20, 30, 40, 50, 60, 70, 80, or 90% or more of the total length of the construct or the total length of the construct minus the poly-A tail. Further, engineered binding sites and conjugation of mRNA for poly-A binding protein may enhance expression.

Additionally, multiple distinct mRNA may be linked together to the PABP (Poly-A binding protein) through the 3'-end using modified nucleotides at the 3'-terminus of the poly-A tail. Transfection experiments can be conducted in relevant cell lines at and protein production can be assayed by ELISA at 12 hr, 24 hr, 48 hr, 72 hr and day 7 post-transfection.

In some embodiments, the mRNA are designed to include a polyA-G Quartet. The G-quartet is a cyclic hydrogen bonded array of four guanine nucleotides that can be formed by G-rich sequences in both DNA and RNA. In this embodiment, the G-quartet is incorporated at the end of the poly-A tail.

Stop Codons

In some embodiments, the mRNA may include one stop codon. In some embodiments, the mRNA may include two stop codons. In some embodiments, the mRNA may include three stop codons. In some embodiments, the mRNA may include at least one stop codon. In some embodiments, the mRNA may include at least two stop codons. In some embodiments, the mRNA may include at least three stop codons. As non-limiting examples, the stop codon may be selected from TGA, TAA and TAG.

In some embodiments, the mRNA includes the stop codon TGA and one additional stop codon. In a further embodiment the addition stop codon may be TAA.

Circular RNA (oRNA)

In some embodiments, the originator construct and/or the benchmark construct is a circular RNA (oRNA). As used herein, the terms "oRNA" or "circular RNA" are used interchangeably and can refer to a RNA that forms a circular structure through covalent or non-covalent bonds.

In some embodiments, the oRNA may be non-immunogenic in a mammal (e.g., a human, non-human primate, rabbit, rat, and mouse).

In some embodiments, the oRNA may be capable of replicating or replicates in a cell from an aquaculture animal (e.g., fish, crabs, shrimp, oysters etc.), a mammalian cell, a cell from a pet or zoo animal (e.g., cats, dogs, lizards, birds, lions, tigers and bears etc.), a cell from a farm or working animal (e.g., horses, cows, pigs, chickens etc.), a human cell, cultured cells, primary cells or cell lines, stem cells, progenitor cells, differentiated cells, germ cells, cancer cells (e.g., tumorigenic, metastatic), non-tumorigenic cells (e.g., normal cells), fetal cells, embryonic cells, adult cells, mitotic cells, non-mitotic cells, or any combination thereof.

In some embodiments, the oRNA has a half-life of at least that of a linear counterpart. In some embodiments, the oRNA has a half-life that is increased over that of a linear counterpart. In some embodiments, the half-life is increased by about 5%, 10%, 15%, 20%, 25%, 30%, 35%, 40%, 45%, 50%, or greater. In some embodiments, the oRNA has a half-life or persistence in a cell for at least about 1 hour to about 30 days, or at least about 2 hours, 6 hours, 12 hours, 18 hours, 24 hours (1 day), 2 days, 3, days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 60 days, or longer or any time therebetween. In some embodiments, the oRNA has a half-life or persistence in a cell for no more than about 10 mins to about 7 days, or no more than about 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 24 hours (1 day), 36 hours (1.5 days), 48 hours (2 days), 60 hours (2.5 days), 72 hours (3 days), 4 days, 5 days, 6 days, or 7 days.

In some embodiments, the oRNA has a half-life or persistence in a cell while the cell is dividing. In some embodiments, the oRNA has a half-life or persistence in a cell post division. In certain embodiments, the oRNA has a half-life or persistence in a dividing cell for greater than about 10 minutes to about 30 days, or at least about 10 minutes, 15 minutes, 30 minutes, 45 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 24 hours (1 day), 2 days, 3, days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 60 days, or longer or any time therebetween.

In some embodiments, the oRNA modulates a cellular function, e.g., transiently or long term. In certain embodiments, the cellular function is stably altered, such as a modulation that persists for at least about 1 hour to about 30 days, or at least about 2 hours, 6 hours, 12 hours, 18 hours, 24 hours (1 day), 2 days, 3, days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 60 days, or longer. In certain embodiments, the cellular function is transiently altered, e.g., such as a modulation that persists for no more than about 30 mins to about 7 days, or no more than about 30 minutes, 45 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours (1 day), 36 hours (1.5 days), 48 hours (2 days), 60 hours (2.5 days), 72 hours (3 days), 4 days, 5 days, 6 days, or 7 days.

In some embodiments, the oRNA is at least about 20 nucleotides, at least about 30 nucleotides, at least about 40 nucleotides, at least about 50 nucleotides, at least about 75 nucleotides, at least about 100 nucleotides, at least about 200 nucleotides, at least about 300 nucleotides, at least about 400 nucleotides, at least about 500 nucleotides, at least about 1,000 nucleotides, at least about 2,000 nucleotides, at least about 5,000 nucleotides, at least about 6,000 nucleotides, at least about 7,000 nucleotides, at least about 8,000 nucleotides, at least about 9,000 nucleotides, at least about 10,000 nucleotides, at least about 12,000 nucleotides, at least about 14,000 nucleotides, at least about 15,000 nucleotides, at least about 16,000 nucleotides, at least about 17,000 nucleotides, at least about 18,000 nucleotides, at least about 19,000 nucleotides, or at least about 20,000 nucleotides. In some embodiments, the oRNA may be of a sufficient size to accommodate a binding site for a ribosome.

In some embodiments, the maximum size of the oRNA may be limited by the ability of packaging and delivering the RNA to a target. In some embodiments, the size of the oRNA is a length sufficient to encode polypeptides, and thus, lengths of at least 20,000 nucleotides, at least 15,000 nucleotides, at least 10,000 nucleotides, at least 7,500 nucleotides, or at least 5,000 nucleotides, at least 4,000 nucleotides, at least 3,000 nucleotides, at least 2,000 nucleotides, at least 1,000 nucleotides, at least 500 nucleotides, at least 400 nucleotides, at least 300 nucleotides, at least 200 nucleotides, at least 100 nucleotides may be useful.

In some embodiments, the oRNA comprises one or more elements described elsewhere herein. In some embodiments, the elements may be separated from one another by a spacer sequence or linker. In some embodiments, the elements may be separated from one another by 1 nucleotide, 2 nucleotides, about 5 nucleotides, about 10 nucleotides, about 15 nucleotides, about 20 nucleotides, about 30 nucleotides, about 40 nucleotides, about 50 nucleotides, about 60 nucleotides, about 80 nucleotides, about 100 nucleotides, about 150 nucleotides, about 200 nucleotides, about 250 nucleotides, about 300 nucleotides, about 400 nucleotides, about 500 nucleotides, about 600 nucleotides, about 700 nucleotides, about 800 nucleotides, about 900 nucleotides, about 1000 nucleotides, up to about 1 kb, at least about 1000 nucleotides.

In some embodiments, one or more elements are contiguous with one another, e.g., lacking a spacer element.

In some embodiments, one or more elements is conformationally flexible. In some embodiments, the conformational flexibility is due to the sequence being substantially free of a secondary structure.

In some embodiments, the oRNA comprises a secondary or tertiary structure that accommodates a binding site for a ribosome, translation, or rolling circle translation.

In some embodiments, the oRNA comprises particular sequence characteristics. For example, the oRNA may comprise a particular nucleotide composition. In some such embodiments, the oRNA may include one or more purine rich regions (adenine or guanosine). In some such embodiments, the oRNA may include one or more purine rich regions (adenine or guanosine). In some embodiments, the oRNA may include one or more AU rich regions or elements (AREs). In some embodiments, the oRNA may include one or more adenine rich regions.

In some embodiments, the oRNA comprises one or more modifications described elsewhere herein.

In some embodiments, the oRNA comprises one or more expression sequences and is configured for persistent expression in a cell of a subject in vivo. In some embodiments, the oRNA is configured such that expression of the one or more expression sequences in the cell at a later time point is equal to or higher than an earlier time point. In such embodiments, the expression of the one or more expression sequences can be either maintained at a relatively stable level or can increase over time. The expression of the expression sequences can be relatively stable for an extended period of time. For instance, in some cases, the expression of the one or more expression sequences in the cell over a time period of at least 7, 8, 9, 10, 12, 14, 16, 18, 20, 22, 23 or more days does not decrease by 50%, 45%, 40%, 35%, 30%, 25%, 20%, 15%, 10%, or 5%. In some cases, in some cases, the expression of the one or more expression sequences in the cell is maintained at a level that does not vary by more than 50%, 45%, 40%, 35%, 30%, 25%, 20%, 15%, 10%, or 5% for at least 7, 8, 9, 10, 12, 14, 16, 18, 20, 22, 23 or more days.

Regulatory Elements

In some embodiments, the oRNA comprises a regulatory element. As used herein, a "regulatory element" is a sequence that modifies expression of an expression sequence. The regulatory element may include a sequence that is located adjacent to a payload or cargo region. The regulatory element may be operatively linked operatively to a payload or cargo region.

In some embodiments, a regulatory element may increase an amount of payload or cargo expressed as compared to an amount expressed when no regulatory element exists. As a non-limiting example, one regulatory element can increase an amount of payloads or cargos expressed for multiple payload or cargo sequences attached in tandem.

In some embodiments, a regulatory element may comprise a sequence to selectively initiates or activates translation of a payload or cargo.

In some embodiments, a regulatory element may comprise a sequence to initiate degradation of the oRNA or the payload or cargo. Non-limiting examples of the sequence to initiate degradation includes, but is not limited to, riboswitch aptazymes and miRNA binding sites.

In some embodiments, a regulatory element can modulate translation of the payload or cargo in the oRNA. The modulation can create an increase (enhancer) or decrease (suppressor) in the payload or cargo. The regulatory element may be located adjacent to the payload or cargo (e.g., on one side or both sides of the payload or cargo).

In some embodiments, a translation initiation sequence functions as a regulatory element. In some embodiments, the translation initiation sequence comprises an AUG/ATG codon. In some embodiments, a translation initiation sequence comprises any eukaryotic start codon such as, but not limited to, AUG/ATG, CUG/CTG, GUG/GTG, UUG/TTG, ACG, AUC/ATC, AUU, AAG, AUA/ATA, or AGG. In some embodiments, a translation initiation sequence comprises a Kozak sequence. In some embodiments, translation begins at an alternative translation initiation sequence, e.g., translation initiation sequence other than AUG/ATG codon, under selective conditions, e.g., stress induced conditions. As a non-limiting example, the translation of the circular polyribonucleotide may begin at alternative translation initiation sequence, such as ACG. As another non-limiting example, the circular polyribonucleotide translation may begin at alternative translation initiation sequence, CUG/CTG. As another non-limiting example, the translation may begin at alternative translation initiation sequence, GUG/GTG. As yet another non-limiting example, the translation may begin at a repeat-associated non-AUG (RAN) sequence, such as an alternative translation initiation sequence that includes short stretches of repetitive RNA e.g. CGG, GGGGCC, CAG, CTG.

Masking Agents

Masking any of the nucleotides flanking a codon that initiates translation may be used to alter the position of translation initiation, translation efficiency, length and/or structure of the oRNA. In some embodiments, a masking agent may be used near the start codon or alternative start codon in order to mask or hide the codon to reduce the probability of translation initiation at the masked start codon or alternative start codon. Non-limiting examples of masking agents include antisense locked nucleic acids (LNA) oligonucleotides and exon junction complexes (EJCs). In some embodiments, a masking agent may be used to mask a start codon of the oRNA in order to increase the likelihood that translation will initiate at an alternative start codon.

Translation Initiation Sequence

In some embodiments, the oRNA encodes a polypeptide or peptide and may comprise a translation initiation sequence. The translation initiation sequence may comprise, but is not limited to a start codon, a non-coding start codon, a Kozak sequence or a Shine-Dalgarno sequence. The translation initiation sequence may be located adjacent to the payload or cargo (e.g., on one side or both sides of the payload or cargo).

In some embodiments, the translation initiation sequence provides conformational flexibility to the oRNA. In some embodiments, the translation initiation sequence is within a substantially single stranded region of the oRNA.

The oRNA may include more than 1 start codon such as, but not limited to, at least 2, at least 3, at least 4, at least 5, at least 6, at least 7, at least 8, at least 9, at least 10, at least 11, at least 12, at least 13, at least 14, at least 15 or more than 15 start codons. Translation may initiate on the first start codon or may initiate downstream of the first start codon.

In some embodiments, the oRNA may initiate at a codon which is not the first start codon, e.g., AUG. Translation of the circular polyribonucleotide may initiate at an alternative translation initiation sequence, such as, but not limited to, ACG, AGG, AAG, CUG/CTG, GUG/GTG, AUA/ATA, AUU/ATT, UUG/TTG. In some embodiments, translation begins at an alternative translation initiation sequence under selective conditions, e.g., stress induced conditions. As a non-limiting example, the translation of the oRNA may begin at alternative translation initiation sequence, such as ACG. As another non-limiting example, the oRNA translation may begin at alternative translation initiation sequence, CUG/CTG. As yet another non-limiting example, the oRNA translation may begin at alternative translation initiation sequence, GTG/GUG. As yet another non-limiting example, the oRNA may begin translation at a repeat-associated non-AUG (RAN) sequence, such as an alternative translation initiation sequence that includes short stretches of repetitive RNA e.g. CGG, GGGGCC, CAG, CTG.

IRES Sequences

In some embodiments, the oRNA described herein comprises an internal ribosome entry site (IRES) element capable of engaging an eukaryotic ribosome. In some embodiments, the IRES element is at least about 5 nucleotides, at least about 8 nucleotides, at least about 9 nucleotides, at least about 10 nucleotides, at least about 15 nucleotides, at least about 20 nucleotides, at least about 25 nucleotides, at least about 30 nucleotides, at least about 40 nucleotides, at least about 50 nucleotides, at least about 100 nucleotides, at least about 200 nucleotides, at least about 250 nucleotides, at least about 350 nucleotides, or at least about 500 nucleotides. In one embodiment, the IRES element is derived from the DNA of an organism including, but not limited to, a virus, a mammal, and a *Drosophila*. Such viral DNA may be derived from, but is not limited to, picornavirus complementary DNA (cDNA), with encephalomyocarditis virus (EMCV) cDNA and poliovirus cDNA. In one embodiment, *Drosophila* DNA from which an IRES element is derived includes, but is not limited to, an Antennapedia gene from *Drosophila melanogaster.*

In some embodiments, the IRES element is at least partially derived from a virus, for instance, it can be derived from a viral IRES element, such as ABPV_IGRpred, AEV, ALPV_IGRpred, BQCV_IGRpred, BVDV1_1-385, BVDV1_29-391, CrPV_5NCR, CrPV_IGR, crTMV_IREScp, crTMV_IRESmp75, crTMV_IRESmp228, crTMV_IREScp, crTMV_IREScp, CSFV, CVB3, DCV_IGR, EMCV-R, EoPV_5NTR, ERAV 245-961, ERBV 162-920, EV71_1-748, FeLV-Notch2, FMDV_type_C, GBV-A, GBV-B, GBV-C, gypsy_env, gypsyD5, gypsyD2, HAV_HM175, HCV_type_1a, HiPV_IGRpred, HIV-1, HoCV1_IGRpred, HRV-2, IAPV_IGRpred, idefix, KBV_IGRpred, LINE-1_ORF1_-101_to_-1, LINE-1_ORF1-302_to_-202, LINE-1_ORF2-138_to_-86, LINE-1_ORF1_-44to_-1, PSIV_IGR, PV_type1_Mahoney, PV_type3_Leon, REV-A, RhPV_5NCR, RhPV_IGR, SINV1_IGRpred, SV40_661-830, TMEV, TMV_UI_IRESmp228, TRV_5NTR, TrV_IGR, or TSV_IGR. In some embodiments, the IRES element is at least partially derived from a cellular IRES, such as AML1/RUNX1, Antp-D, Antp-DE, Antp-CDE, Apaf-1, Apaf-1, AQP4, AT1R_var1, AT1R_var2, AT1R_var3, AT1R_var4, BAG1_p36delta236 nt, BAG1_p36, BCL2, BiP_-222-3, c-IAP1_285-1399, c-IAP1_1313-1462, c-jun, c-myc, Cat-1224, CCND1, DAPS, eIF4G, eIF4GI-ext, eIF4GII, eIF4GII-long, ELG1, ELH, FGF1A, FMR1, Gtx-133-141, Gtx-1-166, Gtx-1-120, Gtx-1-196, hairless, HAP4, HIF1a, hSNM1, Hsp101, hsp70, hsp70, Hsp90, IGF2_leader2, Kv1.4_1.2, L-myc, LamB1_-335_-1, LEF1, MNT_75-267, MNT_36-160, MTG8a, MYB, MYT2_997-1152, n-MYC, NDST1, NDST2, NDST3, NDST4L, NDST4S, NRF_-653_-17, NtHSF1, ODC1, p27kip1, 03_128-269, PDGF2/c-sis, Pim-1, PITSLRE_p58, Rbm3, reaper, Scamper, TFIID, TIF4631, Ubx_1-966, Ubx_373-961, UNR, Ure2, UtrA, VEGF-A-133-1, XIAP_5-464, XIAP_305-466, or YAP1.

Termination Element

In some embodiments, the oRNA includes one or more cargo or payload sequences (also referred to as expression sequences) and each cargo or payload sequence may or may not have a termination element.

In some embodiments, the oRNA includes one or more cargo or payload sequences and the sequences lack a termination element, such that the oRNA is continuously translated. Exclusion of a termination element may result in rolling circle translation or continuous expression of the encoded peptides or polypeptides as the ribosome will not stalling or fall-off. In such an embodiment, rolling circle translation expresses a continuous expression through each cargo or payload sequence.

In some embodiments, one or more cargo or payload sequences in the oRNA comprise a termination element.

In some embodiments, not all of the cargo or payload sequences in the oRNA comprise a termination element. In such instances, the cargo or payload may fall off the ribosome when the ribosome encounters the termination element and terminates translation. In some embodiments, translation is terminated while at least one region of the ribosome remains in contact with the oRNA.

Rolling Circle Translation

In some embodiments, once translation of the oRNA is initiated, the ribosome bound to the oRNA does not disengage from the oRNA before finishing at least one round of translation of the oRNA. In some embodiments, the oRNA as described herein is competent for rolling circle translation. In some embodiments, during rolling circle translation, once translation of the oRNA is initiated, the ribosome bound to the oRNA does not disengage from the oRNA before finishing at least 2 rounds, at least 3 rounds, at least 4 rounds, at least 5 rounds, at least 6 rounds, at least 7 rounds, at least 8 rounds, at least 9 rounds, at least 10 rounds, at least 11 rounds, at least 12 rounds, at least 13 rounds, at least 14 rounds, at least 15 rounds, at least 20 rounds, at least 30 rounds, at least 40 rounds, at least 50 rounds, at least 60 rounds, at least 70 rounds, at least 80 rounds, at least 90 rounds, at least 100 rounds, at least 150 rounds, at least 200 rounds, at least 250 rounds, at least 500 rounds, at least 1000 rounds, at least 1500 rounds, at least 2000 rounds, at least 5000 rounds, at least 10000 rounds, at least 10.sup.5 rounds, or at least 10.sup.6 rounds of translation of the oRNA.

In some embodiments, the rolling circle translation of the oRNA leads to generation of polypeptide that is translated from more than one round of translation of the oRNA. In some embodiments, the oRNA comprises a stagger element, and rolling circle translation of the oRNA leads to generation of polypeptide product that is generated from a single round of translation or less than a single round of translation of the oRNA.

Circularization

In one embodiment, a linear RNA may be cyclized, or concatemerized. In some embodiments, the linear RNA may be cyclized in vitro prior to formulation and/or delivery. In some embodiments, the linear RNA may be cyclized within a cell.

In some embodiments, the mechanism of cyclization or concatemerization may occur through at least 3 different routes: 1) chemical, 2) enzymatic, and 3) ribozyme catalyzed. The newly formed 5'-/3'-linkage may be intramolecular or intermolecular.

In the first route, the 5'-end and the 3'-end of the nucleic acid contain chemically reactive groups that, when close together, form a new covalent linkage between the 5'-end and the 3'-end of the molecule. The 5'-end may contain an NHS-ester reactive group and the 3'-end may contain a 3'-amino-terminated nucleotide such that in an organic solvent the 3'-amino-terminated nucleotide on the 3'-end of a synthetic mRNA molecule will undergo a nucleophilic attack on the 5'-NHS-ester moiety forming a new 5'-/3'-amide bond.

In the second route, T4 RNA ligase may be used to enzymatically link a 5'-phosphorylated nucleic acid molecule to the 3'-hydroxyl group of a nucleic acid forming a new phosphorodiester linkage. In an example reaction, ^g of a nucleic acid molecule is incubated at 37° C. for 1 hour with 1-10 units of T4 RNA ligase (New England Biolabs, Ipswich, MA) according to the manufacturer's protocol. The ligation reaction may occur in the presence of a split oligonucleotide capable of base-pairing with both the 5'- and 3'-region in juxtaposition to assist the enzymatic ligation reaction.

In the third route, either the 5'- or 3'-end of the cDNA template encodes a ligase ribozyme sequence such that during in vitro transcription, the resultant nucleic acid molecule can contain an active ribozyme sequence capable of ligating the 5'-end of a nucleic acid molecule to the 3'-end of a nucleic acid molecule. The ligase ribozyme may be derived from the Group I Intron, Group I Intron, Hepatitis Delta Virus, Hairpin ribozyme or may be selected by SELEX (systematic evolution of ligands by exponential enrichment). The ribozyme ligase reaction may take 1 to 24 hours at temperatures between 0 and 37° C.

In some embodiments, the oRNA is made via circularization of a linear RNA.

Extracellular Circularization

In some embodiments, the linear RNA is cyclized, or concatemerized using a chemical method to form an oRNA. In some chemical methods, the 5'-end and the 3'-end of the nucleic acid (e.g., a linear RNA) includes chemically reactive groups that, when close together, may form a new covalent linkage between the 5'-end and the 3'-end of the molecule. The 5'-end may contain an NHS-ester reactive group and the 3'-end may contain a 3'-amino-terminated nucleotide such that in an organic solvent the 3'-amino-terminated nucleotide on the 3'-end of a linear RNA will undergo a nucleophilic attack on the 5'-NHS-ester moiety forming a new 5'-/3'-amide bond.

In one embodiment, a DNA or RNA ligase may be used to enzymatically link a 5'-phosphorylated nucleic acid molecule (e.g., a linear RNA) to the 3'-hydroxyl group of a nucleic acid (e.g., a linear nucleic acid) forming a new phosphorodiester linkage. In an example reaction, a linear RNA is incubated at 37 C for 1 hour with 1-10 units of T4 RNA ligase according to the manufacturer's protocol. The ligation reaction may occur in the presence of a linear nucleic acid capable of base-pairing with both the 5'- and 3'-region in juxtaposition to assist the enzymatic ligation reaction. In one embodiment, the ligation is splint ligation where a single stranded polynucleotide (splint), like a single stranded RNA, can be designed to hybridize with both termini of a linear RNA, so that the two termini can be juxtaposed upon hybridization with the single-stranded splint. Splint ligase can thus catalyze the ligation of the juxtaposed two termini of the linear RNA, generating an oRNA.

In one embodiment, a DNA or RNA ligase may be used in the synthesis of the oRNA. As a non-limiting example, the ligase may be a circ ligase or circular ligase.

In one embodiment, either the 5'- or 3'-end of the linear RNA can encode a ligase ribozyme sequence such that during in vitro transcription, the resultant linear RNA includes an active ribozyme sequence capable of ligating the 5'-end of the linear RNA to the 3'-end of the linear RNA. The ligase ribozyme may be derived from the Group I Intron, Hepatitis Delta Virus, Hairpin ribozyme or may be selected by SELEX (systematic evolution of ligands by exponential enrichment).

In one embodiment, a linear RNA may be cyclized or concatemerized by using at least one non-nucleic acid moiety. In one aspect, the at least one non-nucleic acid moiety may react with regions or features near the 5' terminus and/or near the 3' terminus of the linear RNA in order to cyclize or concatermerize the linear RNA. In another aspect, the at least one non-nucleic acid moiety may be located in or linked to or near the 5' terminus and/or the 3' terminus of the linear RNA. The non-nucleic acid moieties contemplated may be homologous or heterologous. As a non-limiting example, the non-nucleic acid moiety may be a linkage such as a hydrophobic linkage, ionic linkage, a biodegradable linkage and/or a cleavable linkage. As another non-limiting example, the non-nucleic acid moiety is a ligation moiety. As yet another non-limiting example, the non-nucleic acid moiety may be an oligonucleotide or a peptide moiety, such as an aptamer or a non-nucleic acid linker as described herein.

In one embodiment, a linear RNA may be cyclized or concatemerized due to a non-nucleic acid moiety that causes an attraction between atoms, molecular surfaces at, near or linked to the 5' and 3' ends of the linear RNA. As a non-limiting example, one or more linear RNA may be cyclized or concatemerized by intermolecular forces or intramolecular forces. Non-limiting examples of intermolecular forces include dipole-dipole forces, dipole-induced dipole forces, induced dipole-induced dipole forces, Van der Waals forces, and London dispersion forces. Non-limiting examples of intramolecular forces include covalent bonds, metallic bonds, ionic bonds, resonant bonds, agnostic bonds, dipolar bonds, conjugation, hyperconjugation and antibonding.

In one embodiment, the linear RNA may comprise a ribozyme RNA sequence near the 5' terminus and near the 3' terminus. The ribozyme RNA sequence may covalently link to a peptide when the sequence is exposed to the remainder of the ribozyme. In one aspect, the peptides covalently linked to the ribozyme RNA sequence near the 5' terminus and the 3' terminus may associate with each other causing a linear RNA to cyclize or concatemerize. In another aspect, the peptides covalently linked to the ribozyme RNA near the 5' terminus and the 3' terminus may cause the linear RNA to cyclize or concatemerize after being subjected to ligated using various methods known in the art such as, but not limited to, protein ligation.

In some embodiments, the linear RNA may include a 5' triphosphate of the nucleic acid converted into a 5' monophosphate, e.g., by contacting the 5' triphosphate with RNA 5' pyrophosphohydrolase (RppH) or an ATP diphosphohydrolase (apyrase). Alternately, converting the 5' triphosphate of the linear RNA into a 5' monophosphate may occur by a two-step reaction comprising: (a) contacting the 5' nucleotide of the linear RNA with a phosphatase (e.g., Antarctic Phosphatase, Shrimp Alkaline Phosphatase, or Calf Intestinal Phosphatase) to remove all three phosphates; and (b) contacting the 5' nucleotide after step (a) with a kinase (e.g., Polynucleotide Kinase) that adds a single phosphate.

In some embodiments, RNA may be circularized using the methods described in WO2017222911 and WO2016197121, the contents of each of which are herein incorporated by reference in their entirety.

In some embodiments, RNA may be circularized, for example, by backsplicing of a non-mammalian exogenous intron or splint ligation of the 5' and 3' ends of a linear RNA. In one embodiment, the circular RNA is produced from a recombinant nucleic acid encoding the target RNA to be made circular. As a non-limiting example, the method comprises: a) producing a recombinant nucleic acid encoding the target RNA to be made circular, wherein the recombinant nucleic acid comprises in 5' to 3' order: i) a 3' portion of an exogenous intron comprising a 3' splice site, ii) a nucleic acid sequence encoding the target RNA, and iii) a 5' portion of an exogenous intron comprising a 5' splice site; b) performing transcription, whereby RNA is produced from the recombinant nucleic acid; and c) performing splicing of the RNA, whereby the RNA circularizes to produce a oRNA.

While not wishing to be bound by theory, circular RNAs generated with exogenous introns are recognized by the immune system as “non-self” and trigger an innate immune response. On the other hand, circular RNAs generated with endogenous introns are recognized by the immune system as “self” and generally do not provoke an innate immune response, even if carrying an exon comprising foreign RNA. Accordingly, circular RNAs can be generated with either an endogenous or exogenous intron to control immunological self/nonself discrimination as desired. Numerous intron sequences from a wide variety of organisms and viruses are known and include sequences derived from genes encoding proteins, ribosomal RNA (rRNA), or transfer RNA (tRNA).

Circular RNAs can be produced from linear RNAs in a number of ways. In some embodiments, circular RNAs are produced from a linear RNA by backsplicing of a downstream 5' splice site (splice donor) to an upstream 3' splice site (splice acceptor). Circular RNAs can be generated in this manner by any nonmammalian splicing method. For example, linear RNAs containing various types of introns, including self-splicing group I introns, self-splicing group II introns, spliceosomal introns, and tRNA introns can be circularized. In particular, group I and group II introns have the advantage that they can be readily used for production of circular RNAs in vitro as well as in vivo because of their ability to undergo self-splicing due to their autocatalytic ribozyme activity.

In some embodiments, circular RNAs can be produced in vitro from a linear RNA by chemical or enzymatic ligation of the 5' and 3' ends of the RNA. Chemical ligation can be performed, for example, using cyanogen bromide (BrCN) or ethyl-3-(3'-dimethylaminopropyl) carbodiimide (EDC) for activation of a nucleotide phosphomonoester group to allow phosphodiester bond formation. See e.g., Sokolova (1988) FEBS Lett 232: 153-155; Dolinnaya et al. (1991) Nucleic Acids Res., 19:3067-3072; Fedorova (1996) Nucleosides Nucleotides Nucleic Acids 15: 1 137-1 147; herein incorporated by reference. Alternatively, enzymatic ligation can be used to circularize RNA. Exemplary ligases that can be used include T4 DNA ligase (T4 Dnl), T4 RNA ligase 1 (T4 Rnl 1), and T4 RNA ligase 2 (T4 Rnl 2).

In some embodiments, splint ligation using an oligonucleotide splint that hybridizes with the two ends of a linear RNA can be used to bring the ends of the linear RNA together for ligation. Hybridization of the splint, which can be either a DNA or a RNA, orientates the 5'-phosphate and 3'-OH of the RNA ends for ligation. Subsequent ligation can be performed using either chemical or enzymatic techniques, as described above. Enzymatic ligation can be performed, for example, with T4 DNA ligase (DNA splint required), T4 RNA ligase 1 (RNA splint required) or T4 RNA ligase 2 (DNA or RNA splint). Chemical ligation, such as with BrCN or EDC, in some cases is more efficient than enzymatic ligation if the structure of the hybridized splint-RNA complex interferes with enzymatic activity.

In some embodiments, the oRNA may further comprise an internal ribosome entry site (IRES) operably linked to an RNA sequence encoding a polypeptide. Inclusion of an IRES permits the translation of one or more open reading frames from a circular RNA. The IRES element attracts a eukaryotic ribosomal translation initiation complex and promotes translation initiation. See, e.g., Kaufman et al., Nuc. Acids Res. (1991) 19:4485-4490; Gurtu et al., Biochem. Biophys. Res. Comm. (1996) 229:295-298; Rees et al., BioTechniques (1996) 20: 102-110; Kobayashi et al., BioTechniques (1996) 21:399-402; and Mosser et al., BioTechniques 1997 22 150-161).

In some embodiments, the circularization efficiency of the circularization methods provided herein is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 95%, or 100%. In some embodiments, the circularization efficiency of the circularization methods provided herein is at least about 40%.

Splicing Element

In some embodiments, the oRNA includes at least one splicing element. The splicing element can be a complete splicing element that can mediate splicing of the oRNA or the spicing element can be a residual splicing element from a completed splicing event. For instance, in some cases, a splicing element of a linear RNA can mediate a splicing event that results in circularization of the linear RNA, thereby the resultant oRNA comprises a residual splicing element from such splicing-mediated circularization event. In some cases, the residual splicing element is not able to mediate any splicing. In other cases, the residual splicing element can still mediate splicing under certain circumstances. In some embodiments, the splicing element is adjacent to at least one expression sequence. In some embodiments, the oRNA includes a splicing element adjacent each expression sequence. In some embodiments, the splicing element is on one or both sides of each expression sequence, leading to separation of the expression products, e.g., peptide(s) and or polypeptide(s).

In some embodiments, the oRNA includes an internal splicing element that when replicated the spliced ends are joined together. Some examples may include miniature introns (<100 nt) with splice site sequences and short inverted repeats (30-40 nt) such as AluSq2, AluJr, and AluSz, inverted sequences in flanking introns, Alu elements in flanking introns, and motifs found in (suptable4 enriched motifs) cis-sequence elements proximal to backsplice events such as sequences in the 200 bp preceding (upstream of) or following (downstream from) a backsplice site with flanking exons. In some embodiments, the oRNA includes at least one repetitive nucleotide sequence described elsewhere herein as an internal splicing element. In such embodiments, the repetitive nucleotide sequence may include repeated sequences from the Alu family of introns. See, e.g., U.S. Pat. No. 11,058,706.

In some embodiments, the oRNA may include canonical splice sites that flank head-to-tail junctions of the oRNA.

In some embodiments, the oRNA may include a bulge-helix-bulge motif, comprising a 4-base pair stem flanked by two 3-nucleotide bulges. Cleavage occurs at a site in the bulge region, generating characteristic fragments with terminal 5'-hydroxyl group and 2',3'-cyclic phosphate. Circularization proceeds by nucleophilic attack of the 5'-OH group onto the 2',3'-cyclic phosphate of the same molecule forming a 3',5'-phosphodiester bridge.

In some embodiments, the oRNA may include a sequence that mediates self-ligation. Non-limiting examples of sequences that can mediate self-ligation include a self-circularizing intron, e.g., a 5' and 3' slice junction, or a self-circularizing catalytic intron such as a Group I, Group II or Group III Introns. Non-limiting examples of group I intron self-splicing sequences may include self-splicing permuted intron-exon sequences derived from T4 bacteriophage gene td, and the intervening sequence (IVS) rRNA of Tetrahymena.

Other Circularization Methods

In some embodiments, linear RNA may include complementary sequences, including either repetitive or nonrepetitive nucleic acid sequences within individual introns or across flanking introns. In some embodiments, the oRNA includes a repetitive nucleic acid sequence. In some embodiments, the repetitive nucleotide sequence includes poly CA or poly UG sequences. In some embodiments, the oRNA includes at least one repetitive nucleic acid sequence that hybridizes to a complementary repetitive nucleic acid sequence in another segment of the oRNA, with the hybridized segment forming an internal double strand. In some embodiments, repetitive nucleic acid sequences and complementary repetitive nucleic acid sequences from two separate oRNA that hybridize to generate a single oRNA, with the hybridized segments forming internal double strands. In some embodiments, the complementary sequences are found at the 5' and 3' ends of the linear RNA. In some embodiments, the complementary sequences include about 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, or more paired nucleotides.

In some embodiments, chemical methods of circularization may be used to generate the oRNA. Such methods may include, but are not limited to click chemistry (e.g., alkyne and azide based methods, or clickable bases), olefin metathesis, phosphoramidate ligation, hemiaminal-imine crosslinking, base modification, and any combination thereof.

In some embodiments, enzymatic methods of circularization may be used to generate the oRNA. In some embodiments, a ligation enzyme, e.g., DNA or RNA ligase, may be used to generate a template of the oRNA or complement, a complementary strand of the oRNA, or the oRNA.

Small Interfering RNAs (siRNAs)

In some embodiments, the payload region may be or encode an RNA interference (RNAi) sequence which can be used to reduce or inhibit the expression of a gene. RNAi (also known as post-transcriptional gene silencing (PTGS), quelling, or co-suppression) is a post-transcriptional gene silencing process in which RNA molecules, in a sequence specific manner, reduce or inhibit gene expression, typically by causing the destruction of specific mRNA molecules. The active components of RNAi are short/small double stranded RNAs (dsRNAs), called small interfering RNAs (siRNAs), that typically contain 15-30 nucleotides (e.g., 19 to 25, 19 to 24 or 19-21 nucleotides) and 2 nucleotide 3' overhangs and that match the nucleic acid sequence of the target gene. These short RNA species may be naturally produced in vivo by Dicer-mediated cleavage of larger dsRNAs and they are functional in mammalian cells.

Naturally expressed small RNA molecules, named microRNAs (miRNAs), elicit gene silencing by regulating the expression of mRNAs. The miRNAs-containing RNA Induced Silencing Complex (RISC) targets mRNAs presenting a perfect sequence complementarity with nucleotides 2-7 in the 5'region of the miRNA which is called the seed region, and other base pairs with its 3'region. miRNA-mediated down-regulation of gene expression may be caused by cleavage of the target mRNAs, translational inhibition of the target mRNAs, or mRNA decay. miRNA targeting sequences are usually located in the 3'-UTR of the target mRNAs. A single miRNA may target more than 100 transcripts from various genes, and one mRNA may be targeted by different miRNAs.

siRNA duplexes or dsRNA targeting a specific mRNA may be designed and synthesized in vitro and introduced into cells for activating RNAi processes. It has been previously shown that 21-nucleotide siRNA duplexes (termed small interfering RNAs) were capable of effecting potent and specific gene knockdown without inducing immune response in mammalian cells. Now post-transcriptional gene silencing by siRNAs has quickly emerged as a powerful tool for genetic analysis in mammalian cells and has the potential to produce novel therapeutics.

In vitro synthetized siRNA sequences may be introduced into cells in order to activate RNAi. An exogenous siRNA duplex, when it is introduced into cells, similar to the endogenous dsRNAs, can be assembled to form the RNA Induced Silencing Complex (RISC), a multiunit complex that interacts with RNA sequences that are complementary to one of the two strands of the siRNA duplex (i.e., the antisense strand). During the process, the sense strand (or passenger strand) of the siRNA is lost from the complex, while the antisense strand (or guide strand) of the siRNA is matched with its complementary RNA. In particular, the targets of siRNA containing RISC complexes are mRNAs presenting a perfect sequence complementarity. Then, siRNA mediated gene silencing occurs by cleaving, releasing and degrading the target.

The siRNA duplex comprised of a sense strand homologous to the target mRNA and an antisense strand that is complementary to the target mRNA offers much more advantage in terms of efficiency for target RNA destruction compared to the use of the single strand (ss)-siRNAs (e.g. antisense strand RNA or antisense oligonucleotides). In many cases, it requires higher concentration of the ss-siRNA to achieve the effective gene silencing potency of the corresponding duplex.

Design and Sequences of siRNA Duplexes

Some guidelines for designing siRNAs have been proposed in the art. These guidelines generally recommend generating a 19-nucleotide duplexed region, symmetric 2-3 nucleotide 3'overhangs, 5'-phosphate and 3'-hydroxyl groups targeting a region in the gene to be silenced. Other rules that may govern siRNA sequence preference include, but are not limited to, (i) A/U at the 5' end of the antisense strand; (ii) G/C at the 5' end of the sense strand; (iii) at least five A/U residues in the 5' terminal one-third of the antisense strand; and (iv) the absence of any GC stretch of more than 9 nucleotides in length. In accordance with such consideration, together with the specific sequence of a target gene, highly effective siRNA constructs essential for suppressing mammalian target gene expression may be readily designed.

In some embodiments, siRNA constructs (e.g., siRNA duplexes or encoded dsRNA) that target a specific gene are designed. Such siRNA constructs can specifically, suppress gene expression and protein production. In some aspects, the siRNA constructs are designed and used to selectively "knock out" gene variants in cells, i.e., mutated transcripts that are identified in patients or that are the cause of various diseases and/or disorders. In some aspects, the siRNA constructs are designed and used to selectively "knock down" variants of the gene in cells. In other aspects, the siRNA constructs are able to inhibit or suppress both the wild type and mutated versions of the gene.

In some embodiments, an siRNA sequence comprises a sense strand and a complementary antisense strand in which both strands are hybridized together to form a duplex structure. The antisense strand has sufficient complementarity to the mRNA sequence to direct target-specific RNAi, i.e., the siRNA sequence has a sequence sufficient to trigger the destruction of the target mRNA by the RNAi machinery or process.

In some embodiments, an siRNA sequence comprises a sense strand and a complementary antisense strand in which both strands are hybridized together to form a duplex structure and where the start site of the hybridization to the mRNA is between nucleotide 100 and 10,000 on the mRNA sequence. As a non-limiting example, the start site may be between nucleotide 100-150, 150-200, 200-250, 250-300, 300-350, 350-400, 400-450, 450-500, 500-550, 550-600, 600-650, 650-700, 700-70, 750-800, 800-850, 850-900, 900-950, 950-1000, 1000-1050, 1050-1100, 1100-1150, 1150-1200, 1200-1250, 1250-1300, 1300-1350, 1350-1400, 1400-1450, 1450-1500, 1500-1550, 1550-1600, 1600-1650, 1650-1700, 1700-1750, 1750-1800, 1800-1850, 1850-1900, 1900-1950, 1950-2000, 2000-2050, 2050-2100, 2100-2150, 2150-2200, 2200-2250, 2250-2300, 2300-2350, 2350-2400, 2400-2450, 2450-2500, 2500-2550, 2550-2600, 2600-2650, 2650-2700, 2700-2750, 2750-2800, 2800-2850, 2850-2900, 2900-2950, 2950-3000, 3000-3050, 3050-3100, 3100-3150, 3150-3200, 3200-3250, 3250-3300, 3300-3350, 3350-3400, 3400-3450, 3450-3500, 3500-3550, 3550-3600, 3600-3650, 3650-3700, 3700-3750, 3750-3800, 3800-3850, 3850-3900, 3900-3950, 3950-4000, 4000-4050, 4050-4100, 4100-4150, 4150-4200, 4200-4250, 4250-4300, 4300-4350, 4350-4400, 4400-4450, 4450-4500, 4500-4550, 4550-4600, 4600-4650, 4650-4700, 4700-4750, 4750-4800, 4800-4850, 4850-4900, 4900-4950, 4950-5000, 5000-5050, 5050-5100, 5100-5150, 5150-5200, 5200-5250, 5250-5300, 5300-5350, 5350-5400, 5400-5450, 5450-5500, 5500-5550, 5550-5600, 5600-5650, 5650-5700, 5700-5750, 5750-5800, 5800-5850, 5850-5900, 5900-5950, 5950-6000, 6000-6050, 6050-6100, 6100-6150, 6150-6200, 6200-6250, 6250-6300, 6300-6350, 6350-6400, 6400-6450, 6450-6500, 6500-6550, 6550-6600, 6600-6650, 6650-6700, 6700-6750, 6750-6800, 6800-6850, 6850-6900, 6900-6950, 6950-7000, 7000-7050, 7050-7100, 7100-7150, 7150-7200, 7200-7250, 7250-7300, 7300-7350, 7350-7400, 7400-7450, 7450-7500, 7500-7550, 7550-7600, 7600-7650, 7650-7700, 7700-7750, 7750-7800, 7800-7850, 7850-7900, 7900-7950, 7950-8000, 8000-8050, 8050-8100, 8100-8150, 8150-8200, 8200-8250, 8250-8300, 8300-8350, 8350-8400, 8400-8450, 8450-8500, 8500-8550, 8550-8600, 8600-8650, 8650-8700, 8700-8750, 8750-8800, 8800-8850, 8850-8900, 8900-8950, 8950-9000, 9000-9050, 9050-9100, 9100-9150, 9150-9200, 9200-9250, 9250-9300, 9300-9350, 9350-9400, 9400-9450, 9450-9500, 9500-9550, 9550-9600, 9600-9650, 9650-9700, 9700-9750, 9750-9800, 9800-9850, 9850-9900, 9900-9950, 9950-10000 on the mRNA sequence.

In some embodiments, the antisense strand and target mRNA sequences have 100% complementary. The antisense strand may be complementary to any part of the target mRNA sequence.

In other embodiments, the antisense strand and target mRNA sequences comprise at least one mismatch. As a non-limiting example, the antisense strand and the target mRNA sequence have at least 30%, 40%, 50%, 60%, 70%, 80%, 81%, 82%, 83%, 84%, 85%, 86%, 87%, 88%, 89%, 90%, 91%, 92%, 93%, 94%, 95%, 96%, 97%, 98% or 99% or at least 20-30%, 20-40%, 20-50%, 20-60%, 20-70%, 20-80%, 20-90%, 20-95%, 20-99%, 30-40%, 30-50%, 30-60%, 30-70%, 30-80%, 30-90%, 30-95%, 30-99%, 40-50%, 40-60%, 40-70%, 40-80%, 40-90%, 40-95%, 40-99%, 50-60%, 50-70%, 50-80%, 50-90%, 50-95%, 50-99%, 60-70%, 60-80%, 60-90%, 60-95%, 60-99%, 70-80%, 70-90%, 70-95%, 70-99%, 80-90%, 80-95%, 80-99%, 90-95%, 90-99% or 95-99% complementarity.

In some embodiments, the siRNA sequence has a length from about 10-50 or more nucleotides, i.e., each strand comprising 10-50 nucleotides (or nucleotide analogs). Preferably, the siRNA sequence has a length from about 15-30, e.g., 15, 16, 17, 18, 19, 20, 21, 22, 23, 24, 25, 26, 27, 28, 29, or 30 nucleotides in each strand, wherein one of the strands is sufficiently complementarity to a target region. In some embodiments, the siRNA sequence has a length from about 19 to 25, 19 to 24 or 19 to 21 nucleotides.

In some embodiments, the siRNA sequences can be synthetic RNA duplexes comprising about 19 nucleotides to about 25 nucleotides, and two overhanging nucleotides at the 3-end. In some aspects, the siRNA constructs may be unmodified RNA molecules. In other aspects, the siRNA constructs may contain at least one modified nucleotide, such as base, sugar or backbone modifications.

In some embodiments, the siRNA sequences can be encoded in plasmid vectors, viral vectors or other nucleic acid expression vectors for delivery to a cell. DNA expression plasmids can be used to stably express the siRNA duplexes or dsRNA in cells and achieve long-term inhibition of the target gene expression. In one aspect, the sense and antisense strands of a siRNA duplex are typically linked by a short spacer sequence leading to the expression of a stem-loop structure termed short hairpin RNA (shRNA). The hairpin is recognized and cleaved by Dicer, thus generating mature siRNA constructs.

In some embodiments, the sense and antisense strands of a siRNA duplex may be linked by a short spacer sequence, which may optionally be linked to additional flanking sequence, leading to the expression of a flanking arm-stem-loop structure termed primary microRNA (pri-miRNA). The pri-miRNA may be recognized and cleaved by Drosha and Dicer, and thus generate mature siRNA constructs.

In some embodiments, the siRNA duplexes or encoded dsRNA suppress (or degrade) target mRNA. Accordingly, the siRNA duplexes or encoded dsRNA can be used to substantially inhibit gene expression in a cell. In some aspects, the inhibition of gene expression refers to an inhibition by at least about 20%, preferably by at least about 30%, 40%, 50%, 60%, 70%, 80%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100%. Accordingly, the protein product of the targeted gene may be inhibited by at least about 20%, preferably by at least about 30%, 40%, 50%, 60%, 70%, 80%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100%.

In some embodiments, the siRNA constructs comprise a miRNA seed match for the target located in the guide strand. In another embodiment, the siRNA constructs comprise a miRNA seed match for the target located in the passenger strand. In yet another embodiment, the siRNA duplexes or encoded dsRNA targeting gene do not comprise a seed match for the target located in the guide or passenger strand.

In some embodiments, the siRNA duplexes or encoded dsRNA targeting the gene may have almost no significant full-length off targets for the guide strand. In another embodiment, the siRNA duplexes or encoded dsRNA targeting the gene may have almost no significant full-length off target effects for the passenger strand. The siRNA duplexes or encoded dsRNA targeting the gene may have less than 1%, 2%, 3%, 4%, 5%, 6%, 7%, 8%, 9%, 10%, 11%, 12%, 13%, 14%, 15%, 20%, 25%, 30%, 35%, 40%, 45%, 50%, 1-5%, 2-6%, 3-7%, 4-8%, 5-9%, 5-10%, 6-10%, 5-15%, 5-20%, 5-25% 5-30%, 10-20%, 10-30%, 10-40%, 10-50%, 15-30%, 15-40%, 15-45%, 20-40%, 20-50%, 25-50%, 30-40%, 30-50%, 35-50%, 40-50%, 45-50% full-length off target effects for the passenger strand. In yet another embodiment, the siRNA duplexes or encoded dsRNA targeting the gene may have almost no significant full-length off targets for the guide strand or the passenger strand. The siRNA duplexes or encoded dsRNA targeting the gene may have less than 1%, 2%, 3%, 4%, 5%, 6%, 7%, 8%, 9%, 10%, 11%, 12%, 13%, 14%, 15%, 20%, 25%, 30%, 35%, 40%, 45%, 50%, 1-5%, 2-6%, 3-7%, 4-8%, 5-9%, 5-10%, 6-10%, 5-15%, 5-20%, 5-25% 5-30%, 10-20%, 10-30%, 10-40%, 10-50%, 15-30%, 15-40%, 15-45%, 20-40%, 20-50%, 25-50%, 30-40%, 30-50%, 35-50%, 40-50%, 45-50% full-length off target effects for the guide or passenger strand.

In some embodiments, the siRNA duplexes or encoded dsRNA targeting the gene may have high activity in vitro. In another embodiment, the siRNA constructs may have low activity in vitro. In yet another embodiment, the siRNA duplexes or dsRNA targeting the gene may have high guide strand activity and low passenger strand activity in vitro.

In some embodiments, the siRNA constructs have a high guide strand activity and low passenger strand activity in vitro. The target knock-down (KD) by the guide strand may be at least 40%, 50%, 60%, 65%, 70%, 75%, 80%, 85%, 90%, 95%, 99%, 99.5% or 100%. The target knock-down by the guide strand may be 40-50%, 45-50%, 50-55%, 50-60%, 60-65%, 60-70%, 60-75%, 60-80%, 60-85%, 60-90%, 60-95%, 60-99%, 60-99.5%, 60-100%, 65-70%, 65-75%, 65-80%, 65-85%, 65-90%, 65-95%, 65-99%, 65-99.5%, 65-100%, 70-75%, 70-80%, 70-85%, 70-90%, 70-95%, 70-99%, 70-99.5%, 70-100%, 75-80%, 75-85%, 75-90%, 75-95%, 75-99%, 75-99.5%, 75-100%, 80-85%, 80-90%, 80-95%, 80-99%, 80-99.5%, 80-100%, 85-90%, 85-95%, 85-99%, 85-99.5%, 85-100%, 90-95%, 90-99%, 90-99.5%, 90-100%, 95-99%, 95-99.5%, 95-100%, 99-99.5%, 99-100% or 99.5-100%. As a non-limiting example, the target knock-down (KD) by the guide strand is greater than 70%. As a non-limiting example, the target knock-down (KD) by the guide strand is greater than 60%.

In some embodiments, the guide to passenger (G:P) (also referred to as the antisense to sense) strand ratio expressed is 1:10, 1:9, 1:8, 1:7, 1:6, 1:5, 1:4, 1:3, 1:2, 1;1, 2:10, 2:9, 2:8, 2:7, 2:6, 2:5, 2:4, 2:3, 2:2, 2:1, 3:10, 3:9, 3:8, 3:7, 3:6, 3:5, 3:4, 3:3, 3:2, 3:1, 4:10, 4:9, 4:8, 4:7, 4:6, 4:5, 4:4, 4:3, 4:2, 4:1, 5:10, 5:9, 5:8, 5:7, 5:6, 5:5, 5:4, 5:3, 5:2, 5:1, 6:10, 6:9, 6:8, 6:7, 6:6, 6:5, 6:4, 6:3, 6:2, 6:1, 7:10, 7:9, 7:8, 7:7, 7:6, 7:5, 7:4, 7:3, 7:2, 7:1, 8:10, 8:9, 8:8, 8:7, 8:6, 8:5, 8:4, 8:3, 8:2, 8:1, 9:10, 9:9, 9:8, 9:7, 9:6, 9:5, 9:4, 9:3, 9:2, 9:1, 10:10, 10:9, 10:8, 10:7, 10:6, 10:5, 10:4, 10:3, 10:2, 10:1, 1:99, 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, 95:5, or 99:1 in vitro or in vivo. The guide to passenger ratio refers to the ratio of the guide strands to the passenger strands after the intracellular processing of the pri-microRNA. For example, a 80:20 guide-to-passenger ratio would have 8 guide strands to every 2 passenger strands processed from the precursor. As a non-limiting example, the guide-to-passenger strand ratio is 8:2 in vitro. As a non-limiting example, the guide-to-passenger strand ratio is 8:2 in vivo. As a non-limiting example, the guide-to-passenger strand ratio is 9:1 in vitro. As a non-limiting example, the guide-to-passenger strand ratio is 9:1 in vivo.

In some embodiments, the guide to passenger (G:P) (also referred to as the antisense to sense) strand ratio expressed is greater than 1. In some embodiments, the guide to passenger (G:P) (also referred to as the antisense to sense) strand ratio expressed is greater than 2. In some embodiments, the guide to passenger (G:P) (also referred to as the antisense to sense) strand ratio expressed is greater than 5. In some embodiments, the guide to passenger (G:P) (also referred to as the antisense to sense) strand ratio expressed is greater than 10. In some embodiments, the guide to passenger (G:P) (also referred to as the antisense to sense) strand ratio expressed is greater than 20. In some embodiments, the guide to passenger (G:P) (also referred to as the antisense to sense) strand ratio expressed is greater than 50. In some embodiments, the guide to passenger (G:P) (also referred to as the antisense to sense) strand ratio expressed is at least 3:1. In some embodiments, the guide to passenger (G:P) (also referred to as the antisense to sense) strand ratio expressed is at least 5:1. In some embodiments, the guide to passenger (G:P) (also referred to as the antisense to sense) strand ratio expressed is at least 10:1. In some embodiments, the guide to passenger (G:P) (also referred to as the antisense to sense) strand ratio expressed is at least 20:1. In some embodiments, the guide to passenger (G:P) (also referred to as the antisense to sense) strand ratio expressed is at least 50:1.

In some embodiments, the passenger to guide (P:G) (also referred to as the sense to antisense) strand ratio expressed is 1:10, 1:9, 1:8, 1:7, 1:6, 1:5, 1:4, 1:3, 1:2, 1;1, 2:10, 2:9, 2:8, 2:7, 2:6, 2:5, 2:4,2:3,2:2, 2:1, 3:10, 3:9, 3:8, 3:7, 3:6, 3:5, 3:4, 3:3, 3:2, 3:1, 4:10, 4:9, 4:8, 4:7, 4:6, 4:5, 4:4, 4:3,4:2, 4:1, 5:10, 5:9, 5:8, 5:7, 5:6, 5:5, 5:4, 5:3, 5:2, 5:1, 6:10, 6:9, 6:8, 6:7, 6:6, 6:5, 6:4, 6:3, 6:2, 6:1, 7:10, 7:9, 7:8, 7:7, 7:6, 7:5, 7:4, 7:3, 7:2, 7:1, 8:10, 8:9, 8:8, 8:7, 8:6, 8:5, 8:4, 8:3, 8:2, 8:1, 9:10, 9:9, 9:8, 9:7, 9:6, 9:5, 9:4, 9:3, 9:2, 9:1, 10:10, 10:9, 10:8, 10:7, 10:6, 10:5, 10:4, 10:3, 10:2, 10:1, 1:99, 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, 95:5, or 99:1 in vitro or in vivo. The passenger to guide ratio refers to the ratio of the passenger strands to the guide strands after the excision of the guide strand. For example, a 80:20 passenger to guide ratio would have 8 passenger strands to every 2 guide strands processed from the precursor. As a non-limiting example, the passenger-to-guide strand ratio is 80:20 in vitro. As a non-limiting example, the passenger-to-guide strand ratio is 80:20 in vivo. As a non-limiting example, the passenger-to-guide strand ratio is 8:2 in vitro. As a non-limiting example, the passenger-to-guide strand ratio is 8:2 in vivo. As a non-limiting example, the passenger-to-guide strand ratio is 9:1 in vitro. As a non-limiting example, the passenger-to-guide strand ratio is 9:1 in vivo.

In some embodiments, the passenger to guide (P:G) (also referred to as the sense to antisense) strand ratio expressed is greater than 1. In some embodiments, the passenger to guide (P:G) (also referred to as the sense to antisense) strand ratio expressed is greater than 2. In some embodiments, the passenger to guide (P:G) (also referred to as the sense to antisense) strand ratio expressed is greater than 5. In some embodiments, the passenger to guide (P:G) (also referred to as the sense to antisense) strand ratio expressed is greater than 10. In some embodiments, the passenger to guide (P:G) (also referred to as the sense to antisense) strand ratio expressed is greater than 20. In some embodiments, the passenger to guide (P:G) (also referred to as the sense to antisense) strand ratio expressed is greater than 50. In some embodiments, the passenger to guide (P:G) (also referred to as the sense to antisense) strand ratio expressed is at least 3:1. In some embodiments, the passenger to guide (P:G) (also referred to as the sense to antisense) strand ratio expressed is at least 5:1. In some embodiments, the passenger to guide (P:G) (also referred to as the sense to antisense) strand ratio expressed is at least 10:1. In some embodiments, the passenger to guide (P:G) (also referred to as the sense to antisense) strand ratio expressed is at least 20:1. In some embodiments, the passenger to guide (P:G) (also referred to as the sense to antisense) strand ratio expressed is at least 50:1.

In some embodiments, a passenger-guide strand duplex is considered effective when the pri- or pre-microRNAs demonstrate, but methods known in the art and described herein, greater than 2-fold guide to passenger strand ratio when processing is measured. As a non-limiting examples, the pri- or pre-microRNAs demonstrate great than 2-fold, 3-fold, 4-fold, 5-fold, 6-fold, 7-fold, 8-fold, 9-fold, 10-fold, 11-fold, 12-fold, 13-fold, 14-fold, 15-fold, or 2 to 5-fold, 2 to 10-fold, 2 to 15-fold, 3 to 5-fold, 3 to 10-fold, 3 to 15-fold, 4 to 5-fold, 4 to 10-fold, 4 to 15-fold, 5 to 10-fold, 5 to 15-fold, 6 to 10-fold, 6 to 15-fold, 7 to 10-fold, 7 to 15-fold, 8 to 10-fold, 8 to 15-fold, 9 to 10-fold, 9 to 15-fold, 10 to 15-fold, 11 to 15-fold, 12 to 15-fold, 13 to 15-fold, or 14 to 15-fold guide to passenger strand ratio when processing is measured.

In some embodiments, the vector genome encoding the dsRNA comprises a sequence which is at least 60%, 65%, 70%, 75%, 80%, 85%, 90%, 95%, 99% or more than 99% of the full length of the construct. As a non-limiting example, the vector genome comprises a sequence which is at least 80% of the full length sequence of the construct.

In some embodiments, the siRNA constructs may be used to silence a wild type or mutant gene by targeting at least one exon on the sequence.

siRNA Modification

In some embodiments, the siRNA constructs, when not delivered as a precursor or DNA, may be chemically modified to modulate some features of RNA molecules, such as, but not limited to, increasing the stability of siRNAs in vivo. The chemically modified siRNA constructs can be used in human therapeutic applications, and are improved without compromising the RNAi activity of the siRNA constructs. As a non-limiting example, the siRNA constructs modified at both the 3' and the 5' end of both the sense strand and the antisense strand.

In some embodiments, the modified nucleotides may be on just the sense strand.

In some embodiments, the modified nucleotides may be on just the antisense strand.

In some embodiments, the modified nucleotides may be in both the sense and antisense strands.

In some embodiments, the chemically modified nucleotide does not affect the ability of the antisense strand to pair with the target mRNA sequence.

microRNA (miR) Scaffolds

In some embodiments, the siRNA constructs may be encoded in a polynucleotide sequence which also comprises a microRNA (miR) scaffold construct. As used herein a "microRNA (miR) scaffold construct" is a framework or starting molecule that forms the sequence or structural basis against which to design or make a subsequent molecule.

In some embodiments, the miR scaffold construct comprises at least one 5' flanking region. As a non-limiting example, the 5' flanking region may comprise a 5' flanking sequence which may be of any length and may be derived in whole or in part from wild type microRNA sequence or be a completely artificial sequence.

In some embodiments, the miR scaffold construct comprises at least one 3' flanking region. As a non-limiting example, the 3' flanking region may comprise a 3' flanking sequence which may be of any length and may be derived in whole or in part from wild type microRNA sequence or be a completely artificial sequence.

In some embodiments, the miR scaffold construct comprises at least one loop motif region. As a non-limiting example, the loop motif region may comprise a sequence which may be of any length.

In some embodiments, the miR scaffold construct comprises a 5' flanking region, a loop motif region and/or a 3' flanking region.

In some embodiments, at least one payload (e.g., siRNA, miRNA or other RNAi agent described herein) may be encoded by a polynucleotide which may also comprise at least one miR scaffold construct. The miR scaffold construct may comprise a 5' flanking sequence which may be of any length and may be derived in whole or in part from wild type microRNA sequence or be completely artificial. The 3' flanking sequence may mirror the 5' flanking sequence and/or a 3' flanking sequence in size and origin. Either flanking sequence may be absent. The 3' flanking sequence may optionally contain one or more CNNC motifs, where "N" represents any nucleotide.

In some embodiments, the 5' arm of the stem loop structure of the polynucleotide comprising or encoding the miR scaffold construct comprises a sequence encoding a sense sequence.

In some embodiments, the 3' arm of the stem loop of the polynucleotide comprising or encoding the miR scaffold construct comprises a sequence encoding an antisense sequence. The antisense sequence, in some instances, comprises a "G" nucleotide at the 5' most end.

In some embodiments, the sense sequence may reside on the 3' arm while the antisense sequence resides on the 5' arm of the stem of the stem loop structure of the polynucleotide comprising or encoding the miR scaffold construct.

In some embodiments, the sense and antisense sequences may be completely complementary across a substantial portion of their length. In other embodiments the sense sequence and antisense sequence may be at least 70, 80, 90, 95 or 99% complementarity across independently at least 50, 60, 70, 80, 85, 90, 95, or 99% of the length of the strands.

Neither the identity of the sense sequence nor the homology of the antisense sequence need to be 100% complementarity to the target sequence.

In some embodiments, separating the sense and antisense sequence of the stem loop structure of the polynucleotide is a loop sequence (also known as a loop motif, linker or linker motif). The loop sequence may be of any length, between 4-30 nucleotides, between 4-20 nucleotides, between 4-15 nucleotides, between 5-15 nucleotides, between 6-12 nucleotides, 6 nucleotides, 7 nucleotides, 8 nucleotides, 9 nucleotides, 10 nucleotides, 11 nucleotides, 12 nucleotides, 13 nucleotides, 14 nucleotides, and/or 15 nucleotides.

In some embodiments, the loop sequence comprises a nucleic acid sequence encoding at least one UGUG motif. In some embodiments, the nucleic acid sequence encoding the UGUG motif is located at the 5' terminus of the loop sequence.

In some embodiments, spacer regions may be present in the polynucleotide to separate one or more modules (e.g., 5' flanking region, loop motif region, 3' flanking region, sense sequence, antisense sequence) from one another. There may be one or more such spacer regions present.

In some embodiments, a spacer region of between 8-20, i.e., 8, 9, 10, 11, 12, 13, 14, 15, 16, 17, 18, 19, or 20 nucleotides may be present between the sense sequence and a flanking region sequence.

In some embodiments, the length of the spacer region is 13 nucleotides and is located between the 5' terminus of the sense sequence and the 3' terminus of the flanking sequence. In some embodiments, a spacer is of sufficient length to form approximately one helical turn of the sequence.

In some embodiments, a spacer region of between 8-20, i.e., 8, 9, 10, 11, 12, 13, 14, 15, 16, 17, 18, 19, or 20 nucleotides may be present between the antisense sequence and a flanking sequence.

In some embodiments, the spacer sequence is between 10-13, i.e., 10, 11, 12 or 13 nucleotides and is located between the 3' terminus of the antisense sequence and the 5' terminus of a flanking sequence. In some embodiments, a spacer is of sufficient length to form approximately one helical turn of the sequence.

In some embodiments, the polynucleotide comprises in the 5' to 3' direction, a 5' flanking sequence, a 5' arm, a loop motif, a 3' arm and a 3' flanking sequence. As a non-limiting example, the 5' arm may comprise a sense sequence and the 3' arm comprises the antisense sequence. In another non-limiting example, the 5' arm comprises the antisense sequence and the 3' arm comprises the sense sequence.

In some embodiments, the 5' arm, payload (e.g., sense and/or antisense sequence), loop motif and/or 3' arm sequence may be altered (e.g., substituting 1 or more nucleotides, adding nucleotides and/or deleting nucleotides). The alteration may cause a beneficial change in the function of the construct (e.g., increase knock-down of the target sequence, reduce degradation of the construct, reduce off target effect, increase efficiency of the payload, and reduce degradation of the payload).

In some embodiments, the miR scaffold construct of the polynucleotides is aligned in order to have the rate of excision of the guide strand be greater than the rate of excision of the passenger strand. The rate of excision of the guide or passenger strand may be, independently, 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 99% or more than 99%. As a non-limiting example, the rate of excision of the guide strand is at least 80%. As another non-limiting example, the rate of excision of the guide strand is at least 90%.

In some embodiments, the rate of excision of the guide strand is greater than the rate of excision of the passenger strand. In one aspect, the rate of excision of the guide strand may be at least 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 99% or more than 99% greater than the passenger strand.

In some embodiments, the efficiency of excision of the guide strand is at least 60%, 65%, 70%, 75%, 80%, 85%, 90%, 95%, 99% or more than 99%. As a non-limiting example, the efficiency of the excision of the guide strand is greater than 80%.

In some embodiments, the efficiency of the excision of the guide strand is greater than the excision of the passenger strand from the miR scaffold construct. The excision of the guide strand may be 2, 3, 4, 5, 6, 7, 8, 9, 10 or more than 10 times more efficient than the excision of the passenger strand from the miR scaffold construct.

In some embodiments, the miR scaffold construct comprises a dual-function targeting polynucleotide. As used herein, a "dual-function targeting" polynucleotide is a polynucleotide where both the guide and passenger strands knock down the same target or the guide and passenger strands knock down different targets.

In some embodiments, the miR scaffold construct of the polynucleotides described herein may comprise a 5' flanking region, a loop motif region and a 3' flanking region.

In some embodiments, the polynucleotide is designed using at least one of the following properties: loop variant, seed mismatch/bulge/wobble variant, stem mismatch, loop variant and vassal stem mismatch variant, seed mismatch and basal stem mismatch variant, stem mismatch and basal stem mismatch variant, seed wobble and basal stem wobble variant, or a stem sequence variant.

In some embodiments, the miR scaffold construct may be a natural pri-miRNA scaffold.

In some embodiments, the selection of a miR scaffold construct is determined by a method of comparing polynucleotides in pri-miRNA.

In some embodiments, the selection of a miR scaffold construct is determined by a method of comparing polynucleotides in natural pri-miRNA and synthetic pri-miRNA.

Transfer RNA (tRNA)

Transfer RNAs (tRNAs) are RNA molecules that translate mRNA into proteins. tRNA include a cloverleaf structure that comprise a 3' acceptor site, 5' terminal phosphate, D arm, T arm, and anticodon arm. The main purpose of a tRNA is to carry amino acids on its 3' acceptor site to a ribosome complex with the help of aminoacyl-tRNA synthetases which are enzymes that load the appropriate amino acid onto a free tRNA to synthesize proteins. Once an amino acid is bound to tRNA, the tRNA is considered an aminoacyl-tRNA. The type of amino acid on a tRNA is dependent on the mRNA codon. The anticodon arm of the tRNA is the site of the anticodon, which is complementary to an mRNA codon and dictates which amino acid to carry. tRNAs are also known to have a role in the regulation of apoptosis by acting as a cytochrome c scavenger.

In some embodiments, the originator construct and/or the benchmark construct comprises or encodes a tRNA.

Ribosomal RNA (rRNA)

Ribosomal RNAs (rRNAs) are RNA which form ribosomes. Ribosomes are essential to protein synthesis and contain a large and small ribosomal subunit. In prokaryotes, a small 30S and large 50S ribosomal subunit make up a 70S ribosome. In eukaryotes, the 40S and 60S subunit form an 80S ribosome. In order to bind aminoacyl-tRNAs and link amino acids together to create polypeptides, the ribosome contains 3 sites: an exit site (E), a peptidyl site (P), and acceptor site (A).

In some embodiments, the originator construct and/or the benchmark construct comprises or encodes a rRNA.

microRNA (miRNA)

microRNAs (or miRNA) are 19-25 nucleotide long noncoding RNAs that bind to the 3'UTR of nucleic acid molecules and down-regulate gene expression either by reducing nucleic acid molecule stability or by inhibiting translation. The originator constructs and/or benchmark constructs may comprise one or more microRNA target sequences, microRNA sequences, or microRNA seeds.

A microRNA sequence comprises a "seed" region, i.e., a sequence in the region of positions 2-8 of the mature microRNA, which sequence has perfect Watson-Crick complementarity to the miRNA target sequence. A microRNA seed may comprise positions 2-8 or 2-7 of the mature microRNA. In some embodiments, a microRNA seed may comprise 7 nucleotides (e.g., nucleotides 2-8 of the mature microRNA), wherein the seed-complementary site in the corresponding miRNA target is flanked by an adenine (A) opposed to microRNA position 1. In some embodiments, a microRNA seed may comprise 6 nucleotides (e.g., nucleotides 2-7 of the mature microRNA), wherein the seed-complementary site in the corresponding miRNA target is flanked by an adenine (A) opposed to microRNA position 1. The bases of the microRNA seed have complete complementarity with the target sequence. By engineering microRNA target sequences into the 3' UTR of the mRNA one can target the molecule for degradation or reduced translation, provided the microRNA in question is available. This process will reduce the hazard of off target effects upon nucleic acid molecule delivery.

As used herein, the term "microRNA site" refers to a microRNA target site or a microRNA recognition site, or any nucleotide sequence to which a microRNA binds or associates. It should be understood that "binding" may follow traditional Watson-Crick hybridization rules or may reflect any stable association of the microRNA with the target sequence at or adjacent to the microRNA site.

Non-limiting examples of tissues where microRNA are known to regulate mRNA, and thereby protein expression, include, but are not limited to, liver (miR-122), muscle (miR-133, miR-206, miR-208), endothelial cells (miR-17-92, miR-126), myeloid cells (miR-142-3p, miR-142-5p, miR-16, miR-21, miR-223, miR-24, miR-27), adipose tissue (let-7, miR-30c), heart (miR-1d, miR-149), kidney (miR-192, miR-194, miR-204), and lung epithelial cells (let-7, miR-133, miR-126). MicroRNA can also regulate complex biological processes such as angiogenesis (miR-132).

For example, if the nucleic acid molecule is an mRNA and is not intended to be delivered to the liver but ends up there, then miR-122, a microRNA abundant in liver, can inhibit the expression of the gene of interest if one or multiple target sites of miR-122 are engineered into the 3' UTR of the mRNA. Introduction of one or multiple binding sites for different microRNA can be engineered to further decrease the longevity, stability, and protein translation of a mRNA.

Conversely, microRNA binding sites can be engineered out of (i.e. removed from) sequences in which they naturally occur in order to increase protein expression in specific tissues. For example, miR-122 binding sites may be removed to improve protein expression in the liver. Regulation of expression in multiple tissues can be accomplished through introduction or removal or one or several microRNA binding sites.

Long Non-Coding RNA (lncRNA)

Long non-coding RNAs (lncRNAs) are regulatory RNA molecules that do not code for proteins but influence a vast array of biological processes. The lncRNA designation is generally restricted to non-coding transcripts longer than about 200 nucleotides. The length designation differentiates lncRNA from small regulatory RNAs such as short interfering RNA (siRNA) and micro RNA (miRNA). In vertebrates, the number of lncRNA species is thought to greatly exceed the number of protein-coding species. It is also thought that lncRNAs drive biologic complexity observed in vertebrates compared to invertebrates. Evidence of this complexity is seen in many cellular compartments of a vertebrate organism such as the T lymphocyte compartment of the adaptive immune system. Differences in expression and function of lncRNA can be major contributors to human disease.

In some embodiments, the originator constructs and/or the benchmark constructs comprise lncRNAs.

RNA Modifications

In some aspects, the originator constructs or benchmark constructs may contain one or more modified nucleotides such as, but not limited to, sugar modified nucleotides, nucleobase modifications and/or backbone modifications. In some aspects, the originator constructs or benchmark constructs may contain combined modifications, for example, combined nucleobase and backbone modifications.

In some embodiments, the modified nucleotide may be a sugar-modified nucleotide. Sugar modified nucleotides include, but are not limited to 2'-fluoro, 2'-amino and 2'-thio modified ribonucleotides, e.g. 2'-fluoro modified ribonucleotides. Modified nucleotides may be modified on the sugar moiety, as well as nucleotides having sugars or analogs thereof that are not ribosyl. For example, the sugar moieties may be, or be based on, mannoses, arabinoses, glucopyranoses, galactopyranoses, 4'-thioribose, and other sugars, heterocycles, or carbocycles.

In some embodiments, the modified nucleotide may be a nucleobase-modified nucleotide.

In some embodiments, the modified nucleotide may be a backbone-modified nucleotide. In some embodiments, the originator constructs or benchmark constructs may further comprise other modifications on the backbone. A normal "backbone", as used herein, refers to the repeating alternating sugar-phosphate sequences in a DNA or RNA molecule. The deoxyribose/ribose sugars are joined at both the 3'-hydroxyl and 5'-hydroxyl groups to phosphate groups in ester links, also known as "phosphodiester" bonds/linker (PO linkage). The PO backbones may be modified as "phosphorothioate backbone (PS linkage). In some cases, the natural phosphodiester bonds may be replaced by amide bonds but the four atoms between two sugar units are kept. Such amide modifications can facilitate the solid phase synthesis of oligonucleotides and increase the thermodynamic stability of a duplex formed with siRNA complement.

Modified bases refer to nucleotide bases such as, but not limited to, adenine, guanine, cytosine, thymine, uracil, xanthine, inosine, and queuosine that have been modified by the replacement or addition of one or more atoms or groups. Some examples of modifications on the nucleobase moieties include, but are not limited to, alkylated, halogenated, thiolated, aminated, amidated, or acetylated bases, individually or in combination. More specific examples include, for example, 5-propynyluridine, 5-propynylcytidine, 6-methyladenine, 6-methylguanine, N,N,-dimethyladenine, 2-propyladenine, 2-propylguanine, 2-aminoadenine, 1-methylinosine, 3-methyluridine, 5-methylcytidine, 5-methyluridine and other nucleotides having a modification at the 5 position, 5-(2-amino)propyl uridine, 5-halocytidine, 5-halouridine, 4-acetylcytidine, 1-methyladenosine, 2-methyladenosine, 3-methylcytidine, 6-methyluridine, 2-methylguanosine, 7-methylguanosine, 2,2-dimethylguanosine, 5-methylaminoethyluridine, 5-methyloxyuridine, deazanucleotides such as 7-deaza-adenosine, 6-azouridine, 6-azocytidine, 6-azothymidine, 5-methyl-2-thiouridine, other thio bases such as 2-thiouridine and 4-thiouridine and 2-thiocytidine, dihydrouridine, pseudouridine, queuosine, archaeosine, naphthyl and substituted naphthyl groups, any O- and N-alkylated purines and pyrimidines such as N6-methyladenosine, 5-methylcarbonylmethyluridine, uridine 5-oxyacetic acid, pyridine-4-one, pyridine-2-one, phenyl and modified phenyl groups such as aminophenol or 2,4,6-trimethoxy benzene, modified cytosines that act as G-clamp nucleotides, 8-substituted adenines and guanines, 5-substituted uracils and thymines, azapyrimidines, carboxyhydroxyalkyl nucleotides, carboxyalkylaminoalkyl nucleotides, and alkylcarbonylalkylated nucleotides.

The originator constructs and/or benchmark constructs may include one or more substitutions, insertions and/or additions, deletions, and covalent modifications with respect to reference sequences, in particular, the parent RNA, are included within the scope of this disclosure.

In some embodiments, the originator constructs and/or benchmark constructs includes one or more post-transcriptional modifications (e.g., capping, cleavage, polyadenylation, splicing, poly-A sequence, methylation, acylation, phosphorylation, methylation of lysine and arginine residues, acetylation, and nitrosylation of thiol groups and tyrosine residues, etc). The one or more post-transcriptional modifications can be any post-transcriptional modification, such as any of the more than one hundred different nucleoside modifications that have been identified in RNA (Rozenski, J, Crain, P, and McCloskey, J. (1999). The RNA Modification Database: 1999 update. Nucl Acids Res 27: 196-197) In some embodiments, the first isolated nucleic acid comprises messenger RNA (mRNA). In some embodiments, the originator constructs and/or benchmark constructs comprise at least one nucleoside selected from the group consisting of pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, and 4-methoxy-2-thio-pseudouridine. In some embodiments, the mRNA comprises at least one nucleoside selected from the group consisting of 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, and 4-methoxy-1-methyl-pseudoisocytidine. In some embodiments, the mRNA comprises at least one nucleoside selected from the group consisting of 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, and 2-methoxy-adenine. In some embodiments, mRNA comprises at least one nucleoside selected from the group consisting of inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

The originator constructs and/or benchmark constructs may include any useful modification, such as to the sugar, the nucleobase, or the internucleoside linkage (e.g. to a linking phosphate/to a phosphodiester linkage/to the phosphodiester backbone). One or more atoms of a pyrimidine nucleobase may be replaced or substituted with optionally substituted amino, optionally substituted thiol, optionally substituted alkyl (e.g., methyl or ethyl), or halo (e.g., chloro or fluoro). In certain embodiments, modifications (e.g., one or more modifications) are present in each of the sugar and the internucleoside linkage. Modifications may be modifications of ribonucleic acids (RNAs) to deoxyribonucleic acids (DNAs), threose nucleic acids (TNAs), glycol nucleic acids (GNAs), peptide nucleic acids (PNAs), locked nucleic acids (LNAs) or hybrids thereof). Additional modifications are described herein.

In some embodiments, the originator constructs and/or benchmark constructs includes at least one N(6)methyladenosine (m6A) modification to increase translation efficiency. In some embodiments, the N(6)methyladenosine (m6A) modification can reduce immunogenicity of the originator constructs and/or benchmark constructs.

In some embodiments, the modification may include a chemical or cellular induced modification. For example, some nonlimiting examples of intracellular RNA modifications are described by Lewis and Pan in "RNA modifications and structures cooperate to guide RNA-protein interactions" from Nat. Reviews Mol. Cell Biol., 2017, 18:202-210.

In some embodiments, chemical modifications to the RNA may enhance immune evasion. The RNA may be synthesized and/or modified by methods well established in the art, such as those described in "Current protocols in nucleic acid chemistry," Beaucage, S. L. et al. (Eds.), John Wiley & Sons, Inc., New York, N.Y., USA, which is hereby incorporated herein by reference. Modifications include, for example, end modifications, e.g., 5' end modifications (phosphorylation (mono-, di- and tri-), conjugation, inverted linkages, etc.), 3' end modifications (conjugation, DNA nucleotides, inverted linkages, etc.), base modifications (e.g., replacement with stabilizing bases, destabilizing bases, or bases that base pair with an expanded repertoire of partners), removal of bases (abasic nucleotides), or conjugated bases. The modified ribonucleotide bases may also include 5-methylcytidine and pseudouridine. In some embodiments, base modifications may modulate expression, immune response, stability, subcellular localization, to name a few functional effects, of the RNA. In some embodiments, the modification includes a bi-orthogonal nucleotides, e.g., an unnatural base. See for example, Kimoto et al., Chem Commun (Camb), 2017, 53:12309, DOI: 10.1039/c7cc06661a, which is hereby incorporated by reference.

In some embodiments, sugar modifications (e.g., at the 2' position or 4' position) or replacement of the sugar one or more RNA may, as well as backbone modifications, include modification or replacement of the phosphodiester linkages. Specific examples of modifications include modified backbones or no natural internucleoside linkages such as internucleoside modifications, including modification or replacement of the phosphodiester linkages. RNA having modified backbones include, among others, those that do not have a phosphorus atom in the backbone. For the purposes of this application, and as sometimes referenced in the art, modified RNAs that do not have a phosphorus atom in their internucleoside backbone can also be considered to be oligonucleosides. In particular embodiments, the RNA will include ribonucleotides with a phosphorus atom in its internucleoside backbone.

Modified RNA backbones may include, for example, phosphorothioates, chiral phosphorothioates, phosphorodithioates, phosphotriesters, aminoalkylphosphotriesters, methyl and other alkyl phosphonates such as 3'-alkylene phosphonates and chiral phosphonates, phosphinates, phosphoramidates such as 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included. In some embodiments, the RNA may be negatively or positively charged.

The modified nucleotides can be modified on the internucleoside linkage (e.g., phosphate backbone). Herein, in the context of the polynucleotide backbone, the phrases "phosphate" and "phosphodiester" are used interchangeably. Backbone phosphate groups can be modified by replacing one or more of the oxygen atoms with a different substituent. Further, the modified nucleosides and nucleotides can include the wholesale replacement of an unmodified phosphate moiety with another internucleoside linkage as described herein. Examples of modified phosphate groups include, but are not limited to, phosphorothioate, phosphoroselenates, boranophosphates, boranophosphate esters, hydrogen phosphonates, phosphoramidates, phosphorodiamidates, alkyl or aryl phosphonates, and phosphotriesters. Phosphorodithioates have both non-linking oxygens replaced by sulfur. The phosphate linker can also be modified by the replacement of a linking oxygen with nitrogen (bridged phosphoramidates), sulfur (bridged phosphorothioates), and carbon (bridged methylene-phosphonates).

The a-thio substituted phosphate moiety is provided to confer stability to RNA and DNA polymers through the unnatural phosphorothioate backbone linkages. Phosphorothioate DNA and RNA have increased nuclease resistance and subsequently a longer half-life in a cellular environment. Phosphorothioate linked to the RNA is expected to reduce the innate immune response through weaker binding/activation of cellular innate immune molecules.

In specific embodiments, a modified nucleoside includes an alpha-thio-nucleoside (e.g., 5'-O-(1-thiophosphate)-adenosine, 5'-O-(1-thiophosphate)-cytidine (a-thio-cytidine), 5'-O-(1-thiophosphate)-guanosine, 5'-O-(1-thiophosphate)-uridine, or 5'-O-(1-thiophosphate)-pseudouridine).

Other internucleoside linkages that may be employed according to the present disclosure, including internucleoside linkages which do not contain a phosphorous atom, are described herein.

In some embodiments, the RNA may include one or more cytotoxic nucleosides. For example, cytotoxic nucleosides may be incorporated into RNA, such as bifunctional modification. Cytotoxic nucleoside may include, but are not limited to, adenosine arabinoside, 5-azacytidine, 4'-thio-aracytidine, cyclopentenylcytosine, cladribine, clofarabine, cytarabine, cytosine arabinoside, 1-(2-C-cyano-2-deoxy-beta-D-arabino-pentofuranosyl)-cytosine, decitabine, 5-fluorouracil, fludarabine, floxuridine, gemcitabine, a combination of tegafur and uracil, tegafur ((RS)-5-fluoro-1-(tetrahydrofuran-2-yl)pyrimidine-2,4(1H,3H)-dione), troxacitabine, tezacitabine, 2'-deoxy-2'-methylidenecytidine (DMDC), and 6-mercaptopurine. Additional examples include fludarabine phosphate, N4-behenoyl-1-beta-D-arabinofuranosylcytosine, N4-octadecyl-1-beta-D-arabinofuranosylcytosine, N4-palmitoyl-1-(2-C-cyano-2-deoxy-beta-D-arabino-pentofuranosyl) cytosine, and P-4055 (cytarabine 5'-elaidic acid ester).

In some embodiments, the RNA sequence includes or comprises natural nucleosides (e.g., adenosine, guanosine, cytidine, uridine), nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), and/or modified phosphate groups (e.g., phosphorothioates and 5'-N-phosphoramidite linkages). In one embodiment, the RNA sequence includes or comprises incorporates pseudouridine (y). In another embodiment, the RNA sequence includes or comprises 5-methylcytosine (m5C).

The RNA may or may not be uniformly modified along the entire length of the molecule. For example, one or more or all types of nucleotide (e.g., naturally-occurring nucleotides, purine or pyrimidine, or any one or more or all of A, G, U, C, I, pU) may or may not be uniformly modified in the RNA, or in a given predetermined sequence region thereof. In some embodiments, the RNA includes a pseudouridine. In some embodiments, the RNA includes an inosine, which may aid in the immune system characterizing the RNA as endogenous versus viral RNAs. The incorporation of inosine may also mediate improved RNA stability/reduced degradation.

In some embodiments, all nucleotides in the RNA (or in a given sequence region thereof) are modified. In some embodiments, the modification may include an m6A, which may augment expression, an inosine, which may attenuate an immune response, pseudouridine, which may increase RNA stability, or translational readthrough (stagger element), an m5C, which may increase stability, and a 2,2,7-trimethylguanosine, which aids subcellular translocation (e.g., nuclear localization).

Different sugar modifications, nucleotide modifications, and/or internucleoside linkages (e.g., backbone structures) may exist at various positions in the RNA. One of ordinary skill in the art will appreciate that the nucleotide analogs or other modification(s) may be located at any position(s) of the RNA, such that the function of the RNA is not substantially decreased. A modification may also be a non-coding region modification. The RNA may include from about 1% to about 100% modified nucleotides (either in relation to overall nucleotide content, or in relation to one or more types of nucleotide, i.e. any one or more of A, G, U or C) or any intervening percentage (e.g., from 1% to 20%>, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100%).

Codon Optimization

A nucleotide sequence of the originator construct and/or benchmark construct may be codon optimized. Codon optimization methods are known in the art and may be useful in efforts to achieve one or more of several goals. These goals include to match codon frequencies in target and host organisms to ensure proper folding, bias GC content to increase mRNA stability or reduce secondary structures, minimize tandem repeat codons or base runs that may impair gene construction or expression, customize transcriptional and translational control regions, insert or remove protein trafficking sequences, remove/add post translation modification sites in encoded protein (e.g. glycosylation sites), add, remove or shuffle protein domains, insert or delete restriction sites, modify ribosome binding sites and mRNA degradation sites, to adjust translational rates to allow the various domains of the protein to fold properly, or to reduce or eliminate problem secondary structures within the mRNA. Codon optimization tools, algorithms and services are known in the art, non-limiting examples include services from GeneArt (Life Technologies), DNA2.0 (Menlo Park CA) and/or proprietary methods. In some embodiments, the ORF sequence is optimized using optimization algorithms.

III. Lipids

The present disclosure provides ionizable lipids that demonstrates high efficacy along with low toxicity, low sustained lipid levels in the relevant tissues, and for local delivery to various tissues. The ionizable lipids may be cationic lipids.

In some embodiments, Lipids of the Disclosure comprise an acyclic core. In some embodiments, Lipids of the Disclosure are selected from any lipid in Table (I) below or a pharmaceutically acceptable salt thereof:

TABLE (I)

| Non-Limiting Examples of Ionizable Lipids with an Acyclic Core | |
|---|---|
| Structure | Cpd. |
| 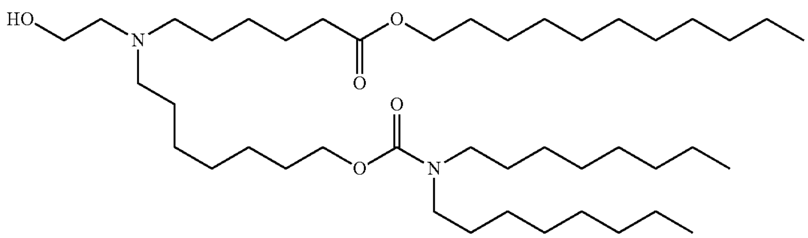 [SMILES: CCCCCCCCCCCOC(=O)CCCCCN(CCO)CCCCCCCOC(=O)N(CCCCCCCC)CCCCCCCC] | 1 |

TABLE (I)-continued
Non-Limiting Examples of Ionizable Lipids with an Acyclic Core
| Structure | Cpd. |
|---|---|
| 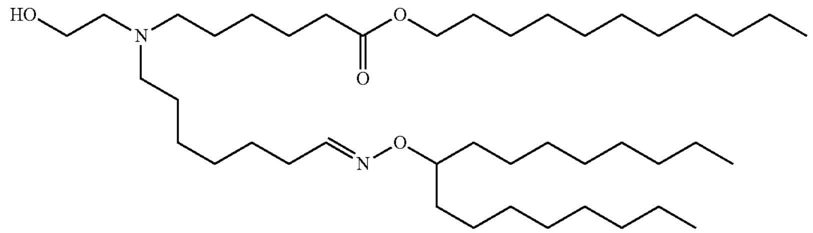 [SMILES: CCCCCCCCCCCOC(=O)CCCCCN(CCO)CCCCCC/C=N/OC(CCCCCCCC)CCCCCCCC] | 2 |
| 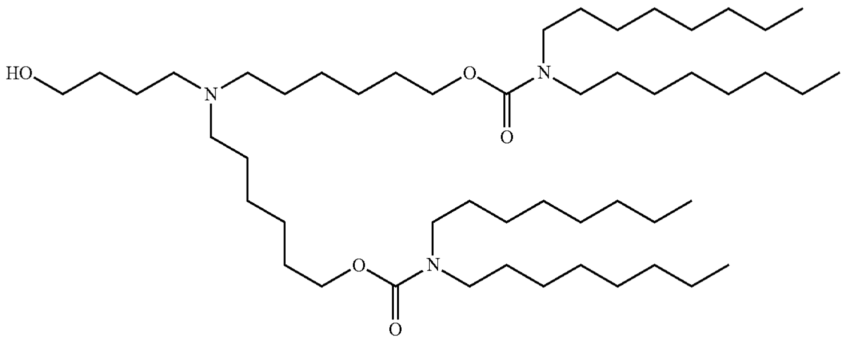 [SMILES: CCCCCCCCN(CCCCCCCC)C(=O)OCCCCCCN(CCCCO)CCCCCCOC(=O)N(CCCCCCCC)CCCCCCCC] | 3 |
| 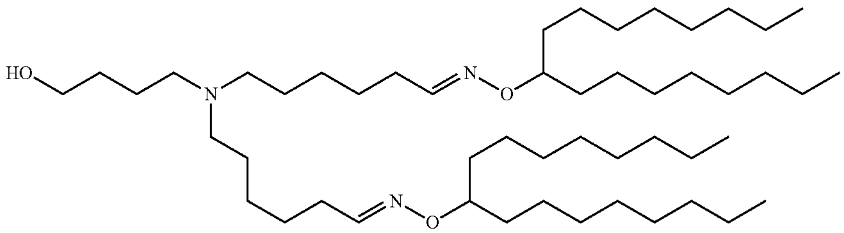 [SMILES: CCCCCCCCC(CCCCCCCC)O/N=C/CCCCCN(CCCCO)CCCCC/C=N/OC(CCCCCCCC)CCCCCCCC] | 4 |
| 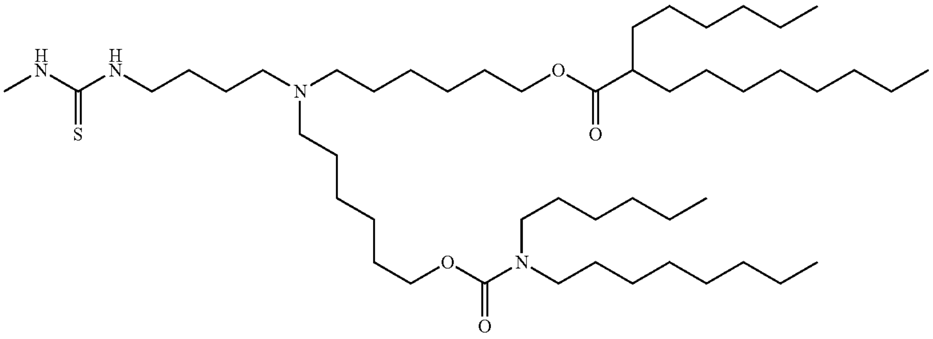 [SMILES: CCCCCCCCC(CCCCCC)C(=O)OCCCCCCN(CCCCCCOC(=O)N(CCCCCC)CCCCCCCC)CCCCNC(=S)NC] | 5 |
| 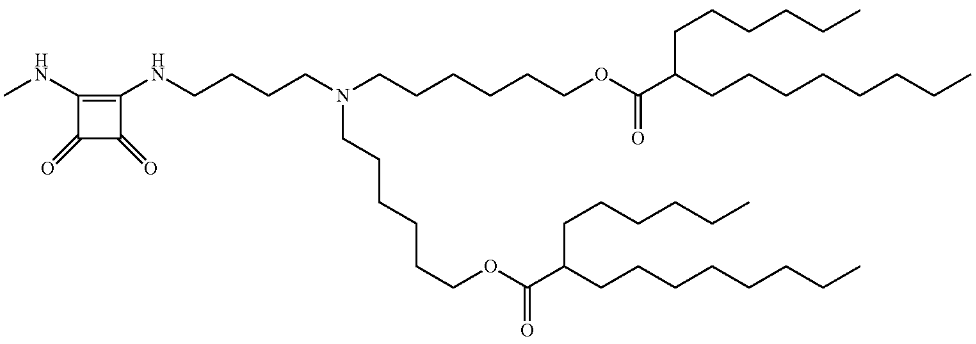 [SMILES: CCCCCCCCC(CCCCCC)C(=O)OCCCCCCN(CCCCCCOC(=O)C(CCCCCC)CCCCCCCC)CCCCNc1c(NC)c(=O)c1=O] | 6 |

TABLE (I)-continued
| Non-Limiting Examples of Ionizable Lipids with an Acyclic Core | |
|---|---|
| Structure | Cpd. |
| 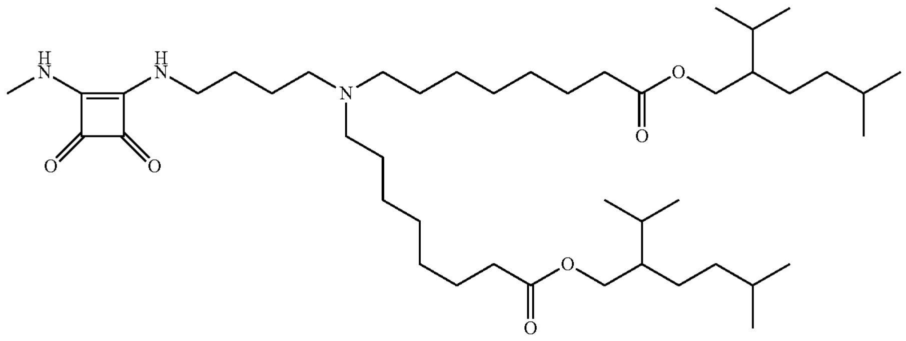 [SMILES: CNc1c(NCCCCN(CCCCCCCC(=O)OCC(CCC(C)C)C(C)C)CCCCCCCC(=O)OCC(CCC(C)C)C(C)C)c(=O)c1=O] | 7 |
| 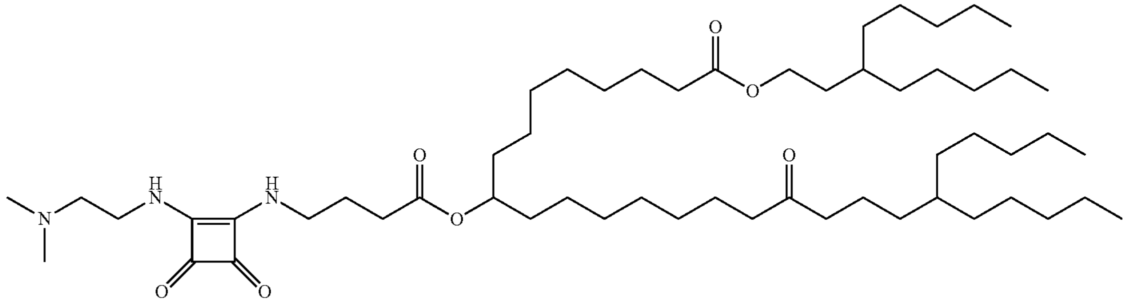 [SMILES: CCCCCC(CCCCC)CCCC(=O)CCCCCCCC(CCCCCCCC(=O)OCCC(CCCCC)CCCCC)OC(=O)CCCNc1c(NCCN(C)C)c(=O)c1=O] | 8 |
| 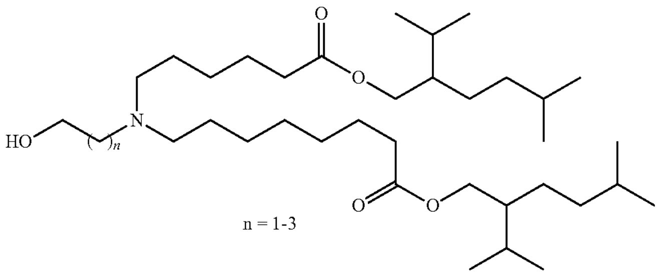 n = 1-3 | 9 |
| 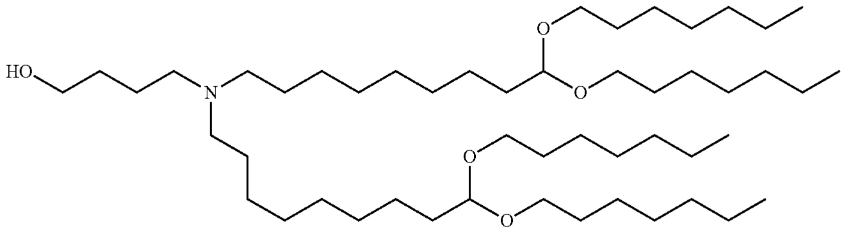 [SMILES: CCCCCCCOC(CCCCCCCCN(CCCCO)CCCCCCCCC(OCCCCCCC)OCCCCCCC)OCCCCCCC] | 10 |
| 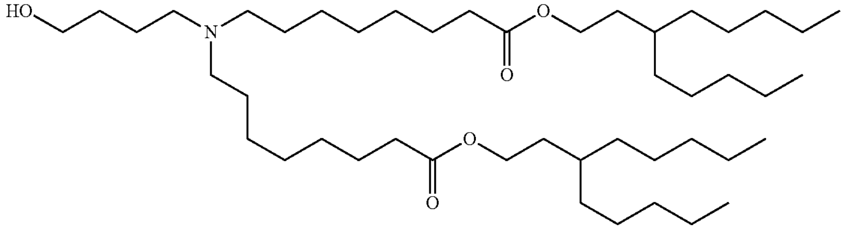 [SMILES: CCCCCC(CCCCC)CCOC(=O)CCCCCCCN(CCCCO)CCCCCCCC(=O)OCCC(CCCCC)CCCCC] | 11 |

TABLE (I)-continued
| Non-Limiting Examples of Ionizable Lipids with an Acyclic Core | |
|---|---|
| Structure | Cpd. |
| 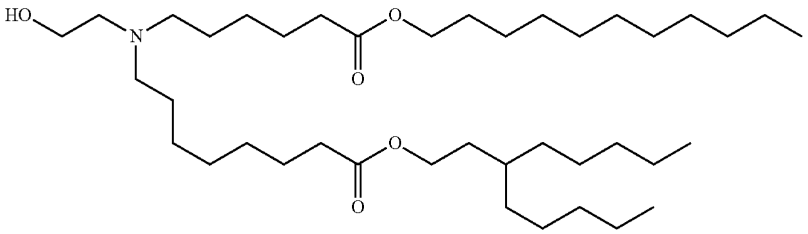 [SMILES: CCCCCCCCCCCOC(=O)CCCCCN(CCO)CCCCCCCC(=O)OCCC(CCCCC)CCCCC] | 13 |
| 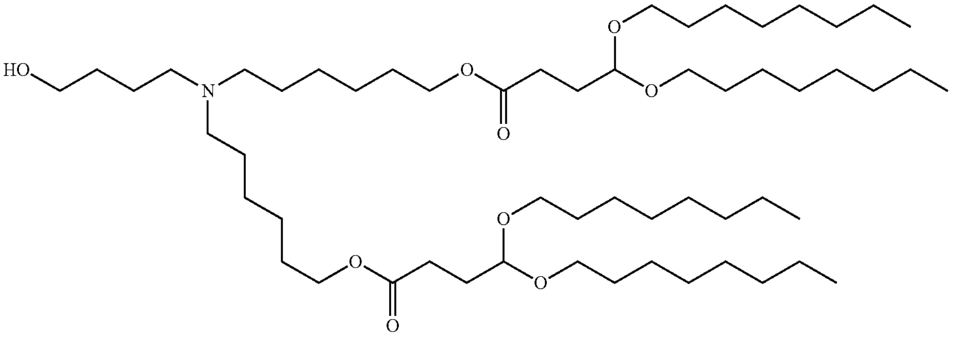 [SMILES: CCCCCCCCOC(CCC(=O)OCCCCCCN(CCCCO)CCCCCCOC(=O)CCC(OCCCCCCCC)OCCCCCCCC)OCCCCCCCC] | 14 |
| 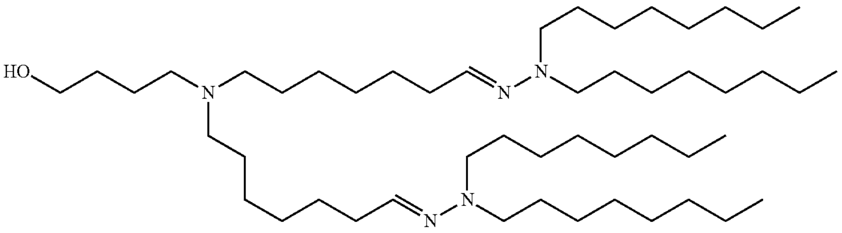 [SMILES: CCCCCCCCN(CCCCCCCC)/N=C/CCCCCCN(CCCCO)CCCCCC/C=N/N(CCCCCCCC)CCCCCCCC] | 15 |
| 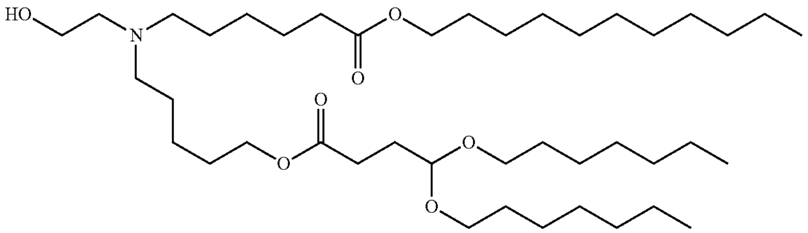 [SMILES: CCCCCCCCCCCOC(=O)CCCCCN(CCO)CCCCCOC(=O)CCC(OCCCCCCC)OCCCCCCC] | 16 |
| 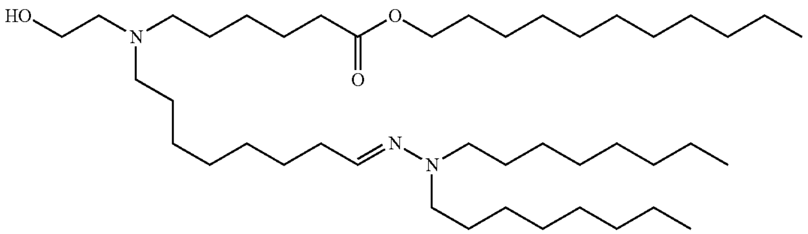 [SMILES: CCCCCCCCCCCOC(=O)CCCCCN(CCO)CCCCCCC/C=N/N(CCCCCCCC)CCCCCCCC] | 17 |

TABLE (I)-continued
Non-Limiting Examples of Ionizable Lipids with an Acyclic Core
| Structure | Cpd. |
|---|---|
| 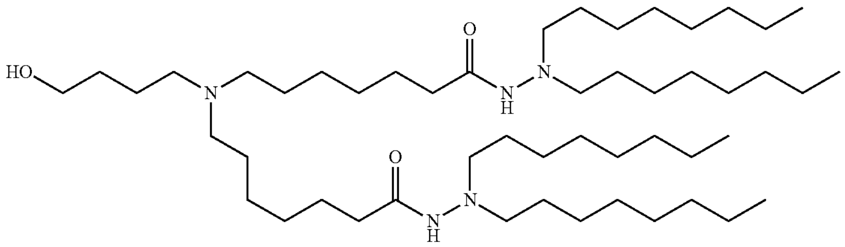 [SMILES: CCCCCCCCN(CCCCCCCC)NC(=O)CCCCCCN(CCCCO)CCCCCCC(=O)NN(CCCCCCCC)CCCCCCCC] | 18 |
| 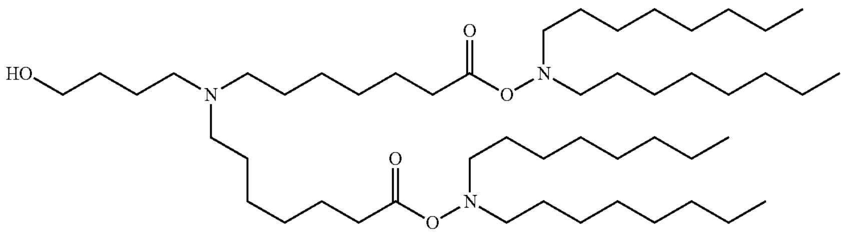 [SMILES: CCCCCCCCN(CCCCCCCC)OC(=O)CCCCCCN(CCCCO)CCCCCCC(=O)ON(CCCCCCCC)CCCCCCCC] | 19 |
| 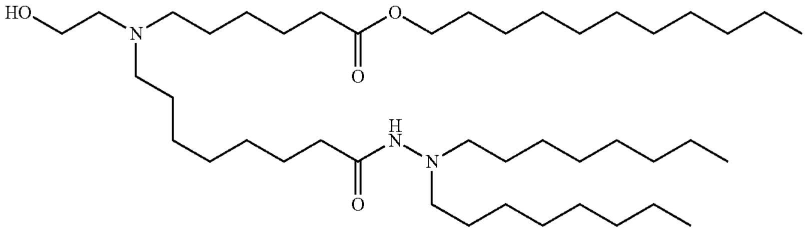 [SMILES: CCCCCCCCCCCOC(=O)CCCCCN(CCO)CCCCCCCC(=O)NN(CCCCCCCC)CCCCCCCC] | 20 |
| 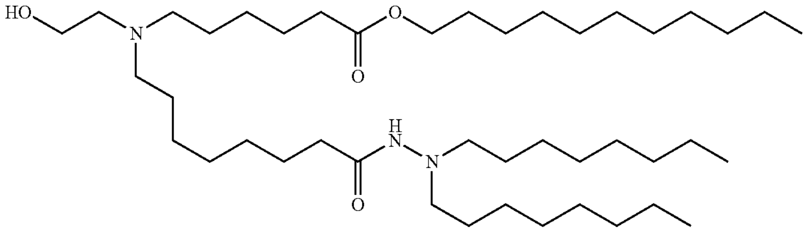 [SMILES: CCCCCCCCCCCOC(=O)CCCCCN(CCO)CCCCCCCC(=O)NN(CCCCCCCC)CCCCCCCC] | 21 |
| 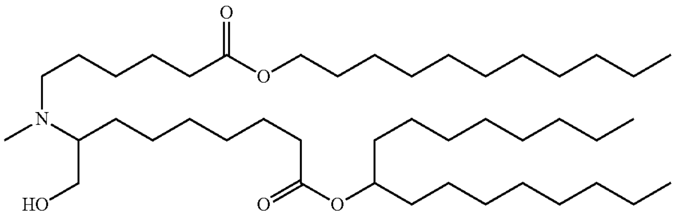 [SMILES: CCCCCCCCCCCOC(=O)CCCCCN(C)C(CO)CCCCCCC(=O)OC(CCCCCCCC)CCCCCCCC] | 22 |
| 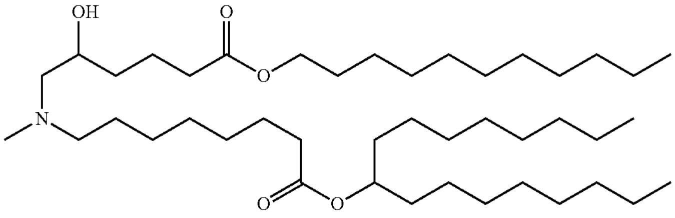 [SMILES: CCCCCCCCCCCOC(=O)CCCC(O)CN(C)CCCCCCCC(=O)OC(CCCCCCCC)CCCCCCCC] | 23 |

TABLE (I)-continued
| Non-Limiting Examples of Ionizable Lipids with an Acyclic Core | |
|---|---|
| Structure | Cpd. |
| 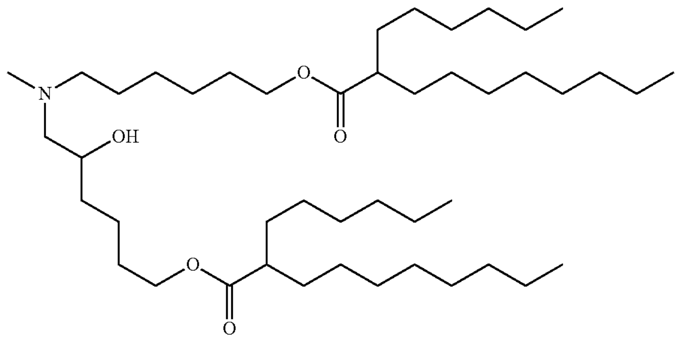 [SMILES: CCCCCCCCC(CCCCCC)C(=O)OCCCCCCN(C)CC(O)CCCCOC(=O)C(CCCCCC)CCCCCCCC] | 24 |
| 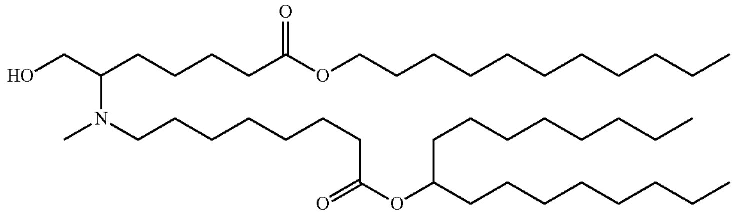 [SMILES: CCCCCCCCCCCOC(=O)CCCCC(CO)N(C)CCCCCCCC(=O)OC(CCCCCCCC)CCCCCCCC] | 25 |
| 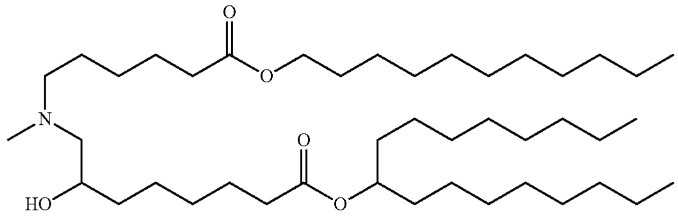 [SMILES: CCCCCCCCCCCOC(=O)CCCCCN(C)CC(O)CCCCCC(=O)OC(CCCCCCCC)CCCCCCCC] | 26 |
| 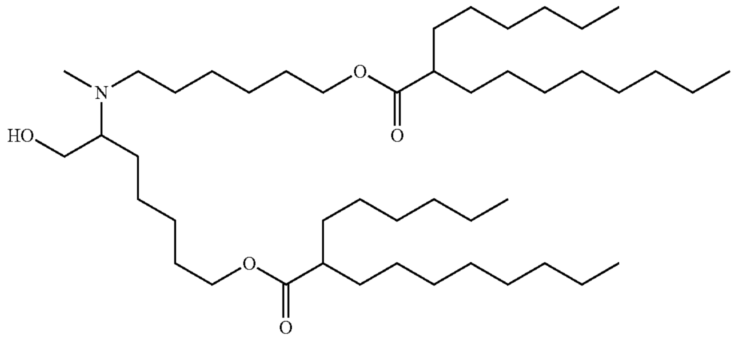 [SMILES: CCCCCCCCC(CCCCCC)C(=O)OCCCCCCN(C)C(CO)CCCCCOC(=O)C(CCCCCC)CCCCCCCC] | 27 |
| 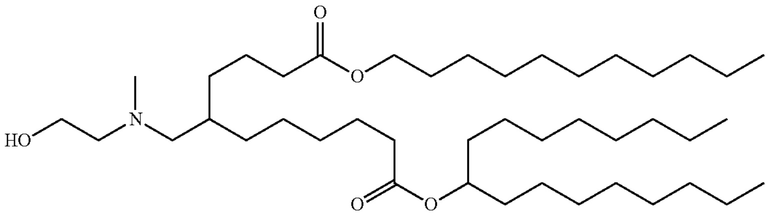 [SMILES: CCCCCCCCCCCOC(=O)CCCC(CCCCCC(=O)OC(CCCCCCCC)CCCCCCCC)CN(C)CCO] | 28 |

TABLE (I)-continued
| Non-Limiting Examples of Ionizable Lipids with an Acyclic Core | |
|---|---|
| Structure | Cpd. |
| 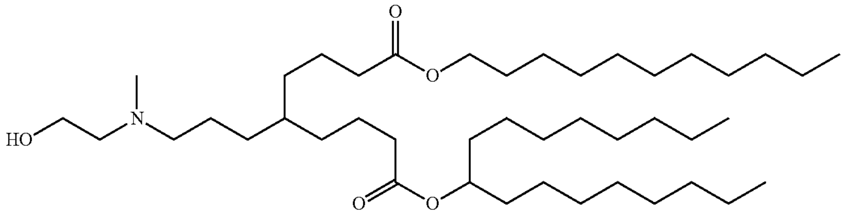 [SMILES: CCCCCCCCCCCOC(=O)CCCC(CCCC(=O)OC(CCCCCCCC)CCCCCCCC)CCCN(C)CCO] | 29 |
| 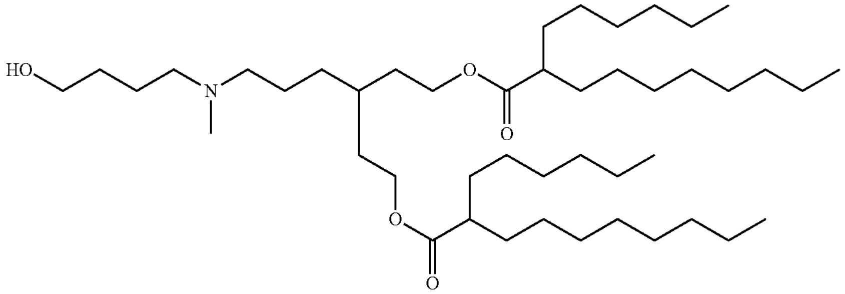 [SMILES: CCCCCCCCC(CCCCCC)C(=O)OCCC(CCCN(C)CCCCO)CCOC(=O)C(CCCCCC)CCCCCCCC] | 30 |
| 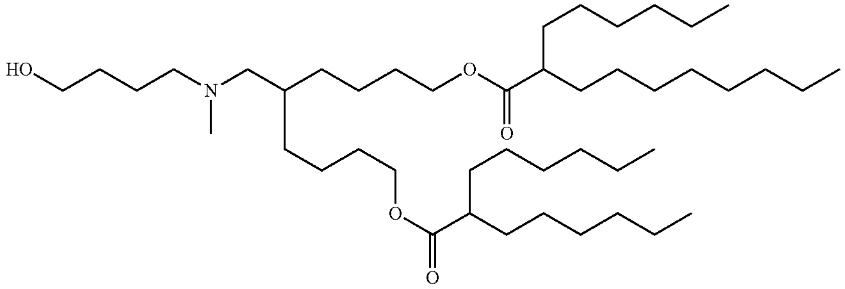 [SMILES: CCCCCCCCC(CCCCCC)C(=O)OCCCCC(CCCCOC(=O)C(CCCCCC)CCCCCC)CN(C)CCCCO] | 31 |
| 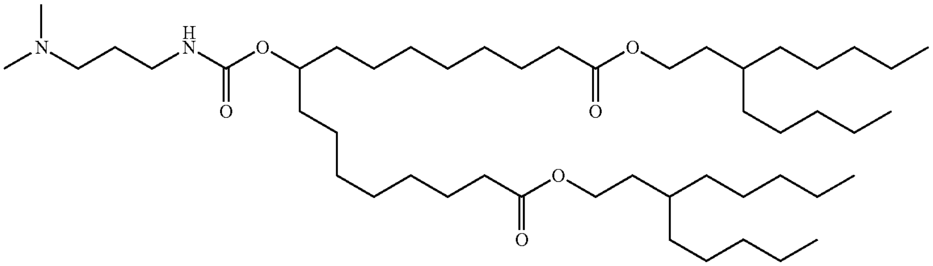 [SMILES: CCCCCC(CCCCC)CCOC(=O)CCCCCCCC(CCCCCCCC(=O)OCCC(CCCCC)CCCCC)OC(=O)NCCCN(C)C] | 32 |
| 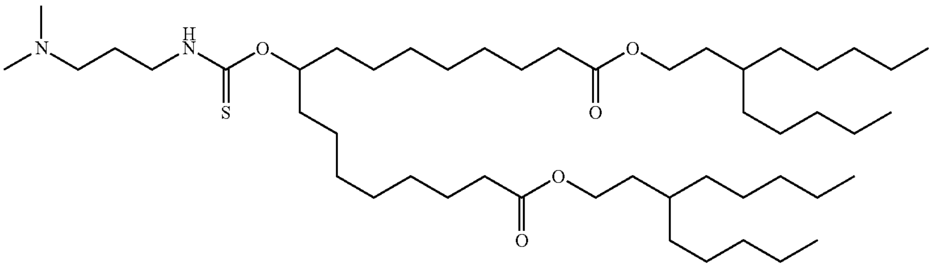 [SMILES: CCCCCC(CCCCC)CCOC(=O)CCCCCCCC(CCCCCCCC(=O)OCCC(CCCCC)CCCCC)OC(=S)NCCCN(C)C] | 33 |

TABLE (I)-continued
| Non-Limiting Examples of Ionizable Lipids with an Acyclic Core | |
|---|---|
| Structure | Cpd. |
| 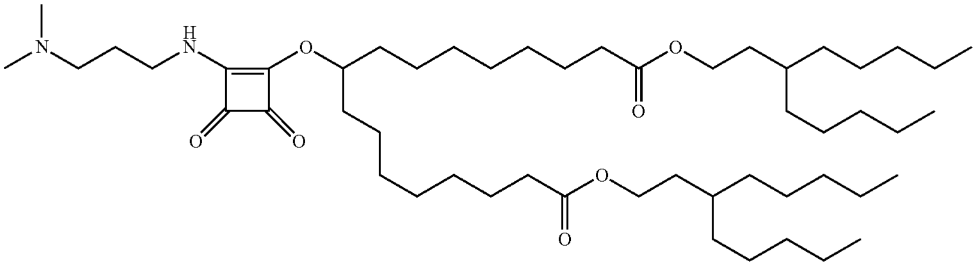 [SMILES: CCCCCC(CCCCC)CCOC(=O)CCCCCCCC(CCCCCCCC(=O)OCCC(CCCCC)CCCCC)Oc1c(NCCCN(C)C)c(=O)c1=O] | 34 |
| 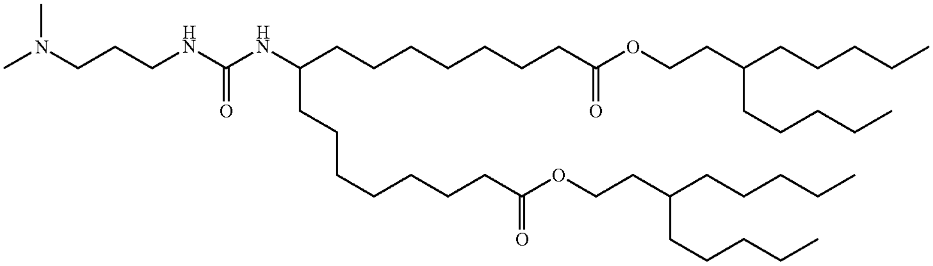 [SMILES: CCCCCC(CCCCC)CCOC(=O)CCCCCCCC(CCCCCCCC(=O)OCCC(CCCCC)CCCCC)NC(=O)NCCCN(C)C] | 35 |
| 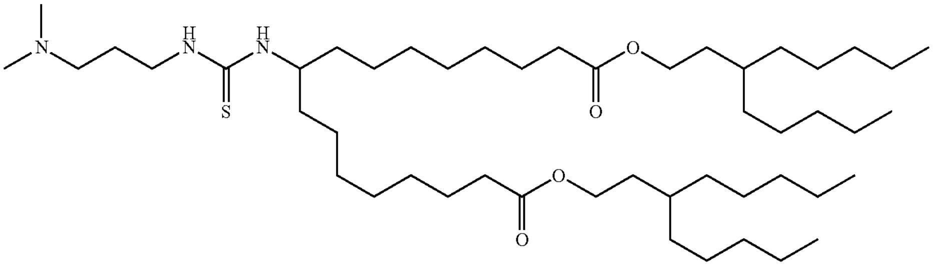 [SMILES: CCCCCC(CCCCC)CCOC(=O)CCCCCCCC(CCCCCCCC(=O)OCCC(CCCCC)CCCCC)NC(=S)NCCCN(C)C] | 36 |
| 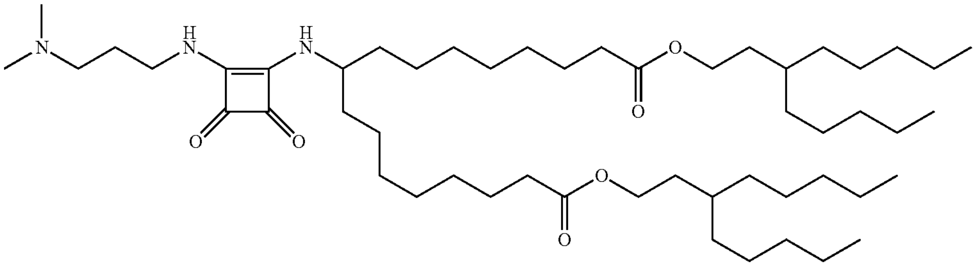 [SMILES: CCCCCC(CCCCC)CCOC(=O)CCCCCCCC(CCCCCCCC(=O)OCCC(CCCCC)CCCCC)Nc1c(NCCCN(C)C)c(=O)c1=O] | 37 |
| 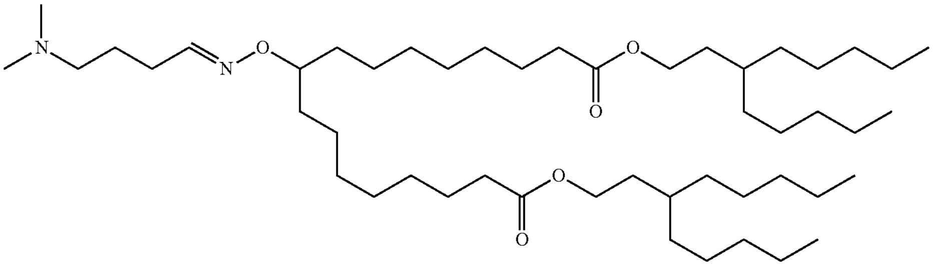 [SMILES: CCCCCC(CCCCC)CCOC(=O)CCCCCCCC(CCCCCCCC(=O)OCCC(CCCCC)CCCCC)O/N=C/CCCN(C)C] | 38 |

TABLE (I)-continued
| Non-Limiting Examples of Ionizable Lipids with an Acyclic Core | |
|---|---|
| Structure | Cpd. |
| 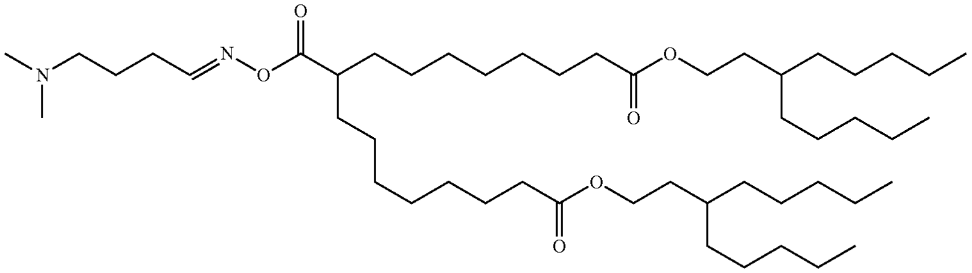 [SMILES: CCCCCC(CCCCC)CCOC(=O)CCCCCCCC(CCCCCCCC(=O)OCCC(CCCCC)CCCCC)C(=O)O/N=C/CCCN(C)C] | 39 |
| 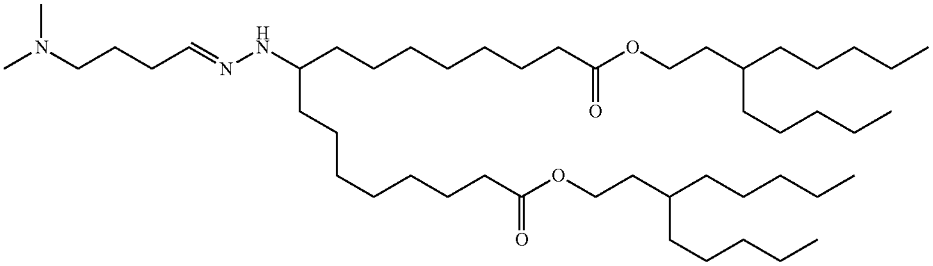 [SMILES: CCCCCC(CCCCC)CCOC(=O)CCCCCCCC(CCCCCCCC(=O)OCCC(CCCCC)CCCCC)N/N=C/CCCN(C)C] | 40 |
| 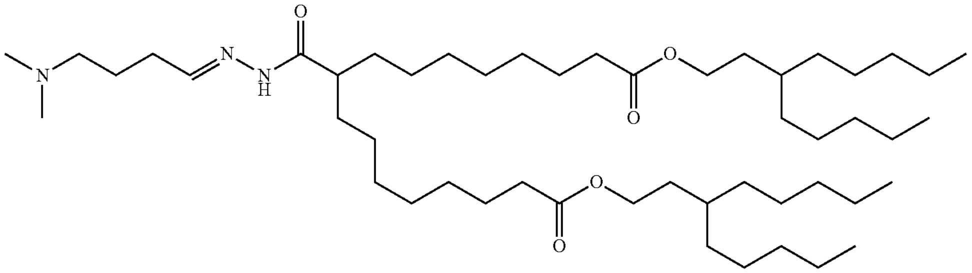 [SMILES: CCCCCC(CCCCC)CCOC(=O)CCCCCCCC(CCCCCCCC(=O)OCCC(CCCCC)CCCCC)C(=O)N/N=C/CCCN(C)C] | 41 |
| 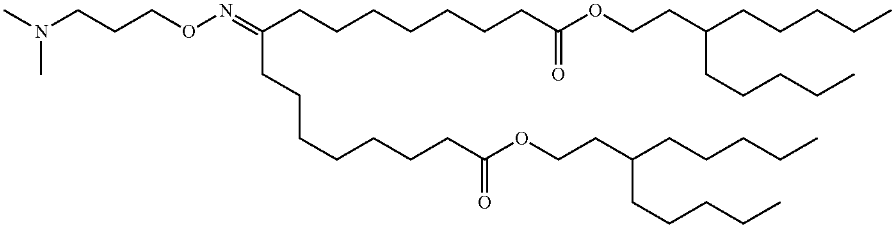 [SMILES: CCCCCC(CCCCC)CCOC(=O)CCCCCCCC(CCCCCCCC(=O)OCCC(CCCCC)CCCCC)=NOCCCN(C)C] | 42 |
| 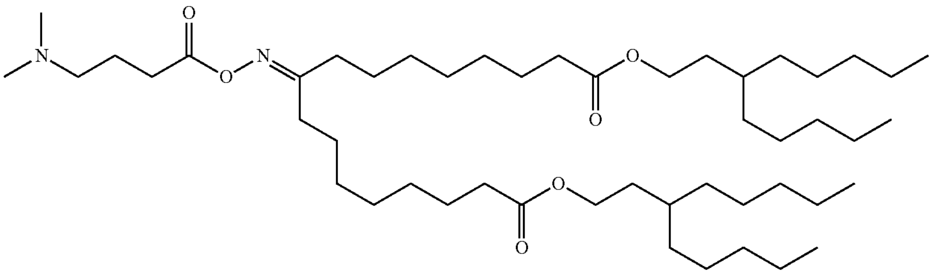 [SMILES: CCCCCC(CCCCC)CCOC(=O)CCCCCCCC(CCCCCCCC(=O)OCCC(CCCCC)CCCCC)=NOC(=O)CCCN(C)C] | 43 |

TABLE (I)-continued
| Non-Limiting Examples of Ionizable Lipids with an Acyclic Core | |
|---|---|
| Structure | Cpd. |
| 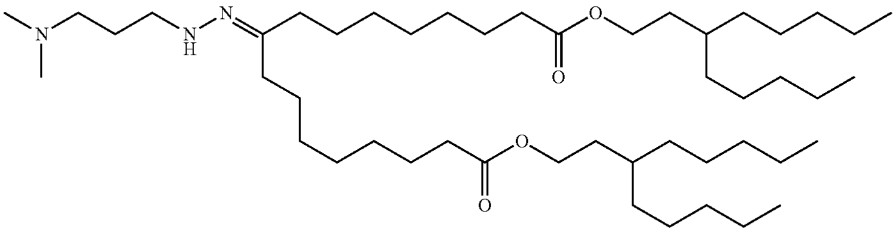 [SMILES: CCCCCC(CCCCC)CCOC(=O)CCCCCCCC(CCCCCCCC(=O)OCCC(CCCCC)CCCCC)=NNCCCN(C)C] | 44 |
| 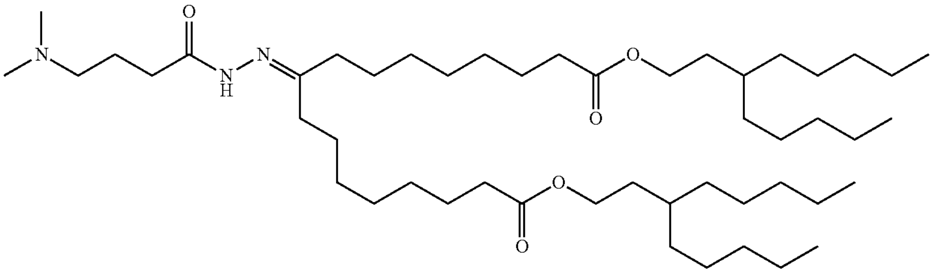 [SMILES: CCCCCC(CCCCC)CCOC(=O)CCCCCCCC(CCCCCCCC(=O)OCCC(CCCCC)CCCCC)=NNC(=O)CCCN(C)C] | 45 |
| 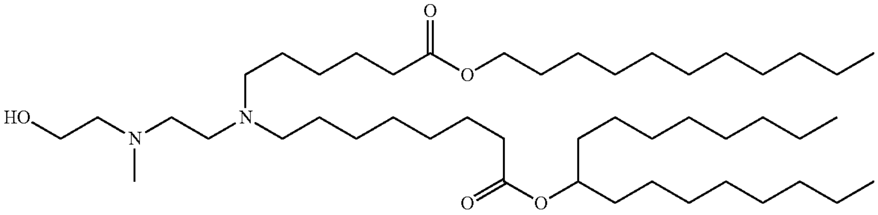 [SMILES: CCCCCCCCCCCOC(=O)CCCCCN(CCCCCCCC(=O)OC(CCCCCCCC)CCCCCCCC)CCN(C)CCO] | 46 |
| 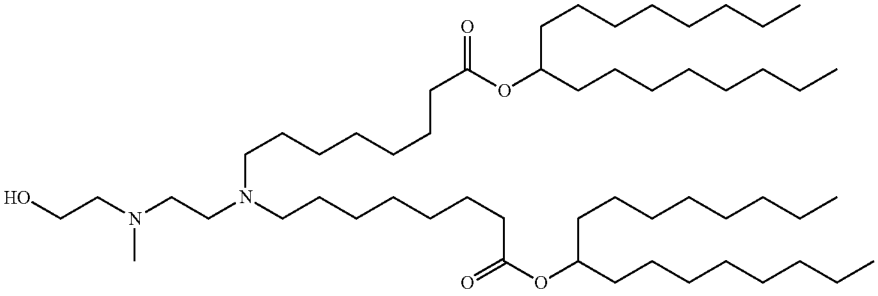 [SMILES: CCCCCCCCC(CCCCCCCC)OC(=O)CCCCCCCN(CCCCCCCC(=O)OC(CCCCCCCC)CCCCCCCC)CCN(C)CCO] | 47 |
| 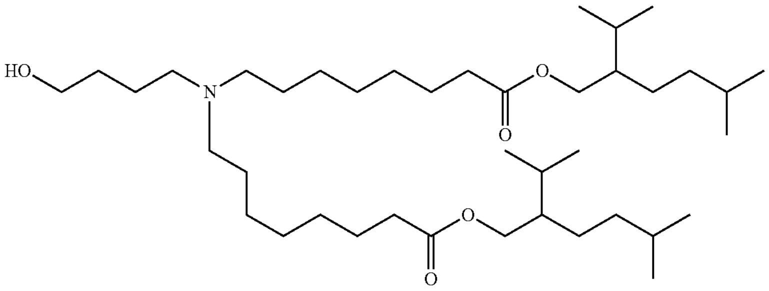 [SMILES: CC(C)CCC(COC(=O)CCCCCCCN(CCCCO)CCCCCCCC(=O)OCC(CCC(C)C)C(C)C)C(C)C] | 48 |

TABLE (I)-continued
| Non-Limiting Examples of Ionizable Lipids with an Acyclic Core | |
|---|---|
| Structure | Cpd. |
| 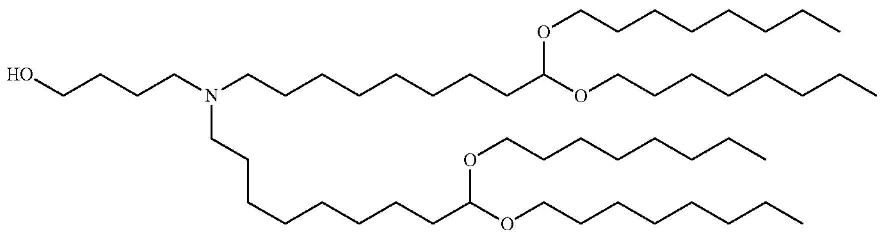 [SMILES: CCCCCCCCOC(CCCCCCCCN(CCCCO)CCCCCCCCC(OCCCCCCCC)OCCCCCCCC)OCCCCCCCC] | 49 |
| 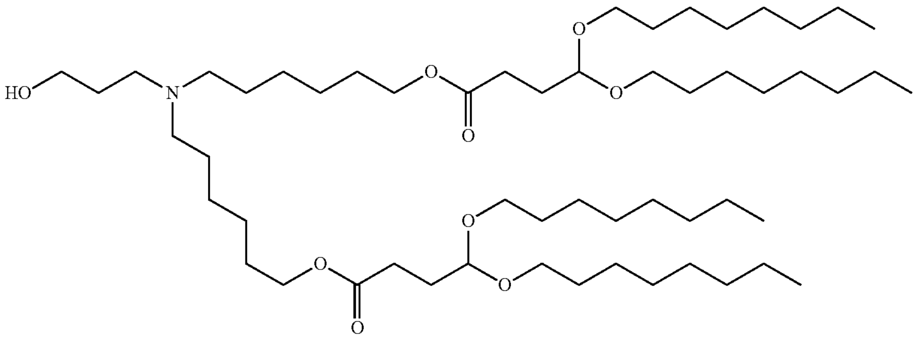 [SMILES: CCCCCCCCOC(CCC(=O)OCCCCCCN(CCCO)CCCCCCOC(=O)CCC(OCCCCCCCC)OCCCCCCCC)OCCCCCCCC] | 50 |
| | 51 |
| | 52 |
| | 53 |
| | 54 |
| | 55 |
| 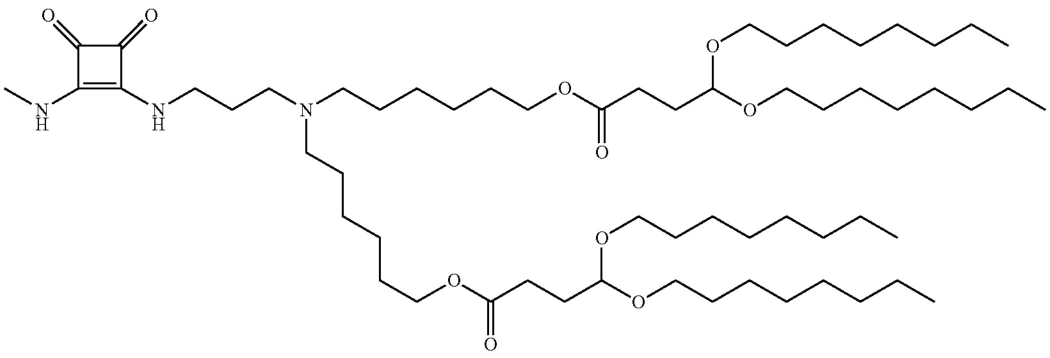 [SMILES: CCCCCCCCOC(CCC(=O)OCCCCCCN(CCCCCCOC(=O)CCC(OCCCCCCCC)OCCCCCCCC)CCCNc1c(NC)c(=O)c1=O)OCCCCCCCC] | 56 |
| 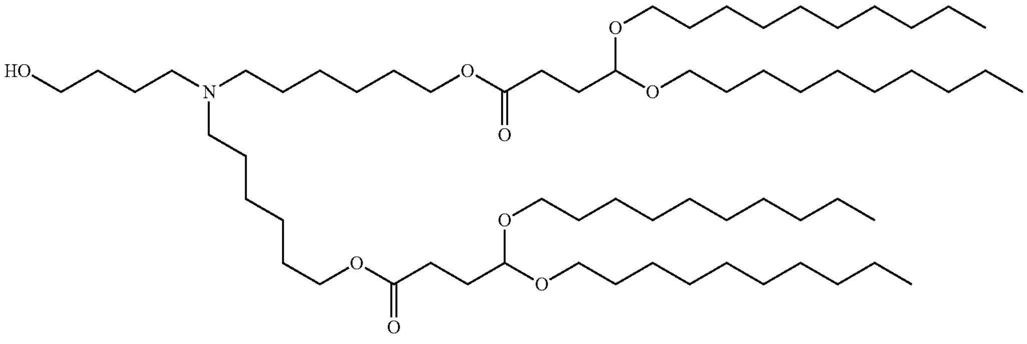 [SMILES: CCCCCCCCCCOC(CCC(=O)OCCCCCCN(CCCCO)CCCCCCOC(=O)CCC(OCCCCCCCCCC)OCCCCCCCCCC)OCCCCCCCCCC] | 57 |

TABLE (I)-continued
Non-Limiting Examples of Ionizable Lipids with an Acyclic Core
| Structure | Cpd. |
| --- | --- |
| 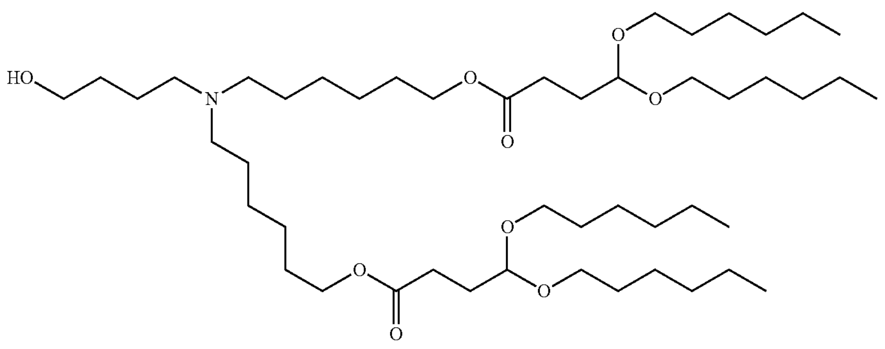 [SMILES: CCCCCCOC(CCC(=O)OCCCCCCN(CCCCO)CCCCCCOC(=O)CCC(OCCCCCC)OCCCCCC)OCCCCCC] | 58 |
| 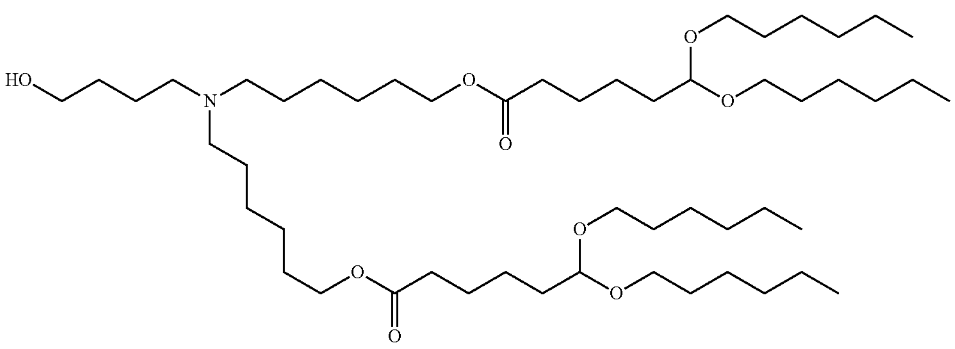 [SMILES: CCCCCCOC(CCCCC(=O)OCCCCCCN(CCCCO)CCCCCCOC(=O)CCCCC(OCCCCCC)OCCCCCC)OCCCCCC] | 59 |
| 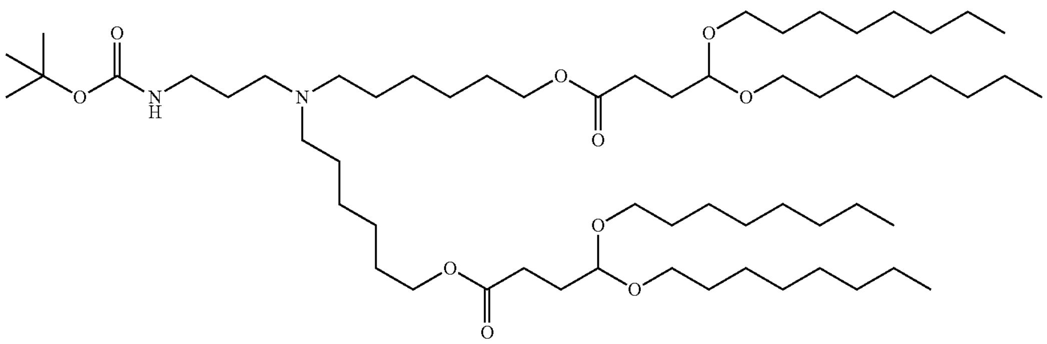 [SMILES: CCCCCCCCOC(CCC(=O)OCCCCCCN(CCCCCCOC(=O)CCC(OCCCCCCCC)OCCCCCCCC)CCCNC(=O)OC(C)(C)C)OCCCCCCCC] | 60 |
| 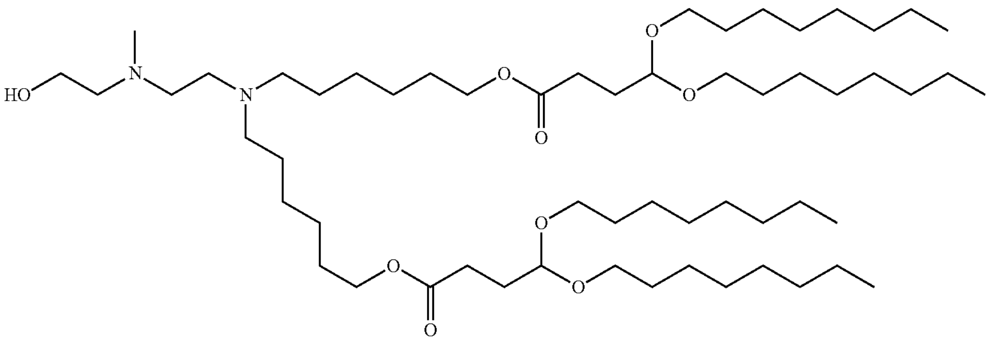 [SMILES: CCCCCCCCOC(CCC(=O)OCCCCCCN(CCCCCCOC(=O)CCC(OCCCCCCCC)OCCCCCCCC)CCN(C)CCO)OCCCCCCCC] | 61 |

TABLE (I)-continued
Non-Limiting Examples of Ionizable Lipids with an Acyclic Core
| Structure | Cpd. |
| --- | --- |
| 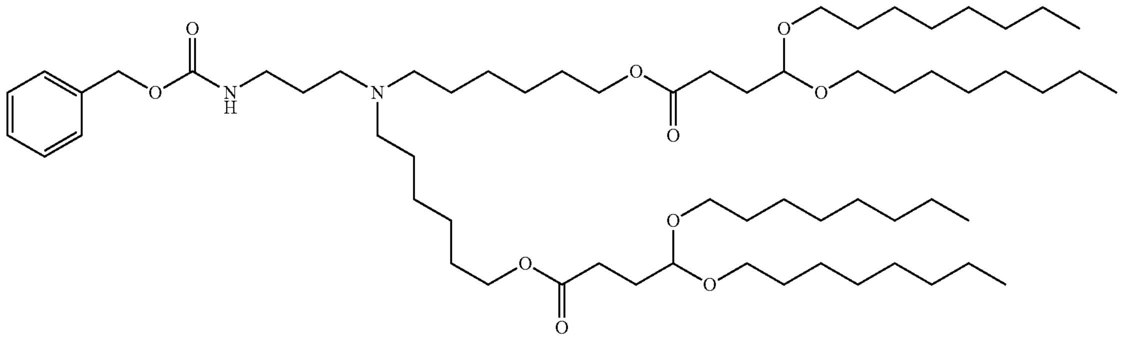 [SMILES: CCCCCCCCOC(CCC(=O)OCCCCCCN(CCCCCCOC(=O)CCC(OCCCCCCCC)OCCCCCCCC)CCCNC(=O)OCc1ccccc1)OCCCCCCCC] | 62 |
| 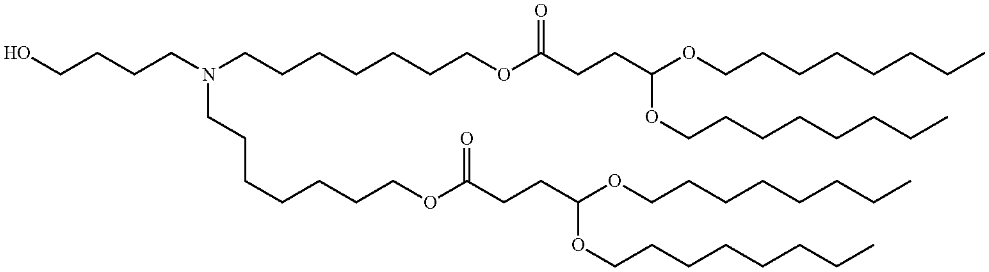 [SMILES: CCCCCCCCOC(CCC(=O)OCCCCCCCN(CCCCO)CCCCCCCOC(=O)CCC(OCCCCCCCC)OCCCCCCCC)OCCCCCCCC] | 64 |
| 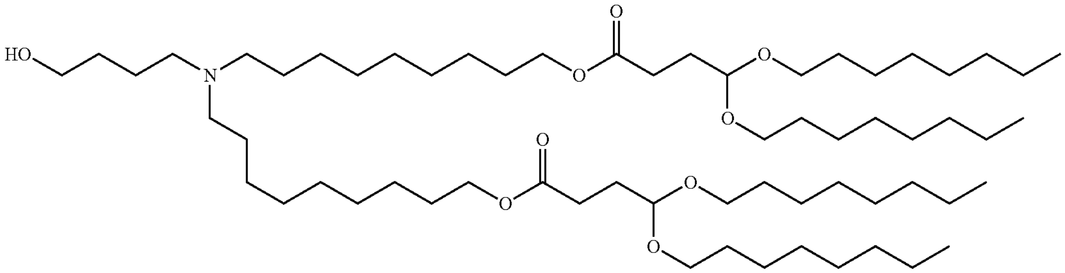 [SMILES: CCCCCCCCOC(CCC(=O)OCCCCCCCCCN(CCCCO)CCCCCCCCCOC(=O)CCC(OCCCCCCCC)OCCCCCCCC)OCCCCCCCC] | 65 |
| 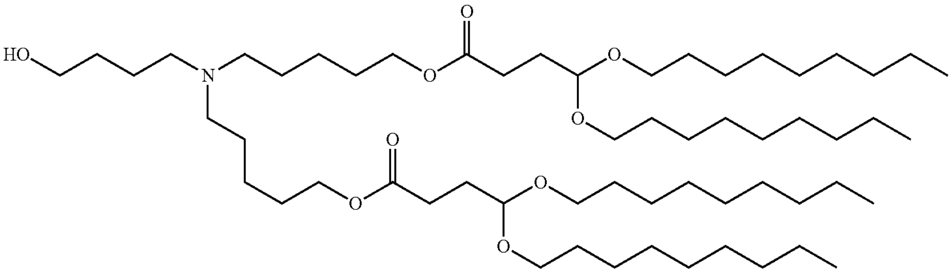 [SMILES: CCCCCCCCCOC(CCC(=O)OCCCCCN(CCCCO)CCCCCOC(=O)CCC(OCCCCCCCCC)OCCCCCCCCC)OCCCCCCCCC] | 66 |
| 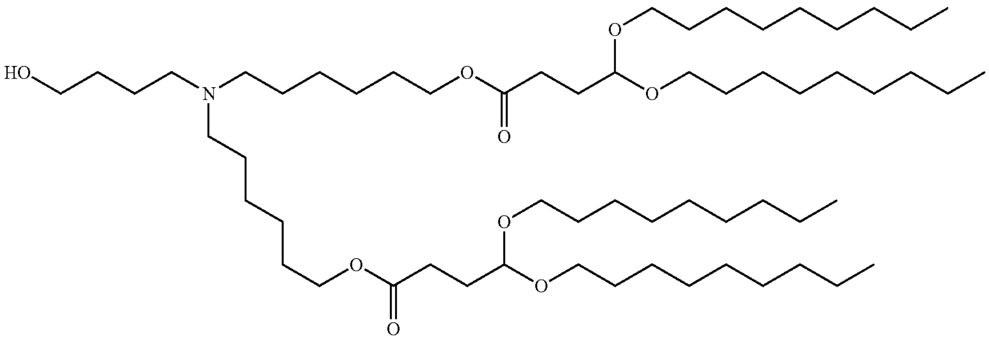 [SMILES: CCCCCCCCCOC(CCC(=O)OCCCCCCN(CCCCO)CCCCCCOC(=O)CCC(OCCCCCCCCC)OCCCCCCCCC)OCCCCCCCCC] | 67 |

TABLE (I)-continued
| Non-Limiting Examples of Ionizable Lipids with an Acyclic Core | |
|---|---|
| Structure | Cpd. |
| 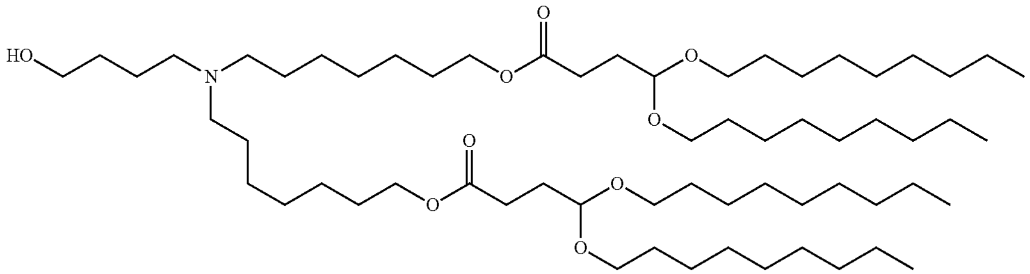 [SMILES: CCCCCCCCCOC(CCC(=O)OCCCCCCCN(CCCCO)CCCCCCCOC(=O)CCC(OCCCCCCCCC)OCCCCCCCCC)OCCCCCCCCC] | 68 |
| 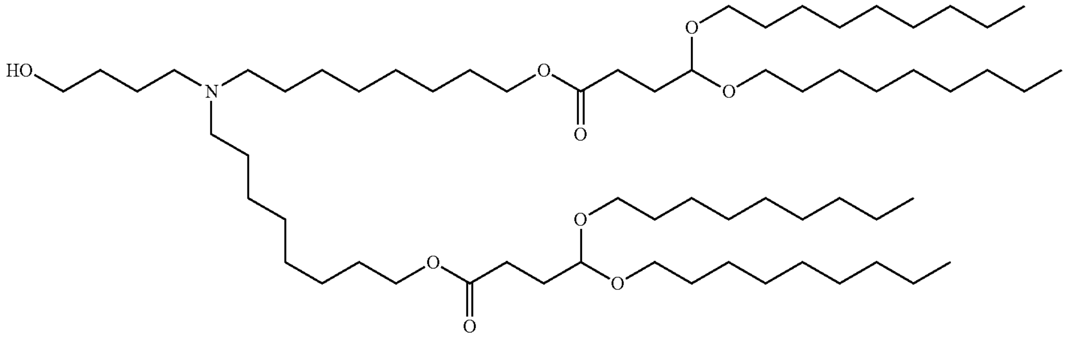 [SMILES: CCCCCCCCCOC(CCC(=O)OCCCCCCCCN(CCCCO)CCCCCCCCOC(=O)CCC(OCCCCCCCCC)OCCCCCCCCC)OCCCCCCCCC] | 69 |
| 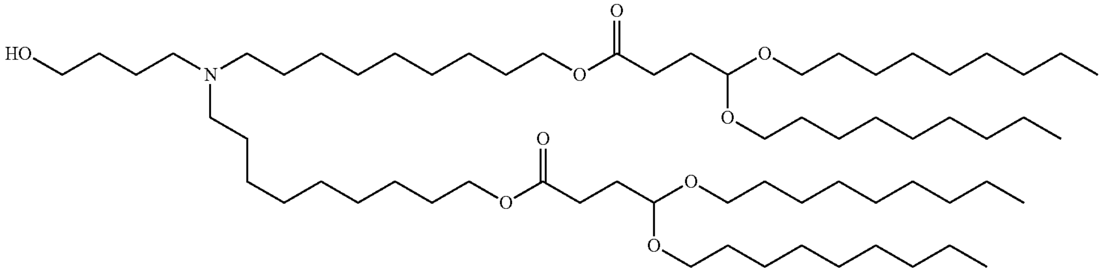 [SMILES: CCCCCCCCCOC(CCC(=O)OCCCCCCCCCN(CCCCO)CCCCCCCCCOC(=O)CCC(OCCCCCCCCC)OCCCCCCCCC)OCCCCCCCCC] | 70 |
| 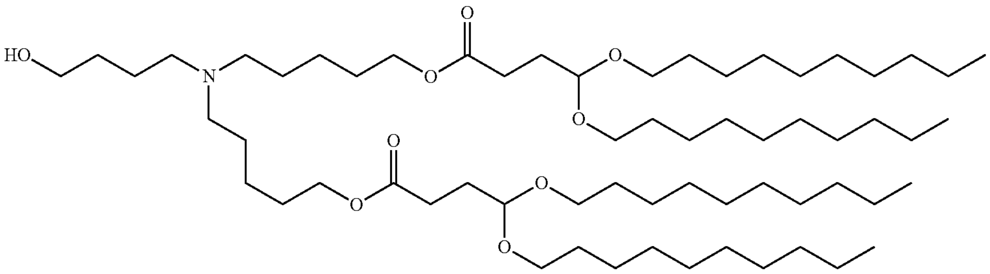 [SMILES: CCCCCCCCCCOC(CCC(=O)OCCCCCN(CCCCO)CCCCCOC(=O)CCC(OCCCCCCCCCC)OCCCCCCCCCC)OCCCCCCCCCC] | 71 |
| 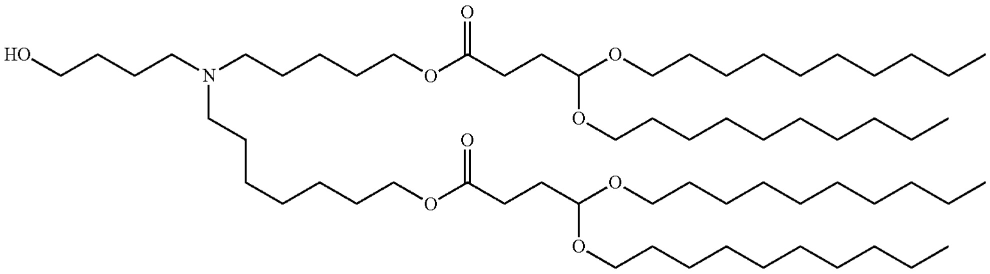 [SMILES: CCCCCCCCCCOC(CCC(=O)OCCCCCCCN(CCCCO)CCCCCOC(=O)CCC(OCCCCCCCCCC)OCCCCCCCCCC)OCCCCCCCCCC] | 72 |

TABLE (I)-continued
Non-Limiting Examples of Ionizable Lipids with an Acyclic Core
| Structure | Cpd. |
| --- | --- |
| 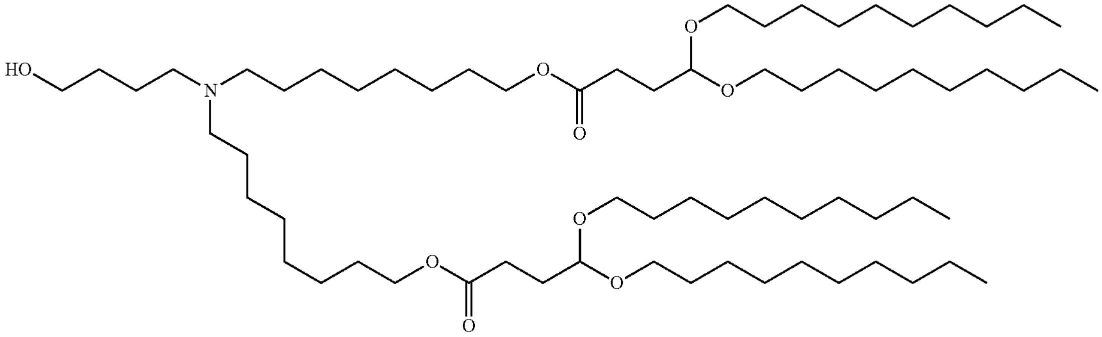 [SMILES: CCCCCCCCCCOC(CCC(=O)OCCCCCCCCN(CCCCO)CCCCCCCCOC(=O)CCC(OCCCCCCCCCC)OCCCCCCCCCC)OCCCCCCCCCC] | 73 |
| 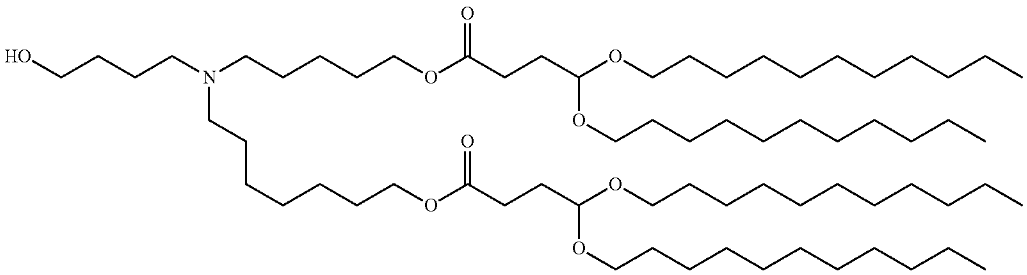 [SMILES: CCCCCCCCCCCOC(CCC(=O)OCCCCCCCN(CCCCO)CCCCCOC(=O)CCC(OCCCCCCCCCCC)OCCCCCCCCCCC)OCCCCCCCCCCC] | 74 |
| 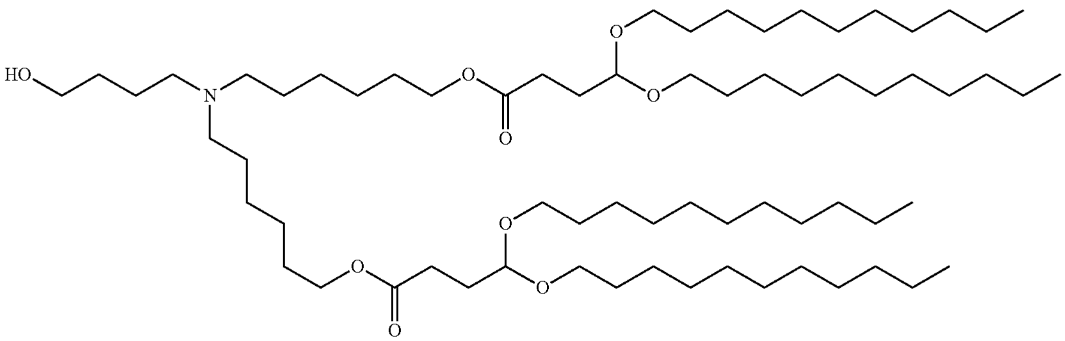 [SMILES: CCCCCCCCCCCOC(CCC(=O)OCCCCCCN(CCCCO)CCCCCCOC(=O)CCC(OCCCCCCCCCCC)OCCCCCCCCCCC)OCCCCCCCCCCC] | 75 |
| 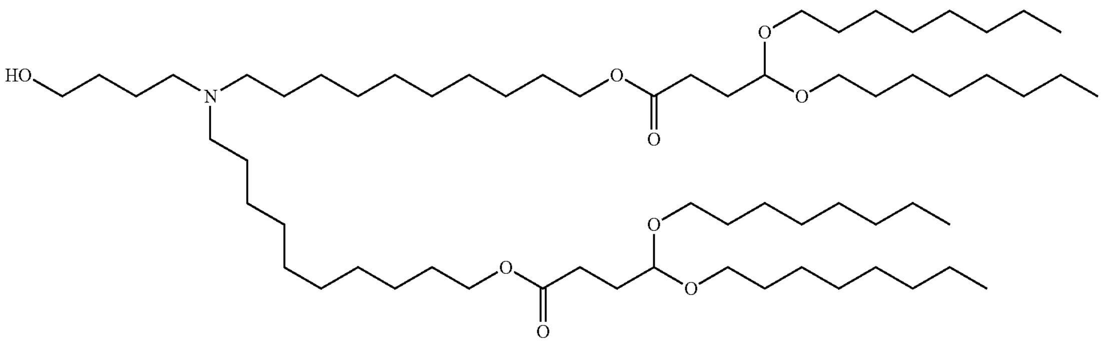 [SMILES: CCCCCCCCOC(CCC(=O)OCCCCCCCCCCN(CCCCO)CCCCCCCCCCOC(=O)CCC(OCCCCCCCC)OCCCCCCCC)OCCCCCCCC] | 76 |

TABLE (I)-continued
| Non-Limiting Examples of Ionizable Lipids with an Acyclic Core | |
|---|---|
| Structure | Cpd. |
| 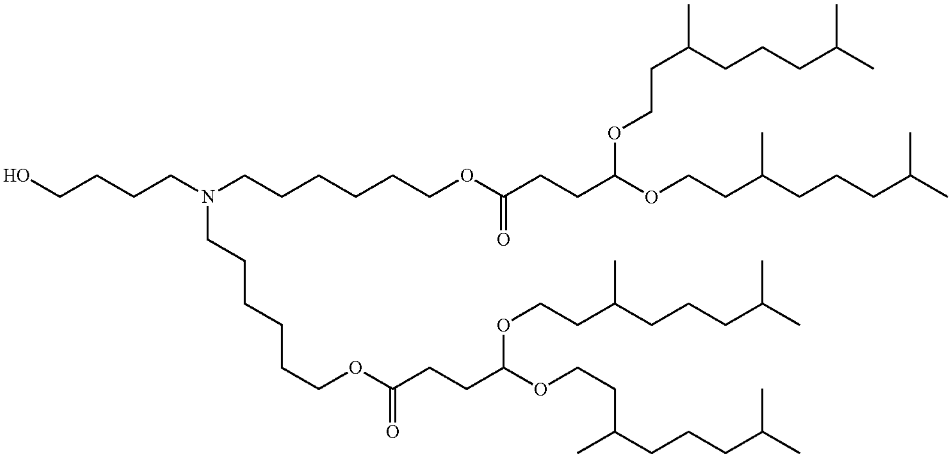 [SMILES: CC(C)CCCC(C)CCOC(CCC(=O)OCCCCCCN(CCCCO)CCCCCCOC(=O)CCC(OCCC(C)CCCC(C)C)OCCC(C)CCCC(C)C)OCCC(C)CCCC(C)C] | 77 |
| 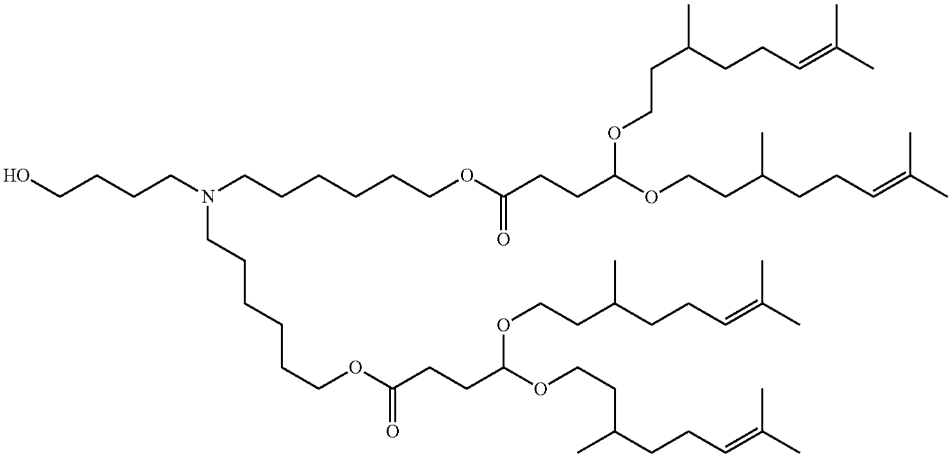 [SMILES: CC(C)=CCCC(C)CCOC(CCC(=O)OCCCCCCN(CCCCO)CCCCCCOC(=O)CCC(OCCC(C)CCC=C(C)C)OCCC(C)CCC=C(C)C)OCCC(C)CCC=C(C)C] | 78 |
| 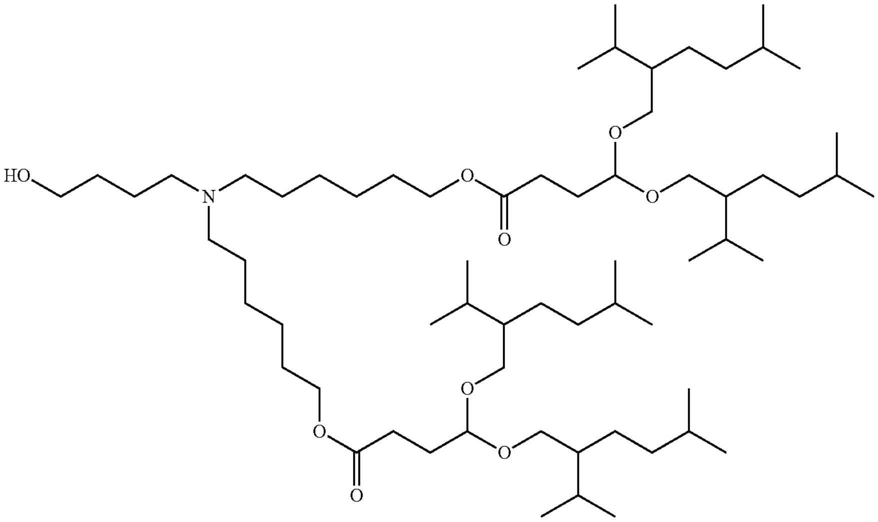 [SMILES: CC(C)CCC(COC(CCC(=O)OCCCCCCN(CCCCO)CCCCCCOC(=O)CCC(OCC(CCC(C)C)C(C)C)OCC(CCC(C)C)C(C)C)OCC(CCC(C)C)C(C)C)C(C)C] | 79 |

TABLE (I)-continued
Non-Limiting Examples of Ionizable Lipids with an Acyclic Core
| Structure | Cpd. |
| --- | --- |
| 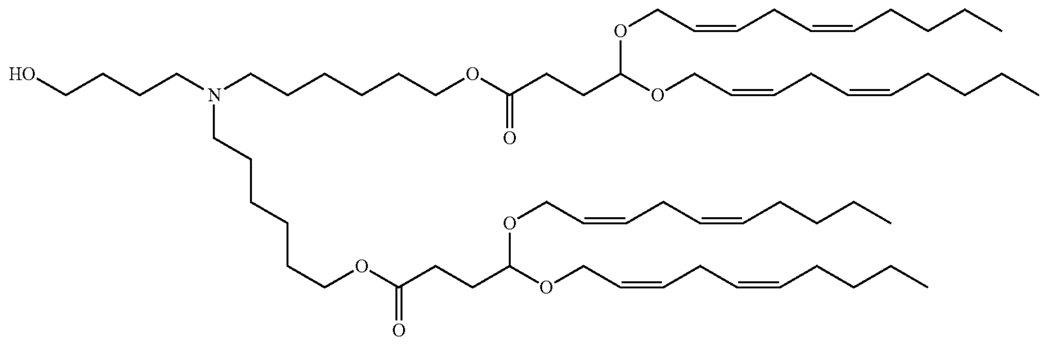 [SMILES: CCCC/C=C\C/C=C\COC(CCC(=O)OCCCCCCN(CCCCO)CCCCCCOC(=O)CCC(OC/C=C\C/C=C\CCCC)OC/C=C\C/C=C\CCCC)OC/C=C\C/C=C\CCCC] | 80 |
| 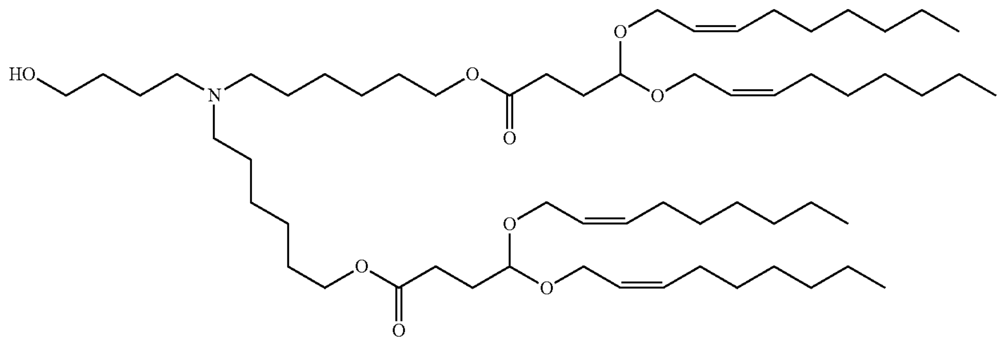 [SMILES: CCCCCC/C=C\COC(CCC(=O)OCCCCCCN(CCCCO)CCCCCCOC(=O)CCC(OC/C=C\CCCCCC)OC/C=C\CCCCCC)OC/C=C\CCCCCC] | 81 |
| 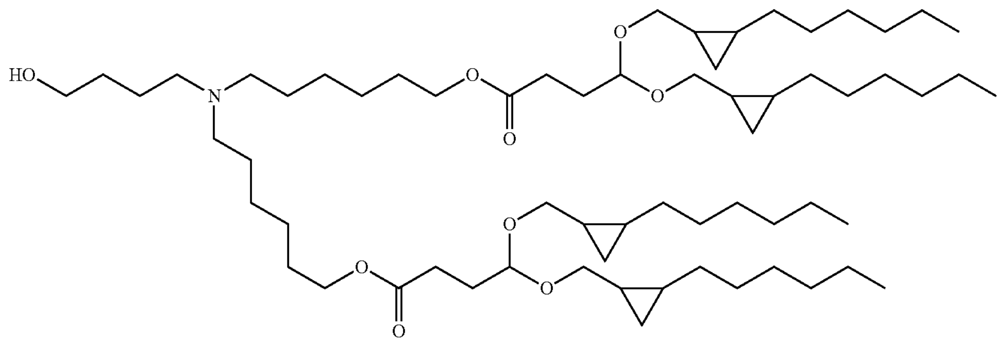 [SMILES: CCCCCCC1CC1COC(CCC(=O)OCCCCCCN(CCCCO)CCCCCCOC(=O)CCC(OCC1CC1CCCCCC)OCC1CC1CCCCCC)OCC1CC1CCCCCC] | 82 |

TABLE (I)-continued
| Non-Limiting Examples of Ionizable Lipids with an Acyclic Core | |
|---|---|
| Structure | Cpd. |
| 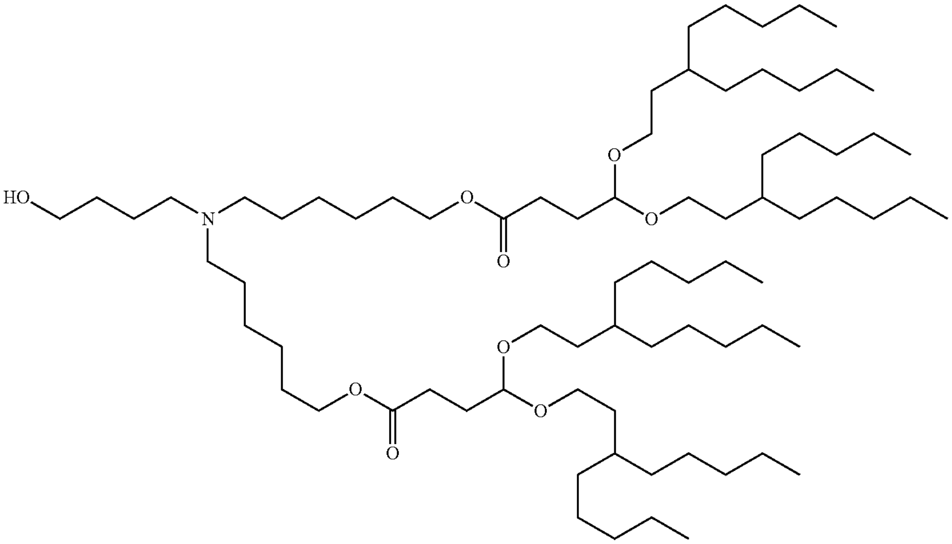 [SMILES: CCCCCC(CCCCC)CCOC(CCC(=O)OCCCCCCN(CCCCO)CCCCCCOC(=O)CCC(OCCC(CCCCC)CCCCC)OCCC(CCCCC)CCCCC)OCCC(CCCCC)CCCCC] | 83 |
| 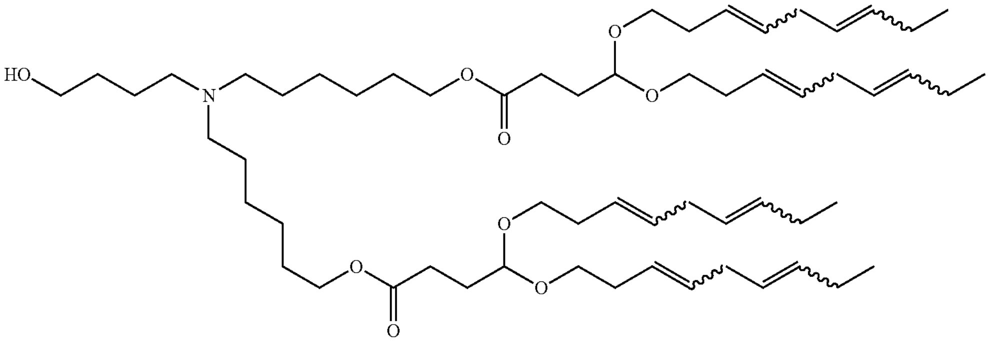 [SMILES: CCC=CCC=CCCOC(CCC(=O)OCCCCCCN(CCCCO)CCCCCCOC(=O)CCC(OCCC=CCC=CCC)OCCC=CCC=CCC)OCCC=CCC=CCC] | 84 |
| 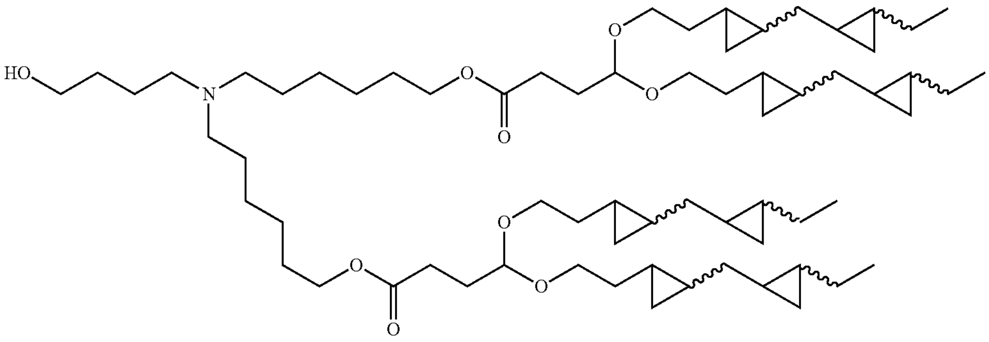 [SMILES: CCC1CC1CC1CC1CCOC(CCC(=O)OCCCCCCN(CCCCO)CCCCCCOC(=O)CCC(OCCC1CC1CC1CC1CC)OCCC1CC1CC1CC1CC)OCCC1CC1CC1CC1CC] | 85 |

TABLE (I)-continued
| Non-Limiting Examples of Ionizable Lipids with an Acyclic Core | |
|---|---|
| Structure | Cpd. |
| 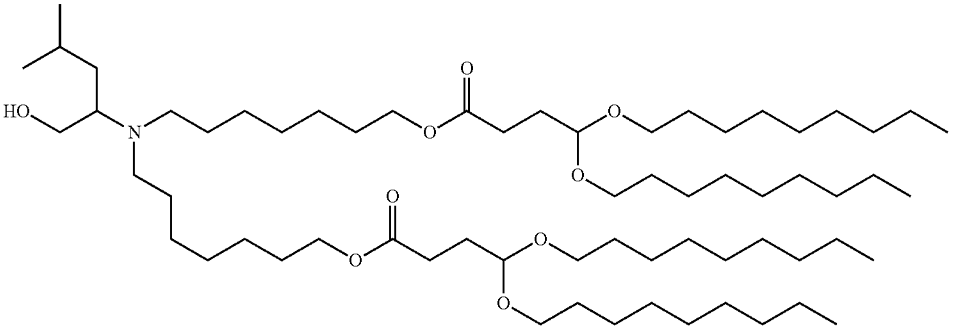 [SMILES: CCCCCCCCCOC(CCC(=O)OCCCCCCCN(CCCCCCCOC(=O)CCC(OCCCCCCCCC)OCCCCCCCCC)C(CO)CC(C)C)OCCCCCCCCC] | 86 |
| 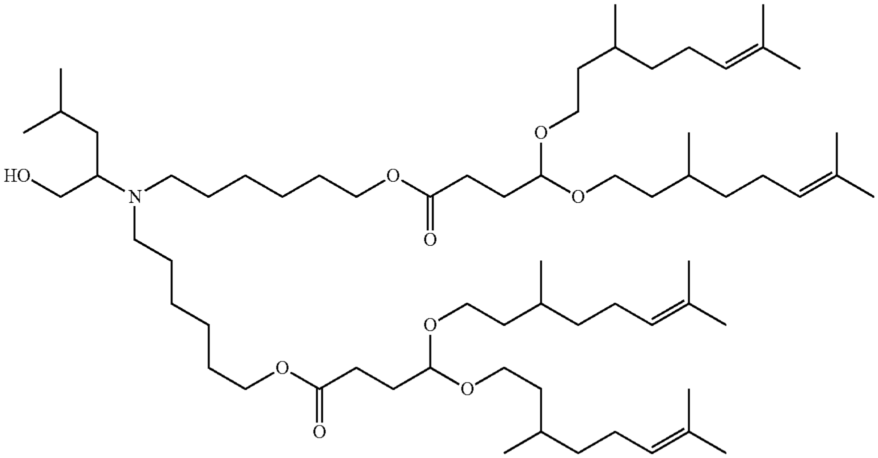 [SMILES: CC(C)=CCCC(C)CCOC(CCC(=O)OCCCCCCN(CCCCCCOC(=O)CCC(OCCC(C)CCC=C(C)C)OCCC(C)CCC=C(C)C)C(CO)CC(C)C)OCCC(C)CCC=C(C)C] | 87 |
| 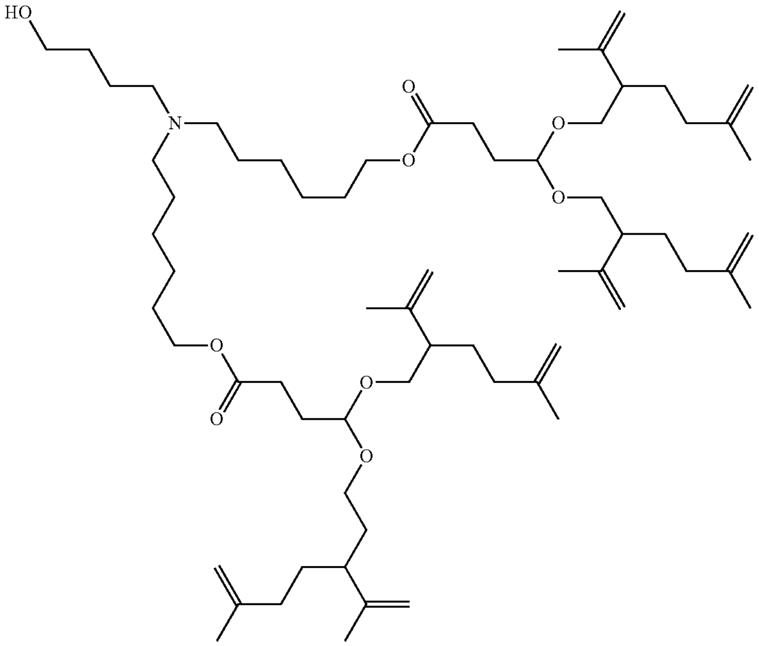 [SMILES: C=C(C)CCC(CCOC(CCC(=O)OCCCCCCN(CCCCO)CCCCCCOC(=O)CCC(OCC(CCC(=C)C)C(=C)C)OCC(CCC(=C)C)C(=C)C)OCC(CCC(=C)C)C(=C)C)C(=C)C] | 88 |

TABLE (I)-continued

| Non-Limiting Examples of Ionizable Lipids with an Acyclic Core | |
|---|---|
| Structure | Cpd. |
| 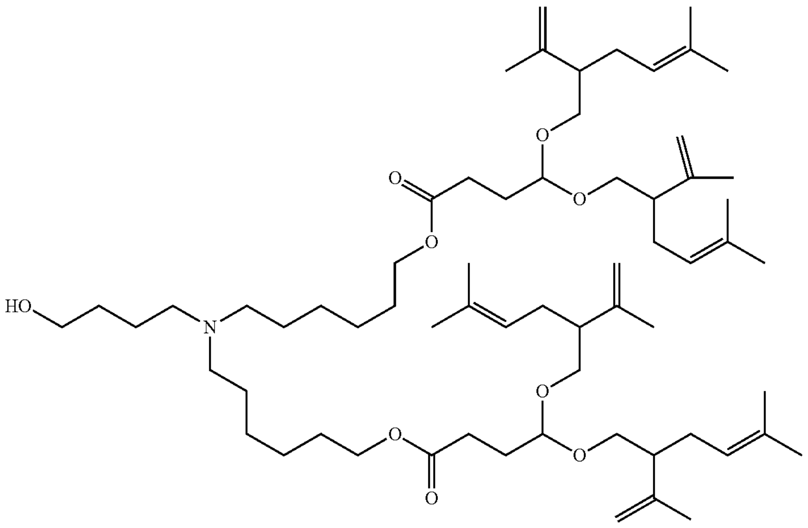 [SMILES: C=C(C)C(CC=C(C)C)COC(CCC(=O)OCCCCCCN(CCCCO)CCCCCCOC(=O)CCC(OCC(CC=C(C)C)C(=C)C)OCC(CC=C(C)C)C(=C)C)OCC(CC=C(C)C)C(=C)C] | 89 |

In some embodiments, Lipids of the Disclosure have a structure of Formula (VII-A):

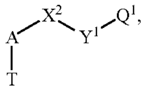

(VII-A)

or a pharmaceutically acceptable salt thereof, wherein:

A is $-N(-X^1R^1)-$, $-C(R')(-L^1\text{-}N(R'')R^6)-$, $-C(R')(-OR^{7a})-$, $-C(R')(-N(R'')R^{8a})-$, $-C(R')(-C(=O)OR^{9a})-$, $-C(R')(-C(=O)N(R'')R^{10a})-$, or $-C(=N-R^{11a})-$;

T is $-X^{2a}-Y^{1a}\text{-}Q^{1a}$ or $-X^3-C(=O)OR^4$;

$X^1$ is optionally substituted $C_2$-$C_6$ alkylenyl;

$R^1$ is $-OH$, $-R^{1a}$,

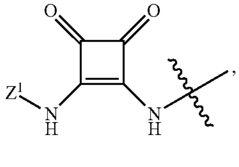

, or

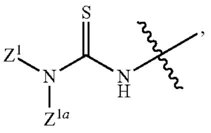

, $Z^1$ is optionally substituted $C_1$-$C_6$ alkyl;

$Z^{1a}$ is hydrogen or optionally substituted $C_1$-$C_6$ alkyl;

$X^2$ and $X^{2a}$ are independently optionally substituted $C_2$-$C_{14}$ alkylenyl or optionally substituted $C_2$-$C_{14}$ alkenylenyl;

$X^3$ is optionally substituted $C_2$-$C_{14}$ alkylenyl or optionally substituted $C_2$-$C_{14}$ alkenylenyl;

(i) $Y^1$ is

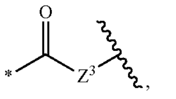

,

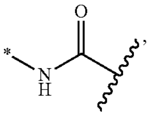

,

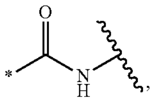

,

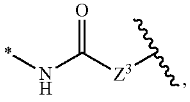

,

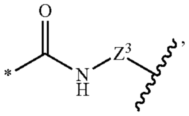

,

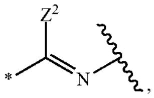

, or

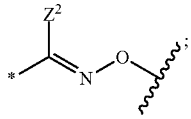

;

wherein the bond marked with an "*" is attached to $X^2$; $Y^{1a}$ is

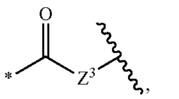

,

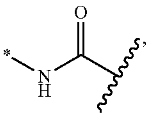

,

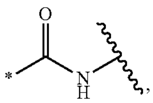

,

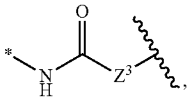

,

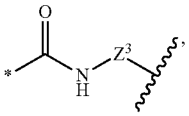

,

-continued

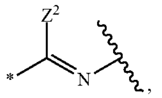, or 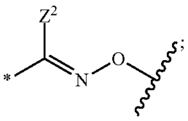;

wherein the bond marked with an "*" is attached to $X^{2a}$; each $Z^2$ is independently H or optionally substituted $C_1$-$C_8$ alkyl;

each $Z^3$ is indpendently optionally substituted $C_1$-$C_6$ alkylenyl;

$Q^1$ is —$NR^2R^3$, —$CH(OR^2)(OR^3)$, —$CR^2$=$C(R^3)(R^{12})$, or —$C(R^2)(R^3)(R^{12})$;

$Q^{1a}$ is —$NR^{2'}R^{3'}$, —$CH(OR^{2'})(OR^{3'})$, —$CR^{2'}$=$C(R^{3'})(R^{12'})$, or —$C(R^{2'})(R^{3'})(R^{12'})$; or (ii) $Y^1$ is

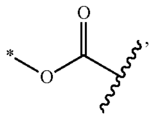, 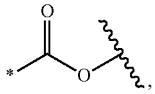, 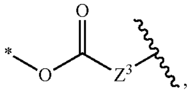, or 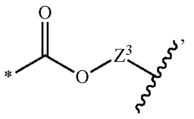, wherein the bond marked with an "*" is attached to $X^2$;

$Y^{1a}$ is

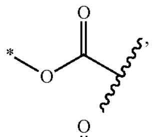, 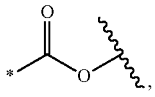, 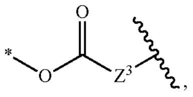, or 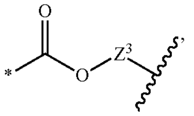, wherein the bond marked with an "*" is attached to $X^{2a}$:

each $Z^2$ is independently H or optionally substituted $C_1$-$C_8$ alkyl;

each $Z^3$ is independently optionally substituted $C_1$-$C_6$ alkylenyl;

$Q^1$ is —$NR^2R^3$;

$Q^{1a}$ is —$NR^{2'}R^{3'}$;

$R^2$, $R^3$, and $R^{12}$ are independently hydrogen, optionally substituted $C_1$-$C_{14}$ alkyl, optionally substituted $C_2$-$C_{14}$ alkenylenyl, or —$(CH_2)_m$-G-$(CH_2)_n$H;

$R^{2'}$, $R^{3'}$, and $R^{12'}$ are independently hydrogen, optionally substituted $C_1$-$C_{14}$ alkyl, optionally substituted $C_2$-$C_{14}$ alkenylenyl, or —$(CH_2)_m$-G-$(CH_2)_n$H;

G is a $C_3$-$C_8$ cycloalkylenyl;

each m is independently 0, 1, 2, 3, 4, 5, 6, 7, 8, 9, 10, 11, or 12;

each n is independently 0, 1, 2, 3, 4, 5, 6, 7, 8, 9, 10, 11, or 12;

$X^3$ is optionally substituted $C_2$-$C_{14}$ alkylenyl;

$R^4$ is optionally substituted $C_4$-$C_{14}$ alkyl;

$L^1$ is $C_1$-$C_8$ alkylenyl;

$R^6$ is $C_1$-$C_6$ alkyl, (hydroxy)$C_1$-$C_6$ alkyl, or (amino)$C_1$-$C_6$ alkyl $R^{7a}$ is —C(=O)N(R''')$R^{7b}$, —C(=S)N(R''')$R^{7b}$, —N=C$(R^{7b})(R^{7c})$, or

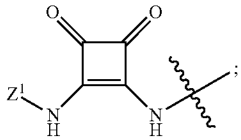;

$R^{7b}$ is $C_1$-$C_6$ alkyl, (hydroxy)$C_1$-$C_6$ alkyl, or (amino)$C_1$-$C_6$ alkyl;

$R^{7c}$ is hydrogen or $C_1$-$C_6$ alkyl;

$R^{8a}$ is —C(=O)N(R''')$R^{8b}$, —C(=S)N(R''')$R^{8b}$, —N=C$(R^{8b})(R^{8c})$, or

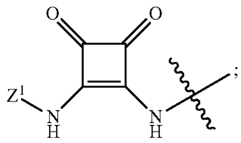;

$R^{8b}$ is $C_1$-$C_6$ alkyl, (hydroxy)$C_1$-$C_6$ alkyl, or (amino)$C_1$-$C_6$ alkyl;

$R^{8c}$ is hydrogen or $C_1$-$C_6$ alkyl;

$R^{9a}$ is —N=C$(R^{9b})(R^{9c})$;

$R^{9b}$ is $C_1$-$C_6$ alkyl, (hydroxy)$C_1$-$C_6$ alkyl, or (amino)$C_1$-$C_6$ alkyl;

$R^{9c}$ is hydrogen or $C_1$-$C_6$ alkyl;

$R^{10a}$ is —N=C$(R^{10b})(R^{10c})$;

$R^{10b}$ is $C_1$-$C_6$ alkyl, (hydroxy)$C_1$-$C_6$ alkyl, or (amino)$C_1$-$C_6$ alkyl;

$R^{10c}$ is hydrogen or $C_1$-$C_6$ alkyl;

$R^{11a}$ is —$OR^{11b}$, —N(R'')$R^{11b}$, —OC(=O)$R^{11b}$ or —N(R'')C(=O)$R^{11b}$;

$R^{11b}$ is $C_1$-$C_6$ alkyl, (hydroxy)$C_1$-$C_6$ alkyl, or (amino)$C_1$-$C_6$ alkyl;

R' is hydrogen or $C_1$-$C_6$ alkyl;

R'' is hydrogen or $C_1$-$C_6$ alkyl; and

R''' is hydrogen or $C_1$-$C_6$ alkyl

In some embodiments, Lipids of the Disclosure have a structure of Formula (VII-A), wherein the Lipids of the Disclosure have a structure of Formula (VIII-A):

(VIII-A)

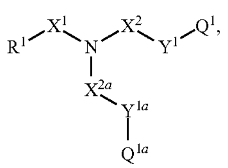

or a pharmaceutically acceptable salt thereof.

In some embodiments, Lipids of the Disclosure have a structure of Formula (VII-A), wherein the Lipids of the Disclosure have a structure of Formula (IX-A):

(IX-A)

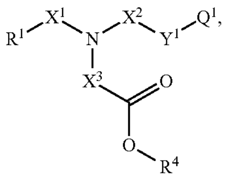

or a pharmaceutically acceptable salt thereof.

In some embodiments, Lipids of the Disclosure have a structure of Formula (VII-A), wherein A is —N(—$X^1R^1$)—.

In some embodiments, Lipids of the Disclosure have a structure of Formula (VII-A), wherein T is —$X^{2a}$—$Y^{1a}$-$Q^{1a}$.

In some embodiments, Lipids of the Disclosure have a structure of Formula (VII-A), wherein T is —$X^3$—C(═O)$OR^4$.

In some embodiments, Lipids of the Disclosure have a structure of Formula (VII-A), (VIII-A), or (IX-A), wherein $X^2$ and/or $X^{2a}$ are/is optionally substituted $C_2$-$C_{14}$ alkylenyl (e.g., $C_4$-$C_{10}$ alkylenyl, $C_5$-$C_7$ alkylenyl, $C_5$, $C_6$, or $C_7$ alkylenyl). In some embodiments, Lipids of the Disclosure have a structure of Formula (VII-A), (VIII-A), or (IX-A), wherein $X^2$ is $C_4$-$C_{10}$ alkylenyl. In some embodiments, Lipids of the Disclosure have a structure of Formula (VII-A), (VIII-A), or (IX-A), wherein $X^{2a}$ is $C_4$-$C_{10}$ alkylenyl. In some embodiments, Lipids of the Disclosure have a structure of Formula (VII-A), (VIII-A), or (IX-A), wherein $X^2$ is $C_5$ alkylenyl. In some embodiments, Lipids of the Disclosure have a structure of Formula (VII-A), (VIII-A), or (IX-A), wherein $X^2$ is $C_6$ alkylenyl. In some embodiments, Lipids of the Disclosure have a structure of Formula (VII-A), (VIII-A), or (IX-A), wherein $X^{2a}$ is $C_5$ alkylenyl. In some embodiments, Lipids of the Disclosure have a structure of Formula (VII-A), (VIII-A), or (IX-A), wherein $X^{2a}$ is $C_6$ alkylenyl.

In some embodiments, Lipids of the Disclosure have a structure of Formula (VII-A), (VIII-A), or (IX-A), wherein $Y^1$ and/or $Y^{1a}$ are/is

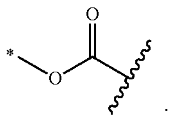 [SMILES: *C(=O)OC]

.

In some embodiments, Lipids of the Disclosure have a structure of Formula (VII-A), (VIII-A), or (IX-A), wherein $Y^1$ is

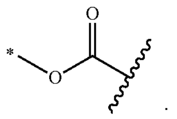 [SMILES: *C(=O)OC]

.

In some embodiments, Lipids of the Disclosure have a structure of Formula (VII-A), (VIII-A), or (IX-A), wherein $Y^{1a}$ is

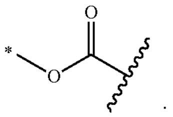 [SMILES: *C(=O)OC]

.

In some embodiments, Lipids of the Disclosure have a structure of Formula (VII-A), (VIII-A), or (IX-A), wherein $Y^1$ and/or $Y^{1a}$ are/is

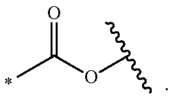 [SMILES: *OC(C)=O]

.

In some embodiments, Lipids of the Disclosure have a structure of Formula (VII-A), (VIII-A), or (IX-A), wherein $Y^1$ is

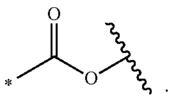 [SMILES: *OC(C)=O]

.

In some embodiments, Lipids of the Disclosure have a structure of Formula (VII-A), (VIII-A), or (IX-A), wherein $Y^{1a}$ is

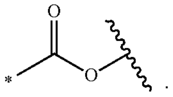 [SMILES: *OC(C)=O]

.

In some embodiments, Lipids of the Disclosure have a structure of Formula (VII-A), (VIII-A), or (IX-A), wherein $Y^1$ and/or $Y^{1a}$ are/is

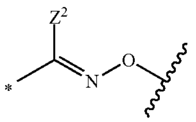

, wherein $Z^2$ is hydrogen.

In some embodiments, Lipids of the Disclosure have a structure of Formula (VII-A), (VIII-A), or (IX-A), wherein $Y^1$ is

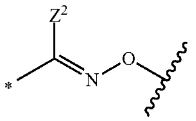

, wherein $Z^2$ is hydrogen.

In some embodiments, Lipids of the Disclosure have a structure of Formula (VII-A), (VIII-A), or (IX-A), wherein $Y^{1a}$ is

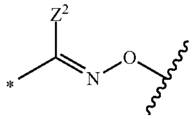

, wherein $Z^2$ is hydrogen.

In some embodiments, Lipids of the Disclosure have a structure of Formula (VII-A), (VIII-A), or (IX-A), wherein $Y^1$ and/or $Y^{1a}$ are/is

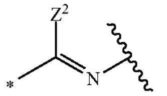

, wherein $Z^2$ is hydrogen.

In some embodiments, Lipids of the Disclosure have a structure of Formula (VII-A), (VIII-A), or (IX-A), wherein $Y^1$ is

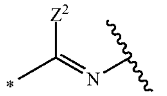

, wherein $Z^2$ is hydrogen.

In some embodiments, Lipids of the Disclosure have a structure of Formula (VII-A), (VIII-A), or (IX-A), wherein $Y^{1a}$ is

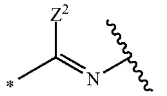

, wherein $Z^2$ is hydrogen.

In some embodiments, Lipids of the Disclosure have a structure of Formula (VII-A), (VIII-A), or (IX-A), wherein $Y^1$ and $Y^{1a}$ are independently

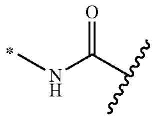

or

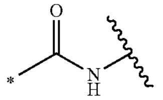

.

In some embodiments, Lipids of the Disclosure have a structure of Formula (VII-A), (VIII-A), or (IX-A), wherein $Y^1$ is independently

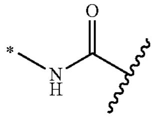

or

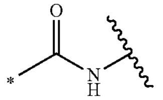

.

In some embodiments, Lipids of the Disclosure have a structure of Formula (VII-A), (VIII-A), or (IX-A), wherein $Y^{1a}$ is independently

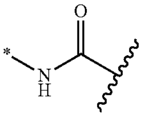

or

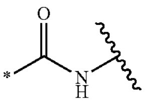

.

In some embodiments, Lipids of the Disclosure have a structure of Formula (VII-A), (VIII-A), or (IX-A), wherein $Q^1$ and/or $Q^{1a}$ are/is —$NR^2R^3$. In some embodiments, Lipids of the Disclosure have a structure of Formula (VII-A), (VIII-A), or (IX-A), wherein $Q^1$ is —$NR^2R^3$. In some embodiments, Lipids of the Disclosure have a structure of Formula (VII-A), (VIII-A), or (IX-A), wherein $Q^{1a}$ is —$NR^2R^3$.

In some embodiments, Lipids of the Disclosure have a structure of Formula (VII-A), (VIII-A), or (IX-A), wherein $Q^1$ and/or $Q^{1a}$ are/is —$CH(OR^2)(OR^3)$. In some embodiments, Lipids of the Disclosure have a structure of Formula (VII-A), (VIII-A), or (IX-A), wherein $Q^1$ is —$CH(OR^2)(OR^3)$. In some embodiments, Lipids of the Disclosure have a structure of Formula (VII-A), (VIII-A), or (IX-A), wherein $Q^{1a}$ is —$CH(OR^2)(OR^3)$.

In some embodiments, Lipids of the Disclosure have a structure of Formula (VII-A), (VIII-A), or (IX-A), wherein $Q^1$ and/or $Q^{1a}$ are/is —$CR^2$═$C(R^3)(R^{12})$. In some embodiments, Lipids of the Disclosure have a structure of Formula (VII-A), (VIII-A), or (IX-A), wherein $Q^1$ is —$CR^2$═$C(R^3)(R^{12})$. In some embodiments, Lipids of the Disclosure have a structure of Formula (VII-A), (VIII-A), or (IX-A), wherein $Q^{1a}$ is —$CR^2$═$C(R^3)(R^{12})$.

In some embodiments, Lipids of the Disclosure have a structure of Formula (VII-A), (VIII-A), or (IX-A), wherein $Q^1$ and/or $Q^{1a}$ are/is —$C(R^{2'})(R^{3'})(R^{12'})$. In some embodiments, Lipids of the Disclosure have a structure of Formula (VII-A), (VIII-A), or (IX-A), wherein $Q^1$ is —$C(R^{2'})(R^{3'})(R^{12'})$. In some embodiments, Lipids of the Disclosure have a structure of Formula (VII-A), (VIII-A), or (IX-A), wherein $Q^{1a}$ is —$C(R^{2'})(R^{3'})(R^{12'})$.

In some embodiments, Lipids of the Disclosure have a structure of Formula (VII-A), (VIII-A), or (IX-A), wherein $X^3$ is optionally substituted $C_2$-$C_{14}$ alkylenyl (e.g., $C_4$-$C_{10}$ alkylenyl, $C_5$-$C_7$ alkylenyl, $C_5$, $C_6$, or $C_7$ alkylenyl). In some embodiments, Lipids of the Disclosure have a structure of Formula (VII-A), (VIII-A), or (IX-A), wherein $X^3$ is $C_5$-$C_7$ alkylenyl. In some embodiments, Lipids of the Disclosure have a structure of Formula (VII-A), (VIII-A), or (IX-A), wherein $X^3$ is $C_5$ alkylenyl.

In some embodiments, Lipids of the Disclosure have a structure of Formula (VII-A), (VIII-A), or (IX-A), wherein $R^2$, $R^3$, $R^{12}$, $R^{2'}$, $R^{3'}$, and/or $R^{12'}$ are hydrogen. In some embodiments, Lipids of the Disclosure have a structure of Formula (VII-A), (VIII-A), or (IX-A), wherein $R^2$ is hydrogen. In some embodiments, Lipids of the Disclosure have a structure of Formula (VII-A), (VIII-A), or (IX-A), wherein $R^3$, is hydrogen. In some embodiments, Lipids of the Disclosure have a structure of Formula (VII-A), (VIII-A), or (IX-A), wherein $R^{12}$ is hydrogen. In some embodiments, Lipids of the Disclosure have a structure of Formula (VII-A), (VIII-A), or (IX-A), wherein $R^{2'}$ is hydrogen. In some embodiments, Lipids of the Disclosure have a structure of Formula (VII-A), (VIII-A), or (IX-A), wherein $R^{3'}$ is hydrogen. In some embodiments, Lipids of the Disclosure have a structure of Formula (VII-A), (VIII-A), or (IX-A), wherein $R^{12'}$ is hydrogen.

In some embodiments, Lipids of the Disclosure have a structure of Formula (VII-A), (VIII-A), or (IX-A), wherein $R^2$, $R^3$, $R^{12}$, $R^{2'}$, $R^{3'}$, and/or $R^{12'}$ are optionally substituted $C_1$-$C_{14}$ alkyl (e.g., $C_5$-$C_{14}$, $C_5$-$C_{10}$, $C_6$-$C_9$, $C_5$, $C_6$, $C_7$, $C_8$, $C_9$, $C_{10}$ alkyl). In some embodiments, Lipids of the Disclosure have a structure of Formula (VII-A), (VIII-A), or (IX-A), wherein $R^2$ is $C_5$-$C_{10}$ alkyl. In some embodiments, Lipids of the Disclosure have a structure of Formula (VII-A), (VIII-A), or (IX-A), wherein $R^3$ is $C_5$-$C_{10}$ alkyl. In some embodiments, Lipids of the Disclosure have a structure of Formula (VII-A), (VIII-A), or (IX-A), wherein $R^{12}$ is $C_5$-$C_{10}$ alkyl. In some embodiments, Lipids of the Disclosure have a structure of Formula (VII-A), (VIII-A), or (IX-A), wherein $R^{2'}$ is $C_5$-$C_{10}$ alkyl. In some embodiments, Lipids of the Disclosure have a structure of Formula (VII-A), (VIII-A), or (IX-A), wherein $R^{3'}$ is $C_5$-$C_{10}$ alkyl. In some embodiments, Lipids of the Disclosure have a structure of Formula (VII-A), (VIII-A), or (IX-A), wherein $R^{12'}$ is $C_5$-$C_{10}$ alkyl. In some embodiments, Lipids of the Disclosure have a structure of Formula (VII-A), (VIII-A), or (IX-A), wherein $R^2$ is $C_8$ alkyl. In some embodiments, Lipids of the Disclosure have a structure of Formula (VII-A), (VIII-A), or (IX-A), wherein $R^3$ is $C_8$ alkyl. In some embodiments, Lipids of the Disclosure have a structure of Formula (VII-A), (VIII-A), or (IX-A), wherein $R^{12}$ is $C_8$ alkyl. In some embodiments, Lipids of the Disclosure have a structure of Formula (VII-A), (VIII-A), or (IX-A), wherein $R^{2'}$ is $C_8$ alkyl. In some embodiments, Lipids of the Disclosure have a structure of Formula (VII-A), (VIII-A), or (IX-A), wherein $R^{3'}$ is $C_8$ alkyl. In some embodiments, Lipids of the Disclosure have a structure of Formula (VII-A), (VIII-A), or (IX-A), wherein $R^{12'}$ is $C_8$ alkyl.

In some embodiments, Lipids of the Disclosure have a structure of Formula (VII-A) or (IX-A), wherein $R^4$ is optionally substituted $C_4$-$C_{14}$ alkyl (e.g., $C_6$-$C_{12}$, $C_8$-$C_{12}$, $C_6$, $C_7$, $C_8$, $C_9$, $C_{10}$, $C_{11}$, $C_{12}$ alkyl). In some embodiments, Lipids of the Disclosure have a structure of Formula (VII-A) or (IX-A), wherein $R^4$ is $C_6$-$C_{12}$ alkyl. In some embodiments, Lipids of the Disclosure have a structure of Formula (VII-A), (VIII-A), or (IX-A), wherein $R^4$ is $C_{11}$ alkyl.

In some embodiments, Lipids of the Disclosure have a structure of Formula (VII-A), (VIII-A), or (IX-A), wherein $R^1$ is OH.

In some embodiments, Lipids of the Disclosure have a structure of Formula (VII-A), (VIII-A), or (IX-A), wherein $X^1$ is $C_{24}$ alkylenyl (e.g., $C_2$, $C_3$, or $C_4$ alkylenyl). In some embodiments, Lipids of the Disclosure have a structure of Formula (VII-A), (VIII-A), or (IX-A), wherein $X^1$ is $C_2$ alkylenyl. In some embodiments, Lipids of the Disclosure have a structure of Formula (VII-A), (VIII-A), or (IX-A), wherein $X^1$ is $C_4$ Alkylenyl.

In some embodiments, Lipids of the Disclosure have a structure of Formula (VII-B):

(VII-B)

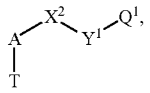

or a pharmaceutically acceptable salt thereof, wherein:

A is —C(R')(-$L^1$-N(R")$R^6$)—, —C(R')(—$OR^{7a}$)—, —C(R')(—N(R")$R^{8a}$)—, —C(R')(—C(=O)$OR^{9a}$)—, —C(R')(—C(=O)N(R")$R^{10a}$)—, or —C(=N—$R^{11a}$)—;

T is —$X^{2a}$—$Y^{1a}$-$Q^{1a}$ or —$X^3$—C(=O)$OR^4$;

$X^2$ and $X^{2a}$ are independently optionally substituted $C_2$-$C_{14}$ alkylenyl or optionally substituted $C_2$-$C_{14}$ alkenylenyl;

$X^3$ is optionally substituted $C_1$-$C_{14}$ alkylenyl or optionally substituted $C_2$-$C_{14}$ alkenylenyl; $Y^1$ is

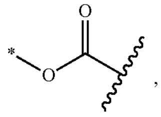 [SMILES: *OC(*)=O], 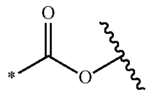,

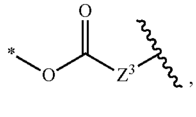, or 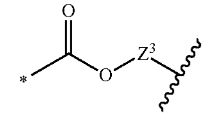, wherein the bond marked with an "*" is attached to $X^2$; $Y^{1a}$ is

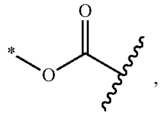 [SMILES: *OC(*)=O], 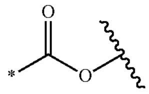,

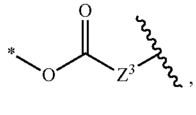, or 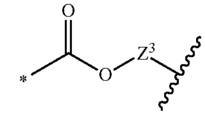, wherein the bond marked with an "*" is attached to $X^{2a}$;

each $Z^3$ is independently optionally substituted $C_1$-$C_6$ alkylenyl or optionally substituted $C_2$-$C_{14}$ alkenylenyl;

$Q^1$ is —$NR^2R^3$, —CH($OR^2$)($OR^3$), —$CR^2$=C($R^3$)($R^{12}$), or —C($R^2$)($R^3$)($R^{12}$);

$Q^{1a}$ is —$NR^{2'}R^{3'}$, —CH($OR^{2'}$)($OR^{3'}$), —$CR^{2'}$=C($R^{3'}$)($R^{12'}$), or —C($R^{2'}$)($R^{3'}$)($R^{12'}$);

$R^2$, $R^3$, and $R^{12}$ are independently hydrogen, optionally substituted $C_1$-$C_{14}$ alkyl, optionally substituted $C_2$-$C_{14}$ alkenylenyl, or —$(CH_2)_m$-G-$(CH_2)_n$H;

$R^{2'}$, $R^{3'}$, and $R^{12'}$ are independently hydrogen, optionally substituted $C_1$-$C_{14}$ alkyl, optionally substituted $C_2$-$C_{14}$ alkenylenyl, or —$(CH_2)_m$-G-$(CH_2)_n$H;

G is a $C_3$-$C_8$ cycloalkylenyl;

each m is independently 0, 1, 2, 3, 4, 5, 6, 7, 8, 9, 10, 11, or 12;

each n is independently 0, 1, 2, 3, 4, 5, 6, 7, 8, 9, 10, 11, or 12;

$X^3$ is optionally substituted $C_2$-$C_{14}$ alkylenyl;

$R^4$ is optionally substituted $C_4$-$C_{14}$ alkyl;

$L^1$ is $C_1$-$C_8$ alkylenyl;

$R^6$ is (hydroxy)$C_1$-$C_6$ alkyl, or (amino)$C_1$-$C_6$ alkyl.

$R^{7a}$ is —C(=O)N(R"')$R^{7b}$, —C(=S)N(R"')$R^{7b}$, —N=C($R^{7b}$)($R^{7c}$),

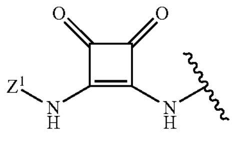, 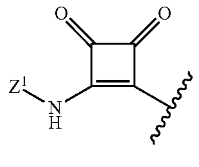, or

-continued

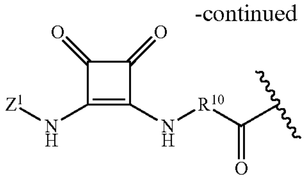;

$Z^1$ is optionally substituted $C_1$-$C_6$ alkyl;

$R^{10}$ is $C_1$-$C_6$ alkylenyl;

$R^{7b}$ is $C_1$-$C_6$ alkyl, (hydroxy)$C_1$-$C_6$ alkyl, or (amino)$C_1$-$C_6$ alkyl;

$R^{7c}$ is hydrogen or $C_1$-$C_6$ alkyl;

$R^{8a}$ is —C(═O)N(R''')$R^{8b}$, —C(═S)N(R''')$R^{8b}$, —N═C($R^{8b}$)($R^{8c}$),

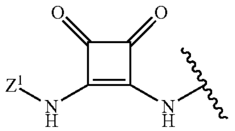, or 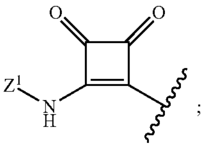;

$R^{8b}$ is $C_1$-$C_6$ alkyl, (hydroxy)$C_1$-$C_6$ alkyl, or (amino)$C_1$-$C_6$ alkyl;

$R^{8c}$ is hydrogen or $C_1$-$C_6$ alkyl;

$R^{9a}$ is —N═C($R^{9b}$)($R^{9c}$);

$R^{9b}$ is $C_1$-$C_6$ alkyl, (hydroxy)$C_1$-$C_6$ alkyl, or (amino)$C_1$-$C_6$ alkyl;

$R^{9c}$ is hydrogen or $C_1$-$C_6$ alkyl;

$R^{10a}$ is —N═C($R^{10b}$)($R^{10c}$);

$R^{10b}$ is $C_1$-$C_6$ alkyl, (hydroxy)$C_1$-$C_6$ alkyl, or (amino)$C_1$-$C_6$ alkyl;

$R^{10c}$ is hydrogen or $C_1$-$C_6$ alkyl;

$R^{11a}$ is —$OR^{11b}$, —N(R'')$R^{11b}$, —OC(═O)$R^{11b}$, or —N(R'')C(═O)$R^{11b}$;

$R^{11b}$ is $C_1$-$C_6$ alkyl, (hydroxy)$C_1$-$C_6$ alkyl, or (amino)$C_1$-$C_6$ alkyl;

R' is hydrogen or $C_1$-$C_6$ alkyl;

R'' is hydrogen or $C_1$-$C_6$ alkyl; and

R''' is hydrogen or $C_1$-$C_6$ alkyl.

In some embodiments, Lipids of the Disclosure have a structure of Formula (VII-B), wherein A is —C(R')(-$L^1$-N(R'')$R^6$)—.

In some embodiments, Lipids of the Disclosure have a structure of Formula (VII-B), wherein A is —C(R')(—$OR^{7a}$)—.

In some embodiments, Lipids of the Disclosure have a structure of Formula (VII-B), wherein A is —C(R')(—N(R'')$R^{8a}$).

In some embodiments, Lipids of the Disclosure have a structure of Formula (VII-B), wherein A is —C(R')(—C(═O)$OR^{9a}$).

In some embodiments, Lipids of the Disclosure have a structure of Formula (VII-B), wherein A is —C(R')(—C(═O)N(R'')$R^{10a}$)—.

In some embodiments, Lipids of the Disclosure have a structure of Formula (VII-B), wherein A is —C(═N—$R^{11a}$)—.

In some embodiments, Lipids of the Disclosure have a structure of Formula (VII-B), wherein T is —$X^{2a}$-$Y^{1a}$_$Q^{1a}$.

In some embodiments, Lipids of the Disclosure have a structure of Formula (VII-B), wherein T is —$X^3$—C(═O)$OR^4$.

In some embodiments, Lipids of the Disclosure have a structure of Formula (VII-B), wherein $X^2$ and/or $X^{2a}$ are/is optionally substituted $C_2$-$C_{14}$ alkylenyl (e.g., $C_2$-$C_{10}$ alkylenyl, $C_2$-$C_5$ alkylenyl, $C_2$, $C_3$, $C_4$, $C_5$, $C_6$, $C_7$, or $C_8$ alkylenyl). In some embodiments, Lipids of the Disclosure have a structure of Formula (VII-B), wherein $X^2$ is $C_2$-$C_{14}$ alkylenyl. In some embodiments, Lipids of the Disclosure have a structure of Formula (VII-B), wherein $X^{2a}$ is $C_2$-$C_{14}$ alkylenyl In some embodiments, Lipids of the Disclosure have a structure of Formula (VII-B), wherein $Y^1$ and/or $Y^{1a}$ are/is

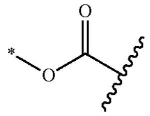.

In some embodiments, Lipids of the Disclosure have a structure of Formula (VII-B), wherein $Y^1$ is

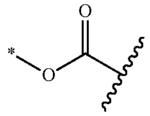.

In some embodiments, Lipids of the Disclosure have a structure of Formula (VII-B), wherein $Y^{1a}$ is

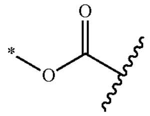.

In some embodiments, Lipids of the Disclosure have a structure of Formula (VII-B), wherein $Y^1$ and/or $Y^{1a}$ are/is

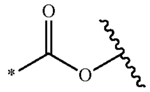.

In some embodiments, Lipids of the Disclosure have a structure of Formula (VII-B), wherein $Y^1$ is

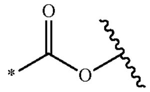.

In some embodiments, Lipids of the Disclosure have a structure of Formula (VII-B), wherein $Y^{1a}$ is

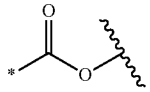.

In some embodiments, Lipids of the Disclosure have a structure of Formula (VII-B), wherein $Y^1$ and/or $Y^{1a}$ are/is

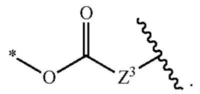

In some embodiments, Lipids of the Disclosure have a structure of Formula (VII-B), wherein $Y^1$ is

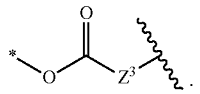

In some embodiments, Lipids of the Disclosure have a structure of Formula (VII-B), wherein $Y^{1a}$ is

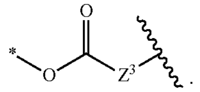

In some embodiments, Lipids of the Disclosure have a structure of Formula (VII-B), wherein $Y^1$ and/or $Y^{1a}$ are/is

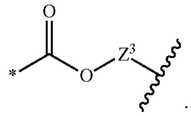

In some embodiments, Lipids of the Disclosure have a structure of Formula (VII-B), wherein $Y^1$ is

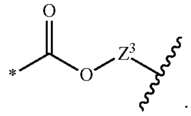

In some embodiments, Lipids of the Disclosure have a structure of Formula (VII-B), wherein $Y^{1a}$ is

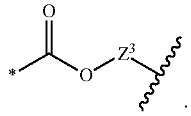

In some embodiments, Lipids of the Disclosure have a structure of Formula (VII-B), wherein $Q^1$ and/or $Q^{1a}$ are/is —$C(R^{2'})(R^{3'})(R^{12'})$. In some embodiments, Lipids of the Disclosure have a structure of Formula (VII-B), wherein $Q^1$ is —$C(R^{2'})(R^{3'})(R^{12'})$. In some embodiments, Lipids of the Disclosure have a structure of Formula (VII-B), wherein $Q^{1a}$ is —$C(R^{2'})(R^{3'})(R^{12'})$.

In some embodiments, Lipids of the Disclosure have a structure of Formula (VII-B), wherein $X^3$ is optionally substituted $C_1$-$C_{14}$ alkylenyl (e.g., $C_1$-$C_6$, $C_1$-$C_4$ alkylenyl). In some embodiments, Lipids of the Disclosure have a structure of Formula (VII-B), wherein $X^3$ is $C_1$-$C_{14}$ alkylenyl.

In some embodiments, Lipids of the Disclosure have a structure of Formula (VII-B), wherein $R^2$, $R^3$, $R^{12}$, $R^{2'}$, $R^{3'}$, and/or $R^{12'}$ are hydrogen. In some embodiments, Lipids of the Disclosure have a structure of Formula (VII-B), wherein $R^2$ is hydrogen. In some embodiments, Lipids of the Disclosure have a structure of Formula (VII-B), wherein $R^3$ is hydrogen. In some embodiments, Lipids of the Disclosure have a structure of Formula (VII-B), wherein $R^{12}$ is hydrogen. In some embodiments, Lipids of the Disclosure have a structure of Formula (VII-B), wherein $R^{2'}$ is hydrogen. In some embodiments, Lipids of the Disclosure have a structure of Formula (VII-B), wherein $R^{3'}$ is hydrogen. In some embodiments, Lipids of the Disclosure have a structure of Formula (VII-B), wherein $R^{12'}$ is hydrogen.

In some embodiments, Lipids of the Disclosure have a structure of Formula (VII-B), wherein $R^2$, $R^3$, $R^{12}$, $R^{2'}$, R', and/or $R^{12'}$ are optionally substituted $C_1$-$C_{14}$ alkyl (e.g., $C_4$-$C_{10}$ alkyl, $C_5$, $C_6$. $C_7$. $C_8$, $C_9$ alkyl). In some embodiments, Lipids of the Disclosure have a structure of Formula (VII-B), wherein $R^2$ is $C_4$-$C_{10}$ alkyl. In some embodiments, Lipids of the Disclosure have a structure of Formula (VII-B), wherein $R^3$ is $C_4$-$C_{10}$ alkyl. In some embodiments, Lipids of the Disclosure have a structure of Formula (VII-B), wherein $R^{12}$ is $C_4$-$C_{10}$ alkyl. In some embodiments, Lipids of the Disclosure have a structure of Formula (VII-B), wherein $R^{2'}$ is $C_4$-$C_{10}$ alkyl. In some embodiments, Lipids of the Disclosure have a structure of Formula (VII-B), wherein $R^{3'}$ is $C_4$-$C_{10}$ alkyl. In some embodiments, Lipids of the Disclosure have a structure of Formula (VII-B), wherein $R^{12'}$ is $C_4$-$C_{10}$ alkyl.

In some embodiments, Lipids of the Disclosure have a structure of Formula (VII-B), wherein $R^4$ is optionally substituted $C_4$-$C_{14}$ alkyl (e.g., $C_8$-$C_{14}$ alkyl, linear $C_8$-$C_{14}$ alkyl, $C_8$, $C_9$, $C_{10}$, $C_{11}$, $C_{12}$, $C_{13}$, or $C_{14}$ alkyl). In some embodiments, Lipids of the Disclosure have a structure of Formula (VII-B), wherein $R^4$ is linear $C_8$-$C_{14}$ alkyl. In some embodiments, Lipids of the Disclosure have a structure of Formula (VII-B), wherein $R^4$ is linear $C_{11}$ alkyl.

In some embodiments, Lipids of the Disclosure have a structure of Formula (VII-B), wherein $L^1$ is $C_1$-$C_3$ alkylenyl.

In some embodiments, Lipids of the Disclosure have a structure of Formula (VII-B), wherein $R^6$ is (hydroxy)$C_1$-$C_6$ alkyl.

In some embodiments, Lipids of the Disclosure have a structure of Formula (VII-B), wherein $R^{7a}$ is

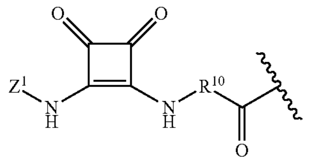

or

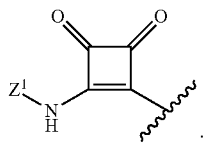

In some embodiments, Lipids of the Disclosure have a structure of Formula (VII-B), wherein $R^{7a}$ is

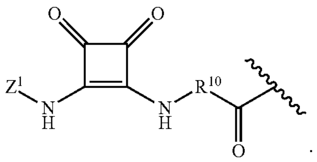.

In some embodiments, Lipids of the Disclosure have a structure of Formula (VII-B), wherein $R^{7a}$ is

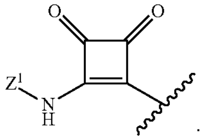.

In some embodiments, Lipids of the Disclosure have a structure of Formula (VII-B), wherein $R^{7a}$ is selected from the group consisting of —C(═O)N(R')$R^{7b}$, —C(═S)N(R''')$R^{7b}$, and —N═C($R^{7b}$)($R^{7c}$). In some embodiments, Lipids of the Disclosure have a structure of Formula (VII-B), wherein $R^{7a}$ is —C(═O)N(R')$R^{7b}$. In some embodiments, Lipids of the Disclosure have a structure of Formula (VII-B), wherein $R^{7a}$ is —C(═S)N(R')$R^{7b}$. In some embodiments, Lipids of the Disclosure have a structure of Formula (VII-B), wherein $R^{7a}$ is —N═C($R^{7b}$)($R^{7c}$).

In some embodiments, Lipids of the Disclosure have a structure of Formula (VII-B), wherein $R^{8a}$ is selected from the group consisting of —C(═O)N(R''')$R^{8b}$, —C(═S)N(R''')$R^{8b}$, and —N═C($R^{8b}$)($R^{8c}$). In some embodiments, Lipids of the Disclosure have a structure of Formula (VII-B), wherein $R^{8a}$ is —C(═O)N(R''')$R^{8b}$. In some embodiments, Lipids of the Disclosure have a structure of Formula (VII-B), wherein $R^{8a}$ is —C(═S)N(R''')$R^{8b}$. In some embodiments, Lipids of the Disclosure have a structure of Formula (VII-B), wherein $R^{8a}$ is —N═C($R^{8b}$)($R^{8c}$).

In some embodiments, Lipids of the Disclosure have a structure of Formula (VII-B), wherein $R^{8a}$ is

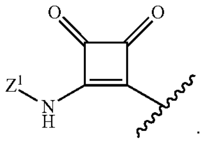.

In some embodiments, Lipids of the Disclosure have a structure of Formula (VII-B), wherein $R^{9b}$ is (hydroxy)$C_1$-$C_6$ alkyl.

In some embodiments, Lipids of the Disclosure have a structure of Formula (VII-B), wherein $R^{10b}$ is (amino)$C_1$-$C_6$ alkyl.

In some embodiments, Lipids of the Disclosure have a structure of Formula (VII-B), wherein $R^{11a}$ is —O$R^{11b}$ or —OC(═O)$R^{11b}$. In some embodiments, Lipids of the Disclosure have a structure of Formula (VII-B), wherein $R^{11a}$ is —O$R^{11b}$. In some embodiments, Lipids of the Disclosure have a structure of Formula (VII-B), wherein $R^{11a}$ is —OC(═O)$R^{11b}$.

In some embodiments, Lipids of the Disclosure have a structure of Formula (VII-B), wherein $R^{11a}$ is —N(R'')$R^{11b}$ or —N(R'')C(═O)$R^{11b}$. In some embodiments, Lipids of the Disclosure have a structure of Formula (VII-B), wherein $R^{11a}$ is —N(R'')$R^{11b}$ In some embodiments, Lipids of the Disclosure have a structure of Formula (VII-B), wherein $R^{11a}$ is —N(R'')C(═O)$R^{11b}$.

In some embodiments, Lipids of the Disclosure have a structure of Formula (VII-B), wherein $R^{11b}$ is (amino)$C_1$-$C_6$ alkyl.

In some embodiments, Lipids of the Disclosure have a structure of Formula (VII-C):

(VII-C)

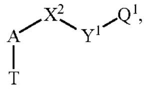

or a pharmaceutically acceptable salt thereof, wherein:

A is —N(—$X^1R^1$)—;

T is —$X^{2a}$—$Y^{1a}$-$Q^{1a}$ or —$X^3$—C(═O)O$R^4$;

(i) $X^1$ is optionally substituted $C_2$-$C_3$ alkylenyl;

$R^1$ is

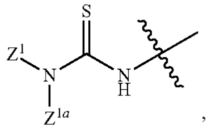,

—NR''C(O)O$R^{20}$, or —NR''$R^{21}$; or (ii) $X^1$ is $C_4$-$C_6$alkylenyl, and $R^1$ is

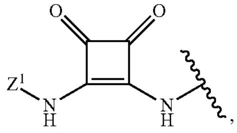, 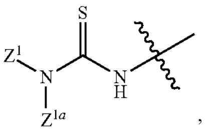,

—NR''C(O)O$R^{20}$, or —NR''$R^{21}$ $Z^1$ is optionally substituted $C_1$-$C_6$ alkyl;

$Z^{1a}$ is hydrogen or optionally substituted $C_1$-$C_6$ alkyl;

$R^{20}$ is optionally substituted $C_1$-$C_6$alkyl;

$R^{21}$ is —($C_2$ alkylenyl)-OH;

$X^2$ and $X^{2a}$ are independently optionally substituted $C_2$-$C_{14}$ alkylenyl or optionally substituted $C_2$-$C_{14}$ alkenylenyl;

$X^3$ is optionally substituted $C_2$-$C_{14}$ alkylenyl or optionally substituted $C_2$-$C_{14}$ alkenylenyl;

$Y^1$ is a bond,

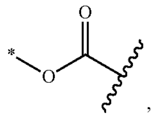, 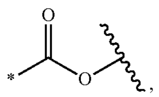,

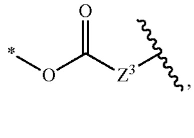, or 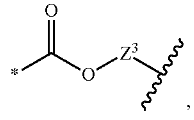, wherein the bond marked with an "*" is attached to $X^2$;

$Y^{1a}$ is

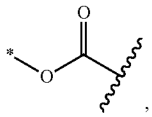
,
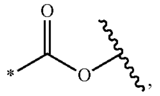
,
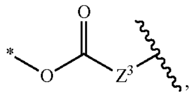
, or
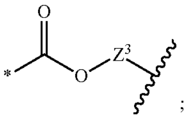
;

wherein the bond marked with an "*" is attached to $X^{2a}$; wherein $Y^1$ and $Y^{1a}$ are

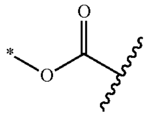
or
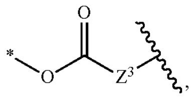
, when $R^1$ is

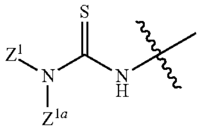
or
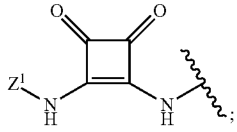
;

each $Z^2$ is independently H or optionally substituted $C_1$-$C_8$alkyl;

each $Z^3$ is independently optionally substituted $C_1$-$C_6$ alkylenyl or optionally substituted $C_2$-$C_{14}$ alkenylenyl;

$Q^1$ is —$NR^2R^3$, —$CH(OR^2)(OR^3)$, —$CR^2$═$C(R^3)(R^{12})$, or —$C(R^2)(R^3)(R^{12}$ $Q^{1a}$ is —$NR^{2'}R^{3'}$, —$CH(OR^{2'})(OR^{3'})$, —$CR^{2}$═$C(R^{3'})(R^{12'})$, or —$C(R^{2'})(R^{3'})(R^{12'})$;

wherein $Q^1$ is-$CH(OR^2)(OR^3)$ and $Q^{1a}$ is —$CH(OR^{2'})(OR^{3'})$ when $R^1$ is —NR"C(O)$OR^{20}$;

$R^2$, $R^3$, and $R^{12}$ are independently hydrogen, optionally substituted linear $C_1$-$C_{14}$ alkyl, optionally substituted $C_2$-$C_{14}$ alkenylenyl, or —$(CH_2)_m$-G-$(CH_2)_n$H;

$R^{2'}$, $R^{3'}$, and $R^{12'}$ are independently hydrogen, optionally substituted linear $C_1$-$C_{14}$ alkyl, or optionally substituted $C_2$-$C_{14}$ alkenylenyl;

$X^3$ is optionally substituted $C_2$-$C_{14}$ alkylenyl;

$R^4$ is optionally substituted $C_4$-$C_{14}$ alkyl; and

R" is hydrogen or $C_1$-$C_6$ alkyl.

In some embodiments, Lipids of the Disclosure have a structure of Formula (VII-C), wherein $R^1$ is

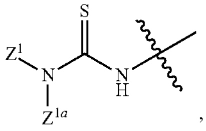
, wherein $Z^1$ is methyl and $Z^{1a}$ is hydrogen or methyl.

In some embodiments, Lipids of the Disclosure have a structure of Formula (VII-C), wherein $R^1$ is

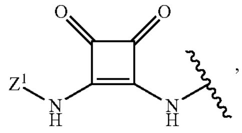
, wherein $Z^1$ is methyl.

In some embodiments, Lipids of the Disclosure have a structure of Formula (VII-C), wherein $R^1$ is —NR"C(O)$OR^{20}$.

In some embodiments, Lipids of the Disclosure have a structure of Formula (VII-C), wherein $R^1$ is —NR"$R^{21}$.

In some embodiments, Lipids of the Disclosure have a structure of Formula (VII-C), wherein $R^{20}$ is t-butyl or benzyl.

In some embodiments, Lipids of the Disclosure have a structure of Formula (VII-C), wherein $X^2$ and/or $X^{2a}$ are/is optionally substituted $C_2$-$C_{14}$ alkylenyl (e.g., $C_4$-$C_8$alkylenyl, $C_4$, $C_5$, $C_6$, $C_7$, $C_8$ alkylenyl). In some embodiments, Lipids of the Disclosure have a structure of Formula (VII-C), wherein $X^2$ is $C_4$-$C_8$alkylenyl. In some embodiments, Lipids of the Disclosure have a structure of Formula (VII-C), wherein $X^{2a}$ is $C_4$-$C_8$alkylenyl.

In some embodiments, Lipids of the Disclosure have a structure of Formula (VII-C), wherein $Y^1$ and/or $Y^{1a}$ are/is

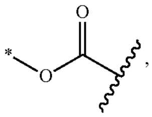
,

In some embodiments, Lipids of the Disclosure have a structure of Formula (VII-C), wherein $Y^1$ is

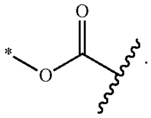
.

In some embodiments, Lipids of the Disclosure have a structure of Formula (VII-C), wherein $Y^{1a}$ is

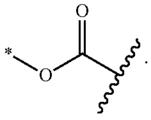
.

In some embodiments, Lipids of the Disclosure have a structure of Formula (VII-C), wherein $Y^1$ and/or $Y^{1a}$ are/is

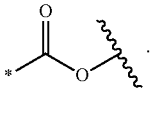 [SMILES: *OC(*)=O]
.

In some embodiments, Lipids of the Disclosure have a structure of Formula (VII-C), wherein $Y^1$ is

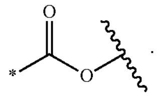

In some embodiments, Lipids of the Disclosure have a structure of Formula (VII-C), wherein $Y^{1a}$ is

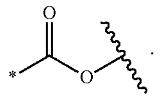 [SMILES: *OC(*)=O]

In some embodiments, Lipids of the Disclosure have a structure of Formula (VII-C), wherein $Y^1$ and/or $Y^{1a}$ are/is

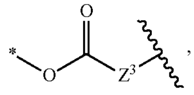

wherein $Z^3$ is $C_2$ alkylenyl.

In some embodiments, Lipids of the Disclosure have a structure of Formula (VII-C), wherein $Y^1$ is

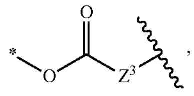

wherein $Z^3$ is $C_2$ alkylenyl.

In some embodiments, Lipids of the Disclosure have a structure of Formula (VII-C), wherein $Y^{1a}$ is

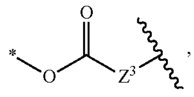

wherein $Z^3$ is $C_2$ alkylenyl.

In some embodiments, Lipids of the Disclosure have a structure of Formula (VII-C), wherein $Y^1$ and/or $Y^{1a}$ are/is

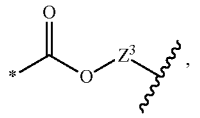

wherein $Z^3$ is $C_2$ alkylenyl.

In some embodiments, Lipids of the Disclosure have a structure of Formula (VII-C), wherein $Y^1$ is

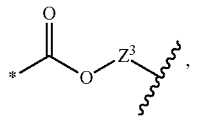

wherein $Z^3$ is $C_2$ alkylenyl.

In some embodiments, Lipids of the Disclosure have a structure of Formula (VII-C), wherein $Y^{1a}$ is

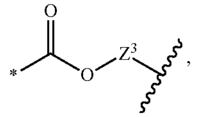

wherein $Z^3$ is $C_2$ alkylenyl.

In some embodiments, Lipids of the Disclosure have a structure of Formula (VII-C), wherein $Q^1$ and/or $Q^{1a}$ are/is —$CH(OR^2)(OR^3)$. In some embodiments, Lipids of the Disclosure have a structure of Formula (VII-C), wherein $Q^{1a}$ is —$CH(OR^2)(OR^3)$. In some embodiments, Lipids of the Disclosure have a structure of Formula (VII-C), wherein $Q^1$ is —$CH(OR^2)(OR^3)$.

In some embodiments, Lipids of the Disclosure have a structure of Formula (VII-C), wherein $Q^1$ and/or $Q^{1a}$ are/is —$C(R^{2'})(R^{3'})(R^{12'})$. In some embodiments, Lipids of the Disclosure have a structure of Formula (VII-C), wherein $Q^1$ is —$C(R^{2'})(R^{3'})(R^{12'})$. In some embodiments, Lipids of the Disclosure have a structure of Formula (VII-C), wherein $Q^{1a}$ is —$C(R^{2'})(R^{3'})(R^{12'})$.

In some embodiments, Lipids of the Disclosure have a structure of Formula (VII-C), wherein $R^2$, $R^3$, $R^{12}$, $R^{2'}$, $R^{3'}$, and $R^{12'}$ are independently hydrogen, optionally substituted linear $C_1$-$C_{14}$ alkyl (e.g., $C_4$-$C_{10}$alkyl, $C_6$-$C_8$alkyl, $C_5$, $C_6$, $C_7$, $C_8$, $C_9$ alkyl). In some embodiments, Lipids of the Disclosure have a structure of Formula (VII-C), wherein $R^2$ is hydrogen. In some embodiments, Lipids of the Disclosure have a structure of Formula (VII-C), wherein $R^3$ is hydrogen. In some embodiments, Lipids of the Disclosure have a structure of Formula (VII-C), wherein $R^{12}$ is hydrogen. In some embodiments, Lipids of the Disclosure have a structure of Formula (VII-C), wherein $R^{2'}$ is hydrogen. In some embodiments, Lipids of the Disclosure have a structure of Formula (VII-C), wherein $R^{3'}$ is hydrogen. In some embodiments, Lipids of the Disclosure have a structure of Formula (VII-C), wherein $R^{12'}$ is hydrogen. In some embodiments, Lipids of the Disclosure have a structure of Formula (VII-C), wherein $R^2$ is linear $C_4$-$C_{10}$alkyl. In some embodiments, Lipids of the Disclosure have a structure of Formula (VII-C), wherein $R^3$ is linear $C_4$-$C_{10}$alkyl. In some embodiments, Lipids of the Disclosure have a structure of Formula (VII-C), wherein $R^{12}$ is linear $C_4$-$C_{10}$alkyl. In some embodiments, Lipids of the Disclosure have a structure of Formula (VII-C), wherein $R^{2'}$ is linear $C_4$-$C_{10}$alkyl. In some embodiments, Lipids of the Disclosure have a structure of Formula (VII-C), wherein $R^{3'}$ is linear $C_4$-$C_{10}$alkyl. In some embodiments, Lipids of the Disclosure have a structure of Formula (VII-C), wherein $R^{12'}$ is linear $C_4$-$C_{10}$alkyl.

In some embodiments, Lipids of the Disclosure have a structure of Formula (I-A):

(I-A)

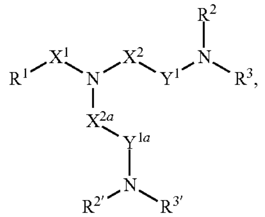

or a pharmaceutically acceptable salt thereof, wherein:

R is —OH, —$R^{1a}$,

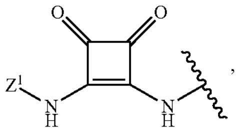

, or

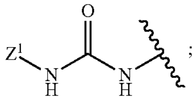

;

$Z^1$ is optionally substituted $C_1$-$C_6$ alkyl;

$X^1$ is optionally substituted $C_2$-$C_6$ alkylenyl;

$X^2$ and $X^{2a}$ are independently optionally substituted $C_2$-$C_{14}$ alkylenyl;

$Y^1$ and $Y^{1a}$ are independently a bond,

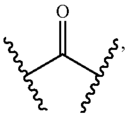

,

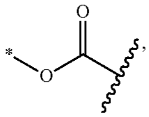

,

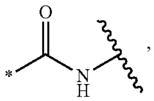

,

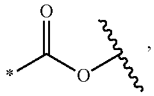

,

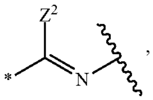

, or

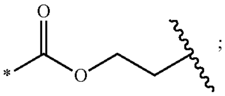

;

wherein the bond marked with an "*" is attached to X or $X^{2a}$;

$Z^2$ is H or optionally substituted $C_1$-$C_8$alkyl;

$R^2$ and $R^3$ are independently optionally substituted $C_4$-$C_{14}$ alkyl;

$R^{2'}$ and $R^{3'}$ are independently optionally substituted $C_4$-$C_{14}$ alkyl;

$R^{1a}$ is:

$R^{1a}$-1

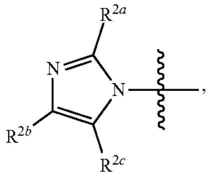

, $R^{1a}$-2

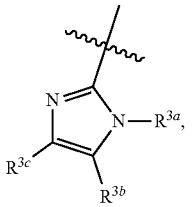

, $R^{1a}$-3

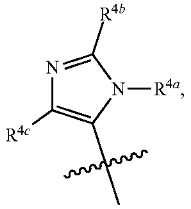

, or

-continued $R^{1a}$-4

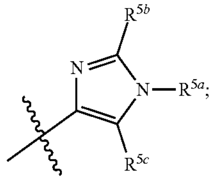

;

$R^{2a}$, $R^{2b}$, and $R^{2c}$ are independently hydrogen or $C_1$-$C_6$ alkyl;

$R^{3a}$, $R^{3b}$, and $R^{3c}$ are independently hydrogen or $C_1$-$C_6$ alkyl;

$R^{4a}$, $R^{4b}$, and $R^{4c}$ are independently hydrogen or $C_1$-$C_6$ alkyl; and $R^{5a}$, $R^{5b}$, and $R^{5c}$ are independently hydrogen or $C_1$-$C_6$ alkyl.

In some embodiments, Lipids of the Disclosure have a structure of Formula (I-A), wherein $R^1$ is OH.

In some embodiments, Lipids of the Disclosure have a structure of Formula (I-A), wherein $Y^1$ and $Y^{1a}$ are independently

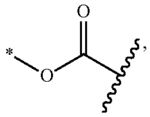

,

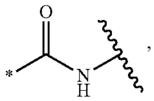

,

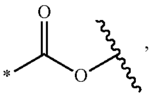

, or

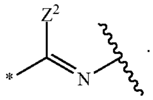

.

In some embodiments, Lipids of the Disclosure have a structure of Formula (I-A), wherein $Y^1$ is

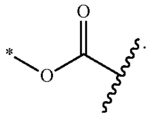 [SMILES: *OC(*)=O]

.

In some embodiments, Lipids of the Disclosure have a structure of Formula (I-A), wherein $Y^1$ is

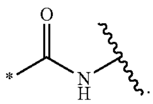 [SMILES: *NC(*)=O]

.

In some embodiments, Lipids of the Disclosure have a structure of Formula (I-A), wherein $Y^1$ is

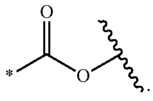 [SMILES: *OC(*)=O]

.

In some embodiments, Lipids of the Disclosure have a structure of Formula (I-A), wherein $Y^1$ is

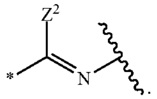

In some embodiments, Lipids of the Disclosure have a structure of Formula (I-A), wherein $Y^{1a}$ is

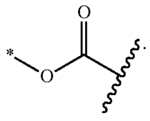 [SMILES: *OC(*)=O]

In some embodiments, Lipids of the Disclosure have a structure of Formula (I-A), wherein $Y^{1a}$ is

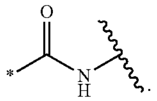

In some embodiments, Lipids of the Disclosure have a structure of Formula (I-A), wherein $Y^{1a}$ is

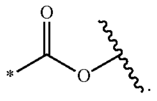

In some embodiments, Lipids of the Disclosure have a structure of Formula (I-A), wherein $Y^{1a}$ is

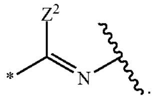

In some embodiments, Lipids of the Disclosure have a structure of Formula (I-A), wherein $Z^2$ is H.

In some embodiments, Lipids of the Disclosure have a structure of Formula (I-A), wherein $X^1$ is optionally substituted $C_2$ or $C_4$ alkylenyl.

In some embodiments, Lipids of the Disclosure have a structure of Formula (I-A), wherein $X^2$ and $X^{2a}$ are independently $C_4$-$C_5$ alkylenyl (e.g., $C_6$ alkylenyl). In some embodiments, Lipids of the Disclosure have a structure of Formula (I-A), wherein $X^2$ is $C_6$ alkylenyl. In some embodiments, Lipids of the Disclosure have a structure of Formula (I-A), wherein $X^{2a}$ is $C_6$ alkylenyl.

In some embodiments, Lipids of the Disclosure have a structure of Formula (I-A), wherein $R^2$, $R^3$, $R^{2'}$ and $R^{3'}$ are independently $C_4$-$C_{14}$ alkyl (e.g., $C_6$-$C_8$ alkyl, $C_6$, $C_7$, $C_8$ alkyl). In some embodiments, Lipids of the Disclosure have a structure of Formula (I-A), wherein $R^2$ is $C_6$-$C_8$ alkyl. In some embodiments, Lipids of the Disclosure have a structure of Formula (I-A), wherein $R^3$ is $C_6$-$C_8$ alkyl. In some embodiments, Lipids of the Disclosure have a structure of Formula (I-A), wherein $R^{2'}$ is $C_6$-$C_8$ alkyl. In some embodiments, Lipids of the Disclosure have a structure of Formula (I-A), wherein $R^{3'}$ is $C_6$-$C_8$ alkyl.

In some embodiments, Lipids of the Disclosure have a structure of Formula (II):

(II)

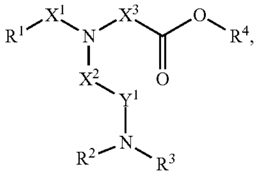

or a pharmaceutically acceptable salt thereof, wherein:

$R^1$ is —OH, —$R^{1a}$,

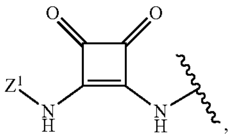

, or

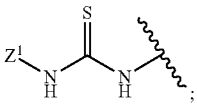

;

$Z^1$ is optionally substituted $C_1$-$C_6$ alkyl;

$X^1$ is optionally substituted $C_2$-$C_6$ alkylenyl;

$X^2$ is optionally substituted $C_2$-$C_{14}$ alkylenyl;

$Y^1$ is a bond,

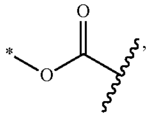

,

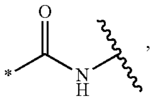

,

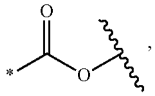

,

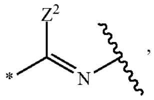

, or

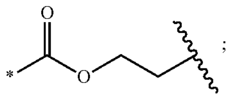

;

wherein the bond marked with an "*" is attached to $X^2$ $Z^2$ is H or optionally substituted $C_1$-$C_8$ alkyl;

$R^2$ and $R^3$ are independently optionally substituted $C_4$-$C_{14}$ alkyl;

$X^3$ is optionally substituted $C_2$-$C_{14}$ alkylenyl;

$R^4$ is optionally substituted $C_4$-$C_{14}$ alkyl;

$R^{1a}$ is:

$R^{1a}$-2

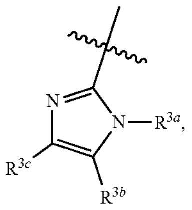

$R^{1a}$-3

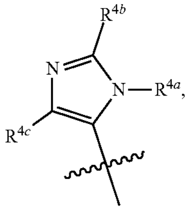

, or

-continued

R$^{1a}$-4

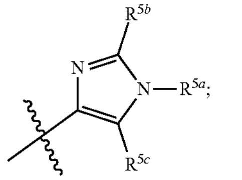

$R^{2a}$, $R^{2b}$, and $R^{2c}$ are independently hydrogen or $C_1$-$C_6$ alkyl;

$R^{3a}$, $R^{3b}$, and $R^{3c}$ are independently hydrogen or $C_1$-$C_6$ alkyl;

$R^{4a}$, $R^{4b}$, and $R^{4c}$ are independently hydrogen or $C_1$-$C_6$ alkyl; and $R^{5a}$, $R^{5b}$, and $R^{5c}$ are independently hydrogen or $C_1$-$C_6$ alkyl.

In some embodiments, Lipids of the Disclosure have a structure of Formula (II), wherein $R^1$ is —OH.

In some embodiments, Lipids of the Disclosure have a structure of Formula (II), wherein $X^1$ is $C_2$-$C_4$ alkylenyl (e.g., $C_2$ alkylenyl). In some embodiments, Lipids of the Disclosure have a structure of Formula (II), wherein $X^1$ is $C_2$ alkylenyl.

In some embodiments, Lipids of the Disclosure have a structure of Formula (II), wherein $X^2$ is $C_4$-$C_{10}$ alkylenyl (e.g., $C_5$, $C_6$, $C_7$, $C_8$, $C_9$ alkyl).

In some embodiments, Lipids of the Disclosure have a structure of Formula (II), wherein $Y^1$ is

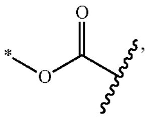, 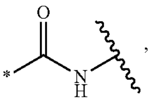, 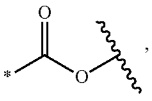, or

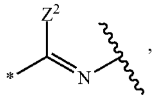, wherein $Z^2$ is hydrogen. In some embodiments, Lipids of the Disclosure have a structure of Formula (II), wherein $Y^1$ is

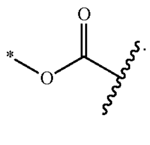 [SMILES: *OC(*)=O].

In some embodiments, Lipids of the Disclosure have a structure of Formula (II), wherein $Y^1$ is

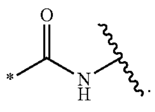.

In some embodiments, Lipids of the Disclosure have a structure of Formula (II), wherein $Y^1$ is

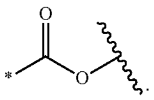 [SMILES: *OC(*)=O].

In some embodiments, Lipids of the Disclosure have a structure of Formula (II), wherein $Y^1$ is

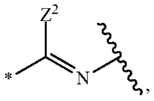, wherein $Z^2$ is hydrogen.

In some embodiments, Lipids of the Disclosure have a structure of Formula (II), wherein $R^2$ and $R^3$ are independently optionally substituted $C_4$-$C_{10}$ alkyl (e.g., $C_8$ alkyl). In some embodiments, Lipids of the Disclosure have a structure of Formula (II), wherein $R^2$ and $R^3$ are independently $C_4$-$C_{10}$ alkyl. In some embodiments, Lipids of the Disclosure have a structure of Formula (II), wherein $R^2$ and $R^3$ are independently $C_8$ alkyl.

In some embodiments, Lipids of the Disclosure have a structure of Formula (II), wherein $X^3$ is optionally substituted $C_4$-$C_{10}$ alkylenyl (e.g., $C_5$ alkylenyl). In some embodiments, Lipids of the Disclosure have a structure of Formula (II), wherein $X^3$ is $C_4$-$C_{10}$alkylenyl. In some embodiments, Lipids of the Disclosure have a structure of Formula (II), wherein $X^3$ is $C_5$ alkylenyl.

In some embodiments, Lipids of the Disclosure have a structure of Formula (II), wherein $R^4$ is optionally substituted $C_6$-$C_{12}$ alkyl (e.g., $C_{11}$ alkyl). In some embodiments, Lipids of the Disclosure have a structure of Formula (II), wherein $R^4$ is $C_6$-$C_{12}$ alkyl. In some embodiments, Lipids of the Disclosure have a structure of Formula (II), wherein $R^4$ is $C_{11}$ alkyl.

In some embodiments, Lipids of the Disclosure have a structure of Formula (III-B):

(III-B)

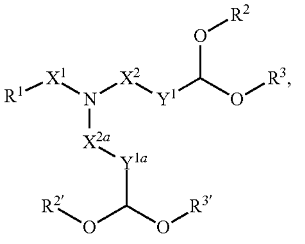

or a pharmaceutically acceptable salt thereof, wherein $R^1$ is

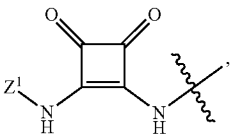, or 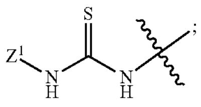;

$Z^1$ is optionally substituted $C_1$-$C_6$ alkyl;

$X^1$ is optionally substituted $C_2$-$C_6$ alkylenyl;

$X^2$ and $X^{2a}$ are independently optionally substituted $C_2$-$C_{14}$ alkylenyl;

$Y^1$ and $Y^{1a}$ are independently

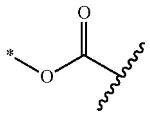 or 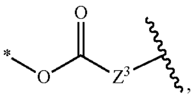, $Z^3$ is independently optionally substituted $C_2$-$C_6$ alkylenyl;

$R^2$ and $R^3$ are independently optionally substituted $C_4$-$C_{14}$ alkyl;

$R^{2'}$ and $R^{3'}$ are independently optionally substituted $C_4$-$C_{14}$ alkyl.

In some embodiments, Lipids of the Disclosure have a structure of Formula (III-B), wherein $R^1$ is

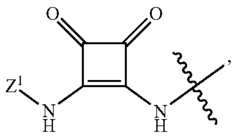, wherein $Z^1$ is methyl.

In some embodiments, Lipids of the Disclosure have a structure of Formula (II), wherein $X^1$ is $C_2$-$C_4$ alkylenyl (e.g., $C_3$ alkylenyl). n some embodiments, Lipids of the Disclosure have a structure of Formula (II), wherein $X^1$ is $C_3$ alkylenyl.

In some embodiments, Lipids of the Disclosure have a structure of Formula (II), wherein $X^2$ is $C_4$-$C_{10}$ alkylenyl (e.g., $C_6$ alkyl). In some embodiments, Lipids of the Disclosure have a structure of Formula (II), wherein $X^2$ is $C_6$ alkyl.

In some embodiments, Lipids of the Disclosure have a structure of Formula (II), wherein $R^2$ and $R^3$ are independently optionally substituted $C_4$-$C_{10}$ alkyl (e.g., $C_8$ alkyl). In some embodiments, Lipids of the Disclosure have a structure of Formula (II), wherein $R^2$ and $R^3$ are independently $C_8$ alkyl.

In some embodiments, Lipids of the Disclosure have a structure of Formula (III-C):

(III-C)

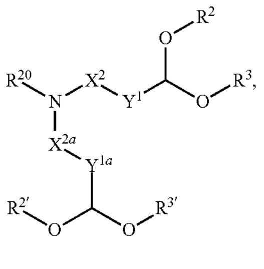

or a pharmaceutically acceptable salt thereof, wherein $R^{20}$ is $C_1$-$C_6$ alkylenyl-$NR^{20'}C(O)OR^{20''}$;

$R^{20'}$ is hydrogen or optionally substituted $C_1$-$C_6$ alkyl;

$R^{20''}$ is optionally substituted $C_1$-$C_6$ alkyl, phenyl, or benzyl;

$Z^1$ is optionally substituted $C_1$-$C_6$ alkyl;

$X^2$ and $X^{2a}$ are independently optionally substituted $C_2$-$C_{14}$ alkylenyl;

$Y^1$ and $Y^{1a}$ are independently

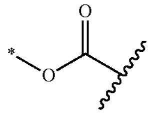 or 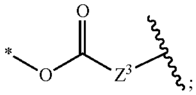;

wherein the bond marked with an "*" is attached to $X^2$ or $X^{2a}$;

$Z^3$ is independently optionally substituted $C_2$-$C_6$ alkylenyl;

$R^2$ and $R^3$ are independently optionally substituted $C_4$-$C_{14}$ alkyl; and $R^{2'}$ and $R^{3'}$ are independently optionally substituted $C_4$-$C_{14}$ alkyl.

In some embodiments, Lipids of the Disclosure have a structure of Formula (III-C), wherein $R^{20}$ is —$CH_2CH_2CH_2NHC(O)O$-t-butyl or —$CH_2CH_2CH_2NHC(O)O$-benzyl. In some embodiments, Lipids of the Disclosure have a structure of Formula (III-C), wherein $R^{20}$ is —$CH_2CH_2CH_2NHC(O)O$-t-butyl. In some embodiments, Lipids of the Disclosure have a structure of Formula (III-C), wherein $R^{20}$ is —$CH_2CH_2CH_2NHC(O)O$-benzyl.

In some embodiments, Lipids of the Disclosure have a structure of Formula (III-C), wherein $X^2$ and $X^{2a}$ are independently $C_4$-$C_5$ alkylenyl (e.g., $C_5$, $C_6$, $C_7$ alkylenyl). In some embodiments, Lipids of the Disclosure have a structure of Formula (III-C), wherein $X^2$ is $C_6$ alkylenyl. In some embodiments, Lipids of the Disclosure have a structure of Formula (III-C), wherein $X^{2a}$ is $C_6$ alkylenyl.

In some embodiments, Lipids of the Disclosure have a structure of Formula (III-C), wherein $Y^1$ and $Y^{1a}$ are

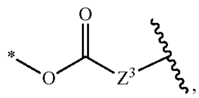, wherein $Z^3$ is $C_2$-$C_4$alkylenyl (e.g., $C_2$ alkylenyl). In some embodiments, Lipids of the Disclosure have a structure of Formula (III-C), wherein $Y^1$ is

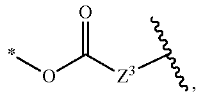, wherein $Z^3$ is $C_2$-$C_4$alkylenyl (e.g., $C_2$ alkylenyl). In some embodiments, Lipids of the Disclosure have a structure of Formula (III-C), wherein $Y^{1a}$ is

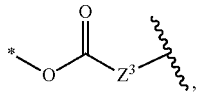, wherein $Z^3$ is $C_2$-$C_4$alkylenyl (e.g., $C_2$ alkylenyl).

In some embodiments, Lipids of the Disclosure have a structure of Formula (III-C), wherein $R^2$, $R^3$, $R^{2'}$ and $R^{3'}$ are independently optionally substituted $C_4$-$C_{10}$ alkyl (e.g., $C_6$-$C_9$alkyl, $C_6$, $C_7$, $C_8$, $C_9$ alkyl). In some embodiments, Lipids of the Disclosure have a structure of Formula (III-C), wherein $R^2$ is $C_6$-$C_9$alkyl. In some embodiments, Lipids of the Disclosure have a structure of Formula (III-C), wherein $R^3$ is $C_6$-$C_9$alkyl. In some embodiments, Lipids of the Disclosure have a structure of Formula (III-C), wherein $R^{2'}$ is $C_6$-$C_9$alkyl. In some embodiments, Lipids of the Disclosure have a structure of Formula (III-C), wherein $R^{3'}$ is $C_6$-$C_9$alkyl.

In some embodiments, Lipids of the Disclosure have a structure of Formula (III-D):

(III-D)

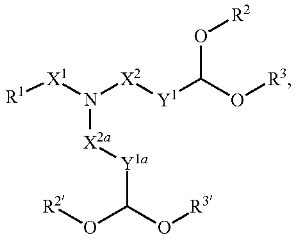

or a pharmaceutically acceptable salt thereof, wherein $R^1$ is —OH;

$X^1$ is optionally substituted $C_4$ alkylenyl;

$X^2$ and $X^{2a}$ are independently optionally substituted $C_2$-$C_{14}$ alkylenyl;

$Y^1$ and $Y^{1a}$ are independently

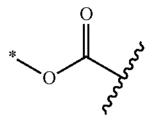

or

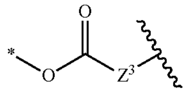

;

$Z^3$ is independently optionally substituted $C_2$-$C_6$ alkylenyl;

$R^2$ and $R^3$ are independently optionally substituted $C_4$-$C_{14}$ alkyl or $C_1$-$C_2$ alkyl substituted with optionally substituted cyclopropyl; or $R^{2'}$ and $R^{3'}$ are independently optionally substituted $C_4$-$C_{14}$ alkyl or $C_1$-$C_2$ alkyl substituted with optionally substituted cyclopropyl.

In some embodiments, Lipids of the Disclosure have a structure of Formula (III-D), wherein $X^1$ is $C_4$ alkylenyl.

In some embodiments, Lipids of the Disclosure have a structure of Formula (III-D), wherein $X^2$ and $X^{2a}$ are independently optionally substituted $C_4$-$C_{10}$ alkylenyl (e.g., $C_5$, $C_6$, $C_7$, $C_8$, $C_9$, or $C_{10}$ alkylenyl). In some embodiments, Lipids of the Disclosure have a structure of Formula (III-D), wherein $X^2$ is $C_4$-$C_{10}$ alkylenyl. In some embodiments, Lipids of the Disclosure have a structure of Formula (III-D), wherein $X^{2a}$ is $C_4$-$C_{10}$ alkylenyl.

In some embodiments, Lipids of the Disclosure have a structure of Formula (III-D), wherein $Y^1$ and $Y^{1a}$ are independently

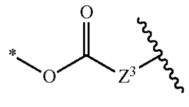

, wherein $Z^3$ is independently $C_2$-$C_4$ alkylenyl (e.g., $C_2$, $C_4$ alkylenyl).

In some embodiments, Lipids of the Disclosure have a structure of Formula (III-D), wherein $R^2$, $R^3$, $R^{2'}$ and $R^{3'}$ are independently $C_6$-$C_{14}$ alkyl (e.g., $C_6$, $C_7$, $C_8$, $C_9$, $C_{10}$, $C_{11}$, $C_{12}$, $C_{13}$, or $C_{14}$ alkyl) or $C_1$-$C_2$ alkyl substituted with optionally substituted cyclopropyl. In some embodiments, Lipids of the Disclosure have a structure of Formula (III-D), wherein $R^2$, $R^3$, $R^{2'}$ and $R^{3'}$ are independently $C_6$-$C_{14}$ alkyl (e.g., $C_6$, $C_7$, $C_8$, $C_9$, $C_{10}$, $C_{11}$, $C_{12}$, $C_{13}$, or $C_{14}$ alkyl). In some embodiments, Lipids of the Disclosure have a structure of Formula (III-D), wherein $R^2$ is $C_6$-$C_{14}$ alkyl. In some embodiments, Lipids of the Disclosure have a structure of Formula (III-D), wherein $R^3$ is $C_6$-$C_{14}$ alkyl. In some embodiments, Lipids of the Disclosure have a structure of Formula (III-D), wherein $R^{2'}$ is $C_6$-$C_{14}$ alkyl. In some embodiments, Lipids of the Disclosure have a structure of Formula (III-D), wherein $R^{3'}$ is $C_6$-$C_{14}$ alkyl. In some embodiments, Lipids of the Disclosure have a structure of Formula (III-D), wherein $R^2$ is $C_1$-$C_2$ alkyl substituted with substituted cyclopropyl. In some embodiments, Lipids of the Disclosure have a structure of Formula (III-D), wherein $R^3$ is $C_1$-$C_2$ alkyl substituted with substituted cyclopropyl. In some embodiments, Lipids of the Disclosure have a structure of Formula (III-D), wherein $R^{2'}$ is $C_1$-$C_2$ alkyl substituted with substituted cyclopropyl. In some embodiments, Lipids of the Disclosure have a structure of Formula (III-D), wherein $R^{3'}$ is $C_1$-$C_2$alkyl substituted with substituted cyclopropyl In some embodiments, Lipids of the Disclosure have a structure of Formula (III-D), wherein $R^2$, $R^3$, $R^{2'}$ and $R^{3'}$ are independently $C_1$-$C_2$ alkyl substituted with cyclopropylene-($C_1$-$C^6$alkylenyl optionally substituted with cyclopropylene substituted with $C_1$-$C_6$alkyl). In some embodiments, Lipids of the Disclosure have a structure of Formula (III-D), wherein $R^2$ is $C_1$-$C_2$ alkyl substituted with cyclopropylene-($C_1$-$C_6$alkylenyl optionally substituted with cyclopropylene substituted with $C_1$-$C_6$alkyl). In some embodiments, Lipids of the Disclosure have a structure of Formula (III-D), wherein $R^3$ is $C_1$-$C_2$ alkyl substituted with cyclopropylene-($C_1$-$C^6$alkylenyl optionally substituted with cyclopropylene substituted with $C_1$-$C_6$alkyl). In some embodiments, Lipids of the Disclosure have a structure of Formula (III-D), wherein $R^{2'}$ is $C_1$-$C_2$ alkyl substituted with cyclopropylene-($C_1$-$C^6$alkylenyl optionally substituted with cyclopropylene substituted with $C_1$-$C_6$alkyl). In some embodiments, Lipids of the Disclosure have a structure of Formula (III-D), wherein $R^{3'}$ is $C_1$-$C_2$ alkyl substituted with cyclopropylene-($C_1$-$C^6$alkylenyl optionally substituted with cyclopropylene substituted with $C_1$-$C_6$alkyl).

In some embodiments, Lipids of the Disclosure have a structure of Formula (III-E):

(III-E)

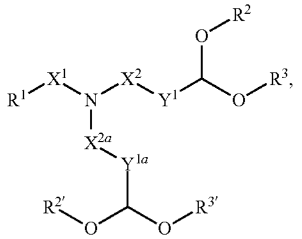

or a pharmaceutically acceptable salt thereof, wherein $R^1$ is —OH;

$X^1$ is branched $C_2$-$C_5$ alkylenyl $X^2$ and $X^{2a}$ are independently optionally substituted $C_2$-$C_{14}$ alkylenyl;

$Y^1$ and $Y^{1a}$ are independently

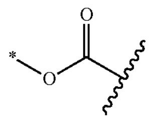

or

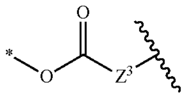

;

$Z^3$ is independently optionally substituted $C_2$-$C_6$ alkylenyl;

$R^2$ and $R^3$ are independently optionally substituted $C_4$-$C_{14}$ alkyl;

$R^{2'}$ and $R^{3'}$ are independently optionally substituted $C_4$-$C_{14}$ alkyl.

In some embodiments, Lipids of the Disclosure have a structure of Formula (III-E), wherein $X^1$ is branched $C_6$ alkylenyl.

In some embodiments, Lipids of the Disclosure have a structure of Formula (III-E), wherein $X^2$ and $X^{2a}$ are independently $C_4$-$C_{10}$ alkylenyl (e.g., $C_6$, $C_7$, $C_8$alkylenyl). In some embodiments, Lipids of the Disclosure have a structure of Formula (III-E), wherein $X^2$ is $C_4$-$C_{10}$ alkylenyl. In some embodiments, Lipids of the Disclosure have a structure of Formula (III-E), wherein $X^{2a}$ is $C_4$-$C_{10}$ alkylenyl.

In some embodiments, Lipids of the Disclosure have a structure of Formula (III-E), wherein $Y^1$ and $Y^{1a}$ are

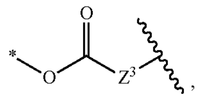

, wherein $Z^3$ is independently optionally substituted $C_2$ alkylenyl. In some embodiments, Lipids of the Disclosure have a structure of Formula (III-E), wherein $Y^1$ is

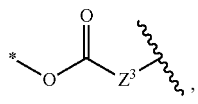

, wherein $Z^3$ is independently optionally substituted $C_2$ alkylenyl. In some embodiments, Lipids of the Disclosure have a structure of Formula (III-E), wherein $Y^{1a}$ is

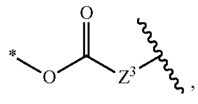

, wherein $Z^3$ is independently optionally substituted $C_2$ alkylenyl.

In some embodiments, Lipids of the Disclosure have a structure of Formula (III-E), wherein $R^2$, $R^3$, RT and $R^Y$ are independently $C_6$-$C_{12}$ alkyl (e.g., $C_9$ alkyl) or $C_4$-$C_{10}$ alkyl (e.g., $C_4$, $C_6$ alkyl) optionally substituted with $C_2$-$C_8$alkenylene (e.g., $C_4$, $C_6$ alkenylene). In some embodiments, Lipids of the Disclosure have a structure of Formula (III-E), wherein $R^2$ is $C_6$-$C_{12}$ alkyl. In some embodiments, Lipids of the Disclosure have a structure of Formula (III-E), wherein $R^3$ is $C_6$-$C_{12}$ alkyl. In some embodiments, Lipids of the Disclosure have a structure of Formula (III-E), wherein $R^{2'}$ is $C_6$-$C_{12}$ alkyl. In some embodiments, Lipids of the Disclosure have a structure of Formula (III-E), wherein $R^{3'}$ is $C_6$-$C_{12}$ alkyl. In some embodiments, Lipids of the Disclosure have a structure of Formula (III-E), wherein $R^2$ is $C_4$-$C_{10}$ alkyl optionally substituted with $C_2$-$C_8$alkenylene. In some embodiments, Lipids of the Disclosure have a structure of Formula (III-E), wherein $R^3$ is $C_4$-$C_{10}$ alkyl optionally substituted with $C_2$-$C_8$alkenylene. In some embodiments, Lipids of the Disclosure have a structure of Formula (III-E), wherein $R^{2'}$ is $C_4$-$C_{10}$ alkyl optionally substituted with $C_2$-$C_8$alkenylene. In some embodiments, Lipids of the Disclosure have a structure of Formula (III-E), wherein $R^{3'}$ is $C_4$-$C_{10}$ alkyl optionally substituted with $C_2$-$C_8$alkenylene.

In some embodiments, Lipids of the Disclosure have a structure of Formula (III-F):

(III-F)

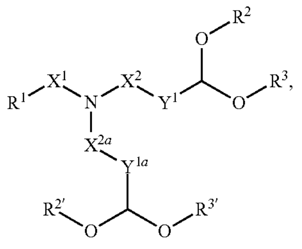

or a pharmaceutically acceptable salt thereof, wherein $R^1$ is —OH;

$X^1$ is optionally substituted $C_2$-$C_6$ alkylenyl;

$X^2$ and $X^{2a}$ are independently optionally substituted $C_2$-$C_{14}$ alkylenyl;

each of $Y^1$ and $Y^{1a}$ is a bond;

$R^2$ and $R^3$ are independently optionally substituted $C_4$-$C_{14}$ alkyl; and $R^{2'}$ and $R^{3'}$ are independently optionally substituted $C_4$-$C_{14}$ alkyl.

In some embodiments, Lipids of the Disclosure have a structure of Formula (III-E), wherein $X^1$ is $C_4$ alkylenyl.

In some embodiments, Lipids of the Disclosure have a structure of Formula (III-E), wherein $X^2$ and $X^{2a}$ are independently $C_4$-$C_{10}$ alkylenyl (e.g., $C_6$-$C_8$ alkylenyl, $C_6$, $C_7$, $C_8$ alkylenyl). In some embodiments, Lipids of the Disclosure have a structure of Formula (III-E), wherein $X^2$ is $C_4$-$C_{10}$ alkylenyl. In some embodiments, Lipids of the Disclosure have a structure of Formula (III-E), wherein $X^{2a}$ is $C_4$-$C_{10}$ alkylenyl.

In some embodiments, Lipids of the Disclosure have a structure of Formula (III-E), wherein $R^2$, $R^3$, $R^{2'}$ and $R^{3'}$ are independently $C_6$-$C_{10}$ alkyl (e.g., $C_7$. $C_8$ alkyl). In some embodiments, Lipids of the Disclosure have a structure of Formula (III-E), wherein $R^2$ is $C_6$-$C_{10}$ alkyl. In some embodiments, Lipids of the Disclosure have a structure of Formula (III-E), wherein $R^3$ is $C_6$-$C_{10}$ alkyl. In some embodiments, Lipids of the Disclosure have a structure of Formula (III-E), wherein $R^{2'}$ is $C_6$-$C_{10}$ alkyl. In some embodiments, Lipids of the Disclosure have a structure of Formula (III-E), wherein $R^{3'}$ is $C_6$-$C_{10}$ alkyl.

In some embodiments, Lipids of the Disclosure have a structure of Formula (VIII-B):

(VIII-B)

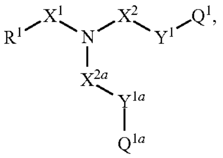

or a pharmaceutically acceptable salt thereof, wherein:

$X^1$ is a bond, $R^1$ is $C_1$-$C_6$ alkyl, $X^2$ is $C_2$-$C_6$ alkylenyl, $X^{2a}$ is $C_2$-$C_{14}$ alkylenyl, wherein $X^2$ or $X^{2a}$ is substituted with OH or $C_{1-4}$alkylenyl-OH, $Y^1$ is

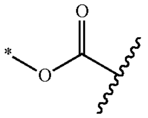, 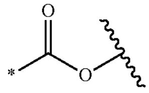,

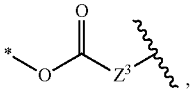, or 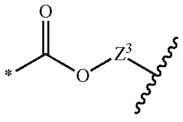, wherein the bond marked with an "*" is attached to $X^2$;

$Y^{1a}$ is

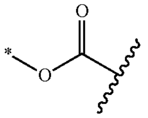, 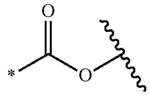,

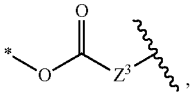, or 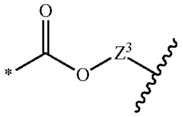, wherein the bond marked with an "*" is attached to $X^{2a}$;

each $Z^3$ is independently optionally substituted $C_1$-$C_6$ alkylenyl or optionally substituted $C_2$-$C_{14}$ alkenylenyl;

$Q^1$ is —$C(R^2)(R^3)(R^{12})$;

$Q^{1a}$ is —$C(R^{2'})(R^{3'})(R^{12'})$;

$R^2$, $R^3$, and $R^{12}$ are independently hydrogen, optionally substituted $C_1$-$C_{14}$ alkyl, or optionally substituted $C_2$-$C_{14}$ alkenylenyl, and $R^{2'}$, $R^{3'}$, and $R^{12'}$ are independently hydrogen, optionally substituted $C_1$-$C_{14}$ alkyl, or optionally substituted $C_2$-$C_{14}$ alkenylenyl.

In some embodiments, Lipids of the Disclosure have a structure of Formula (VIII-B), wherein $R^1$ is methyl.

In some embodiments, Lipids of the Disclosure have a structure of Formula (VIII-B), wherein $X^2$ is $C_4$, $C_5$, or $C_6$ alkylenyl.

In some embodiments, Lipids of the Disclosure have a structure of Formula (VIII-B), wherein $X^{2a}$ is $C_4$-$C_8$ alkylenyl (e.g., $C_5$, $C_6$, or $C_7$ alkylenyl).

In some embodiments, Lipids of the Disclosure have a structure of Formula (VIII-B), wherein $Y^1$ is

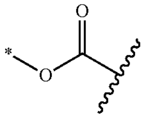 or 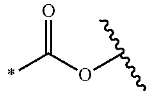, and $Y^{1a}$ is

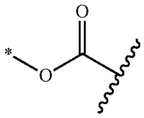 or 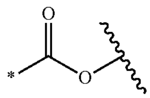.

In some embodiments, Lipids of the Disclosure have a structure of Formula (VIII-B), wherein $Y^1$ is

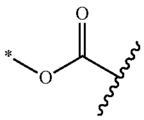.

In some embodiments, Lipids of the Disclosure have a structure of Formula (VIII-B), wherein $Y^1$ is

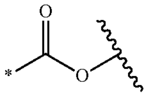.

In some embodiments, Lipids of the Disclosure have a structure of Formula (VIII-B), wherein $Y^{1a}$ is

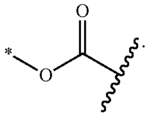 [SMILES: *OC(*)=O].

In some embodiments, Lipids of the Disclosure have a structure of Formula (VIII-B), wherein $Y^{1a}$ is

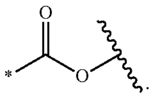 [SMILES: *OC(*)=O].

In some embodiments, Lipids of the Disclosure have a structure of Formula (VIII-B), wherein $R^2$, $R^3$, $R^{12}$, $R^{2'}$, $R^{3'}$, and $R^{12'}$ are independently hydrogen or $C_5$-$C_{12}$ alkyl (e.g., $C_6$, $C_7$, $C_8$, $C_9$, $C_{10}$, $C_{11}$ alkyl). In some embodiments, Lipids of the Disclosure have a structure of Formula (VIII-B), wherein $R^2$ is hydrogen. In some embodiments, Lipids of the Disclosure have a structure of Formula (VIII-B), wherein $R^3$ is hydrogen. In some embodiments, Lipids of the Disclosure have a structure of Formula (VIII-B), wherein $R^{2'}$ is hydrogen. In some embodiments, Lipids of the Disclosure have a structure of Formula (VIII-B), wherein $R^{3'}$ is hydrogen. In some embodiments, Lipids of the Disclosure have a structure of Formula (VIII-B), wherein $R^2$ is $C_5$-$C_{12}$ alkyl. In *some embodiments, Lipids of the Disclosure have a structure of Formula (VIII-B), wherein $R^3$* is $C_5$-$C_{12}$ alkyl. In some embodiments, Lipids of the Disclosure have a structure of Formula (VIII-B), wherein $R^{2'}$ is $C_5$-$C_{12}$ alkyl. In some embodiments, Lipids of the Disclosure have a structure of Formula (VIII-B), wherein $R^{3'}$ is $C_5$-$C_{12}$ alkyl.

In some embodiments, Lipids of the Disclosure have a structure of Formula (IV):

(IV)

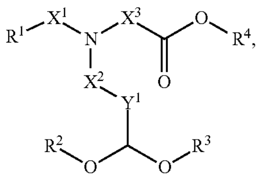

or a pharmaceutically acceptable salt thereof, wherein $R^1$ is —OH, —$R^{1a}$, $X^1$ is optionally substituted $C_2$-$C_6$ alkylenyl;

(i) $Y^1$ is

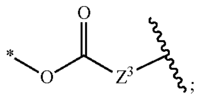

$Z^3$ is optionally substituted $C_2$-$C_6$ alkylenyl; and $R^2$ and $R^3$ are independently optionally substituted $C_4$-$C_{14}$ alkyl;

$X^2$ and $X^3$ are $C_5$ alkylenyl; or (ii) $Y^1$ is a bond $R^2$ and $R^3$ are independently $C_4$-$C_7$alkyl;

$X^2$ is optionally substituted $C_2$-$C_{14}$ alkylenyl;

$X^3$ is optionally substituted $C_5$ alkylenyl;

$R^4$ is optionally substituted $C_4$-$C_{14}$ alkyl;

$R^{1a}$ is:

$R^{1a}$-1

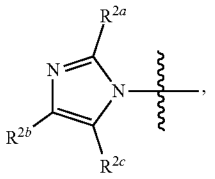

$R^{1a}$-2

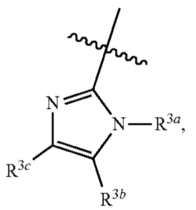

$R^{1a}$-3

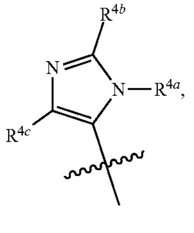

or

-continued $R^{1a}$-4

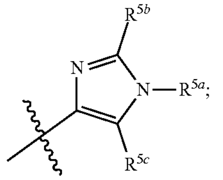

$R^{2a}$, $R^{2b}$, and $R^{2c}$ are independently hydrogen and $C_1$-$C_6$ alkyl;

$R^{3a}$, $R^{3b}$, and $R^{3c}$ are independently hydrogen and $C_1$-$C_6$ alkyl;

$R^{4a}$, $R^{4b}$, and $R^{40}$ are independently hydrogen and $C_1$-$C_6$ alkyl; and $R^{5a}$, $R^{5b}$, and $R^{5c}$ are independently hydrogen and $C_1$-$C_6$ alkyl.

In some embodiments, Lipids of the Disclosure have a structure of Formula (IV), wherein $R^1$ is OH.

In some embodiments, Lipids of the Disclosure have a structure of Formula (IV), wherein $X^1$ is $C_2$ alkylenyl.

In some embodiments, Lipids of the Disclosure have a structure of Formula (IV), wherein $Y^1$ is

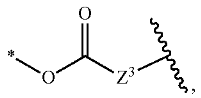

wherein $Z^3$ is $C_2$ alkylenyl.

In some embodiments, Lipids of the Disclosure have a structure of Formula (IV), wherein $R^2$ and $R^3$ are independently $C_6$-$C_{12}$ alkyl ($C_7$, $C_8$, $C_9$, $C_{10}$, $C_{11}$ alkyl). In some embodiments, Lipids of the Disclosure have a structure of Formula (IV), wherein $R^2$ is $C_6$-$C_{12}$ alkyl. In some embodiments, Lipids of the Disclosure have a structure of Formula (IV), wherein $R^3$ is $C_6$-$C_{12}$ alkyl.

In some embodiments, Lipids of the Disclosure have a structure of Formula (IV), wherein $Y^1$ is a bond.

In some embodiments, Lipids of the Disclosure have a structure of Formula (IV), wherein $R^2$ and $R^3$ are $C_4$-$C_7$alkyl (e.g., $C_7$alkyl). In some embodiments, Lipids of the Disclosure have a structure of Formula (IV), wherein $R^2$ is $C_4$-$C_7$ alkyl. In some embodiments, Lipids of the Disclosure have a structure of Formula (IV), wherein $R^3$ is $C_4$-$C_7$ alkyl.

In some embodiments, Lipids of the Disclosure have a structure of Formula (IV), wherein $X^2$ is $C_6$-$C_{12}$ alkylenyl (e.g., $C_7$, $C_8$, $C_9$, $C_{10}$ alkylenyl).

In some embodiments, Lipids of the Disclosure have a structure of Formula (VI):

(VI)

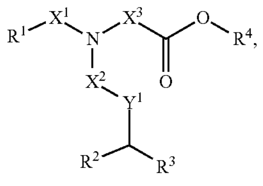

or a pharmaceutically acceptable salt thereof, wherein $R^1$ is —OH,

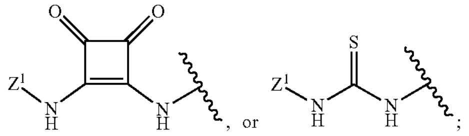

$Z^1$ is optionally substituted $C_1$-$C_6$ alkyl;
$X^1$ is optionally substituted $C_2$-$C_6$ alkylenyl;
$X^2$ is optionally substituted $C_2$-$C_{14}$ alkylenyl;
$X^3$ is optionally substituted $C_2$-$C_{14}$ alkylenyl;
$Y^1$ is

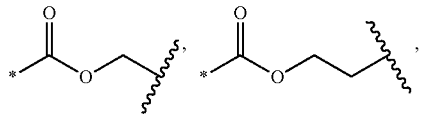

, or

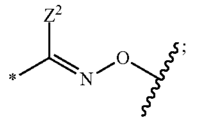

wherein the bond marked with an "*" is attached to $X^2$;
$Z^2$ is H or optionally substituted $C_1$-$C_5$ alkyl;
$R^2$ and $R^3$ are independently optionally substituted $C_3$-$C_{14}$ alkyl; and
(i) $R^4$ is linear $C_4$-$C_{14}$ alkyl; or
(ii) $R^4$ is linear $C_4$-$C_{14}$ alkyl substituted by 1 or 2 isopropyl groups.

In some embodiments, Lipids of the Disclosure have a structure of Formula (VI), wherein $R^1$ is —OH.

In some embodiments, Lipids of the Disclosure have a structure of Formula (VI), wherein $R^1$ is

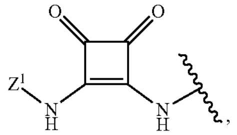

wherein $Z^1$ is $C_1$-$C_6$ alkyl (e.g., methyl).

In some embodiments, Lipids of the Disclosure have a structure of Formula (VI), wherein $X^1$ is optionally substituted $C_2$-$C_4$ alkylenyl (e.g., $C_2$, $C_3$, $C_4$ alkylenyl). In some embodiments, Lipids of the Disclosure have a structure of Formula (VI), wherein $X^1$ is $C_2$-$C_4$ alkylenyl.

In some embodiments, Lipids of the Disclosure have a structure of Formula (VI), wherein $X^2$ is $C_4$-$C_8$ alkylenyl (e.g., $C_5$, $C_6$, $C_7$, $C_8$ alkylenyl).

In some embodiments, Lipids of the Disclosure have a structure of Formula (VI), wherein $X^3$ is $C_4$-$C_8$ alkylenyl (e.g., $C_5$, $C_6$, $C_7$, $C_8$ alkylenyl).

In some embodiments, Lipids of the Disclosure have a structure of Formula (VI), wherein $Y^1$ is

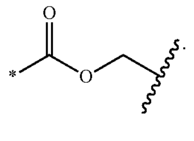 [SMILES: *COC(*)=O]

In some embodiments, Lipids of the Disclosure have a structure of Formula (VI), wherein $Y^1$ is

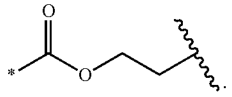 [SMILES: *CCOC(*)=O]

In some embodiments, Lipids of the Disclosure have a structure of Formula (VI), wherein $Y^1$ is

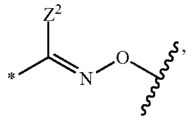

wherein $Z^2$ is hydrogen.

In some embodiments, Lipids of the Disclosure have a structure of Formula (VI), wherein $R^2$ and $R^3$ are independently $C_3$-$C_8$ alkyl (e.g., $C_3$ alkyl, $C_5$ alkyl, $C_8$ alkyl). In some embodiments, Lipids of the Disclosure have a structure of Formula (VI), wherein $R^2$ is $C_3$-$C_8$ alkyl. In some embodiments, Lipids of the Disclosure have a structure of Formula (VI), wherein $R^3$ is $C_3$-$C_8$ alkyl.

In some embodiments, Lipids of the Disclosure have a structure of Formula (VI), wherein $R^4$ is linear $C_8$-$C_{14}$ alkyl (e.g., $C_{10}$, $C_{11}$, $C_{12}$ alkyl).

In some embodiments, Lipids of the Disclosure have a structure of Formula (VI), wherein $R^4$ is linear $C_4$-$C_5$ alkyl (e.g., $C_4$alkyl) substituted by 1 or 2 isopropyl groups.

In some embodiments, Lipids of the Disclosure have a structure of Formula (X):

(X)

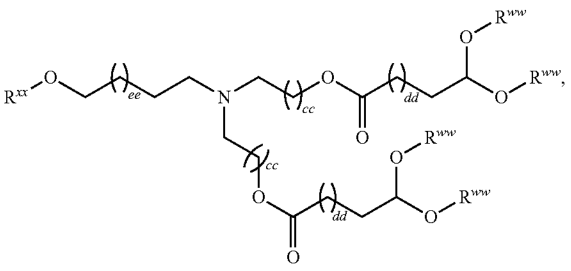

or a pharmaceutically acceptable salt thereof, wherein
each cc is independently selected from 3 to 9;
$R^{xx}$ is selected from hydrogen and optionally substituted $C_1$-$C_6$ alkyl; and (i) ee is 1,
each dd is independently selected from 1 to 4; and
each $R^{ww}$ is independently selected from the group consisting of $C_4$-$C_{14}$ alkyl, branched $C_4$-$C_{12}$ alkenyl, $C_4$-$C_{12}$ alkenyl comprising at least two double bonds, and $C_9$-$C_{12}$ alkenyl, wherein any $—(CH_2)_2—$ of the $C_4$-$C_{14}$ alkyl can be optionally replaced with $C_2$-$C_6$ cycloalkylenyl;
(ii) ee is 0,
each dd is 1; and
each $R^{ww}$ is linear $C_4$-$C_{12}$ alkyl.

In some embodiments, Lipids of the Disclosure have a structure of Formula (X), wherein $R^{xx}$ is H. In some embodiments, Lipids of the Disclosure have a structure of Formula (X), wherein $R^{xx}$ is optionally substituted $C_1$-$C_6$ alkyl. In some embodiments, Lipids of the Disclosure have a structure of Formula (X), wherein $R^{xx}$ is $C_1$ alkyl. In some embodiments, Lipids of the Disclosure have a structure of Formula (X), wherein $R^{xx}$ is $C_2$ alkyl. In some embodiments, Lipids of the Disclosure have a structure of Formula (X), wherein $R^{xx}$ is $C_3$ alkyl. In some embodiments, Lipids of the Disclosure have a structure of Formula (X), wherein $R^{xx}$ is $C_4$ alkyl. In some embodiments, Lipids of the Disclosure have a structure of Formula (X), wherein $R^{xx}$ is $C_5$ alkyl. In some embodiments, Lipids of the Disclosure have a structure of Formula (X), wherein $R^{xx}$ is $C_6$ alkyl.

In some embodiments, Lipids of the Disclosure have a structure of Formula (X), wherein each $R^{ww}$ is independently selected from the group consisting of $C_4$-$C_{14}$ alkyl, branched $C_4$-$C_{12}$ alkenyl, $C_4$-$C_{12}$ alkenyl comprising at least two double bonds, and $C_9$-$C_{12}$ alkenyl, wherein any —$(CH_2)_2$— of the $C_4$-$C_{14}$ alkyl can be optionally replaced with $C_2$-$C_6$ cycloalkylenyl. In some embodiments, Lipids of the Disclosure have a structure of Formula (X), wherein each $R^{ww}$ is $C_4$-$C_{14}$ alkyl, wherein any —$(CH_2)_2$— of the $C_4$-$C_{14}$ alkyl can be optionally replaced with $C_2$-$C_6$ cycloalkylenyl. In some embodiments, Lipids of the Disclosure have a structure of Formula (X), wherein each $R^{ww}$ is $C_4$-$C_{14}$ alkyl, wherein any —$(CH_2)_2$— of the $C_4$-$C_{14}$ alkyl can be optionally replaced with cyclopropylene. In some embodiments, Lipids of the Disclosure have a structure of Formula (X), wherein each $R^{ww}$ is branched $C_4$-$C_{12}$ alkenyl. In some embodiments, Lipids of the Disclosure have a structure of Formula (X), wherein each $R^{ww}$ is $C_4$-$C_{12}$ alkenyl comprising at least two double bonds. In some embodiments, Lipids of the Disclosure have a structure of Formula (X), wherein each $R^{ww}$ is $C_9$-$C_{12}$ alkenyl. In some embodiments, Lipids of the Disclosure have a structure of Formula (X), wherein each $R^{ww}$ is linear $C_4$-$C_{12}$ alkyl. In some embodiments, Lipids of the Disclosure have a structure of Formula (X), wherein each $R^{ww}$ is independently selected from the group consisting of $C_6$-$C_{14}$ alkyl, branched $C_8$-$C_{12}$ alkenyl, $C_8$-$C_{12}$ alkenyl comprising at least two double bonds, and $C_9$-$C_{12}$ alkenyl, wherein any —$(CH_2)_2$— of the $C_6$-$C_{14}$ alkyl can be optionally replaced with cyclopropylene. In some embodiments, Lipids of the Disclosure have a structure of Formula (X), wherein each $R^{ww}$ is $C_6$-$C_{14}$ alkyl, wherein any —$(CH_2)_2$— of the $C_6$-$C_{14}$ alkyl can be optionally replaced with cyclopropylene. In some embodiments, Lipids of the Disclosure have a structure of Formula (X), wherein each $R^{ww}$ is branched $C_8$-$C_{12}$ alkenyl, e.g., (linear or branched $C_3$-$C_5$ alkylenyl)-(branched $C_5$-$C_7$alkenyl), e.g., (branched $C_5$ alkylenyl)-(branched $C_5$ alkenyl), e.g.,

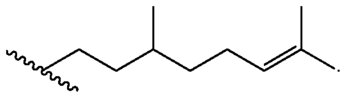

In some embodiments, Lipids of the Disclosure have a structure of Formula (X), wherein each $R^{ww}$ is $C_8$-$C_{12}$ alkenyl comprising at least two double bonds. In some embodiments, Lipids of the Disclosure have a structure of Formula (X), wherein each $R^{ww}$ is $C_9$-$C_{12}$ alkenyl.

In some embodiments, Lipids of the Disclosure have a structure of Formula (X), wherein each $R^{ww}$ is independently selected from the group consisting of $C_6$-$C_{14}$ alkyl (e.g., $C_6$, $C_8$, $C_9$, $C_{10}$, $C_{11}$, $C_{13}$ alkyl), wherein any —$(CH_2)_2$— of the $C_6$-$C_{14}$ alkyl can be optionally replaced with cyclopropylene.

In some embodiments, Lipids of the Disclosure have a structure of Formula (X), wherein each $R^{ww}$ is independently branched $C_8$-$C_{12}$ alkenyl (e.g., branched $C_{10}$ alkenyl).

In some embodiments, Lipids of the Disclosure have a structure of Formula (X), wherein each $R^{ww}$ is independently $C_8$-$C_{12}$ alkenyl comprising at least two double bonds (e.g., $C_9$ or $C_{10}$ alkenyl comprising two double bonds).

In some embodiments, Lipids of the Disclosure have a structure of Formula (X), wherein each $R^{ww}$ is independently ($C_1$ alkylenyl)-(cyclopropylene-$C_6$ alkyl) or ($C_2$ alkylenyl)-(cyclopropylene-$C_2$ alkyl). In some embodiments, Lipids of the Disclosure have a structure of Formula (X), wherein each $R^{ww}$ is independently ($C_1$ alkylenyl)-(cyclopropylene-$C_6$ alkyl). In some embodiments, Lipids of the Disclosure have a structure of Formula (X), wherein each $R^{ww}$ is independently ($C_2$ alkylenyl)-(cyclopropylene-$C_2$ alkyl).

In some embodiments, Lipids of the Disclosure have a structure of Formula (X), wherein each $R^{ww}$ is $C_4$ alkyl. In some embodiments, Lipids of the Disclosure have a structure of Formula (X), wherein each $R^{ww}$ is $C_5$ alkyl. In some embodiments, Lipids of the Disclosure have a structure of Formula (X), wherein each $R^{ww}$ is $C_6$ alkyl. In some embodiments, Lipids of the Disclosure have a structure of Formula (X), wherein each $R^{ww}$ is $C_7$ alkyl. In some embodiments, Lipids of the Disclosure have a structure of Formula (X), wherein each $R^{ww}$ is $C_8$ alkyl. In some embodiments, Lipids of the Disclosure have a structure of Formula (X), wherein each $R^{ww}$ is $C_9$ alkyl. In some embodiments, Lipids of the Disclosure have a structure of Formula (X), wherein each $R^{ww}$ is $C_{10}$ alkyl. In some embodiments, Lipids of the Disclosure have a structure of Formula (X), wherein each $R^{ww}$ is $C_{11}$ alkyl. In some embodiments, Lipids of the Disclosure have a structure of Formula (X), wherein each $R^{ww}$ is $C_{12}$ alkyl. In some embodiments, Lipids of the Disclosure have a structure of Formula (X), wherein each $R^{ww}$ is $C_{13}$ alkyl. In some embodiments, Lipids of the Disclosure have a structure of Formula (X), wherein each $R^{ww}$ is $C_{14}$ alkyl.

In some embodiments, Lipids of the Disclosure have a structure of Formula (X), wherein each $R^{ww}$ is $C_9$ alkenyl. In some embodiments, Lipids of the Disclosure have a structure of Formula (X), wherein each $R^{ww}$ is $C_{10}$ alkenyl. In some embodiments, Lipids of the Disclosure have a structure of Formula (X), wherein each $R^{ww}$ is $C_{11}$ alkenyl. In some embodiments, Lipids of the Disclosure have a structure of Formula (X), wherein each $R^{ww}$ is $C_{12}$ alkenyl.

In some embodiments, Lipids of the Disclosure have a structure of Formula (X), wherein each $R^{ww}$ is $C_8$ alkenyl comprising at least two double bonds. In some embodiments, Lipids of the Disclosure have a structure of Formula (X), wherein each $R^{ww}$ is $C_9$ alkenyl comprising at least two double bonds. In some embodiments, Lipids of the Disclosure have a structure of Formula (X), wherein each $R^{ww}$ is $C_{10}$ alkenyl comprising at least two double bonds. In some embodiments, Lipids of the Disclosure have a structure of Formula (X), wherein each $R^{ww}$ is $C_{11}$ alkenyl comprising at least two double bonds. In some embodiments, Lipids of the Disclosure have a structure of Formula (X), wherein each $R^{ww}$ is $C_{12}$ alkenyl comprising at least two double bonds. In some embodiments, Lipids of the Disclosure have a structure of Formula (X), wherein each $R^{ww}$ is $C_{13}$ alkenyl comprising at least two double bonds. In some embodiments, Lipids of the Disclosure have a structure of Formula (X), wherein each $R^{ww}$ is $C_{14}$ alkenyl comprising at least two double bonds.

In some embodiments, Lipids of the Disclosure have a structure of Formula (X), wherein each $R^{ww}$ is $C_9$ alkyl, wherein one —$(CH_2)_2$— of the $C_9$ alkyl is replaced with $C_2$-$C_6$ cycloalkylenyl. In some embodiments, Lipids of the Disclosure have a structure of Formula (X), wherein each $R^{ww}$ is $C_9$ alkyl, wherein one —$(CH_2)_2$— of the $C_9$ alkyl is replaced with cyclopropylene. In some embodiments, Lipids of the Disclosure have a structure of Formula (X), wherein each $R^{ww}$ is $C_9$ alkyl, wherein two —$(CH_2)_2$— of the $C_9$ alkyl are replaced with $C_2$-$C_6$ cycloalkylenyl. In some embodiments, Lipids of the Disclosure have a structure of Formula (X), wherein each $R^{ww}$ is $C_9$ alkyl, wherein two —$(CH_2)_2$— of the $C_9$ alkyl are replaced with cyclopropylene.

In some embodiments, Lipids of the Disclosure have a structure of Formula (X), wherein each $R^{ww}$ is linear $C_4$ alkyl. In some embodiments, Lipids of the Disclosure have a structure of Formula (X), wherein each $R^{ww}$ is linear $C_5$ alkyl. In some embodiments, Lipids of the Disclosure have a structure of Formula (X), wherein each $R^{ww}$ is linear $C_6$ alkyl. In some embodiments, Lipids of the Disclosure have a structure of Formula (X), wherein each $R^{ww}$ is linear $C_7$ alkyl. In some embodiments, Lipids of the Disclosure have a structure of Formula (X), wherein each $R^{ww}$ is linear $C_8$ alkyl. In some embodiments, Lipids of the Disclosure have a structure of Formula (X), wherein each $R^{ww}$ is linear $C_9$ alkyl. In some embodiments, Lipids of the Disclosure have a structure of Formula (X), wherein each $R^{ww}$ is linear $C_{10}$ alkyl. In some embodiments, Lipids of the Disclosure have a structure of Formula (X), wherein each $R^{ww}$ is linear $C_{11}$ alkyl. In some embodiments, Lipids of the Disclosure have a structure of Formula (X), wherein each $R^{ww}$ is linear $C_{12}$ alkyl. In some embodiments, Lipids of the Disclosure have a structure of Formula (X), wherein each $R^{ww}$ is linear $C_{13}$ alkyl. In some embodiments, Lipids of the Disclosure have a structure of Formula (X), wherein each $R^{ww}$ is linear $C_{14}$ alkyl.

In some embodiments, Lipids of the Disclosure have a structure of Formula (X), wherein each $R^{ww}$ is branched $C_8$ alkenyl. In some embodiments, Lipids of the Disclosure have a structure of Formula (X), wherein each $R^{ww}$ is branched $C_9$ alkenyl. In some embodiments, Lipids of the Disclosure have a structure of Formula (X), wherein each $R^{ww}$ is branched $C_{10}$ alkenyl. In some embodiments, Lipids of the Disclosure have a structure of Formula (X), wherein each $R^{ww}$ is branched $C_{11}$ alkenyl. In some embodiments, Lipids of the Disclosure have a structure of Formula (X), wherein each $R^{ww}$ is branched $C_{12}$ alkenyl.

In some embodiments, Lipids of the Disclosure have a structure of Formula (X), wherein each cc is independently selected from 3 to 7. In some embodiments, Lipids of the Disclosure have a structure of Formula (X), wherein each cc is 3. In some embodiments, Lipids of the Disclosure have a structure of Formula (X), wherein each cc is 4. In some embodiments, Lipids of the Disclosure have a structure of Formula (X), wherein each cc is 5. In some embodiments, Lipids of the Disclosure have a structure of Formula (X), wherein each cc is 6. In some embodiments, Lipids of the Disclosure have a structure of Formula (X), wherein each cc is 7. In some embodiments, Lipids of the Disclosure have a structure of Formula (X), wherein each cc is 8. In some embodiments, Lipids of the Disclosure have a structure of Formula (X), wherein each cc is 9.

In some embodiments, Lipids of the Disclosure have a structure of Formula (X), wherein each dd is independently selected from 1 to 4. In some embodiments, Lipids of the Disclosure have a structure of Formula (X), wherein each dd is 1. In some embodiments, Lipids of the Disclosure have a structure of Formula (X), wherein each dd is 2. In some embodiments, Lipids of the Disclosure have a structure of Formula (X), wherein each dd is 3. In some embodiments, Lipids of the Disclosure have a structure of Formula (X), wherein each dd is 4.

In some embodiments, Lipids of the Disclosure have a structure of Formula (X), wherein ee is 1.

In some embodiments, Lipids of the Disclosure have a structure of Formula (X), wherein ee is 0.

In some embodiments, Lipids of the Disclosure have a structure of Formula (X), wherein the Lipids of the Disclosure have a structure of Formula (X-A):

(X-A)

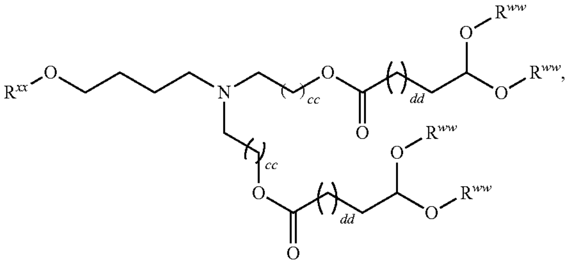

or a pharmaceutically acceptable salt thereof, wherein each cc is independently selected from 3 to 7;

each dd is independently selected from 1 to 4;

$R^{xx}$ is selected from hydrogen and optionally substituted $C_1$-$C_6$ alkyl; and each $R^{ww}$ is independently selected from the group consisting of $C_4$-$C_{14}$ alkyl or (linear or branched $C_3$-$C_5$ alkylenyl)-(branched $C_5$-$C_7$alkenyl).

In some embodiments, Lipids of the Disclosure have a structure of Formula (X-A), wherein $R^{xx}$ is hydrogen. In some embodiments, Lipids of the Disclosure have a structure of Formula (X-A), wherein $R^{xx}$ is $C_1$ alkyl. In some embodiments, Lipids of the Disclosure have a structure of Formula (X-A), wherein $R^{xx}$ is $C_2$ alkyl. In some embodiments, Lipids of the Disclosure have a structure of Formula (X-A), wherein $R^{xx}$ is $C_3$ alkyl. In some embodiments, Lipids of the Disclosure have a structure of Formula (X-A), wherein $R^{xx}$ is $C_4$ alkyl. In some embodiments, Lipids of the Disclosure have a structure of Formula (X-A), wherein $R^{xx}$ is $C_5$ alkyl. In some embodiments, Lipids of the Disclosure have a structure of Formula (X-A), wherein $R^{xx}$ is $C_6$ alkyl.

In some embodiments, Lipids of the Disclosure have a structure of Formula (X-A), wherein each cc is 4, 5, 6, or 7. In some embodiments, Lipids of the Disclosure have a structure of Formula (X-A), wherein each cc is 3. In some embodiments, Lipids of the Disclosure have a structure of Formula (X-A), wherein each cc is 4. In some embodiments, Lipids of the Disclosure have a structure of Formula (X-A), wherein each cc is 5. In some embodiments, Lipids of the Disclosure have a structure of Formula (X-A), wherein each cc is 6. In some embodiments, Lipids of the Disclosure have a structure of Formula (X-A), wherein each cc is 7.

In some embodiments, Lipids of the Disclosure have a structure of Formula (X-A), wherein each dd is 1 or 3. In some embodiments, Lipids of the Disclosure have a structure of Formula (X-A), wherein each dd is 1. In some embodiments, Lipids of the Disclosure have a structure of Formula (X-A), wherein each dd is 2. In some embodiments, Lipids of the Disclosure have a structure of Formula (X-A), wherein each dd is 3. In some embodiments, Lipids of the Disclosure have a structure of Formula (X-A), wherein each dd is 4.

In some embodiments, Lipids of the Disclosure have a structure of Formula (X-A), wherein each $R^{ww}$ is $C_4$-$C_{14}$ alkyl. In some embodiments, Lipids of the Disclosure have a structure of Formula (X-A), wherein each $R^{ww}$ is $C_4$ alkyl. In some embodiments, Lipids of the Disclosure have a structure of Formula (X-A), wherein each $R^{ww}$ is $C_5$ alkyl. In some embodiments, Lipids of the Disclosure have a structure of Formula (X-A), wherein each $R^{ww}$ is $C_6$ alkyl. In some embodiments, Lipids of the Disclosure have a structure of Formula (X-A), wherein each $R^{ww}$ is $C_7$ alkyl. In some embodiments, Lipids of the Disclosure have a structure of Formula (X-A), wherein each $R^{ww}$ is $C_8$ alkyl. In some embodiments, Lipids of the Disclosure have a structure of Formula (X-A), wherein each $R^{ww}$ is $C_9$ alkyl. In some embodiments, Lipids of the Disclosure have a structure of Formula (X-A), wherein each $R^{ww}$ is $C_{10}$ alkyl. In some embodiments, Lipids of the Disclosure have a structure of Formula (X-A), wherein each $R^{ww}$ is $C_{11}$ alkyl. In some embodiments, Lipids of the Disclosure have a structure of Formula (X-A), wherein each $R^{ww}$ is $C_{12}$ alkyl. In some embodiments, Lipids of the Disclosure have a structure of Formula (X-A), wherein each $R^{ww}$ is $C_{13}$ alkyl. In some embodiments, Lipids of the Disclosure have a structure of Formula (X-A), wherein each $R^{ww}$ is $C_{14}$ alkyl.

In some embodiments, Lipids of the Disclosure have a structure of Formula (X-A), wherein each $R^{ww}$ is (linear or branched $C_3$-$C_5$ alkylenyl)-(branched $C_5$-$C_7$alkenyl), e.g., (branched $C_5$ alkylenyl)-(branched $C_5$alkenyl), e.g.,

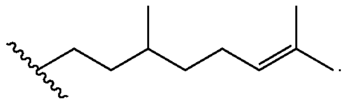 [SMILES: *CCC(C)CCC=C(C)C]

IV. Delivery Vehicles and Tracking Systems

Originator constructs and benchmark constructs described herein may be formulated in a delivery vehicle. Non-limiting examples of delivery vehicles include lipid nanoparticles, non-lipid nanoparticles, exosomes, liposomes, micelles, viral particles, and polymeric delivery technology.

In some embodiments, the delivery vehicle comprises at least one Lipid of the Disclosure.

In some embodiments, the delivery vehicle comprises at least two Lipids of the Disclosure.

In some embodiments, the delivery vehicle comprises at least three Lipids of the Disclosure.

In some embodiments, the delivery vehicle comprises at least four Lipids of the Disclosure.

The total weight percentage of the Lipids of the Disclosure in the delivery vehicle is between about 10% to about 95%, such as between about 10% to about 20%, between about 21% to about 30%, between about 31% to about 40%, between about 41% to about 50%, between about 51% to about 60%, between about 61% to about 70%, between about 71% to about 80%, between about 81% to about 90%, or between about 91% to about 95%.

The total mole percentage of the Lipids of the Disclosure in the delivery vehicle is between about 10% to about 95%, such as between about 10% to about 20%, between about 21% to about 30%, between about 31% to about 40%, between about 41% to about 50%, between about 51% to about 60%, between about 61% to about 70%, between about 71% to about 80%, between about 81% to about 90%, or between about 91% to about 95%.

In some embodiments, at least one lipid in the delivery vehicle has a structure of Formula (VII-A), (VIII-A), (IX-A), (VII-B), (VII-C), (I-A), (II), (III-B), (III-C), (III-D), (III-E), (III-F), (VIII-B), (IV), (VI), (X), or (X-A).

In some embodiments, at least two lipids in the delivery vehicle have a structure of Formula (VII-A), (VIII-A), (IX-A), (VII-B), (VII-C), (I-A), (II), (III-B), (III-C), (III-D), (III-E), (III-F), (VIII-B), (IV), (VI), (X), or (X-A).

In some embodiments, at least three lipids in the delivery vehicle have a structure of Formula (VII-A), (VIII-A), (IX-A), (VII-B), (VII-C), (I-A), (II), (III-B), (III-C), (III-D), (III-E), (III-F), (VIII-B), (IV), (VI), (X), or (X-A).

In some embodiments, at least four lipids in the delivery vehicle have a structure of Formula (VII-A), (VIII-A), (IX-A), (VII-B), (VII-C), (I-A), (II), (III-B), (III-C), (III-D), (III-E), (III-F), (VIII-B), (IV), (VI), (X), or (X-A).

The total weight percentage of the lipid(s) having a structure of Formula (VII-A), (VIII-A), (IX-A), (VII-B), (VII-C), (I-A), (II), (III-B), (III-C), (III-D), (III-E), (III-F), (VIII-B), (IV), (VI), (X), or (X-A) in the delivery vehicle is between 10%-95%, such as between about 10% to about 20%, between about 21% to about 30%, between about 31% to about 40%, between about 41% to about 50%, between about 51% to about 60%, between about 61% to about 70%, between about 71% to about 80%, between about 81% to about 90%, or between about 91% to about 95%.

The total mole percentage of the lipid(s) having a structure of Formula (VII-A), (VIII-A), (IX-A), (VII-B), (VII-C), (I-A), (II), (III-B), (III-C), (III-D), (III-E), (III-F), (VIII-B), (IV), (VI), (X), or (X-A) in the delivery vehicle is between 10%-95%, such as between about 10% to about 20%, between about 21% to about 30%, between about 31% to about 40%, between about 41% to about 50%, between about 51% to about 60%, between about 61% to about 70%, between about 71% to about 80%, between about 81% to about 90%, or between about 91% to about 95%.

In some embodiments, the delivery vehicle further comprises at least one additional lipid. Non-limiting examples include an additional cationic lipid, a neutral lipid, an anionic lipid, a helper lipid, a stealth lipid, or a polyethylene glycol (PEG) lipid.

"Helper lipids" are lipids that enhance transfection, such as transfection of the delivery vehicle including the payloads and cargos. The mechanism by which the helper lipid enhances transfection may include enhancing particle stability and/or enhancing membrane fusogenicity. Helper lipids include steroids and alkyl resorcinols. Helper lipids suitable for use in the present disclosure include, but are not limited to, cholesterol, 5-heptadecylresorcinol, and cholesterol hemisuccinate.

"Stealth lipids" are lipids that extend the length of time for which the delivery vehicle can exist in vivo (e.g. in the blood). Stealth lipids suitable for use in a lipid composition of the present disclosure include, but are not limited to, stealth lipids having a hydrophilic head group linked to a lipid moiety.

Non-limiting examples of cationic lipids suitable for use in the delivery vehicle of the present disclosure include, but are not limited to, N,N-dioleyl-N,N-dimethylammonium chloride (DODAC), N,N-distearyl-N,N-dimethylammonium bromide (DDAB), N-(1-(2,3-dioleoyloxy) propyl)-N,N,N-trimethylammonium chloride (DOTAP), 1,2-Dioleoyl-3-Dimethylammonium-propane (DODAP), N-(1-(2,3-dioleyloxy)propyl)-N,N,N-trimethylammonium chloride (DOTMA), 1,2-Dioleoylcarbamyl-3-Dimethylammonium-propane (DOCDAP), 1,2-Dilineoyl-3-Dimethylammonium-propane (DLINDAP), dilauryl(C12:0) trimethyl ammonium propane (DLTAP), Dioctadecylamidoglycyl spermine (DOGS), DC-Choi, Dioleoyloxy-N-[2-sperminecarboxamido)ethyl]-N,N-dimethyl-1-propanaminiumtrifluoroacetate (DOSPA), 1,2-Dimyristyloxypropyl-3-dimethyl-hydroxyethyl ammonium bromide (DMRIE), 3-Dimethylamino-2-(Cholest-5-en-3-beta-oxybutan-4-oxy)-1-(cis,cis-9,12-octadecadienoxy)propane (CLinDMA), N,N-dimethyl-2,3-dioleyloxy)propylamine (DODMA), 2-[5'-(cholest-5-en-3[beta]-oxy)-3'-oxapentoxy)-3-dimethyl-1-(cis,cis-9',12'-octadecadienoxy) propane (CpLinDMA) and N,N-Dimethyl-3,4-dioleyloxybenzylamine (DMOBA), and 1,2-N,N'-Dioleylcarbamyl-3-dimethylaminopropane (DOcarbDAP).

Non-limiting example of neutral lipids suitable for use in the delivery vehicle of the present disclosure include a variety of neutral, uncharged or zwitterionic lipids. Examples of neutral phospholipids suitable for use in the present disclosure include, but are not limited to: 5-heptadecylbenzene-1,3-diol (resorcinol), dipalmitoylphosphatidylcholine (DPPC), distearoylphosphatidylcholine (DSPC), phosphocholine (DOPC), dimyristoylphosphatidylcholine (DMPC), phosphatidylcholine (PLPC), 1,2-distearoyl-sn-glycero-3-phosphocholine (DAPC), phosphatidylethanolamine (PE), egg phosphatidylcholine (EPC), dilauryloylphosphatidylcholine (DLPC), dimyristoylphosphatidylcholine (DMPC), 1-myristoyl-2-palmitoyl phosphatidylcholine (MPPC), 1-palmitoyl-2-myristoyl phosphatidylcholine (PMPC), 1-palmitoyl-2-stearoyl phosphatidylcholine (PSPC), 1,2-diarachidoyl-sn-glycero-3-phosphocholine (DBPC), 1-stearoyl-2-palmitoyl phosphatidylcholine (SPPC), 1,2-dieicosenoyl-sn-glycero-3-phosphocholine (DEPC), palmitoyloleoyl phosphatidylcholine (POPC), lysophosphatidyl choline, dioleoyl phosphatidylethanolamine (DOPE), dilinoleoylphosphatidylcholine distearoylphophatidylethanolamine (DSPE), dimyristoyl phosphatidylethanolamine (DMPE), dipalmitoyl phosphatidylethanolamine (DPPE), palmitoyloleoyl phosphatidylethanolamine (POPE), lysophosphatidylethanolamine and combinations thereof.

Non-limiting examples of anionic lipids suitable for use in the delivery vehicle of the present disclosure include, but are not limited to, phosphatidylglycerol, cardiolipin, diacylphosphatidylserine, diacylphosphatidic acid, N-dodecanoyl phosphatidyl ethanoloamine, N-succinyl phosphatidylethanolamine, N-glutaryl phosphatidylethanolamine cholesterol hemisuccinate (CHEMS), and lysylphosphatidylglycerol.

In some embodiments, the weight ratio of the delivery vehicle (including all the lipids) and the payload is between about 100:1 to about 1:1, such as between about 100:1 to about 90:1, between about 89:1 to about 80:1, between about 79:1 to about 70:1, between about 69:1 to about 60:1, between about 59:1 to about 50:1, between about 49:1 to about 40:1, between about 39:1 to about 30:1, between about 29:1 to about 20:1, between about 19:1 to about 10:1, and between about 9:1 to about 1:1.

In some embodiments, the delivery vehicle comprises an originator construct or a benchmark construct with at least one cargo or payload. The cargo or payload may be any DNA, RNA or polypeptide described herein.

In some embodiments, the delivery vehicle comprises an originator construct or a benchmark construct with at least one cargo or payload which is a coding RNA.

In some embodiments, the delivery vehicle comprises an originator construct or a benchmark construct with at least one cargo or payload which is a non-coding RNA.

In some embodiments, the delivery vehicle comprises an originator construct or a benchmark construct with at least one cargo or payload which is a oRNA.

In some embodiments, the delivery vehicle comprises an originator construct or a benchmark construct with at least one cargo or payload which is an mRNA.

In some embodiments, the at least one RNA compound is comprised of a functional RNA where the RNA results in at least one change in a cell, tissue, organ and/or organism. Said changes in state may include, but are not limited to, altering the expression level of a polypeptide, altering the translation level of a nucleic acid, altering the expression level of a nucleic acid, altering the amount of a polypeptide present in a cell, tissue, organ and/or organism, changing a genetic sequence of a cell, tissue, organ and/or organism, adding nucleic acids to a target genome, subtracting nucleic acids from a target genome, altering physiological activity in a cell, tissue, organ and/or organism or any combination thereof.

In some embodiments, the delivery vehicle comprises an originator construct or a benchmark construct with at least one cargo or payload which is DNA.

In some embodiments, the delivery vehicle comprises an originator construct or a benchmark construct with two cargos or payloads which are DNA. The DNA may be the same DNA or different DNA. As a non-limiting example, the DNA are the same. As a non-limiting example, the DNA are different. As a non-limiting example, the DNA are different but encode the same payload or cargo. As a non-limiting example, the DNA are different pieces of a larger payload or cargo (e.g., heavy chain or light chain of an antibody) that can come together using natural systems or synthetic methods known in the art to produce a functional polypeptide (e.g., antibody).

In some embodiments, the delivery vehicle comprises an originator construct or a benchmark construct with three cargos or payloads which are DNA. The DNA may be the same DNA or different DNA. As a non-limiting example, the DNA are the same. As a non-limiting example, the DNA are different. As a non-limiting example, two DNA are the same and one is different. As a non-limiting example, the first DNA is different from the second and third DNA. As a non-limiting example, the first DNA, second DNA and third DNA are all different. As a non-limiting example, the first DNA is different from the second and third DNA but they all encode the same payload or cargo. As a non-limiting example, the first DNA is different from the second and third DNA but the second and third DNA encode the same payload or cargo.

In some embodiments, the delivery vehicle comprises an originator construct or a benchmark construct with at least one cargo or payload which is a polypeptide.

In some embodiments, the delivery vehicle comprises an originator construct or a benchmark construct with two cargos or payloads which are polypeptide. The polypeptide may be the same polypeptide or different polypeptide As a non-limiting example, the polypeptide are the same. As a non-limiting example, the polypeptide are different. As a non-limiting example, the polypeptides are different pieces of a larger payload or cargo (e.g., heavy chain or light chain of an antibody) that can come together using natural systems or synthetic methods known in the art to produce a functional polypeptide (e.g., antibody).

In some embodiments, the delivery vehicle comprises an originator construct or a benchmark construct with three cargos or payloads which are polypeptide. The polypeptide may be the same polypeptide or different polypeptide. As a non-limiting example, the polypeptide are the same. As a non-limiting example, the polypeptide are different. As a non-limiting example, two polypeptide are the same and one is different. As a non-limiting example, the first polypeptide is different from the second and third polypeptide. As a non-limiting example, the first polypeptide, second polypeptide and third polypeptide are all different. As a non-limiting example, the first polypeptide is different from the second and third polypeptide but they all encode the same payload or cargo. As a non-limiting example, the first polypeptide is different from the second and third polypeptide but the second and third polypeptide encode the same payload or cargo.

In some embodiments, the delivery vehicle comprises an originator construct or a benchmark construct with at least one cargo or payload which is a peptide.

In some embodiments, the delivery vehicle comprises an originator construct or a benchmark construct with two cargos or payloads which are peptide. The peptide may be the same peptide or different peptide. As a non-limiting example, the peptide are the same. As a non-limiting example, the peptides are different. As a non-limiting example, the peptides are different pieces of a larger payload or cargo (e.g., heavy chain or light chain of an antibody) that can come together using natural systems or synthetic methods known in the art to produce a functional polypeptide (e.g., antibody).

In some embodiments, the delivery vehicle comprises an originator construct or a benchmark construct with three cargos or payloads which are peptide. The peptide may be the same peptide or different peptide. As a non-limiting example, the peptides are the same. As a non-limiting example, the peptides are different. As a non-limiting example, two peptides are the same and one is different. As a non-limiting example, the first peptide is different from the second and third peptide. As a non-limiting example, the first peptide, second peptide and third peptide are all different. As a non-limiting example, the first peptide is different from the second and third peptide but they all encode the same payload or cargo. As a non-limiting example, the first peptide is different from the second and third peptide but the second and third peptide encode the same payload or cargo.

In some embodiments, the delivery vehicle comprises an originator construct or a benchmark construct with at least one cargo or payload which is RNA.

In some embodiments, the delivery vehicle comprises an originator construct or a benchmark construct with two cargos or payloads which are RNA. The RNA may be the same RNA or different RNA. As a non-limiting example, the RNAs are the same. As a non-limiting example, the RNAs are different. As a non-limiting example, the RNAs are different but encode the same payload or cargo. As a non-limiting example, the RNAs are different pieces of a larger payload or cargo (e.g., heavy chain or light chain of an antibody) that can come together using natural systems or synthetic methods known in the art to produce a functional polypeptide (e.g., antibody).

In some embodiments, the delivery vehicle comprises an originator construct or a benchmark construct with three cargos or payloads which are RNA. The RNA may be the same RNA or different RNA. As a non-limiting example, the RNA are the same. As a non-limiting example, the RNA are different. As a non-limiting example, two RNA are the same and one is different. As a non-limiting example, the first RNA is different from the second and third RNA. As a non-limiting example, the first RNA, second RNA and third RNA are all different. As a non-limiting example, the first RNA is different from the second and third RNA but they all encode the same payload or cargo. As a non-limiting example, the first RNA is different from the second and third RNA but the second and third RNA encode the same payload or cargo.

In some embodiments, the delivery vehicle comprises an originator construct or a benchmark construct with two cargos or payloads where one is RNA and one is DNA. The RNA and DNA may encode the same peptide or polypeptide or may encode different peptides or polypeptides. As a non-limiting example, the RNA and DNA may encode the same peptide or polypeptide. As a non-limiting example, the RNA and DNA may encode different peptides or polypeptides. As a non-limiting example, the RNA and DNA are different pieces of a larger payload or cargo (e.g., heavy chain or light chain of an antibody) that can come together using natural systems or synthetic methods known in the art to produce a functional polypeptide (e.g., antibody).

In some embodiments, the delivery vehicle comprises an originator construct or a benchmark construct with two cargos or payloads where one is RNA and one is a peptide. The RNA may encode the same peptide as the peptide cargo/payload the RNA may encode a different peptide. As a non-limiting example, the RNA encodes the same peptide. As a non-limiting example, the RNA encodes a different peptides. As a non-limiting example, the RNA and peptide are different pieces of a larger payload or cargo (e.g., heavy chain or light chain of an antibody) that can come together using natural systems or synthetic methods known in the art to produce a functional polypeptide (e.g., antibody).

In some embodiments, the delivery vehicle comprises an originator construct or a benchmark construct with two cargos or payloads where one is RNA and one is a polypeptide. The RNA may encode the same polypeptide as the polypeptide cargo/payload the RNA may encode a different polypeptide. As a non-limiting example, the RNA encodes the same polypeptide. As a non-limiting example, the RNA encodes a different polypeptide. As a non-limiting example, the RNA and polypeptide are different pieces of a larger payload or cargo (e.g., heavy chain or light chain of an antibody) that can come together using natural systems or synthetic methods known in the art to produce a functional polypeptide (e.g., antibody).

In some embodiments, the delivery vehicle comprises an originator construct or a benchmark construct with two cargos or payloads where one is DNA and one is a peptide. The DNA may encode the same peptide as the peptide cargo/payload the DNA may encode a different peptide. As a non-limiting example, the DNA encodes the same peptide. As a non-limiting example, the DNA encodes a different peptide. As a non-limiting example, the DNA and peptide are different pieces of a larger payload or cargo (e.g., heavy chain or light chain of an antibody) that can come together using natural systems or synthetic methods known in the art to produce a functional polypeptide (e.g., antibody).

In some embodiments, the delivery vehicle comprises an originator construct or a benchmark construct with two cargos or payloads where one is DNA and one is a polypeptide. The DNA may encode the same polypeptide as the polypeptide cargo/payload the DNA may encode a different polypeptide. As a non-limiting example, the DNA encodes the same polypeptide. As a non-limiting example, the DNA encodes a different polypeptide. As a non-limiting example, the DNA and polypeptide are different pieces of a larger payload or cargo (e.g., heavy chain or light chain of an antibody) that can come together using natural systems or synthetic methods known in the art to produce a functional polypeptide (e.g., antibody).

Delivery Vehicles

Nanoparticles

In some embodiments, the delivery vehicle is a nanoparticle. The term "nanoparticle" as used herein refers to any particle ranging in size from 10-1000 nm. The nanoparticle may be 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995, or 1000 nm.

Lipid Nanoparticles

In some embodiments, the nanoparticles may be a lipid nanoparticle (LNP). In general, LNPs can be characterized as small solid or semi-solid particles possessing an exterior lipid layer with a hydrophilic exterior surface that is exposed to the non-LNP environment, an interior space which may aqueous (vesicle like) or non-aqueous (micelle like), and at least one hydrophobic inter-membrane space. LNP membranes may be lamellar or non-lamellar and may be comprised of 1, 2, 3, 4, 5 or more layers. In some embodiments, LNPs may comprise a cargo or a payload into their interior space, into the inter membrane space, onto their exterior surface, or any combination thereof.

LNPs useful herein are known in the art and generally comprise cholesterol (aids in stability and promotes membrane fusion), a phospholipid (which provides structure to the LNP bilayer and also may aid in endosomal escape), a polyethylene glycol (PEG) derivative (which reduces LNP aggregation and "shields" the LNP from non-specific endocytosis by immune cells), and an ionizable lipid (complexes negatively charged RNA and enhances endosomal escape), which form the LNP-forming composition.

The components of the LNP may be selected based on the desired target, cargo, size, etc. As a non-limiting example, previous studies have shown that that polymeric nanoparticles made of low molecular weight polyamines and lipids can deliver nucleic acids to endothelial cells with high efficiency. (Dahlman, et al., In vivo endothelial siRNA delivery using polymeric nanoparticles with low molecular weight, Nat Nanotechnol. 2014 August; 9(8): 648-655; the contents of which is herein incorporated by reference in its entirety).

In some embodiments, the originator constructs and benchmark constructs of the present disclosure may be incorporated into lipid nanoparticles (LNPs). In some embodiments a lipid nanoparticle may be comprised of at least one cationic lipid, at least one non-cationic lipid, at least one sterol, at least one particle-activity-modifying-agent, or any combination thereof. In some embodiments a lipid nanoparticle may be comprised of at least one cationic lipid, at least one non-cationic lipid, at least one sterol, and at least one particle-activity-modifying-agent. In some embodiments, the LNP may be comprised of at least one cationic lipid, at least one non-cationic lipid, and at least one sterol. In some embodiments, the LNP may be comprised of at least one cationic lipid, at least one non-cationic lipid, and at least one particle-activity-modifying-agent. In some embodiments, the LNP may be comprised of at least one non-cationic lipid, at least one sterol, and at least one particle-activity-modifying-agent. In some embodiments, the LNP may be comprised of at least one cationic lipid and at least one non-cationic lipid. In some embodiments, the LNP may be comprised of at least one cationic lipid and at least one sterol. In some embodiments, the LNP may be comprised of at least one cationic lipid and at least one particle-activity-modifying-agent. In some embodiments, the LNP may be comprised of at least one non-cationic lipid and at least one sterol. In some embodiments, the LNP may be comprised of at least one non-cationic lipid and at least one particle-activity-modifying-agent. In some embodiments, the LNP may be comprised of at least one sterol and at least one particle-activity-modifying-agent. In some embodiments, the LNP may be comprised of at least one cationic lipid. In some embodiments, the LNP may be comprised of at least one non-cationic lipid. In some embodiments, a LNP may be comprised of a sterol. In some embodiments, the LNP may be comprised of a particle-activity-modifying-agent.

In some embodiments, the at least one cationic lipid may comprise any of at least one ionizable cationic lipid, at least one amino lipid, at least one saturated cationic lipid, at least one unsaturated cationic lipid, at least one zwitterionic lipid, at least one multivalent cationic lipid, or any combination thereof. In some embodiments, the LNP may be essentially devoid of the at least one cationic lipid. In some embodiments, the LNP may contain no amount of the at least one cationic lipid.

In some embodiments, at least one cationic lipid may be selected from, but not limited to, at least one of 1,3-Bis-(1,2-bis-tetradecyloxy-propyl-3-dimethylethoxyammonium-bromide)-propan-2-ol ((R)-PLC-2), 2-(Dinonylamino)ethan-1-ol (17-10), 2-(Didodecylamino)ethan-1-ol (17-11), 3-(Didodecylamino)propan-1-ol (17-12), 4-(Didodecylamino)butan-1-ol (17-13), 2-(Hexyl((9Z,12Z)-octadeca-9,12-dien-1-yl)amino)ethan-1-ol (17-2), 2-(Nonyl((9Z,12Z)-octadeca-9,12-dien-1-yl)amino)ethan-1-ol (17-3), 2-(Dodecyl((9Z,12Z)-octadeca-9,12-dien-1-yl)amino)ethan-1-ol (17-4), 2-(((9Z,12Z)-Octadeca-9,12-dien-1-yl)(tetradecyl)amino)ethan-1-ol (17-5), 2-(((9Z,12Z)-Octadeca-9,12-dien-1-yl)(octadecyl)amino)ethan-1-ol (17-6), 2-(Ditetradecylamino)ethan-1-ol (17-7), 2-(Di((Z)-octadec-9-en-1-yl)amino)ethan-1-ol (17-8), (9Z,12Z)—N-(2-Methoxyethyl)-N-((9Z,12Z)-octadeca-9,12-dien-1-yl)octadeca-9,12-dien-1-amine (17-9), N-Nonyl-N-(2-(piperazin-1-yl)ethyl)nonan-1-amine (19-1), N-Dodecyl-N-(2-(piperazin-1-yl)ethyl)dodecan-1-amine (19-2), (9Z,12Z)—N-((9Z,12Z)-Octadeca-9,12-dien-1-yl)-N-(2-(piperazin-1-yl)ethyl)octadeca-9,12-dien-1-amine (19-3), N-Dodecyl-N-(2-(4-methylpiperazin-1-yl)ethyl)dodecan-1-amine1ntermediate1:2-(Didodecylamino)ethan-1-ol (19-4), N-Dodecyl-N-(2-(4-(4-methoxybenzyl)piperazin-1-yl)ethyl)dodecan-1-amine (19-5), (9Z,12Z)—N-(2-(4-Dodecylpiperazin-1-yl)ethyl)-N-((9Z,12Z)-octadeca-9,12-dien-1-yl)octadeca-9,12-dien-1-amine (19-6), (3-((6Z,9Z,28Z,31Z)-heptatriaconta-6,9,28,31-tetraen-19-yloxy)-N,N-dimethylpropan-1-amine) (1-B1 1), N-(2-(Didodecylamino)ethyl)-N-dodecylglycine (20-1), Dinonyl8,8'-((2-(dodecyl (2-hydroxyethyl)amino)ethyl)azanediyl)dioctanoate (20-10), 3-((2-(Ditetradecylamino)ethyl)(dodecyl)amino)propan-1-ol (20-11), 2-((2-(Ditetradecylamino)ethyl)(tetradecyl)amino)ethan-1-ol (20-12), 2-((2-(Di((9Z,12Z)-octadeca-9,12-dien-1-yl)amino)ethyl)(dodecyl)amino)ethan-1-ol (20-13), 2-((2-(Di((9Z,12Z)-octadeca-9,12-dien-1-yl)amino)ethyl)((9Z,12Z)-octadeca-9,12-dien-1-yl)amino)ethan-1-ol (20-14), 2-((2-(Didodecylamino)ethyl)(hexyl)amino)ethan-1-ol (20-15), 2-((2-(Dinonylamino)ethyl)(nonyl)amino)ethan-1-ol (20-16), 2-((2-(Didodecylamino)ethyl)(nonyl)amino)ethan-1-ol (20-17), 2-((2-(Dinonylamino)ethyl)(dodecyl)amino)ethan-1-ol (20-18), 2-((2-(Didodecylamino)ethyl)amino)ethan-1-ol (20-19), Pentyl6-(dodecyl(2-(dodecyl(2-hydroxyethyl)amino)ethyl)amino)hexanoate (20-2), 2-((2-(Didodecylamino)ethyl)(dodecyl)amino)ethan-1-ol (20-20), 3-((2-(Didodecylamino)ethyl)(dodecyl)amino)propan-1-ol (20-21), 4-((2-(Didodecylamino)ethyl)(dodecyl)amino)butan-1-ol (20-22), (Z)-2-((2-(Didodecylamino)ethyl)(dodec-6-en-1-yl)amino)ethan-1-ol (20-23), 2-((2-(Didodecylamino)ethyl)(tetradecyl)amino)ethan-1-ol (20-24), 2-((2-(Didodecylamino)ethyl)((9Z,12Z)-octadeca-9,12-dien-1-yl)amino)ethan-1-ol (20-25), Pentyl6-((2-(didodecylamino)ethyl)(2-hydroxyethyl)amino)hexanoate (20-3), Dipentyl6,6'-((2-(dodecyl(2-hydroxyethyl)amino)ethyl)azanediyl)dihexanoate (20-4), Diheptyl6,6'-((2-(((6-(heptyloxy)-6-oxohexyl)(2hydroxyethyl)amino)ethyl)azanediyl)dihexanoate (20-5), Pentyl6-((2-(dinonylamino)ethyl)(2-hydroxyethyl)amino)hexanoate (20-6), Heptyl6-(dodecyl(2-(dodecyl(2-hydroxyethyl)amino)ethyl)amino)hexanoate (20-7), Nonyl8-((2-(didodecylamino)ethyl)(2-hydroxyethyl)amino)octanoate (20-8), Heptadecan-9-yl8-((2-(didodecylamino)ethyl)(2-hydroxyethyl)amino)octanoate (20-9), 1-(2,2-Di((9Z,12Z)-octadeca-9,12-dien-1-yl)cyclopropyl)-N,N-dimethylmethanamine (21-1), 3,3-Di((9Z,12Z)-octadeca-9,12-dien-1-yl)cyclobutyl4-(dimethylamino)butanoate (21-2), 3,3-Di((9Z,12Z)-octadeca-9,12-dien-1-yl)cyclopentyl3-(dimethylamino)propanoate (21-3), 3,3-Di((9Z,12Z)-octadeca-9,12-dien-1-yl)cyclopentyl4-(dimethylamino)butanoate (21-4), 1-(2,3-Di((8Z,11Z)-heptadeca-8,11-dien-1-yl)cyclopropyl)-N,N-dimethylmethanamine (21-6), Unknown (75-016B), poly{4-((2-(dimethylamino)ethyl)thio)tetrahydro-2H-pyran-2-one}-r-poly{4-(octylthio)tetrahydro-2H-pyran-2-one}(A7), (3aR5s,6aS)—N,N-dimethyl-2,2-di((9Z,12Z)-octadeca-9,12-dienyl)tetrahydro-3aH-cyclopentad1,3dioxol-5-amine (ALN100), (3aR,5s,6aS)—N,N-dimethyl-2,2-di((9Z,12Z)-octadeca-9,12-dienyl)tetrahydro-3aHcyclopenta[d][1,3]dioxol-5-amine (ALN1001), ((3aR,5s,6aS)—N,N-dimethyl-2,2-di((9Z,12Z)-octadeca-9,12-dienyl)tetrahydro-3aH-cyclopenta[d][1,3]dioxol-5-amine)) (ALNY-100), dimyristoyltrimethylammoniumpropane (Amino Lipid 6), Benzami7di7-dialkylcarboxylicacid (BADACA), N,N-dihydroxyethylmethyl-N-2-(cholesteryloxycarbonylamino)ethylammoniumbromide (BHEM-Chol), N,N-bis-(2-hydroxyethyl)-N-methyl-N-(2-cholesteryloxycarbonylamino-ethyl)ammoniumbromide (BHEM-Chol1), 2-{4-[(3β)-cholest-5-en-3-yloxy]butoxy}-iV?N-dimethyl-3-[(9Z,12Z)-octadeca-9!12-dien-1-yloxy]propan-1-amine (Butyl-CLinDMA), (2JR)-2-{4-[(30)-cholest-5-en-3-yloxy]butoxy}-Ar^dimethyl-3-[(9Z,12Z)-octadeca-9!12-dien-1-yloxyjpropan-1-amine (Butyl-CLinDMA (2R)), (25)-2-{4-[(3p)-cholest-5-en-3-yloxy]butoxy}-iVy/V-dimethyl-3-[(9Z,12Z)-octadeca-9,12-dien-1-yloxy]propan-1-amine (Butyl-CLinDMA (2S)), 1,1'-(2-(4-(2-((2-(bis(2-hydroxydodecyl)amino)ethyl)(2-hydroxydodecyl)amino)ethyl)piperazin-1-yl)ethylazanediyl)didodecan-2-ol (C12-200), 1,1'-((2-(4-(2-((2-(bis(2-hydroxydodecyl)amino)ethyl)(2-hydroxydodecyl)amino)ethyl)piperazin-1-yl)ethyl)azanediyl)bis(dodecan-2-ol) (C12-200), Cholesteryl-succinyl Silane (C2), (9Z,9'Z,12Z,12'Z)-2-((4-(((3-(dimethylamino)propoxy)carbonyl)oxy)hexadecanoyl)oxy)propane-1,3-diylbis(octadeca-9,12-dienoate) (Cationic Lipid A2), 9Z,12Z)-3-((4,4-bis(octyloxy)butanoyl)oxy)-2-((((3-(diethylamino)propoxy)carbonyl)oxy)methyl)propyloctadeca-9,12-dienoate (Cationic Lipid A3), 1-(3-cholesteryl)-oxycarbonyl-aminomethylimidazole (CHIM), [(2-Morpholine-4-yl-ethylcarbamoyl)methyl]-carbamicacidcholesterylester (Chol-C3N-Mo2), [(2-Morpholine-4-yl-ethylcarbamoyl)-ethyl]-carbamicacidcholesterylesterChol-DMC3N-Mo2[1-Methyl-2-(2-morpholine-4-yl-ethylcarbamoyl)-propyl]-carbamicacidcholesterylester (Chol-C4N-Mo2), 1,17-bis(2-octylcyclopropyl)heptadecan-9-yl4-(dimethylamino)butanoate (CL), heptatriaconta-6,9,28,31-tetraen-19-yl-4-(dimethylamino)-butanoate (CLO1), cholesteryl3-(dimethylamino)propanoate (CL06), cholesteryl2-(dimethylamino)acetate (CL08), N,N-dimethyl-2,3-bis(((9Z,12Z)-octadeca-9,12-dien-1-yl)oxy)propan-1-amine (CL-1), N-methyl-2-(((9Z,12Z)-octadeca-9,12-dien-1-yl)oxy)-N-(2-((((9Z,12Z)-octadeca-9,12-diene-1-yl)oxy)ethyl)ethan-1-amine (CL-11), (3R,4R)-3,4-bis(((Z)-hexadec-9-en-1-yl)oxy)-1-methylpyrrolidine (CompoundCL-12) (CL-12), 2-(Dimethylamino)-N-((6Z,9Z,28Z,31Z)-Heptatriaconta-6,9,28,31-tetraen-19-yl)acetamide (CL-13), 3-(Dimethylamino)propane-1,2-diyl(9Z,9'Z,12Z,12'Z)-bis(octadeca-9,12-dienoate) (CL-14), (9Z,12Z)-di((9Z,12Z)-octadeca-9,12-dien-1-yl)amine (CL-15), 7-Hydroxy7-(4-((1-methylpiperidine-4-carbonyl)oxy)butyl)tridecane-1,13-diyldidodecanoate (CL15B6), 7-Hydroxy7-(4-((1-methylpiperidine-4-carbonyl)oxy)butyl)tridecane-1,13-diylditetradecanoate (CL15C6), 7-Hydroxy7-(4-((1-methylpiperidine-4-carbonyl)oxy)butyl)tridecane-1,13-diyldipalmitate (CL15D6), 7-Hydroxy7-(4-((1-methylpiperidine-4-carbonyl)oxy)butyl)tridecane-1,13-diyldioleate (CL15H6), Bis(2-(((9Z,12Z)-octadeca-9,12-dien-1-yl)oxy)ethyl)amine (CL-16), (9Z,12Z)—N-Methyl-N-(2-(((9Z,12Z)-octadeca-9,12-dien-1-yl)oxy)ethyl)octadeca-9,12-dien-1-amine (CL-17), (9Z,12Z)—N-(3-(((9Z,12Z)-octadeca-9,12-dien-1-yl)oxy)propyl)octadeca-9,12-dien-1-amine (CL-18), (1-Methylpiperidin-3-yl)methyldi((11Z,14Z)-icosa-11,14-dien-1-yl)carbamate (CL-19), N-methyl-N,N-bis(2-((Z)-hexadec-9-enyloxy)ethyl)amine (CL-2), (13Z,16Z)—N,N-Dimethyl-4-((9Z,12Z)-octadeca-9,12-dien-1-yl)docosa-3,13,16-trien-1-amine (CL-20), (S)-2-Amino-3-hydroxy-N,N-bis(2-(((Z)-octadeca-9-en-1-yl)oxy)ethyl)propanamide (CL-21), C2:N,N-dihexadecyl-N'-(3-triethoxysilylpropyl)succinamide (CL3), trans-1-Methyl-3,4-bis((((Z)-octadec-9-en-1-yl)oxy)methyl)pyrrolidine (CL-3), trans-1-methylpyrrolidine-3,4-diyl)bis(methylene)(9Z,9'Z,12Z,12'Z)-bis(octadeca-9,12-dienoate) (CL-4), 7-(4-(Diisopropylamino)butyl)-7-hydroxytridecane-1,13-diylditetradecanoate (CL4C6), 7-(4-(Diisopropylamino)butyl)-7-hydroxytridecane-1,13-diyldipalmitate (CL4D6), 11-(4-(Diisopropylamino)butyl)-11-hydroxyhenicosane-1,21-diyldioleate (CL4H10), 7-(4-(Diisopropylamino)butyl)-7-hydroxytridecane-1,13-diyldioleate (CL4H6), 9-(4-(Diisopropylamino)butyl)-7-hydroxyheptadecane-1,17-diyldioleate (CL4H8), (6Z,9Z,28Z,31Z)-Heptatriaconta-6,9,28,31-tetraen-19-yl4-(dimethylamino)butanoate (CL-5), 2-(Dimethylamino)-N-(2-(((Z)-octadeca-9-en-1-yl)oxy)ethyl)-N-((9Z,12Z)-octadeca-9,12-diene-1-yl)acetamide (CL-53), 3-((2-(((Z)-octadeca-9-en-1-yl)oxy)ethyl)((9Z,12Z)-octadeca-9,12-dien-1-yl)amino)propane-1-All (CL-54), 1-Methyl-3,3-bis ((((9Z,12Z)-octadeca-9,12-dien-1-yl)oxy)methyl)azetidine (CL-55), 1-Methyl-3,3-bis(2-(((9Z,12Z)-octadeca-9,12-dien-1-yl)oxy)ethyl)azetidine (CL-56), 1-Methyl-3,3-bis(2-(((9Z,12Z)-octadeca-9,12-dien-1-yl)oxy)propyl)azetidine (CL-57), 2-(3,3-di((9Z,12Z)-octadeca-9,12-dien-1-yl)azetidin-1-yl)ethan-1-ol (CL-58), 2-(3,3-di((9Z,12Z)-octadeca-9,12-dien-1-yl)azetidin-1-yl)propan-1-ol (CL-59), 3-(Di((9Z,12Z)-octadeca-9,12-dien-1-yl)amino)propan-1-o (CL-6), 3-(Dimethylamino)propyl3,3-di((9Z,12Z)-octadeca-9,12-dien-1-yl)azetidine-1-carboxylate (CL-60), 2-(Di((Z)-octadeca-9-en-1-yl)amino)ethane-1-ol (CL-61), 3-(Di((Z)-octadeca-9-en-1-yl)amino)propan-1-ol (CL-62), (11Z,14Z)-2-((Dimethylamino)methyl)-2-((9Z,12Z)-octadeca-9,12-dien-1-yl)icosa-11,14-dien-1-ol (CL-63), (11Z,14Z)-2-(Dimethylamino)-2-((9Z,12Z)-octadeca-9,12-dien-1-yl) icosa-11,14-dien-1-ol (CL-64), 3-(Dimethylamino)-2,2-bis ((((9Z,12Z)-octadeca-9,12-dien-1-yl)oxy)methyl)propan-1-ol (CL-65), (9Z,12Z)—N-(2-(((Z)-Octadeca-9-en-1-yl)oxy) ethyl)octadeca-9,12-dien-1-amine (CL-7), 1-Methyl-3,3-di ((9Z,12Z)-octadeca-9,12-dien-1-yl)azetidine (CL-8), N,2-Dimethyl-1,3-bis(((9Z,12Z)-octadeca-9,12-dien-1-yl)oxy) propan-2-amine (CL-9), 3-Dimethylamino-2-(Cholest-5-en-3B-oxybutan-4-oxy)-1-(cis,cis-9,12-octadecadienoxy) propane (CLinDMA), 2-[5'-(cholest-5-en-3-oxy)-3'-oxapentoxy)-3-dimethy-1-(cis,cis-9',12'-octadecadienoxy) propane (CpLinDMA), cetyltrimethylammoniumbromide (CTAB), 1^-Diarachidonyloxy-^TV-dimethy^-propyl-S-amine (DAraDMA), 0,0'-ditetradecanoyl-N-(α-trimethylammonioacetyl)diethanolaminechloride (DC-6-14), 30-[N—(N',N'-dimethylaminoethane)carbamoyl]cholesterol (DC-Chol), dimethyldioctadecylammonium (DDA), dimethyldioctadecylammoniumbromide (DDA), N,N-distearyl-N,N-dimethylammoniumbromide (DDAB), 1,2-Didocosahexaenyloxy-(7V,N-dimethyl)-propyl-3-amine (DDocDMA), N-(2-(dimethylamino)ethyl)-4,5-bis(dodecylthio)pentanamide (DEDPA), 3-Dimethylamino-2-(Cholest-5-en-3β-oxypent-3-oxa-an-5-oxy)-1-(cis,cis-9,12-octadecadienoxy)propane (DEG-CLinDMA), 1,6-DileoylTriethylenetetramide (dio-TETA), N1,N19-bis((S,23E,25E,27E,29E)-16-((2E,4E,6E,8E)-3,7-dimethyl-9-(2,6,6-trimethylcyclohex-1-en-1-yl)nona-2,4,6,8-tetraenamido)-24,28-dimethyl-15,22-dioxo-30-(2,6,6-trimethylcyclohex-1-en-1-yl)-4,7,10-trioxa-14,21-diazatriaconta-23,25,27,29-tetraen-1-yl)-4,7,10,13,16-pentaoxanonadecane-1,19-diamide (diVA-PEG-diVA), DiLin-N-Methylpiperazine (DL-033), DiLin-N,N-DimethylGlycine (DL-036), Dioleyl-N,N-DimethylGlycine (DL-048), 3-((1,3-bis(((9Z,12Z)-octadeca-9,12-dienoyl)oxy)propan-2-yl)amino)propanoicacid (DLAPA), 1,2-dilinolenyloxy-3-dimethylaminopropane (DLenDMA), 1-Linoleoyl-2-linoleyloxy-3-dimethylaminopropane (DLin-2-DMAP), 3-(N,N-Dilinoleylamino)-1,2-propanediol (DLinAP), 1,2-N,N'-Dilinoleylcarbamyl-3-dimethylaminopropane (DLincarbDAP), 1,2-Dilinoleoylcarbamyl-3-dimethylaminopropane (DLinCDAP), 1,2-Dilinoleylcarbamoyloxy-3-dimethylaminopropane (DLin-C-DAP), 1,2-Dilinoleyoxy-3-(dimethylamino)acetoxypropane (DLin-DAC), 1,2-Dilinoleoyl-3-dimethylaminopropane (DLinDAP), 1,2-DiLinoleyloxy-N,N-dimethylaminopropane (DLinDMA), 1,2-dilinoleyloxy-3-dimethylaminopropane (DLinDMA 1), 1,2-Dilinoleyloxo-3-(2-N,N-dimethylamino)ethoxypropane (DLin-EG-DMA), dilinoleoyl-4-aminobutyricacid (DLinFAB), 2,2-dilinoleyl-4-(2-dimethylaminoethyl)-[1,3]-dioxolane (DLin-K-C2-DMA), 2,2-Dilinoleyl-4-dimethylaminomethyl-[1,3]-dioxolane (DLin-K-DMA), 1,2-Dilinoleyoxy-3-morpholinopropane (DLin-MA), (6Z,9Z,28Z,31Z)-heptatriacont-6,9,28,31-tetraene-19-yl4-(dimethylamino) butanoate (DLin-MC3-DMA), 1,2-Dilinoleyloxy-3-(N-methylpiperazino)propane (DLinMPZ), 1,2-Dilinoleyloxy-3-(N-methylpiperazino)propane (DLin-MPZ), Dilinoleyloxy3-piperidinopropylamine (DLinPip), 1.2Dilinoleyloxy3-(3'-hvdroxypiperidino)-propylamine (DLinPip-30H), 1,2Dilinoleyloxy3-(4'-hvdroxypiperidino)-propylamine (DLinPip-40H), 1,2-Dilinoleyloxy-3-hvdroxypropane (DLinPO), 1,2-Dilinoleylthio-3-dimethylaminopropane (DLin-S-DMA), 1,2-Dilinoleoyl-3-trimethylaminopropane (DLinTAP), 1,2-Dilinoleoyl-3-trimethylaminopropanechloridesalt (DLin-TAP.Cl), 1,2-Dilinoleyloxy-3-trimethylaminopropane (DLinTMA), 1,2-Dilinoleyloxy-3-trimethylaminopropanechloridesalt (DLin-TMA.Cl), 3-((1,3-bis(((9Z,12Z.15Z)-octadeca-9,12,15-trienoyl)oxy)propan-2-yl) amino)propanoicacid (DLLAPA), 1,2Dilinoleyloxy3-(N, NdimethyD-propylamme (DLmDEA), 1,2-Dilauroyl-sn-Glicero-3-Phosphoethanolamine (DLPE), 1,2-Dilauroyl-sn-Glicero-3-Glycerol (DLPG), N,N-Dimethyl-3,4-dioleyloxybenzylamine (DMOBA), dimyristoylphosphatidylserine (DMPS), N-[1-(2,3-dimyristyloxy)propyl]-N,N-dimethyl-N-(2-hydroxyethyl)ammoniumbromide (DMRIE), 1,2-Dimyristyloxypropyl-3-dimethyl-hydroxyethylammoniumbromide (DMRIE1), 1,2-dimyristoyl-3-trimethylammoniumpropane (DMTAP), 3-(N,N-Dioleylamino)-1,2-propanedio (DOAP), 3-((1,3-bis (oleoyloxy)propan-2-yl)amino)propanoicacid (DOAPA), 1,2-N,N'-dioleylcarbamyl-3-dimethylaminopropane (DOcarbDAP), 1,2-Dioleoylcarbamyl-3-Dimethylammonium-propane (DOCDAP), N,N-dioleyl-N,N-dimethylammoniumchloride (DODAC), 1,2-Dioleoyl-3-Dimethylammonium-propane (DODAP), N,N-dihydroxyethylN,N-dioctadecylammoniumchloride (DODEAC), N,N-dimethyl-2,3-dioleyloxypropylamine (DODMA), dioleoyl-4-aminobutyricacid (DOFAB), Dioctadecylamidoglycylspermine (DOGS), 1,2-Dioleoyl-3-methyl-(methoxycarbonyl-ethyl)ammonium-Propane (DOMCAP), 1,2-Dioleoyl-3-N-pyrrolidine-propane (DOP5P), 1,2-Dioleoyl-3-N-pyrridinium-propane, bromidesalt (DOP6P), 1,2-dioleoyl-3-dimethyl-hydroxyethylammoniumbromide (DORI), 1,2-dioleyloxypropyl-3-dimethyl-hydroxyethylammoniumbromide (DORIE), 1,2-dioleyloxypropyl-3-dimethyl-hydroxybutylammoniumbromide (DORIE-HB), 1,2-dioleyloxypropyl-3-dimetyl-hydroxypropylammoniumbromide (DORIE-HP), 1,2-dioleyloxypropyl-3-dimethyl-hydroxypentylammoniumbromide (DORIE-Hpe), 2,3-dioleyloxy-N-[2(spermine-carboxamido)ethyl]-N,N-dimethyl-1-propanaminiumtrifluoroacetate (DOSPA), 1,3-dioleoyloxy-2-(6-carboxy-spermyl)-propylamide (DOSPER), N-(1-(2,3-dioleoyloxy)propyl)-N,N,N-trimethylammoniumchloride (DOTAP), 1,2-dioleoyl-3-trimethyl-ammonium-propane (DOTAP1), N-[5'-(2',3'-dioleoyl)uridine]-N',N',N'-trimethylammoniumtosylate (DOTAU), 1-[2-(9(Z)-octadecenoyloxy)ethyl]-2-(8(Z)-heptadecenyl-3-(2-hydroxyethyl)imidazoliniumchloride (DOTIM), N-(1-(2,3-dioleyloxy)propyl)-N,N,N-trimethylammoniumchloride (DOTMA), dioleylphosphatidyluridinephosphatidylcholine (DOUPC), 1,2-Diphvtanyloxy-W.N-dimemyl)-butyl-4-amme (DPan-C2-DMA), 1,2-Diphytanyloxy-3-(iV,7V-dimethyl)-propylamine (DPanDMA), 2,3-bis(dodecylthio)propyl(2-(dimethylamino)ethyl)carbamate (DPDEC), dipalmitoyl-4-aminobutyricacid (DPFAB), 1,2-dipalmityloxypropyl-3-dimethyl-hydroxyethylammoniumbromide (DPRIE), 1,2-dipalmitoyl-3-trimethylammoniumpropane (DPTAP), 1-[2-(hexadecanoyloxy)ethyl]-2-pentadecyl-3-(2-hydroxyethyl)imidazoliniumchloride (DPTIM), 3-((1,3-bis(stearoyloxy)propan-2-yl)amino)propanoicacid (DSAPA), distearyldimethylammonium (DSDMA), 1,2-distearloxy-N,N-dimethylaminopropane (DSDMA1), 1,2-disteryloxypropyl-3-dimethyl-hydroxyethylammoniumbromide (DSRIE), 1,2-disteroyl-3-trimethylammoniumpropane (DSTAP), ditetradecyltrimethylammonium (DTDTMA), 1,2-dioleoyl-sn-glycero-3-ethylphosphocholine (EDOPC), N2-[N2,N5-bis(3-aminopropyl)-L-ormithyl]-N,N-dioctadecyl-L-glutaminetetrahydrotrifluoroacetate (GC33), Cholest-5-en-3-ol(3P)-,3-[(3-aminopropyl)[4-[(3-aminopropyl)amino]butyl]carbamate](GL67), glycerylmonooleate (GMO), Guanidino-dialkyl-carboxylicacid (GUADACA), 2-(bis(2-(tetradecanoyloxy)ethyl)amino)-N-(2-hydroxyethyl)-N,N-dimethyl-2-oxoethan-aminiumbromide (HEDC), 2,2'-(tert-butoxycarbonylazanediyl)bis(ethane-2,1-diyl)ditetradecanoate (HEDC-BOC-TN), 1-(2-(((3S,10R,13R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yldisulfanyl)ethyl)guanidine (HGT4002), (15Z,18Z)—N,N-dimethyl-6-(9Z,12Z)-octadeca-9,12-dien-1-yl)tetracosa-15,18-dien-1-amine (HGT5000), (15Z,18Z)—N,N-dimethyl-6-((9Z,12Z)-octadeca-9,12-dien-1-yl)tetracosa-4,15,18-trien-1-amine (HGT5001), Histaminyl-Cholesterolhemisuccinat (His-Chol), histidinylcholesterolhemisuccinate (Hist-Chol), HydroSoyPC (HSPC), imidazolecholesterolester (ICE), 3-(didodecylamino)-N1,N1,4-tridodecyl-1-piperazineethanamine (KL10), N1-[2-(didodecylamino)ethyl]-N1,N4,N4-tridodecyl-1,4-piperazinediethanamine (KL22), 14,25-ditridecyl-15,18,21,24-tetraaza-octatriacontane (KL25), N,N-di-n-letradecyl,N-methyl-N-(2-guanidinyl) ethylammonium (Lipid 1), N,N-di-n-octadecyl,N-methyl-N-(2-guanidinyl)ethylammoniumchloride (Lipid 2), 3-((4,4-bis(octyloxy)butanoyl)oxy)-2-((((3-(diethylamino)propoxy) carbonyl)oxy)methyl)propyl(9Z,12Z)-octadeca-9,12-dienoate (Lipid A), (9Z,12Z)-3-((4,4-bis(octyloxy)butanoyl) oxy)-2-((((3-(diethylamino)propoxy)carbonyl)oxy)methyl) propyloctadeca-9,12-dienoate (Lipid A1), 2,2-Dilinoleyl-4-dimethylaminoethyl-[1,3]-dioxolane (Lipid A2), ((5-((dimethylamino)methyl)-1,3-phenylene)bis(oxy))bis (octane-8,1-diyl)bis(decanoate) (Lipid B), 2-((4-(((3-(dimethylamino)propoxy)carbonyl)oxy)hexadecanoyl)oxy) propane-1,3-diyl9Z,9'Z,12Z,12'Z)-bis(octadeca-9,12-dienoate) (Lipid C), 3-(((3-(dimethylamino)propoxy) carbonyl)oxy)-13-(octanoyloxy)tridecyl3-octylundecanoate (Lipid D), (6Z,16Z)-12-((Z)-dec-4-en-1-yl)docosa-6,16-dien-11-yl5-(dimethylamino)pentanoate (Lipid I), Dioctadecyl-(2-hydroxyl-3-propylamino)aminopolylysine (Lipid T), (3-((6Z,9Z,28Z,31Z)-heptatriaconta-6,9,28,31-tetraen-19-yloxy)-N,N-dimethylpropan-1-amine (MC3 Ether), described in U.S. Provisional Application No. 61/384,050 (MC3 Thioester), (4-((6Z,9Z,28Z,31Z)-heptatriaconta-6,9,28,31-tetraen-19-yloxy)-N,N-dimethylbutan-1-amine (MC4 Ether), 3-((2-(((9Z,12Z)-octadeca-9,12-dienoyl)oxy)ethyl) amino)propanoicacid (MLAPA), 3-((2-(((9Z,12Z,15Z)-octadeca-9,12,15-trienoyl)oxy)ethvnamino)propanoicacid (MLLAPA), mon-omycolylglycerol (MMG), 3-((2-(oleoyloxy)ethyl)amino)propanoicacid (MOAPA), 4-(2-Aminoethyl)-Morpholino-Cholesterolhemisuccinat (MoChol), 1,2-Dioleoyl-3-N-morpholine-propane (MoDO), Methylpyridiyl-dialkyl-carboxylicacid (MPDACA), monopalmitoylphosphatidylcholin (MPPC), 3-((2-(stearoyloxy)ethyl)amino)propanoicacid (MSAPA), N1-[2-((1S)-1-[(3-aminopropyl)amino]-4-[di(3-amino-propyl)amino]butylcarboxamido)ethyl]-3,4-di[oleyloxy]-benzamide (MVL5), 2-({8-[(3p)-cholest-5-en-3-yloxy]octyl}oxy)-N,N-dimethyl-3-[(9Z,12Z)-octadeca-9,12-dien-1-yloxy]propan-1-amine (Octyl-CLinDMA), (2R)-2-({8-[(3)-cholest-5-en-3-yloxy]octyl}oxy)-N,N-dimethyl-3-[(9Z,12Z)-octadeca-9,12-dien-1-yloxy]propan-1-amine (Octyl-CLinDMA (2R)), phosphatidylcholines (PC), 1,3-Bis-(1,2-bis-tetradecyloxy-propyl-3-dimemylethoxyammoniumbromide)-propane-2-ol (PCL-2), palmitoyi-oieoyl-nor-arginine (PONA), stearylamine (STA), 2-(((tert-Butyldimethylsilyl)oxy)methyl)-2-(hydroxymethyl)propane-1,3-diol), 3-((tert-Butyl(dimethyl)silyl)oxy)-2,2-bis(((9Z)-tetradec-9-enoyloxy)methyl)propyl(9Z)-tetradec-9-enoate), 3-Hydroxy-2,2-bis(((9Z)-tetradec-9-enoyloxy)methyl)propyl(9Z)-tetradec-9-enoate), 3-((4-(Dimethylamino)butanoyl)oxy)-2,2-bis(((9Z)-tetradec-9-enoyloxy)methyl)propyl(9Z)-tetradec-9-enoate), 3-(5-(bis(2-hydroxydodecyl)amino)pentan-2-yl)-6-(5-((2-hydroxydodecyl)(2-hydroxyundecyl)amino)pentan-2-yl)-1,4-dioxane-2,5-dione) (Target 24), trehalose6'6'-dibehenate (TDB), 1,1'-(2-(4-(2-((2-(bis(2hydroxydodecyl)amino) ethyl)(2-hydroxydodecyl)amino)ethyl)piperazin-1-yl)ethylazanediyl)didodecan-2-ol (Tech G1), 3-((1,3-bis(((9Z,12Z)-octadeca-9,12-dienoyl)oxy)-2-((((9Z,12Z)-octadeca-9,12-dienoyl)oxy)methyl)propan-2-yl)amino)propanoicacid (TLAPA), (1-(2,3-linoleyloxypropoxy)-2-(linoleyloxy)-(7V,Λ/-dimethyl)-propyl-3-amine) (TLinDMA), 3-((1,3-bis(((9Z.12Z.15Z)-octadeca-9.12.15-trienoyl)oxy)-2-((((9Z.12Z.15E)-octadeca-9,12,15-trienoyl)oxy)methyl) propan-2-yl)amino)propanoicacid (TLLAPA), N-(α-trimethylammonioacetyl)-didodecyl-D-glutamatechloride (TMAG), 3-((1,3-bis(((Z)-octadec-9-enoyl)oxy)-2-((((Z)-octadec-9-enoyl)oxy)methyl)propan-2-yl)amino)propanoicacid (TOAPA), 3-((1,3-bis(stearoyloxy)-2-((stearoyloxy)methyl)propan-2-yl)amino)propanoicacid (TSAPA), 1,N19-bis((16E,18E,20E,22E)-17,21-dimethyl-15-oxo-23-(2,6,6-trimethylcyclohex-1-en-1-yl)-4,7,10-trioxa-14-azatricosa-16,18,20,22-tetraen-1-yl)-4,7,10,13,16-pentaoxanonadecane-1,19-diamide (VA-PEG-VA), 2,2-Dillinoleyl-4-dimethylaminoethyl-[1,3]-dioxolane (XTC), disclosed in Non-Patent Literature 11 (YSK05), 1,2-di-γ-linolenyloxy-N,N-dimethylaminopropane (γ-DLenDMA), a-D-Tocopherolhemisuccinoyl, (9Z,9,Z,12Z,12,Z)-2-((2-(((3-(dimethylamino)propoxy)carbonyl)oxy)tetradecanoyl) oxy)propane-1,3-diylbis(octadeca-9,12-dienoate), 2-(((13Z,16Z)-4-(((3-(diethylamino)propoxy)carbonyl)oxy)docosa-13,16-dienoyl)oxy)propane-1,3-diyldioctanoate, 2-(((13Z,16Z)-4-(((3-(dimethylamino)propoxy)carbonyl)oxy) docosa-13,16-dienoyl)oxy)propane-1,3-diyldioctanoate, 2-((4-(((3-(ethyl(methyl)amino)propoxy)carbonyl)oxy) hexadecanoyl)oxy)propane-1,3-diyldioctanoate, 2-((4-(((3-(ethyl(methyl)amino)propoxy)carbonyl)oxy)hexadecanoyl) oxy)propane-1,3-diylbis(decanoate), 2-((4-(((3-(diethylamino)propoxy)carbonyl)oxy)hexadecanoyl)oxy) propane-1,3-diylbis(decanoate), 2-(10-dodecyl-3-ethyl-8,14-dioxo-7,9,13-trioxa-3-azaicosan-20-yl)propane-1,3-diyldioctanoate, 2-(((4-(dimethylamino)butanoyl)oxy) methyl)-2-((octanoyloxy)methyl)propane-1,3-diyl(9Z,9'Z) bis-tetradec-9-enoate, (9Z,9'Z,12Z,12'Z)-2-(((1-(cyclopropylmethyl)piperidine-4-carbonyl)oxy)methyl) propane-1,3-diylbis(octadeca-9,12-dienoate), ((2-(((1-isopropylpiperidine-4-carbonyl)oxy)methyl)-1,4-phenylene)bis(oxy))bis(octane-8,1-diyl)bis(decanoate), 2-((4-(((3-(ethyl(methyl)amino)propoxy)carbonyl)oxy) hexadecanoyl)oxy)propane-1,3-diyldidodecanoate, 2-((4-(((3-(diethylamino)propoxy)carbonyl)oxy)hexadecanoyl) oxy)propane-1,3-diyldidodecanoate, 2-((4-(((3-(dimethylamino)propoxy)carbonyl)oxy)hexadecanoyl)oxy) propane-1,3-diyldidodecanoate, 2-((4-(((3-(ethyl(methyl) amino)propoxy)carbonyl)oxy)hexadecanoyl)oxy)propane- 1,3-diylditetradecanoate, 2-((4-(((3-(dimethylamino)propoxy)carbonyl)oxy)hexadecanoyl)oxy)propane-1,3-diylditetradecanoate, 2-((4-(((3-(diethylamino)propoxy)carbonyl)oxy)hexadecanoyl)oxy)propane-1,3-diylditetradecanoate, (Z)-2-((4-(((3-(dimethylamino)propoxy)carbonyl)oxy)hexadecanoyl)oxy)propane-1,3-diyldioleate, (9Z,9,Z,12Z,12,Z,15Z,15,Z)-2-((4-(((3-(dimethylamino)propoxy)carbonyl)oxy)hexadecanoyl)oxy)propane-1,3-diylbis(octadeca-9,12,15-trienoate), (9Z,9,Z,12Z,12,Z)-2-((4-(((3-(diethylamino)propoxy)carbonyl)oxy)hexadecanoyl)oxy)propane-1,3-diylbis(octadeca-9,12-dienoate), (9Z,9,Z,12Z,12,Z)-2-((4-(((3-(dimethylamino)propoxy)carbonyl)oxy)hexadecanoyl)oxy)propane-1,3-diylbis(octadeca-9,12-dienoate), N,N,N-trimethyl-5-oxo-5-(3-((3-pentyloctanoyl)oxy)-2,2-bis(((3-pentyloctanoyl)oxy)methyl)propoxy)pentane-1-Aminiumiodide3-((5-(dimethylamino)pentanoyl)oxy)-2,2-bis(((3-pentyloctanoyl)oxy)methyl)propyl3-pentyloctanoate, 3-dimethylaminopropylcarbonate(9Z,12Z)-octacosa-19,22-dien-11-yl, 2-(((N,N-dimethyl-β-alanyl)oxy]methyl}-2-[(octanoyloxy)methyl)propane-1,3-diyl(9Z,9'Z)bis-tetradec-9-enoate, O'I,O1-(2-(7-dodecyl-14-methyl-3,9-dioxo-2,4,8,10-tetraoxa-14-azapentadecyl)propane-1,3-diyl)8-dimethyldioctanedioate, 8-dimethylO'I,O1-(2-(((1-methylpyrrolidine-3-carbonyl)oxy)methyl)propane-1,3-diyl)dioctanedioate, 1-(3-((6,6-bis((2-propylpentyl)oxy)hexanoyl)oxy)-2-(((1,4-dimethylpiperidine-4-carbonyl)oxy)methyl)propyl)8-methyloctanedioate, (9Z,12Z)-5-(((3-(dimethylamino)propoxy)carbonyl)oxy)-7-octylpentadecyloctadeca-9,12-dienoate, 5-(((3-(dimethylamino)propoxy)carbonyl)oxy)-7-octylpentadecyloctanoate, 1-(3-((6,6-bis((2-propylpentyl)oxy)hexanoyl)oxy)-2-(((1,4-dimethylpiperidine-4-carbonyl)oxy)methyl)propyl)10-octyldecanedioate, 3-(((3-(dimethylamino)propoxy)carbonyl)oxy)-5-octyltridecyldecanoate, 1-(16-(((4,4-bis(octyloxy)butanoyl)oxy)methyl)-9-dodecyl-2-methyl-7,13-dioxo-6,8,12,14-tetraoxa-2-azaheptadecan-17-yl)8-methyloctanedioate, 3-((5-(dimethylamino)pentanoyl)oxy)-2,2-bis(((9Z)-tetradec-9-enoyloxy)methyl)propyl(9Z,12Z)-octadec-9,12-dienoate, 3-((5-(Dimethylamino)pentanoyl)oxy)-2,2-bis(((3-pentyloctanoyl)oxy)methyl)propyl3-pentyloctanoate, (9Z,9'Z,12Z,12'Z)-2-(((3-(diethylamino)propanoyl)oxy)methyl)propane-1,3-diylbis(octadeca-9,12-dienoate), ((2-(((4-(dimethylamino)butanoyl)oxy)methyl)-1,4-phenylene)bis(oxy))bis(octane-8,1-diyl)bis(decanoate), 1-(3-((4,4-bis(octyloxy)butanoyl)oxy)-2-(((1-methylpyrrolidine-3-carbonyl)oxy)methyl)propyl)8-methyloctanedioate, 3-((4,4-bis(octyloxy)butanoyl)oxy)-2-((palmitoyloxy)methyl)propyl1-methylpyrrolidine-3-carboxylate, 3-((4,4-bis(octyloxy)butanoyl)oxy)-2-((tetradecanoyloxy)methyl)propyl1-methylpyrrolidine-3-carboxylate, 3-(((3-(dimethylamino)propoxy)carbonyl)oxy)-13-(octanoyloxy)tridecyl9-pentyltetradecanoate, 3-((4,4-bis(octyloxy)butanoyl)oxy)-2-((dodecanoyloxy)methyl)propyl1-methylpyrrolidine-3-carboxylate, 3-(((3-(dimethylamino)propoxy)carbonyl)oxy)-13-hydroxytridecyl9-pentyltetradecanoate, 3-(((3-(dimethylamino)propoxy)carbonyl)oxy)-13-(octanoyloxy)tridecyl7-hexyltridecanoate, 2-(5-(3-((1-methylpyrrolidine-3-carbonyl)oxy)-2-((tetradecanoyloxy)methyl)propoxy)-5-oxopentyl)propane-1,3-diyldioctanoate, 3-(((3-(dimethylamino)propoxy)carbonyl)oxy)-13-(octanoyloxy)tridecyl5-heptyldodecanoate, 2-(5-(3-((1-methylpyrrolidine-3-carbonyl)oxy)-2-((palmitoyloxy)methyl)propoxy)-5-oxopentyl)propane-1,3-diyldioctanoate, 3-(((3-(dimethylamino)propoxy)carbonyl)oxy)-13-hydroxytridecyl5-heptyldodecanoate, 2-(((1-methylpyrrolidine-3-carbonyl)oxy)methyl)propane-1,3-diylbis(6,6-bis(octyloxy)hexanoate), (9Z,12Z)-3-(((3-dimethylamino)propoxy)carbonyl)oxy)-13-(octanoyloxy)tridecyloctadeca-9,12-dienoate, 3-((5-(dimethylamino)pentanoyl)oxy)-2,2-bis(((9Z)-tetradec-9-enoyloxy)methyl)propyl(9Z)-octadec-9-enoate, 2-(10-dodecyl-3-ethyl-8,14-dioxo-7,9,13-trioxa-3-azanonadecan-19-yl)propane-1,3-diyldioctanoate, ((2-(((1-methylpiperidine-4-carbonyl)oxy)methyl)-1,4-phenylene)bis(oxy))bis(octane-8,1-diyl)bis(decanoate), 2-(((3-(dimethylamino)propanoyl)oxy)methyl)propane-1,3-diylbis(4,4-bis(octyloxy)butanoate), (9Z,12Z)-2-(((11Z,14Z)-2-((3-(dimethylamino)propanoyl)oxy)icosa-11,14-dien-1-yl)oxy)ethyloctadeca-9,12-dienoate, 2-(((1,3-dimethylpyrrolidine-3-carbonyl)oxy)methyl)propane-1,3-diylbis(4,4-bis(octyloxy)butanoate), (13Z,16Z)-4-(((3-(dimethylamino)propoxy)carbonyl)oxy)docosa-13,16-dien-1-ylheptadecan-9-ylsuccinate, 2,2-bis(heptyloxy)ethyl3-((3-ethyl-10-((9Z,12Z)-octadeca-9,12-dien-1-yl)-8,15-dioxo-7,9,14-trioxa-3-azaheptadecan-17-yl)disulfanyl)propanoate, 2-(((1-methylpyrrolidine-3-carbonyl)oxy)methyl)propane-1,3-diylbis(4,4-bis(octyloxy)buta, 1-(3-((1,3-dimethylpyrrolidine-3-carbonyl)oxy)-2-(((9Z,12Z)-octadeca-9,12-dienoyloxy)methyl)propyl)10-octyldecanedioate, (13Z,16Z)-4-(((3-(diethylamino)propoxy)carbonyl)oxy)docosa-13,16-dien-1-yl2,2-bis(heptyloxy)acetate, (13Z,16Z)-4-(((2-(dimethylamino)ethoxy)carbonyl)oxy)docosa-13,16-dien-1-yl2,2-bis(heptyloxy)acetate, Aceticacid(20,23R)-2-methyl-9-[(9Z,12Z)-octadeca-9,12-dien-1-yl]-7-oxo-6,8,11-trioxa-2-azanonacosa-20-En-23-yl3-(dimethylamino)propylcarbonate(11Z,14Z)-1-{[(9Z,12R)-12-hydroxyoctadec-9-en-1-yl], (12Z,15Z)-1-((((9Z,12Z)-octadeca-9,12-dien-1-yloxy)carbonyl)oxy)henicosa-12,15-dien-3-yl3-(dimethylamino)propanoate, (9Z,12Z)-3-((4,4-bis(octyloxy)butanoyl)oxy)-2-((((3-(dimethylamino)propyl)carbamoyl)oxy)methyl)propyloctadeca-9,12-dienoate, (12Z,15Z)-3-((4-(dimethylamino)butanoyl)oxy)henicosa-12,15-dien-1-yl9-pentyltetradecanoate, (9Z,12Z)-3-((4,4-bis(octyloxy)butanoyl)oxy)-2-(((((1,2,2,6,6-pentamethylpiperidin-4-yl)oxy)carbonyl)oxy)methyl)propyloctadeca-9,12-dienoate, (12Z,15Z)-3-((4-(dimethylamino)butanoyl)oxy)henicosa-12,15-dien-1-yl7-hexyltridecanoate, (9Z,12Z)-3-((4,4-bis(octyloxy)butanoyl)oxy)-2-(((((1-methylpiperidin-4-yl)methoxy)carbonyl)oxy)methyl)propyloctadeca-9,12-dienoate, (12Z,15Z)-3-((4-(dimethylamino)butanoyl)oxy)henicosa-12,15-dien-1-yl5-heptyldodecanoate, (9Z,12Z)-3-((4,4-bis(octyloxy)butanoyl)oxy)-2-(((((1-ethylpiperidin-4-yl)oxy)carbonyl)oxy)methyl)propyloctadeca-9,12-dienoate, (12Z,15Z)-3-((4-(dimethylamino)butanoyl)oxy)henicosa-12,15-dien-1-yl3-octylundecanoate, formate salt, 3-((5-(dimethylamino)pentanoyl)oxy)-2,2-bis(((9Z)-tetradec-9-enoyloxy)methyl)propyl(9Z)-hexadec-9-enoate, (9Z,12Z)-3-((4,4-bis(octyloxy)butanoyl)oxy)-2-(((((1-methylazetidin-3-yl)oxy)carbonyl)oxy)methyl)propyloctadeca-9,12-dienoate, (9Z,12Z)-(12Z,15Z)-3-((3-(dimethylamino)propanoyl)oxy)henicosa-12,15-dien-1-yloctadeca-9,12-dienoate, 2-(((3-(diethylamino)propoxy)carbonyl)oxy)tetradecyl4,4-bis((2-ethylhexyl)oxy)butanoate, (9Z,12Z)-3-((4,4-bis(octyloxy)butanoyl)oxy)-2-(((((1-methylpiperidin-4-yl)oxy)carbonyl)oxy)methyl)propyloctadeca-9,12-dienoate, (9Z,12Z)-3-((4,4-bis(octyloxy)butanoyl)oxy)-2-(((((1-methylpyrrolidin-3-yl)oxy)carbonyl)oxy)methyl)propyloctadeca-9,12-dienoate, (9Z,12Z)-3-(((2-(dimethylamino)ethoxy)carbonyl)oxy)pentadecyloctadeca-9,12-dienoate, (9Z,12Z)-3-((4,4-bis(octyloxy)butanoyl)oxy)-2-((((3-(4-methylpiperazin-1-yl)propoxy)carbonyl)oxy)methyl)propyloctadeca-9,12-dienoate, 3-(Dimethylamino)propyltriacontan-11-ylcarbonateTriacontan-11-ol, (9Z,12Z)-3-((4,4-bis(octyloxy)butanoyl)oxy)-2-((((3-(pyrrolidin-1-yl)propoxy)carbonyl)oxy)methyl)propyloctadeca-9,12-dienoate, (9Z,12Z)-3-(((3-(ethyl(methyl)amino)propoxy)carbonyl)oxy)pentadecyloctadeca-9,12-dienoate, 3-((4,4-bis(octyloxy)butanoyl)oxy)-2-(((9Z,12Z)-octadeca-9,12-dienoyloxy)methyl)propyl4-((diethylamino)methyl)benzoate, (9Z,12Z)-3-(((3-(diethylamino)propoxy)carbonyl)oxy)pentadecyloctadeca-9,12-dienoate, 3-((4,4-bis(octyloxy)butanoyl)oxy)-2-(((9Z,12Z)-octadeca-9,12-dienoyloxy)methyl)propyl3-((dimethylamino)methyl)benzoate, (9Z,12Z)-3-(((3-(dimethylamino)propoxy)carbonyl)oxy)pentadecyloctadeca-9,12-dienoate, 3-((4,4-bis(octyloxy)butanoyl)oxy)-2-(((9Z,12Z)-octadeca-9,12-dienoyloxy)methyl)propyl1-methylpiperidine-3-carboxylate, 3-((4,4-bis(octyloxy)butanoyl)oxy)-2-(((9Z,12Z)-octadeca-9,12-dienoyloxy)methyl)propyl1-methylpiperidine-4-carboxylate, 3-((4,4-bis(octyloxy)butanoyl)oxy)-2-(((9Z,12Z)-octadeca-9,12-dienoyloxy)methyl)propyl1,4-dimethylpiperidine-4-carboxylate, 3-((4-(dimethylamino)butanoyl)oxy)-2,2-bis(((9Z)-tetradec-9-enoyloxy)methyl)propyl(9Z)-hexadec-9-enoate, 2-(10-dodecyl-3-ethyl-8,14-dioxo-7,9,13-trioxa-3-azahexadecan-16-yl)propane-1,3-diyldioctanoate, (9Z,9'Z,12Z,12'Z)-2-(((4-(piperidin-1-yl)butanoyl)oxy)methyl)propane-1,3-diylbis(octadeca-9,12-dienoate), 3-((4,4-bis(octyloxy)butanoyl)oxy)-2-(((9Z,12Z)-octadeca-9,12-dienoyloxy)methyl)propyl4-methylmorpholine-2-carboxylate, (2R)-3-((4,4-bis(octyloxy)butanoyl)oxy)-2-(((9Z,12Z)-octadeca-9,12-dienoyloxy)methyl)propyl1-methylpyrrolidine-2-carboxylate, (2S)-3-((4,4-bis(octyloxy)butanoyl)oxy)-2-(((9Z,12Z)-octadeca-9,12-dienoyloxy)methyl)propyl1-methylpyrrolidine-2-carboxylate, (9Z,9'Z,12Z,12'Z)-2-((((3-(diethylamino)propoxy)carbonyl)oxy)methyl)-2-(((9Z,12Z)-octadeca-9,12-dienoyloxy)methyl)propane-1,3-diylbis(octadeca-9,12-dienoate), (9Z,12Z)-3-((4,4-bis(octyloxy)butanoyl)oxy)-2-(((((1-ethylpiperidin-3-yl)methoxy)carbonyl)oxy)methyl)propyloctadeca-9,12-dienoate, 3-((4,4-bis(octyloxy)butanoyl)oxy)-2-(((9Z,12Z)-octadeca-9,12-dienoyloxy)methyl)propyl1-(cyclopropylmethyl)piperidine-4-carboxylate, 3-((4,4-bis(octyloxy)butanoyl)oxy)-2-(((9Z,12Z)-octadeca-9,12-dienoyloxy)methyl)propyl1-isopropylpiperidine-4-carboxylate, (9Z,12Z)-3-((4,4-bis(octyloxy)butanoyl)oxy)-2-(((3-(dimethylamino)propanoyl)oxy)methyl)propyloctadeca-9,12-dienoate, 4-(dimethylamino)butylcarbonate(6Z,9Z,26Z,29Z)-pentatriaconta-6,9,26,29-tetraen-18-yl, 3-((6-(dimethylamino)hexanoyl)oxy)-2,2-bis(((9Z)-tetradec-9-enoyloxy)methyl)propyl(9Z)-tetradec-9-enoate, 2,5-bis((9Z,12Z)-octadeca-9,12-dienyloxy)benzyl3-(dimethylamino)propylcarbonate, (9Z,9'Z,12Z,12'Z)-2-(((4-(pyrrolidin-1-yl)butanoyl)oxy)methyl)propane-1,3-diylbis(octadeca-9,12-dienoate), 3-(((3-(dimethylamino)propoxy)carbonyl)oxy)pentadecyl5-heptyldodecanoate, Aceticacid (7R,9Z)-18-({[3-(dimethylamino)propyloxy]carbonyl}oxy)octacosa-9-en-7-yl, 3-(((3-(dimethylamino)propoxy)carbonyl)oxy)pentadecyl9-pentyltetradecanoate, (9Z,12Z)-3-((6,6-bis(octyloxy)hexanoyl)oxy)-2-((((3-(diethylamino)propoxy)carbonyl)oxy)methyl)propyloctadeca-9,12-dienoate, 3-(((3-(dimethylamino)propoxy)carbonyl)oxy)pentadecyl7-hexyltridec-6-enoate, (9Z,12Z)-3-(2,2-bis(heptyloxy)acetoxy)-2-((((2-(dimethylamino)ethoxy)carbonyl)oxy)methyl)propyloctadeca-9,12-dienoate, 3-(((3-(dimethylamino)propoxy)carbonyl)oxy)pentadecyl3-octylundec-2-enoate, (9Z,12Z)-3-(((3-(diethylamino)propoxy)carbonyl)oxy)-2-(((5-heptyldodecanoyl)oxy)methyl)propyloctadeca-9,12-dienoate, 3-(((3-dimethylamino)propoxy)carbonyl)oxy)pentadecyl3octylundecanoate, (9Z,12Z)-3-(((3-(diethylamino)propoxy)carbonyl)oxy)-2-(((9-pentyltetradecanoyl)oxy)methyl)propyloctadeca-9,12-dienoate, Diaceticacid(7R,9Z,26Z,29R)-18-({1[3-(dimethylamino)propoxy]carbonyl}oxy)pentatriaconta-9,26-diene-7,29-diyl, 3-(((3-(dimethylamino)propoxy)carbonyl)oxy)pentadecyl8,8-bis((2-propylpentyl)oxy)octanoate, (9Z,12Z)-3-(((3-(diethylamino)propoxy)carbonyl)oxy)-2-(((7-hexyltridecanoyl)oxy)methyl)propyloctadeca-9,12-dienoate, 3-(((3-(ethyl(methyl)amino)propoxy)carbonyl)oxy)pentadecyl8,8-bis((2-propylpentyl)oxy)octanoate, (9Z,12Z)-3-(((3-(diethylamino)propoxy)carbonyl)oxy)-2-(((3-octylundecanoyl)oxy)methyl)propyloctadeca-9,12-dienoate, 3-(((3-(diethylamino)propoxy)carbonyl)oxy)pentadecyl8,8-bis((2-propylpentyl)oxy)octanoate, 3-(((3-(diethylamino)propoxy)carbonyl)oxy)pentadecyl8,8-dibutoxyoctanoate, 3-((5-(dimethylamino)pentanoyl)oxy)-2,2-bis(((9Z)-tetradec-9-enoyloxy)methyl)propyl(9Z)-tetradec-9-enoate, 3-(Dimethylamino)propylcarbonate(6Z,9Z,26Z,29Z)-pentatriacontour-6,9,26,29-tetraen-18-yl, 2,5-bis((9Z,12Z)-octadeca-9,12-dien-1-yloxy)benzyl3-(dimethylamino)propanoate, (9Z,9'Z,12Z,12'Z)-2-(((3-(4-methylpiperazin-1-yl)propanoyl)oxy)methyl)propane-1,3-diylbis(octadeca-9,12-dienoate), 3-(((3-(diethylamino)propoxy)carbonyl)oxy)pentadecyl8,8-bis(octyloxy)octanoate, 3-(Dimethylamino)propyloctacosane-11-ylcarbonate, 2,4-bis((9Z,12Z)-octadeca-9,12-dienyloxy)benzyl4-(dimethylamino)butanoate, (9Z,12Z)-3-(((3-(diethylamino)propoxy)carbonyl)oxy)-2-(((2-heptylundecanoyl)oxy)methyl)propyloctadeca-9,12-dienoate, 3-(((3-(diethylamino)propoxy)carbonyl)oxy)pentadecyl6,6-bis((2-ethylhexyl)oxy)hexanoate, 2-((((3-(dimethylamino)propoxy)carbonyl)oxy)methyl)propane-1,3-diylbis(2-heptylundecanoate), 3-(((3-(diethylamino)propoxy)carbonyl)oxy)pentadecyl6,6-bis(hexyloxy)hexanoate, 4-methyl-2,5-bis((9Z,12Z)-octadeca-9,12-dien-1-yloxy)benzyl4-(dimethylamino)butanoate, 3-(((3-(diethylamino)propoxy)carbonyl)oxy)pentadecyl6,6-bis(octyloxy)hexanoate, 4-(dimethylamino)butyl4-methyl-2,5-bis((9Z,12Z)-octadeca-9,12-dienyloxy)benzylcarbonate, 3-(((3-(dimethylamino)propoxy)carbonyl)oxy)pendadecyl4,4-bis((2-propylpentyl)oxy)butanoate, 2-(12-dodecyl-3-ethyl-8,14-dioxo-7,9,13-trioxa-3-azaoctadecan-18-yl)propane-1,3-diyldioctanoate, 2-(5-oxo-5-((3-(((3-(piperidin-1-yl)propoxy)carbonyl)oxy)pentadecyl)oxy)pentyl)propane-1,3-diyldioctanoate, 3-(dimethylamino)propyl4-methyl-2,5-bis((9Z,12Z)-octadeca-9,12-dien-1-yloxy)benzylcarbonate, 3-(((3-(ethyl(methyl)amino)propoxy)carbonyl)oxy)pentadecyl4,4-bis((2-propylpentyl)oxy)butanoate, 2-(11-dodecyl-3-ethyl-9,15-dioxo-8,10,14-trioxa-3-azanonadecan-19-yl)propane-1,3-diyldioctanoate, 2-(10-dodecyl-3-ethyl-8,15-dioxo-7,9,14-trioxa-3-azanonadecan-19-yl)propane-1,3-diyldioctanoate, 2-(5-((4-((((1-methylpiperidin-4-yl)oxy)carbonyl)oxy)hexadecyl)oxy)-5-oxopentyl)propane-1,3-diyldioctanoate, 2-(5-((4-((((1-ethylpiperidin-3-yl)methoxy)carbonyl)oxy)hexadecyl)oxy)-5-oxopentyl)propane-1,3-diyldioctanoate, 2-(5-((4-(((((R)-1-methylpyrrolidin-3-yl)oxy)carbonyl)oxy)hexadecyl)oxy)-5-oxopentyl)propane-1,3-diyldioctanoate, 2-(5-((4-(((((S)-1-methylpyrrolidin-3-yl)oxy)carbonyl)oxy)hexadecyl)oxy)-5-oxopentyl)propane-1,3-diyldioctanoate, 2-(5-oxo-5-((4-(((S)-pyrrolidine-2-carbonyl)oxy)hexadecyl)oxy)pentyl)propane-1,3-diyldioctanoate, 2-(5-((4-((1,3-dimethylpyrrolidine-3-carbonyl)oxy)hexadecyl)oxy)-5-oxopentyl)propane-1,3-diyldioctanoate, 2-(5-((4-((1,4-dimethylpiperidine-4-carbonyl)oxy)hexadecyl)oxy)-5-oxopentyl)propane-1,3-diyldioctanoate, 4,4-bis(octyloxy)butyl(3-(diethylamino)propyl)pentadecane-1,3-diyldicarbonate, 3-(((3-(diethylamino)propoxy)carbonyl)oxy)pentadecyl4,4-bis((2-propylpentyl)oxy)butanoate, ((2-((((3-(diethylamino)propoxy)carbonyl)oxy)methyl)-1,4-phenylene)bis(oxy))bis(octane-8,1-diyl)bis(decanoate), 4,4-bis(octyloxy)butyl5-(((3-(diethylamino)propoxy)carbonyl)oxy)heptadecanoate, 6-((6,6-bis(octyloxy)hexanoyl)oxy)-4-(((3-(diethylamino)propoxy)carbonyl)oxy)hexyloctanoate, (12Z,15Z)-3-(((3-(diethylamino)propoxy)carbonyl)oxy)henicosa-12,15-dien-1-yl6,6-bis(octyloxy)hexanoate, 3-(((3-(diethylamino)propoxy)carbonyl)oxy)tridecyl6,6-bis(octyloxy)hexanoate, 3-(((3-(diethylamino)propoxy)carbonyl)oxy)undecyl6,6-bis(octyloxy)hexanoate, 3-(((3-(diethylamino)propoxy)carbonyl)oxy)pentadecyl5-(4,6-diheptyl-1,3-dioxan-2-yl)pentanoate, 3-((5-(diethylamino)pentanoyl)oxy)pentadecyl6,6-bis(octyloxy)hexanoate, 1-((6,6-bis(octyloxy)hexanoyl)oxy)pentadecan-3-yl1,4-dimethylpiperidine-4-carboxylate, 3-((3-(1-methylpiperidin-4-yl)propanoyl)oxy)pentadecyl6,6-bis(octyloxy)hexanoate, 1-((6,6-bis(octyloxy)hexanoyl)oxy)pentadecan-3-yl1,3-dimethylpyrrolidine-3-carboxylate, 3-(((3-(diethylamino)propoxy)carbonyl)oxy)pentadecyl4,4-bis((2-ethylhexyl)oxy)butanoate, 2-(((1,3-dimethylpyrrolidine-3-carbonyl)oxy)methyl)propane-1,3-diylbis(8-(octanoyloxy)octanoate), ((2-((((3-(dimethylamino)propoxy)carbonyl)oxy)methyl)-1,4-phenylene)bis(oxy))bis(octane-8,1-diyl)bis(decanoate), (2R)-1-((6,6-bis(octyloxy)hexanoyl)oxy)pentadecan-3-ylpyrrolidine-2-carboxylate, (2S)-1-((6,6-bis(octyloxy)hexanoyl)oxy)pentadecan-3-yl1-methylpyrrolidine-2-carboxylate, (2R)-1-((6,6-bis(octyloxy)hexanoyl)oxy)pentadecan-3-yl1-methylpyrrolidine-2-carboxylate, 3-(((3-(dimethylamino)propoxy)carbonyl)oxy)pentadecyl6,6-bis((3-ethylpentyl)oxy)hexanote, 3-(((3-(dimethylamino)propoxy)carbonyl)oxy)pentadecyl6,6-bis((2-propylpentyl)oxy)hexanoate, 3-(((3-(diethylamino)propoxy)carbonyl)oxy)pentadecyl6,6-bis((2-propylpentyl)oxy)hexanoate, 3-(((2-(diethylamino)ethoxy)carbonyl)oxy)pentadecyl6,6-bis(octyloxy)hexanoate, 3-(((3-morpholinoproproxy)carbonyl)oxy)pentadecyl6,6-bis(octyloxy)hexanoate, 3-((((1-methylpiperidin-4-yl)methoxy)carbonyl)oxy)pentadecyl6,6-bis(octyloxy)hexanoate, 3-(((3-(4-methylpiperazin-1-yl)propoxy)carbonyl)oxy)pentadecyl6,6-bis(octyloxy)hexanoate, 3-(((3-(diethylamino)propoxy)carbonyl)oxy)pentadecyl4,4-bis(octyloxy)butanoate, 2-(((4-(dimethylamino)butanoyl)oxy)methyl)-2-((dodecanoyloxy)methyl)propane-1,3-diyl (9Z,9'Z)bis-tetradec-9-enoate, (9Z,9'Z,12Z,12'Z)-2-(((4-(dimethylamino)butanoyl)oxy)methyl)propane-1,3-diylbis(octadeca-9,12-dienoate), 3-(((4-(diethylamino)butoxy)carbonyl)oxy)pentadecyl6,6-bis(octyloxy)hexanote, 3-(((3-(piperazin-1-yl)propoxy)carbonyl)oxy)pentadecyl6,6-bis(octyloxy)hexanoate, 3-(((3-piperidin-1-yl)propoxy)carbonyl)oxy)pentadecyl6.6-bis(octyloxy)hexanoate, 3-(((3-(dimethylamino)propoxy)carbonyl)oxy)pentadecyl4,4-bis(octyloxy)butanoate, (9Z,9'Z,12Z,12'Z)-2-(9-dodecyl-2-methyl-7,12-dioxo-6,8,13-trioxa-2-azatetradecan-14-yl)propane-1,3-diylbis(octadeca-9,12-dienoate), (9Z,12Z)-10-dodecyl-3-ethyl-14-(2-((9Z,12Z)-octadeca-9,12-dienoyloxy)ethyl)-8,13-dioxo-7,9-dioxa-3,14-diazahexadecan-16-yloctadeca-9,12-dienoate, 2-((2-(((3-(diethylamino)propoxy)carbonyl)oxy)tetradecanoyl)oxy)propane-1,3-diyldioctanoate, 2-(9-dodecyl-2-methyl-7,13-dioxo-6,8,12-trioxa-2-azanonadecan-19-yl)propane-1,3-diyldioctanoate, 2-((decanoyloxy)methyl)-2-(((4-(dimethylamino)butanoyl)oxy)methyl)propane-1,3-diyl(9Z,9'Z)bis-tetradec-9-enoate, (9Z,9'Z,12Z,12'Z)-2-(((3-morpholinopropanoyl)oxy)methyl)propane-1,3-diylbis(octadeca-9,12-dienoate), 3-(Dimethylamino)propylcarbonate(6Z,9Z,28Z,31Z)-heptatriconta-6,9,28,31-tetraen-19-yl, 2,5-bis((9Z,12Z)-octadeca-9,12-dien-1-yloxy)benzyl4-(dimethylamino)butanoate, 2-(10-dodecyl-3-ethyl-8,14-dioxo-7,9,13-trioxa-3-azaoctadecan-18-yl)propane-1,3-diyldioctanoate, (9Z,9'Z,12Z,12'Z)-2-(((1,3-dimethylpyrrolidine-3-carbonyl)oxy)methyl)propane-1,3-diylbis(octadeca-9,12-dienoate), ((5-((dimethylamino)methyl)benzene-1,2,3-triyl)tris(oxy))tris(decane10,1-diyl)trioctanoate, 0',0-(((5-((dimethylamino)methyl)-1,3-phenylene)bis(oxy))bis(propane-3,1-diyl))9-dioctyldinonanedioate, (9Z,12Z)-3-(3-((dimethylamino)methyl)-5-(3-((3-octylundecanoyl)oxy)propoxy)phenoxy)propyloctadeca-9,12-dienoate, ((((5-((dimethylamino)methyl)-1,3-phenylene)bis(oxy))bis(propane-3,1-diyl))bis(oxy))bis(4-oxobutane-4,1-diyl)bis(decanoate), (R)-4-(3-((R)-3,4-bis(octanoyloxy)butoxy)-5-((dimethylamino)methyl)phenoxy)butane-1,2-diyldioctanoate, (S)-4-(3-((S)-3,4-bis(octanoyloxy)butoxy)-5-((dimethylamino)methyl)phenoxy)butane-1,2-diyldioctanoate, (R)-4-(3-((S)-3,4-bis(octanoyloxy)butoxy)-5-((dimethylamino)methyl)phenoxy)butane-1,2-diyldioctanoate, 4,4'-((5-((dimethylamino)methyl)-1,3-phenylene)bis(oxy))bis(butane1,2-diyl)tetraoctanoate, didodecyl6,6'-((5-((dimethylamino)methyl)-1,3-phenylene)bis(oxy))dihexanoate, di((9Z,12Z)-octadeca-9,12-dien-1-yl)5,5'-((5-((dimethylamino)methyl)-1,3-phenylene)bis(oxy))dipentanoate, (((5-((dimethylamino)methyl)-1,3-phenylene)bis(methylene))bis(oxy))bis(6-oxohexane-6,1-diyl)bis(decanoate), (5-((dimethylamino)methyl)-1,3-phenylene)bis(methylene)bis(8-(octanoyloxy)octanoate), (5-((dimethylamino)methyl)-1,3-phenylene)bis(methylene)bis(10-(octanoyloxy)decanoate), (((5-((dimethylamino)methyl)-1,3-phenylene)bis(methylene))bis(oxy))bis(6-oxohexane-6,1-diyl)dioctanoate, (((5-((dimethylamino)methyl)-1,3-phenylene)bis(methylene))bis(oxy))bis(8-oxooctane-8,1-diyl)bis(decanoate), (9Z,9'Z,12Z,12'Z)-(((5-((dimethylamino)methyl)-1,3-phenylene)bis(methylene))bis(oxy))bis(4-oxobutane-4,1-diyl)bis(octadeca-9,12-dienoate), 0',0-((5-((dimethylamino)methyl)-1,3-phenylene)bis(methylene))8-dinonyldioctanedioate, 0,0'-((5-((dimethylamino)methyl)-1,3-phenylene)bis(methylene))bis(10-(octanoyloxy)decyl)disuccinate, 0,0'-((5-((dimethylamino)methyl)-1,3-phenylene)bis(methylene))di((9Z,12Z)-octadeca-9,12-dien-1-yl)disuccinate, (9Z,9'Z,12Z,12'Z)-(5-((((3-(diethylamino)propoxy)carbonyl)oxy)methyl)-1,3-phenylene)bis(methylene)bis(octadeca-9,12-dienoate), (9Z,12Z)-4-(3-((dimethylamino)methyl)-5-(4-(oleoyloxy)butoxy)phenoxy)butyloctadeca-9,12-dienoate, (9Z,9'Z,12Z,12'Z,15Z,15'Z)-((5-((dimethylamino)methyl)-1,3-phenylene)bis(oxy))bis(butane-4,1-diyl)bis(octadeca-9,12,15-trienoate), ((5-((dimethylamino)methyl)-1,3-phenylene)bis(oxy))bis(butane-4,1-diyl)ditetradecanoate, (Z)-((5-((dimethylamino)methyl)-1,3-phenylene)bis(oxy))bis(butane-4,1-diyl)dioleate, ((5-((dimethylamino)methyl)-1,3-phenylene)bis(oxy))bis(hexane-6,1-diyl)didodecanoate, (9Z,9'Z,12Z,12'Z)-((((5-((diethylamino)methyl)-1,3-phenylene)bis(oxy))bis(ethane-2,1-diyl))bis(oxy))bis(ethane-2,1-diyl)bis(octadeca-9,12-dienoate), didecyl8,8'-((5-((dimethylamino)methyl)-1,3-phenylene)bis(oxy))dioctanoate, ((5-((dimethylamino)methyl)-1,3-phenylene)bis(oxy))bis(propane-3,1-diyl)bis(3-octylundecanoate), (9Z.9'Z.12Z.12'Z)-((5-((diethylamino)methvn-2-methyl-1.3-phenylene)bis(oxy))bis(butane-4,1-diyl)bis(octadeca-9,12-dienoate), ((5-((dimethylamino)methyl)-1,3-phenylene)

bis(oxy))bis(octane-8,1-diyl)didodecanoate, ((5-((dimethylamino)methyl)-1,3-phenylene)bis(oxy))bis(octane-8,1-diyl)bis(decanoate), (9Z.9'Z.12Z.12'Z)-((5-((dimethylamino)methvn-2-methyl-1.3-phenylene)bis(oxy))bis(butane-4,1-diyl)bis(octadeca-9,12-dienoate), (8Z,8'Z)-((5-((dimethylamino)methyl)-1,3-phenylene)bis(oxy))bis(hexane-bis(dodec-8-enoate), (9Z,9'Z,12Z,12'Z)-((5-((3-hydroxyazetidin-1-yl)methyl)-1,3-phenylene)bis(oxy))bis(butane-4,1-diyl)bis(octadeca-9,12-dienoate), ((5-((dimethylamino)methyl)-1,3-phenylene)bis(oxy))bis(hexane-6,1-diyl)dioctanoate, ((5-((dimethylamino)methyl)-1,3-phenylene)bis(oxy))bis(hexane-6,1-diyl)bis(decanoate), (9Z.9'Z.12Z.12'Z)-((5-((dimethylamino)methvn-1.3-phenylene)bis(oxy))bis(octane-8,1-diyl)bis(octadeca-9,12-dienoate), (9Z,9'Z,12Z,12'Z)-((5-((dimethylamino)methyl)-1,3-phenylene)bis(oxy))bis(hexane-6,1-diyl)bis(octadeca-9,12-dienoate), ((5-((dimethylamino)methyl)-1,3-phenylene)bis(oxy))bis(decane-10,1-diyl)dihexanoate, ((5-((dimethylamino)methyl)-1,3-phenylene)bis(oxy))bis(decane-10,1-diyl)dioctanoate, ((5-((dimethylamino)methyl)-1,3-phenylene)bis(oxy))bis(octane-8,1-diyl)dioctanoate, ((5-((dimethylamino)methyl)-1,3-phenylene)bis(oxy))bis(octane-8,1-diyl)dihexanoate, (9Z,9'Z,12Z,12'Z)-((5-((dimethylamino)methyl)-1,3-phenylene)bis(oxy))bis(ethane-2,1-diyl)bis(octadeca-9,12-dienoate), (9Z,9'Z,12Z,12'Z)-((5-((dimethylamino)methyl)-1,3-phenylene)bis(oxy))bis(propane-3,1-diyl)bis(octadeca-9,12-dienoate), (9Z,9'Z,12Z,12'Z)-((5-((dimethylamino)methyl)-1,3-phenylene)bis(oxy))bis(butane-4,1-diyl)bis(octadeca-9,12-dienoate), (5-((dimethylamino)methyl)-1,3-phenylene)bis(methylene)ditridecanoate, (9Z,9'Z,12Z,12'Z)-(5-((dimethylamino)methyl)-1,3-phenylene)bis(methylene)bis(octadeca-9,12-dienoate), (2,6-bis((9Z,12Z)-octadeca-9,12-dien-1-yloxy)pyridin-4-yl)methyl3-(dimethylamino)propanoate, (9Z,9'Z,12Z,12'Z)-5-(((3-(dimethylamino)propanoyl)oxy)methyl)-1,3-phenylenebis(octadeca-9,12-dienoate), 1-(3,5-bis((9Z,12Z)-octadeca-9,12-dien-1-yloxy)phenyl)-N,Ndimethylmethanamine, 3,5-bis((9Z,12Z)-octadeca-9,12-dien-1-yloxy)benzyl3-(dimethylamino)propanoate, 1-(3,5-bis(4,4-bis(octyloxy)butoxy)phenyl)-N,N-dimethylmethanamine, ((((5-((dimethylamino)methyl)-1,3-phenylene)bis(oxy))bis(butane-4,1-diyl))bis(oxy))bis(propane-3,2,1-triyl)tetraoctanoate, ((5-(((4-(dimethylamino)butanoyl)oxy)methyl)-1,3-phenylene)bis(oxy))bis(octane-8,1-diyl)bis(decanoate), ((5-(((3-(dimethylamino)propanoyl)oxy)methyl)-1,3-phenylene)bis(oxy))bis(octane-8,1-diyl)bis(decanoate), (9Z,9'Z,12Z,12'Z)-((5-(3-morpholinopropyl)-1,3-phenylene)bis(oxy))bis(butane4,1-diyl)bis(octadeca-9,12-dienoate), (9Z,9'Z,12Z,12'Z)-((5-(3-(dimethylamino)propyl)-1,3-phenylene)bis(oxy))bis(butane-4,1-diyl)bis(octadeca-9,12-dienoate), (9Z,9'Z,12Z,12'Z)-((5-(3-(piperidin-1-yl)propyl)-1,3-phenylene)bis(oxy))bis(butane-4,1-diyl)bis(octadeca-9,12-dienoate), (5-((dimethylamino)methyl)-1,3-phenylene)bis(methylene)bis(9-pentyltetradecanoate), (5-((dimethylamino)methyl)-1,3-phenylene)bis(methylene)bis(7-hexyltridecanoate), (5-((dimethylamino)methyl)-1,3-phenylene)bis(methylene)bis(5-heptyldodecanoate), ((5-((dimethylamino)methyl)-1,3-phenylene)bis(oxy))bis(butane-4,1-diyl)bis(3-octylundecanoate), ((5-((dimethylamino)methyl)-1,3-phenylene)bis(oxy))bis(butane-4,1-diyl)bis(5-heptyldodecanoate), ((5-((dimethylamino)methyl)-1,3-phenylene)bis(oxy))bis(butane-4,1-diyl)bis(9-pentyltetradecanoate), ((5-((dimethylamino)methyl)-1,3-phenylene)bis(oxy))bis(butane-4,1-diyl)bis(7-hexyltridecanoate), (9Z,9'Z,12Z,12'Z)-((5-(pyrrolidin-1-ylmethyl)-1,3-phenylene)bis(oxy))bis(butan4,1-diyl)bis(octadeca-9,12-dienoate), (((5-((dimethylamino)methyl)-1,3-phenylene)bis(oxy))bis(methylene))bis(propane-3,2,1-triyl)tetraoctanoate, (((5-((dimethylamino)methyl)-1,3-phenylene)bis(oxy))bis(butane-4,1-diyl))bis(propane-3,2,1-triyl)tetraoctanoate, (9Z.12Z)-4-(3-((dimethylamino)methvn-5-(4-((3-octylundecanoyl)oxy)butoxy)phenoxy)butyloctadeca-9,12-dienoate, bis(1,3-bis(octanoyloxy)propan-2-yl)0,0'-((5-((dimethylamino)methyl)-1,3-phenylene)bis(methylene))disuccinate, (5-((dimethylamino)methyl)-1,3-phenylene)bis(methylene)bis(6-(((nonyloxy)carbonyl)oxy)hexanoate), 2-(3-(4-(5-((dimethylamino)methyl)-2-methyl-3-((9Z,12Z)-octadeca9,12-dien-1-yloxy)phenoxy)butoxy)-3-oxopropyl)propane-1,3-diyldihexanoate, 3-((dimethylamino)methyl)-5-(((8-(octanoyloxy)octanoyl)oxy)methyl)benzyl3-octylundecanoate, ((5-((diethylamino)methyl)benzene-1,2,3-triyl)tris(oxy))tris(decane-10,1-diyl)trioctanoate, 1-(3,5-bis((Z)-octadec-9-en-1-yloxy)phenyl)-N,N-dimethylmethanamine, N'-methyl-N',N".N"-tris((2E.6E)-3.7.11-trimethyldodeca-2.6.10-trien-1-ynpropane-1,3-diamine, 1,17-bis(2-((2-pentylcyclopropyl)methyl)cyclopropyl)heptadecan-9-yl4-(dimethylamino)butanoate, ethyl(7Z)-17-{[4-(dimethylamino)butanoyl]oxy}hexacos-7-enoate, (Z)-methyl6-(2-(dimethylamino)-3-(octadec-9-en-1-yloxy)propoxy)hexanoate, 2-(Didodecylamino)-1-(4-(N-(2-(dinonylamino)ethyl)-N-dodecylglycyl)piperazin-1-yl)ethan-1-one, 3-((3-(1-(3-((2-(Dinonylamino)ethyl)(nonyl)amino)propanoyl)piperidin-4-yl)propyl)(nonyl)amino)propylhexanoate, 3-((3-(4-(3-((2-(Dinonylamino)ethyl)(nonyl)amino)propanoyl)piperazin-1-yl)-3-oxopropyl)(nonyl)amino)propylhexanoate, 3-((2-(Dinonylamino)ethyl)(nonyl)amino)-1-(4-(3-(dinonylamino)propyl)piperidin-1-yl)propan-1-one, Pentyl4-((3-(1-(3-((2-(dinonylamino)ethyl)(nonyl)amino)propanoyl)piperidin-4-yl)propyl)(nonyl)amino)butano, Pentyl4-((2-(1-(N-(2-(dinonylamino)ethyl)-N-nonylglycyl)piperidin-4-yl)ethyl)(nonyl)amino)butanoate, Pentyl4-(((1-(N-(2-(dinonylamino)ethyl)-N-nonylglycyl)pyrrolidin-3-yl)methyl)(nonyl)amino)butanoate, Pentyl4-((2-(1-(N-(2-(dinonylamino)ethyl)-N-nonylglycyl)pyrrolidin-3-yl)ethyl)(nonyl)amino)butanoate, Pentyl4-((2-(1-(N-(2-(dinonylamino)ethyl)-N-nonylglycyl)piperidin-3-yl)ethyl)(nonyl)amino)butanoate, 2-(Didodecylamino)-1-(4-(N-(2-(dinonylamino)ethyl)-N-nonylglycyl)piperazin-1-yl)ethan-1-one, 2-((2-(Dinonylamino)ethyl)(nonyl)amino)-1-(3-(2-(dinonylamino)ethyl)piperidin-1-yl)ethan-1-one, Dipentyl4,4'-((2-(4-(N-(2-(dinonylamino)ethyl)-N-nonylglycyl)piperazin-1-yl)-2-oxoethyl)azanediyl)dibutyrate, Pentyl4-(nonyl(2-(4-(N-nonyl-N-(2-(nonyl(4-oxo-4-(penlyloxy)buryl)amino)ethyl)glycyl)piperazin-1-yl)-2-oxoethyl)amino)butanoate, 2-((2-(Dinonylamino)ethyl)(nonyl)amino)-1-(3-((dinonylamino)methyl)pyrrolidin-1-yl)ethan-1-one, 2-((2-(Didodecylamino)ethyl)(dodecyl)amino)-1-(4-(dinonylglycyl)piperazin-1-yl)ethan-1-one, 2-((2-(Dinonylamino)ethyl)(nonyl)amino)-1-(3-(2-(dinonylamino)ethyl)pyrrolidin-1-yl)ethan-1-one, Pentyl4-((3-(4-(3-((2-(dinonylamino)ethyl)(nonyl)amino)propanoyl)piperazin-1-yl)-3-oxopropyl)(nonyl)amino)butanoate, 3-((2-(1-(N-(2-(Dinonylamino)ethyl)-N-nonylglycyl)piperidin-4-yl)ethyl)(nonyl)amino)propylhexanoate, Butyl5-((2-(1-(N-(2-(dinonylamino)ethyl)-N-nonylglycyl)piperidin-4-yl)ethyl)(nonyl)amino)pentanoate, 2-((2-(Didodecylamino)ethyl)(nonyl)amino)-1-(4-(dinonylglycyl)piperazin-1-yl)ethan-1-one, Propyl6-((2-(1-(N-(2-(dinonylamino)ethyl)-N-nonylglycyl)piperidin-4-yl)ethyl)(nonyl)amino)hexanoate, Ethyl7-((2-(1-(N-(2-(dinonylamino)ethyl)-N-nonylglycyl)piperidin-4-yl)ethyl)

(nonyl)amino)heptanoate, Methyl8-((2-(1-(N-(2-(dinonylamino)ethyl)-N-nonylglycyl)piperidin-4-yl)ethyl)(nonyl)amino)octanoate, 3-((2-(4-(N-(2-(Dinonylamino)ethyl)-N-nonylglycyl)piperazin-1-yl)-2-oxoethyl)(nonyl)amino)propylhexanoate, Butyl5-((2-(4-(N-(2-(dinonylamino)ethyl)-N-nonylglycyl)piperazin-1-yl)-2-oxoethyl)(nonyl)amino)pentanoate, Propyl6-((2-(4-(N-(2-(dinonylamino)ethyl)-N-nonylglycyl)piperazin-2-oxoethyl)(nonyl)amino)hexanoate, Ethyl7-((2-(4-(N-(2-(dinonylamino)ethyl)-N-nonylglycyl)piperazin-1-yl)-2-oxoethyl)(nonyl)amino)heptanoate, 3-(Dinonylamino)-1-(4-(3-((2-(dinonylamino)ethyl)(nonyl)amino)propanoyl)piperazin-1-yl)propan-1-one, 2-((2-(Dinonylamino)ethyl)(nonyl)amino)-1-(4-(ditetradecylglycyl)piperazin-1-yl)ethan-1-one, 2-(Dinonylamino)-1-(4-(2-((2-(dinonylamino)ethyl)(nonyl)amino)ethyl)piperidin-1-yl)ethan-1-one, 2-(Dinonylamino)-1-(4-(N-(2-(dinonylamino)ethyl)-N-dodecylglycyl)piperazin-1-yl)ethan-1-one, 2-((2-(Dinonylamino)ethyl)(nonyl)amino)-1-(4-(2-(dinonylamino)ethyl)piperidin-1-yl)ethan-1-one, Methyl8-((2-(4-(dinonylglycyl)piperazin-1-yl)-2-oxoethyl)(2-((8-methoxy-8-oxooctyl)(nonyl)amino)ethyl)amino)octanoate, Methyl8-((2-(dinonylamino)ethyl)(2-(4-(dinonylglycyl)piperazin-1-yl)-2-oxoethyl)amino)octanoate, Methyl8-((2-((2-(4-(dinonylglycyl)piperazin-1-yl)-2-oxoethyl)(nonyl)amino)ethyl)(nonyl)amino)octanoate, Pentyl4-((2-(4-(N-(2-(dinonylamino)ethyl)-N-nonylglycyl)piperazin-2-oxoethyl)(nonyl)amino)butanoate, Methyl8-((2-(4-(N-(2-(dinonylamino)ethyl)-N-nonylglycyl)piperazin-1-yl)-2-oxoethyl)(nonyl)amino)octanoate, 2-((2-(Didodecylamino)ethyl)(dodecyl)amino)-1-(5-(dinonylglycyl)-2,5-diazabicyclo[2.2.1]heptan-2-yl)ethan-1-one3, 2-(Dinonylamino)-1-(5-(N-(2-(dinonylamino)ethyl)-N-nonylglycyl)-2,5-diazabicyclo[2.2.1]heptan-2-yl)ethan-1-one, N1,N1,N2-Tri((9Z,12Z)-octadeca-9,12-dien-1-yl)-N2-(2-(piperazin-1-yl)ethyl)ethane-1,2-diamine, N1,N1,N2-Tri((Z)-octadec-9-en-1-yl)-N2-(2-(piperazin-1-yl)ethyl)ethane-1,2-diamine, 2-(Dinonylamino)-1-(4-(N-(2-(dinonylamino)ethyl)-N-nonylglycyl)piperazin-1-yl)ethan-1-one, N1,N1,N2-Tridodecyl-N2-(2-(piperazin-1-yl)ethyl)ethane-1,2-diamine, N1,N1,N2-Trinonyl-N2-(2-(piperazin-1-yl)ethyl)ethane-1,2-diamine, N1,N1,N2-Trihexyl-N2-(2-(piperazin-1-yl)ethyl)ethane-1,2-diamine, N1-(2-(4-(2-(Didodecylamino)ethyl)piperazin-1-yl)ethyl)-N1,N2,N2-tri((9Z,12Z)-octadeca-9,12-dien-1-yl)ethane-1,2-diamine, N1-(2-(4-(2-(Didodecylamino)ethyl)piperazin-1-yl)ethyl)-N1,N2,N2-tri((Z)-octadec-9-en-1-yl)ethane-1,2-diamine, N1-(2-(4-(2-(Ditetradecylamino)ethyl)piperazin-1-yl)ethyl)-N1,N2,N2-tritetradecylethane-1,2-diamine, N1-(2-(4-(2-(Didodecylamino)ethyl)piperazin-1-yl)ethyl)-N1,N2,N2-tritetradecylethane-1,2-diamine, N1-(2-(4-(2-(Dinonylamino)ethyl)piperazin-1-yl)ethyl)-N1,N2,N2-tritetradecylethane-1,2-diamine, 2-(Didodecylamino)-1-(4-(2-((2-(didodecylamino)ethyl)(dodecyl)amino)ethyl)piperazin-1-yl)ethan-1-one, N1-(2-(4-(2-(Di((9Z,12Z)-octadeca-9,12-dien-1-yl)amino)ethyl)piperazin-1-yl)ethyl)-N1,N2,N2-tridodecylethane-1,2-diamine, N1-(2-(4-(2-(Di((Z)-octadec-9-en-1-yl)amino)ethyl)piperazin-1-yl)ethyl)-N1,N2,N2-tridodecylethane-1,2-diamine, N1,N1,N2-Tridodecyl-N2-(2-(4-(2-(dodecyl((9Z,12Z)-octadeca-9,12-dien-1-yl)amino)ethyl)piperazin-1-yl)ethyl)ethane-1,2-diamine, N1-(2-(4-(2-(Ditetradecylamino)ethyl)piperazin-1-yl)ethyl)-N1,N2,N2-tridodecylethane-1,2-diamine, N1-(2-(4-(2-(Di((Z)-dodec-6-en-1-yl)amino)ethyl)piperazin-1-yl)ethyl)-N1,N2,N^tridodecylethane-1,2-diamine, (Z)-N1-(2-(4-(2-(Dodec-6-en-1-yl(dodecyl)amino)ethyl)piperazin-1-yl)ethyl)-N,N2,N2-tridodecylethane-1,2-diamine, N1-(2-(4-(2-(Dinonylamino)ethyl)piperazin-1-yl)ethyl)-N1,N2,N2-tridodecylethane-1,2-diamine, N1-(2-(4-(2-(Dioctylamino)ethyl)piperazin-1-yl)ethyl)-N1,N2,N2-tridodecylethane-1,2-diamine, N1-(2-(4-(2-(Dihexylamino)ethyl)piperazin-1-yl)ethyl)-N1,N2,N2-tridodecylethan-1,2-diamine, N1-(2-(4-(2-(Ditetradecylamino)ethyl)piperazin-1-yl)ethyl)-N1,N2,N2-trinonylethane-1,2-diamine, 2-((2-(Didodecylamino)ethyl)(dodecyl)amino)-1-(4-(2-(didodecylamino)ethyl)piperazin-1-yl)ethan-1-one, N1-(2-(4-(2-(Didodecylamino)ethyl)piperazin-1-yl)ethyl)-N1,N2,N2-trinonylethane-1,2-diamine, N1-(2-(4-(2-(Dinonylamino)ethyl)piperazin-1-yl)ethyl)-N1,N2,N2-trinonylethane-1,2-diamine, N1-(2-(4-(2-(Didodecylamino)ethyl)piperazin-1-yl)ethyl)-N1,N2,N2-trihexylethane-1,2-diamine, Dimethyl12,12'-((2-(4-(2-((2-(didodecylamino)ethyl)(dodecyl)amino)ethyl)piperazin-1-yl)ethyl)azanediyl)didodecanoate, Methyl12-((2-(4-(2-((2-(didodecylamino)ethyl)(dodecyl)amino)ethyl)piperazin-1-yl)ethyl)(dodecyl)amino)dodecanoate, Dipentyl6,6'-((2-(4-(2-((2-(didodecylamino)ethyl)(dodecyl)amino)ethyl)piperazin-1-yl)ethyl)azanediyl)dihexanoate, Pentyl6-((2-(4-(2-((2-(ditetradecylamino)ethyl)(tetradecyl)amino)ethyl)piperazin-1-yl)ethyl)(dodecyl)amino)hexanoate, Pentyl6-((2-(4-(2-((2-(didodecylamino)ethyl)(dodecyl)amino)ethyl)piperazin-1-yl)ethyl)(dodecyl)amino)hexanoate, 2-(Didodecylamino)-1-(4-(N-(2-(didodecylamino)ethyl)-N-dodecylglycyl)piperazin-1-yl)ethan-1-one, 2-(Didodecylamino)-1-(4-(N-(2-(didodecylamino)ethyl)-N-nonylglycyl)piperazin-1-yl)ethan-1-one, 2-(Didodecylamino)-N-(2-(4-(2-(didodecylamino)ethyl)piperazin-1-yl)ethyl)-N-dodecylacetamide, ((2-((3,S',4R)-3,4-dihydroxypyrrolidin-1-yl)acetyl)azanediyl)bis(ethane-2,1-diyl)(9Z,9'Z,12Z,12'Z)-bis(octadeca-9,12-dienoate), 2-amino-N,N-dihexadecyl-3-(1H-imidazol-5-yl)propanamide, (2-amino-N,N-dihexadecyl-3-(1H-imidazol-5-yl)propanamide, methyl(9Z)-19-[2-(dimethylamino)ethyl]heptacos-9-enoate, methyl8-(2-{9-[2-(dimethylamino)ethyl]octadecyl}cyclopropyl)octanoate, methyl(9Z)-19-[2-(dimethylamino)ethyl]octacos-9-enoate, ethyl8-(2-{11-[(dimethylamino)methyl]heptadecyl}cyclopropyl)octanoate, ethyl8-(2-{11-[(dimethylamino)methyl]octadecyl}cyclopropyl)octanoate, di((9Z,12Z)-octadeca-9,12-dien-1-yl)3-(((2-(dimethylamino)ethoxy)carbonyl)amino)pentanedioate, Heptyl6-((2-(1-(N-(2-(dinonylamino)ethyl)-N-nonylglycyl)piperidin-4-yl)ethyl)(tetradecyl)amino)hexanoate, ethyl8-(2-{11-[(dimethylamino)methyl]nonadecyl}cyclopropyl)octanoate, Pentyl8-((2-(1-(N-(2-(dinonylamino)ethyl)-N-nonylglycyl)piperidin-4-yl)ethyl)(tetradecyl)amino)octanoate, ethyl8-(2-{11-[(dimethylamino)methyl]icosyl}cyclopropyl)octanoate, ethyl8-(2-{9-[(dimethylamino)methyl]pentadecyl}cyclopropyl)octanoate, 3-((2-(1-(N-(2-(Dinonylamino)ethyl)-N-nonylglycyl)piperidin-4-yl)ethyl)(tetradecyl)amino)propyldecanoate, Heptyl6-((2-(4-(N-(2-(dinonylamino)ethyl)-N-nonylglycyl)piperazin-1-yl)-2-oxoethyl)(tetradecyl)amino)hexanoate, ethyl8-(2-{9-[(dimethylamino)methyl]hexadecyl}cyclopropyl)octanoate, Pentyl8-((2-(4-(N-(2-(dinonylamino)ethyl)-N-nonylglycyl)piperazin-2-oxoethyl)(tetradecyl)amino)octanoate, ethyl8-(2-{9-[(dimethylamino)methyl]heptadecyl}cyclopropyl)octanoate, methyl6-(2-(8-(2-(dimethylamino)-3-(nonyloxy)propoxy)octyl)cyclopropyl)hexanoate, methyl(9Z)-21-(dimethylamino)heptacos-9-enoate, methyl(9Z)-21-{[4-(dimethylamino)butanoyl]oxy}heptacos-9-enoate, (2R)—N,N-dimethyl-1-[(9Z,12Z)-octadeca-9,12-dien-1-yloxy]dodecan-2-amine, (15Z,18Z)—N,N-dimethyltetracoda-15,18-dien-5-amine, ethyl8-(2-{9-[(dimethylamino)methyl]octadecyl}cyclopropyl)octanoate, 3-((2-(4-(N-(2-

(Dinonylamino)ethyl)-N-nonylglycyl)piperazin-1-yl)-2-oxoethyl)(tetradecyl)amino)propyldecanoate, ethyl4-(2-{11-[(dimethylamino)methyl]icosyl}cyclopropyl)butanoate, ethyl8-(2-{7-[(dimethylamino)methyl]hexadecyl}cyclopropyl)octanoate, 3-((3-(1-(3-((2-(Dinonylamino)ethyl)(nonyl)amino)propanoyl)piperidin-4-yl)propyl)(nonyl)amino)propylhexanoate, ethyl6-(2-{9-[(dimethylamino)methyl]pentadecyl}cyclopropyl)hexanoate, 3-((3-(4-(3-((2-(Dinonylamino)ethyl)(nonyl)amino)propanoyl)piperazin-1-yl)-3-oxopropyl)(nonyl)amino)propylhexanoate, ethyl6-(2-{9-[(dimethylamino)methyl]hexadecyl}cyclopropyl)hexanoate, 3-((2-(Dinonylamino)ethyl)(nonyl)amino)-1-(4-(3-(dinonylamino)propyl)piperidin-1-yl)propan-1-one, Pentyl4-((3-(1-(3-((2-(dinonylamino)ethyl)(nonyl)amino)propanoyl)piperidin-4-yl)propyl)(nonyl)amino)buta^, ethyl6-(2-{9-[(dimethylamino)methyl]heptadecyl}cyclopropyl)hexanoate, Pentyl4-((2-(1-(N-(2-(dinonylamino)ethyl)-N-nonylglycyl)piperidin-4-yl)ethyl)(nonyl)amino)butanoate, ethyl6-(2-{9-[(dimethylamino)methyl]octadecyl}cyclopropyl)hexanoate, Pentyl4-(((1-(N-(2-(dinonylamino)ethyl)-N-nonylglycyl)pyrrolidin-3-yl)methyl)(nonyl)amino)butanoate, ethyl(9Z)-21-[(dimethylamino)methyl]heptacos-9-enoate, Pentyl4-((2-(1-(N-(2-(dinonylamino)ethyl)-N-nonylglycyl)pyrrolidin-3-yl)ethyl)(nonyl)amino)butanoate, ethyl(9Z)-21-[(dimethylamino)methyl]octacos-9-enoate, ((2-((3,S',4R)-3,4-dihydroxypyrrolidin-1-yl)acetyl)azanediyl)bis(ethane-2,1-diyl)(9Z,9'Z,12Z,12'Z)-bis(octadeca-9,12-dienoate), Pentyl4-((2-(1-(N-(2-(dinonylamino)ethyl)-N-nonylglycyl)piperidin-3-yl)ethyl)(nonyl)amino)butanoate, ethyl(9Z)-21-[(dimethylamino)methyl]nonacos-9-enoate, methyl6-(2-(8-(2-(dimethylamino)-3-(heptyloxy)propoxy)octyl)cyclopropyl)hexanoate, methyl(9Z)-21-{1[4-(dimethylamino)butanoyl]oxy}octacos-9-enoate, methyl (9Z)-21-(dimethylamino)octacos-9-enoate, 2-(Didodecylamino)-1-(4-(N-(2-(dinonylamino)ethyl)-N-nonylglycyl)piperazin-1-yl)ethan-1-, (2S)—N.N-dimethyl-1-[(9Z,12Z)-octadeca-9,12-dien-1-yloxy]nonan-2-amine, (18Z,21Z)—N,N-dimethylheptacosa-18,21-dien-10-amine, ethyl(9Z)-21-[(dimethylamino)methyl]triacont-9-enoate, ethyl(9Z)-19-[(dimethylamino)methyl]pentacos-9-enoate, ethyl(9Z)-19-[(dimethylamino)methyl]hexacos-9-enoate, ethyl(9Z)-19-[(dimethylamino)methyl]heptacos-9-enoate, ethyl(9Z)-19-[(dimethylamino)methyl]octacos-9-enoate, ethyl(5Z)-17-[(dimethylamino)methyl]hexacos-5-enoate, ethyl(9Z)-17-[(dimethylamino)methyl]hexacos-9-enoate, 2-((2-(Dinonylamino)ethyl)(nonyl)amino)-1-(3-(2-(dinonylamino)ethyl)piperidin-1-yl)ethan-1-one, ethyl(7Z)-17-[(dimethylamino)methyl]tricos-7-enoate, Dipentyl4,4'-((2-(4-(N-(2-(dinonylamino)ethyl)-N-nonylglycyl)piperazin-1-yl)-2-oxoethyl)azanediyl)dibutyrate, Pentyl4-(nonyl(2-(4-(N-nonyl-N-(2-(nonyl(4-oxo-4-(pentyloxy)butyl)amino)ethyl)glycyl)piperazin-1-yl)-2-oxoethyl)amino)butanoate, ethyl(7Z)-17-[(dimethylamino)methyl]tetracos-7-enoate, ethyl(7Z)-17-[(dimethylamino)methyl]pentacos-7-enoate, 2-((2-(Dinonylamino)ethyl)(nonyl)amino)-1-(3-((dinonylamino)methyl)pyrrolidin-1-yl)ethan-1-one, trans-3-[(3}7-dimethyloctyl)oxy]-1-methyl-4-[(9Z,12Z)-octadeca-9512-dien-1-yloxyjpyrrolidine, methyl6-(2-(8-(2-(dimethylamino)-3-(hexyloxy)propoxy)octyl)cyclopropyl)hexanoate, methyl(9Z)-21-{1[4-(dimethylamino)butanoyl]oxy}nonacos-9-enoate, methyl(9Z)-21-(dimethylamino)nonacos-9-enoate, (2S)—N,N-dimethyl-1-[(9Z,12Z)-octadeca-9,12-dien-1-yloxy]tridecan-2-amine, (15Z,18Z)—N,N-dimethyltetracosa-15,18-dien-7-amine, ethyl(7Z)-17-[(dimethylamino)methyl]hexacos-7-enoate, 2-((2-(Dinonylamino)ethyl)(nonyl)amino)-1-(3-(2-(dinonylamino)ethyl)pyrrolidin-1-yl)ethan-1-one, methyl6-(2-{11-[(dimethylamino)methyl]icosyl}cyclopropyl)hexanoate, methyl10-(2-{7-[(dimethylamino)methyl]hexadecyl}cyclopropyl)decanoate, methyl8-(2-{11-[(dimethylamino)methyl]heptadecyl}cyclopropyl)octanoate, methyl8-(2-{11-[(dimethylamino)methyl]octadecyl}cyclopropyl)octanoate, methyl8-(2-{11-[(dimethylamino)methyl]nonadecyl}cyclopropyl)octanoate, methyl8-(2-{11-[(dimethylamino)methyl]icosyl}cyclopropyl)octanoate, Pentyl4-((3-(4-(3-((2-(dinonylamino)ethyl)(nonyl)amino)propanoyl)piperazin-1-yl)-3-oxopropyl)(nonyl)amino)butanoate, methyl8-(2-{9-[(dimethylamino)methyl]pentadecyl}cyclopropyl)octanoate, methyl8-(2-{9-[(dimethylamino)methyl]hexadecyl}cyclopropyl)octanoate, 3-((2-(1-(N-(2-(Dinonylamino)ethyl)-N-nonylglycyl)piperidin-4-yl)ethyl)(nonyl)amino)propylhexanoate, methyl8-(2-{9-[(dimethylamino)methyl]heptadecyl}cyclopropyl)octanoate, methyl8-(2-(dimethylamino)-3-((6-((2-octylcyclopropyl)methoxy)-6-oxohexyl)oxy)propoxy)octanoate, Butyl5-((2-(1-(N-(2-(dinonylamino)ethyl)-N-nonylglycyl)piperidin-4-yl)ethyl)(nonyl)amino)pentanoate, trans-1-methyl-3-[(12Z)-octadec-12-en-1-yloxy]-4-(octyloxy)pyrrolidine, methyl(9Z)-21-{1[4-(dimethylamino)butanoyl]oxy}triacont-9-enoate, methyl(9Z)-21-(dimethylamino)triacont-9-enoate, 2-((2-(Didodecylamino)ethyl)(nonyl)amino)-1-(4-(dinonylglycyl)piperazin-1-yl)ethan-1-oneStep1:MethylN-(2-(didodecylamino)ethyl)-N-nonylglycinate, 1-((2R,3S,5R)-3-(bis(hexadecyloxy)methoxy)-5-(5-methyl-2,4-dioxo-3,4-dihydropyrimidin-1(2H)-yl)tetrahydrofumethanesulfonate, (Z)-methyl16-(3-(decyloxy)-2-(dimethylamino)propoxy)hexadec-7-enoate, (2S)-1-[(9Z,12Z)-octadeca-9,12-dien-1-yloxy]nonan-2-amine, (14Z,17Z)—N,N-dimethyltricosa-14,17-dien-6-amine, Propyl6-((2-(1-(N-(2-(dinonylamino)ethyl)-N-nonylglycyl)piperidin-4-yl)ethyl)(nonyl)amino)hexanoate, methyl7-(2-(dimethylamino)-3-((6-((2-octylcyclopropyl)methoxy)-6-oxohexyl)oxy)propoxy)heptanoate, methyl (7Z)-19-[(dimethylamino)methyl]octacos-7-enoate, methyl (HZ)-19-[(dimethylamino)methyl]octacos-11-enoate, Ethyl7-((2-(1-(N-(2-(dinonylamino)ethyl)-N-nonylglycyl)piperidin-4-yl)ethyl)(nonyl)amino)heptanoate, (2-octylcyclopropyl)methyl6-(2-(dimethylamino)-3-((5-methoxy-5-oxopentyl)oxy)propoxy)hexanoate, Methyl8-((2-(1-(N-(2-(dinonylamino)ethyl)-N-nonylglycyl)piperidin-4-yl)ethyl)(nonyl)amino)octanoate, methyl(9Z)-21-[(dimethylamino)methyl]heptacos-9-enoate, (2-octylcyclopropyl)methyl6-(2-(dimethylamino)-3-(4-methoxy-4-oxobutoxy)propoxy)hexanoate, methyl(9Z)-21-[(dimethylamino)methyl]octacos-9-enoate, 3-((2-(4-(N-(2-(Dinonylamino)ethyl)-N-nonylglycyl)piperazin-1-yl)-2-oxoethyl)(nonyl)amino)propylhexanoate, (Z)-methyl8-(2-(dimethylamino)-3-((6-oxo-6-(undec-2-en-1-yloxy)hexyl)oxy)propoxy)octanoate, methyl(9Z)-21-[(dimethylamino)methyl]nonacos-9-enoate, Butyl5-((2-(4-(N-(2-(dinonylamino)ethyl)-N-nonylglycyl)piperazin-1-yl)-2-oxoethyl)(nonyl)amino)pentanoate, (Z)-methyl7-(2-(dimethylamino)-3-((6-oxo-6-(undec-2-en-1-yloxy)hexyl)oxy)propoxy)heptanoate, Propyl6-((2-(4-(N-(2-(dinonylamino)ethyl)-N-nonylglycyl)piperazin-1-yl)-2-oxoethyl)(nonyl)amino)hexanoate, methyl(9Z)-21-[(dimethylamino)methyl]triacont-9-enoate, (Z)-undec-2-en-1-yl6-(2-(dimethylamino)-3-((5-methoxy-5-oxopentyl)oxy)propoxy)hexanoate, methyl(9Z)-19-[(dimethylamino)methyl]pentacos-9-enoate, Ethyl7-((2-(4-(N-(2-(dinonylamino)ethyl)-N-nonylglycyl)piperazin-1-yl)-2-oxoethyl)(nonyl)amino)heptanoate, (Z)-undec-2-en-1-yl6-

(2-(dimethylamino)-3-(4-methoxy-4-oxobutoxy)propoxy) hexanoate, methyl6-(2-(dimethylamino)-3-((6-((2-octylcyclopropyl)methoxy)-6-oxohexyl)oxy)propoxy) hexanoate, methyl(9Z)-19-[(dimethylamino)methyl] hexacos-9-enoate, 3-(Dinonylamino)-1-(4-(3-((2-(dinonylamino)ethyl)(nonyl)amino)propanoyl)piperazin-1-yl)propan-1-one, methyl(9Z)-19-[(dimethylamino)methyl] heptacos-9-enoate, 2-((2-(Dinonylamino)ethyl)(nonyl) amino)-1-(4-(ditetradecylglycyl)piperazin-1-yl)ethan-1-one, (Z)-methyl6-(2-(dimethylamino)-3-((6-oxo-6-(undec-2-en-1-yloxy)hexyl)oxy)propoxy)hexanoate, methyl8-(2-(dimethylamino)-3-((8-(2-(6-methoxy-6-oxohexyl) cyclopropyl)octyl)oxy)propoxy)octanoate, methyl8-(2-{9-[(dimethylamino)methyl]octadecyl}cyclopropyl)octanoate, 2-(Dinonylamino)-1-(4-(2-((2-(dinonylamino)ethyl)(nonyl) amino)ethyl)piperidin-1-yl)ethan-1-one, trans-1-methyl-3-[(9Z)-octadec-9-en-1-yloxy]-4-(octyloxy)pyrrolidine, methyl(9Z)-19-{[4-(dimethylamino)butanoyl] oxy}pentacos-9-enoate, methyl(9Z)-19-(dimethylamino) pentacos-9-enoate, (Z)-methyl16-(2-(dimethylamino)-3-(nonyloxy)propoxy)hexadec-7-enoate, (2S)-1-[(9Z,12Z)-octadeca-9,12-dien-1-yloxy]decan-2-amine, (12Z,15Z)—N, N-dimethylhenicosa-12,15-dien-4-amine, methyl7-(2-(dimethylamino)-3-((8-(2-(6-methoxy-6-oxohexyl) cyclopropyl)octyl)oxy)propoxy)heptanoate, methyl(9Z)-19-[(dimethylamino)methyl]octacos-9-enoate, 2-((2-(Dinonylamino)ethyl)(nonyl)amino)-1-(4-(2-(dinonylamino)ethyl)piperidin-1-yl)ethan-1-one, Methyl8-((2-(4-(dinonylglycyl)piperazin-1-yl)-2-oxoethyl)(2-((8-methoxy-8-oxooctyl)(nonyl)amino)ethyl)amino)octanoate, methyl6-(2-(8-(2-(dimethylamino)-3-((5-methoxy-5-oxo-pentyl)oxy)propoxy)octyl)cyclopropyl)hexanoate, ethyl8-{2-[11-(dimethylamino)heptadecyl]cyclopropyl}octanoate, Methyl8-((2-(dinonylamino)ethyl)(2-(4-(dinonylglycyl)piperazin-1-yl)-2-oxoethyl)amino)octanoate, methyl6-(2-(8-(2-(dimethylamino)-3-(4-methoxy-4-oxobutoxy)propoxy)octyl)cyclopropyl)hexanoate, ethyl8-{2-[11-(dimethylamino) octadecyl]cyclopropyl}octanoate, Methyl8-((2-((2-(4-(dinonylglycyl)piperazin-1-yl)-2-oxoethyl)(nonyl)amino) ethyl)(nonyl)amino)octanoate, ethyl8-{2-[11-(dimethylamino)nonadecyl]cyclopropyl}octanoate, (Z)-methyl16-(2-(dimethylamino)-3-((8-methoxy-8-oxooctyl) oxy)propoxy)hexadec-7-enoate, Pentyl4-((2-(4-(N-(2-(dinonylamino)ethyl)-N-nonylglycyl)piperazin-1-yl)-2-oxoethyl)(nonyl)amino)butanoate, ethyl8-{2-[11-(dimethylamino)icosyl]cyclopropyl}octanoate, (Z)-methyl16-(2-(dimethylamino)-3-((7-methoxy-7-oxoheptyl) oxy)propoxy)hexadec-7-enoate, Methyl8-((2-(4-(N-(2-(dinonylamino)ethyl)-N-nonylglycyl)piperazin-1-yl)-2-oxoethyl)(nonyl)amino)octanoate, ethyl8-{2-[9-(dimethylamino)pentadecyl]cyclopropyl}octanoate, (Z)-methyl16-(2-(dimethylamino)-3-((5-methoxy-5-oxopentyl) oxy)propoxy)hexadec-7-enoate, (11E,20Z,23Z)—N,N-dimethylnonacosa-11,20,23-trien-10-amine, N,N-dimethyl-1-[(1S,2R)-2-octylcyclopropyl]pentadecan-8-amine, ethyl8-{2-[9-(dimethylamino)hexadecyl]cyclopropyl}octanoate, 2-((2-(Didodecylamino)ethyl)(dodecyl)amino)-1-(5-(dinonylglycyl)-2,5-diazabicyclo[2.2.1]heptan-2-yl)ethan-1-one3, (Z)-methyl16-(2-(dimethylamino)-3-(4-methoxy-4-oxobutoxy)propoxy)hexadec-7-enoate, methyl6-(2-(8-(2-(dimethylamino)-3-((6-methoxy-6-oxohexyl)oxy)propoxy)octyl) cyclopropyl)hexanoate, ethyl8-{2-[9-(dimethylamino) heptadecyl]cyclopropyl}octanoate, 2-(Dinonylamino)-1-(5-(N-(2-(dinonylamino)ethyl)-N-nonylglycyl)-2,5-diazabicyclo[2.2.1]heptan-2-yl)ethan-1-one, 1-[(1S,2R)-2-decylcyclopropyl]-N,N-dimethylpentadecan-6-amine, N1,N1,N2-Tri((9Z,12Z)-octadeca-9,12-dien-1-yl)-N2-(2-(piperazin-1-yl)ethyl)ethane-1,2-diamine, ethyl8-{2-[9-(dimethylamino)octadecyl]cyclopropyl}octanoate, 1-[(1R,2S)-2-heptylcyclopropyl]-N,N-dimethyloctadecan-9-amine, (Z)-methyl16-(2-(dimethylamino)-3-((6-methoxy-6-oxohexyl)oxy)propoxy)hexadec-7-enoate, N1,N1,N2-Tri((Z)-octadec-9-en-1-yl)-N2-(2-(piperazin-1-yl)ethyl)ethane-1,2-diamine, N,N-dimethyl-3-{7-[(1S,2R)-2-octylcyclopropyl] heptyl}dodecan-1-amine, methyl8-(2-(dimethylamino)-3-((8-(2-((2-pentylcyclopropyl)methyl)cyclopropyl)octyl) oxy)propoxy)octanoate, ethyl4-{2-[11-(dimethylamino) icosyl]cyclopropyl}butanoate, trans-1-Methyl-3-[((9Z,12Z)-octadeca-9,12-dienyl)oxy]-4-octyloxy-pyrrolidine, methyl(9Z)-19-(dimethylamino)hexacos-9-enoate, methyl (9Z)-19-{1[4-(dimethylamino)butanoyl]oxy}hexacos-9-enoate, (Z)-methyl16-(2-(dimethylamino)-3-(heptyloxy) propoxy)hexadec-7-enoate, (2R)-1-[(9Z,12Z)-octadeca-9,12-dien-1-yloxy]dodecan-2-amine, (13Z,16Z)—N,N-dimethyldocosa-13,16-dien-5-amine, N,N-dimethyl-1-[(1R,2S)-2-undecylcyclopropyl]tetradecan-5-amine, methyl7-(2-(dimethylamino)-3-((8-(2-((2-pentylcyclopropyl)methyl) cyclopropyl)octyl)oxy)propoxy)heptanoate, ethyl8-{2-[7-(dimethylamino)hexadecyl]cyclopropyl}octanoate, 2-(Didodecylamino)-N-dodecyl-N-(2-(piperazin-1-yl)ethyl) acetamide, N,N-dimethyl-1-[(1S,2R)-2-octylcyclopropyl] hexadecan-8-amine, N1-(2-(Piperazin-1-yl)ethyl)-N1,N2,N2-tritetradecylethane-1,2-diamine, methyl6-(2-(dimethylamino)-3-((8-(2-((2-pentylcyclopropyl)methyl) cyclopropyl)octyl)oxy)propoxy)hexanoate, ethyl6-{2-[9-(dimethylamino)pentadecyl]cyclopropyl}hexanoate, N,N-dimethyl-1-[(1S,2S)-2-{[(1R,2R)-2-pentylcyclopropyl] methyl}cyclopropyl]nonadecan-10-amine, NN1,N2-Tridodecyl-N2-(2-(piperazin-1-yl)ethyl)ethane-1,2-diamine, methyl5-(2-(dimethylamino)-3-((8-(2-((2-pentylcyclopropyl)methyl)cyclopropyl)octyl)oxy)propoxy) pentanoate, ethyl6-{2-[9-(dimethylamino)hexadecyl] cyclopropyl}hexanoate, N,N-dimethyl-21-[(1S,2R)-2-octylcyclopropyl]henicosan-10-amine, NNN2-Trinonyl-N2-(2-(piperazin-1-yl)ethyl)ethane-1,2-diamine, methyl4-(2-(dimethylamino)-3-((8-(2-((2-pentylcyclopropyl)methyl) cyclopropyl)octyl)oxy)propoxy)butanoate, ethyl6-{2-[9-(dimethylamino)heptadecyl]cyclopropyl}hexanoate, N,N-dimethyl-1-[(1S,2R)-2-octylcyclopropyl]nonadecan-10-amine, N1,N1,N2-Trihexyl-N2-(2-(piperazin-1-yl)ethyl) ethane-1,2-diamine, methyl8-(2-(dimethylamino)-3-((9Z,12Z)-octadeca-9,12-dien-1-yloxy)propoxy)octanoate, ethyl6-{2-[9-(dimethylamino)octadecyl] cyclopropyl}hexanoate, N1-(2-(4-(2-(Didodecylamino) ethyl)piperazin-1-yl)ethyl)-N1,N2,N2-tri((9Z,12Z)-octadeca-9,12-dien-1-yl)ethane-1,2-diamine, methyl7-(2-(dimethylamino)-3-((9Z,12Z)-octadeca-9,12-dien-1-yloxy) propoxy)heptanoate, ethyl(9Z)-21-(dimethylamino) heptacos-9-enoate, 1-[(1S,2R)-2-hexylcyclopropyl]-N,N-dimethylnonadecan-10-amine, 1-methyl18-[(2Z)-non-2-en-1-yl]9-{[4-(dimethylamino)butanoyl] oxy}octadecanedioate, N1-(2-(4-(2-(Didodecylamino) ethyl)piperazin-1-yl)ethyl)-N1,N2,N2-tri((Z)-octadec-9-en-1-yl)ethane-1,2-diamine, N,N-dimethyl-1-[(1S,2R)-2-octylcyclopropyl]heptadecan-8-amine, methyl6-(2-(dimethylamino)-3-((9Z,12Z)-octadeca-9,12-dien-1-yloxy) propoxy)hexanoate, ethyl(9Z)-21-(dimethylamino)octacos-9-enoate, dimethyl(9Z)-19-{[4-(dimethylamino)butanoyl] oxy}heptacos-9-enedioate, N1-(2-(4-(2-(Ditetradecylamino)ethyl)piperazin-1-yl)ethyl)-N1,N2,N2-tritetradecylethane-1,2-diamine, methyl5-(2-(dimethylamino)-3-((9Z,12Z)-octadeca-9,12-dien-1-yloxy) propoxy)pentanoate, ethyl8-{[4-(dimethylamino)butanoyl] oxy}-15-(2-octylcyclopropyl)pentadecanoate, ethyl(9Z)-21-

(dimethylamino)nonacos-9-enoate, (13Z,16Z)—N,N-dimethyl-3-nonyldocosa-13,16-dien-1-amine, N1-(2-(4-(2-(Didodecylamino)ethyl)piperazin-1-yl)ethyl)-N1,N2,N2-tritetradecylethane-1,2-diamine, methyl9-{1[4-(dimethylamino)butanoyl]oxy}-16-(2-octylcyclopropyl) hexadecanoate, methyl4-(2-(dimethylamino)-3-((9Z,12Z)-octadeca-9,12-dien-1-yloxy)propoxy)butanoate, ethyl(9Z)-21-(dimethylamino)triacont-9-enoate, (12Z,15Z)—N,N-dimethyl-2-nonylhenicosa-12,15-dien-1-amine, methyl8-(2-(dimethylamino)-3-((8-(2-octylcyclopropyl)octyl)oxy) propoxy)octanoate, ethyl(9Z)-19-(dimethylamino)pentacos-9-enoate, ethyl(18Z,21Z)-8-{[4-(dimethylamino)butanoyl] oxy}heptacosa-18,21-dienoate, (16Z)—N,N-dimethylpentacos-16-en-8-amine, methyl(9Z)-19-{[4-(dimethylamino)butanoyl]oxy}heptacos-9-enoate, methyl (9Z)-19-(dimethylamino)heptacos-9-enoate, 2-(Didodecylamino)-1-(4-(2-((2-(didodecylamino)ethyl) (dodecyl)amino)ethyl)piperazin-1-yl)ethan-1-one, (Z)-methyl16-(2-(dimethylamino)-3-(hexyloxy)propoxy)hexadec-7-enoate, (2S)-1-[(9Z,12Z)-octadeca-9,12-dien-1-yloxy]dodecan-2-amine, (16Z,19Z)—N,N-dimethylpentacosa-16,19-dien-8-amine, N1-(2-(4-(2-(Dinonylamino)ethyl)piperazin-1-yl)ethyl)-N1,N2^V2-tritetradecylethane-1,2-diamine, methyl7-(2-(dimethylamino)-3-((8-(2-octylcyclopropyl)octyl)oxy) propoxy)heptanoate, methyl(19Z,22Z)-9-{1[4-(dimethylamino)butanoyl]oxy}octacosa-19,22-dienoate, ethyl(9Z)-19-(dimethylamino)hexacos-9-enoate, (22Z)—N, N-dimethylhentriacont-22-en-10-amine, N1-(2-(4-(2-(Di ((Z)-octadec-9-en-1-yl)amino)ethyl)piperazin-1-yl)ethyl)-!^^-tridodecylethane-1,2-diamine, methyl5-(2-(dimethylamino)-3-((8-(2-octylcyclopropyl)octyl)oxy) propoxy)pentanoate, ethyl(9Z)-19-(dimethylamino) heptacos-9-enoate, (2-butylcyclopropyl)methyl12-{[4-(dimethylamino)butanoyl]oxy}henicosanoate, (20Z)—N,N-dimethylnonacos-20-en-10-amine, N1,N1,N2-Tridodecyl-N2-(2-(4-(2-(dodecyl((9Z,12Z)-octadeca-9,12-dien-1-yl) amino)ethyl)piperazin-1-yl)ethyl)ethane-1,2-diamine, methyl4-(2-(dimethylamino)-3-((8-(2-octylcyclopropyl)octyl)oxy)propoxy)butanoate, ethyl(9Z)-19-(dimethylamino) octacos-9-enoate, (2-octylcyclopropyl)methyl8-{1[4-(dimethylamino)butanoyl]oxy}heptadecanoate, (24Z)—N,N-dimethyltritriacont-24-en-10-amine, N1-(2-(4-(2-(Ditetradecylamino)ethyl)piperazin-1-yl)ethyl)-N1,N2,N2-tridodecylethane-1,2-diamine, ethyl(5Z)-17-(dimethylamino)hexacos-5-enoate, (Z)-methyl8-(2-(dimethylamino)-3-(octadec-9-en-1-yloxy)propoxy) octanoate, (2Z)-hept-2-en-1-yl12-{[4-(dimethylamino) butanoyl]oxy}henicosanoate, (17Z)—N,N-dimethylnonacos-17-en-10-amine, N1-(2-(4-(2-(Di((Z)-dodec-6-en-1-yl)amino)ethyl)piperazin-1-yl)ethyl)-N1,N2, N2-tridodecylethane-1,2,-diamine, ethyl(9Z)-17-(dimethylamino)hexacos-9-enoate, (Z)-methyl7-(2-(dimethylamino)-3-(octadec-9-en-1-yloxy)propoxy) heptanoate, (2Z)-undec-2-en-1-yl8-{[4-(dimethylamino) butanoyl]oxy}heptadecanoate, (14Z)—N,N-dimethylnonacos-14-en-10-amine, ethyl(7Z)-17-(dimethylamino)tricos-7-enoate, (Z)-N1-(2-(4-(2-(Dodec-6-en-1-yl(dodecyl)amino)ethyl)piperazin-N!^^-tridodecylethane-1,2-diamine, (Z)-methyl5-(2-(dimethylamino)-3-(octadec-9-en-1-yloxy)propoxy) pentanoate, (2-hexylcyclopropyl)methyl10-{[4-(dimethylamino)butanoyl]oxy}nonadecanoate, (15Z)—N, N-dimethylheptacos-15-en-10-amine, ethyl(7Z)-17-(dimethylamino)tetracos-7-enoate, (Z)-methyl4-(2-(dimethylamino)-3-(octadec-9-en-1-yloxy)propoxy) butanoate, (2Z)-non-2-en-1-yl10-{[4-(dimethylamino) butanoyl]oxy}nonadecanoate, (20Z)—N,N-dimethylheptacos-20-en-10-amine, N1-(2-(4-(2-(Dioctylamino)ethyl)piperazin-1-yl)ethyl)-N1,N2^V2-tridodecylethane-1,2-diamine, methyl6-(2-(dimethylamino)-3-((8-(2-octylcyclopropyl)octyl)oxy) propoxy)hexanoate, ethyl6-[2-(9-{[4-(dimethylamino) butanoyl]oxy}octadecyl)cyclopropyl]hexanoate, ethyl(7Z)-17-(dimethylamino)pentacos-7-enoate, 1-[(11Z,14Z)-1-nonylicosa-11,14-dien-1-yl]pyrrolidine, ethyl(7Z)-17-(dimethylamino)hexacos-7-enoate, (20Z,23Z)—N-ethyl-N-methylnonacosa-20,23-dien-10-amine, N,N-dimethylheptacosan-10-amine, methyl6-{2-[11-(dimethylamino)icosyl]cyclopropyl}hexanoate, methyl6-[2-(11-{[4-(dimethylamino)butanoyl]oxy}icosyl)cyclopropyl] hexanoate, (2-octylcyclopropyl)methyl6-(3-(decyloxy)-2-(dimethylamino)propoxy)hexanoate, methyl8-{2-[9-(dimethylamino)octadecyl]cyclopropyl}octanoate, methyl8-[2-(9-{[4-(dimethylamino)butanoyl] oxy}octadecyl)cyclopropyl]octanoate, methyl7-(2-(8-(2-(dimethylamino)-3-(octyloxy)propoxy)octyl)cyclopropyl) heptanoate, Heptadecan-9-yl8-((2-hydroxyethyl) (tetradecyl)amino)octanoateRepresentative, 2-((2-(Didodecylamino)ethyl)(dodecyl)amino)-1-(4-(2-(didodecylamino)ethyl)piperazin-1-yl)ethan-1-one, (2S)-1-[(9Z,12Z)-octadeca-9,12-dien-1-yloxy]undecan-2-amine, (17Z,20Z)—N,N-dimemylhexacosa-17,20-dien-9-amine, (18Z)-heptacos-18-en-10-yl4-(dimethylamino)butanoate, (2S)-1-({6-[3B))-cholest-5-en-3-yloxy]hexyl}oxy)-N,N-dimethyl-3-[(9Z)-octadec-9-en-1-yloxy]propan-2-amine, methyl10-{2-[7-(dimethylamino)hexadecyl] cyclopropyl}decanoate, methyl10-[2-(7-{[4-(dimethylamino)butanoyl]oxy}hexadecyl)cyclopropyl]decanoate, (2S)—N,N-dimethyl-1-({8-[(1R,2R)-2-{[(S,2S)-2-pentylcyclopropyl]methyl}cyclopropyl]octyl}oxy)tridecan-2-amine, (2-octylcyclopropyl)methyl6-(2-(dimethylamino)-3-(nonyloxy)propoxy)hexanoate, (19Z,22Z)—N,N-dimethyloctacosa-19,22-dien-7-amine, 4-((N-(2-(Dinonylamino)ethyl)-N-nonylglycyl)oxy)pentan-2-yldinonylglycinate, 3-Hydroxybutan-2-ylN-(2-(dinonylamino)ethyl)-N-nonyl, Di(heptadecan-9-yl)8,8'-(26,28-dimethyl-11,24,30,43-tetraoxo-10,25,29,44-tetraoxa-19,35-diazatripentacontane-19,35-diyl) dioctanoate, Di(heptadecan-9-yl)8,8'-(26,27-dimethyl-11, 24,29,42-tetraoxo-10,25,28,43-tetraoxa-19,34-diazadopentacontane-19,34-diyl)dioctanoate, Di(heptadecan-9-yl)8,8'-(11,24,29,42-tetraoxo-10,25,28,43-tetraoxa-19,34-diazadopentacontane-19,34-diyl)dioctanoate, Di(heptadecan-9-yl)8,8'-((piperazine-1,4-diylbis(5-oxopentane-5,1-diyl))bis((8-(nonyloxy)-8-oxooctyl)azanediyl)) dioctanoate, Di(heptadecan-9-yl)15,18-dimethyl-9,24-bis (8-(nonyloxy)-8-oxooctyl)-14,19-dioxo-9,15,18,24-tetraazadotriacontanedioate, Di(heptadecan-9-yl)15,19-dimethyl-9,25-bis(8-(nonyloxy)-8-oxooctyl)-14,20-dioxo-9,15,19,25-tetraazatritriacontanedioate, Di(heptadecan-9-yl)15,18-diethyl-9,24-bis(8-(nonyloxy)-8-oxooctyl)-14,19-dioxo-9,15,18,24-tetraazadotriacontanedioate, N,N-dimethyl-3-{[(9Z,12Z)-octadeca-9,12-dien-1-yloxy] methyl}dodecan-1-amine, methyl8-[2-(11-{[4-(dimethylamino)butanoyl]oxy}octadecyl)cyclopropyl] octanoate, methyl8-{2-[11-(dimethylamino)heptadecyl] cyclopropyl}octanoate (Compound 18), Heptadecan-9-yl8-((2-hydroxyethyl)(8-(nonyloxy)-8-oxooctyl)amino) octanoate, (2-octylcyclopropyl)methyl6-(2-(dimethylamino)-3-(heptyloxy)propoxy)hexanoate, (17Z)—N,N-dimethylhexacos-17-en-9-amine, N1-(2-(4-(2-(Didodecylamino)ethyl)piperazin-1-yl)ethyl)-N1^V2,N2-trihexylethane-1,2-diamine, N,N-dimethyl-2-{[(9Z,12Z)- octadeca-9,12-dien-1-yloxy]methyl}undecan-1-amine, methyl8-{2-[11-(dimethylamino)octadecyl]cyclopropyl}octanoate, (2-octylcyclopropyl)methyl6-(2-(dimethylamino)-3-(hexyloxy)propoxy)hexanoate, (18Z)—N,N-dimethylheptacos-18-en-10-amine, 2-((2-(Dinonylamino)ethyl)(nonyl)amino)ethyltetradecanoate, 2-((2-(Dinonylamino)ethyl)(nonyl)amino)ethylnonanoate, Tetradecy1N-(2-(dinonylamino)ethyl)-N-nonylglycinate, NonylN-(2-(dinonylamino)ethyl)-N-nonylglycinate, 4-(2-((2-(dinonylamino)ethyl)(nonyl)amino)acetamido)butyl-pentanoate, 1,1'-(Piperazine-1,4-diyl)bis(5-(didecylamino)pentan-1-one, 2-((2-(dinonylamino)ethyl)(nonyl)armno)-N-tetradecylacetamide, N-decyl-2-((2-(dinonylamino)ethyl)(nonyl)amino), N1-(3-(3-(dinonylamino)propoxy)propyl)-N1,N2,N2-trinonylethane-1,2-diamine, N1-(2-(dinonylamino)ethyl)-NN8,N8-trinonyloctane-1,8-diamine, methyl8-[2-(11-{1[4-(dimethylamino)butanoyl]oxy}nonadecyl)cyclopropyl]octanoate, methyl8-{2-[11-(dimethylamino)nonadecyl]cyclopropyl}octanoate, (Z)-undec-2-en-1-yl6-(3-(decyloxy)-2-(dimethylamino)propoxy)hexanoate, (2R,12Z,15Z)—N,N-dimethyl-1-(undecyloxy)henicosa-12,15-dien-2-amine, (21Z,24Z)—N,N-dimethyltriaconta-21,24-dien-9-amine, 2-(dinonylamino)-N-(4-(2-((2-(dinonylamino)ethyl)(nonyl)amino)-N-methylacetamido)butyl)-N-methylacetamide, 7,10-dimethyl-13,16-dinonyl-6,11-dioxo-4-tetradecyl-4,7,10,13,16-pentaazapentacosyldecanoate, 2-(dinonylamino)-N-(2-(2-((2-(dinonylamino)ethyl)(nonyl)amino)-N-ethylacetamido)ethyl)-N-ethylacetamide, 2-(dinonylamino)-N-(3-(2-((2-(dinonylamino)ethyl)(nonyl)amino)-N-methylacetamido)propyl)-N-methylacetamide, 2-((2-(di((Z)-non-3-en-1-yl)amino)ethyl)((Z)-non-3-en-1-yl)amino)-N-(2-(2-(dinonylamino)-N-methylacetamido)ethyl)-N-methylacetamide, 2-(dinonylamino)-N-(2-(2-((2-(dinonylamino)ethyl)(nonyl)amino)acetamido)ethyl)acetamide, Pentyl8,11-dimethyl-5,14,17-trinonyl-7,12-dioxo-5,8,11,14,17-pentaazahexacosanoate2-((2-(Dinonylamino)ethyl)(nonyl)amino)-N-methyl-N-(2-(methylandno)ethyl)acetami, 2-(Dinonylamino)-N-(2-(2-((2-(dinonylamino)ethyl)(nonyl)amino)-N-methylacetamido)ethyl)-N-methylacetamide2-(Dinonylamino)-N-methyl-N-(2-(methylamino)ethyl)acetamide, 2-((N-(2-(Dinonylamino)ethyl)-N-nonylglycyl)oxy)ethyldinonylglycinate2-Hydroxyethyldinonylglycinate, methyl8-[2-(11-{1[4-(dimethylamino)butanoyl]oxy}icosyl)cyclopropyl]octanoate, methyl8-{2-[11-(dimethylamino)icosyl]cyclopropyl}octanoate, (Z)-undec-2-en-1-yl6-(2-(dimethylamino)-3-(nonyloxy)propoxy)hexanoate, (2R,12Z,15Z)-1-(hexadecyloxy)-N,N-dimethylhenicosa-12,15-dien-2-amine, (22Z,25Z)—N,N-dimethylhentriaconta-22,25-dien-10-amine, 1,1-(Piperazine-1,4-diyl)bis(4-(didecylamino)butan-1-one)fert-Butyl4-(didecylaminobutanoate, Heptyl5-(4-(N-(2-(dinonylamino)ethyl)-N-nonylglycyl)piperazin-1-yl)-5-oxopentanoate5-(Heptloxy)-5-oxopentanoicacid, Heptyl5-(4-(N-(2-(dinonylamino)ethyl)-N-nonylglycyl)piperazin-1-yl)-5-oxopentanoate5-(Heptloxy)-5-oxopentanoic, (Z)-4-((2-(4-(N-(2-(dinonylamino)ethyl)-N-nonylglycyl)piperazin-1-yl)-2-oxoethyl)(tetradecyl)amino)but-2-en-1-ylnonanoate(Z)-4-Hydroxybut-2-en-1-ylnonanoate, (Z)-3-((2-(4-(N-(2-(Dinonylamino)ethyl)-N-nonylglycyl)piperazin-1-yl)-2-oxoethyl)(tetradec-9-en-1-yl)amino)propyldecanoate(Z)-Tetradec-9-en-1-ylmethanesulfonate, methyl8-[2-(9-{1[4-(dimethylamino)butanoyl]oxy}pentadecyl)cyclopropyl]octanoate, methyl8-{2-[9-(dimethylamino)pentadecyl]cyclopropyl}octanoate, (Z)-undec-2-en-1-yl6-(2-(dimethylamino)-3-(heptyloxy)propoxy)hexanoate, (2R,12Z,15Z)-1-(hexyloxy)-N,N-dimethylhenicosa-12,15-dien-2-amine, (16Z,19Z)—N,N-dimethylpentacosa-16,19-dien-6-amine, Methyl8-((2-(4-(N-(2-(Di((Z)-non-3-en-1-yl)amino)ethyl)-N—((Z)-non-3-en-1-yl)glycyl)piperazin-1-yl)-2-oxoethyl)(nonyl)amino)octanoatefert-Butyl4-(nonylglycyl)piperazine-1-carboxylate, 3-((2-(4-(N-(2-(Dinonylamino)ethyl)-N-nonylglycyl)piperazin-1-yl)-2-oxoethyl)(tetradecyl)amino)propyl(Z)-dec-3-enoate(Z)-Dec-3-en-1-ol, 2-((2-(Di((Z)-non-3-en-1-yl)amino)ethyl)((Z)-non-3-en-1-yl)amino)-1-(4-(dinonylglycyl)piperazin-1-yl)ethan-1-one(Z)-1-Bromonon-4-ene, 3-((2-(4-(N-(2-(Dinonylamino)ethyl)-N-nonylglycyl)piperazin-oxoethyl)(dodecyl)amino)propyloctanoatetot-Butyldodecylglycinate, S-Pentyl4-((2-(4-(N-(2-(dinonylamino)ethyl)-N-nonylglycyl)piperazin-1-yl)-2-oxoethyl)(nonyl)amino)butanethioate, 3-((2-(1-(N-(2-(Dinonylamino)ethyl)-N-nonylglycyl)piperidin-ˆyl)ethyl)(nonyl)amino)propyl3-methylhexanoatefert-Butyl4-(2-((3-((3-methylhexanoyl)oxy)propyl)(nonyl)amino)ethyl)piperidine-1-, 3-((2-(1-(N-(2-(Dinonylamino)ethyl)-N-nonylglycyl)piperidin-4-yl)ethyl)(nonyl)amino)-2-methylpropylhexanoate, 3-((2-(4-(N-(2-(Dinonylamino)ethyl)-N-nonylglycyl)piperazin-oxoethyl)(nonyl)amino)propyl3-methylhexanoate, 3-((2-(4-(N-(2-(Dinonylamino)ethyl)-N-nonylglycyl)piperazin-oxoethyl)(nonyl)amino)-2-methylpropylhexanoate, methyl8-[2-(9-{1[4-(dimethylamino)butanoyl]oxy}hexadecyl)cyclopropyl]octanoate, methyl8-{2-[9-(dimethylamino)hexadecyl]cyclopropyl}octanoate, (Z)-undec-2-en-1-yl6-(2-(dimethylamino)-3-(hexyloxy)propoxy)hexanoate, (2R,12Z,15Z)-1-(decyloxy)-N,N-dimethylhenicosa-12,15-dien-2-amine, (17Z,20Z)—N,N-dimethylhexacosa-17,20-dien-7-amine, 2-((2-(Dinonylamino)ethyl)(nonyl)amino)ethyll-(dinonylglycyl)piperidine-4-carboxylate, 1-(2-(Dinonylamino)ethyl)4-(2-((2-(dinonylamino)ethyl)(nonyl)amino)ethyl)cyclohexane-1,4-dicarboxylate2-(Dinonylamino)ethan-1-ol, Methyl12-((2-(1-(N-(2-(dinonylamino)ethyl)-N-nonylglycyl)pyrrolidin-3-yl)ethyl)(tetradecyl)amino)dodecanoatefert-Butyl3-(2-((12-methoxy-12-oxododecyl)(tetradecyl)amino)ethyl)pyrrolidine-1-carboxylate, 3-((2-(1-(N-(2-(Dinonylamino)ethyl)-N-nonylglycyl)pyrrolidin-3-yl)ethyl)(tetradecyl)amino)propyldecanoateter/-Butyl3-(2-((3-(decanoyloxy)propyl)(tetradecyl)amino)ethyl)pyrrolidine-1-carboxylate, "Heptyl6-((2-(1-(N-(2-(dinonylamino)ethyl)-N-nonylglycyl)pyrrolidin-3-yl)ethyl)(tetradecyl)amino)hexanoatetot-Butyl3-(2-((6-(heptyloxy)-6-oxohexyl)(tetradecyl)amino)ethyl)pyrrolidine-1-carboxylate,", Pentyl8-((2-(1-(N-(2-(dinonylamino)ethyl)-N-nonylglycyl)pyrrolidin-3-yl)ethyl)(tetradecyl)amino)octanoate/er/-Butyl3-(2-(tetradecylamino)ethyl)pyrrolidine-1-carboxylate, Methyl12-((2-(1-(N-(2-(dinonylamino)ethyl)-N-nonylglycyl)piperidin-3-yl)ethyl)(tetradecyl)amino)dodecanoate-Butyl3-(2-((12-methoxy-12-oxododecyl)(tetradecyl)amino)ethyl)piperidine-1-carboxylate, 3-((2-(1-(N-(2-(Dinonylamino)ethyl)-N-nonylglycyl)piperidin-3-yl)ethyl)(tetradecyl)amino)propyldecanoate, Heptyl6-((2-(1-(N-(2-(dinonylamino)ethyl)-N-nonylglycyl)piperidin-3-yl)ethyl)(tetradecyl)amino)hexanoate, Pentyl8-((2-(1-(N-(2-(dinonylamino)ethyl)-N-nonylglycyl)piperidin-3-yl)ethyl)(tetradecyl)amino)octanoate, Pentyl6-((2-(4-(2-((2-(didodecylamino)ethyl)(dodecyl)amino)ethyl)piperazin-1-yl)ethyl)(dodecyl)amino)hexanoateStep1:Pentyl6-bromohexanoate, methyl8-[2-(9-{[4-(dimethylamino)butanoyl]oxy}heptadecyl)cyclopropyl]octanoate, methyl8-{2-[9-(dimethylamino)heptadecyl]cyclopropyl}octanoate, (2S,12Z,15Z)—N,N-dimethyl-1-(octyloxy)henicosa-12,15-dien-2-amine, (2-octylcyclopropyl)methyl6-(2-(dimethylamino)-3-(octyloxy)propoxy)hexanoate, (18Z,21Z)—N,N-dimethylheptacosa-18,21-dien-8-amine, trans-1-methyl-3,4-bis(((Z)-hexadec-9-enoyloxy)methyl)pyrrolidine, (Z)-Non-2-en-1-yl4-((2-(4-(N-(2-(dinonylamino)ethyl)-N-nonylglycyl)piperazin-1-yl)-2-oxoethyl)(tetradecyl)amino) butanoate, trans-1-methyl-3,4-bis(((9Z,12Z)-octadeca-9,12-dienoyloxy)methyl)pyrrolidine, Methyl12-((2-(4-(N-(2-(dinonylamino)ethyl)-N-nonylglycyl)piperazin-1-yl)-2-oxoethyl)(tetradecyl)amino)dodecanoate, ethyl(7Z)-17-[2-(dimethylamino)ethyl]hexacos-7-enoate, trans-1-methyl-3, 4-bis(((Z)-octadeca-9-enoyloxy)methyl)pyrrolidine, methyl6-(2-{]11-^2-(dimethylamino)ethyl] icosyl}cyclopropyl)hexanoate, Methyl12-((2-(1-(N-(2-(di-nonylamino)ethyl)-N-nonylglycyl)piperidin-4-yl)ethyl)(tetradecyl)amino)dodecanoate, methyl10-(2-V-^2-ethylamino) ethyl]hexadecyl}cyclopropyl)decanoate, methyl8-(2-{111-; 2-(dimethylamino)ethyl]heptadecyl}cyclopropyl)octanoate, 2-(1-(N-(2-(Dinonylamino)ethyl)-N-nonylglycyl)piperidin-4-yl)ethyldinonylglycinatefert-Butyl4-(2-((dinonylglycyl) oxy)ethyl)piperidine-1-carboxylate, methyl8-(2-{1L1-;2-(dimethylamino)ethyl]octadecyl}cyclopropyl)octanoate, methyl8-(2-{ ]11-^2-(dimethylamino)ethyl] nonadecyl}cyclopropyl)octanoate, 1,-(piperazine-1,4-diyl) bis(2-(dinonylamino)ethan-1-one), methyl8-[2-{]11-^2-(dimethylamino)ethyl]icosyl}cyclopropyl)octanoate, methyl8-(2-{9-[2-(dimethylamino)ethyl]pentadecyl}cyclopropyl) octanoate, methyl(7Z)-19-{[4-(dimethylamino)butanoyl] oxy}octacos-7-enoate, methyl(7Z)-19-(dimethylamino) octacos-7-enoate, cis-1-methyl-3-[(9Z,12Z)-octadeca-9,12-dien-1-yloxy]-4-(octyloxy)pyrrolidine, 2-(Didodecylamino)-1-(4-(N-(2-(didodecylamino)ethyl)-N-dodecylglycyl)piperazin-1-yl)ethan-1-one, (Z)-undec-2-en-1-yl6-(2-(dimethylamino)-3-(octyloxy)propoxy)hexanoate, (2SN,N-dimethyl-1-[(9Z,12Z)-octadeca-9,12-dien-1-yloxy] decan-2-amine(Compound11), (19Z,22Z)—N,N-dimeihy-loctacosa-19,22-dien-9-amine, methyl8-(2-{9-[2-(dimethyl-amino)ethyl]hexadecyl}cyclopropyl)octanoate, 5-((2-(4-(N-(2-(Dinonylamino)ethyl)-N-nonylglycyl)piperazin-oxoethyl)(nonyl)amino)pentylmethylcarbonate, methyl8-(2-{9-[2-(dimethylamino)ethyl]heptadecyl}cyclopropyl) octanoate, methyl(7Z)-19-[2-(dimethylamino)ethyl] octacos-7-enoate, (Z)-Pent-2-en-1-yl4-((2-(4-(N-(2-(dinonylamino)ethyl)-N-nonylglycyl)piperazin-1-yl)-2-oxoethyl)(nonyl)amino)butanoate, methyl(11Z)-19-[2-(dimethylamino)ethyl]octacos-11-enoate, methyl(9Z)-21-[2-(dimethylamino)ethyl]heptacos-9-enoate, methyl(9Z)-21-[2-(dimethylamino)ethyl]octacos-9-enoate, methyl(9Z)-21-[2-(dimethylamino)ethyl]nonacos-9-enoate, 2-(1-(N-(2-(Dinonylamino)ethyl)-N-nonylglycyl)pyrrolidin-3-yl) ethyldinonylglycinate, methyl(9Z)-21-[2-(dimethylamino) ethyl]triacont-9-enoate, (1-(N-(2-(Dinonylamino)ethyl)-N-nonylglycyl)pyrrolidin-3-yl)methyldinonylglycinate, methyl(9Z)-19-[2-(dimethylamino)ethyl]pentacos-9-enoate, methyl(9Z)-19-[2-(dimethylamino)ethyl]hexacos-9-enoate, methyl6-(2-(8-(3-(decyloxy)-2-(dimethylamino)propoxy) octyl)cyclopropyl)hexanoate, methyl(11Z)-19-{[4-(dimethylamino)butanoyl]oxy}octacos-ll-enoate, methyl(11Z)-19-(dimethylamino)octacos-11-enoate, (2S)—N,N-dimethyl-1-[(9Z,12Z)-octadeca-9,12-dien-1-yloxy]dodecan-2-amine, (14Z,17Z)—N,N-dimethyltricosa-14,17-dien-4-amine, Methyldi((9Z,12Z)-octadeca-9,12-dienyl)amine, methyl (9Z)-19-{1[4-(dimethylamino)butanoyl]oxy}octacos-9-enoate, methyl(9Z)-19-(dimethylamino)octacos-9-enoate, (Z)-methyl17-(2-(dimethylamino)-3-(octyloxy)propoxy) heptadec-8-enoate, (3R,4R)-3,4-bis((Z)-hexadec-9-enyloxy)-1-methylpyrrolidine, (2S)—N,N-dimethyl-1-[(9Z,12Z)-octadeca-9,12-dien-1-yloxy]undecan-2-amine, (20Z,23Z)-nonacosa-20,23-dien-10-yl4-(dimethylamino) butanoate, (20Z,23Z)—N,N-dimethylnonacosa-20,23-dien-10-amine, 3-((6Z,9Z,28Z,31Z)-heptatriaconta-6,9,28,31-tetraen-19-yloxy)-N,N-dimethylpropan-1-amine, 3-((6Z,9Z,28Z,31Z)-heptatriaconta-6,9,28,31-tetraen-19-yloxy)-N,N-dimethylpropan-1-amine, (6Z,9Z,28Z,31Z)-heptatriaconta-6,9,28,31-tetraen-19-yl4-(dimethylamino)butanoate), (6Z,16Z)-12-((Z)-dec-4-enyl)docosa-6,16-dien-11-yl5-(dimethylamino)pentanoate, (6Z,16Z)-12-((Z)-dec-4-enyl) docosa-6,16-dien-11-yl5-(dimethylamino)pentanoat, (6Z,16Z)-12-((Z)-dec-4-enyl)docosa-6,16-dien-11-yl5-(dimethylamino)pentanoate, L-arginine-alpha-(2,3-dilauryloxy)propylamide, L-lysine-alpha-(2,3-dilauryloxy) propylamide, 2,3-dioleyloxypropylamine, 2,3-distearyloxypropylamine, 2,3-dilauryloxypropylamine, dilinoleylmethyl4-(dimethylamino)propylether), dilinoleylmethyl4-(dimethylamino)butylether), and 2,2-dilinoleyl-4-(2-dimethylaminoethyl)-[1,3]-dioxolane.

In some embodiments, the at least one non-cationic lipid comprises at least one phospholipid, at least one fusogenic lipid, at least one anionic lipid, at least one helper lipid, at least one neutral lipid, or any combination thereof. In some embodiments, the LNP may be essentially devoid of the at least one non-cationic lipid. In some embodiments, the LNP may contain no amount of the at least one non-cationic lipid.

In some embodiments, at least one non-cationic lipid may be selected from, but is not limited to, at least one of 1,2-di-O-octadecenyl-sn-glycero-3-phosphocholine (18:0 Diether PC), DSPC but with 3 unsaturated double bonds pertail (18:3 PC), Acylcarnosine (AC), 1-hexadecyl-sn-glycero-3-phosphocholine (C16 Lyso PC), N-oleoyl-SPM (C18:1), N-lignocerylSPM (C24:0), N-nervacylC (C24:1), carbamoyl]cholesterol (Cet-P), cholesterolhemisuccinate (CHEMS), cholesterol (Chol), Cholesterolhemidodecanedicarboxylic acid (Chol-C12), 12-Cholesteryloxycarbonylaminododecanoic acid (Chol-C13N), Cholesterolhemioxalate (Chol-C2), Cholesterolhemimalonate (Chol-C3), N-(Cholesteryl-oxycarbonyl)glycine (Chol-C3N), Cholesterolhemiglutarate (Chol-C5), Cholesterolhemiadipate (Chol-C6), Cholesterolhemipimelate (Chol-C7), Cholesterolhemisuberate (Chol-C8), Cardiolipid (CL), 1,2-bis(tricosa-10,12-diynoyl)-sn-glycero-3-phosphocholine (DC8-9PC), dicetylphosphate (DCP), dihexadecylphosphate (DCP1), 1,2-Dipalmitoyglycerol-3-hemisuccinate (DGSucc), short-chainbis-n-heptadecanoylphosphatidylcholine (DHPC), dihexadecoylphosphoethanolamine (DHPE), 1,2-dilinoleoyl-sn-glycero-3-phosphocholine (DLPC), 1,2-dilauroyl-sn-glycero-3-PE (DLPE), Dimyristoylglycerolhemisuccinate (DMGS), dimyristoylphosphatidylcholine (DMPC), dimyristoylphosphoethanolamine (DMPE), dimyristoylphosphatidylglycerol (DMPG), dioleyloxybenzylalcohol (DOBA), 1,2-dioleoylglyceryl-3-hemisuccinate (DOGHEMS), N-[2-(2-{2-[2-(2,3-Bis-octadec-9-enyloxy-propoxy)-ethoxy]-ethoxy}-ethoxy)-ethyl]-3-(3,4,5-lrihydroxy-6-hydroxymethyl-1etrahydro-pyran-2-ylsulfanyl)-propionamide (DOGP4uMan), dioleoylphosphatidylcholine (DOPC), dioleoylphosphatidylethanolamine (DOPE), dioleoyl-phosphatidylethanolamine4-(N-maleimidomethyl)-cyclohexane-1-carboxylate (DOPE-mal), dioleoylphosphatidylglycerol (DOPG), 1,2-dioleoyl-sn-glycero-3-(phospho-L-serine) (DOPS), a cell-fusogenic phospholipid (DPhPE), dipalmitoylphosphatidylcholine (DPPC), dipalmitoylphosphatidylethanolamine (DPPE), dipalmitoylphosphatidylglycerol (DPPG), dipalmitoylphosphatidylserine (DPPS), distearoylphosphatidylcholine (DSPC), distearoyl-phosphatidyl-ethanolamine (DSPE), distearoylphosphoethanolamineimidazole (DS- PEI), 1,2-diundecanoyl-sn-glycero-phosphocholine (DUPC), eggphosphatidylcholine (EPC), N-histidinylcholesterolcarbamate (HCChol), histaminedistearoylglycerol (HDSG), N-histidinylcholesterolhemisuccinate (HistChol), 1,2-Dipalmitoylglycerol-hemisuccinate-Nα-Histidinyl-Hemisuccinate (HistSuccDG), N-(5'-hydroxy-3'-oxypentyl)-10-12-pentacosadiynamide (h-Pegi-PCDA), 2-[1-hexyloxyethyl]-2-devinylpyropheophorbide-a (HPPH), hydrogenatedsoybeanphosphatidylcholine (HSPC), 1,2-Dipalmitoylglycerol-Oα-histidinyl-Nα-hemisuccinate (IsohistsuccDG), mannosialized dipalmitoylphosphatidylethanolamine (ManDOG), 1,2-Dioleoyl-sn-Glycero-3-Phosphoethanolamine-N-[4-(p-maleimidomethyl) cyclohexane-carboxamide](MCC-PE), 1,2-diphytanoyl-sn-glycero-3-phosphoethanolamine (ME 16.0 PE), 1-myristoyl-2-hydroxy-sn-glycero-phosphocholine (MHPC), a thiol-reactive maleimide head group lipid, e.g., 1,2-dioleoyl-sn-glycero-3-phosphoethanolamine-N-[4-(p-maleimidophenyl)but-yramid (MPB-PE), Nervonic Acid (NA), sodiumcholate (NaChol), 1,2-dioleoyl-sn-glycero-3-[phosphoethanolamine-N-dodecanoyl (NC12-DOPE), defined by synthesis example in WO2008042973A2 (ND98), "N-glutarylphosphatidylethanolamine(s) of Formula 1" (NG-PE), N-hydroxysulfosuccinimide (NHS-'x'), "N-(co)-dicarboxylicacid-derivatized phosphatidylethanolamines encompassed by Formula 1" (N(OPE-'x'), OleicAcid (OA), 1-oleoyl-2-cholesterylhemisuccinoyl-sn-glycero-3-phosphocholine (OChemsPC), phosphatidicacid (PA), phosphatidylethanolamine lipid (PE), PE lipid conjugated with polyethyleneglycol (PEG). One example of PEG-PE can be polyethyleneglycol-distearoylphosphatidylethanolamine lipid (PEG-PE), phosphatidylglycerol (PG), partially hydrogenated soy phosphatidylchloline (PHSPC), phosphatidylinositol lipid (PI), phosphotidylinositol-4-phosphate (PIP), palmitoyloleoylphosphatidylcholine (POPC), phosphatidylethanolamine (POPE), palmitoyloleyolphosphatidylglycerol (POPG), phosphatidylserine (PS), lissaminerhodamineB-phosphatidylethanolamine lipid (Rh-PE), purifiedsoy-derived mixture of phospholipids (SIOO), phosphatidylcholine (SM), 18-1-transPE,1-stearoyl-2-oleoyl-phosphatidyethanolamine (SOPE), soybeanphosphatidylcholine (SPC), sphingomyelins (SPM), alpha.alpha'-trehalose6,6'-dibehenate (TDB), 1,2-dielaidoyl-sn-glycero-3-phophoethanolamine (transDOPE), ((23S,5R)-3-(bis (hexadecyloxy)methoxy)-5-(5-methyl-2,4-dioxo-3,4-dihydropyrimidin-1(2H)-yl)tetrahydrofuran-2-yl) methylmethylphosphate, 1,2-diarachidonoyl-sn-glycero-3-phosphocholine, 1,2-diarachidonoyl-sn-glycero-3-phosphoethanolamine, 1,2-didocosahexaenoyl-sn-glycero-3-phosphocholine, 1,2-didocosahexaenoyl-sn-glycero-3-phosphoethanolamine, 1,2-dilinolenoyl-sn-glycero-3-phosphocholine, 1,2-dilinolenoyl-sn-glycero-3-phosphoethanolamine, 1,2-dilinoleoyl-sn-glycero-3-phosphoethanolamine, 1,2-dioleyl-sn-glycero-3-phosphoethanolamine, 1,2-distearoyl-sn-glycero-3-phosphoethanolamine, 16-O-monomethyl PE, 16-O-dimethyl PE, and dioleylphosphatidylethanolamine.

In some embodiments, the LNP comprises an ionizable lipid or lipid-like material. As a non-limiting example, the ionizable lipid may be C12-200, CKK-E12, 5A2-SC8, BAMEA-016B, or 7C1. Other ionizable lipids are known in the art and are useful herein.

In some embodiments, the LNP comprises a phospholipid. As a non-limiting example, the phospholipid (helper) may be DOPE, DSPC, DOTAP, or DOTMA.

In some embodiments, the LNP comprises a PEG derivative. As a non-limiting example, the PEG derivative may be a lipid-anchored such as PEG is C14-PEG2000, C14-PEG1000, C14-PEG3000, C14-PEG5000, C12-PEG1000, C12-PEG2000, C12-PEG3000, C12-PEG5000, C16-PEG1000, C16-PEG2000, C16-PEG3000, C16-PEG5000, C18-PEG1000, C18-PEG2000, C18-PEG3000, or C18-PEG5000.

In some embodiments, the at least one sterol comprises at least one cholesterol or cholesterol derivative. In some embodiments, the LNP may be essentially devoid of an at least one sterol. In some embodiments, the LNP may contain no amount of the at least one sterol.

In some embodiments, the at least one particle-activity-modifying-agent comprises at least one component that reduced aggregation of particles, at least one component that decreases clearing of the LNP from circulation in a subject, at least component that increases the LNP's ability to traverse mucus layers, at least one component that decreases a subjects immune response to administration of the LNP, at least one component that modifies membrane fluidity of the LNP, at least one component that contributes to the stability of the LNP, or any combination thereof. In some embodiments, the LNP may be essentially devoid of the at least one particle-activity-modifying-agent. In some embodiments, the LNP may contain no amount of the at least one particle-activity-modifying-agent.

In some embodiments, the particle-activity-modifying-agent may be comprised of a polymer. In some embodiments, the polymer comprising the particle-activity-modifying-agent may be comprised of at least one polyethylene glycol (PEG), at least one polypropylene glycol (PPG), poly(2-oxazoline) (POZ), at least one polyamide (ATTA), at least one cationic polymer, or any combination thereof.

In some embodiments, the average molecular weight of the polymer moiety (e.g., PEG) may be between 500 and 20,000 daltons. In some embodiments, the molecular weight of the polymer may be about 500 to 20,000, 1,000 to 20,000, 1,500 to 20,000, 2,000 to 20,000, 2,500 to 20,000, 3,000 to 20,000, 3,500 to 20,000, 4,000 to 20,000, 4,500 to 20,000, 5,000 to 20,000, 5,500 to 20,000, 6,000 to 20,000, 6,500 to 20,000, 7,000 to 20,000, 7,500 to 20,000, 8,000 to 20,000, 8,500 to 20,000, 9,000 to 20,000, 9,500 to 20,000, 10,000 to 20,000, 10,500 to 20,000, 11,000 to 20,000, 11,500 to 20,000, 12,000 to 20,000, 12,500 to 20,000, 13,000 to 20,000, 13,500 to 20,000, 14,000 to 20,000, 14,500 to 20,000, 15,000 to 20,000, 15,500 to 20,000, 16,000 to 20,000, 16,500 to 20,000, 17,000 to 20,000, 17,500 to 20,000, 18,000 to 20,000, 18,500 to 20,000, 19,000 to 20,000, 19,500 to 20,000, 500 to 19,500, 1,000 to 19,500, 1,500 to 19,500, 2,000 to 19,500, 2,500 to 19,500, 3,000 to 19,500, 3,500 to 19,500, 4,000 to 19,500, 4,500 to 19,500, 5,000 to 19,500, 5,500 to 19,500, 6,000 to 19,500, 6,500 to 19,500, 7,000 to 19,500, 7,500 to 19,500, 8,000 to 19,500, 8,500 to 19,500, 9,000 to 19,500, 9,500 to 19,500, 10,000 to 19,500, 10,500 to 19,500, 11,000 to 19,500, 11,500 to 19,500, 12,000 to 19,500, 12,500 to 19,500, 13,000 to 19,500, 13,500 to 19,500, 14,000 to 19,500, 14,500 to 19,500, 15,000 to 19,500, 15,500 to 19,500, 16,000 to 19,500, 16,500 to 19,500, 17,000 to 19,500, 17,500 to 19,500, 18,000 to 19,500, 18,500 to 19,500, 19,000 to 19,500, 1,500 to 19,000, 2,000 to 19,000, 2,500 to 19,000, 3,000 to 19,000, 3,500 to 19,000, 4,000 to 19,000, 4,500 to 19,000, 5,000 to 19,000, 5,500 to 19,000, 6,000 to 19,000, 6,500 to 19,000, 7,000 to 19,000, 7,500 to 19,000, 8,000 to 19,000, 8,500 to 19,000, 9,000 to 19,000, 9,500 to 19,000, 10,000 to 19,000, 10,500 to 19,000, 11,000 to 19,000, 11,500 to 19,000, 12,000 to 19,000, 12,500 to 19,000, 13,000 to 19,000, 13,500 to 19,000, 14,000 to 19,000, 14,500 to 19,000, 15,000 to 19,000, 15,500 to 19,000, 16,000 to 19,000, 16,500 to 19,000, 17,000 to 19,000, 17,500 to 19,000, 18,000 to 19,000, 18,500 to 19,000, 1,500 to 18,500, 2,000 to 18,500, 2,500 to 18,500, 3,000 to 18,500, 3,500 to 18,500, 4,000 to 18,500, 4,500 to 18,500, 5,000 to 18,500, 5,500 to 18,500, 6,000 to 18,500, 6,500 to 18,500, 7,000 to 18,500, 7,500 to 18,500, 8,000 to 18,500, 8,500 to 18,500, 9,000 to 18,500, 9,500 to 18,500, 10,000 to 18,500, 10,500 to 18,500, 11,000 to 18,500, 11,500 to 18,500, 12,000 to 18,500, 12,500 to 18,500, 13,000 to 18,500, 13,500 to 18,500, 14,000 to 18,500, 14,500 to 18,500, 15,000 to 18,500, 15,500 to 18,500, 16,000 to 18,500, 16,500 to 18,500, 17,000 to 18,500, 17,500 to 18,500, 18,000 to 18,500, 1,500 to 18,000, 2,000 to 18,000, 2,500 to 18,000, 3,000 to 18,000, 3,500 to 18,000, 4,000 to 18,000, 4,500 to 18,000, 5,000 to 18,000, 5,500 to 18,000, 6,000 to 18,000, 6,500 to 18,000, 7,000 to 18,000, 7,500 to 18,000, 8,000 to 18,000, 8,500 to 18,000, 9,000 to 18,000, 9,500 to 18,000, 10,000 to 18,000, 10,500 to 18,000, 11,000 to 18,000, 11,500 to 18,000, 12,000 to 18,000, 12,500 to 18,000, 13,000 to 18,000, 13,500 to 18,000, 14,000 to 18,000, 14,500 to 18,000, 15,000 to 18,000, 15,500 to 18,000, 16,000 to 18,000, 16,500 to 18,000, 17,000 to 18,000, 17,500 to 18,000, 1,500 to 17,500, 2,000 to 17,500, 2,500 to 17,500, 3,000 to 17,500, 3,500 to 17,500, 4,000 to 17,500, 4,500 to 17,500, 5,000 to 17,500, 5,500 to 17,500, 6,000 to 17,500, 6,500 to 17,500, 7,000 to 17,500, 7,500 to 17,500, 8,000 to 17,500, 8,500 to 17,500, 9,000 to 17,500, 9,500 to 17,500, 10,000 to 17,500, 10,500 to 17,500, 11,000 to 17,500, 11,500 to 17,500, 12,000 to 17,500, 12,500 to 17,500, 13,000 to 17,500, 13,500 to 17,500, 14,000 to 17,500, 14,500 to 17,500, 15,000 to 17,500, 15,500 to 17,500, 16,000 to 17,500, 16,500 to 17,500, 17,000 to 17,500, 1,500 to 17,000, 2,000 to 17,000, 2,500 to 17,000, 3,000 to 17,000, 3,500 to 17,000, 4,000 to 17,000, 4,500 to 17,000, 5,000 to 17,000, 5,500 to 17,000, 6,000 to 17,000, 6,500 to 17,000, 7,000 to 17,000, 7,500 to 17,000, 8,000 to 17,000, 8,500 to 17,000, 9,000 to 17,000, 9,500 to 17,000, 10,000 to 17,000, 10,500 to 17,000, 11,000 to 17,000, 11,500 to 17,000, 12,000 to 17,000, 12,500 to 17,000, 13,000 to 17,000, 13,500 to 17,000, 14,000 to 17,000, 14,500 to 17,000, 15,000 to 17,000, 15,500 to 17,000, 16,000 to 17,000, 16,500 to 17,000, 1,500 to 16,500, 2,000 to 16,500, 2,500 to 16,500, 3,000 to 16,500, 3,500 to 16,500, 4,000 to 16,500, 4,500 to 16,500, 5,000 to 16,500, 5,500 to 16,500, 6,000 to 16,500, 6,500 to 16,500, 7,000 to 16,500, 7,500 to 16,500, 8,000 to 16,500, 8,500 to 16,500, 9,000 to 16,500, 9,500 to 16,500, 10,000 to 16,500, 10,500 to 16,500, 11,000 to 16,500, 11,500 to 16,500, 12,000 to 16,500, 12,500 to 16,500, 13,000 to 16,500, 13,500 to 16,500, 14,000 to 16,500, 14,500 to 16,500, 15,000 to 16,500, 15,500 to 16,500, 16,000 to 16,500, 1,500 to 16,000, 2,000 to 16,000, 2,500 to 16,000, 3,000 to 16,000, 3,500 to 16,000, 4,000 to 16,000, 4,500 to 16,000, 5,000 to 16,000, 5,500 to 16,000, 6,000 to 16,000, 6,500 to 16,000, 7,000 to 16,000, 7,500 to 16,000, 8,000 to 16,000, 8,500 to 16,000, 9,000 to 16,000, 9,500 to 16,000, 10,000 to 16,000, 10,500 to 16,000, 11,000 to 16,000, 11,500 to 16,000, 12,000 to 16,000, 12,500 to 16,000, 13,000 to 16,000, 13,500 to 16,000, 14,000 to 16,000, 14,500 to 16,000, 15,000 to 16,000, 15,500 to 16,000, 1,500 to 15,500, 2,000 to 15,500, 2,500 to 15,500, 3,000 to 15,500, 3,500 to 15,500, 4,000 to 15,500, 4,500 to 15,500, 5,000 to 15,500, 5,500 to 15,500, 6,000 to 15,500, 6,500 to 15,500, 7,000 to 15,500, 7,500 to 15,500, 8,000 to 15,500, 8,500 to 15,500, 9,000 to 15,500, 9,500 to 15,500, 10,000 to 15,500, 10,500 to 15,500, 11,000 to 15,500, 11,500 to 15,500, 12,000 to 15,500, 12,500 to 15,500, 13,000 to 15,500, 13,500 to 15,500, 14,000 to 15,500, 14,500 to 15,500, 15,000 to 15,500, 1,500 to 15,000, 2,000 to 15,000, 2,500 to 15,000, 3,000 to 15,000, 3,500 to 15,000, 4,000 to 15,000, 4,500 to 15,000, 5,000 to 15,000, 5,500 to 15,000, 6,000 to 15,000, 6,500 to 15,000, 7,000 to 15,000, 7,500 to 15,000, 8,000 to 15,000, 8,500 to 15,000, 9,000 to 15,000, 9,500 to 15,000, 10,000 to 15,000, 10,500 to 15,000, 11,000 to 15,000, 11,500 to 15,000, 12,000 to 15,000, 12,500 to 15,000, 13,000 to 15,000, 13,500 to 15,000, 14,000 to 15,000, 14,500 to 15,000, 1,500 to 14,500, 2,000 to 14,500, 2,500 to 14,500, 3,000 to 14,500, 3,500 to 14,500, 4,000 to 14,500, 4,500 to 14,500, 5,000 to 14,500, 5,500 to 14,500, 6,000 to 14,500, 6,500 to 14,500, 7,000 to 14,500, 7,500 to 14,500, 8,000 to 14,500, 8,500 to 14,500, 9,000 to 14,500, 9,500 to 14,500, 10,000 to 14,500, 10,500 to 14,500, 11,000 to 14,500, 11,500 to 14,500, 12,000 to 14,500, 12,500 to 14,500, 13,000 to 14,500, 13,500 to 14,500, 14,000 to 14,500, 1,500 to 14,000, 2,000 to 14,000, 2,500 to 14,000, 3,000 to 14,000, 3,500 to 14,000, 4,000 to 14,000, 4,500 to 14,000, 5,000 to 14,000, 5,500 to 14,000, 6,000 to 14,000, 6,500 to 14,000, 7,000 to 14,000, 7,500 to 14,000, 8,000 to 14,000, 8,500 to 14,000, 9,000 to 14,000, 9,500 to 14,000, 10,000 to 14,000, 10,500 to 14,000, 11,000 to 14,000, 11,500 to 14,000, 12,000 to 14,000, 12,500 to 14,000, 13,000 to 14,000, 13,500 to 14,000, 1,500 to 13,500, 2,000 to 13,500, 2,500 to 13,500, 3,000 to 13,500, 3,500 to 13,500, 4,000 to 13,500, 4,500 to 13,500, 5,000 to 13,500, 5,500 to 13,500, 6,000 to 13,500, 6,500 to 13,500, 7,000 to 13,500, 7,500 to 13,500, 8,000 to 13,500, 8,500 to 13,500, 9,000 to 13,500, 9,500 to 13,500, 10,000 to 13,500, 10,500 to 13,500, 11,000 to 13,500, 11,500 to 13,500, 12,000 to 13,500, 12,500 to 13,500, 13,000 to 13,500, 1,500 to 13,000, 2,000 to 13,000, 2,500 to 13,000, 3,000 to 13,000, 3,500 to 13,000, 4,000 to 13,000, 4,500 to 13,000, 5,000 to 13,000, 5,500 to 13,000, 6,000 to 13,000, 6,500 to 13,000, 7,000 to 13,000, 7,500 to 13,000, 8,000 to 13,000, 8,500 to 13,000, 9,000 to 13,000, 9,500 to 13,000, 10,000 to 13,000, 10,500 to 13,000, 11,000 to 13,000, 11,500 to 13,000, 12,000 to 13,000, 12,500 to 13,000, 1,500 to 12,500, 2,000 to 12,500, 2,500 to 12,500, 3,000 to 12,500, 3,500 to 12,500, 4,000 to 12,500, 4,500 to 12,500, 5,000 to 12,500, 5,500 to 12,500, 6,000 to 12,500, 6,500 to 12,500, 7,000 to 12,500, 7,500 to 12,500, 8,000 to 12,500, 8,500 to 12,500, 9,000 to 12,500, 9,500 to 12,500, 10,000 to 12,500, 10,500 to 12,500, 11,000 to 12,500, 11,500 to 12,500, 12,000 to 12,500, 1,500 to 12,000, 2,000 to 12,000, 2,500 to 12,000, 3,000 to 12,000, 3,500 to 12,000, 4,000 to 12,000, 4,500 to 12,000, 5,000 to 12,000, 5,500 to 12,000, 6,000 to 12,000, 6,500 to 12,000, 7,000 to 12,000, 7,500 to 12,000, 8,000 to 12,000, 8,500 to 12,000, 9,000 to 12,000, 9,500 to 12,000, 10,000 to 12,000, 10,500 to 12,000, 11,000 to 12,000, 11,500 to 12,000, 1,500 to 11,500, 2,000 to 11,500, 2,500 to 11,500, 3,000 to 11,500, 3,500 to 11,500, 4,000 to 11,500, 4,500 to 11,500, 5,000 to 11,500, 5,500 to 11,500, 6,000 to 11,500, 6,500 to 11,500, 7,000 to 11,500, 7,500 to 11,500, 8,000 to 11,500, 8,500 to 11,500, 9,000 to 11,500, 9,500 to 11,500, 10,000 to 11,500, 10,500 to 11,500, 11,000 to 11,500, 1,500 to 11,000, 2,000 to 11,000, 2,500 to 11,000, 3,000 to 11,000, 3,500 to 11,000, 4,000 to 11,000, 4,500 to 11,000, 5,000 to 11,000, 5,500 to 11,000, 6,000 to 11,000, 6,500 to 11,000, 7,000 to 11,000, 7,500 to 11,000, 8,000 to 11,000, 8,500 to 11,000, 9,000 to 11,000, 9,500 to 11,000, 10,000 to 11,000, 10,500 to 11,000, 1,500 to 10,500, 2,000 to 10,500, 2,500 to 10,500, 3,000 to 10,500, 3,500 to 10,500, 4,000 to 10,500, 4,500 to 10,500, 5,000 to 10,500, 5,500 to 10,500, 6,000 to 10,500, 6,500 to 10,500, 7,000 to 10,500, 7,500 to 10,500, 8,000 to 10,500, 8,500 to 10,500, 9,000 to 10,500, 9,500 to 10,500, 10,000 to 10,500, 1,500 to 10,000, 2,000 to 10,000, 2,500 to 10,000, 3,000 to 10,000, 3,500 to 10,000, 4,000 to 10,000, 4,500 to 10,000, 5,000 to 10,000, 5,500 to 10,000, 6,000 to 10,000, 6,500 to 10,000, 7,000 to 10,000, 7,500 to 10,000, 8,000 to 10,000, 8,500 to 10,000, 9,000 to 10,000, 9,500 to 10,000, 1,500 to 9,500, 2,000 to 9,500, 2,500 to 9,500, 3,000 to 9,500, 3,500 to 9,500, 4,000 to 9,500, 4,500 to 9,500, 5,000 to 9,500, 5,500 to 9,500, 6,000 to 9,500, 6,500 to 9,500, 7,000 to 9,500, 7,500 to 9,500, 8,000 to 9,500, 8,500 to 9,500, 9,000 to 9,500, 1,500 to 9,000, 2,000 to 9,000, 2,500 to 9,000, 3,000 to 9,000, 3,500 to 9,000, 4,000 to 9,000, 4,500 to 9,000, 5,000 to 9,000, 5,500 to 9,000, 6,000 to 9,000, 6,500 to 9,000, 7,000 to 9,000, 7,500 to 9,000, 8,000 to 9,000, 8,500 to 9,000, 1,500 to 8,500, 2,000 to 8,500, 2,500 to 8,500, 3,000 to 8,500, 3,500 to 8,500, 4,000 to 8,500, 4,500 to 8,500, 5,000 to 8,500, 5,500 to 8,500, 6,000 to 8,500, 6,500 to 8,500, 7,000 to 8,500, 7,500 to 8,500, 8,000 to 8,500, 1,500 to 8,000, 2,000 to 8,000, 2,500 to 8,000, 3,000 to 8,000, 3,500 to 8,000, 4,000 to 8,000, 4,500 to 8,000, 5,000 to 8,000, 5,500 to 8,000, 6,000 to 8,000, 6,500 to 8,000, 7,000 to 8,000, 7,500 to 8,000, 1,500 to 7,500, 2,000 to 7,500, 2,500 to 7,500, 3,000 to 7,500, 3,500 to 7,500, 4,000 to 7,500, 4,500 to 7,500, 5,000 to 7,500, 5,500 to 7,500, 6,000 to 7,500, 6,500 to 7,500, 7,000 to 7,500, 1,500 to 7,000, 2,000 to 7,000, 2,500 to 7,000, 3,000 to 7,000, 3,500 to 7,000, 4,000 to 7,000, 4,500 to 7,000, 5,000 to 7,000, 5,500 to 7,000, 6,000 to 7,000, 6,500 to 7,000, 1,500 to 6,500, 2,000 to 6,500, 2,500 to 6,500, 3,000 to 6,500, 3,500 to 6,500, 4,000 to 6,500, 4,500 to 6,500, 5,000 to 6,500, 5,500 to 6,500, 6,000 to 6,500, 1,500 to 6,000, 2,000 to 6,000, 2,500 to 6,000, 3,000 to 6,000, 3,500 to 6,000, 4,000 to 6,000, 4,500 to 6,000, 5,000 to 6,000, 5,500 to 6,000, 1,500 to 5,500, 2,000 to 5,500, 2,500 to 5,500, 3,000 to 5,500, 3,500 to 5,500, 4,000 to 5,500, 4,500 to 5,500, 5,000 to 5,500, 1,500 to 5,000, 2,000 to 5,000, 2,500 to 5,000, 3,000 to 5,000, 3,500 to 5,000, 4,000 to 5,000, 4,500 to 5,000, 1,500 to 4,500, 2,000 to 4,500, 2,500 to 4,500, 3,000 to 4,500, 3,500 to 4,500, 4,000 to 4,500, 1,500 to 4,000, 2,000 to 4,000, 2,500 to 4,000, 3,000 to 4,000, 3,500 to 4,000, 1,500 to 3,500, 2,000 to 3,500, 2,500 to 3,500, 3,000 to 3,500, 1,500 to 3,000, 2,000 to 3,000, 2,500 to 3,000, 1,500 to 2,500, 2,000 to 2,500, and 1,500 to 2,000 daltons.

In some embodiments the polymer (e.g., PEG) is conjugated to at least one lipid. In some embodiments the lipid conjugated to the polymer comprised of at least one neutral lipid, at least one phospholipid, at least one anionic lipid, at least one cationic lipid, at least one cholesterol, at least one cholesterol derivative, or any combination thereof.

In some embodiments, the lipid conjugated to the polymer may be selected from, but is not limited to, at least one of the cationic, non-cationic, or sterol lipids listed previously.

In some embodiments, the at least one PEG-lipid conjugate may be selected from, but is not limited to at least one of Siglec-1L-PEG-DSPE, (R)-2,3-bis(octadecyloxy)propyl-1-(methoxypoly(ethyleneglycol)2000)propylcarbamate, PEG-S-DSG, PEG-S-DMG, PEG-PE, PEG-PAA, PEG-OH DSPE C18, PEG-DSPE, PEG-DSG, PEG-DPG, PEG-DOMG, PEG-DMPE Na, PEG-DMPE, PEG-DMG2000, PEG-DMG C14, PEG-DMG 2000, PEG-DMG, PEG-DMA, PEG-Ceramide C16, PEG-C-DOMG, PEG-c-DMOG, PEG-c-DMA, PEG-cDMA, PEGA, PEG750-C-DMA, PEG400, PEG2k-DMG, PEG2k-C11, PEG2000-PE, PEG2000P, PEG2000-DSPE, PEG2000-DOMG, PEG2000-DMG, PEG2000-C-DMA, PEG2000, PEG200, PEG(2k)-DMG, PEG DSPE C18, PEG DMPE C14, PEG DLPE C12, PEG Click DMG C14, PEG Click C12, PEG Click C10, N(Carbonyl-methoxypolyethylenglycol-2000)-1,2-distearoyl-sn-glycero3-phosphoethanolamine, Myrj52, mPEG-PLA, MPEG-DSPE, mPEG3000-DMPE, MPEG-2000-DSPE, MPEG2000-DSPE, mPEG2000-DPPE, mPEG2000-DMPE, mPEG2000-DMG, mDPPE-PEG2000, 1,2-distearoyl-sn-glycero-3-phosphoethanolamine-PEG2000, HPEG-2K-LIPD, Folate PEG-DSPE, DSPE-PEGMA 500, DSPE-PEGMA, DSPE-PEG6000, DSPE-PEG5000, DSPE-PEG2K-NAG, DSPE-PEG2k, DSPE-PEG2000maleimide, DSPE-PEG2000, DSPE-PEG, DSG-PEGMA, DSG-PEG5000, DPPE-PEG-2K, DPPE-PEG, DPPE-mPEG2000, DPPE-mPEG, DPG-PEGMA, DOPE-PEG2000, DMPE-PEGMA, DMPE-PEG2000, DMPE-Peg, DMPE-mPEG2000, DMG-PEGMA, DMG-PEG2000, DMG-PEG, distearoyl-glycerol-polyethyleneglycol, C18PEG750, C18PEG5000, C18PEG3000, C18PEG2000, C16PEG2000, C14PEG2000, C18-PEG5000, C18PEG, C16PEG, C16 mPEG (polyethylene glycol) 2000 Ceramide, C14-PEG-DSPE200, C14-PEG2000, C14PEG2000, C14-PEG 2000, C14-PEG, C14PEG, 14:0-PEG2KPE, 1,2-distearoyl-sn-glycero-3-phosphoethanolamine-PEG2000, (R)-2,3-bis(octadecyloxy)propyl-1-(methoxypoly(ethyleneglycol)2000) propylcarbamate, (PEG)-C-DOMG, PEG-C-DMA, and DSPE-PEG-X.

In some embodiments, the LNP comprises a Lipid of the Disclosure, distearoylphosphatidylcholine (DSPC), cholesterol, and 1,2-dimyristoyl-rac-glycero-3-methoxypolyethylene glycol-2000 (DMG-PEG2000).

In some embodiments, the LNP comprises a Lipid of the Disclosure, distearoylphosphatidylcholine (DSPC), cholesterol, and 1,2-dimyristoyl-rac-glycero-3-methoxypolyethylene glycol-2000 (DMG-PEG2000) at a molar ratio of about 48.5:10:40:1.5, respectively.

In some embodiments, the LNP comprises a Lipid of the Disclosure, distearoylphosphatidylcholine (DSPC), cholesterol, and 1,2-dimyristoyl-rac-glycero-3-methoxypolyethylene glycol-2000 (DMG-PEG2000) at a molar ratio of about 48.5:10:39:2.5, respectively.

The amounts and ratios of LNP components may be varied by any amount dependent on the desired form, structure, function, cargo, target, or any combination thereof. The amount of each component may be expressed in various embodiments as percent of the total molar mass of all lipid or lipid conjugated components accounted for by the indicated component (mol %), The amount of each component may be expressed in various embodiments as the relative ratio of each component based on molar mass (Molar Ratio). The amount of each component may be expressed in various embodiments as the weight of each component used to formulate the LNP prior to fabrication (mg or equivalent). The amount of each component may be expressed in various embodiments by any other method known in the art. Any formulation given in one representation of component amounts ("units") is expressly meant to encompass any formulation expressed in different units of component amounts, wherein those representations are effectively equivalent when converted into the same units. In some embodiments, "effectively equivalent" means two or more values within about 10% of one another.

In some embodiments, the LNP comprises at least one cationic lipid in an amount of about 0.1 to 100 mol %. In some embodiments, the LNP comprises at least one cationic lipid in an amount of about 20 to 60 mol %. In some embodiments, the LNP comprises at least one cationic lipid in an amount of about 50 to 85 mol %. In some embodiments, the LNP comprises at least one cationic lipid in an amount of less than about 20 mol %. In some embodiments, the LNP comprises at least one cationic lipid in an amount of more than about 60 mol % or about 85 mol %. In some embodiments, the LNP comprises at least one cationic lipid in an amount of about 95 mol % or less. In some embodiments, the LNP comprises a cationic lipid in an amount of less than or equal to about 95, 90, 85, 80, 75, 70, 65, 60, 55, 50, 45, 40, 35, 30, 25, 20, 15, 10, and 5 mol %. In some embodiments, the LNP comprises at least one cationic lipid in an amount of more than or equal to about 5, 10, 15, 20, 25, 30, 35, 40, 45, 50, 55, 60, 65, 70, 75, 80, 85, 90, and 95 mol %. In some embodiments, the LNP comprises at least one cationic lipid in an amount from about 20 to 30 mol %, 20 to 35 mol %, 20 to 40 mol %, 20 to 45 mol %, 20 to 50 mol %, 20 to 55 mol %, 20 to 60 mol %, 20 to 65 mol %, 20 to 70 mol %, 20 to 75 mol %, 20 to 80 mol %, 20 to 85 mol %, 20 to 90 mol %, 25 to 35 mol %, 25 to 40 mol %, 25 to 45 mol %, 25 to 50 mol %, 25 to 55 mol %, 25 to 60 mol %, 25 to 65 mol %, 25 to 70 mol %, 25 to 75 mol %, 25 to 80 mol %, 25 to 85 mol %, 25 to 90 mol %, 30 to 40 mol %, 30 to 45 mol %, 30 to 50 mol %, 30 to 55 mol %, 30 to 60 mol %, 30 to 65 mol %, 30 to 70 mol %, 30 to 75 mol %, 30 to 80 mol %, 30 to 85 mol %, 30 to 90 mol %, 35 to 40 mol %, 35 to 45 mol %, 35 to 50 mol %, 35 to 55 mol %, 35 to 60 mol %, 35 to 65 mol %, 35 to 70 mol %, 35 to 75 mol %, 35 to 80 mol %, 35 to 85 mol %, 35 to 90 mol %, 40 to 45 mol %, 40 to 50 mol %, 40 to 55 mol %, 40 to 60 mol %, 40 to 65 mol %, 40 to 70 mol %, 40 to 75 mol %, 40 to 80 mol %, 40 to 85 mol %, 40 to 90 mol %, 45 to 55 mol %, 45 to 60 mol %, 45 to 65 mol %, 45 to 70 mol %, 45 to 75 mol %, 45 to 80 mol %, 45 to 85 mol %, 45 to 90 mol %, 50 to 60 mol %, 50 to 65 mol %, 50 to 70 mol %, 50 to 75 mol %, 50 to 80 mol %, 50 to 85 mol %, 50 to 90 mol %, 55 to 65 mol %, 55 to 70 mol %, 55 to 75 mol %, 55 to 80 mol %, 55 to 85 mol %, 55 to 90 mol %, 60 to 70 mol %, 60 to 75 mol %, 60 to 80 mol %, 60 to 85 mol %, 60 to 90 mol %, 65 to 75 mol %, 65 to 80 mol %, 65 to 85 mol %, 65 to 90 mol %, 70 to 80 mol %, 70 to 85 mol %, 70 to 90 mol %, 75 to 85 mol %, 75 to 90 mol %, 80 to 90 mol % or 85 to 95 mol %.

In some embodiments, the LNP comprises at least one non-cationic lipid in an amount of about 0.1 to 100 mol %. In some embodiments, the LNP comprises at least one non-one cationic lipid in an amount of about 5 to 35 mol %. In some embodiments, the LNP comprises at least one cationic lipid in an amount of about 5 to 25 mol %. In some embodiments, the LNP comprises at least one non-cationic lipid in an amount of less than about 5 mol %. In some embodiments, the LNP comprises at least one non-cationic lipid in an amount of more than about 25 mol % or about 35 mol %. In some embodiments, the LNP comprises at least one non-cationic lipid in an amount of about 95 mol % or less. In some embodiments, the LNP comprises at least one non-cationic lipid in an amount of less than or equal to about 95, 90, 85, 80, 75, 70, 65, 60, 55, 50, 45, 40, 35, 30, 25, 20, 15, 10, and 5 mol %. In some embodiments, the LNP comprises at least one non-cationic lipid in an amount of more than or equal to about 5, 10, 15, 20, 25, 30, 35, 40, 45, 50, 55, 60, 65, 70, 75, 80, 85, 90, and 95 mol %. In some embodiments, the LNP comprises at least one non-cationic lipid in an amount from about 5 to 15 mol %, 5 to 25 mol %, 5 to 35 mol %, 5 to 45 mol %, 5 to 55 mol %, 10 to 20 mol %, 10 to 30 mol %, 10 to 40 mol %, 10 to 50 mol %, 15 to 25 mol %, 15 to 35 mol %, 15 to 45 mol %, 20 to 30 mol %, 20 to 40 mol %, 20 to 50 mol %, 25 to 35 mol %, 25 to 45 mol %, 30 to 40 mol %, 30 to 50 mol %, and 35 to 45 mol %.

In some embodiments, the LNP comprises at least one sterol in an amount of about 0.1 to 100 mol %. In some embodiments, the LNP comprises at least one sterol in an amount of about 20 to 45 mol %. In some embodiments, the LNP comprises at least one sterol in an amount of about 25 to 55 mol %. In some embodiments, the LNP comprises at least one sterol in an amount of less than about 20 mol %. In some embodiments, the LNP comprises at least one sterol in an amount of more than about 45 mol % or about 55 mol %. In some embodiments, the LNP comprises at least one sterol in an amount of about 95 mol % or less. In some embodiments, the LNP comprises at least one sterol in an amount of less than or equal to about 95, 90, 85, 80, 75, 70, 65, 60, 55, 50, 45, 40, 35, 30, 25, 20, 15, 10, and 5 mol %. In some embodiments, the LNP comprises at least one sterol in an amount of more than or equal to about 5, 10, 15, 20, 25, 30, 35, 40, 45, 50, 55, 60, 65, 70, 75, 80, 85, 90, and 95 mol %. In some embodiments, the LNP comprises at least one sterol in an amount from about 10 to 20 mol %, 10 to 30 mol %, 10 to 40 mol %, 10 to 50 mol %, 10 to 60 mol %, 15 to 25 mol %, 15 to 35 mol %, 15 to 45 mol %, 15 to 55 mol %, 15 to 65 mol %, 20 to 30 mol %, 20 to 40 mol %, 20 to 50 mol %, 20 to 60 mol %, 25 to 35 mol %, 25 to 45 mol %, 25 to 55 mol %, 25 to 65 mol %, 30 to 40 mol %, 30 to 50 mol %, 30 to 60 mol %, 35 to 45 mol %, 35 to 55 mol %, 35 to 65 mol %, 40 to 50 mol %, 40 to 60 mol %, 45 to 55 mol %, 45 to 65 mol %, 50 to 60 mol %, and 55 to 65 mol %.

In some embodiments, the LNP comprises at least one particle-activity-modifying-agent in an amount of about 0.1 to 100 mol %. In some embodiments, the LNP comprises at least one particle-activity-modifying-agent in an amount of about 0.5 to 15 mol %. In some embodiments, the LNP comprises at least one particle-activity-modifying-agent in an amount of about 15 to 40 mol %. In some embodiments, the LNP comprises at least one particle-activity-modifying-agent in an amount of less than about 0.1 mol %. In some embodiments, the LNP comprises at least one particle-activity-modifying-agent in an amount of more than about 15 mol % or about 40 mol %. In some embodiments, the LNP comprises at least one particle-activity-modifying-agent in an amount of about 95 mol % or less. In some embodiments, the LNP comprises at least one particle-activity-modifying-agent in an amount of less than or equal to about 95, 90, 85, 80, 75, 70, 65, 60, 55, 50, 45, 40, 35, 30, 25, 20, 15, 10, and 5 mol %. In some embodiments, the LNP comprises at least one particle-activity-modifying-agent in an amount of more than or equal to about 5, 10, 15, 20, 25, 30, 35, 40, 45, 50, 55, 60, 65, 70, 75, 80, 85, 90, and 95 mol %. In some embodiments, the LNP comprises at least one particle-activity-modifying-agent in an amount from about 0.1 to 1 mol %, 0.1 to 2 mol %, 0.1 to 3 mol %, 0.1 to 4 mol %, 0.1 to 5 mol %, 0.1 to 6 mol %, 0.1 to 7 mol %, 0.1 to 8 mol %, 0.1 to 9 mol %, 0.1 to 10 mol %, 0.1 to 15 mol %, 0.1 to 20 mol %, 0.1 to 25 mol %, 1 to 2 mol %, 1 to 3 mol %, 1 to 4 mol %, 1 to 5 mol %, 1 to 6 mol %, 1 to 7 mol %, 1 to 8 mol %, 1 to 9 mol %, 1 to 10 mol %, 1 to 15 mol %, 1 to 20 mol %, 1 to 25 mol %, 2 to 3 mol %, 2 to 4 mol %, 2 to 5 mol %, 2 to 6 mol %, 2 to 7 mol %, 2 to 8 mol %, 2 to 9 mol %, 2 to 10 mol %, 2 to 15 mol %, 2 to 25 mol %, 3 to 4 mol %, 3 to 5 mol %, 3 to 6 mol %, 3 to 7 mol %, 3 to 8 mol %, 3 to 9 mol %, 3 to 10 mol %, 3 to 15 mol %, 3 to 20 mol %, 3 to 25 mol %, 4 to 5 mol %, 4 to 6 mol %, 4 to 7 mol %, 4 to 8 mol %, 4 to 9 mol %, 4 to 10 mol %, 4 to 15 mol %, 4 to 20 mol %, 4 to 25 mol %, 5 to 10 mol %, 5 to 15 mol %, 5 to 20 mol %, 5 to 25 mol %, 10 to 15 mol %, 10 to 20 mol %, 10 to 25 mol %, 15 to 20 mol %, 15 to 25 mol %, and 20 to 25 mol %.

In some embodiments, the LNP is comprised of about 30-60 mol % of at least one cationic lipid, about 0-30 mol % of at least one non-cationic lipid (e.g., a phospholipid), about 18.5-48.5 mol % of at least one sterol (e.g., cholesterol), and about 0-10 mol % of at least one particle-activity-modifying-agent (e.g., a PEGylated lipid).

In some embodiments, the LNP is comprised of about 35-55 mol % of at least one cationic lipid, about 5-25 mol % of at least one non-cationic lipid (e.g., a phospholipid), about 30-40 mol % of at least one sterol (e.g., cholesterol), and about 0-10 mol % of at least one particle-activity-modifying-agent (e.g., a PEGylated lipid).

In some embodiments, the LNP is comprised of about 35-45 mol % of at least one cationic lipid, about 25-35 mol % of at least one non-cationic lipid (e.g., a phospholipid), about 20-30 mol % of at least one sterol (e.g., cholesterol), and about 0-10 mol % of at least one particle-activity-modifying-agent (e.g., a PEGylated lipid).

In some embodiments, the LNP is comprised of about 45-65 mol % of at least one cationic lipid, about 5-10 mol % of at least one non-cationic lipid (e.g., a phospholipid), about 25-40 mol % of at least one sterol (e.g., cholesterol), and about 0.5-10 mol % of at least one particle-activity-modifying-agent (e.g., a PEGylated lipid).

In some embodiments, the LNP is comprised of about 40-60 mol % of at least one cationic lipid, about 5-15 mol % of at least one non-cationic lipid (e.g., a phospholipid), about 35-45 mol % of at least one sterol (e.g., cholesterol), and about 0.5-3 mol % of at least one particle-activity-modifying-agent (e.g., a PEGylated lipid).

In some embodiments, the LNP is comprised of about 30-60 mol % of at least one cationic lipid, about 0-30 mol % of at least one non-cationic lipid (e.g., a phospholipid), about 15-50 mol % of at least one sterol (e.g., cholesterol), and about 0.01-10 mol % of at least one particle-activity-modifying-agent (e.g., a PEGylated lipid).

In some embodiments, the LNP is comprised of about 10-75 mol % of at least one cationic lipid, about 0.5-50 mol % of at least one non-cationic lipid (e.g., a phospholipid), about 5-60 mol % of at least one sterol (e.g., cholesterol), and about 0.1-20 mol % of at least one particle-activity-modifying-agent (e.g., a PEGylated lipid).

In some embodiments, the LNP is comprised of about 50-65 mol % of at least one cationic lipid, about 3-15 mol % of at least one non-cationic lipid (e.g., a phospholipid), about 30-40 mol % of at least one sterol (e.g., cholesterol), and about 0.5-2 mol % of at least one particle-activity-modifying-agent (e.g., a PEGylated lipid).

In some embodiments, the LNP is comprised of about 50-85 mol % of at least one cationic lipid, about 3-15 mol % of at least one non-cationic lipid (e.g., a phospholipid), about 30-40 mol % of at least one sterol (e.g., cholesterol), and about 0.5-2 mol % of at least one particle-activity-modifying-agent (e.g., a PEGylated lipid).

In some embodiments, the LNP is comprised of about 25-75 mol % of at least one cationic lipid, about 0.1-15 mol % of at least one non-cationic lipid (e.g., a phospholipid), about 5-50 mol % of at least one sterol (e.g., cholesterol), and about 0.5-20 mol % of at least one particle-activity-modifying-agent (e.g., a PEGylated lipid).

In some embodiments, the LNP is comprised of about 50-65 mol % of at least one cationic lipid, about 5-10 mol % of at least one non-cationic lipid (e.g., a phospholipid), about 25-35 mol % of at least one sterol (e.g., cholesterol), and about 5-10 mol % of at least one particle-activity-modifying-agent (e.g., a PEGylated lipid).

In some embodiments, the LNP is comprised of about 20-60 mol % of at least one cationic lipid, about 5-25 mol % of at least one non-cationic lipid (e.g., a phospholipid), about 25-55 mol % of at least one sterol (e.g., cholesterol), and about 0.5-15 mol % of at least one particle-activity-modifying-agent (e.g., a PEGylated lipid).

In some embodiments, the LNPs can be characterized by their shape. In some embodiments, the LNPs are essentially spherical. In some embodiments, the LNPs are essentially rod-shaped (i.e., cylindrical). In some embodiments, the LNPs are essentially disk shaped.

In some embodiments, the LNPs can be characterized by their size. In some embodiments, the size of an LNP can be defined as the diameter of its largest circular cross section, referred to herein simply as its diameter. In some embodiments the LNPs may have a diameter between 30 nm to about 150 nm. In some embodiments, the LNP may have diameters ranging between about 40 to 150 nm 50 to 150 nm, 60 to 150 nm, about 70 to 150 nm, or 80 to 150 nm, 90 to 150 nm, 100 to nm, 110 to 150 nm, 120 to 150 nm, 130 to 150 nm, 140 to 150 nm, 30 to 30 to 140 mol %, 40 to 140 mol %, 50 to 140 mol %, 60 to 140 mol %, 70 to 140 mol %, 80 to 140 mol %, 90 to 140 mol %, 100 to 140 mol %, 110 to 140 mol %, 120 to 140 mol %, 130 to 140 mol %, 140 to 140 mol %, 30 to 140 mol %, 40 to 130 mol %, 50 to 130 mol %, 60 to 130 mol %, 70 to 130 mol %, 80 to 130 mol %, 90 to 130 mol %, 100 to 130 mol %, 110 to 130 mol %, 120 to 130 mol %, 30 to 120 mol %, 40 to 120 mol %, 50 to 120 mol %, 60 to 120 mol %, 70 to 120 mol %, 80 to 120 mol %, 90 to 120 mol %, 100 to 120 mol %, 110 to 120 mol %, 30 to 110 mol %, 40 to 110 mol %, 50 to 110 mol %, 60 to 110 mol %, 70 to 110 mol %, 80 to 110 mol %, 90 to 110 mol %, 100 to 110 mol %, 30 to 100 mol %, 40 to 100 mol %, 50 to 100 mol %, 60 to 100 mol %, 70 to 100 mol %, 80 to 100 mol %, 90 to 100 mol %, 30 to 90 mol %, 40 to 90 mol %, 50 to 90 mol %, 60 to 90 mol %, 70 to 90 mol %, 80 to 90 mol %, 30 to 80 mol %, 40 to 80 mol %, 50 to 80 mol %, 60 to 80 mol %, 70 to 80 mol %, 30 to 70 mol %, 40 to 70 mol %, 50 to 70 mol %, 60 to 70 mol %, 30 to 60 mol %, 40 to 60 mol %, 50 to 60 mol %, 30 to 50 mol %, 40 to 50 mol %, and 30 to 40 mol %.

In some embodiments, a population of LNPs, such as those resulting from the same formulation, may be characterized by measuring the uniformity of size, shape, or mass of the particles in the population. Uniformity may be expressed in some embodiments as the polydispersity index (PI) of the population. In some embodiments uniformity may be expressed in some embodiments as the disparity (D) of the population. The terms "polydispersity index" and "disparity" are understood herein to be equivalent and may be used interchangeably. In some embodiments, a population of LNPs resulting from a given formulation will have a PI of between about 0.1 and 1. In some embodiments, a population of LNPs resulting from a giving formulation will have a PI of less than about 1, less than about 0.5, less than about 0.4, less than about 0.3, less than about 0.2, less than about 0.1. In some embodiments, a population of LNPs resulting from a given formulation will have a PI of between about 0.1 to 1, 0.1 to 0.8, 0.1 to 0.6, 0.1 to 0.4, 0.1 to 0.2, 0.2 to 1, 0.2 to 0.8, 0.2 to 0.6, 0.2 to 0.4, 0.4 to 1, 0.4 to 0.8, 0.4 to 0.6, 0.6 to 1, 0.6 to 0.8, and 0.8 to 1.

In some embodiments, the LNP may fully or partially encapsulate a cargo, such as the originator constructs and benchmark constructs of the present disclosure. In some embodiments, essentially 0% of the cargo present in the final formulation is exposed to the environment outside of the LNP (i.e., the cargo is fully encapsulated. In some embodiments, the cargo is associated with the LNP but is at least partially exposed to the environment outside of the LNP. In some embodiments, the LNP may be characterized by the % of the cargo not exposed to the environment outside of the LNP, e.g., the encapsulation efficiency. For the sake of clarity, an encapsulation efficiency of about 100% refers to an LNP formulation where essentially all the cargo is fully encapsulated by the LNP, while an encapsulation rate of about 0% refers to an LNP where essential none of the cargo is encapsulated in the LNP, such as with an LNP where the cargo is bound to the external surface of the LNP. On some embodiments, an LNP may have an encapsulation efficiency of less than about 100%, less than about 95%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15% less than about 10%, or less than 5%. In some embodiments, an LNP may have an encapsulation efficiency of between about 90 to 100%, 80 to 100%, 70 to 100%, 60 to 100%, 50 to 100%, 40 to 100%, 30 to 100%, 20 to 100%, 10 to 100%, 80 to 90%, 70 to 90%, 60 to 90%, 50 to 90%, 40 to 90%, 30 to 90%, 20 to 90%, 10 to 90%, 70 to 80%, 60 to 80%, 50 to 80%, 40 to 80%, 30 to 80%, 20 to 80%, 10 to 80%, 60 to 70%, 50 to 70%, 40 to 70%, 30 to 70%, 20 to 70%, 10 to 70%, 40 to 50%, 30 to 50%, 20 to 50%, 10 to 50%, 30 to 40%, 20 to 40%, 10 to 40%, 20 to 30%, 10 to 30%, and 10 to 20%.

Figure 5:
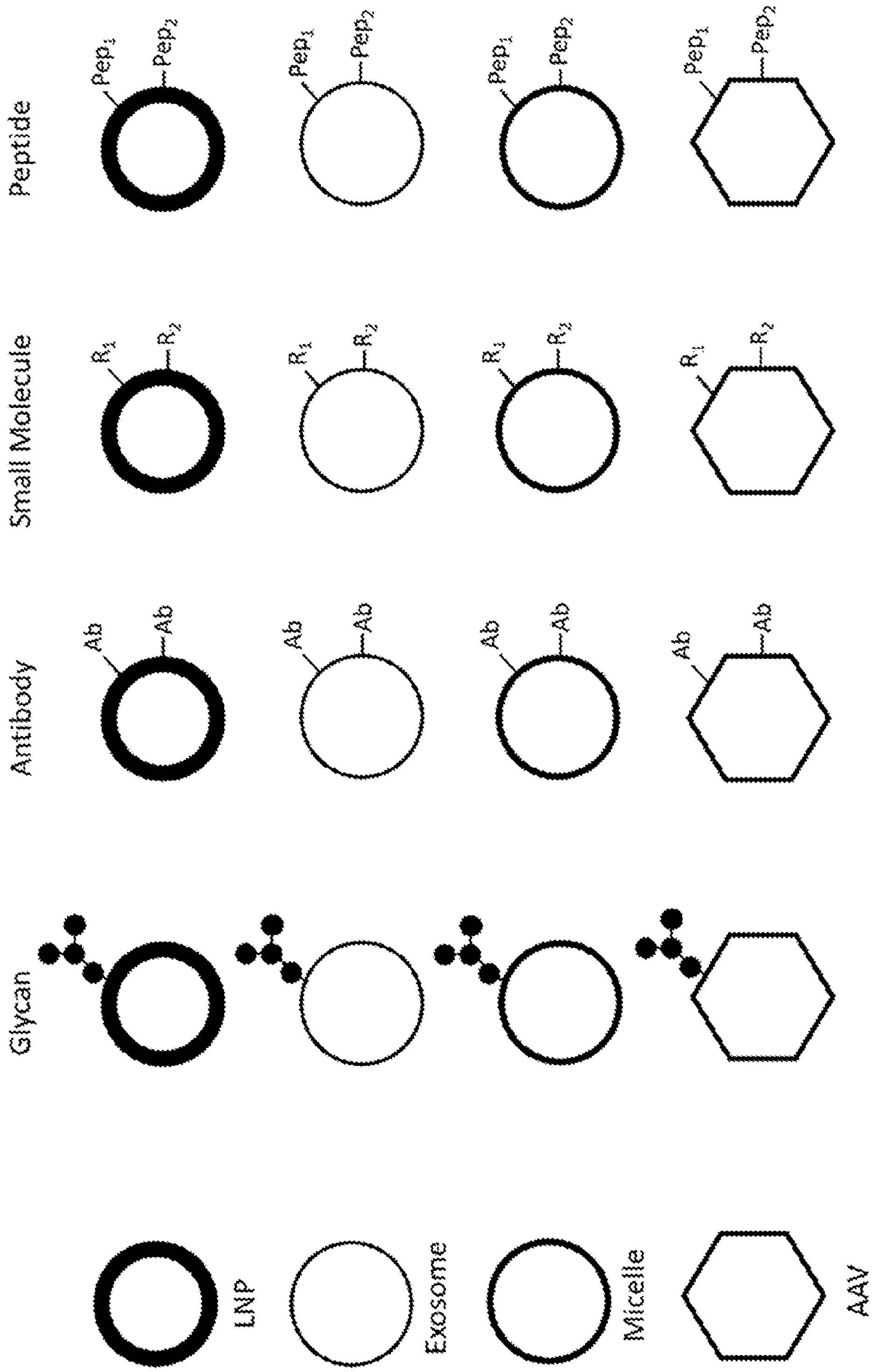
FIG. 5 is a diagram illustrating a series of delivery vehicles of the present disclosure.

In some embodiments, a LNP may include at least one identifier moiety as shown in FIG. 5. Non-limiting examples of an identifier moiety include glycans, antibodies, peptides, small molecules, and any combination thereof. In some embodiments, the at least one targeting agent may be incorporated into the lipid membrane of the lipid-based nanoparticle. In some embodiments, the at least one targeting agent may be presented on the external surface of the nanoparticle. In some embodiments, the at least one targeting agent may be conjugated to a lipid-component of the nanoparticle. In some embodiments, the at least one targeting agent may be conjugated to a polymer component of the nanoparticle. In some embodiments, the at least one targeting agent may be anchored to the nanoparticle via hydrophobic ad hydrophilic interactions among the at least one targeting agent, the nanoparticle membrane, and the aqueous environments inside or outside the nanoparticle. In some embodiments, the at least one targeting agent is conjugated to a peptide/protein component of the nanoparticle membrane. In some embodiments, the at least one targeting agent is conjugated to a suitable linker moiety which is conjugated to a component of the nanoparticle membrane. In some embodiments, any combination of forces and bonds can result in the targeting agent being associated with the nanoparticle.

The LNPs described herein may be formed using techniques known in the art. As a non-limiting example, an organic solution containing the lipids is mixed together with an acidic aqueous solution containing the originator construct or benchmark construct in a microfluidic channel resulting in the formation of targeting system (delivery vehicle and the benchmark construct).

In some embodiments, each LNP formulation includes a benchmark construct having a uniquely identifiable nucleotide identifier sequence (e.g., barcode). The unique identifier sequence provides the ability to identify the specific LNP which produces the desired result. The LNP formulation may also differ in the LNP-forming composition used to generate the LNP. For example, the LNP-forming compositions can be varied in the molar amount and/or structure of the ionizable lipid, the molar amount and/or structure of the helper lipid, the molar amount/or structure of PEG, and/or the molar amount of cholesterol. Additionally, or alternatively, the LNP formulation may comprise benchmark constructs which differ in the coding sequence for the biologically active molecule. Additionally, or alternatively, the LNP formulation may comprise benchmark constructs which differ in the modifications made to the nucleic acid sequence.

In some embodiments, the lipid compositions described according to the respective molar ratios of the component lipids in the formulation. As a non-limiting example, the mol-% of the ionizable lipid may be from about 10 mol-% to about 80 mol-%. As a non-limiting example, the mol-% of the ionizable lipid may be from about 20 mol-% to about 70 mol-%. As a non-limiting example, the mol-% of the ionizable lipid may be from about 30 mol-% to about 60 mol-%. As a non-limiting example, the mol-% of the ionizable lipid may be from about 35 mol-% to about 55 mol-%. As a non-limiting example, the mol-% of the ionizable lipid may be from about 40 mol-% to about 50 mol-%. As a non-limiting example, the ionizable lipid mol-% of the transfer vehicle batch will be ±30%, ±25%, ±20%, ±15%, ±10%, ±5%, or ±2.5% of the target mol-%. In some embodiments, transfer vehicle variability between lots will be less than 15%, less than 10% or less than 5%.

In some embodiments, the mol-% of the helper lipid may be from about 1 mol-% to about 50 mol-%. In some embodiments, the mol-% of the helper lipid may be from about 2 mol-% to about 45 mol-%. In some embodiments, the mol-% of the helper lipid may be from about 3 mol-% to about 40 mol-%. In some embodiments, the mol-% of the helper lipid may be from about 4 mol-% to about 35 mol-%. In some embodiments, the mol-% of the helper lipid may be from about 5 mol-% to about 30 mol-%. In some embodiments, the mol-% of the helper lipid may be from about 10 mol-% to about 20 mol-%. In some embodiments, the helper lipid mol-% of the transfer vehicle batch will be ±30%, ±25%, ±20%, ±15%, ±10%, ±5%, or ±2.5% of the target mol-%.

In some embodiments, the mol-% of the structural lipid may be from about 10 mol-% to about 80 mol-%. In some embodiments, the mol-% of the structural lipid may be from about 20 mol-% to about 70 mol-%. In some embodiments, the mol-% of the structural lipid may be from about 30 mol-% to about 60 mol-%. In some embodiments, the mol-% of the structural lipid may be from about 35 mol-% to about 55 mol-%. In some embodiments, the mol-% of the structural lipid may be from about 40 mol-% to about 50 mol-%. In some embodiments, the structural lipid mol-% of the transfer vehicle batch will be ±30%, ±25%, ±20%, ±15%, ±10%, ±5%, or ±2.5% of the target mol-%.

In some embodiments, the mol-% of the PEG modified lipid may be from about 0.1 mol-% to about 10 mol-%. In some embodiments, the mol-% of the PEG modified lipid may be from about 0.2 mol-% to about 5 mol-%. In some embodiments, the mol-% of the PEG modified lipid may be from about 0.5 mol-% to about 3 mol-%. In some embodiments, the mol-% of the PEG modified lipid may be from about 1 mol-% to about 2 mol-%. In some embodiments, the mol-% of the PEG modified lipid may be about 1.5 mol-%. In some embodiments, the PEG modified lipid mol-% of the transfer vehicle batch will be ±30%, ±25%, ±20%, ±15%, ±10%, ±5%, or ±2.5% of the target mol-%.

In some embodiments, the delivery vehicle may be any of the lipid nanoparticles described in WO2021113777, the contents of which are herein incorporated by reference in their entirety.

In some embodiments, the delivery vehicle is a lipid nanoparticle which comprises any of the ionizable lipids (e.g., amine lipids), PEG lipids, non-cationic (helper) lipids, or structural lipids in WO2021113777, the contents of which are herein incorporated by reference in their entirety.

In some embodiments, a lipid nanoparticle formulation may be prepared by the methods described in International Publication Nos. WO2011127255 or WO2008103276, the contents of each of which is herein incorporated by reference in their entirety. In some embodiments, lipid nanoparticle formulations may be as described in International Publication No. WO2019131770, the contents of which is herein incorporated by reference in its entirety.

In some embodiments, a lipid nanoparticle formulation may be prepared by the methods described in International Publication No. WO2020237227, the contents of each of which is herein incorporated by reference in their entirety. In some embodiments, lipid nanoparticle formulations may be as described in International Publication No. WO2020237227, the contents of which is herein incorporated by reference in its entirety.

Non-Lipid Nanoparticle

In some embodiments, the nanoparticle is a non-lipid-based nanoparticle. Non-lipid-based nanoparticles include, but are not limited to, silicon-based nanoparticles (i.e., porous silicon nanoparticles), gold nanoparticles, polypeptide-based nanoparticles, nucleotide-based nanoparticles, and carbon-based nanoparticle.

Exosomes

In some embodiments, the delivery vehicle comprises at least one exosome. As used herein, "exosomes" refer to small membrane bound vesicles with an endocytic origin. Without wishing to be bound by theory, exosomes are generally released into an extracellular environment from host/progenitor cells post fusion of multivesicular bodies the cellular plasma membrane. As such, exosomes will tend to include components of the progenitor membrane in addition to designed components and cargos. Exosome membranes are generally lamellar, composed of a bilayer of lipids, with an aqueous inter-nanoparticle space.

In some embodiments, an exosome may include at least one identifier moiety as shown in FIG. 5. Non-limiting examples of an identifier moiety include glycans, antibodies, peptides, small molecules, and any combination thereof.

Liposomes

In some embodiments, the delivery vehicles comprise of at least one liposome. As used herein, "liposomes" are small vesicles comprised of at least one lipid bilayer membrane surrounding an aqueous inner-nanoparticle space that is generally not derived from a progenitor/host cell. Liposomes can be (large) multilamellar vesicle (MLV), potentially hundreds of nanometers in diameter comprising a series of concentric bilayers separated by narrow aqueous spaces, small unicellular vesicle (SUV), potentially smaller than 50 nm in diameter, and a large unilamellar vesicle (LUV), potentially between 50 and 500 nm in diameter. In some embodiments, liposomes may be comprised of any or all the same components and same component amounts as a lipid nanoparticle, differing principally in their method of manufacture.

Micelles

In some embodiments, the delivery vehicles comprise of at least one micelle. As used herein, "micelles" refer to small particles which do not have an aqueous intra-particle space. Without wishing to be bound by theory, the intra-particle space of micelles is occupied by the hydrophobic tails of the lipids comprising the micelle membrane and possible associated cargo, rather than any additional lipid-head groups. In some embodiments, micelles may be comprised of any or all the same components as a lipid-nanoparticle, differing principally in their method of manufacture.

In some embodiments, a micelle may include at least one identifier moiety as shown in FIG. 5. Non-limiting examples of an identifier moiety include glycans, antibodies, peptides, small molecules, and any combination thereof.

Viral Particle

In some embodiments, the delivery vehicle comprises at least one virus like particle. As used herein, "virus like particles" refer to a vesicle predominantly of a protein capsid, sheath, shell, or coat (all used interchangeably herein) derived from a virus which can be loaded with a cargo moiety. In general, virus like particle are non-infection and may be synthesized using cellular machinery to express viral capsid protein sequences, which then self-assemble and incorporate the associated cargo moiety, though it is possible to form virus like particles by providing the capsid and cargo components without expression related cellular machinery and allowing them to self-assemble.

In some embodiments, the virus like particle may be derived from at least one of species of virus such as, but not limited to, Parvoviridae, Retroviridae, Flaviviridae, Paramyxoviridae, and bacteriophages. In some embodiments, the virus like particle may be derived from an adeno-associated virus, HIV, Hepatitis C virus, HPV, or any combination thereof.

In some embodiments, the virus like particle is an AAV particle and the AAV particle may include at least one identifier moiety as shown in FIG. 5. Non-limiting examples of an identifier moiety include glycans, antibodies, peptides, small molecules, and any combination thereof.

Polymeric Delivery Technology

In some embodiments, the delivery vehicle may comprise at least one polymeric delivery agent. As used herein, "polymeric delivery agents" refer to non-aggregating delivery agents comprised of soluble polymers conjugated to cargo moieties via various linkage groups. In some embodiments, polymeric delivery agents may comprise any of the polymers described herein.

Tracking Systems

The tropism discovery platform disclosed herein may utilize a variety of tracking systems which include identifier sequences and moieties (also referred to as a "barcode") in order to allow qualification of the delivery vehicles and/or the benchmark constructs, cargo and payloads post-administration.

In some embodiments, the tracking system is a single identifier sequence or moiety. The identifier sequence or moiety may be located in the delivery vehicle, benchmark construct, cargo or payload region, 5' UTR, 3'UTR, promoter region or tailing region. As a non-limiting example, the identifier sequence or moiety is located in or on the delivery vehicle. As a non-limiting example, the identifier sequence or moiety is located in or on the benchmark construct. As a non-limiting example, the identifier sequence or moiety is located in or on the 5' UTR. As a non-limiting example, the identifier sequence or moiety is located in or on the 3' UTR. As a non-limiting example, the identifier sequence or moiety is located in or on the promoter region.

As a non-limiting example, the identifier sequence or moiety is located in or on the payload region. As a non-limiting example, the identifier sequence or moiety is located in or on the tailing region.

In some embodiments, the tracking system is a set of identifier sequences or moieties with a first identifier sequence or moiety for the delivery vehicle and a second identifier sequence or moiety for the benchmark construct, cargo and payload. The first and second identifier sequence or moiety may be the same or different. If there are additional benchmark constructs, cargos and payloads in the delivery vehicle then each benchmark constructs, cargo and payloads may have its own identifier sequence or moiety or it may be the same at the second identifier sequence or moiety.

In some embodiments, the tropism discovery platform is comprised of multiple tracking systems, wherein each tracking system allows for detecting the delivery vehicle and/or benchmark constructs, cargo and payloads at different levels of resolution.

In some embodiments, the tracking systems comprises at least one barcode sequence. As used herein, a "barcode" or "barcode sequence" is any sequence which can be detected using methods known in the art and is distinct from the sequences in the cell, tissue, organ and/or organism or any sequences being administered. The barcode sequence may be included in or attached to the delivery vehicle and/or in the benchmark construct, cargo and payload. As a non-limiting example, the delivery vehicle comprises the barcode sequence. As a non-limiting example, the cargo or payload comprises the barcode sequence. As a non-limiting example, the benchmark construct comprises the barcode sequence.

In some embodiments, the location of the identifier sequence or moiety in the targeting system is random. As a non-limiting example, the identifier sequence or moiety is in the delivery vehicle. As a non-limiting example, the identifier sequence or moiety is in the delivery vehicle. As a non-limiting example, the identifier sequence or moiety is in the benchmark construct. As a non-limiting example, the identifier sequence or moiety is in the cargo or payload. As a non-limiting example, the identifier sequence or moiety is in the delivery vehicle and the benchmark construct. As a non-limiting example, the identifier sequence or moiety is in the delivery vehicle and the cargo or payload. As a non-limiting example, the identifier sequence or moiety is in the benchmark construct and the cargo or payload. As a non-limiting example, the identifier sequence or moiety is in the delivery vehicle, benchmark construct, and the cargo or payload.

In some embodiments, the location of the identifier sequence or moiety in the targeting system is pre-determined. As a non-limiting example, the identifier sequence or moiety is in the delivery vehicle. As a non-limiting example, the identifier sequence or moiety is in the delivery vehicle. As a non-limiting example, the identifier sequence or moiety is in the benchmark construct. As a non-limiting example, the identifier sequence or moiety is in the cargo or payload. As a non-limiting example, the identifier sequence or moiety is in the delivery vehicle and the benchmark construct. As a non-limiting example, the identifier sequence or moiety is in the delivery vehicle and the cargo or payload. As a non-limiting example, the identifier sequence or moiety is in the benchmark construct and the cargo or payload. As a non-limiting example, the identifier sequence or moiety is in the delivery vehicle, benchmark construct, and the cargo or payload.

In some embodiments, the location of the identifier sequence or moiety in the targeting system is inverted. As a non-limiting example, the identifier sequence or moiety is in the delivery vehicle. As a non-limiting example, the identifier sequence or moiety is in the delivery vehicle. As a non-limiting example, the identifier sequence or moiety is in the benchmark construct. As a non-limiting example, the identifier sequence or moiety is in the cargo or payload. As a non-limiting example, the identifier sequence or moiety is in the delivery vehicle and the benchmark construct. As a non-limiting example, the identifier sequence or moiety is in the delivery vehicle and the cargo or payload. As a non-limiting example, the identifier sequence or moiety is in the benchmark construct and the cargo or payload. As a non-limiting example, the identifier sequence or moiety is in the delivery vehicle, benchmark construct, and the cargo or payload.

In some embodiments, the identifier sequence is a randomly generated sequences which serve to avoid duplication during deep sequencing. In some embodiments, the identifier sequence is a repeating sequence of nucleotides or amino acids. In some embodiments, the identifier sequence is a fragment of a larger sequence such as, but not limited to, a cargo or payload. The identifier sequence may be designed to any length available using synthesis technology (See Clement et al., AmpUMI: design and analysis of unique molecular identifiers for deep amplicon sequencing, Bioinformatics, Volume 34, Issue 13, 1 Jul. 2018, Pages i202-i210; the contents of which is herein incorporated herein by reference in its entirety).

In some embodiments, the identifier sequence has a length between 2 and 1000 nucleotides. For example, the identifier sequence may have a length of 2, 3, 4, 5, 6, 7, 8, 9, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 or more than 1000 nucleotides. The identifier sequence may have a length between 2-5, 2-10, 2-15, 2-20, 2-30, 2-50, 2-70, 2-90, 2-100, 2-250, 2-300, 2-350, 2-400, 2-450, 2-500, 2-550, 2-600, 2-650, 2-700, 2-750, 2-800, 2-850, 2-900, 2-950, 2-1000, 5-10, 5-15, 5-20, 5-30, 5-50, 5-70, 5-90, 5-100, 5-250, 5-300, 5-350, 5-400, 5-450, 5-500, 5-550, 5-600, 5-650, 5-700, 5-750, 5-800, 5-850, 5-900, 5-950, 5-1000, 10-30, 10-50, 10-70, 10-90, 10-100, 10-250, 10-300, 10-350, 10-400, 10-450, 10-500, 10-550, 10-600, 10-650, 10-700, 10-750, 10-800, 10-850, 10-900, 10-950, 10-1000, 20-30, 20-50, 20-70, 20-90, 20-100, 20-250, 20-300, 20-350, 20-400, 20-450, 20-500, 20-550, 20-600, 20-650, 20-700, 20-750, 20-800, 20-850, 20-900, 20-950, 20-1000, 30-50, 30-70, 30-90, 30-100, 30-250, 30-300, 30-350, 30-400, 30-450, 30-500, 30-550, 30-600, 30-650, 30-700, 30-750, 30-800, 30-850, 30-900, 30-950, 30-1000, 40-50, 40-70, 40-90, 40-100, 40-250, 40-300, 40-350, 40-400, 40-450, 40-500, 40-550, 40-600, 40-650, 40-700, 40-750, 40-800, 40-850, 40-900, 40-950, 40-1000, 50-70, 50-90, 50-100, 50-250, 50-300, 50-350, 50-400, 50-450, 50-500, 50-550, 50-600, 50-650, 50-700, 50-750, 50-800, 50-850, 50-900, 50-950, 50-1000, 60-70, 60-90, 60-100, 60-250, 60-300, 60-350, 60-400, 60-450, 60-500, 60-550, 60-600, 60-650, 60-700, 60-750, 60-800, 60-850, 60-900, 60-950, 60-1000, 70-90, 70-100, 70-250, 70-300, 70-350, 70-400, 70-450, 70-500, 70-550, 70-600, 70-650, 70-700, 70-750, 70-800, 70-850, 70-900, 70-950, 70-1000, 80-90, 80-100, 80-250, 80-300, 80-350, 80-400, 80-450, 80-500, 80-550, 80-600, 80-650, 80-700, 80-750, 80-800, 80-850, 80-900, 80-950, 80-1000, 90-100, 90-250, 90-300, 90-350, 90-400, 90-450, 90-500, 90-550, 90-600, 90-650, 90-700, 90-750, 90-800, 90-850, 90-900, 90-950, 90-1000, 100-250, 100-300, 100-350, 100-400, 100-450, 100-500, 100-550, 100-600, 100-650, 100-700, 100-750, 100-800, 100-850, 100-900, 100-950, 100-1000, 150-250, 150-300, 150-350, 150-400, 150-450, 150-500, 150-550, 150-600, 150-650, 150-700, 150-750, 150-800, 150-850, 150-900, 150-950, 150-1000, 200-250, 200-300, 200-350, 200-400, 200-450, 200-500, 200-550, 200-600, 200-650, 200-700, 200-750, 200-800, 200-850, 200-900, 200-950, 200-1000, 250-300, 250-350, 250-400, 250-450, 250-500, 250-550, 250-600, 250-650, 250-700, 250-750, 250-800, 250-850, 250-900, 250-950, 250-1000, 300-350, 300-400, 300-450, 300-500, 300-550, 300-600, 300-650, 300-700, 300-750, 300-800, 300-850, 300-900, 300-950, 300-1000, 350-400, 350-450, 350-500, 350-550, 350-600, 350-650, 350-700, 350-750, 350-800, 350-850, 350-900, 350-950, 350-1000, 400-450, 400-500, 400-550, 400-600, 400-650, 400-700, 400-750, 400-800, 400-850, 400-900, 400-950, 400-1000, 450-500, 450-550, 450-600, 450-650, 450-700, 450-750, 450-800, 450-850, 450-900, 450-950, 450-1000, 500-550, 500-600, 500-650, 500-700, 500-750, 500-800, 500-850, 500-900, 500-950, 500-1000, 550-600, 550-650, 550-700, 550-750, 550-800, 550-850, 550-900, 550-950, 550-1000, 600-650, 600-700, 600-750, 600-800, 600-850, 600-900, 600-950, 600-1000, 650-700, 650-750, 650-800, 650-850, 650-900, 650-950, 650-1000, 700-750, 700-800, 700-850, 700-900, 700-950, 700-1000, 750-800, 750-850, 750-900, 750-950, 750-1000, 800-850, 800-900, 800-950, 800-1000, 850-900, 850-950, 850-1000, 900-950, 900-1000, 950-1000 or over 1000 nucleotides.

In some embodiments, the identifier sequence or moiety may produce a signal that is detectable immediately after administration. In some embodiments, the identifier sequence or moiety may produce a signal that is detectable for an indefinite amount of time after administration. In some embodiments, the identifier sequence or moiety may produce a signal that is detectable for more than 1 day, 2 days, 3 days, 4 days, 5 days, 6 days or 7 days post administration. In some embodiments, the identifier sequence or moiety may produce a signal that is detectable for about 1 to 24 hours. As a non-limiting example, the signal may be detectable for about 1 to 6, 1 to 12, 1 to 18, 6 to 12, 6 to 18, 6 to 24, or 18 to 24 hours, or 1, 2, 3, 4, 5, 6, 7, 8, 9, 10, 11, 12, 13, 14, 15, 16, 17, 18, 19, 20, 21, 22, 23, or 24 hours. In some embodiments, the identifier sequence or moiety may produce a signal that is detectable for about 1-60 minutes such as, but not limited to, 1-5, 1-10, 1-20, 1-30, 1-40, 1-50, 10-20, 10-30, 10-40, 10-50, 10-60, 20-30, 20-40, 20-50, 20-60, 30-40, 30-50, 30-60, 40-50, 40-60, or 50-60 minutes, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 minutes. In some embodiments, the identifier sequence or moiety may produce a signal that is detectable for less than 1 minute post administration.

In some embodiments, the identifier sequence or moiety may produce a signal that is detectable from outside the body of a subject. In some embodiments, the identifier sequence or moiety may produce a signal that is detectable from via non-invasive imagery techniques, for example from outside a subject's organs or tissues but within the subject's body. In some embodiments, the identifier sequence or moiety may produce a signal that is detectable on a macroscopic level. In some embodiments, the identifier sequence or moiety may produce a signal that is detectable on the microscopic level. In some embodiments, the identifier sequence or moiety may produce a signal that is detectable on the nanoscopic level. In some embodiments, the identifier sequence or moiety may produce a signal that is only detectable after target cells are harvested and assayed, for non-limiting example via mass spectrometer, electrophoresis, flow cytometry, or deep sequencing.

In some embodiments, the delivery vehicle comprises or is operably linked to an identifier moiety.

In some embodiments, the delivery vehicle comprises or is operably linked to an identifier moiety that binds to an immune cell antigen. As a non-limiting example, the immune cell antigen may be a T cell antigen such as CD2, CD3, CD5, CD7, CD8, CD4, beta 7 integrin, beta 2 integrin, and C1q. As a non-limiting example, the immune cell antigen may be a NK cell, an NKT cell, a macrophage or a neutrophil. As a non-limiting example, the immune cell antigen may be a macrophage antigen such as mannose receptor, CD206 and C1q.

In some embodiments, the delivery vehicle comprises or is operably linked to an identifier moiety which is a small molecule that binds to an ectoenzyme on an immune cell. The ectoenzyme may be, but is not limited to, CD38, CD73, adenosine 2a receptor and adenosine 2b receptor.

In some embodiments, the delivery vehicle comprises or is operably linked to an identifier moiety which is a small molecule such as, but not limited to, mannose, lectin, acivicin, biotin, or digoxigenin.

In some embodiments, the delivery vehicle comprises or is operably linked to an identifier moiety which is a single chain Fv (scFv) fragment, nanobody, peptide, peptide-based macrocycle, minibody, small molecule ligand (e.g., folate, arginylglycylaspartic acid (RGD), or phenol-soluble modulin alpha 1 peptide (PSMA1)), heavy chain variable region, light chain variable region or fragment thereof.

Tracking System: Fluorescence

In some embodiments, the at least one tracking system comprises an identifier sequence or moieties that is detectable by florescence.

In some embodiments, florescence is achieved via the inclusion of at least one fluorescent dye in the delivery vehicle. In some embodiments, the at least one fluorescent dye may be selected from, but is not limited to, fluorescein, TAMRA (carboxytetramethylrhodamine), Cy dyes, Texas red, HEX, JOE, Oregon green, rhodamine 6 G, coumarin, pyrene, and DiOC6 (3,3'-dihexyloxacarbocyanine iodide).

In some embodiments, florescence is achieved via the inclusion of at least one fluorescent protein in the, or associated with, the delivery vehicle. In some embodiments, at least one fluorescent protein is encoded in the benchmark construct or the benchmark construct comprises the fluorescent protein. Non-limiting examples of fluorescent protein include Green Fluorescent Protein (GFP), Yellow Fluorescent Protein (YFP), Red Fluorescent Protein (RFP), Sirius, excitable blue fluorescent protein (EBFP2), cyan fluorescent protein (CFP), Cerulean, excitable green fluorescent protein (EGFP), excitable yellow fluorescent protein (EYFP), mOrange, mCherry, mPlum, NIR, iRFP, EosFP, PamCherry, Dronpa, Dreiklang, asFP595, mMaple, mGeo, mEos2, Dendra2, psCFP2, and 2,3,5,6-tetracarbazole-4-cyano-pyridine (CPy).

In some embodiments, florescence is achieved via the inclusion of at least one fluorescent nanoparticle associated with the delivery vehicle or the benchmark construct. In some embodiments, the fluorescent nanoparticle may be, but is not limited to, carbon dots, graphene quantum dots, gold nanorods, polymer-based nanoparticles, aggregation-induced emission dots, Conjugated Polymer nanoparticles (CP-dots), Gold nanospheres, Gold nano shells, Gold nanocages, and AIE pheromone.

In some embodiments, florescence is achieved via inclusion of at least one fluorescent lipid associated with or included in the delivery vehicle. In some embodiments, the fluorescent lipid may be, but is not limited to, DiR, DiD, DiO, and DiI, other members of the Di series of phospholipids, Bodipy, and FL-Sphingomyelin.

In some embodiments, florescence is achieved via the inclusion of at least one luciferase in or associated with the delivery vehicle. In some embodiments, at least one luciferase protein is encoded in the benchmark construct or the benchmark construct comprises the luciferase. Non-limiting examples of the types of luciferase which may be used include *Renilla* luciferase, *Gaussia* luciferase, Nanoluc luciferase, Firefly luciferase, and Click Beetle luciferases.

In some embodiments, florescence is achieved via inclusion of β-galactosidase (β-gal) associated with or included in the delivery vehicle. In some embodiments, at least one β-galactosidase (β-gal) protein is encoded in the benchmark construct or the benchmark construct comprises β-galactosidase (β-gal).

In some embodiments, florescence is achieved via inclusion of at least one quencher molecule associated with or included in the delivery vehicle. In some embodiments, florescence is achieved via inclusion of at least one quencher molecule associated with or encoded by the benchmark construct. Non-limiting examples of quencher molecules include dimethylaminophenylazobenzoic acid (DABCYL), QSY 7, Cu(II) ion, Dabcyl, QSY 35, BHQ-0, Eclipse, BHQ-1, QSY 9, BHQ-2, ElleQuencher, Iowa Black, QSY 21, and BHQ-3.

Tracking System: Fluorophores and Radioactive Phosphates

In some embodiments, the at least one tracking system comprises an identifier sequence or moieties that is a fluorophore or radioactive phosphate.

In some embodiments, the at least one tracking system comprises the inclusion of at least one fluorophore associated with or included in the delivery vehicle. In some embodiments, the at least one tracking system comprises the inclusion of at least one fluorophore associated with, encoded in or included in the benchmark construct. Non-limiting examples of fluorophores includes quantum dot and organic small molecule.

In some embodiments, the at least one tracking system comprises the inclusion of at least one quantum dot associated with or included in the delivery vehicle. In some embodiments, the at least one tracking system comprises the inclusion of at least one quantum dot associated with, encoded in or included in the benchmark construct. Non-limiting examples of quantum dots include CdSe/ZnS, CdTe/ZnS, CdTe/CdSe, CdSe/ZnTe, CdSe/CdTe/ZnSe, nAs/ZnSe, InAs/CdSe, InAs/InP, Cu:InP/ZnSe, InAsxP1-x/InP/ZnSe, CdS/CdSe, ZnSe/CdSe, ZnSe/InP/ZnS, ZnSe/InP/ZnS, CdTe/ZnSe, QD585, and QD655.

In some embodiments, the at least one tracking system comprises the inclusion of at least one organic small molecule associated with or included in the delivery vehicle. In some embodiments, the at least one tracking system comprises the inclusion of at least one organic small molecule associated with, encoded in or included in the benchmark construct. Non-limiting examples of organic small molecules include classes of Coumarins, Naphthalimides, Fluoresceins and rhodamines derivatives, BODIPY, Cyanines, xanthenes, oxazines, Oligothiophenes, and Phthalocyanine derivatives (PcDer). In some embodiments, the at least one organic small molecule may be selected from, but is not limited to, 7-dialkyl-amino-4-trifluoromethyl coumarin, rhodamine B, Coumarin 314, Lucifer Yellow CH, florescein, rhodamine 123, BODIPY FL NHS ester, Cy5, Rhodamine 6G, Silicon-rhodamine (SiR), Cy3, Cy5.5, Cy7, Cy2, ATT0655, ATTO680, ATTO700, Nitrobenzoxadiazole (NBD), 1,6-diphenyl-1,3,5-hexatriene (DPH), ABBERIOR™, ALEXA FLUOR™, ATTO™, DYLIGHT FLUOR™, ALEXA FLUOR 647™, and TOPFLUOR™.

In some embodiments, the at least one tracking system comprises the inclusion of at least one imaging contrast agent associated with or included in the delivery vehicle. In some embodiments, the at least one tracking system comprises the inclusion of at least one imaging contrast agent associated with, encoded in or included in the benchmark construct. Non-limiting examples of imaging contrast agents include gadolinium-based small molecules, gadolinium-encapsulated liposomes, manganese-based small molecules, and iron oxide nanoparticles.

In some embodiments, the at least one tracking system comprises the inclusion of at least one radiolabel associated with or included in the delivery vehicle. In some embodiments, the at least one tracking system comprises the inclusion of at least one radiolabel associated with, encoded in or included in the benchmark construct. Non-limiting examples of radiolabels include $^{111}$In, $^{99m}$Tc, $^{13}$N, $^{68}$Ga, $^{18}$F, 64Cu, $^{86}$Y, $^{76}$Br, $^{89}$Zr, $^{72}$As, 124I, $^{74}$As, fluorine-18, gallium-68, nitrogen-13, copper-64, bromine-76, iodine-125, arsenic-74, carbon-11, iodine-131, $^{153}$Sm, $^{177}$Lu, $^{186}$Re, $^{188}$Re, $^{198}$Au, and $^{225}$Ac.

In some embodiments, the at least one tracking system comprises the inclusion of at least one biotin associated with or included in the delivery vehicle.

In some embodiments, the at least one tracking system comprises the inclusion of at least one digoxygenin associated with or included in the delivery vehicle.

In some embodiments, the at least one tracking system comprises the inclusion of at least one dinitrophenyl (DNP) associated with or included in the delivery vehicle.

In some embodiments, the at least one tracking system comprises the inclusion of at least one Fluorescein associated with or included in the delivery vehicle.

In some embodiments, the at least one tracking system comprises the inclusion of at least one fucose associated with or included in the delivery vehicle.

In some embodiments, the at least one tracking system comprises the inclusion of at least one amine associated with or included in the delivery vehicle.

In some embodiments, the at least one tracking system comprises the inclusion of at least one Texas Red® associated with or included in the delivery vehicle.

In some embodiments, the at least one tracking system comprises the inclusion of at least one biotin associated with, encoded in or included in the benchmark construct.

In some embodiments, the at least one tracking system comprises the inclusion of at least one digoxygenin associated with, encoded in or included in the benchmark construct.

In some embodiments, the at least one tracking system comprises the inclusion of at least one dinitrophenyl (DNP) associated with, encoded in or included in the benchmark construct.

In some embodiments, the at least one tracking system comprises the inclusion of at least one Fluorescein associated with, encoded in or included in the benchmark construct.

In some embodiments, the at least one tracking system comprises the inclusion of at least one fucose associated with, encoded in or included in the benchmark construct.

In some embodiments, the at least one tracking system comprises the inclusion of at least one amine associated with, encoded in or included in the benchmark construct.

In some embodiments, the at least one tracking system comprises the inclusion of at least one Texas Red® associated with, encoded in or included in the benchmark construct.

In some embodiments, the at least one tracking system comprises the inclusion of at least one reporter sequence or protein associated with or included in the delivery vehicle. In some embodiments, the at least one tracking system comprises the inclusion of at least one reporter sequence or protein associated with, encoded in or included in the benchmark construct. Non-limiting examples of reporter sequence or protein include eGFP, luciferase, gene editor (e.g. cas9 edit, DNA readout), ox-40, beta6 integrin, CD45, a surface marker with a HA tag, flag tag with or without a TEV protease site, or any combination thereof.

In some embodiments, the at least one tracking system comprises the inclusion of at least one functional sequence or protein associated with or included in the delivery vehicle. In some embodiments, the at least one tracking system comprises the inclusion of at least one functional sequence or protein associated with, encoded in or included in the benchmark construct. Non-limiting examples of functional sequence or protein include fluorescent protein, a surface protein, Cre-Recombinase, CRISPR/CAS system, surface protein with an epitope tag (e.g., HA, FLAG, etc.) or any combination thereof In some embodiments, the at least one tracking system comprises the inclusion of at least one functional sequence or protein that comprises a protease cleavage site (e.g., TEV) which may be associated with or included in the delivery vehicle. In some embodiments, the at least one tracking system comprises the inclusion of at least one functional sequence or protein that comprises a protease cleavage site (e.g., TEV) which may be associated with, encoded in or included in the benchmark construct.

In some embodiments, the at least one tracking system comprises the inclusion of at least one functional sequence or protein that comprises an affinity tag (e.g. 3×HA, FLAG, His) which may be associated with or included in the delivery vehicle. In some embodiments, the at least one tracking system comprises the inclusion of at least one functional sequence or protein that comprises an affinity tag (e.g. 3×HA, FLAG, His) which may be associated with, encoded in or included in the benchmark construct.

V. Pharmaceutical Composition and Route of Administration

Pharmaceutical Compositions and Formulations

The originator constructs, benchmark constructs, and targeting systems can be formulated using one or more excipients to: (1) increase stability; (2) increase cell transfection or transduction; (3) permit the sustained or delayed expression of the payload; (4) alter the biodistribution (e.g., target the viral particle to specific tissues or cell types); (5) increase the translation of encoded protein; (6) alter the release profile of encoded protein; and/or (7) allow for regulatable expression of the cargo and/or payload.

Formulations can include, without limitation, saline, liposomes, lipid nanoparticles, polymers, peptides, proteins, cells transfected with viral vectors (e.g., for transfer or transplantation into a subject) and combinations thereof.

Formulations of the pharmaceutical compositions described herein may be prepared by any method known or hereafter developed in the art of pharmacology. As used herein the term "pharmaceutical composition" refers to compositions comprising at least one active ingredient and optionally one or more pharmaceutically acceptable excipients.

In general, such preparatory methods include the step of associating the active ingredient with an excipient and/or one or more other accessory ingredients. As used herein, the phrase "active ingredient" generally refers either to an originator construct or benchmark construct with a payload region or cargo or payload as described herein.

Formulations of the originator constructs, benchmark constructs, and targeting systems and pharmaceutical compositions described herein may be prepared by any method known or hereafter developed in the art of pharmacology. In general, such preparatory methods include the step of bringing the active ingredient into association with an excipient and/or one or more other accessory ingredients, and then, if necessary and/or desirable, dividing, shaping and/or packaging the product into a desired single- or multi-dose unit.

A pharmaceutical composition in accordance with the present disclosure may be prepared, packaged, and/or sold in bulk, as a single unit dose, and/or as a plurality of single unit doses. As used herein, a "unit dose" refers to a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

In some embodiments, a pharmaceutically acceptable excipient may be at least 95%, at least 96%, at least 97%, at least 98%, at least 99%, or 100% pure. In some embodiments, an excipient is approved for use for humans and for veterinary use. In some embodiments, an excipient may be approved by United States Food and Drug Administration. In some embodiments, an excipient may be of pharmaceutical grade. In some embodiments, an excipient may meet the standards of the United States Pharmacopoeia (USP), the European Pharmacopoeia (EP), the British Pharmacopoeia, and/or the International Pharmacopoeia.

Relative amounts of the active ingredient, the pharmaceutically acceptable excipient, and/or any additional ingredients in a pharmaceutical composition in accordance with the present disclosure may vary, depending upon the identity, size, and/or condition of the subject being treated and further depending upon the route by which the composition is to be administered. For example, the composition may comprise between 0.1% and 99% (w/w) of the active ingredient. By way of example, the composition may comprise between 0.1% and 100%, e.g., between 0.5 and 50%, between 1-30%, between 5-80%, or at least 80% (w/w) active ingredient.

In one aspect, the present disclosure further provides delivery systems for delivery of a therapeutic payload disclosed herein. In some embodiments, a delivery system suitable for delivery of the therapeutic payload disclosed herein comprises a lipid nanoparticle (LNP) formulation.

In some embodiments, an LNP of the present disclosure comprises an ionizable lipid, a structural lipid, a PEGylated lipid (aka PEG lipid), and a phospholipid. In alternative embodiments, an LNP comprises an ionizable lipid, a structural lipid, a PEGylated lipid (aka PEG lipid), and a zwitterionic amino acid lipid. In some embodiments, an LNP further comprises a $5^{th}$ lipid, besides any of the aforementioned lipid components. In some embodiments, the LNP encapsulates one or more elements of the active agent of the present disclosure. In some embodiments, an LNP further comprises a targeting moiety covalently or non-covalently bound to the outer surface of the LNP. In some embodiments, the targeting moiety is a targeting moiety that binds to, or otherwise facilitates uptake by, cells of a particular organ system.

In some embodiments, an LNP has a diameter of at least about 20 nm, 30 nm, 40 nm, 50 nm, 60 nm, 70 nm, 80 nm, or 90 nm. In some embodiments, an LNP has a diameter of less than about 100 nm, 110 nm, 120 nm, 130 nm, 140 nm, 150 nm, or 160 nm. In some embodiments, an LNP has a diameter of less than about 100 nm. In some embodiments, an LNP has a diameter of less than about 90 nm. In some embodiments, an LNP has a diameter of less than about 80 nm. In some embodiments, an LNP has a diameter of about 60-100 nm. In some embodiments, an LNP has a diameter of about 75-80 nm.

In some embodiments, the lipid nanoparticle compositions of the present disclosure are described according to the respective molar ratios of the component lipids in the formulation. As a non-limiting example, the mol-% of the ionizable lipid may be from about 10 mol-% to about 80 mol-%. As a non-limiting example, the mol-% of the ionizable lipid may be from about 20 mol-% to about 70 mol-%. As a non-limiting example, the mol-% of the ionizable lipid may be from about 30 mol-% to about 60 mol-%. As a non-limiting example, the mol-% of the ionizable lipid may be from about 35 mol-% to about 55 mol-%. As a non-limiting example, the mol-% of the ionizable lipid may be from about 40 mol-% to about 50 mol-%.

In some embodiments, the mol-% of the phospholipid may be from about 1 mol-% to about 50 mol-%. In some embodiments, the mol-% of the phospholipid may be from about 2 mol-% to about 45 mol-%. In some embodiments, the mol-% of the phospholipid may be from about 3 mol-% to about 40 mol-%. In some embodiments, the mol-% of the phospholipid may be from about 4 mol-% to about 35 mol-%. In some embodiments, the mol-% of the phospholipid may be from about 5 mol-% to about 30 mol-%. In some embodiments, the mol-% of the phospholipid may be from about 10 mol-% to about 20 mol-%. In some embodiments, the mol-% of the phospholipid may be from about 5 mol-% to about 20 mol-%.

In some embodiments, the mol-% of the structural lipid may be from about 10 mol-% to about 80 mol-%. In some embodiments, the mol-% of the structural lipid may be from about 20 mol-% to about 70 mol-%. In some embodiments, the mol-% of the structural lipid may be from about 30 mol-% to about 60 mol-%. In some embodiments, the mol-% of the structural lipid may be from about 35 mol-% to about 55 mol-%. In some embodiments, the mol-% of the structural lipid may be from about 40 mol-% to about 50 mol-%.

In some embodiments, the mol-% of the PEG lipid may be from about 0.1 mol-% to about 10 mol-%. In some embodiments, the mol-% of the PEG lipid may be from about 0.2 mol-% to about 5 mol-%. In some embodiments, the mol-% of the PEG lipid may be from about 0.5 mol-% to about 3 mol-%. In some embodiments, the mol-% of the PEG lipid may be from about 1 mol-% to about 2 mol-%. In some embodiments, the mol-% of the PEG lipid may be about 1.5 mol-%.

Excipients and Diluents

Excipients, as used herein, include, but are not limited to, any and all solvents, dispersion media, diluents, or other liquid vehicles, dispersion or suspension aids, surface active agents, isotonic agents, thickening or emulsifying agents, preservatives, and the like, as suited to the particular dosage form desired. Various excipients for formulating pharmaceutical compositions and techniques for preparing the composition are known in the art (see Remington: The Science and Practice of Pharmacy, 21st Edition, A. R. Gennaro, Lippincott, Williams & Wilkins, Baltimore, MD, 2006; incorporated herein by reference in its entirety). The use of a conventional excipient medium may be contemplated within the scope of the present disclosure, except insofar as any conventional excipient medium may be incompatible with a substance or its derivatives, such as by producing any undesirable biological effect or otherwise interacting in a deleterious manner with any other component(s) of the pharmaceutical composition.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and/or combinations thereof.

Ionizable Lipids

In some embodiments, an LNP disclosed herein comprises an ionizable lipid. In some embodiments, an LNP comprises two or more ionizable lipids. In some embodiments, the ionizable lipid is any ionizable lipid disclosed herein, or any combinations thereof.

Structural Lipids

In some embodiments, an LNP comprises a structural lipid. Structural lipids can be selected from the group consisting of, but are not limited to, cholesterol, fecosterol, fucosterol, beta sitosterol, sitosterol, ergosterol, campesterol, stigmasterol, brassicasterol, tomatidine, cholic acid, sitostanol, litocholic acid, tomatine, ursolic acid, alpha-tocopherol, Vitamin D3, Vitamin D2, Calcipotriol, botulin, lupeol, oleanolic acid, beta-sitosterol-acetate and mixtures thereof. In some embodiments, the structural lipid is cholesterol. In some embodiments, the structural lipid is a cholesterol analogue disclosed by Patel, et al., Nat Commun., 11, 983 (2020), which is incorporated herein by reference in its entirety. In some embodiments, the structural lipid includes cholesterol and a corticosteroid (such as prednisolone, dexamethasone, prednisone, and hydrocortisone), or any combinations thereof. In some embodiments, a structural lipid is described in international patent application WO2019152557A1, which is incorporated herein by reference in its entirety.

In some embodiments, a structural lipid is a cholesterol analog. Using a cholesterol analog may enhance endosomal escape as described in Patel et al., Naturally-occurring cholesterol analogues in lipid nanoparticles induce polymorphic shape and enhance intracellular delivery of mRNA, Nature Communications (2020), which is incorporated herein by reference.

In some embodiments, a structural lipid is a phytosterol. Using a phytosterol may enhance endosomal escape as described in Herrera et al., Illuminating endosomal escape of polymorphic lipid nanoparticles that boost mRNA delivery, Biomaterials Science (2020), which is incorporated herein by reference.

In some embodiments, a structural lipid contains plant sterol mimetics for enhanced endosomal release.

PEGylated Lipids

A PEGylated lipid is a lipid modified with polyethylene glycol. In some embodiments, the LNP comprises a compound of Formula I or a pharmaceutically acceptable salt thereof, as described herein above. In some embodiments, the LNP comprises a compound of Formula II or a pharmaceutically acceptable salt thereof, as described herein above. In some embodiments, the LNP comprises a compound set forth in Table (I), as described herein above.

In some embodiments, an LNP comprises an additional PEGylated lipid or PEG-modified lipid. A PEGylated lipid may be selected from the non-limiting group consisting of PEG-modified phosphatidylethanolamines, PEG-modified phosphatidic acids, PEG-modified ceramides, PEG-modified dialkylamines, PEG-modified diacylglycerols, PEG-modified dialkylglycerols, and mixtures thereof. For example, a PEG lipid may be PEG-c-DOMG, PEG-DMG, PEG-DLPE, PEG-DMPE, PEG-DPPC, or a PEG-DSPE lipid.

In some embodiments, the LNP comprises a PEGylated lipid disclosed in one of US 2019/0240354; US 2010/0130588; US 2021/0087135; WO 2021/204179; US 2021/0128488; US 2020/0121809; US 2017/0119904; US 2013/0108685; US 2013/0195920; US 2015/0005363; US 2014/0308304; US 2013/0053572; WO 2019/232095A1; WO 2021/077067; WO 2019/152557; US 2015/0203446; US 2017/0210697; US 2014/0200257; or WO 2019/089828A1, each of which is incorporated by reference herein in their entirety.

In some embodiments, the LNP comprises a PEGylated lipid substitute in place of the PEGylated lipid. All embodiments disclosed herein that contemplate a PEGylated lipid should be understood to also apply to PEGylated lipid substitutes. In some embodiments, the LNP comprises a polysarcosine-lipid conjugate, such as those disclosed in US 2022/0001025 A1, which is incorporated by reference herein in its entirety.

Phospholipids

In some embodiments, an LNP of the present disclosure comprises a phospholipid. Phospholipids useful in the compositions and methods may be selected from the non-limiting group consisting of 1,2-distearoyl-sn-glycero-3-phosphocholine (DSPC), 1,2-dioleoyl-sn-glycero-3-phosphoethanolamine (DOPE), 1,2-dilinoleoyl-sn-glycero-3-phosphocholine (DLPC), 1,2-dimyristoyl-sn-glycero-phosphocholine (DMPC), 1.2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 1-palmitoyl-2-oleoyl-sn-glycero-3-phosphocho line (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), sodium (S)-2-ammonio-3-((((R)-2-(oleoyloxy)-3-(stearoyloxy)propoxy)oxidophosphoryl)oxy)propanoate (L-α-phosphatidylserine; Brain PS), dimyristoyl phosphatidylcholine (DMPC), dimyristoyl phosphoethanolamine (DMPE), dimyristoylphosphatidylglycerol (DMPG), dioleoyl-phosphatidylethanolamine4-(N-maleimidomethyl)-cyclohexane-1-carboxylate (DOPE-mal), dioleoylphosphatidylglycerol (DOPG), 1,2-dioleoyl-sn-glycero-3-(phospho-L-serine) (DOPS), a cell-fusogenic phospholipid (DPhPE), dipalmitoylphosphatidylethanolamine (DPPE), dipalmitoylphosphatidylglycerol (DPPG), dipalmitoylphosphatidylserine (DPPS), distearoylphosphatidylcholine (DSPC), distearoyl-phosphatidyl-ethanolamine (DSPE), distearoyl phosphoethanolamineimidazole (DSPEI), 1,2-diundecanoyl-sn-glycero-phosphocholine (DUPC), egg phosphatidylcholine (EPC), 1,2-dioleoyl-sn-glycero-3-phosphate (18:1 PA; DOPA), ammonium bis((S)-2-hydroxy-3-(oleoyloxy)propyl) phosphate (18:1 DMP; LBPA), 1,2-dioleoyl-sn-glycero-3-phospho-(1'-myo-inositol) (DOPI; 18:1 PI), 1,2-distearoyl-sn-glycero-3-phospho-L-serine (18:0 PS), 1,2-dilinoleoyl-sn-glycero-3-phospho-L-serine (18:2 PS), 1-palmitoyl-2-oleoyl-sn-glycero-3-phospho-L-serine (16:0-18:1 PS; POPS), 1-stearoyl-2-oleoyl-sn-glycero-3-phospho-L-serine (18:0-18:1 PS), 1-stearoyl-2-linoleoyl-sn-glycero-3-phospho-L-serine (18:0-18:2 PS), 1-oleoyl-2-hydroxy-sn-glycero-3-phospho-L-serine (18:1 Lyso PS), 1-stearoyl-2-hydroxy-sn-glycero-3-phospho-L-serine (18:0 Lyso PS), and sphingomyelin. In some embodiments, an LNP includes DSPC. In certain embodiments, an LNP includes DOPE. In some embodiments, an LNP includes both DSPC and DOPE.

In some embodiments, a phospholipid tail may be modified in order to promote endosomal escape as described in U.S. 2021/0121411, which is incorporated herein by reference.

In some embodiments, the LNP comprises a phospholipid disclosed in one of US 2019/0240354; US 2010/0130588; US 2021/0087135; WO 2021/204179; US 2021/0128488; US 2020/0121809; US 2017/0119904; US 2013/0108685; US 2013/0195920; US 2015/0005363; US 2014/0308304; US 2013/0053572; WO 2019/232095A1; WO 2021/077067; WO 2019/152557; US 2017/0210697; or WO 2019/089828A1, each of which is incorporated by reference herein in their entirety.

In some embodiments, phospholipids disclosed in US 2020/0121809 have the following structure:

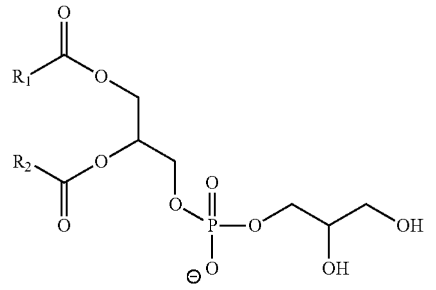

wherein $R_1$ and $R_2$ are each independently a branched or straight, saturated or unsaturated carbon chain (e.g., alkyl, alkenyl, alkynyl).

Targeting Moieties

In some embodiments, the lipid nanoparticle further comprises a targeting moiety. The targeting moiety may be an antibody or a fragment thereof. The targeting moiety may be capable of binding to a target antigen.

In some embodiments, the pharmaceutical composition comprises a targeting moiety that is operably connected to a lipid nanoparticle. In some embodiments, the targeting moiety is capable of binding to a target antigen. In some embodiments, the target antigen is expressed in a target organ. In some embodiments, the target antigen is expressed more in the target organ than it is in the liver.

In some embodiments, the targeting moiety is an antibody as described in WO2016189532A1, which is incorporated herein by reference. For example, in some embodiments, the targeted particles are conjugated to a specific anti-CD38 monoclonal antibody (mAb), which allows specific delivery of the siRNAs encapsulated within the particles at a greater percentage to B-cell lymphocytes malignancies (such as MCL) than to other subtypes of leukocytes.

In some embodiments, the lipid nanoparticles may be targeted when conjugated/attached/associated with a targeting moiety such as an antibody.

Zwitterionic Amino Lipids

In some embodiments, an LNP comprises a zwitterionic lipid. In some embodiments, an LNP comprising a zwitterionic lipid does not comprise a phospholipid.

Zwitterionic amino lipids have been shown to be able to self-assemble into LNPs without phospholipids to load, stabilize, and release mRNAs intracellular as described in U.S. Patent Application 20210121411, which is incorporated herein by reference in its entirety. Zwitterionic, ionizable cationic and permanently cationic helper lipids enable tissue-selective mRNA delivery and CRISPR-Cas9 gene editing in spleen, liver and lungs as described in Liu et al., Membrane-destablizing ionizable phospholipids for organ-selective mRNA delivery and CRISPR-Cas gene editing, Nat Mater. (2021), which is incorporated herein by reference in its entirety.

The zwitterionic lipids may have head groups containing a cationic amine and an anionic carboxylate as described in Walsh et al., Synthesis, Characterization and Evaluation of Ionizable Lysine-Based Lipids for siRNA Delivery, Bioconjug Chem. (2013), which is incorporated herein by reference in its entirety. Ionizable lysine-based lipids containing a lysine head group linked to a long-chain dialkylamine through an amide linkage at the lysine α-amine may reduce immunogenicity as described in Walsh et al., Synthesis, Characterization and Evaluation of Ionizable Lysine-Based Lipids for siRNA Delivery, Bioconjug Chem. (2013).

Additional Lipid Components

In some embodiments, the LNP compositions of the present disclosure further comprise one or more additional lipid components capable of influencing the tropism of the LNP. In some embodiments, the LNP further comprises at least one lipid selected from DDAB, EPC, 14PA, 18BMP, DODAP, DOTAP, and C12-200 (see Cheng, et al. *Nat Nanotechnol.* 2020 April; 15(4): 313-320.; Dillard, et al. *PNAS* 2021 Vol. 118 No. 52.).

Polynucleotides

In some embodiments, an LNP of the present disclosure contains an active agent. In some embodiments, an active agent is a polynucleotide. In some embodiments, a LNP is capable of delivering a polynucleotide to a target organ. A polynucleotide, in its broadest sense of the term, includes any compound and/or substance that is or can be incorporated into an oligonucleotide chain. Exemplary polynucleotides for use in accordance with the present disclosure include, but are not limited to, one or more of deoxyribonucleic acid (DNA), ribonucleic acid (RNA) including messenger mRNA (mRNA), hybrids thereof, RNAi-inducing agents, RNAi agents, siRNAs, shRNAs, miRNAs, antisense RNAs, ribozymes, catalytic DNA, RNAs that induce triple helix formation, aptamers, vectors, etc. RNAs useful in the compositions and methods described herein can be selected from the group consisting of but are not limited to, shortimers, antagomirs, antisense, ribozymes, short interfering RNA (siRNA), asymmetrical interfering RNA (aiRNA), microRNA (miRNA), Dicer substrate RNA (dsRNA), short hairpin RNA (shRNA), transfer RNA (tRNA), messenger RNA (mRNA), and mixtures thereof. In some embodiments, a polynucleotide is mRNA. In some embodiments, a polynucleotide is circular RNA. In some embodiments, a polynucleotide encodes a protein. A polynucleotide may encode any polypeptide of interest, including any naturally or non-naturally occurring or otherwise modified polypeptide. A polypeptide may be of any size and may have any secondary structure or activity. In some embodiments, a polypeptide encoded by an mRNA may have a therapeutic effect when expressed in a cell.

In other embodiments, a polynucleotide is an siRNA. An siRNA may be capable of selectively knocking down or down regulating expression of a gene of interest. For example, an siRNA could be selected to silence a gene associated with a particular disease, disorder, or condition upon administration to a subject in need thereof of a nanoparticle composition including the siRNA. An siRNA may comprise a sequence that is complementary to an mRNA sequence that encodes a gene or protein of interest. In some embodiments, the siRNA may be an immunomodulatory siRNA.

In some embodiments, a polynucleotide is an shRNA or a vector or plasmid encoding the same. An shRNA may be produced inside a target cell upon delivery of an appropriate construct to the nucleus. Constructs and mechanisms relating to shRNA are well known in the relevant arts.

A polynucleotide may include a first region of linked nucleosides encoding a polypeptide of interest (e.g., a coding region), a first flanking region located at the 5'-terminus of the first region (e.g., a 5'-UTR), a second flanking region located at the 3'-terminus of the first region (e.g., a 3'-UTR), at least one 5'-cap region, and a 3'-stabilizing region. In some embodiments, a polynucleotide further includes a poly-A region or a Kozak sequence (e.g., in the 5'-UTR). In some cases, polynucleotides may contain one or more intronic nucleotide sequences capable of being excised from the polynucleotide. In some embodiments, a polynucleotide (e.g., an mRNA) may include a 5'cap structure, a chain terminating nucleotide, a stem loop, a polyA sequence, and/or a polyadenylation signal. Any one of the regions of a nucleic acid may include one or more alternative components (e.g., an alternative nucleoside). For example, the 3'-stabilizing region may contain an alternative nucleoside such as an L-nucleoside, an inverted thymidine, or a 2'-O-methyl nucleoside and/or the coding region, 5'-UTR, 3'-UTR, or cap region may include an alternative nucleoside such as a 5-substituted uridine (e.g., 5-methoxyuridine), a 1-substituted pseudouridine (e.g., 1-methyl pseudouridine or 1-ethyl-pseudouridine), and/or a 5-substituted cytidine (e.g., 5-methyl-cytidine). In some embodiments, a polynucleotide contains only naturally occurring nucleosides.

In some cases, a polynucleotide is greater than 30 nucleotides in length. In another embodiment, the poly nucleotide molecule is greater than 35 nucleotides in length. In another embodiment, the length is at least 40 nucleotides. In another embodiment, the length is at least 45 nucleotides. In another embodiment, the length is at least 55 nucleotides. In another embodiment, the length is at least 50 nucleotides. In another embodiment, the length is at least 60 nucleotides. In another embodiment, the length is at least 80 nucleotides. In another embodiment, the length is at least 90 nucleotides. In another embodiment, the length is at least 100 nucleotides. In another embodiment, the length is at least 120 nucleotides. In another embodiment, the length is at least 140 nucleotides. In another embodiment, the length is at least 160 nucleotides. In another embodiment, the length is at least 180 nucleotides. In another embodiment, the length is at least 200 nucleotides. In another embodiment, the length is at least 250 nucleotides. In another embodiment, the length is at least 300 nucleotides. In another embodiment, the length is at least 350 nucleotides. In another embodiment, the length is at least 400 nucleotides. In another embodiment, the length is at least 450 nucleotides. In another embodiment, the length is at least 500 nucleotides. In another embodiment, the length is at least 600 nucleotides. In another embodiment, the length is at least 700 nucleotides. In another embodiment, the length is at least 800 nucleotides. In another embodiment, the length is at least 900 nucleotides. In another embodiment, the length is at least 1000 nucleotides. In another embodiment, the length is at least 1100 nucleotides. In another embodiment, the length is at least 1200 nucleotides. In another embodiment, the length is at least 1300 nucleotides. In another embodiment, the length is at least 1400 nucleotides. In another embodiment, the length is at least 1500 nucleotides. In another embodiment, the length is at least 1600 nucleotides. In another embodiment, the length is at least 1800 nucleotides. In another embodiment, the length is at least 2000 nucleotides. In another embodiment, the length is at least 2500 nucleotides. In another embodiment, the length is at least 3000 nucleotides. In another embodiment, the length is at least 4000 nucleotides. In another embodiment, the length is at least 5000 nucleotides, or greater than 5000 nucleotides.

In some embodiments, a polynucleotide molecule, formula, composition or method associated therewith comprises one or more polynucleotides comprising features as described in WO2002/098443, WO2003/051401, WO2008/052770, WO2009/127230, WO2006/122828, WO2008/083949, WO2010/088927, WO2010/037539, WO2004/004743, WO2005/016376, WO2006/024518, WO2007/095,976, WO2008/014979, WO2008/077592, WO2009/030481, WO2009/095226, WO2011/069586, WO2011/026641, WO2011/144358, WO2012/019780, WO2012/013326, WO2012/089338, WO2012/113513, WO2012/116811, WO2012/116810, WO2013/113502, WO2013/113501, WO2013/113736, WO2013/143698, WO2013/143699, WO2013/143700, WO2013/120626, WO2013/120627, WO2013/120628, WO2013/120629, WO2013/174409, WO2014/127917, WO2015/024669, WO2015/024668, WO2015/024667, WO2015/024665, WO2015/024666, WO2015/024664, WO2015/101415, WO2015/101414, WO2015/024667, WO2015/062738, WO2015/101416, all of which are incorporated by reference herein.

Polynucleotides, such as circular RNA, may contain an internal ribosome entry site (IRES). An IRES may act as the sole ribosome binding site, or may serve as one of multiple ribosome binding sites of an mRNA. A polynucleotide containing more than one functional ribosome binding site may encode several peptides or polypeptides that are translated independently by the ribosomes (e.g., multicistronic mRNA). When polynucleotides are provided with an IRES, further optionally provided is a second translatable region. Examples of IRES sequences that can be used according to the present disclosure include without limitation, those from picornaviruses (e.g., FMDV), pest viruses (CFFV), polio viruses (PV), encephalomyocarditis viruses (ECMV), foot-and mouth disease viruses (FMDV), hepatitis C viruses (HCV), classical Swine fever viruses (CSFV), murine leukemia virus (MLV), simian immune deficiency viruses (SIV) or cricket paralysis viruses (CrPV).

In some embodiments, a polynucleotide comprises one or more microRNA binding sites. In some embodiments, a microRNA binding site is recognized by a microRNA in a non-target organ. In some embodiments, a microRNA binding site is recognized by a microRNA in the liver. In some embodiments, a microRNA binding site is recognized by a microRNA in hepatic cells.

Inactive Ingredients

In some embodiments, formulations described herein may comprise at least one inactive ingredient. As used herein, the term "inactive ingredient" refers to one or more agents that do not contribute to the activity of the active ingredient of the pharmaceutical composition included in formulations. In some embodiments, all, none or some of the inactive ingredients which may be used in the formulations of the present disclosure may be approved by the US Food and Drug Administration (FDA).

In some embodiments, formulations disclosed herein may include cations or anions. The formulations include metal cations such as, but not limited to, $Zn^{2+}$, $Ca^{2+}$, $Cu^{2+}$, $Mn^{2+}$, $Mg^{2+}$, and combinations thereof. As a non-limiting example, formulations may include polymers and complexes with a metal cation.

Formulations of the disclosure may also include one or more pharmaceutically acceptable salts. As used herein, "pharmaceutically acceptable salts" refers to derivatives of the disclosed compounds wherein the parent compound is modified by converting an existing acid or base moiety to its salt form (e.g., by reacting the free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, acetic acid, adipate, alginate, ascorbate, aspartate, benzenesulfonate, benzene sulfonic acid, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. The pharmaceutically acceptable salts of the present disclosure include the conventional non-toxic salts of the parent compound formed, for example, from non-toxic inorganic or organic acids.

Solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate."

Routes of Administration

The originator constructs, benchmark constructs, and targeting systems described herein may be administered by any delivery route which results in a therapeutically effective outcome. These include, but are not limited to, enteral (into the intestine), gastroenteral, epidural (into the dura mater), oral (by way of the mouth), transdermal, intracerebral (into the cerebrum), intracerebroventricular (into the cerebral ventricles), epicutaneous (application onto the skin), intradermal (into the skin itself), subcutaneous (under the skin), nasal administration (through the nose), intravenous (into a vein), intravenous bolus, intravenous drip, intra-arterial (into an artery), intramuscular (into a muscle), intracardiac (into the heart), intraosseous infusion (into the bone marrow), intrathecal (into the spinal canal), intraparenchymal (into brain tissue), intraperitoneal (infusion or injection into the peritoneum), intravesical infusion, intravitreal (through the eye), intracavernous injection (into a pathologic cavity) intracavitary (into the base of the penis), intravaginal administration, intrauterine, extra-amniotic administration, transdermal (diffusion through the intact skin for systemic distribution), transmucosal (diffusion through a mucous membrane), transvaginal, insufflation (snorting), sublingual, sublabial, enema, eye drops (onto the conjunctiva), ear drops, auricular (in or by way of the ear), buccal (directed toward the cheek), conjunctival, cutaneous, dental (to a tooth or teeth), electro-osmosis, endocervical, endosinusial, endotracheal, extracorporeal, hemodialysis, infiltration, interstitial, intra-abdominal, intra-amniotic, intra-articular, intrabiliary, intrabronchial, intrabursal, intracartilaginous (within a cartilage), intracaudal (within the cauda equine), intracisternal (within the cisterna magna cerebellomedularis), intracorneal (within the cornea), dental intracoronal, intracoronary (within the coronary arteries), intracorporus cavernosum (within the dilatable spaces of the corporus cavernosa of the penis), intradiscal (within a disc), intraductal (within a duct of a gland), intraduodenal (within the duodenum), intradural (within or beneath the dura), intraepidermal (to the epidermis), intraesophageal (to the esophagus), intragastric (within the stomach), intragingival (within the gingivae), intraileal (within the distal portion of the small intestine), intralesional (within or introduced directly to a localized lesion), intraluminal (within a lumen of a tube), intralymphatic (within the lymph), intramedullary (within the marrow cavity of a bone), intrameningeal (within the meninges), intramyocardial (within the myocardium), intraocular (within the eye), intraovarian (within the ovary), intrapericardial (within the pericardium), intrapleural (within the pleura), intraprostatic (within the prostate gland), intrapulmonary (within the lungs or its bronchi), intrasinal (within the nasal or periorbital sinuses), intraspinal (within the vertebral column), intrasynovial (within the synovial cavity of a joint), intratendinous (within a tendon), intratesticular (within the testicle), intrathecal (within the cerebrospinal fluid at any level of the cerebrospinal axis), intrathoracic (within the thorax), intratubular (within the tubules of an organ), intratumor (within a tumor), intratympanic (within the aurus media), intravascular (within a vessel or vessels), intraventricular (within a ventricle), iontophoresis (by means of electric current where ions of soluble salts migrate into the tissues of the body), irrigation (to bathe or flush open wounds or body cavities), laryngeal (directly upon the larynx), nasogastric (through the nose and into the stomach), occlusive dressing technique (topical route administration which is then covered by a dressing which occludes the area), ophthalmic (to the external eye), oropharyngeal (directly to the mouth and pharynx), parenteral, percutaneous, periarticular, peridural, perineural, periodontal, rectal, respiratory (within the respiratory tract by inhaling orally or nasally for local or systemic effect), retrobulbar (behind the pons or behind the eyeball), soft tissue, subarachnoid, subconjunctival, submucosal, topical, transplacental (through or across the placenta), transtracheal (through the wall of the trachea), transtympanic (across or through the tympanic cavity), ureteral (to the ureter), urethral (to the urethra), vaginal, caudal block, diagnostic, nerve block, biliary perfusion, cardiac perfusion, photopheresis, and spinal.

In some embodiments, compositions may be administered in a way which allows them to cross the blood-brain barrier, vascular barrier, or other epithelial barrier. The originator constructs, benchmark constructs, and targeting systems may be administered in any suitable form, either as a liquid solution or suspension, as a solid form suitable for liquid solution or suspension in a liquid solution. The originator constructs, benchmark constructs, and targeting systems may be formulated with any appropriate and pharmaceutically acceptable excipient.

In some embodiments, the originator constructs, benchmark constructs, and targeting systems may be delivered to a subject via a single route administration.

In some embodiments, the originator constructs, benchmark constructs, and targeting systems may be delivered to a subject via a multi-site route of administration. A subject may be administered at 2, 3, 4, 5, or more than 5 sites.

In some embodiments, a subject may be administered the originator constructs, benchmark constructs, and targeting systems using a bolus infusion.

In some embodiments, a subject may be administered originator constructs, benchmark constructs, and targeting systems using sustained delivery over a period of minutes, hours, or days. The infusion rate may be changed depending on the subject, distribution, formulation or another delivery parameter.

In some embodiments, the originator constructs, benchmark constructs, and targeting systems may be delivered by intramuscular delivery route. Non-limiting examples of intramuscular administration include an intravenous injection or a subcutaneous injection.

In some embodiments, the originator constructs, benchmark constructs, and targeting systems may be delivered by oral administration. Non-limiting examples of oral delivery include a digestive tract administration and a buccal administration.

In some embodiments, the originator constructs, benchmark constructs, and targeting systems may be delivered by intraocular delivery route. A non-limiting example of intraocular delivery include an intravitreal injection.

In some embodiments, the originator constructs, benchmark constructs, and targeting systems may be delivered by intranasal delivery route. Non-limiting examples of intranasal delivery include nasal drops or nasal sprays.

In some embodiments, the originator constructs, benchmark constructs, and targeting systems may be administered to a subject by peripheral injections. Non-limiting examples of peripheral injections include intraperitoneal, intramuscular, intravenous, conjunctival, or joint injection.

In some embodiments, the originator constructs, benchmark constructs, and targeting systems may be delivered by injection into the cerebrospinal fluid. Non-limiting examples of delivery to the cerebrospinal fluid include intrathecal and intracerebroventricular administration.

In some embodiments, the originator constructs, benchmark constructs, and targeting systems may be delivered by systemic delivery. As a non-limiting example, the systemic delivery may be by intravascular administration.

In some embodiments, the originator constructs, benchmark constructs, and targeting systems may be administered to a subject by intracranial delivery.

In some embodiments, the originator constructs, benchmark constructs, and targeting systems may be administered to a subject by intraparenchymal administration.

In some embodiments, the originator constructs, benchmark constructs, and targeting systems may be administered to a subject by intramuscular administration.

In some embodiments, the originator constructs, benchmark constructs, and targeting systems are administered to a subject and transduce muscle of a subject. As a non-limiting example, the originator constructs, benchmark constructs, and targeting systems are administered by intramuscular administration.

In some embodiments, the originator constructs, benchmark constructs, and targeting systems may be administered to a subject by intravenous administration.

In some embodiments, the originator constructs, benchmark constructs, and targeting systems may be administered to a subject by subcutaneous administration.

In some embodiments, the originator constructs, benchmark constructs, and targeting systems may be administered to a subject by topical administration.

In some embodiments, the originator constructs, benchmark constructs, and targeting systems may be delivered by more than one route of administration.

The originator constructs, benchmark constructs, and targeting systems described herein may be co-administered in conjunction with one or more originator constructs, benchmark constructs, targeting systems, or therapeutic agents or moieties.

VI. Target Area, Tissue or Cell for Delivery

The delivery of nucleic acid sequences, polypeptides or peptides and formulations thereof can be localized to specific target areas, tissues or cells using the methods and targeted delivery systems described herein.

Tumors

In some embodiments, the delivery of nucleic acid sequences, polypeptides or peptides and formulations thereof can be localized to a tumor. The tumor may be a benign tumor or a malignant tumor.

In some embodiments, the delivery of nucleic acid sequences, polypeptides or peptides and formulations thereof is localized to a connective tissue tumor such as, but not limited to, adult fibrous tissue, embryonic (myxomatous) fibrous tissue, fat tissue, cartilage, bone, and notochord. As a non-limiting example, the tumor is a benign tumor called fibroma located in adult fibrous tissue. As a non-limiting example, the tumor is a malignant tumor called fibrosarcoma located in adult fibrous tissue. As a non-limiting example, the tumor is a benign tumor called myxoma located in embryonic fibrous tissue. As a non-limiting example, the tumor is a malignant tumor called myxosarcoma located in embryonic fibrous tissue. As a non-limiting example, the tumor is a benign tumor called lipoma located in fat tissue. As a non-limiting example, the tumor is a malignant tumor called liposarcoma located in fat tissue. As a non-limiting example, the tumor is a benign tumor called chondroma located in cartilage. As a non-limiting example, the tumor is a malignant tumor called chondrosarcoma located in cartilage. As a non-limiting example, the tumor is a benign tumor called osteoma located in bone. As a non-limiting example, the tumor is a malignant tumor called osteosarcoma located in bone. As a non-limiting example, the tumor is a malignant tumor called chordoma located in notochord. As a non-limiting example, the tumor is a benign tumor called fibrous histiocytoma located in connective tissue. As a non-limiting example, the tumor is a malignant tumor called malignant fibrous histiocytoma located in connective tissue.

In some embodiments, the delivery of nucleic acid sequences, polypeptides or peptides and formulations thereof is localized to endothelium and/or mesothelium tumor tissue such as, but not limited to, blood vessels, lymph vessels and mesothelium. As a non-limiting example, the tumor is a benign tumor called hemangioma located in blood vessels. As a non-limiting example, the tumor is a benign tumor called hemangiopericytoma located in blood vessels. As a non-limiting example, the tumor is a malignant tumor called hemangiosarcoma located in blood vessels. As a non-limiting example, the tumor is a malignant tumor called angiosarcoma located in blood vessels. As a non-limiting example, the tumor is a benign tumor called lymphangioma located in lymph vessels. As a non-limiting example, the tumor is a malignant tumor called lymphangiosarcoma located in lymph vessels. As a non-limiting example, the tumor is a malignant tumor called mesothelioma located in the mesothelium.

In some embodiments, the delivery of nucleic acid sequences, polypeptides or peptides and formulations thereof is localized to blood and lymphoid cell tissue such as, but not limited to, hematopoietic cells and lymphoid tissue. As a non-limiting example, the tumor is a benign tumor called preleukemias located in hematopoietic cells. As a non-limiting example, the tumor is a benign tumor called myeloproliferative disorders located in hematopoietic cells. As a non-limiting example, the tumor is a malignant tumor called leukemia located in hematopoietic cells. As a non-limiting example, the tumor is a benign tumor called plasmacytosis located in lymphoid tissue. As a non-limiting example, the tumor a malignant tumor called plasmacytoma located in lymphoid tissue. As a non-limiting example, the tumor a malignant tumor called multiple myeloma located in lymphoid tissue. As a non-limiting example, the tumor a malignant tumor called Hodgkin lymphoma located in lymphoid tissue. As a non-limiting example, the tumor a malignant tumor called Non-Hodgkin lymphoma located in lymphoid tissue.

In some embodiments, the delivery of nucleic acid sequences, polypeptides or peptides and formulations thereof is localized to muscle tissue such as, but not limited to, smooth muscle and striated muscle. As a non-limiting example, the tumor is a benign tumor called Leiomyoma located in smooth muscle. As a non-limiting example, the tumor is a malignant tumor called leiomyosarcoma located in smooth muscle. As a non-limiting example, the tumor is a benign tumor called rhabdomyoma located in striated muscle. As a non-limiting example, the tumor is a malignant tumor called rhabdomyosarcoma located in striated muscle.

In some embodiments, the delivery of nucleic acid sequences, polypeptides or peptides and formulations thereof is located to epithelial tissue such as, but not limited to, stratified squamous tissue, glandular epithelium tissue (e.g., liver, kidney, bile duct), transitional epithelium tissue, placenta and testis. As a non-limiting example, the tumor is a benign tumor called papilloma located in stratified squamous. As a non-limiting example, the tumor is a benign tumor called seborrheic keratosis located in stratified squamous. As a non-limiting example, the tumor is a malignant tumor called squamous cell carcinoma located in stratified squamous tissue. As a non-limiting example, the tumor is a malignant tumor called epidermoid carcinoma located in stratified squamous tissue. As a non-limiting example, the tumor is a benign tumor called adenoma located in glandular epithelium tissue. As a non-limiting example, the tumor is a benign tumor called hepatic adenoma located in liver glandular epithelium tissue. As a non-limiting example, the tumor is a benign tumor called renal tubular adenoma located in kidney glandular epithelium tissue. As a non-limiting example, the tumor is a benign tumor called bile duct adenoma located in bile duct glandular epithelium tissue. As a non-limiting example, the tumor is a malignant tumor called adenocarcinoma located in glandular epithelium tissue. As a non-limiting example, the tumor is a malignant tumor called hepatoma located in liver glandular epithelium tissue. As a non-limiting example, the tumor is a malignant tumor called hepatocellular carcinoma located in liver glandular epithelium tissue. As a non-limiting example, the tumor is a malignant tumor called renal cell carcinoma located in kidney glandular epithelium tissue. As a non-limiting example, the tumor is a malignant tumor called hypernephroma located in kidney glandular epithelium tissue. As a non-limiting example, the tumor is a malignant tumor called cholangiocarcinoma located in bile duct glandular epithelium tissue. As a non-limiting example, the tumor is a benign tumor called transitional cell papilloma located in transitional epithelium tissue. As a non-limiting example, the tumor is a malignant tumor called transitional cell carcinoma located in transitional epithelium tissue. As a non-limiting example, the tumor is a benign tumor called hydatidiform mole located in the placenta. As a non-limiting example, the tumor is a malignant tumor called choriocarcinoma located in the placenta. As a non-limiting example, the tumor is a malignant tumor called seminoma located in the testis. As a non-limiting example, the tumor is a malignant tumor called embryonal cell carcinoma located in the testis.

In some embodiments, the delivery of nucleic acid sequences, polypeptides or peptides and formulations thereof is located to neural tissue such as, but not limited to, glial cells, nerve cells, meninges, and nerve sheath. As a non-limiting example, the tumor is a malignant tumor called glioma (grades I-III) located in glial cells. As a non-limiting example, the tumor is a malignant tumor called anaplastic glioma (grades I-III) located in glial cells. As a non-limiting example, the tumor is a malignant tumor called glioblastoma multiforme (grade IV) located in glial cells. As a non-limiting example, the tumor is a benign tumor called ganglioneuroma located in nerve cells. As a non-limiting example, the tumor is a malignant tumor called neuroblastoma located in nerve cells. As a non-limiting example, the tumor is a malignant tumor called medulloblastoma located in nerve cells. As a non-limiting example, the tumor is a benign tumor called meningioma located in meninges tissue. As a non-limiting example, the tumor is a malignant tumor called malignant meningioma located in meninges tissue. As a non-limiting example, the tumor is a benign tumor called schwannoma located in the nerve sheath. As a non-limiting example, the tumor is a benign tumor called neurilemmoma located in the nerve sheath. As a non-limiting example, the tumor is a benign tumor called neurofibroma located in the nerve sheath. As a non-limiting example, the tumor is a malignant tumor called malignant meningioma located in the nerve sheath. As a non-limiting example, the tumor is a malignant tumor called malignant schwannoma located in the nerve sheath. As a non-limiting example, the tumor is a malignant tumor called neurofibrosarcoma located in the nerve sheath.

In some embodiments, the delivery of nucleic acid sequences, polypeptides or peptides and formulations thereof is located to the Amine Precursor Uptake and Decarboxylation (APUD) System such as, but not limited to, pituitary tissue, parathyroid tissue, thyroid tissue, bronchial tissue, adrenalmedulla tissue, pancreas tissue, stomach and intestines, carotid body and chemo-receptor system tissue. The APUD system is a series of cells which have endocrine functions and secrete a variety of small amine or polypeptide hormones. As a non-limiting example, the tumor is a benign tumor called basophilic adenoma located in the pituitary tissue. As a non-limiting example, the tumor is a benign tumor called eosinophilic adenoma located in the pituitary tissue. As a non-limiting example, the tumor is a benign tumor called chromophobe adenoma located in the pituitary tissue. As a non-limiting example, the tumor is a benign tumor called parathyroid adenoma located in the parathyroid. As a non-limiting example, the tumor is a malignant tumor called parathyroid carcinoma located in the parathyroid. As a non-limiting example, the tumor is a benign tumor called c cell hyperplasia located in the thyroid tissue (C cells). As a non-limiting example, the tumor is a malignant tumor called medullary carcinoma of thyroid located in the thyroid tissue (C cells). As a non-limiting example, the tumor is a malignant tumor called bronchial carcinooid located in the bronchial lining (Kultschitzky cells). As a non-limiting example, the tumor is a malignant tumor called oat cells carcinoma located in the bronchial lining (Kultschitzky cells). As a non-limiting example, the tumor is a benign tumor called pheochromocytoma located in the adrenalmedulla. As a non-limiting example, the tumor is a malignant tumor called malignant pheochromocytoma located in the adrenalmedualla. As a non-limiting example, the tumor is a benign tumor called islet cell adenoma located in the pancreas. As a non-limiting example, the tumor is a benign tumor called insulinoma located in the pancreas. As a non-limiting example, the tumor is a benign tumor called gastrinoma located in the pancreas. As a non-limiting example, the tumor is a malignant tumor called islet cell carcinoma located in the pancreas. As a non-limiting example, the tumor is a benign tumor called carcinoid located in the stomach and intestines. As a non-limiting example, the tumor is a malignant tumor called malignant carcinoid located in the stomach and intestines. As a non-limiting example, the tumor is a benign tumor called chemodectoma located in the carotid body and chemo-receptor system. As a non-limiting example, the tumor is a benign tumor called paraganglioma located in the carotid body and chemo-receptor system. As a non-limiting example, the tumor a malignant tumor called malignant carcinoid located in the carotid body and chemo-receptor system. As a non-limiting example, the tumor a malignant tumor called malignant paraganglioma located in the carotid body and chemo-receptor system.

In some embodiments, the delivery of nucleic acid sequences, polypeptides or peptides and formulations thereof is located in neural crest-derived cells such as, but not limited to, pigment-producing cells (e.g., skin and eyes), schwann cells of the peripheral nervous system, and merkel cells in the squamous epithelium. As a non-limiting example, the tumor is a benign tumor called nevus located in pigment-producing cells such as the skin and eyes. As a non-limiting example, the tumor a malignant tumor called melanoma located in pigment-producing cells such as the skin and eyes. As a non-limiting example, the tumor is a benign tumor called schwannoma or neurilemmoma located in schwann cells of the peripheral nervous system. As a non-limiting example, the tumor is a malignant tumor called malignant schwannoma located in schwann cells of the peripheral nervous system. As a non-limiting example, the tumor is a malignant tumor called merkel cell neoplasm located in merkel cells in the squamous epithelium.

In some embodiments, the delivery of nucleic acid sequences, polypeptides or peptides and formulations thereof is located in breast tissue. As a non-limiting example, the tumor is a benign tumor called fibroadenoma. As a non-limiting example, the tumor is a malignant tumor called cystosarcoma phylloides.

In some embodiments, the delivery of nucleic acid sequences, polypeptides or peptides and formulations thereof is located in renal anlage tissue. As a non-limiting example, the tumor is a malignant tumor called Wilms tumor.

In some embodiments, the delivery of nucleic acid sequences, polypeptides or peptides and formulations thereof is located in ovary tissue.

In some embodiments, the delivery of nucleic acid sequences, polypeptides or peptides and formulations thereof is located in testis tissue.

In some embodiments, the delivery of nucleic acid sequences, polypeptides or peptides and formulations thereof is located in germ cell tumor tissue. Non-limiting examples of germ cell tumors including seminoma, dysgerminoma, choriocarcinoma, embryonal carcinoma, endodermal sinus tumor, and teratocarcinoma.

In some embodiments, the delivery of nucleic acid sequences, polypeptides or peptides and formulations thereof is located in the connective tissue stroma. Non-limiting examples of these tumors are Sertoli-Leydig cell tumors, arrhenoblastoma, granulose-theca cell tumors, hilar cell tumors, lipid cell tumors.

Organs

In some embodiments, the delivery of nucleic acid sequences, polypeptides or peptides and formulations thereof can be localized to an organ. Non-limiting example of organs include the anal canal, arteries, ascending colon, bladder, bone marrow, brain, bronchi, bronchioles, bulbourethral glands, capillaries, cecum, cerebellum, cerebral hemispheres, cerebrum, cervix, choroid plexus, clitoris, cranial nerves, descending colon, diencephalon, duodenum, ear, enteric nervous system, epididymis, esophagus, external reproductive organs, fallopian tubes, gallbladder, ganglia, gustatory, gut-associated lymphoid tissue, heart, ileum, internal reproductive organs, interstitium, jejunum, joints, kidneys, large intestine, larynx, ligaments, liver, lungs, lymph node, lymphatic vessel, mammary glands, medulla oblongata, mesentery, midbrain, mouth, muscles of breathing, nasal cavity, nerves, olfactory, ovaries, pancreas, parotid glands, penis, pharynx, placenta, pons, prostate, rectum, salivary glands, scrotum, seminal vesicles, sigmoid colon, skeleton, skin, small intestine, spinal nerves, spleen, stomach, subcutaneous tissue, sublingual glands, submandibular glands, teeth, tendons, testes, the brainstem, the spinal cord, the ventricular system, thymus, tongue, tonsils, trachea, transverse colon, ureter, urethra, uterus, vagina, vas deferens, veins, and vulva.

Tissues

In some embodiments, the delivery of nucleic acid sequences, polypeptides or peptides and formulations thereof can be localized to a tissue. Non-limiting example of adrenal medulla, adult fibrous tissue, blood vessels, bone, breast, bronchial lining, carotid body, cartilage, connective tissue, embryonic (myxomatous) fibrous tissue, epithelial, epithelium, fat, glandular epithelium (liver, kidney, bile duct), gonads, hematopoietic cells, lymph vessels, lymphoid tissue, meninges, mesothelium, muscle, nerve sheath, nervous, notochord, ovary, pancreas, parathyroid, pituitary, placenta, renal anlage, smooth muscle, stomach and intestines, stratified squamous, striated muscle, stroma, testis, thyroid, and transitional epithelium. As a non-limiting example, the tissue is connective tissue.

Cells

In some embodiments, the delivery of nucleic acid sequences, polypeptides or peptides and formulations thereof can be localized to a particular cell type. Non-limiting example of cells include adipocytes, adrenergic neural cells, alpha cell, amacrine cells, ameloblast, anterior lens epithelial cell, anterior/intermediate pituitary cells, apocrine sweat gland cell, astrocytes, auditory inner hair cells of organ of corti, auditory outer hair cells of organ of *corti, b* cell, bartholin's gland cell, basal cell (stem cell) of cornea, tongue, mouth, nasal cavity, distal anal canal, distal urethra, and distal vagina, basal cells of olfactory epithelium, basket cells, basophil granulocyte and precursors, beta cell, betz cells, bone marrow reticular tissue fibroblasts, border cells of organ of corti, boundary cells, bowman's gland cell, brown fat cell, brunner's gland cell, bulbourethral gland cell, bushy cells, c cells, cajal-retzius cells, cardiac muscle cell, cardiac muscle cells, cartwheel cells, cells of the zona fasciculata produce glucocorticoids, cells of the zona glomerulosa produce mineralocorticoids, cells of the zona reticularis produce androgens, cells of the adrenal cortex, cementoblast, centroacinar cell, ceruminous gland cell in ear, chandelier cells, chemoreceptor glomus cells of carotid body cell, chief cell, cholinergic neurons, chromaffin cells, club cell, cold-sensitive primary sensory neurons, connective tissue macrophage (all types), corneal fibroblasts (corneal keratocytes), corpus luteum cell of ruptured ovarian follicle secreting progesterone, cortical hair shaft cell, corticotropes, crystallin-containing lens fiber cell, cuticular hair shaft cell, cytotoxic t cell, d cell, delta cell, dendritic cell, double-bouquet cells, duct cell, eccrine sweat gland clear cell, eccrine sweat gland dark cell, efferent ducts cell, elastic cartilage chondrocyte, endothelial cells, enteric glial cells, enterochromaffin cell, enterochromaffin-like cell, enteroendocrine cell, eosinophil granulocyte and precursors, ependymal cells, epidermal basal cell, epidermal langerhans cell, epididymal basal cell, epididymal principal cell, epithelial reticular cell, epsilon cell, erythrocyte, fibrocartilage chondrocyte, fork neurons, foveolar cell, g cell, gall bladder epithelial cell, germ cells, gland of littre cell, gland of moll cell in eyelid, glial cells, golgi cells, gonadal stromal cells, gonadotropes, granule cells, granulosa cell, granulosa lutein cells, grid cells, head direction cells, and hematopoietic stem cells. In some embodiments, the at least one cell type comprise cancerous cells. In some embodiments, the at least one cell type comprise non-cancerous cells. In some embodiments, the at least one cell type comprise both cancerous and non-cancerous type. In some embodiments, the cancerous state of the at least one cell type is unknown.

Physiological Systems

In some embodiments, the delivery of nucleic acid sequences, polypeptides or peptides and formulations thereof can be localized to a physiological system. Non-limiting example of physiological system include the auditory, cardiovascular, central nervous system, chemo-receptor system, circulatory, digestive, endocrine, excretory, exocrine, genital, integumentary, lymphatic, muscular, musculoskeletal, nervous, peripheral nervous system, renal, reproductive, respiratory, urinary, and visual systems.

VII. Methods of Detection and Analysis

Detection of the tropism discovery platform including the targeting systems (e.g., candidate targeting system and validated targeting system) may be carried out through a variety of techniques (i.e., detection techniques or analysis techniques, both of which are used interchangeably herein) which can be selected based on the tracking system used.

In some embodiments, the targeting systems described herein is detected utilizing a nuclear imaging technique. Nuclear imaging techniques, as used herein, are meant to encompass any imaging, detection, counting, or sorting technique that utilizes radioactive emissions, ether emitted from the subject or an external source. Without limitation, nuclear imaging techniques may include X-ray, magnetic resonance imaging (MRI) including functional magnetic resonance imaging (fMRI) and nuclear magnetic resonance imaging, computed tomography (CT), positron emission tomography (PET), single-photon emission computed tomography (SPECT), absorption imaging, or any combination thereof. The general principles and procedures of these approaches are known in the art, see Pérez-Medina, et. al., *Nuclear imaging approaches facilitating nanomedicine translation*. Advanced Drug Delivery Reviews 154-155 (2020) 123-141, the contents of which are herein incorporated by reference in their entirety as it relates to nuclear imaging techniques.

In some embodiments, detection of the targeting systems described herein in a subject may be performed utilizing MRI techniques. This approach may be carried out by any method known or discovered. While not wishing to be bound by theory, MRI utilizes the detection of certain nuclide spin characteristics. In some embodiments, MRI may be used as a non-invasive detection technique along with the targeting systems described herein that comprises an MRI contrast agent such as gadolinium-based small molecules, manganese-based small molecules, iron oxide nanoparticles, $^{19}$F-based compounds, and any combination thereof. MRI techniques may, as an example, allow for a detection of the targeting systems in specific organs and tissues of a subject in vivo, as well as changes in those distributions over time.

In some embodiments, detection of the targeting systems described herein in a subject may be performed utilizing CT techniques. This approach may be carried out by any method known or discovered. While not wishing to be bound by theory, CT utilizes the interaction of X-ray photons with matter, CT may be used as a non-invasive detection technique along with the targeting systems that comprise an CT contrast agent such as a gold high-density lipoprotein nanoparticle (Au-HDL). CT techniques may, as an example, allow for a detection of the targeting systems in specific organs and tissues of a subject in vivo, as well as changes in those distributions over time.

In some embodiments, detection of the targeting systems described herein in a subject may be performed utilizing PET techniques. This approach may be carried out by any method known or discovered. While not wishing to be bound by theory, PET utilize detection of photon emission from exogenously administered radiological substances, i.e., radiotracers. Principally, PET scanners detect the two photons emitted in opposite directions after positron-electron annihilation (the coincidence event). PET may be used as either an invasive or non-invasive detection technique along with the targeting systems that comprise an appropriate radiolabel such as 111In, 99mTc, 13N, 68Ga, 18F, 64Cu, 86Y, 76Br, 89Zr, 72As, 124I, 74As, fluorine-18, gallium-68, nitrogen-13, copper-64, bromine-76, iodine-125, arsenic-74, carbon-11, iodine-131, 153Sm, 177Lu, 186Re, 188Re, 198Au, and 225Ac. These labels maybe conjugated to either the structural elements, the cargo components, or both. PET scans may be performed to detect distribution of the targeting systems either on the subject in vivo, including changes in those distributions over time, or on excised samples of the subject. PET techniques may allow for detection of the targeting systems in a subject from the organ/tissue level down to the cell type level. Some PET techniques may allow for detection of the targeting systems at the intracellular level.

In some embodiments, detection of the targeting systems described herein in a subject may be performed utilizing SPECT techniques. This approach may be carried out by any method known or discovered. While not wishing to be bound by theory, SPECT utilize detection of photon emission from exogenously administered radiological substances, i.e., radiotracers. Principally, SPECT scanners detect X-ray and gamma photons associated with nuclear state transitions. SPECT may be used as either an invasive or non-invasive detection technique along with the targeting systems that comprise an appropriate radiolabel such as 111In, 99mTc, 13N, 68Ga, 18F, 64Cu, 86Y, 76Br, 89Zr, 72As, 124I, 74As, fluorine-18, gallium-68, nitrogen-13, copper-64, bromine-76, iodine-125, arsenic-74, carbon-11, iodine-131, 153Sm, 177Lu, 186Re, 188Re, 198Au, and 225Ac. These labels may be conjugated to either the structural elements, the cargo components, or both. SPECT scans may be performed to detect distribution of the targeting systems either on the subject in vivo, including changes in those distributions over time, or on excised samples of the subject. SPECT techniques may allow for detection of the targeting systems in a subject from the organ/tissue level down to the cell type level. Some SPECT techniques may allow for detection of the targeting systems at the intracellular level.

In some embodiments, multiple nuclear imaging techniques may be used with the targeting systems comprising a single tracking system. In some embodiments, multiple nuclear imaging techniques may be used with the targeting systems comprising multiple tracking systems.

In some embodiments, the targeting systems described herein is detected utilizing an optical imaging technique. Optical imaging techniques, as used herein, are meant to encompass any imaging, detection, counting, or sorting technique that utilizes light emissions and the special properties of photons, ether emitted from the subject or an external source. Without limitation, optical imaging techniques may include visible light microscopy, Raman spectroscopy, fluorescence microscopy, bioluminescence imaging (BLI), optical coherence tomography, or any combination thereof. The general principles and procedures of these approaches are known in the art, see Drummen.

*Fluorescent Probes and Fluorescence* (*Microscopy*) *Techniques—Illuminating Biological and Biomedical Research*. Molecules 2012, 17, 14067-14090, Boutorine, et. al., *Fluorescent Probes for Nucleic Acid Visualization in Fixed and Live Cells*. Molecules 2013, 18, 15357-15397, and Juskowiak, *Nucleic acid-based fluorescent probes and their analytical potential*. Anal. Bioanal. Chem. (2011) 399:3157-3176, the contents of which are herein incorporated by reference in their entirety as relates to optical imaging techniques.

In some embodiments, detection of the targeting systems described herein in a subject may be performed utilizing visible fluorescence microscopy techniques. Fluorescence microscopy techniques include a wide range of techniques known in the art including without limitation confocal fluorescence microscopy, fluorescence reflectance imaging, fluorescence molecular tomographic imaging, and Förster Resonance Energy Transfer (FRET). In general, all fluorescence microscopy techniques utilize detection of light emitted from endogenously present or exogenously administered fluorescent compounds, i.e., compounds which absorb light or other electromagnetic radiation and re-emits it at longer wavelengths. Fluorescence microscopy techniques may be used as either an invasive or non-invasive detection technique along with the targeting systems that comprise at least one tracking system which comprises an appropriate fluorescent compound. Without limitation, such fluorescent compounds may include Green Florescent Protein, Yellow Florescent Protein, Red Florescent Protein, Sirius, EBFP2, CFP, Cerulean, EGFP, EYFP, mOrange, mCherry, mPlum, NIR, iRFP, EosFP, PamCherry, Dronpa, Dreiklang, asFP595, mMaple, mGeo, mEos2, Dendra2, psCFP2, 2,3,5,6-tetracarbazole-4-cyano-pyridine (CPy), florescent nanoparticles, or florescent lipids, fluorescein, TAMRA, Cy dyes, Texas red, HEX, JOE, Oregon green, rhodamine 6 G, coumarin, pyrene, DiOC6 (3,3'-dihexyloxacarbocyanine iodide), or any combination thereof. In some embodiments, a targeting system for detection with fluorescence microscopy will comprise at least one fluorophore which may include, without limitation, a quantum dot, a Coumarins, a Naphthalimide, a Fluorescein, a BODIPY, a Cyanine, a xanthene, an oxazine, an Oligothiophenes, and a Phthalocyanine derivative (PcDer). These fluorescence compounds may be incorporated into the structure of the targeting systems, loaded as a cargo or payload, expressed as the product of a cargo or payload, or any combination thereof. Fluorescence microscopy techniques may be performed to detect distribution of the targeting systems either on the subject in vivo, including changes in those distributions over time, or on excised samples of the subject. Fluorescence microscopy techniques may allow for detection of the targeting systems in a subject from the organ/tissue level down to the cell type level. Some fluorescence microscopy techniques may allow for detection of the targeting systems at the intracellular level. In some embodiments, fluorescence microscopy techniques may be used to sort samples of cells post administration utilizing Fluorescence-activated Cell Sorting (FACS).

In some embodiments, detection of the targeting systems in a subject may be performed utilizing bioluminescence imaging (BLI) techniques. This approach may be carried out by any method known or discovered. While not wishing to be bound by theory, BLI imaging utilizes exogenously supplied compounds which emit light as a product of a chemical reaction under physiological condition. These emissions may be detected through various techniques of light and fluorescence microscopy. In some embodiments, BLI techniques may be used in conjunction with targeting systems which comprise bioluminescent compounds. Such compounds may be incorporated into nanoparticles or as the cargo or payload for expression post-delivery. In some embodiments, bioluminescent compounds may include, but are not limited to, luciferases including *Renilla* luciferase, *Gaussia* luciferase, Nanoluc luciferase, Firefly luciferase, Click Beetle luciferases, or any combination thereof. BLI techniques may be performed to detect distribution of the tropism discovery platform either on the subject in vivo, including changes in those distributions over time, or on excised samples of the subject. BLI may allow for detection of the targeting systems in a subject from the organ/tissue level down to the cell type level. Some BLI techniques may allow for detection of the targeting systems at the intracellular level. In some embodiments, BLI techniques may include quantifying luciferase expression from different organs with an in vivo imaging system (IVIS).

In some embodiments, detection of the targeting systems described herein may be performed utilizing nucleotide sequencing techniques. Nucleotide sequencing techniques maybe used to detect the presence of a known sequence of nucleotides, such as an identifier (e.g., barcode) sequence, in a sample. Non-limiting examples of nucleotide sequencing techniques which may be used to detect the targeting systems include high throughput sequencing, PCR, deep sequencing, and any combination thereof.

In some embodiments, detection of the targeting systems described herein may be performed by detecting the product of a tracking system which comprises a functional polynucleotide (e.g., DNA, mRNA, or oRNA) coding for a known peptide sequence or protein (i.e., a reporter sequence). In some embodiments, the functional polynucleotide may comprise a sequence which codes for a unique non-functional polypeptide sequence (i.e., a peptide or protein). In some embodiments, the reporter sequence may comprise a β-galactosidase (β-gal) sequence. In some embodiments, the reporter sequence may comprise a eGFP, luciferase, gene editor (e.g. cas9 edit, DNA readout), ox-40, beta6 integrin, CD45, a surface marker with (3×)-HA tag, (3×)-flag tag (with or without) a TEV protease site, or any combination thereof. In some embodiments, the reporter sequence may comprise a luciferase or fluorescent compound sequence. In some embodiments, the expression of the functional sequence, and by extension the presence of the targeting systems may be performed by any technique disclosed previously. In some embodiments, detecting the product of a tracking system which comprises a reporter sequence may be performed using any method known or discovered to detect products of expression. Such techniques include, but are not limited to, liquid/gas chromatography, mass spectrometry, light spectrometry (absorbance), gel electrophoresis, quantitative enzyme-linked immunosorbent assays (ELISA), Western blotting, dot blotting, Northern Blotting, protein immunostaining, protein immunoprecipitation, or any combination thereof.

In some embodiments, detection of the targeting systems described herein may be performed by utilizing detections systems chosen to match especially designed tracking systems. As a non-limiting example, the targeting systems described herein may be detected by electron microscopy, thermal imaging, ultrasound imaging, photoacoustic imaging, lab assays, and any combination thereof.

In some embodiments, detection of the targeting systems described herein may be performed by utilizing cell sorting techniques, including but not limited to, magnetic beads, flow cytometry, cleavage of peptide with LC-MS/MS, Fluorescence-activated Cell Sorting (FACS), or any combination thereof, combined with tracking system nanoparticles comprising components recognized by the cell sorting method.

In some embodiments, a detection technique may analyze only one formulation or cargo at a time. In some embodiments, a detection technique may analyze multiple formulations or cargos at a time. In some embodiments, a detection technique may analyze about 1 formulation, 2 formulations, 3 formulations, 4 formulations 5, formulations, 6 formulations, 7, formulations, 8, formulations, 9 formulations, 10 formulations, 11 formulations, 12 formulations, 13 formulations, 14 formulations, 15 formulations, 16 formulations, 17 formulations, 18 formulations, 19 formulations, 20 formulations, 21 formulations, 22 formulations, 23 formulations, 24 formulations, 25 formulations, or more at a time. In some embodiments, a detection technique may analyze between about 1 and 100 formulations. As a non-limiting example, a detection technique may analyze about 1-10, 1-20, 1-30, 1-40. 1-50, 1-60, 1-70. 1-80, or 1-90 formulations. In some embodiments, a detection technique may analyze more than 100 formulations at a time.

In some embodiments, a library of targeting systems may be analyzed. As a non-limiting examples, targeting systems may have the same formulation and different identifier sequences or moieties. As another non-limiting example, targeting systems may have the same formulation and the same identifier sequences or moieties. As another non-limiting example, targeting systems may have different formulations and the same identifier sequence or moieties. As another non-limiting example, targeting systems may have different formulations and different identifier sequences of moieties.

In some embodiments, a library of targeting systems may have one identifier sequence or moiety for analysis.

In some embodiments, a library of targeting systems may have at least two identifier sequences or moieties for analysis. The library may have 2-10 identifier sequences or moieties for analysis. The library may have 2-100 identifier sequences or moieties for analysis. The library may have 2-500 identifier sequences or moieties for analysis. The library may have 100-500 identifier sequences or moieties for analysis. The library may have 2-1000 identifier sequences or moieties for analysis. The library may have 2-2500 identifier sequences or moieties for analysis. The library may have 1000-2500 identifier sequences or moieties for analysis. The library may have 1000-5000 identifier sequences or moieties for analysis. The library may have 2500-5000 identifier sequences or moieties for analysis. The library may have 4000-5000 identifier sequences or moieties for analysis.

In some embodiments, a library of targeting systems may have at least one originator constructs or benchmark constructs formulated in a nanoparticle delivery vehicle. The library may have 1-10000 nanoparticles. The library may have 1-10 nanoparticles. The library may have 1-100 nanoparticles. The library may have 1-500 nanoparticles. The library may have 100-500 nanoparticles. The library may have 1-1000 nanoparticles. The library may have 100-500 nanoparticles. The library may have 1000-5000 nanoparticles. The library may have 2500-5000 nanoparticles. The library may have 1-5000 nanoparticles. The library may have 1-10000 nanoparticles. The library may have 5000-10000 nanoparticles. As a non-limiting example, the nanoparticle may be a lipid nanoparticle.

VIII. Methods of Use

In some embodiments, the tropism delivery systems described herein may be used as a therapeutic to diagnose, prevent, treat and/or manage disease, disorders and conditions, or as a diagnostic. The therapeutic may be used in personalized medicine, immuno-oncology, cancer, vaccines, gene editing (e.g., CRISPR).

In some embodiments, the tropism delivery systems described herein may be used for diagnostic purposes or as diagnostic tools.

In some embodiments, delivery systems described herein may be used to treat a foodborne illness, gastroentities, an infectious disease, a neglected topical disease, a tropical disease, a vector-borne disease, a toxin exposure, The pharmaceutical composition may be delivered as described in PCT Publication WO2012135805, which is incorporated herein by reference in its entirety.

The present disclosure provides methods comprising administering a pharmaceutical composition to a subject in need thereof. The pharmaceutical composition may be administered to a subject using any amount and any route of administration which may be effective for preventing, treating, diagnosing, or imaging a disease, disorder, and/or condition. The exact amount required will vary from subject to subject, depending on factors such as, but not limited to, the species, age, and general condition of the subject, the severity of the disease, the particular composition, its mode of administration, its mode of activity, and the like. The pharmaceutical composition may be administered to animals, such as mammals (e.g., humans, domesticated animals, cats, dogs, monkeys, mice, rats, etc.). The payload of the pharmaceutical composition is a polynucleotide.

In some embodiments, pharmaceutical, prophylactic, diagnostic, or imaging compositions thereof are administered to humans.

In some embodiments, the active agent is administered by one or more of a variety of routes, including, but not limited to, local, oral, intravenous, intramuscular, intra-arterial, intramedullary, intrathecal, subcutaneous, intraventricular, transdermal, interdermal, rectal, intravaginal, intraperitoneal, topical (e.g., by powders, ointments, creams, gels, lotions, and/or drops), mucosal, nasal, buccal, enteral, vitreal, intratumoral, sublingual; by intratracheal instillation, bronchial instillation, and/or inhalation; as an oral spray, nasal spray, and/or aerosol, and/or through a portal vein catheter.

In some embodiments, the active agent is administered by systemic intravenous injection.

In some embodiments, the active agent is administered intravenously and/or orally.

In specific embodiments, the active agent may be administered in a way which allows the active agent to cross the blood-brain barrier, vascular barrier, or other epithelial barrier.

Injectable preparations, for example, sterile injectable aqueous or oleaginous suspensions may be formulated according to the known art using suitable dispersing agents, wetting agents, and/or suspending agents. Sterile injectable preparations may be sterile injectable solutions, suspensions, and/or emulsions in nontoxic parenterally acceptable diluents and/or solvents, for example, as a solution in 1,3-butanediol. Among the acceptable vehicles and solvents that may be employed are water, Ringer's solution, U.S.P., and isotonic sodium chloride solution. Sterile, fixed oils are conventionally employed as a solvent or suspending medium. For this purpose, any bland fixed oil can be employed including synthetic mono- or diglycerides. Fatty acids such as oleic acid can be used in the preparation of injectables.

Injectable formulations can be sterilized, for example, by filtration through a bacterial-retaining filter, and/or by incorporating sterilizing agents in the form of sterile solid compositions which can be dissolved or dispersed in sterile water or other sterile injectable medium prior to use.

Dosage forms for local, topical and/or transdermal administration of a pharmaceutical composition may include ointments, pastes, creams, lotions, gels, powders, solutions, sprays, inhalants and/or patches. Additionally, the present disclosure contemplates the use of transdermal patches, which often have the added advantage of providing controlled delivery of a compound to the body. Such dosage forms may be prepared, for example, by dissolving and/or dispensing the compound in the proper medium. Alternatively or additionally, rate may be controlled by either providing a rate controlling membrane and/or by dispersing the compound in a polymer matrix and/or gel.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of active ingredient may be as high as the solubility limit of the active ingredient in the solvent. Formulations for topical administration may further comprise one or more of the additional ingredients described herein.

A pharmaceutical composition may be prepared, packaged, and/or sold in a formulation suitable for ophthalmic administration. Such formulations may, for example, be in the form of eye drops including, for example, a 0.1/1.0% (w/w) solution and/or suspension of the active ingredient in an aqueous or oily liquid excipient. Such drops may further comprise buffering agents, salts, and/or one or more other of any additional ingredients described herein. Other ophthalmically-administrable formulations which are useful include those which comprise the active ingredient in microcrystalline form and/or in a liposomal preparation. Ear drops and/or eye drops are contemplated as being within the scope of this disclosure.

In general, the most appropriate route of administration will depend upon a variety of factors including the nature of the active agent to be delivered (e.g., its stability in the environment of the gastrointestinal tract, bloodstream, etc), the condition of the patient (e.g., whether the patient is able to tolerate particular routes of administration), etc. The present disclosure encompasses the delivery of the active agent by any appropriate route taking into consideration likely advances in the sciences of drug delivery.

In certain embodiments, pharmaceutical compositions in accordance with the present disclosure may be administered at dosage levels sufficient to deliver from about 0.0001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic, diagnostic or prophylactic effect. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations). When multiple administration is employed, split dosing regimens such as those described herein may be used.

According to the present disclosure, administration of active agent in split-dose regimens may produce higher levels of proteins in mammalian subjects. As used herein, a "split dose" is the division of single unit dose or total daily dose into two or more doses. As used herein, a "single unit dose" is a dose of any therapeutic administered in one dose/at one time/single route/single point of contact, i.e., single administration event. As used herein, a "total daily dose" is an amount given or prescribed in 24 hr period. It may be administered as a single unit dose. In one embodiment, the active agent of the present disclosure are administered to a subject in split doses. In some embodiments, the active agent is formulated in buffer only or in a formulation described herein.

LNPs of the present disclosure may be used or administered in combination with one or more other therapeutic, prophylactic, diagnostic, or imaging agents. By "in combination with," it is not intended to imply that the agents must be administered at the same time and/or formulated for delivery together, although these methods of delivery are within the scope of the present disclosure. Pharmaceutical compositions can be administered concurrently with, prior to, or subsequent to, one or more other desired therapeutics or medical procedures. In general, each agent will be administered at a dose and/or on a time schedule determined for that agent. In some embodiments, the present disclosure encompasses the delivery of pharmaceutical, prophylactic, diagnostic, or imaging compositions in combination with agents that may improve their bioavailability, reduce and/or modify their metabolism, inhibit their excretion, and/or modify their distribution within the body.

It will further be appreciated that therapeutically, prophylactically, diagnostically, or imaging active agents utilized in combination may be administered together in a single pharmaceutical composition or administered separately in different pharmaceutical compositions. In general, it is expected that agents utilized in combination with be utilized at levels that do not exceed the levels at which they are utilized individually. In some embodiments, the levels utilized in combination will be lower than those utilized individually. In one embodiment, the combinations, each or together may be administered according to the split dosing regimens described herein.

The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, a pharmaceutical composition useful for treating cancer in accordance with the present disclosure may be administered concurrently with a chemotherapeutic agent), or they may achieve different effects (e.g., control of any adverse effects).

Pharmaceutical compositions containing LNPs disclosed herein are formulated for administration intramuscularly, transarterially, intraocularly, vaginally, rectally, intraperitoneally, intravenously, intranasally, subcutaneously, endoscopically, transdermally, intramuscularly, intraventricularly, intradermally, intrathecally, topically (e.g. by powders, ointments, creams, gels, lotions, and/or drops), mucosally, nasal, enterally, intratumorally, by intratracheal instillation, bronchial instillation, and/or inhalation; nasal spray and/or aerosol, and/or through a portal vein catheter.

The pharmaceutical compositions may also be formulated for direct delivery to an organ or tissue in any of several ways in the art including, but not limited to, direct soaking or bathing, via a catheter, by gels, powder, ointments, creams, gels, lotions, and/or drops, by using substrates such as fabric or biodegradable materials coated or impregnated with the pharmaceutical compositions, and the like. In some embodiments, the pharmaceutical composition is formulated for extended release. In specific embodiments, the active agent and/or pharmaceutical, prophylactic, diagnostic, or imaging compositions thereof, may be administered in a way which allows the active agent to cross the blood-brain barrier, vascular barrier, or other epithelial barrier.

In some aspects of the present disclosure, the active agent of the present disclosure are spatially retained within or proximal to a target tissue. Provided are methods of providing a pharmaceutical composition to a target tissue of a mammalian subject by contacting the target tissue (which contains one or more target cells) with the pharmaceutical composition under conditions such that the pharmaceutical composition, in particular the active agent component(s) of the pharmaceutical composition, is substantially retained in the target tissue, meaning that at least 10, 20, 30, 40, 50, 60, 70, 80, 85, 90, 95, 96, 97, 98, 99, 99.9, 99.99 or greater than 99.99% of the pharmaceutical composition is retained in the target tissue. Advantageously, retention is determined by measuring the amount of a component of the active agent present in the pharmaceutical composition that enters one or more target cells. For example, at least 1, 5, 10, 20, 30, 40, 50, 60, 70, 80, 85, 90, 95, 96, 97, 98, 99, 99.9, 99.99 or greater than 99.99% of the active agent administered to the subject are present intracellularly at a period of time following administration.

Aspects of the present disclosure are directed to methods of providing a pharmaceutical composition to a target tissue or organ of a mammalian subject, by contacting the target tissue (containing one or more target cells) or organ (containing one or more target cells) with the pharmaceutical composition under conditions such that the pharmaceutical composition is substantially retained in the target tissue or organ. The pharmaceutical composition contains an effective amount of an active agent.

Pharmaceutical compositions which may be administered intramuscularly and/or subcutaneously may include, but are not limited to, polymers, copolymers, and gels. The polymers, copolymers and/or gels may further be adjusted to modify release kinetics by adjusting factors such as, but not limited to, molecular weight, particle size, payload and/or ratio of the monomers. As a nonlimiting example, formulations administered intramuscularly and/or subcutaneously may include a copolymer such as poly(lactic-co-glycolic acid).

Localized delivery of the pharmaceutical compositions described herein may be administered by methods such as, but not limited to, topical delivery, ocular delivery, transdermal delivery, and the like. The pharmaceutical composition may also be administered locally to a part of the body not normally available for localized delivery such as, but not limited to, when a subject's body is open to the environment during treatment. The pharmaceutical composition may further be delivered by bathing, soaking and/or surrounding the body part with the pharmaceutical composition.

However, the present disclosure encompasses the delivery of an active agent disclosed herein, and/or pharmaceutical, prophylactic, diagnostic, or imaging compositions thereof, by any appropriate route taking into consideration likely advances in the sciences of drug delivery.

ii. Pharmaceutical Compositions

In some embodiments, a nanoparticle includes an ionizable lipid, a phospholipid, a PEG lipid, and a structural lipid. In certain embodiments, the lipid component of the nanoparticle composition includes about 30 mol % to about 60 mol % ionizable lipid, about 0 mol % to about 30 mol % phospholipid, about 18.5 mol % to about 48.5 mol % structural lipid, and about 0 mol % to about 10 mol % of PEG lipid, provided that the total mol % does not exceed 100%. In some embodiments, the lipid component of the nanoparticle composition includes about 35 mol % to about 55 mol % ionizable lipid, about 5 mol % to about 25 mol % phospholipid, about 30 mol % to about 40 mol % structural lipid, and about 0 mol % to about 10 mol % of PEG lipid. In a particular embodiment, the lipid component includes about 50 mol % ionizable lipid, about 10 mol % phospholipid, about 38.5 mol % structural lipid, and about 1.5 mol % of PEG lipid. In another particular embodiment, the lipid component includes about 40 mol % ionizable lipid, about 20 mol % phospholipid, about 38.5 mol % structural lipid, and about 1.5 mol % of PEG lipid. In another particular embodiment, the lipid component includes about 48.5 mol % ionizable lipid, about 10 mol % phospholipid, about 40 mol % structural lipid, and about 1.5 mol % of PEG lipid. In another particular embodiment, the lipid component includes about 48.5 mol % ionizable lipid, about 10 mol % phospholipid, about 39 mol % structural lipid, and about 2.5 mol % of PEG lipid. In some embodiments, the phospholipid may be DOPE or DSPC. In other embodiments, the PEG lipid may be PEG-DMG and/or the structural lipid may be cholesterol. The amount of active agent in a nanoparticle composition may depend on the size, composition, desired target and/or application, or other properties of the nanoparticle composition as well as on the properties of the active agent. For example, the amount of active agent useful in a nanoparticle composition may depend on the size, sequence, and other characteristics of the active agent. The relative amounts of active agent and other elements (e.g., lipids) in a nanoparticle composition may also vary. In some embodiments, the wt/wt ratio of the lipid component to an enzyme in a nanoparticle composition may be from about 5:1 to about 60:1, such as 5:1, 6:1, 7:1, 8:1, 9:1, 10:1, 11:1, 12:1, 13:1, 14:1, 15:1, 16:1, 17:1, 18:1, 19:1, 20:1, 25:1, 30:1, 35:1, 40:1, 45:1, 50:1, and 60:1. The amount of a enzyme in a nanoparticle composition may, for example, be measured using absorption spectroscopy (e.g., ultraviolet-visible spectroscopy).

In some embodiments, a nanoparticle composition comprising an active agent of the present disclosure is formulated to provide a specific E:P ratio. The E:P ratio of the composition refers to the molar ratio of nitrogen atoms in one or more lipids to the number of phosphate groups in an RNA active agent. In general, a lower E:P ratio is preferred. The one or more enzymes, lipids, and amounts thereof may be selected to provide an E:P ratio from about 2:1 to about 30:1, such as 2:1, 3:1, 4:1, 5:1, 6:1, 7:1, 8:1, 9:1, 10:1, 12:1, 14:1, 16:1, 18:1, 20:1, 22:1, 24:1, 26:1, 28:1, or 30:1. In certain embodiments, the E:P ratio may be from about 2:1 to about 8:1. In other embodiments, the E:P ratio is from about 5:1 to about 8:1. For example, the E:P ratio may be about 5.0:1, about 5.5:1, about 5.67:1, about 6.0:1, about 6.5:1, or about 7.0:1.

The characteristics of a nanoparticle composition may depend on the components thereof. For example, a nanoparticle composition including cholesterol as a structural lipid may have different characteristics than a nanoparticle composition that includes a different structural lipid. Similarly, the characteristics of a nanoparticle composition may depend on the absolute or relative amounts of its components. For instance, a nanoparticle composition including a higher molar fraction of a phospholipid may have different characteristics than a nanoparticle composition including a lower molar fraction of a phospholipid. Characteristics may also vary depending on the method and conditions of preparation of the nanoparticle composition. Nanoparticle compositions may be characterized by a variety of methods. For example, microscopy (e.g., transmission electron microscopy or scanning electron microscopy) may be used to examine the morphology and size distribution of a nanoparticle composition. Dynamic light scattering or potentiometry (e.g., potentiometric titrations) may be used to measure Zeta potentials. Dynamic light scattering may also be utilized to determine particle sizes. Instruments such as the Zetasizer Nano ZS (Malvern Instruments Ltd, Malvern, Worcestershire, UK) may also be used to measure multiple characteristics of a nanoparticle composition, Such as particle size, polydispersity index, and Zeta potential.

The mean size of a nanoparticle composition may be between 10s of nm and 100s of nm, e.g., measured by dynamic light scattering (DLS). For example, the mean size may be from about 40 nm to about 150 nm, such as about 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm. In some embodiments, the mean size of a nanoparticle composition may be from about 50 nm to about 100 nm, from about 50 nm to about 90 nm, from about 50 nm to about 80 nm, from about 50 nm to about 70 nm, from about 50 nm to about 60 nm, from about 60 nm to about 100 nm, from about 60 nm to about 90 nm, from about 60 nm to about 80 nm, from about 60 nm to about 70 nm, from about 70 nm to about 100 nm, from about 70 nm to about 90 nm, from about 70 nm to about 80 nm, from about 80 nm to about 100 nm, from about 80 nm to about 90 nm, or from about 90 nm to about 100 nm. In certain embodiments, the mean size of a nanoparticle composition may be from about 70 nm to about 100 nm. In a particular embodiment, the mean size may be about 80 nm. In other embodiments, the mean size may be about 100 nm.

A nanoparticle composition may be relatively homogenous. A polydispersity index may be used to indicate the homogeneity of a nanoparticle composition, e.g., the particle size distribution of the nanoparticle compositions. A small (e.g., less than 0.3) polydispersity index generally indicates a narrow particle size distribution. A nanoparticle composition may have a polydispersity index from about 0 to about 0.25, such as 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, or 0.25.

The Zeta potential of a nanoparticle composition may be used to indicate the electrokinetic potential of the composition. For example, the Zeta potential may describe the surface charge of a nanoparticle composition. Nanoparticle compositions with relatively low charges, positive or negative, are generally desirable, as more highly charged species may interact undesirably with cells, tissues, and other elements in the body. In some embodiments, the Zeta potential of a nanoparticle composition may be from about −10 mV to about +20 mV, from about −10 mV to about +15 mV, from about −10 mV to about +10 mV, from about −10 mV to about +5 mV, from about −10 mV to about 0 mV, from about −10 mV to about −5 mV, from about −5 mV to about +20 mV, from about −5 mV to about +15 mV, from about −5 mV to about +10 mV, from about −5 mV to about +5 mV, from about −5 mV to about 0 mV, from about 0 mV, to about +20 mV, from about 0 mV to about +15 mV, from about 0 mV to about +10 mV, from about 0 mV to about +5 mV, from about +5 mV to about +20 mV, from about +5 mV, to about +15 mV, or from about +5 mV to about +10 mV.

The efficiency of encapsulation of a payload describes the amount of payload that is encapsulated or otherwise associated with a nanoparticle composition after preparation, relative to the initial amount provided. The encapsulation efficiency is desirably high (e.g., close to 100%). The encapsulation efficiency may be measured, for example, by comparing the amount of payload in a solution containing the nanoparticle composition before and after breaking up the nanoparticle composition with one or more organic solvents or detergents. Fluorescence may be used to measure the amount of free payload in a solution. For the nanoparticle compositions described herein, the encapsulation efficiency of a therapeutic and/or prophylactic may be at least 50%, for example 50%, 55%, 60%, 65%, 70%, 75%, 80%, 85%, 90%, 91%, 92%, 93%, 94%, 95%, 96%, 97%, 98%, 99%, or 100%. In some embodiments, the encapsulation efficiency may be at least 80%. In certain embodiments, the encapsulation efficiency may be at least 90%.

Lipids and their method of preparation are disclosed in, e.g., U.S. Pat. Nos. 8,569,256, 5,965,542 and U.S. Patent Publication Nos. 2016/0199485, 2016/0009637, 2015/0273068, 2015/0265708, 2015/0203446, 2015/0005363, 2014/0308304, 2014/0200257, 2013/086373, 2013/0338210, 2013/0323269, 2013/0245107, 2013/0195920, 2013/0123338, 2013/0022649, 2013/0017223, 2012/0295832, 2012/0183581, 2012/0172411, 2012/0027803, 2012/0058188, 2011/0311583, 2011/0311582, 2011/0262527, 2011/0216622, 2011/0117125, 2011/0091525, 2011/0076335, 2011/0060032, 2010/0130588, 2007/0042031, 2006/0240093, 2006/0083780, 2006/0008910, 2005/0175682, 2005/017054, 2005/0118253, 2005/0064595, 2004/0142025, 2007/0042031, 1999/009076 and PCT Pub. Nos. WO 99/39741, WO 2017/117528, WO 2017/004143, WO 2017/075531, WO 2015/199952, WO 2014/008334, WO 2013/086373, WO 2013/086322, WO 2013/016058, WO 2013/086373, WO2011/141705, and WO 2001/07548 and Semple et. al, Nature Biotechnology, 2010, 28, 172-176, the full disclosures of which are herein incorporated by reference in their entirety for all purposes.

A nanoparticle composition may include any substance useful in pharmaceutical compositions. For example, the nanoparticle composition may include one or more pharmaceutically acceptable excipients or accessory ingredients such as, but not limited to, one or more solvents, dispersion media, diluents, dispersion aids, suspension aids, granulating aids, disintegrants, fillers, glidants, liquid vehicles, binders, surface active agents, isotonic agents, thickening or emulsifying agents, buffering agents, lubricating agents, oils, preservatives, and other species. Excipients such as waxes, butters, coloring agents, coating agents, flavorings, and perfuming agents may also be included. Pharmaceutically acceptable excipients are well known in the art (see for example Remington's *The Science and Practice of Pharmacy,* $21^{st}$ Edition, A. R. Gennaro: Lippincott, Williams & Wilkins, Baltimore, Md., 2006).

iii. Diseases, Disorders, and Other Uses

Methods of Producing Polypeptides in Cells

The present disclosure provides methods of producing a polypeptide of interest in a mammalian cell. Methods of producing polypeptides involve contacting a cell with a formulation of the disclosure comprising an LNP including an mRNA encoding the polypeptide of interest. Upon contacting the cell with the lipid nanoparticle, the mRNA may be taken up and translated in the cell to produce the polypeptide of interest.

In general, the step of contacting a mammalian cell with a LNP including an mRNA encoding a polypeptide of interest may be performed in vivo, ex vivo, in culture, or in vitro. The amount of lipid nanoparticle contacted with a cell, and/or the amount of mRNA therein, may depend on the type of cell or tissue being contacted, the means of administration, the physiochemical characteristics of the lipid nanoparticle and the mRNA (e.g., size, charge, and chemical composition) therein, and other factors. In general, an effective amount of the lipid nanoparticle will allow for efficient polypeptide production in the cell. Metrics for efficiency may include polypeptide translation (indicated by polypeptide expression), level of mRNA degradation, and immune response indicators.

The step of contacting an LNP including an mRNA with a cell may involve or cause transfection. A phospholipid including in the lipid component of a LNP may facilitate transfection and/or increase transfection efficiency, for example, by interacting and/or fusing with a cellular or intracellular membrane. Transfection may allow for the translation of the mRNA within the cell.

In some embodiments, the lipid nanoparticles described herein may be used therapeutically. For example, an mRNA included in an LNP may encode a therapeutic polypeptide (e.g., in a translatable region) and produce the therapeutic polypeptide upon contacting and/or entry (e.g., transfection) into a cell. In other embodiments, an mRNA included in a LNP may encode a polypeptide that may improve or increase the immunity of a subject. In some embodiments, an mRNA may encode a granulocyte-colony stimulating factor or trastuzumab.

In some embodiments, an mRNA included in an LNP may encode a recombinant polypeptide that may replace one or more polypeptides that may be substantially absent in a cell contacted with the lipid nanoparticle. The one or more substantially absent polypeptides may be lacking due to a genetic mutation of the encoding gene or a regulatory pathway thereof. Alternatively, a recombinant polypeptide produced by translation of the mRNA may antagonize the activity of an endogenous protein present in, on the surface of, or secreted from the cell. An antagonistic recombinant polypeptide may be desirable to combat deleterious effects caused by activities of the endogenous protein, such as altered activities or localization caused by mutation. In another alternative, a recombinant polypeptide produced by translation of the mRNA may indirectly or directly antagonize the activity of a biological moiety present in, on the surface of, or secreted from the cell. Antagonized biological moieties may include, but are not limited to, lipids (e.g., cholesterol), lipoproteins (e.g., low density lipoprotein), nucleic acids, carbohydrates, and small molecule toxins. Recombinant polypeptides produced by translation of the mRNA may be engineered for localization within the cell, such as within a specific compartment such as the nucleus, or may be engineered for secretion from the cell or for translocation to the plasma membrane of the cell.

In some embodiments, contacting a cell with an LNP including an mRNA may reduce the innate immune response of a cell to an exogenous nucleic acid. A cell may be contacted with a first lipid nanoparticle including a first amount of a first exogenous mRNA including a translatable region and the level of the innate immune response of the cell to the first exogenous mRNA may be determined. Subsequently, the cell may be contacted with a second composition including a second amount of the first exogenous mRNA, the second amount being a lesser amount of the first exogenous mRNA compared to the first amount. Alternatively, the second composition may include a first amount of a second exogenous mRNA that is different from the first exogenous mRNA. The steps of contacting the cell with the first and second compositions may be repeated one or more times. Additionally, efficiency of polypeptide production (e.g., translation) in the cell may be optionally determined, and the cell may be re-contacted with the first and/or second composition repeatedly until a target protein production efficiency is achieved.

Methods of Delivering Therapeutic Agents to Cells and Organs

Provided herein are methods of treating a disease or disorder, the methods comprising administering to a subject in need thereof a pharmaceutical composition of the present disclosure, such as a pharmaceutical composition comprising an LNP described herein.

The present disclosure provides methods of delivering an active agent and/or prophylactic, such as a nucleic acid, to a mammalian cell or organ. Delivery of a therapeutic and/or prophylactic to a cell involves administering a formulation of the disclosure that comprises a LNP including the therapeutic and/or prophylactic, such as a nucleic acid, to a subject, where administration of the composition involves contacting the cell with the composition. In some embodiments, a protein, cytotoxic agent, radioactive ion, chemotherapeutic agent, or nucleic acid (such as an RNA, e.g., mRNA) may be delivered to a cell or organ. In the instance that a therapeutic and/or prophylactic is an mRNA, upon contacting a cell with the lipid nanoparticle, a translatable mRNA may be translated in the cell to produce a polypeptide of interest. However, mRNAs that are substantially not translatable may also be delivered to cells. Substantially non-translatable mRNAs may be useful as vaccines and/or may sequester translational components of a cell to reduce expression of other species in the cell.

In some embodiments, an LNP may target a particular type or class of cells (e.g., cells of a particular organ or system thereof). In some embodiments, a LNP including a therapeutic and/or prophylactic of interest may be specifically delivered to a mammalian liver, kidney, spleen, femur, or lung. "Specific delivery" to a particular class of cells, an organ, or a system or group thereof implies that a higher proportion of lipid nanoparticles including a therapeutic and/or prophylactic are delivered to the destination (e.g., tissue) of interest relative to other destinations, e.g., upon administration of an LNP to a mammal. In some embodiments, specific delivery may result in a greater than 2 fold, 5 fold, 10 fold, 15 fold, or 20 fold increase in the amount of therapeutic and/or prophylactic per 1 g of tissue of the targeted destination (e.g., tissue of interest, such as a liver) as compared to another destination (e.g., the spleen). In some embodiments, the tissue of interest is selected from the group consisting of a liver, kidney, a lung, a spleen, a femur, vascular endothelium in vessels (e.g., intra-coronary or intra-femoral) or kidney, and tumor tissue (e.g., via intratumoral injection).

As another example of targeted or specific delivery, an mRNA that encodes a protein-binding partner (e.g., an antibody or functional fragment thereof, a scaffold protein, or a peptide) or a receptor on a cell surface may be included in an LNP. An mRNA may additionally or instead be used to direct the synthesis and extracellular localization of lipids, carbohydrates, or other biological moieties. Alternatively, other therapeutics and/or prophylactics or elements (e.g., lipids or ligands) of an LNP may be selected based on their affinity for particular receptors (e.g., low density lipoprotein receptors) such that a LNP may more readily interact with a target cell population including the receptors. In some embodiments, ligands may include, but are not limited to, members of a specific binding pair, antibodies, monoclonal antibodies, Fv fragments, single chain Fv (scFv) fragments, Fab' fragments, F(ab')2 fragments, single domain antibodies, camelized antibodies and fragments thereof, humanized antibodies and fragments thereof, and multivalent versions thereof; multivalent binding reagents including mono- or bispecific antibodies such as disulfide stabilized Fv fragments, scFv tandems, diabodies, tribodies, or tetrabodies; and aptamers, receptors, and fusion proteins.

In some embodiments, a ligand may be a surface-bound antibody, which can permit tuning of cell targeting specificity. This is especially useful since highly specific antibodies can be raised against an epitope of interest for the desired targeting site. In some embodiments, multiple antibodies are expressed on the surface of a cell, and each antibody can have a different specificity for a desired target. Such approaches can increase the avidity and specificity of targeting interactions.

A ligand can be selected, e.g., by a person skilled in the biological arts, based on the desired localization or function of the cell. In some embodiments an estrogen receptor ligand, such as tamoxifen, can target cells to estrogen-dependent breast cancer cells that have an increased number of estrogen receptors on the cell surface. Other non-limiting examples of ligand/receptor interactions include CCR1 (e.g., for treatment of inflamed joint tissues or brain in rheumatoid arthritis, and/or multiple sclerosis), CCR7, CCR8 (e.g., targeting to lymph node tissue), CCR6, CCR9, CCR10 (e.g., to target to intestinal tissue), CCR4, CCR10 (e.g., for targeting to skin), CXCR4 (e.g., for general enhanced transmigration), HCELL (e.g., for treatment of inflammation and inflammatory disorders, bone marrow), Alpha4beta7 (e.g., for intestinal mucosa targeting), and VLA-4NCAM-1 (e.g., targeting to endothelium). In general, any receptor involved in targeting (e.g., cancer metastasis) can be harnessed for use in the methods and compositions described herein.

Targeted cells may include, but are not limited to, hepatocytes, epithelial cells, hematopoietic cells, epithelial cells, endothelial cells, lung cells, bone cells, stem cells, mesenchymal cells, neural cells, cardiac cells, adipocytes, vascular smooth muscle cells, cardiomyocytes, skeletal muscle cells, beta cells, pituitary cells, synovial lining cells, ovarian cells, testicular cells, fibroblasts, B cells, T cells, reticulocytes, leukocytes, granulocytes, and tumor cells.

In some embodiments, an LNP may target hepatocytes. Apolipoproteins such as apolipoprotein E (apoE) have been shown to associate with neutral or near neutral lipid-containing lipid nanoparticles in the body, and are known to associate with receptors such as low-density lipoprotein receptors (LDLRs) found on the surface of hepatocytes. Thus, an LNP including a lipid component with a neutral or near neutral charge that is administered to a subject may acquire apoE in a subject's body and may subsequently deliver a therapeutic and/or prophylactic (e.g., an RNA) to hepatocytes including LDLRs in a targeted manner.

Methods of Treating Diseases and Disorders

Lipid nanoparticles are useful for treating a disease, disorder, or condition. In particular, such compositions are useful in treating a disease, disorder, or condition characterized by missing or aberrant protein or polypeptide activity. In some embodiments, a formulation of the disclosure that comprises an LNP including an mRNA encoding a missing or aberrant polypeptide may be administered or delivered to a cell. Subsequent translation of the mRNA may produce the polypeptide, thereby reducing or eliminating an issue caused by the absence of or aberrant activity caused by the polypeptide. Because translation may occur rapidly, the methods and compositions may be useful in the treatment of acute diseases, disorders, or conditions such as sepsis, stroke, and myocardial infarction. A therapeutic and/or prophylactic included in an LNP may also be capable of altering the rate of transcription of a given species, thereby affecting gene expression.

Diseases, disorders, and/or conditions characterized by dysfunctional or aberrant protein or polypeptide activity for which a composition may be administered include, but are not limited to, rare diseases, infectious diseases (as both vaccines and therapeutics), cancer and proliferative diseases, genetic diseases (e.g., cystic fibrosis), autoimmune diseases, diabetes, neurodegenerative diseases, cardio- and reno-vascular diseases, and metabolic diseases. Multiple diseases, disorders, and/or conditions may be characterized by missing (or substantially diminished such that proper protein function does not occur) protein activity. Such proteins may not be present, or they may be essentially non-functional. A specific example of a dysfunctional protein is the missense mutation variants of the cystic fibrosis transmembrane conductance regulator (CFTR) gene, which produce a dysfunctional protein variant of CFTR protein, which causes cystic fibrosis. The present disclosure provides a method for treating such diseases, disorders, and/or conditions in a subject by administering a LNP including an RNA and a lipid component including a PEGylated lipid compound disclosed herein, a phospholipid (optionally unsaturated), optionally a second PEGylated lipid, and a structural lipid, wherein the RNA may be an mRNA encoding a polypeptide that antagonizes or otherwise overcomes an aberrant protein activity present in the cell of the subject.

In some embodiments, lipid nanoparticles disclosed herein comprise a polynucleotide encoding an antigen protein. In some embodiments, the polynucleotide is an mRNA or circRNA encoding an antigen protein. In some embodiments, the polynucleotide encodes a protein selected from SEQ ID NOs: 1-54, or a sequence having about 60% sequence identity, about 70% sequence identity, about 80% sequence identity, about 90% sequence identity, or about 95% sequence identity to a protein selected from SEQ ID NOs: 1-54.

In some embodiments, lipid nanoparticles disclosed herein are useful in methods of treating a disease or disorder. In some embodiments, the disease or disorder is a foodbourne illness or gastroenteritis. In some embodiments, the foodbourne illness is caused by a pathogen selected from the group consisting of *Campylobacter jejuni* bacteria, *Clostridium difficile* bacteria, *Entamoeba histolytica*, Enterotoxin B, Norwalk virus/Norovirus, *Helicobacter pylori*, and Rotavirus.

In some embodiments, the disease or disorder is an infectious disease. In some embodiments, the infectious disease is the result of an infection with an agent selected from the group consisting of *Candida* yeast, a coronavirus (e.g., SARS-CoV, SARS-CoV-2, MERS-CoV), enterovirus 71, Epstein-Barr virus, Gram-Negative Bacteria (e.g., *Bordetella*), Gram-Positive bacteria (e.g., *Clostridium Tetani, Francisella tularensis, Streptococcus bacteria, Staphylococcus* bacteria), hepatitis virus, human cytomegalovirus, HIV, HPV, influenza virus, JCV, *Mycobacterium*, poxviruses, pseudomonos *aeruginosa*, toxoplasma *gondii*, vaicella zoster virus, chikungunya virus, dengue virus, rabies virus, typanosoma *cruzi*, ebola virus, *Plasmodium falciparum*, marbug virus, Japanese encephalitis virus, St. Louis encephalitis virus, West Nile Virus, and Yellow Fever virus.

Preventative Applications

In some embodiments, the tropism delivery systems described herein may be used to prevent disease or stabilize the progression of disease.

In some embodiments, the tropism delivery systems described herein may be used as a prophylactic to prevent a disease or disorder in the future.

In some embodiments, the tropism delivery systems described herein may be used to halt further progression of a disease or disorder.

Vaccine

In some embodiments, the tropism delivery systems described herein may be used as, and/or in a manner similar to that of a vaccine. As used herein, a "vaccine" is a biological preparation that improves immunity to a particular disease or infectious agent.

In some embodiments, the tropism delivery systems described herein may be used as, and/or in a manner similar to that of a vaccine for a therapeutic area such as, but not limited to, cardiovascular, CNS, dermatology, endocrinology, oncology, immunology, respiratory, and anti-infective. In some embodiments, the tropism delivery systems described herein may be used as a vaccine to diagnose, prevent, treat and/or manage a foodborne illness. In some embodiments, the tropism delivery systems described herein may be used as a vaccine to diagnose, prevent, treat and/or manage gastroenteritis. In some embodiments, the tropism delivery systems described herein may be used as a vaccine to diagnose, prevent, treat and/or manage influenza. In some embodiments, the tropism delivery systems described herein may be used as a prophylactic to diagnose, prevent, treat and/or manage HIV. In some embodiments, the tropism delivery systems described herein may be used as a prophylactic to diagnose, prevent, treat and/or manage coronavirus. In some embodiments, the tropism delivery systems described herein may be used as a prophylactic to diagnose, prevent, treat and/or manage COVID-19. In some embodiments, the tropism delivery systems described herein may be used as a prophylactic to diagnose, prevent, treat and/or manage polio. In some embodiments, the tropism delivery systems described herein may be used as a prophylactic to diagnose, prevent, treat and/or manage tetanus. In some embodiments, the tropism delivery systems described herein may be used as a prophylactic to diagnose, prevent, treat and/or manage Hepatitis A. In some embodiments, the tropism delivery systems described herein may be used as a prophylactic to diagnose, prevent, treat and/or manage Hepatitis B. In some embodiments, the tropism delivery systems described herein may be used as a prophylactic to diagnose, prevent, treat and/or manage Hepatitis C. In some embodiments, the tropism delivery systems described herein may be used as a prophylactic to diagnose, prevent, treat and/or manage Rubella. In some embodiments, the tropism delivery systems described herein may be used as a prophylactic to diagnose, prevent, treat and/or manage Hib (*Haemophilus influenzae* type b). In some embodiments, the tropism delivery systems described herein may be used as a prophylactic to diagnose, prevent, treat and/or manage Measles. In some embodiments, the tropism delivery systems described herein may be used as a prophylactic to diagnose, prevent, treat and/or manage Pertussis (Whooping Cough). In some embodiments, the tropism delivery systems described herein may be used as a prophylactic to diagnose, prevent, treat and/or manage Pneumococcal Disease. In some embodiments, the tropism delivery systems described herein may be used as a prophylactic to diagnose, prevent, treat and/or manage Rotavirus. In some embodiments, the tropism delivery systems described herein may be used as a prophylactic to diagnose, prevent, treat and/or manage Mumps. In some embodiments, the tropism delivery systems described herein may be used as a prophylactic to diagnose, prevent, treat and/or manage Chickenpox. In some embodiments, the tropism delivery systems described herein may be used as a prophylactic to diagnose, prevent, treat and/or manage Diphtheria.

Contraceptive

In some embodiments, the tropism delivery systems described herein may be used as, and/or in a manner similar to that of a contraceptive. As used herein, the term, "contraceptive" may be defined as any agent or method that may be used to prevent pregnancy.

In some embodiments, the contraceptive may be used short-term or long-term.

In some embodiments, the contraceptive may be reversible or permanent.

Diagnostics

In some embodiments, the tropism delivery systems described herein may be used for diagnostic purposes or as diagnostic tools for any of the aforementioned diseases or disorders.

In some embodiments, the tropism delivery systems described herein may be used to detect a biomarker for disease diagnosis.

In some embodiments, the tropism delivery systems described herein may be used for diagnostic imaging purposes, e.g., MRI, PET, CT or ultrasound.

Research

In some embodiments, the tropism delivery systems described herein may be used for diagnostic purposes or as research tools for any of the aforementioned diseases or disorders.

In some embodiments, the tropism delivery systems described herein may be used to detect a biomarker for research.

In some embodiments, the tropism delivery systems described herein may be used in any research experiment, e.g., in vivo or in vitro experiments.

In some embodiments, the tropism delivery systems described herein may be used in cultured cells. The cultured cells may be derived from any origin known to one with skill in the art, and may be as non-limiting examples, derived from a stable cell line, an animal model or a human patient or control subject.

In some embodiments, the tropism delivery systems described herein may be used in in vivo experiments in animal models (i.e., mouse, rat, rabbit, dog, cat, non-human primate, guinea pig, ferret, *C-elegans, Drosophila*, zebrafish, or any other animal used for research purposes, known in the art).

In some embodiments, the tropism delivery systems described herein may be used in human research experiments or human clinical trials.

In some embodiments, the tropism delivery systems described herein may be used in stem cells and/or cell differentiation

IX. Enumerated Embodiments

In an embodiment of the disclosure, provided herein is a pharmaceutical composition comprising:

a) a polynucleotide encoding at least one protein of interest, and b) a delivery vehicle comprising at least one lipid wherein the composition elicits an immune response in a subject.

In an embodiment, the polynucleotides are DNA.

In an embodiment, the polynucleotides are RNA.

In an embodiment, the RNA are short interfering RNA (siRNA).

In an embodiment, the siRNA inhibits or suppresses the expression of a target of interest in a cell.

In an embodiment, the inhibition or suppression is about 30%, 40%, 50%, 60%, 70%, 80%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100%.

In an embodiment, the polynucleotides are substantially circular.

In an embodiment, polynucleotide comprises an internal ribosome entry site (IRES) sequence that is operably linked to the payload sequence region.

In an embodiment, the IRES sequence comprises a sequence derived from picornavirus complementary DNA, encephalomyocarditis virus (EMCV) complementary DNA, poliovirus complementary DNA, or an Antennapedia gene from *Drosophila melanogaster*.

In an embodiment, the polynucleotide comprises a termination element, wherein the termination element comprises at least one stop codon.

In an embodiment, the polynucleotide comprises a regulatory element.

In an embodiment, the polynucleotide comprises at least one masking agent.

In an embodiment, the substantially circular polynucleotide is produced using in vitro transcription.

In an embodiment, the payload sequence region comprises a non-coding nucleic acid sequence.

In an embodiment, the payload sequence region comprises a coding nucleic acid sequence.

In an embodiment, the coding nucleic acid sequence encodes a protein of interest for *Campylobacter jejuni.*

In an embodiment, the coding nucleic acid sequence encodes a protein of interest for *Clostridium difficile.*

In an embodiment, the coding nucleic acid sequence encodes a protein of interest for *Entamoeba histolytica.*

In an embodiment, the coding nucleic acid sequence encodes a protein of interest for enterotoxin B.

In an embodiment, the coding nucleic acid sequence encodes a protein of interest for Norwalk virus or norovirus.

In an embodiment, the coding nucleic acid sequence encodes a protein of interest for *Helicobacter pylori.*

In an embodiment, the coding nucleic acid sequence encodes a protein of interest for rotavirus.

In an embodiment, the coding nucleic acid sequence encodes a protein of interest for *Candida* yeast.

In an embodiment, the coding nucleic acid sequence encodes a protein of interest for coronavirus.

In an embodiment, the coding nucleic acid sequence encodes a protein of interest for SARS-CoV.

In an embodiment, the coding nucleic acid sequence encodes a protein of interest for SARS-CoV-2.

In an embodiment, the coding nucleic acid sequence encodes a protein of interest for MERS-CoV.

In an embodiment, the coding nucleic acid sequence encodes a protein of interest for Enterovirus 71.

In an embodiment, the coding nucleic acid sequence encodes a protein of interest for Epstein-Barr virus.

In an embodiment, the coding nucleic acid sequence encodes a protein of interest for Gram-Negative Bacteria.

In an embodiment, the Gram-Negative Bacteria is *Bordetella.*

In an embodiment, the coding nucleic acid sequence encodes a protein of interest for Gram-Positive Bacteria.

In an embodiment, the Gram-Positive Bacteria is *Clostridium tetani.*

In an embodiment, the Gram-Positive Bacteria is *Francisella tularensis.*

In an embodiment, the Gram-Positive Bacteria is *Streptococcus* bacteria.

In an embodiment, the Gram-Positive Bacteria is *Staphylococcus* bacteria.

In an embodiment, the coding nucleic acid sequence encodes a protein of interest for Hepatitis.

In an embodiment, the coding nucleic acid sequence encodes a protein of interest for Human Cytomegalovirus.

In an embodiment, the coding nucleic acid sequence encodes a protein of interest for Human Immunodeficiency Virus.

In an embodiment, the coding nucleic acid sequence encodes a protein of interest for Human Papilloma Virus.

In an embodiment, the coding nucleic acid sequence encodes a protein of interest for Influenza.

In an embodiment, the coding nucleic acid sequence encodes a protein of interest for John Cunningham Virus.

In an embodiment, the coding nucleic acid sequence encodes a protein of interest for *Mycobacterium.*

In an embodiment, the coding nucleic acid sequence encodes a protein of interest for Poxviruses.

In an embodiment, the coding nucleic acid sequence encodes a protein of interest for *Pseudomonas aeruginosa.*

In an embodiment, the coding nucleic acid sequence encodes a protein of interest for Respiratory Syncytial Virus.

In an embodiment, the coding nucleic acid sequence encodes a protein of interest for Rubella virus.

In an embodiment, the coding nucleic acid sequence encodes a protein of interest for Varicella zoster virus.

In an embodiment, the coding nucleic acid sequence encodes a protein of interest for Chikungunya virus.

In an embodiment, the coding nucleic acid sequence encodes a protein of interest for Dengue virus.

In an embodiment, the coding nucleic acid sequence encodes a protein of interest for Rabies virus.

In an embodiment, the coding nucleic acid sequence encodes a protein of interest for *Trypanosoma cruzi* and/or Chagas disease.

In an embodiment, the coding nucleic acid sequence encodes a protein of interest for Ebola virus.

In an embodiment, the coding nucleic acid sequence encodes a protein of interest for *Plasmodium falciparum.*

In an embodiment, the coding nucleic acid sequence encodes a protein of interest for Marburg virus.

In an embodiment, the coding nucleic acid sequence encodes a protein of interest for Japanese encephalitis virus.

In an embodiment, the coding nucleic acid sequence encodes a protein of interest for St. Louis encephalitis virus.

In an embodiment, the coding nucleic acid sequence encodes a protein of interest for West Nile Virus.

In an embodiment, the coding nucleic acid sequence encodes a protein of interest for Yellow Fever virus.

In an embodiment, the coding nucleic acid sequence encodes a protein of interest for *Bacillus anthracis.*

In an embodiment, the coding nucleic acid sequence encodes a protein of interest for Botulinum toxin.

In an embodiment, the coding nucleic acid sequence encodes a protein of interest for Ricin.

In an embodiment, the coding nucleic acid sequence encodes a protein of interest for Shiga toxin and/or Shiga-like toxin.

In an embodiment, the polynucleotide comprises at least one modification.

In an embodiment, the at least one modification is pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, and 4-methoxy-2-thio-pseudouridine, 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, and 4-methoxy-1-methyl-pseudoisocytidine, 2-aminopurine, 2, 6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyl-adenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, and 2-methoxy-adenine, inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, or N2,N2-dimethyl-6-thio-guanosine.

In an embodiment, the pharmaceutical composition comprises at least one cationic lipid selected from the group consisting of any lipid in Table (I); any lipid having a structure of Formula (VII-A), (VIII-A), (IX-A), (VII-B), (VII-C), (I-A), (II), (III-B), (III-C), (III-D), (III-E), (III-F), (VIII-B), (IV), (VI), (X), or (X-A); and combinations thereof.

In an embodiment, the pharmaceutical composition comprises at least one cationic lipid having a structure of Formula (VII-A). In an embodiment, the cationic lipid is selected from the group consisting of Compounds 1, 2, 3, 4, 15, 17, 18, 19, 20, and 21.

In an embodiment, the pharmaceutical composition comprises at least one cationic lipid having a structure of Formula (VII-B). In an embodiment, the cationic lipid is selected from the group consisting of Compounds 8, 28, 29, 30, 31, 32, 33, 34, 35, 36, 37, 38, 39, 40, 41, 42, 43, 44, and 45.

In an embodiment, the pharmaceutical composition comprises at least one cationic lipid having a structure of Formula (VII-C). In an embodiment, the cationic lipid is selected from the group consisting of Compounds 5, 6, 46, 47, 54, 60, 61, and 62.

In an embodiment, the pharmaceutical composition comprises at least one cationic lipid having a structure of Formula (I-A). In an embodiment, the cationic lipid is selected from the group consisting of Compounds 3, 15, 18, and 19.

In an embodiment, the pharmaceutical composition comprises at least one cationic lipid having a structure of Formula (II). In an embodiment, the cationic lipid is selected from the group consisting of Compounds 1, 17, 20, and 21.

In an embodiment, the pharmaceutical composition comprises at least one cationic lipid having a structure of Formula (III-B). In an embodiment, the cationic lipid is Compound 56.

In an embodiment, the pharmaceutical composition comprises at least one cationic lipid having a structure of Formula (III-C). In an embodiment, the cationic lipid is selected from the group consisting of Compounds 60 and 62.

In an embodiment, the pharmaceutical composition comprises at least one cationic lipid having a structure of Formula (III-D). In an embodiment, the cationic lipid is selected from the group consisting of Compounds 14, 51, 52, 53, 55, 57, 58, 59, 64, 65, 66, 67, 68, 69, 70, 71, 72, 73, 74, 75, 76, 77, 79, 82, 83, and 85.

In an embodiment, the pharmaceutical composition comprises at least one cationic lipid having a structure of Formula (III-E). In an embodiment, the cationic lipid is selected from the group consisting of Compounds 86 and 87.

In an embodiment, the pharmaceutical composition comprises at least one cationic lipid having a structure of Formula (III-F). In an embodiment, the cationic lipid is selected from the group consisting of Compounds 10 and 49.

In an embodiment, the pharmaceutical composition comprises at least one cationic lipid having a structure of Formula (IV). In an embodiment, the cationic lipid is Compound 16.

In an embodiment, the pharmaceutical composition comprises at least one cationic lipid having a structure of Formula (VI). In an embodiment, the cationic lipid is selected from the group consisting of Compounds 2, 7, 9, 13, and 48.

In an embodiment, the pharmaceutical composition comprises at least one cationic lipid having a structure of Formula (VIII-B). In an embodiment, the cationic lipid is selected from the group consisting of Compounds 22, 23, 24, 25, 26, and 27.

In an embodiment, the pharmaceutical composition comprises at least one cationic lipid having a structure of Formula (VIII-B). In an embodiment, the cationic lipid is selected from the group consisting of Compounds 22, 23, 24, 25, 26, and 27.

In an embodiment, the pharmaceutical composition comprises at least one cationic lipid having a structure of Formula (X). In an embodiment, the cationic lipid is selected from the group consisting of Compounds 14, 50, 51, 52, 53, 55, 57, 58, 59, 64, 66, 67, 68, 69, 71, 72, 73, 74, 75, 77, 78, 79, 80, 81, 82, 83, 84, 85, 88, and 89.

In an embodiment, the cationic lipid is any lipid having a structure disclosed herein.

In an embodiment, the pharmaceutical composition comprises an additional cationic lipid.

In an embodiment, the pharmaceutical composition comprises a neutral lipid.

In an embodiment, the pharmaceutical composition comprises an anionic lipid.

In an embodiment, the pharmaceutical composition comprises a helper lipid.

In an embodiment, the pharmaceutical composition comprises a stealth lipid.

In an embodiment, the weight ratio of the lipids and the polynucleotide is between 100:1 to 1:1.

In an embodiment, the pharmaceutical compositions disclosed herein preferentially target immune cells, e.g., T cells, e.g., T regulatory cells. For example, the disclosed pharmaceutical compositions may preferentially target immune cells over hepatocytes. Exemplary non-limiting immune cells include CD8+, CD4+, or CD8+CD4+ cells. In some embodiments, the disclosed pharmaceutical compositions deliver the cargo or payload to immune cells without the need for peptide-, protein-, or aptamer-based targeting ligands. See, e.g., WO 2021/021634.

In an embodiment, the pharmaceutical compositions disclosed herein are delivered in the absence of a targeting ligand to mammalian liver immune cells, spleen T cells, or lung endothelial cells. Specific delivery to a particular class or type of cells indicates that a higher proportion of the pharmaceutical composition is delivered to target type or class of cells. For example, specific delivery may result in a greater than 2-fold, 3-fold, 4-fold, 5-fold, 10-fold, 15-fold, or 20-fold increase in the amount of cargo or payload per 1 g of tissue of the targeted destination.

In an embodiment, a vaccine formulation comprises the pharmaceutical composition.

In an embodiment, a vaccine is prepared with any of Formulas (I)-(VI).

In an embodiment, provided herein is a method of vaccinating a subject against an infectious agent comprising contacting a subject with the vaccine formulation or preparation and eliciting an immune response.

In an embodiment, the infectious agent is *Campylobacter jejuni, Clostridium difficile, Entamoeba histolytica*, enterotoxin B, Norwalk virus or norovirus, *Helicobacter pylori*, rotavirus, *Candida* yeast, coronavirus including SARS-CoV, SARS-CoV-2 and MERS-CoV, Enterovirus 71, Epstein-Barr virus, Gram-Negative Bacteria including *Bordetella*, Gram-Positive Bacteria including *Clostridium tetani, Francisella tularensis, Streptococcus* bacteria and *Staphylococcus* bacteria, and Hepatitis, Human Cytomegalovirus, Human Immunodeficiency Virus, Human Papilloma Virus, Influenza, John Cunningham Virus, *Mycobacterium*, Poxviruses, *Pseudomonas aeruginosa*, Respiratory Syncytial Virus, Rubella virus, Varicella zoster virus, Chikungunya virus, Dengue virus, Rabies virus, *Trypanosoma cruzi* and/or Chagas disease, Ebola virus, *Plasmodium falciparum*, Marburg virus, Japanese encephalitis virus, St. Louis encephalitis virus, West Nile Virus, Yellow Fever virus, *Bacillus anthracis*, Botulinum toxin, Ricin, or Shiga toxin and/or Shiga-like toxin.

The present disclosure includes the following enumerated embodiments

1. A pharmaceutical composition comprising:
a) a polynucleotide encoding at least one protein of interest, and
b) a delivery vehicle comprising at least one lipid
wherein the composition elicits an immune response in a subject.

2. The pharmaceutical composition of embodiment 1, wherein the polynucleotides are DNA.

3. The pharmaceutical composition of embodiment 1, wherein the polynucleotides are RNA.

4. The pharmaceutical composition of embodiment 3, wherein the RNA are short interfering RNA (siRNA).

5. The pharmaceutical composition of embodiment 4, wherein the siRNA inhibits or suppresses the expression of a target of interest in a cell.

6. The pharmaceutical composition of embodiment 5, wherein the inhibition or suppression is about 30%, 40%, 50%, 60%, 70%, 80%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100%.

7. The pharmaceutical composition of embodiments 2 or 3, wherein the polynucleotides are substantially circular.

8. The pharmaceutical composition of embodiment 7, wherein polynucleotide comprises an internal ribosome entry site (IRES) sequence that is operably linked to the payload sequence region.

9. The pharmaceutical composition of embodiment 8, wherein the IRES sequence comprises a sequence derived from picornavirus complementary DNA, encephalomyocarditis virus (EMCV) complementary DNA, poliovirus complementary DNA, or an Antennapedia gene from *Drosophila melanogaster.*

10. The pharmaceutical composition of embodiment 7, wherein the polynucleotide comprises a termination element, wherein the termination element comprises at least one stop codon.

11. The pharmaceutical composition of embodiment 7, wherein the polynucleotide comprises a regulatory element.

12. The pharmaceutical composition of any of embodiments 7-11, wherein the polynucleotide comprises at least one masking agent.

13. The pharmaceutical composition of any of embodiments 7-12, wherein the substantially circular polynucleotide is produced using in vitro transcription.

14. The pharmaceutical composition of any of embodiments 7-14, wherein the payload sequence region comprises a non-coding nucleic acid sequence.

15. The pharmaceutical composition of any of embodiments 7-13, wherein the payload sequence region comprises a coding nucleic acid sequence.

16. The pharmaceutical composition of embodiment 15, wherein the coding nucleic acid sequence encodes a protein of interest for *Campylobacter jejuni.*

17. The pharmaceutical composition of embodiment 15, wherein the coding nucleic acid sequence encodes a protein of interest for *Clostridium difficile.*

18. The pharmaceutical composition of embodiment 15, wherein the coding nucleic acid sequence encodes a protein of interest for *Entamoeba histolytica.*

19. The pharmaceutical composition of embodiment 15, wherein the coding nucleic acid sequence encodes a protein of interest for enterotoxin B.

20. The pharmaceutical composition of embodiment 15, wherein the coding nucleic acid sequence encodes a protein of interest for Norwalk virus or norovirus.

21. The pharmaceutical composition of embodiment 15, wherein the coding nucleic acid sequence encodes a protein of interest for *Helicobacter pylori.*

22. The pharmaceutical composition of embodiment 15, wherein the coding nucleic acid sequence encodes a protein of interest for rotavirus.

23. The pharmaceutical composition of embodiment 15, wherein the coding nucleic acid sequence encodes a protein of interest for *Candida* yeast.

24. The pharmaceutical composition of embodiment 15, wherein the coding nucleic acid sequence encodes a protein of interest for coronavirus.

25. The pharmaceutical composition of embodiment 15, wherein the coding nucleic acid sequence encodes a protein of interest for SARS-CoV.

26. The pharmaceutical composition of embodiment 15, wherein the coding nucleic acid sequence encodes a protein of interest for SARS-CoV-2.

27. The pharmaceutical composition of embodiment 15, wherein the coding nucleic acid sequence encodes a protein of interest for MERS-CoV.

28. The pharmaceutical composition of embodiment 15, wherein the coding nucleic acid sequence encodes a protein of interest for Enterovirus 71.

29. The pharmaceutical composition of embodiment 15, wherein the coding nucleic acid sequence encodes a protein of interest for Epstein-Barr virus.

30. The pharmaceutical composition of embodiment 15, wherein the coding nucleic acid sequence encodes a protein of interest for Gram-Negative Bacteria.

31. The pharmaceutical composition of embodiment 30, wherein the Gram-Negative Bacteria is *Bordetella.*

32. The pharmaceutical composition of embodiment 15, wherein the coding nucleic acid sequence encodes a protein of interest for Gram-Positive Bacteria.

33. The pharmaceutical composition of embodiment 32, wherein the Gram-Positive Bacteria is *Clostridium tetani.*

34. The pharmaceutical composition of embodiment 32, wherein the Gram-Positive Bacteria is *Francisella tularensis.*

35. The pharmaceutical composition of embodiment 32, wherein the Gram-Positive Bacteria is *Streptococcus* bacteria.

36. The pharmaceutical composition of embodiment 32, wherein the Gram-Positive Bacteria is *Staphylococcus* bacteria.

37. The pharmaceutical composition of embodiment 15, wherein the coding nucleic acid sequence encodes a protein of interest for Hepatitis.

38. The pharmaceutical composition of embodiment 15, wherein the coding nucleic acid sequence encodes a protein of interest for Human Cytomegalovirus.

39. The pharmaceutical composition of embodiment 15, wherein the coding nucleic acid sequence encodes a protein of interest for Human Immunodeficiency Virus.

40. The pharmaceutical composition of embodiment 15, wherein the coding nucleic acid sequence encodes a protein of interest for Human Papilloma Virus.

41. The pharmaceutical composition of embodiment 15, wherein the coding nucleic acid sequence encodes a protein of interest for Influenza.

42. The pharmaceutical composition of embodiment 15, wherein the coding nucleic acid sequence encodes a protein of interest for John Cunningham Virus.

43. The pharmaceutical composition of embodiment 15, wherein the coding nucleic acid sequence encodes a protein of interest for *Mycobacterium.*

44. The pharmaceutical composition of embodiment 15, wherein the coding nucleic acid sequence encodes a protein of interest for Poxviruses.

45. The pharmaceutical composition of embodiment 15, wherein the coding nucleic acid sequence encodes a protein of interest for *Pseudomonas aeruginosa.*

46. The pharmaceutical composition of embodiment 15, wherein the coding nucleic acid sequence encodes a protein of interest for Respiratory Syncytial Virus.

47. The pharmaceutical composition of embodiment 15, wherein the coding nucleic acid sequence encodes a protein of interest for Rubella virus.

48. The pharmaceutical composition of embodiment 15, wherein the coding nucleic acid sequence encodes a protein of interest for Varicella zoster virus.

49. The pharmaceutical composition of embodiment 15, wherein the coding nucleic acid sequence encodes a protein of interest for Chikungunya virus.

50. The pharmaceutical composition of embodiment 15, wherein the coding nucleic acid sequence encodes a protein of interest for Dengue virus.

51. The pharmaceutical composition of embodiment 15, wherein the coding nucleic acid sequence encodes a protein of interest for Rabies virus.

52. The pharmaceutical composition of embodiment 15, wherein the coding nucleic acid sequence encodes a protein of interest for *Trypanosoma cruzi* and/or Chagas disease.

53. The pharmaceutical composition of embodiment 15, wherein the coding nucleic acid sequence encodes a protein of interest for Ebola virus.

54. The pharmaceutical composition of embodiment 15, wherein the coding nucleic acid sequence encodes a protein of interest for *Plasmodium falciparum.*

55. The pharmaceutical composition of embodiment 15, wherein the coding nucleic acid sequence encodes a protein of interest for Marburg virus.

56. The pharmaceutical composition of embodiment 15, wherein the coding nucleic acid sequence encodes a protein of interest for Japanese encephalitis virus.

57. The pharmaceutical composition of embodiment 15, wherein the coding nucleic acid sequence encodes a protein of interest for St. Louis encephalitis virus.

58. The pharmaceutical composition of embodiment 15, wherein the coding nucleic acid sequence encodes a protein of interest for West Nile Virus.

59. The pharmaceutical composition of embodiment 15, wherein the coding nucleic acid sequence encodes a protein of interest for Yellow Fever virus.

60. The pharmaceutical composition of embodiment 15, wherein the coding nucleic acid sequence encodes a protein of interest for *Bacillus anthracis.*

61. The pharmaceutical composition of embodiment 15, wherein the coding nucleic acid sequence encodes a protein of interest for Botulinum toxin.

62. The pharmaceutical composition of embodiment 15, wherein the coding nucleic acid sequence encodes a protein of interest for Ricin.

63. The pharmaceutical composition of embodiment 15, wherein the coding nucleic acid sequence encodes a protein of interest for Shiga toxin and/or Shiga-like toxin.

64. The pharmaceutical composition of any one of embodiments 3-63, wherein the polynucleotide comprises at least one modification.

65. The pharmaceutical composition of embodiment 64, wherein at least 20% of the bases are modified.

66. The pharmaceutical composition of embodiment 64, wherein at least 30% of the bases are modified.

67. The pharmaceutical composition of embodiment 64, wherein at least 40% of the bases are modified.

68. The pharmaceutical composition of embodiment 64, wherein at least 50% of the bases are modified.

69. The pharmaceutical composition of embodiment 64, wherein at least 60% of the bases are modified.

70. The pharmaceutical composition of embodiment 64, wherein at least 70% of the bases are modified.

71. The pharmaceutical composition of embodiment 64, wherein at least 80% of the bases are modified.

72. The pharmaceutical composition of embodiment 64, wherein at least 90% of the bases are modified.

73. The pharmaceutical composition of embodiment 64, wherein at least 100% of the bases are modified.

74. The pharmaceutical composition of embodiment 64, wherein a specific base comprises at least one modification.

75. The pharmaceutical composition of embodiment 74, wherein the base is adenine.

76. The pharmaceutical composition of embodiment 75, wherein at least 20% of the adenine bases are modified.

77. The pharmaceutical composition of embodiment 75, wherein at least 30% of the adenine bases are modified.

78. The pharmaceutical composition of embodiment 75, wherein at least 40% of the adenine bases are modified.

79. The pharmaceutical composition of embodiment 75, wherein at least 50% of the adenine bases are modified.

80. The pharmaceutical composition of embodiment 75, wherein at least 60% of the adenine bases are modified.

81. The pharmaceutical composition of embodiment 75, wherein at least 70% of the adenine bases are modified.

82. The pharmaceutical composition of embodiment 75, wherein at least 80% of the adenine bases are modified.

83. The pharmaceutical composition of embodiment 75, wherein at least 90% of the adenine bases are modified.

84. The pharmaceutical composition of embodiment 75, wherein at least 100% of the adenine bases are modified.

85. The pharmaceutical composition of embodiment 74, wherein the base is guanine.

86. The pharmaceutical composition of embodiment 85, wherein at least 20% of the guanine bases are modified.

87. The pharmaceutical composition of embodiment 85, wherein at least 30% of the guanine bases are modified.

88. The pharmaceutical composition of embodiment 85, wherein at least 40% of the guanine bases are modified.

89. The pharmaceutical composition of embodiment 85, wherein at least 50% of the guanine bases are modified.

90. The pharmaceutical composition of embodiment 85, wherein at least 60% of the guanine bases are modified.

91. The pharmaceutical composition of embodiment 85, wherein at least 70% of the guanine bases are modified.

92. The pharmaceutical composition of embodiment 85, wherein at least 80% of the guanine bases are modified.

93. The pharmaceutical composition of embodiment 85, wherein at least 90% of the guanine bases are modified.

94. The pharmaceutical composition of embodiment 85, wherein at least 100% of the guanine bases are modified.

95. The pharmaceutical composition of embodiment 74, wherein the base is cytosine.

96. The pharmaceutical composition of embodiment 95, wherein at least 20% of the cytosine bases are modified.

97. The pharmaceutical composition of embodiment 95, wherein at least 30% of the cytosine bases are modified.

98. The pharmaceutical composition of embodiment 95, wherein at least 40% of the cytosine bases are modified.

99. The pharmaceutical composition of embodiment 95, wherein at least 50% of the cytosine bases are modified.

100. The pharmaceutical composition of embodiment 95, wherein at least 60% of the cytosine bases are modified.

101. The pharmaceutical composition of embodiment 95, wherein at least 70% of the cytosine bases are modified.

102. The pharmaceutical composition of embodiment 95, wherein at least 80% of the cytosine bases are modified.

103. The pharmaceutical composition of embodiment 95, wherein at least 90% of the cytosine bases are modified.

104. The pharmaceutical composition of embodiment 95, wherein at least 100% of the cytosine bases are modified.

105. The pharmaceutical composition of embodiment 74, wherein the base is uracil.

106. The pharmaceutical composition of embodiment 105, wherein at least 20% of the uracil bases are modified.

107. The pharmaceutical composition of embodiment 105, wherein at least 30% of the uracil bases are modified.

108. The pharmaceutical composition of embodiment 105, wherein at least 40% of the uracil bases are modified.

109. The pharmaceutical composition of embodiment 105, wherein at least 50% of the uracil bases are modified.

110. The pharmaceutical composition of embodiment 105, wherein at least 60% of the uracil bases are modified.

111. The pharmaceutical composition of embodiment 105, wherein at least 70% of the uracil bases are modified.

112. The pharmaceutical composition of embodiment 105, wherein at least 80% of the uracil bases are modified.

113. The pharmaceutical composition of embodiment 105, wherein at least 90% of the uracil bases are modified.

114. The pharmaceutical composition of embodiment 105, wherein at least 100% of the uracil bases are modified.

115. The pharmaceutical composition of any of embodiments 64-114, wherein the at least one modification is pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, and 4-methoxy-2-thio-pseudouridine, 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, and 4-methoxy-1-methyl-pseudoisocytidine, 2-aminopurine, 2, 6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, and 2-methoxy-adenine, inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, or N2,N2-dimethyl-6-thio-guanosine.

116. The pharmaceutical composition of embodiment 1, further comprising at least one cationic lipid selected from the group consisting of any lipid in Table (I); any lipid having a structure of Formula (VII-A), (VIII-A), (IX-A), (VII-B), (VII-C), (I-A), (II), (III-B), (III-C), (III-D), (III-E), (III-F), (VIII-B), (IV), (VI), (X), or (X-A); and combinations thereof.

125. The pharmaceutical composition of any of embodiments 116-124, further comprises an additional cationic lipid.

126. The pharmaceutical composition of any of embodiments 116-125, further comprising a neutral lipid.

127. The pharmaceutical composition of any of embodiments 116-126, further comprising an anionic lipid.

128. The pharmaceutical composition of any of embodiments 116-127, further comprises a helper lipid.

129. The pharmaceutical composition of any of embodiments 116-128, further comprises a stealth lipid.

130. The pharmaceutical composition of any of embodiments 116-129, wherein the weight ratio of the lipids and the polynucleotide is from about 100:1 to about 1:1.

131. A vaccine formulation comprising the pharmaceutical composition of any of embodiments 1-130.

132. A vaccine preparation comprising the pharmaceutical composition of any of embodiments 116-130.

133. A method of vaccinating a subject against an infectious agent comprising:

a) contacting a subject with the vaccine formulation of embodiment 131 or the vaccine preparation of embodiment 132, and b) eliciting an immune response.

134. The method of embodiment 133, wherein the infectious agent is *Campylobacter jejuni, Clostridium difficile, Entamoeba histolytica*, enterotoxin B, Norwalk virus or norovirus, *Helicobacter pylori*, rotavirus, *Candida* yeast, coronavirus including SARS-CoV, SARS-CoV-2 and MERS-CoV, Enterovirus 71, Epstein-Barr virus, Gram-Negative Bacteria including *Bordetella*, Gram-Positive Bacteria including *Clostridium tetani, Francisella tularensis, Streptococcus* bacteria and *Staphylococcus* bacteria, and Hepatitis, Human Cytomegalovirus, Human Immunodeficiency Virus, Human Papilloma Virus, Influenza, John Cunningham Virus, *Mycobacterium*, Poxviruses, *Pseudomonas aeruginosa*, Respiratory Syncytial Virus, Rubella virus, Varicella zoster virus, Chikungunya virus, Dengue virus, Rabies virus, *Trypanosoma cruzi* and/or Chagas disease, Ebola virus, *Plasmodium falciparum*, Marburg virus, Japanese encephalitis virus, St. Louis encephalitis virus, West Nile Virus, Yellow Fever virus, *Bacillus anthracis*, Botulinum toxin, Ricin, or Shiga toxin and/or Shiga-like toxin.

135. The method of embodiment 133, wherein the contacting is enteral (into the intestine), gastroenteral, epidural (into the dura mater), oral (by way of the mouth), transdermal, intracerebral (into the cerebrum), intracerebroventricular (into the cerebral ventricles), epicutaneous (application onto the skin), intradermal (into the skin itself), subcutaneous (under the skin), nasal administration (through the nose), intravenous (into a vein), intravenous bolus, intravenous drip, intra-arterial (into an artery), intramuscular (into a muscle), intracardiac (into the heart), intraosseous infusion (into the bone marrow), intrathecal (into the spinal canal), intraparenchymal (into brain tissue), intraperitoneal (infusion or injection into the peritoneum), intravesical infusion, intravitreal (through the eye), intracavernous injection (into a pathologic cavity) intracavitary (into the base of the penis), intravaginal administration, intrauterine, extra-amniotic administration, transdermal (diffusion through the intact skin for systemic distribution), transmucosal (diffusion through a mucous membrane), transvaginal, insufflation (snorting), sublingual, sublabial, enema, eye drops (onto the conjunctiva), ear drops, auricular (in or by way of the ear), buccal (directed toward the cheek), conjunctival, cutaneous, dental (to a tooth or teeth), electro-osmosis, endocervical, endosinusial, endotracheal, extracorporeal, hemodialysis, infiltration, interstitial, intra-abdominal, intra-amniotic, intra-articular, intrabiliary, intrabronchial, intrabursal, intra-cartilaginous (within a cartilage), intracaudal (within the cauda equine), intracisternal (within the cisterna magna cerebellomedularis), intracorneal (within the cornea), dental intracoronal, intracoronary (within the coronary arteries), intracorporus cavernosum (within the dilatable spaces of the corporus cavernosa of the penis), intradiscal (within a disc), intraductal (within a duct of a gland), intraduodenal (within the duodenum), intradural (within or beneath the dura), intraepidermal (to the epidermis), intraesophageal (to the esophagus), intragastric (within the stomach), intragingival (within the gingivae), intraileal (within the distal portion of the small intestine), intralesional (within or introduced directly to a localized lesion), intraluminal (within a lumen of a tube), intralymphatic (within the lymph), intramedullary (within the marrow cavity of a bone), intrameningeal (within the meninges), intramyocardial (within the myocardium), intraocular (within the eye), intraovarian (within the ovary), intrapericardial (within the pericardium), intrapleural (within the pleura), intraprostatic (within the prostate gland), intrapulmonary (within the lungs or its bronchi), intrasinal (within the nasal or periorbital sinuses), intraspinal (within the vertebral column), intrasynovial (within the synovial cavity of a joint), intratendinous (within a tendon), intratesticular (within the testicle), intrathecal (within the cerebrospinal fluid at any level of the cerebrospinal axis), intrathoracic (within the thorax), intratubular (within the tubules of an organ), intratumor (within a tumor), intratympanic (within the aurus media), intravascular (within a vessel or vessels), intraventricular (within a ventricle), iontophoresis (by means of electric current where ions of soluble salts migrate into the tissues of the body), irrigation (to bathe or flush open wounds or body cavities), laryngeal (directly upon the larynx), nasogastric (through the nose and into the stomach), occlusive dressing technique (topical route administration which is then covered by a dressing which occludes the area), ophthalmic (to the external eye), oropharyngeal (directly to the mouth and pharynx), parenteral, percutaneous, periarticular, peridural, perineural, periodontal, rectal, respiratory (within the respiratory tract by inhaling orally or nasally for local or systemic effect), retrobulbar (behind the pons or behind the eyeball), soft tissue, subarachnoid, subconjunctival, submucosal, topical, transplacental (through or across the placenta), transtracheal (through the wall of the trachea), transtympanic (across or through the tympanic cavity), ureteral (to the ureter), urethral (to the urethra), vaginal, caudal block, diagnostic, nerve block, biliary perfusion, cardiac perfusion, photopheresis, or spinal.

136. A method of delivering a polynucleotide encoding at least one protein of interest to an immune cell of a subject in need thereof, the method comprising administering to the subject the pharmaceutical composition of any one of embodiments 1-130.

137. The method of embodiment 136, wherein the immune cell is a T cell.

138. The method of embodiment 137, wherein the T cell is a CD8+ T cell.

139. The method of embodiment 137, wherein the T cell is a T regulatory cell.

140. The method of embodiment 137, wherein the T cell is CD4+ T cell.

141. The method of embodiment 136, wherein the immune cell is a macrophage, dendritic cell, or liver immune cell.

X. Definitions

The term "compound" or "structure," as used herein, is meant to include all stereoisomers, geometric isomers, tautomers, and isotopes of the structures depicted.

The compounds or structures described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C═N double bonds, and the like can also be present in the compounds described herein, and all such stable isomers are contemplated in the present disclosure. Cis and trans geometric isomers of the compounds of the present disclosure are described and may be isolated as a mixture of isomers or as separated isomeric forms.

Compounds or structures of the present disclosure also include tautomeric forms. Tautomeric forms result from the swapping of a single bond with an adjacent double bond and the concomitant migration of a proton. Tautomeric forms include prototropic tautomers which are isomeric protonation states having the same empirical formula and total charge. Examples prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, such as, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds or structures of the present disclosure also include all of the isotopes of the atoms occurring in the intermediate or final compounds. "Isotopes" refers to atoms having the same atomic number but different mass numbers resulting from a different number of neutrons in the nuclei. For example, isotopes of hydrogen include tritium and deuterium.

The compounds or structures and salts of the present disclosure can be prepared in combination with solvent or water molecules to form solvates and hydrates by routine methods.

The term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups.

In some embodiments, a straight chain or branched chain alkyl has 30 or fewer carbon atoms in its backbone (e.g., $C_1$-$C_{30}$ for straight chains, $C_3$-$C_{30}$ for branched chains), 20 or fewer, 12 or fewer, or 7 or fewer. Likewise, in some embodiments cycloalkyls have from 3-10 carbon atoms in their ring structure, e.g., have 5, 6 or 7 carbons in the ring structure. The term "alkyl" (or "lower alkyl") as used throughout the specification, examples, and claims is intended to include both "unsubstituted alkyls" and "substituted alkyls", the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, a hosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons, or from one to six carbon atoms in its backbone structure. Likewise, "lower alkenyl" and "lower alkynyl" have similar chain lengths. In some embodiments, alkyl groups are lower alkyls. In some embodiments, a substituent designated herein as alkyl is a lower alkyl.

The term "alkylenyl" as used herein refers to a divalent radical of a straight-chain or branched-chain alkyl group. In one embodiment, the alkylenyl is a divalent form of a $C_{1-12}$ alkyl, i.e., a $C_1$-$C_{12}$ alkylenyl. In one embodiment, the alkylenyl is a divalent form of a $C_{2-6}$ alkyl, i.e., a $C_1$-$C_{10}$ alkylenyl. In one embodiment, the alkylenyl is a divalent form of a $C_{2-14}$ alkyl, i.e., a $C_1$-$C_8$ alkylenyl. In one embodiment, the alkylenyl is a divalent form of an unsubstituted $C_{1-6}$ alkyl, i.e., a $C_1$-$C_6$ alkylenyl. In another embodiment, the alkylenyl is a divalent form of an unsubstituted $C_{14}$ alkyl, i.e., a $C_1$-$C_4$ alkylenyl. Non-limiting exemplary alkylenyl groups include $—CH_2—$, $—CH_2CH_2—$, $—CH_2CH_2CH_2—$, $—CH_2CH(CH_3)CH_2—$, $—CH_2(CH_2)_2CH_2—$, $—CH(CH_2)_3CH_2—$, and $—CH_2(CH_2)_4CH_2—$.

The term "cycloalkylenyl" as used herein refers to a divalent radical of a cycloalkyl group. In one embodiment, the cycloalkylenyl is a divalent form of a $C_{3-8}$ cycloalkyl, i.e., a $C_3$-$C_8$ cycloalkylenyl. Non-limiting exemplary cycloalkylenyl groups include;

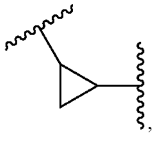,
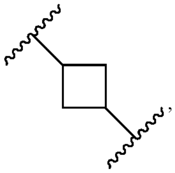,
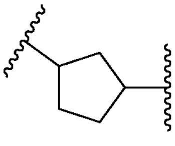, and
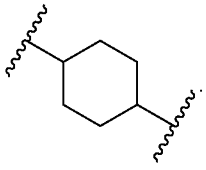.

It will be understood by those skilled in the art that the moieties substituted on the hydrocarbon chain can themselves be substituted, if appropriate. For instance, the substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Cycloalkyls can be substituted in the same manner.

The term "heteroalkyl", as used herein, refers to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups.

The term "alkylthio" refers to an alkyl group, as defined above, having a sulfur radical attached thereto. In some embodiments, the "alkylthio" moiety is represented by one of —S— alkyl, —S-alkenyl, and —S-alkynyl. Representative alkylthio groups include methylthio, and ethylthio. The term "alkylthio" also encompasses cycloalkyl groups, alkene and cycloalkene groups, and alkyne groups. "Arylthio" refers to aryl or heteroaryl groups. Alkylthio groups can be substituted as defined above for alkyl groups.

The terms "alkenyl" and "alkynyl", refer to unsaturated aliphatic groups analogous in length and possible substitution to the alkyls described above, but that contain at least one double or triple bond respectively. In one embodiment, the alkenyl contains one double bond. In another embodiment, the alkenyl contains two double bonds. In another embodiment, the alkenyl contains three double bonds.

The term "alkenylenyl" as used herein refers to a divalent radical of an alkenyl group. In one embodiment, the alkenylenyl is a divalent form of a $C_{2-12}$ alkenyl, i.e., a $C_2$-$C_{12}$ alkenylenyl. In one embodiment, the alkenylenyl is a divalent form of a $C_{2-6}$ alkenyl, i.e., a $C_2$-$C_{10}$ alkenylenyl. In one embodiment, the alkenylenyl is a divalent form of a $C_{2-14}$ alkenyl, i.e., a $C_2$-$C_8$ alkenylenyl. In one embodiment, the alkylenyl is a divalent form of an unsubstituted $C_{2-6}$ alkenyl, i.e., a $C_2$-$C_6$ alkenylenyl. In another embodiment, the alkylenyl is a divalent form of an unsubstituted $C_{24}$ alkyl, i.e., a $C_2$-$C_4$ alkenylenyl. Non-limiting exemplary alkenylenyl groups include —CH═CH—, —$CH_2$CH═CH—, —$CH_2CH_2$CH═$CHCH_2$—, and —$CH_2$CH═$CHCH_2$CH═$CHCH_2CH_2$—.

The terms "alkoxyl" or "alkoxy" as used herein refers to an alkyl group, as defined above, having an oxygen radical attached thereto. Representative alkoxyl groups include methoxy, ethoxy, propyloxy, and tert-butoxy. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, and —O— alkynyl. Aroxy can be represented by —O-aryl or O-heteroaryl, wherein aryl and heteroaryl are as defined below. The alkoxy and aroxy groups can be substituted as described above for alkyl.

The terms "amine" and "amino" are art-recognized and refer to both unsubstituted and substituted amines, e.g., a moiety that can be represented by the general formula:

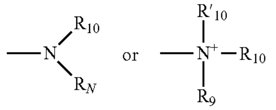

wherein $R_9$, $R_{10}$, and $R'_{10}$ each independently represent a hydrogen, an alkyl, an alkenyl, —$(CH_2)_m$—$R_8$ or $R_9$ and $R_{10}$ taken together with the N atom to which they are attached complete a heterocycle having from 4 to 8 atoms in the ring structure; $R_8$ represents an aryl, a cycloalkyl, a cycloalkenyl, a heterocycle or a polycycle; and m is zero or an integer in the range of 1 to 8. In some embodiments, only one of $R_9$ or $R_{10}$ can be a carbonyl, e.g., $R_9$, $R_{10}$ and the nitrogen together do not form an imide. In still other embodiments, the term "amine" does not encompass amides, e.g., wherein one of $R_9$ and $R_{10}$ represents a carbonyl. In additional embodiments, $R_9$ and $R_{10}$ (and optionally $R'_{10}$) each independently represent a hydrogen, an alkyl or cycloalkly, an alkenyl or cycloalkenyl, or alkynyl. Thus, the term "alkylamine" as used herein means an amine group, as defined above, having a substituted (as described above for alkyl) or unsubstituted alkyl attached thereto, i.e., at least one of $R_9$ and $R_{10}$ is an alkyl group.

The term "amido" is art-recognized as an amino-substituted carbonyl and includes a moiety that can be represented by the general formula:

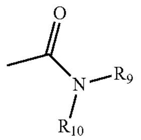

wherein $R_9$ and $R_{10}$ are as defined above.

"Aryl", as used herein, refers to $C_5$-$C_{10}$-membered aromatic, heterocyclic, fused aromatic, fused heterocyclic, biaromatic, or bihetereocyclic ring systems. Broadly defined, "aryl", as used herein, includes 5-, 6-, 7-, 8-, 9-, and 10-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with one or more substituents including, but not limited to, halogen, azide, alkyl, aralkyl, alkenyl, alkynyl, cycloalkyl, hydroxyl, alkoxyl, amino (or quaternized amino), nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN; and combinations thereof.

The term "aryl" also includes polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. One or more of the rings can be substituted as defined above for "aryl".

The term "aralkyl," as used herein, refers to an alkyl group substituted with an aryl group (e.g., an aromatic or heteroaromatic group).

The term "carbocycle," as used herein, refers to an aromatic or non-aromatic ring in which each atom of the ring is carbon.

"Heterocycle" or "heterocyclic," as used herein, refers to a cyclic radical attached via a ring carbon or nitrogen of a monocyclic or bicyclic ring containing 3-10 ring atoms, for example, from 5-6 ring atoms, consisting of carbon and one to four heteroatoms each selected from the group consisting of non-peroxide oxygen, sulfur, and N(Y) wherein Y is absent or is H, O, ($C_1$-$C_{10}$) alkyl, phenyl or benzyl, and optionally containing 1-3 double bonds and optionally substituted with one or more substituents. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxepanyl, oxetanyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydropyranyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. Heterocyclic groups can optionally be substituted with one or more substituents at one or more positions as defined above for alkyl and aryl, for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —CF3, and —CN.

The term "carbonyl" is art-recognized and includes such moieties as can be represented by the general formula:

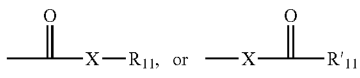

wherein X is a bond or represents an oxygen or a sulfur, and $R_{11}$ represents a hydrogen, an alkyl, a cycloalkyl, an alkenyl, a cycloalkenyl, or an alkynyl, $R'_{11}$ represents a hydrogen, an alkyl, a cycloalkyl, an alkenyl, a cycloalkenyl, or an alkynyl. Where X is an oxygen and $R_{11}$ or $R'_{11}$ is not hydrogen, the formula represents an "ester". Where X is an oxygen and $R_{11}$ is as defined above, the moiety is referred to herein as a carboxyl group, and particularly when $R_{11}$ is a hydrogen, the formula represents a "carboxylic acid". Where X is an oxygen and $R'_{11}$ is hydrogen, the formula represents a "formate". In general, where the oxygen atom of the above formula is replaced by sulfur, the formula represents a "thiocarbonyl" group. Where X is a sulfur and $R_{11}$ or $R'_{11}$ is not hydrogen, the formula represents a "thioester." Where X is a sulfur and $R_{11}$ is hydrogen, the formula represents a "thiocarboxylic acid." Where X is a sulfur and $R'_{11}$ is hydrogen, the formula represents a "thioformate." On the other hand, where X is a bond, and $R_{11}$ is not hydrogen, the above formula represents a "ketone" group. Where X is a bond, and $R_{11}$ is hydrogen, the above formula represents an "aldehyde" group.

The term "heteroatom" as used herein means an atom of any element other than carbon or hydrogen. Examples of heteroatoms are boron, nitrogen, oxygen, phosphorus, sulfur and selenium. Other useful heteroatoms include silicon and arsenic.

As used herein, the term "nitro" means $—NO_2$; the term "halogen" designates —F, —Cl, —Br or —I; the term "sulfhydryl" means —SH; the term "hydroxyl" means —OH; and the term "sulfonyl" means $—SO_2—$.

The term "substituted" as used herein, refers to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, for example, 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, aminoacid, peptide, and polypeptide groups.

As described herein, compounds of the present disclosure may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $—(CH_2)_{0-4}R°$; $—(CH_2)_{0-4}OR°$; $—O(CH_2)_{0-4}R°—O—(CH_2)_{0-4}C(O)OR°$; $—(CH_2)_{0-4}CH(OR°)_2$; $—(CH_2)_{0-4}SR°$; $—(CH_2)_{0-4}Ph$, which may be substituted with R°; $—(CH_2)_{0-4}O(CH_2)_{0-1}Ph$ which may be substituted with R°; —CH═CHPh, which may be substituted with R°; $—(CH_2)_{0-4}O(CH_2)_{0-1}$-pyridyl which may be substituted with R°; $—NO_2$; —CN; $—N_3$; $—(CH_2)_{0-4}N(R°)_2$; $—(CH_2)_{0-4}N(R°)C(O)R°$; —N(R°)C(S)R°; $—(CH_2)_{0-4}N(R°)C(O)NR°_2$; $—N(R°)C(S)NR°_2$; $—(CH_2)_{0-4}N(R°)C(O)OR°$; —N(R°)N(R°)C(O)R°; $—N(R°)N(R°)C(O)NR°_2$; —N(R°)N(R°)C(O)OR°; $—(CH_2)_{0-4}C(O)R°$; —C(S)R°; $—(CH_2)_{0-4}C(O)OR°$; $—(CH_2)_{0-4}C(O)SR°$; $—(CH_2)_{0-4}C(O)OSiR°_3$; $—(CH_2)_{0-4}OC(O)R°$; $—OC(O)(CH_2)_{0-4}SR°$, SC(S)SR°; $—(CH_2)_{0-4}SC(O)R°$; $—(CH_2)_{0-4}C(O)NR°_2$; $—C(S)NR°_2$; —C(S)SR°; —SC(S)SR°, $—(CH_2)_{0-4}OC(O)NR°_2$; —C(O)N(OR°)R°; —C(O)C(O)R°; $—C(O)CH_2C(O)R°$; —C(NOR°)R°; $—(CH_2)_{0-4}SSR°$; $—(CH_2)_{0-4}S(O)_2R°$; $—(CH_2)_{0-4}S(O)_2OR°$; $—(CH_2)_{0-4}OS(O)_2R°$; $—S(O)_2NR°_2$; $—(CH_2)_{0-4}S(O)R°$; $—N(R°)S(O)_2NR°_2$; $—N(R°)S(O)_2R°$; —N(OR°)R°; $—C(NH)NR°_2$; $—P(O)_2R°$; $—P(O)R°_2$; $—OP(O)R°_2$; $—OP(O)(OR°)_2$; $SiR°_3$; —($C_{1-4}$ straight or branched alkylene)O—N(R°)$_2$; or —($C_{1-4}$ straight or branched alkylene)C(O)O—N(R°)$_2$, wherein each R° may be substituted as defined below and is independently hydrogen, $C_{1-6}$ aliphatic, $—CH_2Ph$, $—O(CH_2)_{0-1}Ph$, $—CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, $—(CH_2)_{0-2}R^●$, -(haloR$^●$), $—(CH_2)_{0-2}OH$, $—(CH_2)_{0-2}OR^●$, $—(CH_2)_{0-2}CH(OR^●)_2$; —O(haloR$^●$), —CN, $—N_3$, $—(CH_2)_{0-2}C(O)R^●$, $—(CH_2)_{0-2}C(O)OH$, $—(CH_2)_{0-2}C(O)OR^●$, $—(CH_2)_{0-2}SR^●$, $—(CH_2)_{0-2}SH$, $—(CH_2)_{0-2}NH_2$, $—(CH_2)_{0-2}NHR^●$, $—(CH_2)_{0-2}NR^●_2$, $—NO_2$, $—SiR^●_3$, $—OSiR^●_3$, $—C(O)SR^●$, —($C_{1-4}$ straight or branched alkylene)C(O)OR$^●$, or $—SSR^●$ wherein each R$^●$ is unsubstituted or where preceded by "halo" is substituted only with one or more halogens, and is independently selected from $C_{1-4}$ aliphatic, $—CH_2Ph$, $—O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of R° include ═O and ═S.

Suitable divalent substituents on a saturated carbon atom of an "optionally substituted" group include the following: ═O, ═S, $═NNR^*_2$, ═NNHC(O)R*, ═NNHC(O)OR*, $═NNHS(O)_2R^*$, ═NR*, ═NOR*, $—O(C(R^*_2))_{2-3}O—$, or $—S(C(R^*_2))_{2-3}S—$, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $—O(CR^*_2)_{2-3}O—$, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R$^●$ include halogen, $—R^●$, -(haloR$^●$), —OH, $—OR^●$, —O(haloR$^●$), —CN, —C(O)OH, $—C(O)OR^●$, $—NH_2$, $—NHR^●$, $—NR^●_2$, or $—NO_2$, wherein each R* is unsubstituted or where preceded by "halo" is substituted only with one or more halogens, and is independently $C_{14}$ aliphatic, $—CH_2Ph$, $—O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include $—R^†$, $—NR^†_2$, $—C(O)R^†$, $—C(O)OR^†$, $—C(O)C(O)R^†$, $—C(O)CH_2C(O)R^†$, $—S(O)_2R^†$, $—S(O)_2NR^†_2$, $—C(S)NR^†_2$, $—C(NH)NR^†_2$, or $—N(R^†)S(O)_2R^†$; wherein each $R^†$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^†$ are independently halogen, $—R^●$, -(haloR$^●$), —OH, $—OR^●$, —O(haloR$^●$), —CN, —C(O)OH, $—C(O)OR^●$, $—NH_2$, $—NHR^●$, $—NR^●_2$, or $—NO_2$, wherein each R$^●$ is unsubstituted or where preceded by "halo" is substituted only with one or more halogens, and is independently $C_{1-4}$ aliphatic, $—CH_2Ph$, $—O(CH_2)_{0-1}Ph$, or a 5-6-membered saturated, partially unsaturated, or aryl ring having 0-4 heteroatoms independently selected from nitrogen, oxygen, or sulfur.

Heteroatoms such as nitrogen may have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e., a compound that does not spontaneously undergo transformation, for example, by rearrangement, cyclization, or elimination.

In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. The heteroatoms such as nitrogen may have hydrogen substituents and/or any permissible substituents of organic compounds described herein which satisfy the valencies of the heteroatoms.

In various embodiments, the substituent is selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, and thioketone, each of which optionally is substituted with one or more suitable substituents. In some embodiments, the substituent is selected from alkoxy, aryloxy, alkyl, alkenyl, alkynyl, amide, amino, aryl, arylalkyl, carbamate, carboxy, cycloalkyl, ester, ether, formyl, haloalkyl, heteroaryl, heterocyclyl, ketone, phosphate, sulfide, sulfinyl, sulfonyl, sulfonic acid, sulfonamide, and thioketone, wherein each of the alkoxy, aryloxy, alkyl, alkenyl, alkynyl, amide, amino, aryl, arylalkyl, carbamate, carboxy, cycloalkyl, ester, ether, formyl, haloalkyl, heteroaryl, heterocyclyl, ketone, phosphate, sulfide, sulfinyl, sulfonyl, sulfonic acid, sulfonamide, and thioketone can be further substituted with one or more suitable substituents.

Examples of substituents include, but are not limited to, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, thioketone, ester, heterocyclyl, —CN, aryl, aryloxy, perhaloalkoxy, aralkoxy, heteroaryl, heteroaryloxy, heteroarylalkyl, heteroaralkoxy, azido, alkylthio, oxo, acylalkyl, carboxy esters, carboxamido, acyloxy, aminoalkyl, alkylaminoaryl, alkylaryl, alkylaminoalkyl, alkoxyaryl, arylamino, aralkylamino, alkylsulfonyl, carboxamidoalkylaryl, carboxamidoaryl, hydroxyalkyl, haloalkyl, alkylaminoalkylcarboxy, aminocarboxamidoalkyl, cyano, alkoxyalkyl, perhaloalkyl, arylalkyloxyalkyl, and the like. In some embodiments, the substituent is selected from cyano, halogen, hydroxyl, and nitro.

Antibodies: As used herein, the term "antibody" is referred to in the broadest sense and specifically covers various embodiments including, but not limited to monoclonal antibodies, polyclonal antibodies, multispecific antibodies (e.g., bispecific antibodies formed from at least two intact antibodies), and antibody fragments (e.g., diabodies) so long as they exhibit a desired biological activity (e.g., "functional"). Antibodies are primarily amino-acid based molecules but may also comprise one or more modifications (including, but not limited to the addition of sugar moieties, fluorescent moieties, chemical tags, etc.). Non-limiting examples of antibodies or fragments thereof include VH and VL domains, scFvs, Fab, Fab', F(ab')2, Fv fragment, diabodies, linear antibodies, single chain antibody molecules, multispecific antibodies, bispecific antibodies, intrabodies, monoclonal antibodies, polyclonal antibodies, humanized antibodies, codon-optimized antibodies, tandem scFv antibodies, bispecific T-cell engagers, mAb2 antibodies, chimeric antigen receptors (CAR), tetravalent bispecific antibodies, biosynthetic antibodies, native antibodies, miniaturized antibodies, unibodies, maxibodies, antibodies to senescent cells, antibodies to conformers, antibodies to disease specific epitopes, or antibodies to innate defense molecules.

Associated: As used herein, the terms "associated with," "conjugated," "linked," "attached," and "tethered," when used with respect to two or more moieties, means that the moieties are physically associated or connected with one another, either directly or via one or more additional moieties that serves as a linking agent, to form a structure that is sufficiently stable so that the moieties remain physically associated under the conditions in which the structure is used, e.g., physiological conditions. An "association" need not be strictly through direct covalent chemical bonding. It may also suggest ionic or hydrogen bonding or a hybridization based connectivity sufficiently stable such that the "associated" entities remain physically associated.

Cargo: As used herein, the term "cargo" or "payload" can refer to one or more molecules or structures encompassed in a delivery vehicle for delivery to or into a cell or tissue. Non-limiting examples of cargo can include a nucleic acid, a polypeptide, a peptide, a protein, a liposome, a label, a tag, a small chemical molecule, a large biological molecule, and any combinations thereof.

Chimeric Antigen Receptors (CARs): As used herein, the term "chimeric antigen receptor" or "CAR" refers to an artificial chimeric protein comprising at least one antigen specific targeting region (ASTR), a transmembrane domain and an intracellular signaling domain, wherein the antigen specific targeting region comprises a full-length antibody or a fragment thereof. Any molecule that is capable of binding a target antigen with high affinity can be used in the ASTR of a CAR. The CAR may optionally have an extracellular spacer domain and/or a co-stimulatory domain. A CAR may also be used to generate a cytotoxic cell carrying the CAR.

Circular RNA: As used herein, the term "circular RNA" or "circRNA" refer to a RNA that forms a circular structure through covalent or non-covalent bonds.

Co-Administered: As used herein, the term "co-administered" or "co-administering" means administering an originator construct, a benchmark construct or a targeting system with one or more additional an originator construct, a benchmark construct, a targeting systems or other therapeutic agents or moieties sufficiently close in time such that the effect of the originator construct, a benchmark construct, a targeting systems or other therapeutic agents or moieties is enhanced.

Complementary and substantially complementary: As used herein, the term "complementary" refers to the ability of polynucleotides to form base pairs with one another. Base pairs are typically formed by hydrogen bonds between nucleotide units in antiparallel polynucleotide strands. Complementary polynucleotide strands can form base pair in the Watson-Crick manner (e.g., A to T, A to U, C to G), or in any other manner that allows for the formation of duplexes. As persons skilled in the art are aware, when using RNA as opposed to DNA, uracil rather than thymine is the base that is considered to be complementary to adenosine. However, when a U is denoted in the context of the present disclosure, the ability to substitute a T is implied, unless otherwise stated. Perfect complementarity or 100% complementarity refers to the situation in which each nucleotide unit of one polynucleotide strand can form hydrogen bond with a nucleotide unit of a second polynucleotide strand. Less than perfect complementarity refers to the situation in which some, but not all, nucleotide units of two strands can form hydrogen bond with each other. For example, for two 20-mers, if only two base pairs on each strand can form hydrogen bond with each other, the polynucleotide strands exhibit 10% complementarity. In the same example, if 18 base pairs on each strand can form hydrogen bonds with each other, the polynucleotide strands exhibit 90% complementarity. As used herein, the term "substantially complementary" means that the siRNA has a sequence (e.g., in the antisense strand) which is sufficient to bind the desired target mRNA, and to trigger the RNA silencing of the target mRNA.

Delivery: As used herein, "delivery" refers to the act or manner of delivering a compound, substance, entity, moiety, cargo or payload.

DNA and RNA: As used herein, the term "RNA" or "RNA molecule" or "ribonucleic acid molecule" refers to a polymer of ribonucleotides; the term "DNA" or "DNA molecule" or "deoxyribonucleic acid molecule" refers to a polymer of deoxyribonucleotides. DNA and RNA can be synthesized naturally, e.g., by DNA replication and transcription of DNA, respectively; or be chemically synthesized. DNA and RNA can be single-stranded (i.e., ssRNA or ssDNA, respectively) or multi-stranded (e.g., double stranded, i.e., dsRNA and dsDNA, respectively). The term "mRNA" or "messenger RNA", as used herein, refers to a single stranded RNA that encodes the amino acid sequence of one or more polypeptide chains.

Encapsulate: As used herein, the term "encapsulate" means to enclose, surround or encase.

Encode: As used herein the term "encode" refers broadly to any process whereby the information in a polymeric macromolecule is used to direct the production of a second molecule that is different from the first. The second molecule may have a chemical structure that is different from the chemical nature of the first molecule.

Enhance expression of a gene: As used herein, the phrase "add-back" or "enhance expression of a gene" means to cause an increase in the amount of an expression product of the gene. The expression product can be an RNA transcribed from the gene (e.g., an mRNA) or a polypeptide translated from an mRNA transcribed from the gene. Typically, an increase in the level of an mRNA results in an increase in the level of a polypeptide translated therefrom. The level of expression may be determined using standard techniques for measuring mRNA or protein.

Exosomes: As used herein, "exosome" is a vesicle secreted by mammalian cells or a complex involved in RNA degradation.

Formulation: As used herein, a "formulation" includes at least one compound, substance, entity, moiety, cargo or payload and a delivery agent.

Fragment: A "fragment," as used herein, refers to a portion. For example, fragments of proteins may comprise polypeptides obtained by digesting full-length protein isolated from cultured cells.

Homology: As used herein, the term "homology" refers to the overall relatedness between polymeric molecules, e.g. between polynucleotide molecules (e.g. DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical or similar. The term "homologous" necessarily refers to a comparison between at least two sequences (polynucleotide or polypeptide sequences). In accordance with the disclosure, two polynucleotide sequences are considered to be homologous if the polypeptides they encode are at least about 50%, 60%, 70%, 80%, 90%, 95%, or even 99% for at least one stretch of at least about 20 amino acids. In some embodiments, homologous polynucleotide sequences are characterized by the ability to encode a stretch of at least 4-5 uniquely specified amino acids. For polynucleotide sequences less than 60 nucleotides in length, homology is determined by the ability to encode a stretch of at least 4-5 uniquely specified amino acids. In accordance with the disclosure, two protein sequences are considered to be homologous if the proteins are at least about 50%, 60%, 70%, 80%, or 90% identical for at least one stretch of at least about 20 amino acids.

Inactive Ingredient: As used herein, the term "inactive ingredient" refers to one or more agents that do not contribute to the activity of the active ingredient of the pharmaceutical composition included in formulations. In some embodiments, all, none or some of the inactive ingredients which may be used in the formulations of the present disclosure may be approved by the US Food and Drug Administration (FDA).

IRES: As used herein, the term "internal ribosome entry site" or "IRES" refers to an RNA sequence or structural element ranging in size form 10 nucleotides to 1,000 nucleotides or more which is capable of initiating translation of a polypeptide in the absence of a normal RNA cap structure.

Identity: As used herein, the term "identity" refers to the overall relatedness between polymeric molecules, e.g., between polynucleotide molecules (e.g. DNA molecules and/or RNA molecules) and/or between polypeptide molecules. Calculation of the percent identity of two polynucleotide sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using methods such as those described in Computational Molecular Biology, Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, Part I, Griffin, A. M., and Griffin, H. G., eds., Humana Press, New Jersey, 1994; and Sequence Analysis Primer, Gribskov, M. and Devereux, J., eds., M Stockton Press, New York, 1991; each of which is incorporated herein by reference. For example, the percent identity between two nucleotide sequences can be determined using the algorithm of Meyers and Miller (CABIOS, 1989, 4:11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using an NWSgapdna.CMP matrix. Methods commonly employed to determine percent identity between sequences include, but are not limited to those disclosed in Carillo, H. and Lipman, D., SIAM J Applied Math., 48:1073 (1988); incorporated herein by reference. Techniques for determining identity are codified in publicly available computer programs. Exemplary computer software to determine homology between two sequences include, but are not limited to, GCG program package, Devereux, J., et al., Nucleic Acids Research, 12(1), 387 (1984)), BLASTP, BLASTN, and FASTA Altschul, S. F. et al., J. Molec. Biol., 215, 403 (1990)).

Inhibit expression of a gene: As used herein, the phrase "knock-down" or "inhibit expression of a gene" means to cause a reduction in the amount of an expression product of the gene. The expression product can be an RNA transcribed from the gene (e.g., an mRNA) or a polypeptide translated from an mRNA transcribed from the gene. Typically, a reduction in the level of an mRNA results in a reduction in the level of a polypeptide translated therefrom. The level of expression may be determined using standard techniques for measuring mRNA or protein.

Ionizable Lipid: As used herein "ionizable lipid" refers to any of a number of lipid species that carry a net positive charge at a selected pH.

Lipid Nanoparticle: As used herein "lipid nanoparticle" or "LNP" refers to a delivery vehicle comprising one or more lipids (e.g., cationic lipids, non-cationic lipids, PEG-modified lipids).

Liposome: As used herein "liposome" generally refers to a vesicle composed of lipids (e.g., amphiphilic lipids) arranged in one or more spherical bilayers or bilayers.

Modified: As used herein "modified" refers to a changed state or structure of a molecule. Molecules may be modified in many ways including chemically, structurally, and functionally.

Non-Cationic Lipid: As used herein "non-cationic lipid" refers to any neutral, zwitterionic or anionic lipid.

Peptide: As used herein, "peptide" is less than or equal to 50 amino acids long, e.g., about 5, 10, 15, 20, 25, 30, 35, 40, 45, or 50 amino acids long.

Pharmaceutical Composition: As used herein the term "pharmaceutical composition" refers to compositions comprising at least one active ingredient and optionally one or more pharmaceutically acceptable excipients.

PEG: As used herein "PEG" means any polyethylene glycol or other polyalkylene ether polymer.

Spacer: As used herein the term "spacer" refers to a region of a polynucleotide or polypeptide ranging from 1 residue to hundreds or thousands of residues separating two other elements in a sequence. The sequence of the spacer can be defined or random. A spacer sequence is typically non-coding but may be a coding sequence.

Sterol: As used herein "sterol" is a subgroup of steroids consisting of steroid alcohols.

Structural Lipid: As used herein "structural lipid" refers to sterols and lipids containing sterol moieties.

Transcription: As used herein the term "transcription" refers to the formation or synthesis of an RNA molecule by an RNA polymerase using a DNA molecule as a template.

Translation: As used herein the term "translation" refers to the formation of a polypeptide molecule by a ribosome based upon a RNA template.

Treat and Prevent: As used herein the terms "treat" or "prevent" as well as words stemming therefrom do not necessarily imply 100% or complete treatment or prevention. Rather there are varying degrees of treatment or prevention of which one of ordinary skill in the art recognizes as having a potential benefit or therapeutic effect. Also, "prevention" can encompass delaying the onset of the disease, symptom or condition thereof.

Unmodified: As used herein, "unmodified" refers to any substance, compound or molecule prior to being changed in any way. Unmodified may, but does not always, refer to the wild type or native form of a biomolecule. Molecules may undergo a series of modifications whereby each modified molecule may serve as the "unmodified" starting molecule for a subsequent modification.

Vector: As used herein, a "vector" is any molecule or moiety which transports, transduces or otherwise acts as a carrier of a heterologous molecule. Vectors of the present disclosure may be produced recombinantly and may be based on and/or may comprise viral parent or reference sequence. Such parent or reference viral sequences may serve as an original, second, third or subsequent sequence for engineering vectors. In non-limiting examples, such parent or reference viral sequences may comprise any one or more of the following sequences: a polynucleotide sequence encoding a polypeptide or multi-polypeptide, which sequence may be wild-type or modified from wild-type and which sequence may encode full-length or partial sequence of a protein, protein domain, or one or more subunits of a protein; a polynucleotide comprising a modulatory or regulatory nucleic acid which sequence may be wild-type or modified from wild-type; and a transgene that may or may not be modified from wild-type sequence. These viral sequences may serve as either the "donor" sequence of one or more codons (at the nucleic acid level) or amino acids (at the polypeptide level) or "acceptor" sequences of one or more codons (at the nucleic acid level) or amino acids (at the polypeptide level). The details of one or more embodiments of the disclosure are set forth in the accompanying description below. Although any materials and methods similar or equivalent to those described herein can be used in the practice or testing of the present disclosure, the preferred materials and methods are now described. Other features, objects and advantages of the disclosure will be apparent from the description. In the description, the singular forms also include the plural unless the context clearly dictates otherwise. Unless defined otherwise, all technical and scientific terms used herein have the same meaning as commonly understood by one of ordinary skill in the art to which this disclosure belongs. In the case of conflict, the present description will control.

XII. Examples

Example 1

Methods of Making the Lipids

The Lipids of the Disclosure may be prepared using any convenient methodology. In a rational approach, the lipids are constructed from their individual components. The components can be covalently bonded to one another through functional groups, as is known in the art, where such functional groups may be present on the components or introduced onto the components using one or more steps, e.g., oxidation reactions, reduction reactions, cleavage reactions and the like. Functional groups that may be used in covalently bonding the components together to produce the lipids: hydroxy, sulfhydryl, amino, and the like. Where necessary and/or desired, certain moieties on the components may be protected using blocking groups, as is known in the art, see, e.g., Green & Wuts, Protective Groups in Organic Synthesis (John Wiley & Sons) (1991).

Alternatively, the lipids can be produced using known combinatorial methods to produce large libraries of potential lipids which may then be screened for identification of a lipid with desired functionalities.

Example 2

Methods of Making the Delivery Vehicles

The delivery vehicles such as LNPs of the present disclosure may be prepared using any convenient methodology. In one non-limiting example, the LNPs are formed by mixing equal volumes of lipids dissolved in alcohol with oligonucleotide payloads dissolved in a citrate buffer by an impinging jet process.

The lipid solution contains a cationic lipid compound of the present disclosure, a helper lipid, a neutral lipid and a PEGylated lipid. The payload to total lipid ratio is approximately 1:20 (wt/wt). The LNPs are formed by mixing equal volumes of lipid solution in ethanol with oligonucleotide payloads dissolved in a citrate buffer by an impinging jet process through a mixing device. The mixed LNP solution is held at room temperature for 0-24 hrs prior to a dilution step.

The solution is then concentrated and diafiltered with suitable buffer by ultrafiltration or dialysis process using membranes. The final product is sterile filtered and stored at 4° C.

Example 3

Evaluation of Candidate LNP Targeting Systems

A library of candidate targeting systems is prepared where the candidate targeting systems comprise at least one identifier sequence or moiety in the formulation and at least one identifier sequence and/or payload in the nucleic acid construct.

Candidate Targeting System Generation

A population of lipid nanoparticle (LNP) formulations are generated where the cationic lipid component is labeled with at least one identifier sequence or moiety. The LNP formulations that are generated may include LNPs where (a) the components are the same for all formulations and the molar ratios of the components are the same for all the LNP formulations, (b) the components are the same for all formulations but the molar ratios of the components are different for all the LNP formulations, or (c) the components are different for the LNP formulations. Each of the different LNP formulation can include different identifier sequence or moiety in order to track targeting system after administration. Nucleic acid constructs including at least one identifier sequence or payload (e.g., a reporter gene) is generated and formulated in the population of LNPs in order to create candidate targeting systems to be administered to a subject.

Screening and Validation of candidate Targeting Systems

The candidate targeting systems are then administered into a subject at a pre-determined dose and dosing interval. After administration the entire subject or a region of the subject is screened to determine the location of the LNP formation and/or the payload of the benchmark construct. The subject can be scanned by various methods known in the art including positron emission tomography (PET) and computed tomography (CT) utilizing the $^{64}Cu$ radiolabel. The localization of the LNP formation and/or the payload will be determined by visual inspection of the PET images for areas with the greatest concentration of $^{64}Cu$ and anatomical position of PET results will be confirmed using the results of the CT scan. The scan can be repeated in order to determine if the localization changes over time.

At the desired time points, samples will be taken from the areas of the subject displaying localization of the LNP and/or the payload in the whole animal localization screening performed above for higher resolution screening of the distribution.

The samples can then be prepared for Fluorescence-activated Cell Sorting (FACS) via the directions supplied with the cell sorter. These populations of cells are then prepared for deep sequencing to determine the presence and identity of the payload and/or identifier sequence.

These results from the screening of the LNP library will provide the tropism of the LNP formulation and the nucleic acid construct that was administered to the subject.

Example 4

Synthesis of Exemplary Ionizable Lipids

Synthesis of Bis(3-pentyloctyl) 8,8'-((4-hydroxybutyl)azanediyl) dioctanoate (Compound 11)

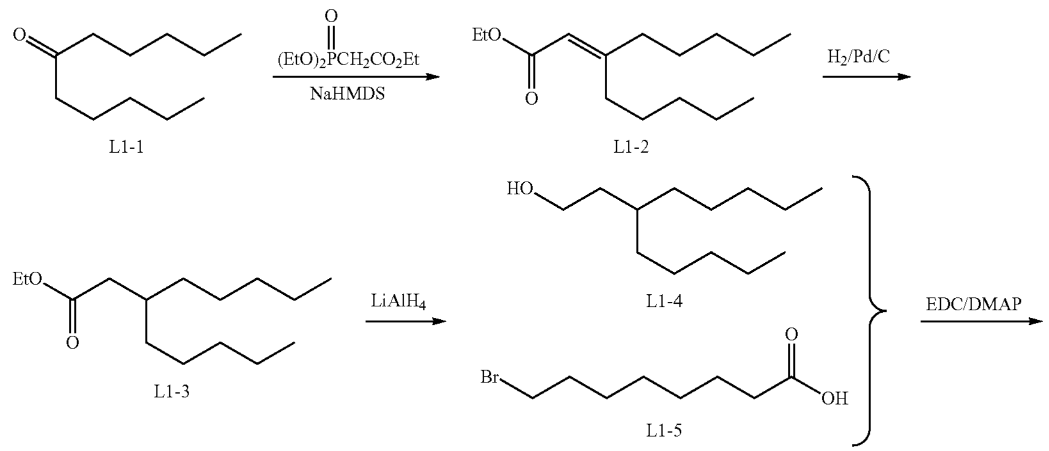

-continued

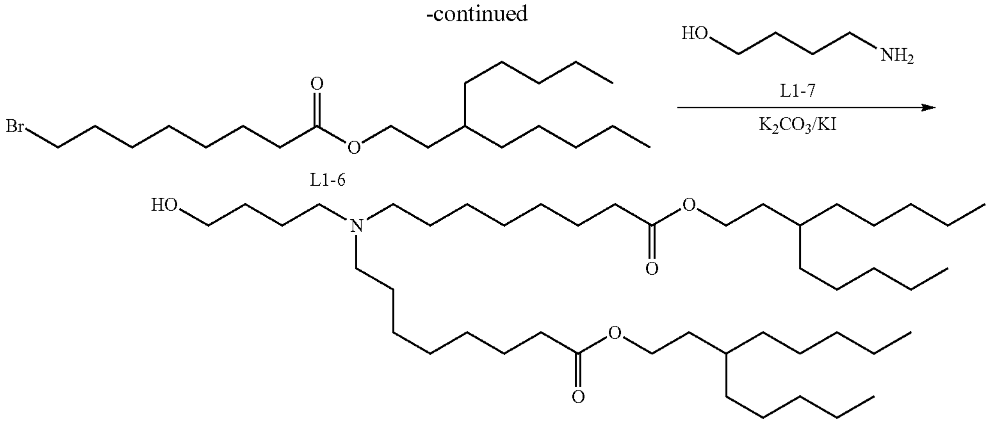

L1-6

Compound 11

Synthesis of ethyl 3-pentyloct-2-enoate (L1-2)

To a solution of triethyl phophonoacetate (26.3 g, 118 mmol) in anhydrous THF (33 mL) was added 1M NaHMDS in THF (118 mL, 118 mmol), dropwise, at −10 to −15° C. under nitrogen atmosphere. After completion of the addition, the mixture was stirred at the same temperature for 30 min and then at 0° C. for 1 h. To this mixture was dropped in 6-undecanone (10.0 g, 59 mmol) at 0° C. and the reaction mixture was allowed to warm to room temperature and stirred overnight. It was then warmed to 45° C. and stirred for an additional 24 h. Aq. sat. $NH_4Cl$ (8 mL) was added and the THF was evaporated. The residue was mixed with $Et_2O$ (80 mL) and $H_2O$ (100 mL) and the resulting phases were separated. The aqueous phase was extracted with $Et_2O$ (80 mL). Combined organic phases were washed with $H_2O$ (100 mL×2) and dried over anhydrous $Na_2SO_4$. Filtration and concentration provided crude material which was purified by flash column chromatography ($SiO_2$: 0 to 4% ethyl acetate in hexane gradient) to yield ethyl 3-pentyloct-2-enoate L1-2 as colorless oil (11.6 g, 82%). $^1$H-NMR (300 MHz, $CDCl_3$) δ 5.60 (s, 1H), 4.13 (q, J=7.1 Hz, 2H), 2.57 (t, J=7.6 Hz, 2H), 2.12 (t, J=7.4 Hz, 2H), 1.52-1.19 (m, 15H), 0.89 (t, J=7.2 Hz, 6H); CIMS m/z 241 $[M+H]^+$.

Synthesis of ethyl 3-pentyloctanoate (L1-3)

To a solution of L1-2 (11.0 g, 2.1 mmol) in EtOAc (90 mL) was added 10% Pd/C (0.5 g). The resulting mixture was stirred under a hydrogen balloon for one day. It was then filtered through Celite. The Celite was rinsed with EtOAc (25 mL×3). The combined filtrate was evaporated to give ethyl 3-pentyloctanoate L1-3 as a light-yellow oil (9.0 g, 83%). $^1$H-NMR (300 MHz, $CDCl_3$) δ 4.10 (q, J=7.1 Hz, 2H), 2.20 (d, J=6.8 Hz, 2H), 1.82 (s, 1H), 1.40-1.12 (m, 19H), 0.88 (t, J=7.0 Hz, 6H).

Synthesis of 3-pentyloctan-1-ol (L1-4)

To a 2.0 M THF solution of lithium aluminum hydride (28 mL, 56 mmol) was added slowly a solution of L1-3 (7.0 g, 29 mmol) in THF (33 mL) at 0° C. under nitrogen atmosphere. The resulting mixture was stirred at 0° C. for 1 h then at room temperature overnight. With ice-water bath cooling, the reaction was quenched by adding saturated aqueous $Na_2SO_4$ solution to give a milky solution. The organic phase was separated, and the aqueous phase was extracted with $Et_2O$ (50 mL×2). The combined organic phases were dried over $Na_2SO_4$. Filtration and concentration provided crude material which was purified by flash column chromatography ($SiO_2$: 0 to 15% ethyl acetate in hexane gradient) to yield 3-pentyloctan-1-ol L1-4 as slightly yellow oil (4.0 g, 70%). $^1$H-NMR (300 MHz, $CDCl_3$) 3.65 (t, J=4.4 Hz, 2H), 1.51 (dd, J=13.7 Hz, 6.8 Hz, 2H), 1.46-1.12 (m, 17H), 0.88 (t, J=7.1 Hz, 6H).

Synthesis of 3-pentyloctyl 8-bromooctanoate (L1-6)

To a solution of L1-4 (0.8 g, 4 mmol) in DCM (10 mL) was added 8-bromooctanoic acid L1-5 (1.0 g, 4.4 mmol) followed by DMAP (0.3 g, 2 mmol) and EDC (1.9 g, 8 mmol). The resulting mixture was stirred at room temperature under nitrogen atmosphere overnight. The reaction mixture was diluted with DCM (10 mL) and washed with saturated $NaHCO_3$ aqueous solution (10 mL), water (10 mL) and brine (10 mL). The organic phase was dried over anhydrous $Na_2SO_4$. Filtration and concentration provided crude material which was purified by flash column chromatography ($SiO_2$: 0 to 10% ethyl acetate in hexane gradient) to yield 3-pentyloctyl 8-bromooctanoate L1-6 as colorless oil (1.0 g, 78%). $^1$H-NMR (300 MHz, $CDCl_3$) δ 4.07 (t, J=7.3 Hz, 2H), 3.39 (t, J=6.9 Hz, 2H), 2.28 (t, J=7.7 Hz, 2H), 1.90-1.15 (m, 29H), 0.88 (t, J=6.9 Hz, 6H).

Synthesis of bis(3-pentyloctyl) 8,8'-((4-hydroxybutyl)azanediyl) dioctanoate (Compound 11)

A solution of L1-6 (650 mg, 1.6 mmol), 4-amino-1-butanol L1-7 (64 mg, 0.7 mmol) in cyclopentyl methyl ether (10 mL) and acetonitrile (10 mL) containing potassium carbonate (400 mg, 2.8 mmol) and potassium iodide (120 mg, 0.7 mmol) was heated at 85° C. for 24 hours. After cooling to room temperature, the reaction mixture was filtered through Celite, washed with ethyl acetate, and then the solvent was removed under vacuum to give the crude product which was purified by flash chromatography ($SiO_2$: ethyl acetate/hexane 0-100% with 1% triethylamine in the eluent) to get Compound 11 (337 mg, 63%) as slightly yellow oil. $^1$H NMR (300 MHz, $CDCl_3$): δ ppm 4.06 (t, J=7.0 Hz, 4H), 3.52 (m, 2H), 2.40 (m, 6H), 2.26 (t, J=7.7 Hz, 4H), 1.70-1.15 (m, 68H), 0.86 (t, J=7.1 Hz, 12H); MS (CI): m/z $[M+H]^+$ 738.7; Analytical HPLC column: Agilent Zorbax SB-C18, 5 μm, 4.6×150 mm, mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: ELSD, $t_R$=10.7 min, purity: 99.61%; UPLC column: Thermo Scientific Hypersil GOLD C4, mobile phase A: acetonitrile with 0.1% trifluoroacetic acid, mobile phase B: water with 0.1% trifluoroacetic acid, use gradient: A in B 60% to 100% in 15 min, flow rate: 0.5 mL/min, column temperature: 20±2° C., detector: CAD, $t_R$=13.1 min, purity: 97.30%.

Synthesis of heptadecan-9-yl 8-((2-((2-hydroxyethyl)(methyl)amino)ethyl)(6-oxo-6-(undecyloxy)hexyl)amino)octanoate (Compound 46)

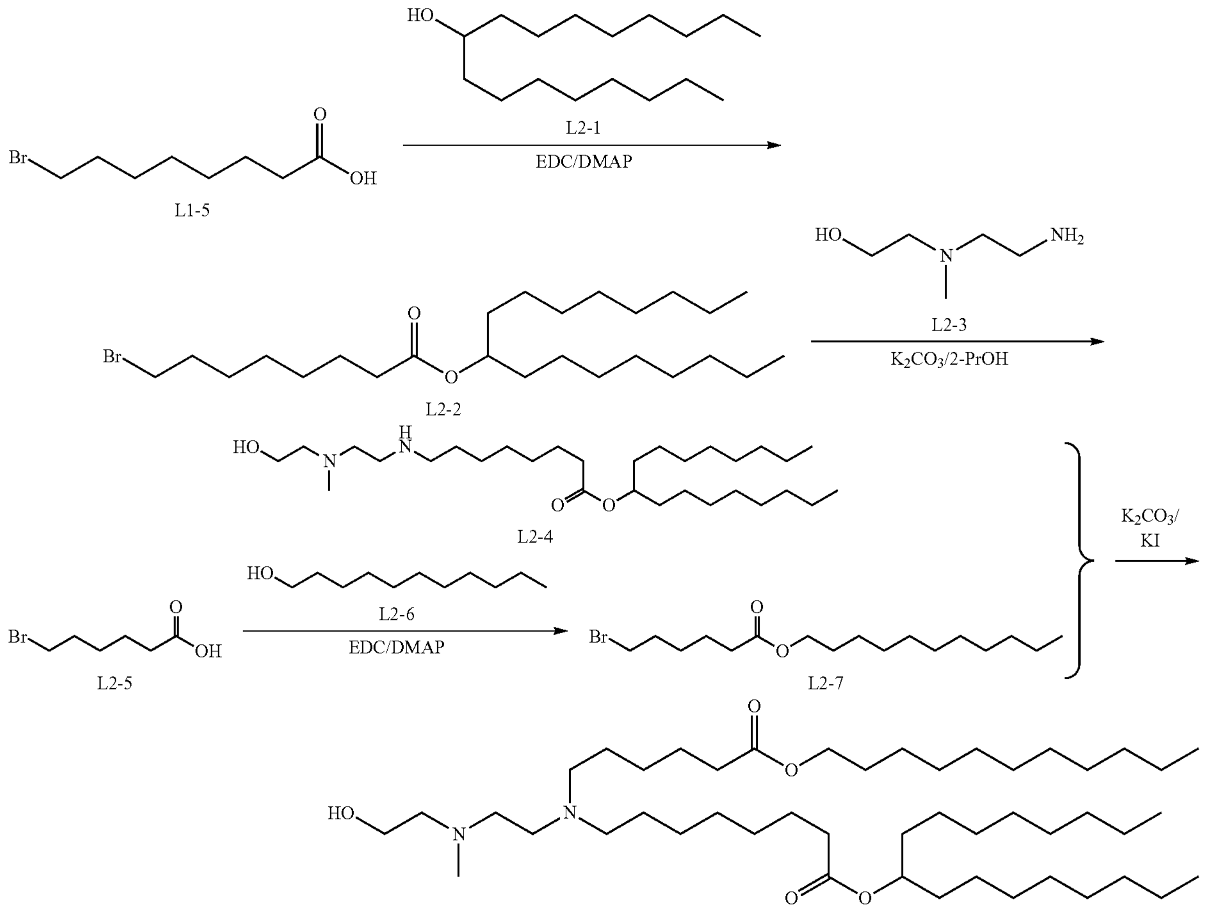

Compound 46

Synthesis of heptadecan-9-yl 8-bromooctanoate (L2-2)

To a solution of L2-1 (2.56 g, 1 mmol) in DCM (60 mL) was added 8-bromooctanoic acid L1-5 (2.22 g, 1 mmol) followed by DMAP (0.61 g, 0.5 mmol) and EDC (3.9 g, 2 mmol). The resulting mixture was stirred at room temperature under nitrogen atmosphere overnight. The reaction mixture was diluted with DCM (50 mL) and washed with saturated $NaHCO_3$ aqueous solution (50 mL), water (30 mL) and brine (30 mL). The organic phase was dried over anhydrous $Na_2SO_4$. Filtration and concentration provided crude material which was purified by flash column chromatography ($SiO_2$: 0 to 10% ethyl acetate in hexane gradient) to yield 3-pentyloctyl 8-bromooctanoate L2-2 as colorless oil (3.2 g, 70%). $^1$H-NMR (300 MHz, $CDCl_3$) δ 4.85 (quintet, J=6.1 Hz, 1H), 3.40 (t, J=6.9 Hz, 2H), 2.28 (t, J=7.7 Hz, 2H), 1.86 (quintet, J=6.0 Hz, 2H), 1.70-1.15 (m, 36H), 0.87 (t, J=6.9 Hz, 6H).

Synthesis of heptadecan-9-yl 8-((2-((2-hydroxyethyl)(methyl)amino)ethyl)amino)octanoate (L2-4) and di(heptadecan-9-yl) 8,8'-((2-((2-hydroxyethyl)(methyl)amino)ethyl)azanediyl)dioctanoate (Compound 47)

A mixture of L2-2 (1.0 g, 2.2 mmol), and 2-[(2-aminoethyl)(methyl)amino]ethanol L2-3 (1.28 g, 11 mmol) in 2-propanol (10 mL) containing potassium carbonate (0.28 g, 2.0 mmol) was heated at 55-60° C. for 3.5 days. After cooling to room temperature, the reaction mixture was filtered through Celite. Concentration gave an oil residue which was purified by flash chromatography ($SiO_2$: ethyl acetate/hexane 0-100% with 1-30% triethylamine in the eluent) to give L2-4 (0.79 g, 72%) as slightly yellow oil. $^1$H NMR (300 MHz, $CDCl_3$): δ ppm 4.85 (quintet, J=6.1 Hz, 1H), 3.59 (t, J=5.2 Hz, 2H), 2.70 (t, J=6.1 Hz, 2H), 2.62-2.48 (m, 6H), 2.29 (s, 3H), 2.27 (t, J=7.7 Hz, 2H), 1.73-1.16 (m, 40H), 0.87 (t, J=6.6 Hz, 6H); MS (CI): m/z $[M+H]^+$ 499; The bis-addition compound product (Compound 47) (69 mg) was also isolated as slightly yellow oil. $^1$H NMR (300 MHz, $CDCl_3$): δ ppm 4.86 (quintet, J=6.3 Hz, 1H), 3.55 (t, J=4.9 Hz, 2H), 2.54 (t, J=5.4 Hz, 2H), 2.49 (s, 4H), 2.40 (t, J=7.4 Hz, 4H), 2.30 (s, 3H), 2.27 (t, J=7.6 Hz, 4H), 1.73-1.16 (m, 84H), 0.87 (t, J=6.6 Hz, 6H); MS (CI): m/z $[M+H]^+$ 879.7; Analytical HPLC column: Agilent Zorbax SB-C18, 5 m, 4.6×150 mm, mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: ELSD, $t_R$=12.0 min, purity: >99%; UPLC column: Thermo Scientific Hypersil GOLD C4, mobile phase A: acetonitrile with 0.1% trifluoroacetic acid, mobile phase B: water with 0.1% trifluoroacetic acid, use gradient: A in B 60% to 100% in 15 min, flow rate: 0.5 mL/min, column temperature: 20±2° C., detector: CAD, $t_R$=14.8 min, purity: 99.42%.

Synthesis of undecyl 6-bromohexanoate (L2-7)

To a solution of L2-6 (5.16 g, 30 mmol) in DCM (160 mL) was added 6-bromohexanoic acid L2-5 (5.85 g, 30 mmol) followed by DMAP (1.8 g, 15 mmol) and EDC (11.9 g, 60 mmol). The resulting mixture was stirred at room temperature under nitrogen atmosphere for 20 h. The reaction mixture was diluted with DCM (150 mL) and washed with saturated $NaHCO_3$ aqueous solution (150 mL), water (100 mL) and brine (100 mL). The organic phase was dried over anhydrous $Na_2SO_4$. Filtration and concentration provided crude material which was purified by flash column chromatography ($SiO_2$: 0 to 10% ethyl acetate in hexane gradient) to yield undecyl 6-bromohexanoate L2-7 as slightly yellow oil (8.5 g, 81%). $^1$H-NMR (300 MHz, $CDCl_3$) δ 4.06 (t, J=6.9 Hz, 2H), 3.40 (t, J=6.6 Hz, 2H), 2.31 (t, J=7.4 Hz, 2H), 1.88 (quintet, J=6.1 Hz, 2H), 1.70-1.15 (m, 19H), 0.88 (t, J=6.9 Hz, 6H).

Synthesis of heptadecan-9-yl 8-((2-((2-hydroxyethyl)(methyl)amino)ethyl)(6-oxo-6-(undecyloxy)hexyl)amino)octanoate (Compound 46)

A mixture of L2-4 (0.4 g, 0.8 mmol) and L2-7 (0.4 g, 1.2 mmol) in cyclopentyl methyl ether (5 mL) and acetonitrile (5 mL) containing potassium carbonate (0.33 g, 2.4 mmol) and potassium iodide (0.134 g, 0.8 mmol) was heated at 80° C. under nitrogen with stirring for one day. After cooling to room temperature, the reaction mixture was filtered through Celite. The filtrate was concentrated to give an oil residue which was purified by flash chromatography ($SiO_2$: ethyl acetate/hexane 0-100% with 1% triethylamine in the eluent) to yield Compound 46 (0.319 g, 52%) as slightly yellow oil. $^1$H NMR (300 MHz, $CDCl_3$): δ ppm 4.85 (quintet, J=6.3 Hz, 1H), 4.04 (t, J=6.6 Hz, 2H), 3.55 (t, J=5.2 Hz, 2H), 2.53 (t, J=5.0 Hz, 2H), 2.49 (s, 4H), 2.40 (m, 4H), 2.30 (s, 3H), 2.27 (t, J=7.4 Hz, 4H), 1.73-1.16 (m, 66H), 0.87 (t, J=6.6 Hz, 6H); MS (CI): m/z $[M+H]^+$ 767.7; Analytical HPLC column: Agilent Zorbax SB-C18, 5 μm, 4.6×150 mm, mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: ELSD, $t_R$=11.1 min, purity: >99%; UPLC column: Thermo Scientific Hypersil GOLD C4, mobile phase A: acetonitrile with 0.1% trifluoroacetic acid, mobile phase B: water with 0.1% trifluoroacetic acid, use gradient: A in B 5% to 95% in 15 min, flow rate: 1 mL/min, A in B 60% to 100% in 15 min, flow rate: 0.5 mL/min, column temperature: 20±2° C., detector: CAD, $t_R$=12.4 min, purity: 98.95%.

Synthesis of 2-Isopropyl-5-methylhexyl 8-((4-hydroxybutyl)(6-((2-isopropyl-5-methylhexyl)oxy)-6-oxohexyl)amino)octanoate (Compound 9)

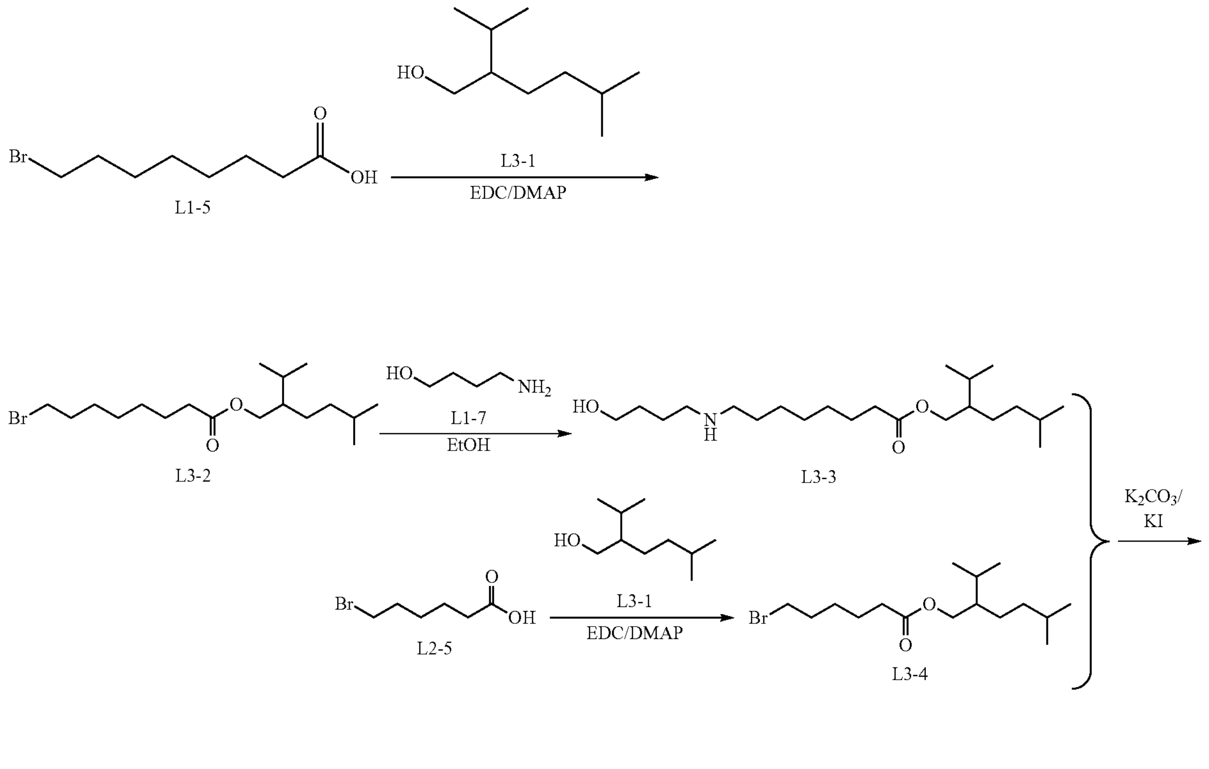

-continued

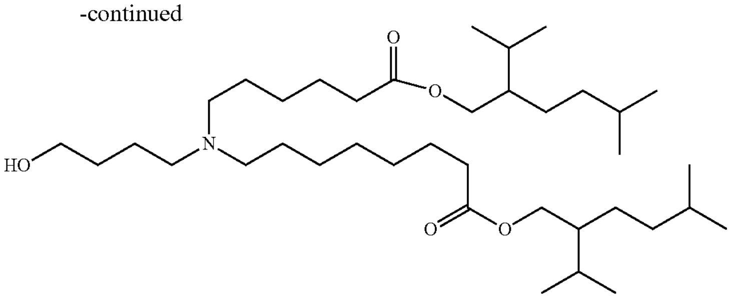

Compound 9

Synthesis of 2-isopropyl-5-methylhexyl 8-bromooctanoate (L3-2)

To a solution of tetrahydrolavandulol L3-1 (1.2 g, 7.6 mmol) in DCM (40 mL) was added 8-bromooctanoic acid L1-5 (1.69 g, 7.6 mmol) followed by DMAP (0.46 g, 3.8 mmol) and EDC (2.9 g, 15.2 mmol). The resulting mixture was stirred at room temperature under nitrogen atmosphere for 20 h. The reaction mixture was diluted with DCM (40 mL) and washed with saturated $NaHCO_3$ aqueous solution (40 mL), water (30 mL) and brine (30 mL). The organic phase was dried over anhydrous $Na_2SO_4$. Filtration and concentration provided crude material which was purified by flash column chromatography ($SiO_2$: 0 to 10% ethyl acetate in hexane gradient) to yield 2-isopropyl-5-methylhexyl 8-bromooctanoate L3-2 as colorless oil (1.8 g, 65%). $^1$H-NMR (300 MHz, $CDCl_3$) δ 4.10-3.91 (m, 2H), 3.40 (t, J=6.6 Hz, 2H), 2.29 (t, J=7.6 Hz, 2H), 1.90-1.10 (m, 17H), 0.93-0.76 (m, 12H).

Synthesis of 2-isopropyl-5-methylhexyl 8-((4-hydroxybutyl)amino)octanoate (L3-3) and bis(2-isopropyl-5-methylhexyl) 8,8'-((4-hydroxybutyl)azanediyl)dioctanoate (Compound 48)

A mixture of L3-2 (1.2 g, 3.3 mmol), 4-amino-1-butanol L1-7 (1.47 g, 16.5 mmol) in abs. EtOH (10 mL) containing potassium carbonate (0.38 g, 3.3 mmol) was heated at 55° C. for 3.5 days. After cooling to room temperature, the reaction mixture was filtered through Celite. The filtrate was concentrated to give an oil residue which was purified by flash chromatography ($SiO_2$: ethyl acetate/hexane 0-100% with 1-30% triethylamine in the eluent) to yield L3-3 (0.67 g, 54%) as slightly yellow oil. $^1$H NMR (300 MHz, $CDCl_3$): δ ppm 4.86 (quintet, J=6.3 Hz, 1H), 3.55 (t, J=4.9 Hz, 2H), 2.54 (t, J=5.4 Hz, 2H), 2.49 (s, 4H), 2.40 (t, J=7.4 Hz, 4H), 2.30 (s, 3H), 2.27 (t, J=7.6 Hz, 4H), 1.73-1.16 (m, 84H), 0.87 (t, J=6.6 Hz, 6H); MS (CI): m/z $[M+H]^+$ 373. The bis-addition product (Compound 48) (62 mg) was also isolated as slightly yellow oil. $^1$H NMR (300 MHz, $CDCl_3$): δ ppm 4.86 (quintet, J=6.3 Hz, 1H), 3.55 (t, J=4.9 Hz, 2H), 2.54 (t, J=5.4 Hz, 2H), 2.49 (s, 4H), 2.40 (t, J=7.4 Hz, 4H), 2.30 (s, 3H), 2.27 (t, J=7.6 Hz, 4H), 1.73-1.16 (m, 84H), 0.87 (t, J=6.6 Hz, 6H); MS (CI): m/z $[M+H]^+$ 654.5; Analytical HPLC column: Agilent Zorbax SB-C18, 5 m, 4.6×150 mm, mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: ELSD, $t_R$=5.42 min, purity: >99%; UPLC column: Thermo Scientific Hypersil GOLD C4, mobile phase A: acetonitrile with 0.1% trifluoroacetic acid, mobile phase B: water with 0.1% trifluoroacetic acid, use gradient: A in B 60% to 100% in 15 min, flow rate: 0.5 mL/min, column temperature: 20±2° C., detector: CAD, $t_R$=9.8 min, purity: 97.20%.

Synthesis of 2-isopropyl-5-methylhexyl 6-bromohexanoate (L3-4)

To a solution of tetrahydrolavandulol L3-1 (0.8 g, 5 mmol) in DCM (25 mL) was added 6-bromohexanoic acid L2-5 (0.98 g, 5 mmol) followed by DMAP (0.3 g, 2.5 mmol) and EDC (1.7 g, 9 mmol). The resulting mixture was stirred at room temperature under nitrogen atmosphere for 20 h. The reaction mixture was diluted with DCM (25 mL) and washed with saturated $NaHCO_3$ aqueous solution (25 mL), water (15 mL) and brine (15 mL). The organic phase was dried over anhydrous $Na_2SO_4$. Filtration and concentration provided crude material which was purified by flash column chromatography ($SiO_2$: 0 to 10% ethyl acetate in hexane gradient) to yield L3-4 as colorless oil (0.76 g, 45%). $^1$H-NMR (300 MHz, $CDCl_3$) δ 4.10-3.92 (m, 2H), 3.40 (t, J=6.6 Hz, 2H), 2.32 (t, J=7.4 Hz, 2H), 1.92-1.10 (m, 13H), 0.93-0.76 (m, 12H).

Synthesis of 2-isopropyl-5-methylhexyl 8-((4-hydroxybutyl)(6-((2-isopropyl-5-methylhexyl)oxy)-6-oxohexyl)amino)octanoate (Compound 9)

A mixture of L3-3 (0.3 g, 0.8 mmol) and L3-4 (0.3 g, 0.9 mmol) in cyclopentyl methyl ether (5 mL) and acetonitrile (5 mL) containing potassium carbonate (0.19 g, 2.4 mmol) and potassium iodide (0.134 g, 0.8 mmol) was heated at 80° C. under nitrogen with stirring for one day. More of L3-4 (0.2 g, 0.6 mmol) was added and the reaction continued for another two days. After cooling to room temperature, the reaction mixture was filtered through Celite. The filtrate was concentrated to give an oil residue which was purified by flash chromatography ($SiO_2$: ethyl acetate/hexane 0-100% with 1% triethylamine in the eluent) to yield Compound 9 (0.276 g, 55%) as slightly yellow oil. $^1$H NMR (300 MHz, $CDCl_3$): δ ppm 4.10-3.91 (m, 4H), 3.53 (t, J=5.2 Hz, 2H), 2.49-2.22 (m, 10H), 1.82-1.12 (m, 35H), 0.93-0.79 (m, 24H); MS (CI): m/z $[M+H]^+$ 626.5; Analytical HPLC column: Agilent Zorbax SB-C18, 5 μm, 4.6×150 mm, mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: ELSD, $t_R$=5.8 min, purity: >99%; UPLC column: Thermo Scientific Hypersil GOLD C4, mobile phase A: acetonitrile with 0.1% trifluoroacetic acid, mobile phase B: water with 0.1% trifluoroacetic acid, use gradient: A in B 60% to 100% in 15 min, flow rate: 0.5 mL/min, column temperature: 20±2° C., detector: CAD, $t_R$=8.8 min, purity: 98.29%.

Synthesis of ((4-hydroxybutyl)azanediyl)bis (hexane-6,1-diyl) bis(4,4-bis(octyloxy)butanoate) (Compound 14)

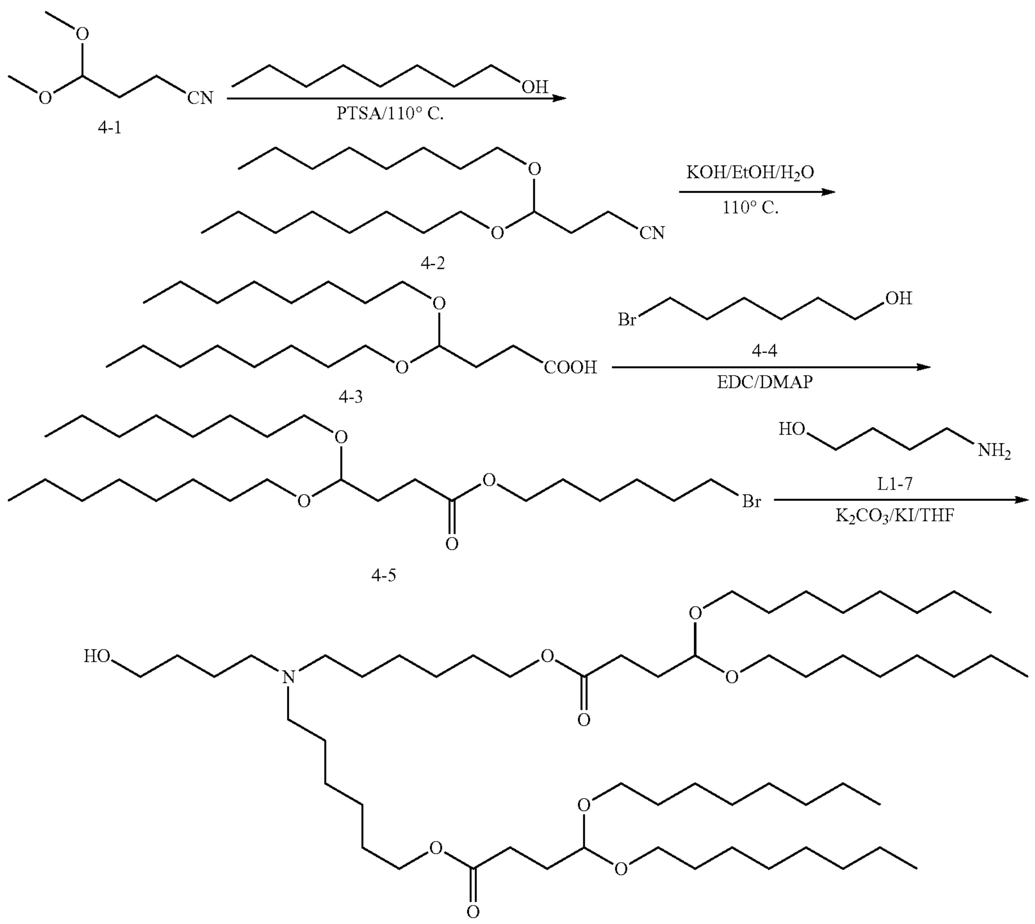

4-1

4-2

4-3

4-4

4-5

Compound 14

Synthesis of 4,4-bis(octyloxy)butanenitrile (L4-2)

To an oven dried 100 mL round bottom flask, 4,4-dimethoxybutanenitrile (10.0 g, 77.4 mmol) and 1-octanol (24.9 g, 232 mmol) were added. The resulting mixture was stirred at 120° C. for 18 h and cooled to room temperature. EtOAc (150 mL) and $H_2O$ (60 mL) were added in, and the resulting phases were separated. The aqueous phase was extracted with EtOAc (50 mL). Combined organic extracts were washed with $H_2O$ (60 mL×2) and dried over anhydrous $MgSO_4$. Filtration and concentration provided crude material which was purified by flash column chromatography ($SiO_2$: 0 to 10% ethyl acetate in hexanes gradient) to yield 4,4-bis(octyloxy)butanenitrile L4-2 as colorless oil (6.9 g, 27%). $^1$H-NMR (300 MHz, $CDCl_3$) δ 4.56-4.53 (t, 1H), 3.61-3.58 (2H, m), 3.44-3.41 (m, 2H), 2.44-2.39 (t, 2H), 1.97-1.90 (q, 2H), 1.58-1.54 (m, 5H), 1.32-1.27 (m, 23H), 0.90-0.85 (m, 6H).

Synthesis of 4,4-bis(octyloxy)butanoic acid (L4-3)

To an oven dried 100 mL round bottom flask containing a solution of 4,4-bis(octyloxy)butanenitrile L4-2 (6.9 g, 21 mmol) in ethanol (25 mL) was added a solution of KOH (3.6 g, 64 mmol) in water (25 mL). After completion of the addition, the mixture was stirred at 110° C. for 18 h. The volatiles were removed, and the reaction pH was adjusted to 5. EtOAc (150 mL) and $H_2O$ (60 mL) were added, and the resulting phases were separated. The aqueous phase was extracted with EtOAc (50 mL). Combined organic extracts were washed with $H_2O$ (60 mL×2) and dried over anhydrous $MgSO_4$. Filtration and concentration provided 4,4-bis(octyloxy)butanoic acid L4-3 (6.75 g, 92%) which was used for the next step without further purification. $^1$H-NMR (300 MHz, $CDCl_3$) δ 4.53-4.49 (t, 1H), 3.59-3.42 (m, 2H), 3.42-3.39 (m, 2H), 2.43-2.41 (t, 2H), 1.96-1.92 (m, 2H), 1.58-1.54 (m, 5H), 1.32-1.27 (m, 23H), 0.90-0.85 (m, 6H).

Synthesis of 6-bromohexyl 4,4-bis(octyloxy)butanoate (L4-5)

To an oven dried 100 mL round bottom flask containing a solution of 4,4-bis(octyloxy)butanoic acid L4-3 (1.5 g, 4.35 mmol) in dichloromethane (20 mL) under nitrogen was added EDC (1.25 g, 6.53 mmol), DMAP (0.106 g, 0.871 mmol) and DIPEA (2.25 g, 17.41 mmol). After completion of the addition, the mixture was stirred at room temperature for 10 min. 6-bromo-1-hexanol L4-4 (1.02 g, 5.66 mmol) was then added and the reaction mixture was stirred for 16 h at room temperature. The reaction mixture was diluted with dichloromethane and water and the resulting phases were separated. The aqueous phase was extracted again with EtOAc (50 mL). Combined organic extracts were washed with $H_2O$ (60 mL×2) and dried over anhydrous $MgSO_4$. Filtration and concentration provided crude product which was purified by flash column chromatography ($SiO_2$: 0 to 10% ethyl acetate in hexanes gradient) to yield 6-bromohexyl 4,4-bis(octyloxy)butanoate L4-5 as colorless oil (0.74 g, 33%). $^1$H-NMR (300 MHz, $CDCl_3$) δ 4.49 (t, 1H), 4.06 (t, 2H), 3.60-3.50 (m, 2H), 3.45-3.34 (m, 4H), 2.38 (t, 2H), 1.96-1.81 (m, 4H), 1.66-1.18 (m, 30H), 0.90-0.85 (m, 6H).

Synthesis of ((4-hydroxybutyl)azanediyl)bis (hexane-6,1-diyl) bis(4,4-bis(octyloxy)butanoate) (Compound 14)

To a solution of compound L4-5 (0.74 g, 1.46 mmol) in $CH_3CN$/CPME (1:1, 10 mL) under nitrogen was treated with compound 4-amino-1-butanol (65.1 mg, 0.731 mmol) and followed by the addition of $K_2CO_3$ (0.708 g, 5.12 mmol) and KI (0.726 g, 4.38 mmol). The reaction mixture was heated at 80° C. for 18 h. After cooling to room temperature, the reaction mixture was filtered through Celite, washed with ethyl acetate, and the solvent was removed under vacuum to give the crude product which was purified by flash chromatography ($SiO_2$: DCM/MeOH 0-10%) to get final Compound 14 as colorless oil (0.3 g, 44%). $^1$H-NMR (300 MHz, $CDCl_3$) δ 4.48 (t, 2H), 4.04 (t, 4H), 3.60-3.50 (m, 6H), 3.42-3.36 (m, 4H), 2.56-2.32 (m, 8H), 1.95-1.88 (q, 4H), 1.68-1.46 (m, 20H), 1.41-1.18 (m, 51H), 0.89-0.85 (t, 12H); CIMS m/z 942.7 $[M+H]^+$; Analytical HPLC column: Agilent Zorbax SB-C18, 5 μm, 4.6×150 mm, mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: ELSD, $t_R$=11.81 min, purity: >99%; UPLC column: Thermo Scientific Hypersil GOLD C4, mobile phase A: acetonitrile with 0.1% trifluoroacetic acid, mobile phase B: water with 0.1% trifluoroacetic acid, use gradient: A in B 60% to 100% in 15 min, flow rate: 0.5 mL/min, column temperature: 20±2° C., detector: CAD, $t_R$=12.9 min, purity: 98.63%.

Synthesis of 4-(Bis(9,9-bis(octyloxy)nonyl)amino) butan-1-ol (Compound 49)

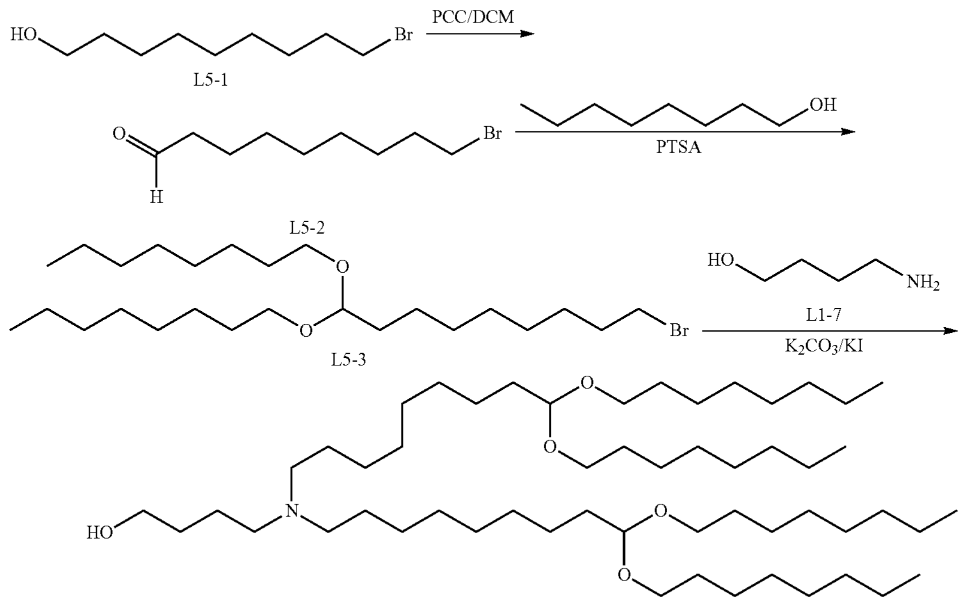

Compound 49

Synthesis of 9-bromononanal (L5-2)

To an oven dried 1000 mL round bottom flask containing a solution of 9-bromononanol (5.0 g, 22.52 mmol) in dichloromethane (400 mL) was added Pyridinium chlorochromate (PCC) (7.74 g, 33.77 mmol) and the reaction mixture was stirred for 3 h at room temperature. The reaction mixture was then passed through a plug of Florisil. Water was added to the filtrate and the resulting phases were separated. The aqueous phase was extracted again with DCM (150 mL). Combined organic extracts were washed with aqueous sodium bicarbonate solution (150 mL) and $H_2O$ (60 mL×2) and dried over anhydrous $MgSO_4$. Filtration and concentration provided crude L5-2 as colorless oil (4.95 g, 100%) which was used for the next step without further purification; $^1$H-NMR (300 MHz, $CDCl_3$) δ 9.76 (s, 1H), 3.40 (m, 2H), 2.43 (m, 2H), 1.85-1.78 (m, 2H), 1.70-1.55 (m, 2H), 1.48-1.19 (m, 8H).

Synthesis of 9-bromo-1,1-bis(octyloxy)nonane (L5-3)

To an oven dried 100 mL round bottom flask containing a solution of L5-2 (5.0 g, 22.61 mmol) in dichloromethane (150 mL) was added 1-octanol (8.83 g, 67.83 mmol), PTSA (0.584 g, 3.39 mmol) and sodium sulfate (9.63 g, 67.83 mmol). After completion of the addition, the mixture was stirred at room temperature for 18 h. Dichloromethane and water were then added to the reaction mixture and the resulting phases were separated. The aqueous phase was extracted again with DCM (150 mL). Combined organic extracts were washed with aqueous sodium bicarbonate solution (150 mL) and $H_2O$ (60 mL×2) and dried over anhydrous $MgSO_4$. Filtration and concentration provided crude material which was purified by flash column chromatography ($SiO_2$: 0 to 20% EtOAc/Hexanes) to yield L5-3 (1.4 g, 14%); $^1$H-NMR (300 MHz, $CDCl_3$) δ 4.45 (t, 1H), 3.57-3.50 (m, 2H), 3.43-3.34 (m, 4H), 1.87-1.80 (m, 2H), 1.62-1.51 (m, 6H), 1.41-1.20 (m, 30H), 0.92-0.85 (m, 6H).

Synthesis of 4-(bis(9,9-bis(octyloxy)nonyl)amino) butan-1-ol (Compound 49)

To a solution of compound L5-3 (0.75 g, 1.62 mmol) in $CH_3CN$/CPME (1:1, 10 mL) under nitrogen was added 4-amino-1-butanol L1-7 (72 mg, 0.811 mmol) followed by the addition of $K_2CO_3$ (0.783 g, 5.67 mmol) and KI (0.807 g, 4.86 mmol). The reaction mixture was heated at 85° C. under nitrogen for 24 h. After cooling to room temperature, the reaction mixture was filtered through Celite, washed with ethyl acetate, and the solvent was removed under vacuum to give the crude product which was purified by flash chromatography (SiO2: DCM/MeOH 0-10%) to provide Compound 49 (0.250 g, 36%) as slightly yellow oil. $^1$H-NMR (300 MHz, $CDCl_3$) δ 4.44 (t, 2H), 3.56-3.53 (m, 6H), 3.41-3.35 (m, 4H), 2.44-2.39 (m, 6H), 1.64-1.20 (m, 81H), 0.89-0.85 (m, 12H). CIMS m/z 854.8 $[M+H]^+$. Analytical HPLC column: Agilent Zorbax SB-C18, 5 m, 4.6× 150 mm, mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: ELSD, $t_R$=11.99 min, purity: >99%; UPLC column: Thermo Scientific Hypersil GOLD C4, mobile phase A: acetonitrile with 0.1% trifluoroacetic acid, mobile phase B: water with 0.1% trifluoroacetic acid, use gradient: A in B 60% to 100% in 15 min, flow rate: 0.5 mL/min, column temperature: 20±2° C., detector: CAD, $t_R$=15.45 min, purity: 91.24%.

Synthesis of undecyl 6-((7-((dioctylcarbamoyl)oxy) heptyl) (2-hydroxyethyl) amino) hexanoate (Compound 1)

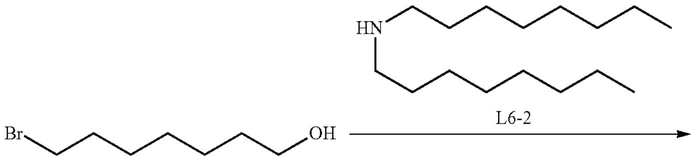

L6-1

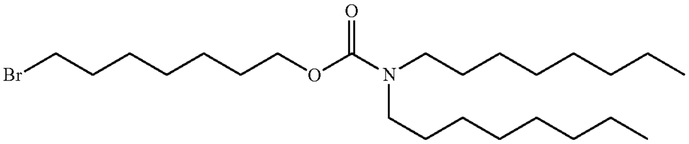

L6-3

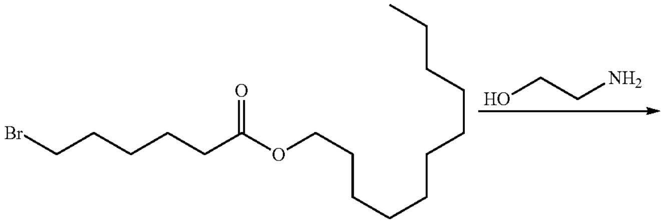

L2-7

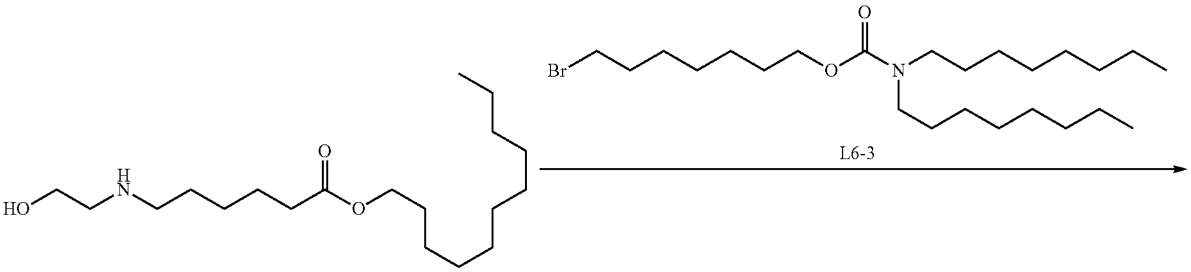

L6-4

-continued

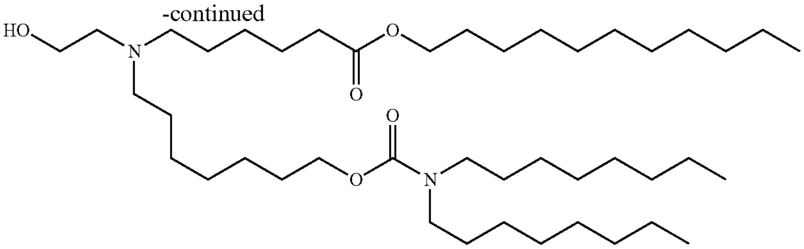

Compound 1

Synthesis of 2,3,3a,4,7,7a-hexahydro-1H-isoindole (L6-3)

To a solution of compound L6-1 (1.0 g, 5.1 mmol) in DCM (20 mL), cooled in an ice-water bath under nitrogen, was added triphosgene (1.5 g, 11.2 mmol) over 5 min followed by the addition of DIPEA (1.98 g, 15.3 mmol) and stirred for 5 min. The reaction was allowed to warm to room temperature and stirred for 1 h and then compound L6-2 (1.2 g, 5.1 mmol) was added in one portion. The resulting mixture was allowed to warm to room temperature and stirred for 12 h. The solvent was removed in vacuo, and the residue was dissolved in ethyl acetate and washed with saturated $NaHCO_3$ and brine and dried ($Na_2SO_4$). The mixture was concentrated in vacuo to give crude product which was purified by silica gel column chromatography eluted with a gradient of hexane/ethyl acetate to obtain L6-3 as colorless oil (1.2 g, 50%). $^1$H-NMR (300 MHz, $CDCl_3$) δ 4.32-4.25 (m, 2H), 4.02 (t, 2H), 3.41-3.36 (m, 3H), 3.15 (s, 3H), 1.86-1.70 (m, 5H), 1.60-1.25 (m, 27H), 0.86 (t, 6H); CIMS m/z 462.56 $[M+H]^+$.

Synthesis of undecyl 6-((2-hydroxyethyl) amino) hexanoate (L6-4)

A solution of compound L2-7 (6.0 g, 17.1 mmol) in ethanol (80 mL) was added dropwise to a solution of ethanolamine (31.4 g, 515 mmol) in EtOH (940 mL) at ambient temperature over 25 minutes. The reaction solution was heated at 60° C.-70° C. for 5 h. The reaction solution was allowed to cool to 35° C. by turning the heater off, and the reaction solution was concentrated in vacuo at 40° C. to give crude residue. The crude residue was diluted in TBME and then the TBME layer was separated from the ethanolamine layer. The ethanolamine layer was back extracted with TBME (200 mL). The combined TBME layers were washed with 5% $NaHCO_3$ solution and then concentrated in vacuo at 40° C. to give pale yellow oil. The crude product was purified by flash chromatography (SiO2: DCM/MeOH 0-100%, 1% $NH_4OH$) to give product L6-4 as colorless oil (2.3 g, 40%). $^1$H-NMR (300 MHz, $CDCl_3$) δ 4.01 (t, 2H), 3.63 (t, 2H), 2.90 (s, 3H), 2.74 (t, 2H), 2.60 (t, 2H), 2.27 (t, 2H), 1.63-1.40 (m, 7H), 1.37-1.19 (m, 15H), 0.84 (t, 3H); CIMS m/z 330.3 $[M+H]^+$.

Synthesis of undecyl 6-((7-((dioctylcarbamoyl)oxy) heptyl) (2-hydroxyethyl) amino) hexanoate (Compound 1)

To a solution of compound L6-3 (500 mg, 1.08 mmol, 1 eq) in CPME (5 mL) and (ACN 5 mL), under nitrogen, was added compound L-2-8 (427 mg, 1.29 mmol, 1.2 eq), followed by the addition of $K_2CO_3$ (597 mg, 4.3 mmol, 4 eq) and KI (179 mg, 1.08 mmol, 1 eq). The reaction mixture was heated at 60° C. for 18 h. After cooling to room temperature, the reaction mixture was filtered through Celite, washed with ethyl acetate, and the solvent was removed under vacuum to give the crude product which was purified by flash chromatography (80 g $SiO_2$: 0 to 100% ethyl acetate in hexane with 0 to 30% triethylamine gradient) to obtain Compound 1 as colorless oil (0.15 g, 20%). $^1$H-NMR (300 MHz, $CDCl_3$) δ 4.06-4.0 (m, 4H), 3.50-3.49 (m, 3H), 3.17 (s, 3H), 2.55 (t, 2H), 2.45-2.39 (m, 5H), 2.28 (t, 3H), 1.64-1.55 (m, 7H), 1.49-1.39 (m, 7H), 1.34-1.24 (m, 43H), 0.84 (t, 9H)); CIMS m/z 711.3 $[M+H]^+$. Analytical HPLC column: Agilent Zorbax SB-C18, 5 m, 4.6×150 mm, mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: ELSD, $t_R$=10.2 min, purity: 92.0%; UPLC column: Thermo Scientific Hypersil GOLD C4, mobile phase A: acetonitrile with 0.1% trifluoroacetic acid, mobile phase B: water with 0.1% trifluoroacetic acid, use gradient: A in B 60% to 100% in 15 min, flow rate: 0.5 mL/min, column temperature: 20±2° C., detector: CAD, $t_R$=12.6 min, purity: 91.05%.

Synthesis of ((4-hydroxybutyl) azanediyl) bis (hexane-6,1-diyl) bis(dioctylcarbamate) (Compound 3)

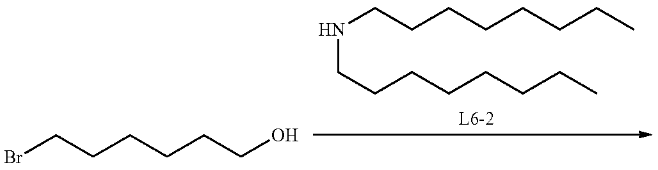

L7-1

-continued

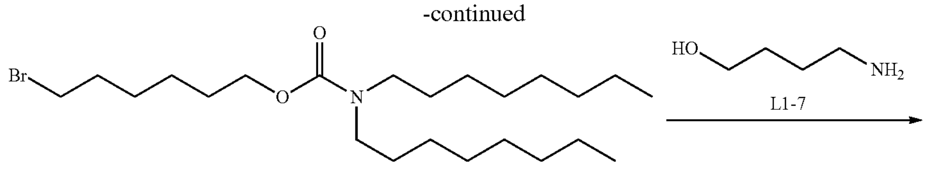

L7-2

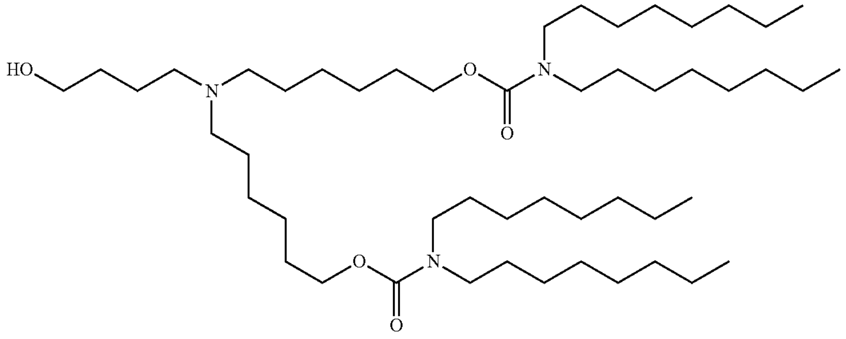

Compound 3

Synthesis of 6-bromohexyl dioctylcarbamate (L7-2)

To a solution of compound L7-1 (1.0 g, 5.52 mmol) in DCM (20 mL), cooled in an ice-water bath and under nitrogen, was treated with triphosgene (1.63 g, 5.52 mmol) over 5 min followed by the addition of DIPEA (2.8 mL, 16.5 mmol) and stirred for 5 min, the mixture was allowed to warm to temperature and stirred for 1 h and then compound-L6-2 was added in one portion. The resulting mixture was allowed to warm to room temperature and stir for 12 h. The solvent was removed in vacuo, and the residue was dissolved in ethyl acetate and washed with saturated $NaHCO_3$ and brine and dried ($Na_2SO_4$). Concentration in vacuo gave crude product which was purified by silica gel column chromatography eluted with a gradient of hexane/ethyl acetate to obtain final Compound L7-2 (1.48 g, 60%); $^1$H-NMR (300 MHz, $CDCl_3$) δ 4.04 (t, 2H), 3.39 (t, 2H), 3.16 (s, 4H), 1.90-1.74 (m, 2H), 1.64-1.58 (m, 2H), 1.51-1.37 (m, 7H), 1.36-1.12 (m, 21H), 0.87 (t, 6H). CIMS m/z 449.2 $[M+H]^+$.

Synthesis of ((4-hydroxybutyl) azanediyl) bis (hexane-6,1-diyl) bis(dioctylcarbamate) (Compound 3)

To a solution of compound L1-7 (0.05 g, 0.5 mmol) in CPME (5 mL) and (ACN 5 mL), under nitrogen, was added compound L7-2 (0.503 g, 1.1 mmol) and followed by the addition of $K_2CO_3$ (0.310 g, 2.2 mmol, 4 eq) and KI (0.093 g, 0.56 mmol). The reaction mixture was heated at 80° C. for 18 h. After cooling to room temperature, the reaction mixture was filtered through Celite, washed with ethyl acetate, and the solvent was removed under vacuum to give the crude product which was purified by flash chromatography (SiO2: DCM/MeOH 0-10%) to give Compound 3 (0.2 g, 45%) as colorless oil; $^1$H-NMR (300 MHz, $CDCl_3$) δ 4.03 (t, 4H), 3.61 (t, 2H), 3.15-3.14 (m, 7H), 2.71-2.69 (m, 5H), 1.78-1.75 (m, 10H), 1.71-1.58 (m, 15H), 1.41-1.26 (m, 46H), 0.84 (t, 12H); CIMS m/z 824.7 $[M+H]^+$. Analytical HPLC column: Agilent Zorbax SB-C18, 5 m, 4.6×150 mm, mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: ELSD, $t_R$=11.4 min, purity: >99%; UPLC column: Thermo Scientific Hypersil GOLD C4, mobile phase A: acetonitrile with 0.1% trifluoroacetic acid, mobile phase B: water with 0.1% trifluoroacetic acid, use gradient: A in B 60% to 100% in 15 min, flow rate: 0.5 mL/min, column temperature: 20±2° C., detector: CAD, $t_R$=13.8 min, purity: 99.38%.

Synthesis of undecyl 6-((8-(2,2-dioctylhydrazineyl)-8-oxooctyl)(2-hydroxyethyl)amino)hexanoate (Compound 20)

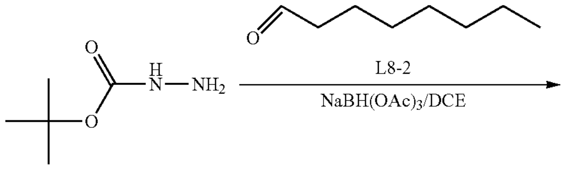

L8-1

-continued

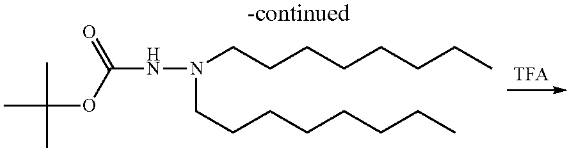

L8-3

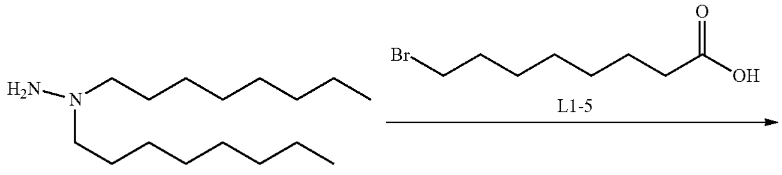

L1-5

L8-4

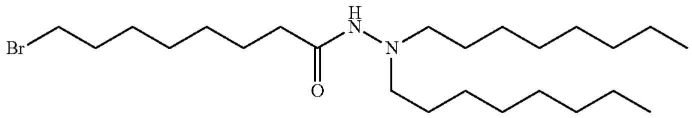

L8-5

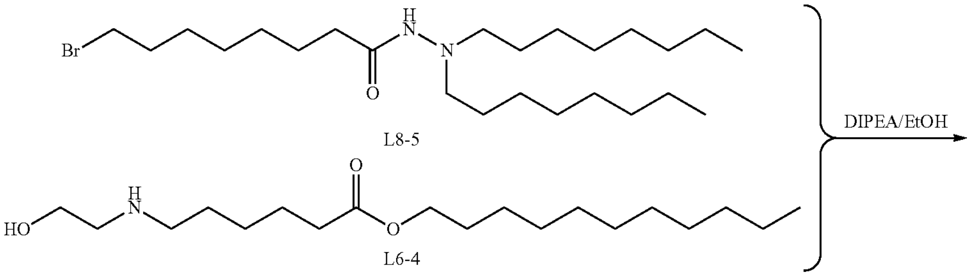

L8-5

L6-4

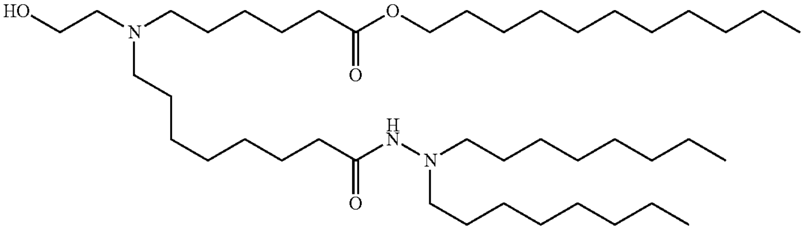

Compound 20

Synthesis of tert-butyl 2,2-dioctylhydrazine-1-carboxylate (L8-3)

To an oven dried 500 mL round bottom flask, to a solution of tert-butyl carbazate (3.0 g, 22.70 mmol), 1-octanal (3.64 g, 28.37 mmol) in dichloroethane (100 mL), was added $NaBH(OAc)_3$ (24.05 g, 113.5 mmol) and the reaction mixture was stirred for 24 h at room temperature. The reaction mixture was then diluted with DCM (300 mL). Water was added and the resulting two phases were separated. The aqueous phase was extracted again with DCM (150 mL). Combined organic extracts were washed with bicarbonate solution (150 mL), and $H_2O$ (60 mL×2) and dried over anhydrous $MgSO_4$. Filtration and concentration provided crude material which was purified by flash column chromatography ($SiO_2$: 0 to 35% EtOAc/Hexanes) to yield L8-3 (3.6 g, 44%); $^1$H-NMR (300 MHz, $CDCl_3$) Rotamers Observed δ 5.16 (bs, 0.68H), 4.71 (bs, 0.23H), 2.70-2.52 (m, 4H), 1.55-1.38 (m, 13H), 1.38-1.15 (m, 20H), 0.92-0.84 (t, 6H). CIMS m/z 357.3 $[M+H]^+$.

Synthesis of 1,1-dioctylhydrazine (L8-4)

To a solution of L8-3 (3.6 g, 10.08 mmol) in dichloromethane (40 mL) was added TFA (20 mL) at 0° C. and the reaction mixture was stirred at room temperature for 16 h. The volatile components were removed under reduced pressure and the crude L8-4 (2.7 g) was used for the next step without further purification. $^1$H-NMR (300 MHz, $CDCl_3$) δ 6.50 (b, 1H), 3.30 (b, 1H), 2.74 (t, 2H), 2.51-2.38 (m, 2H), 1.58-1.46 (m, 3H), 1.32-1.12 (m, 20H), 0.89-0.84 (m, 6H). CIMS m/z 257.2 $[M+H]^+$.

Synthesis of 8-bromo-N',N'-dioctyloctanehydrazide (L8-5)

To an oven dried 100 mL round bottom flask containing a solution of L8-4 (0.400 g, 1.561 mmol) and bromooctanoic acid (0.485 g, 2.185 mmol) in dichloromethane (20 mL) was added EDC (0.449 g, 2.341 mmol) and DMAP (0.038 g, 0.312 mmol). After completion of the addition, the mixture was stirred at room temperature for 16 h. The reaction mixture was diluted with water and the resulting phases were separated. The aqueous phase was extracted with DCM (50 mL). Combined organic extracts were washed with $H_2O$ (60 mL×2) and dried over anhydrous $MgSO_4$. Filtration and concentration provided crude product which was purified by flash column chromatography ($SiO_2$: 0 to 50% ethyl acetate in hexanes gradient) to yield L8-5 as a white solid (0.24 g, 33%). $^1$H-NMR (300 MHz, $CDCl_3$) δ 5.78 (s, 0.19H), 5.64 (s, 0.61H), 3.39 (t, 2H), 2.70-2.64 (m, 2H), 2.43-2.37 (m, 2H), 2.10 (t, 0.65H), 1.87-1.80 (m, 2H), 1.63-1.56 (m, 2H), 1.49-1.20 (m, 30H), 1.03 (t, 1H), 0.88-0.85 (m, 6H). CIMS m/z 461.2, 463.2 $[M+H]^+$.

Synthesis of undecyl 6-((8-(2,2-dioctylhydrazineyl)-8-oxooctyl)(2-hydroxyethyl)amino)hexanoate (Compound 20)

To a solution of compound L8-5 (0.240 g, 0.52 mmol) in EtOH (5 mL) under nitrogen was added compound L6-4 (223 mg, 0.676 mmol) and followed by the addition of DIPEA (0.235 g, 1.82 mmol). The reaction mixture was heated at 80° C. for 24 h. After cooling to room temperature, the reaction mixture was evaporated under vacuum to give the crude product which was purified by flash chromatography (SiO2: DCM/MeOH 0-10%) to give Compound 20 (0.078 g, 30%); $^1$H-NMR (300 MHz, $CDCl_3$) Rotamers observed δ 6.02 (s, 0.23H), 5.71 (s, 0.5H), 4.05 (t, 2H), 3.98-3.86 (m, 2H), 3.15-2.90 (m, 5H), 2.73-2.64 (m, 2H), 2.45-2.29 (m, 4H), 2.11 (t, 0.46H), 1.89-1.56 (m, 10H), 1.46-1.15 (m, 46H), 0.90-0.85 (m, 9H). CIMS m/z 710.6 $[M+H]^+$. Analytical HPLC column: Agilent Zorbax SB-C18, 5 μm, 4.6×150 mm, mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: ELSD, $t_R$=10.4 min, purity: 99.90%; UPLC column: Thermo Scientific Hypersil GOLD C4, mobile phase A: acetonitrile with 0.1% trifluoroacetic acid, mobile phase B: water with 0.1% trifluoroacetic acid, use gradient: A in B 60% to 100% in 15 min, flow rate: 0.5 mL/min, column temperature: 20±2° C., detector: CAD, $t_R$=9.6 min, purity: 93.12%.

Synthesis of 7,7'-((4-hydroxybutyl)azanediyl)bis(N',N'-dioctylheptanehydrazide) (Compound 18)

Synthesis of 7-bromo-N',N'-dioctylheptanehydrazide (L9-2)

To an oven dried 100 mL round bottom flask containing a solution of L8-4 (1.25 g, 4.88 mmol) and bromo-heptanoic acid (1.53 g, 7.32 mmol) in dichloromethane (20 mL) was added DCC (2.01 g, 9.76 mmol) and DMAP (0.06 g, 0.488 mmol). After completion of the addition, the mixture was stirred at room temperature for 16 h. The reaction mixture was then diluted with water and the organic phase was separated. The aqueous phase was extracted with DCM (50 mL). Combined organic extracts were washed with $H_2O$ (60 mL×2) and dried over anhydrous $MgSO_4$. Filtration and concentration provided crude material which was purified by flash column chromatography ($SiO_2$: 0 to 30% ethyl acetate in hexanes gradient) to yield L9-2 as colorless oil (0.59 g, 27%); $^1$H-NMR (300 MHz, $CDCl_3$) Rotamers Observed δ 5.78 (s, 0.3H), 5.66 (s, 1.2H), 3.52 (t, 4H), 3.40 (q, 2H), 2.74-2.60 (m, 5H), 2.48-2.35 (m, 7H), 2.14-2.06 (t, 1H), 1.82-1.78 (m, 3H), 1.68-1.54 (m, 7H), 1.52-1.36 (m, 12H), 1.32-1.15 (m, 55H), 0.88-0.85 (m, 16H). CIMS m/z 447.2, 449.2 $[M+H]^+$.

Synthesis of 7,7'-((4-hydroxybutyl)azanediyl)bis(N',N'-dioctylheptanehydrazide) (Compound 18)

To a solution of compound L9-2 (0.500 g, 1.12 mmol) in CPME (5 mL) and (ACN 5 mL), under nitrogen, was treated with compound 4-amino-1-butanol (40 mg, 0.811 mmol) and followed by the addition of $K_2CO_3$ (0.464 g, 3.36 mmol) and KI (0.557 g, 3.36 mmol). The reaction mixture was heated at 90° C. for 18 h. After cooling to room temperature, the reaction mixture was filtered through Celite, washed with ethyl acetate, and the solvent was removed under vacuum to give the crude product which was purified by flash chromatography (SiO2: DCM/MeOH 0-10%) to provide Compound 18 (0.054 g, 12%) as yellow oil; $^1$H-NMR (300 MHz, $CDCl_3$) δ 6.40 (s, 0.3H), 6.25 (s, 0.15H), 5.70 (s,

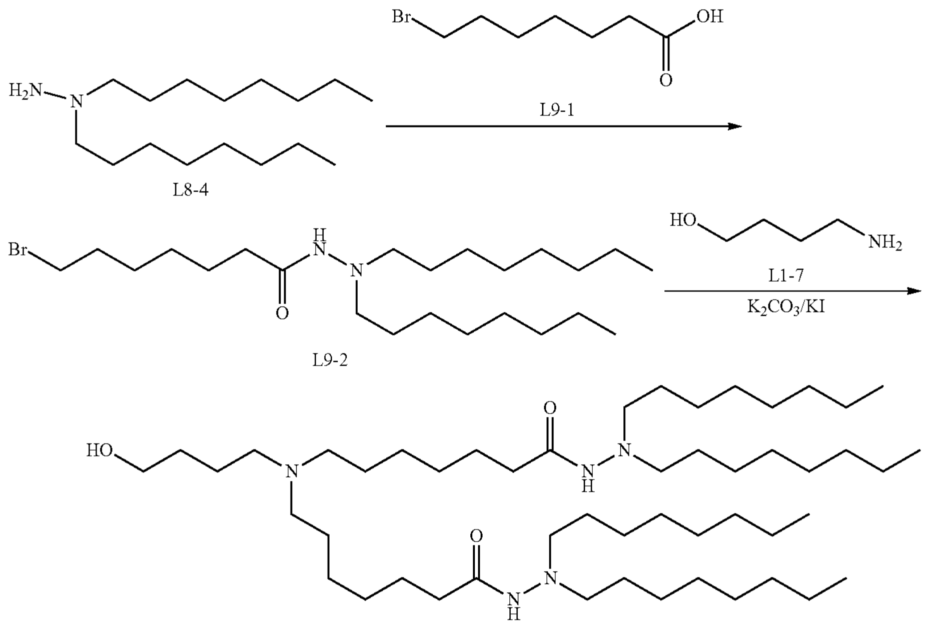

Compound 18

1.13H), 3.68-3.58 (m, 2H), 2.80-2.60 (m, 9H), 2.48-2.36 (m, 5H), 2.12 (t, 1H), 1.80-1.15 (m, 73H), 0.90-0.84 (m, 12H). CIMS m/z 822.7 $[M+H]^+$. Analytical HPLC column: Agilent Zorbax SB-C18, 5 μm, 4.6×150 mm, mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: ELSD, $t_R$=5.26 min, purity: >99%; UPLC column: Thermo Scientific Hypersil GOLD C4, mobile phase A: acetonitrile with 0.1% trifluoroacetic acid, mobile phase B: water with 0.1% trifluoroacetic acid, use gradient: A in B 60% to 100% in 15 min, flow rate: 0.5 mL/min, column temperature: 20±2° C., detector: CAD, $t_R$=8.86 min, purity: 96.15%.

Synthesis of ((4-((2-(methylamino)-3,4-dioxocyclobut-1-en-1-yl)amino)butyl)azanediyl)bis(hexane-6,1-diyl) bis(2-hexyldecanoate) (Compound 6)

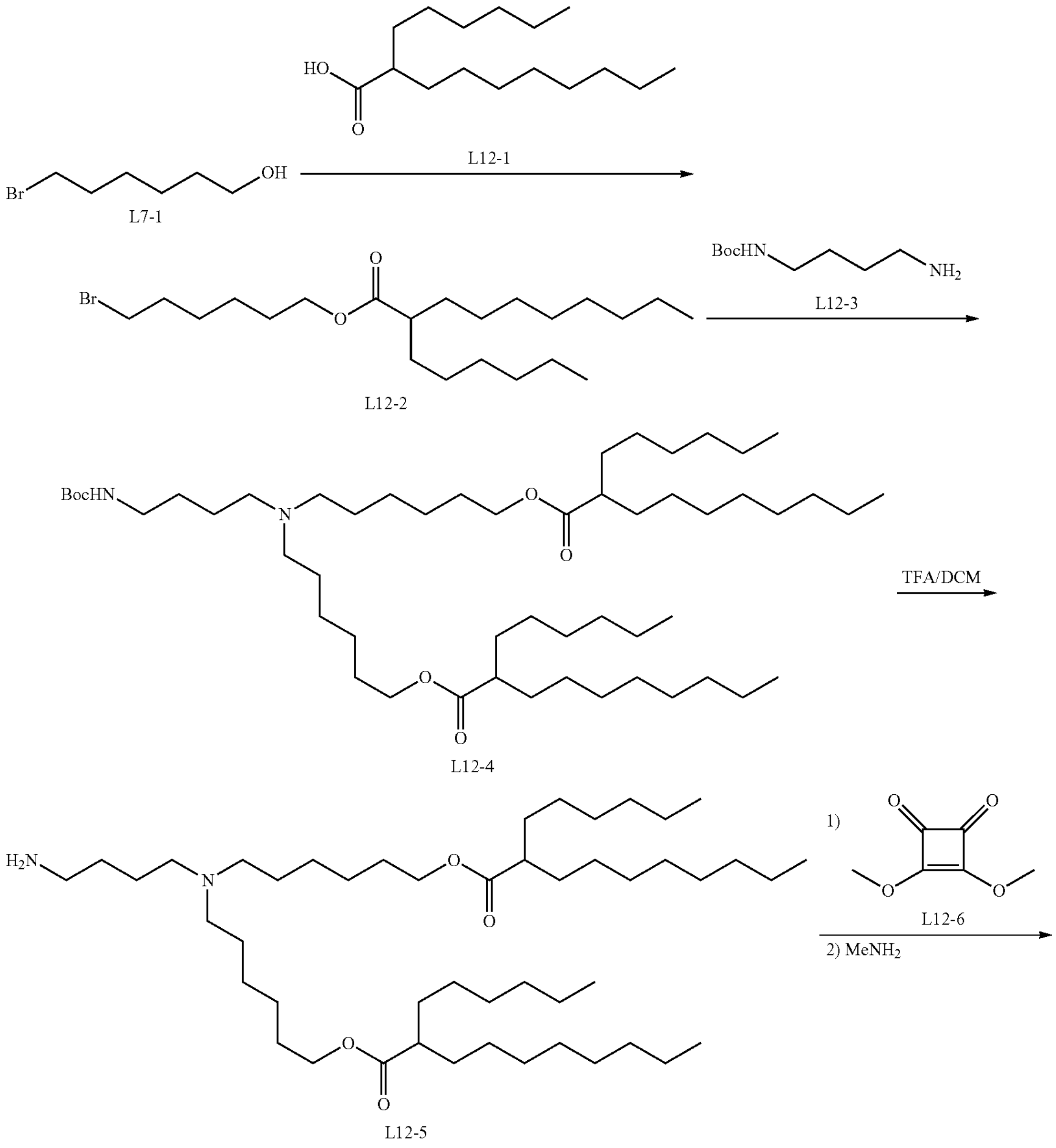

-continued

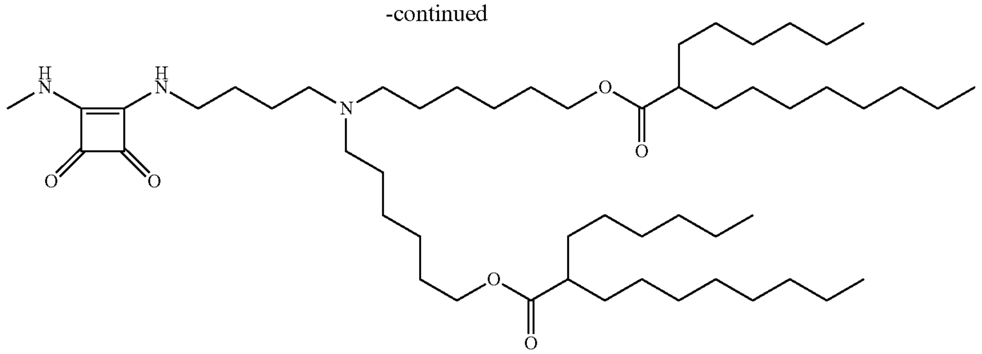

Compound 6

Synthesis of 6-bromohexyl 2-hexyldecanoate (L12-2)

To an oven dried 100 mL round bottom flask containing a solution of 2-hexyldecanoic acid L12-1 (5.0 g, 19.50 mmol) in dichloromethane (50 mL) was added EDC (5.61 g, 29.25 mmol) and DMAP (0.476 g, 3.90 mmol). After completion of the addition, the mixture was stirred at room temperature for 10 min. 6-bromo-1-hexanol L7-1 (3.5 g, 19.50 mmol) was then added and the reaction mixture was stirred at room temperature for 16 h. The reaction was diluted with water and the resulting phases were separated. The aqueous phase was extracted with EtOAc (50 mL×2). Combined organic extracts were washed with $H_2O$ (60 mL×2) and dried over anhydrous $MgSO_4$. Filtration and concentration provided crude material which was purified by flash column chromatography ($SiO_2$: 0 to 30% ethyl acetate in hexanes gradient) to yield 6-bromohexyl 2-hexyldecanoate L12-2 as colorless oil (3.8 g, 47%); CIMS m/z 419.2, 421.2 $[M+H]^+$.

Synthesis of ((4-((tert-butoxycarbonyl)amino)butyl) azanediyl)bis(hexane-6,1-diyl) bis(2-hexyldecanoate) (L12-4)

To a solution of compound L12-2 (2.0 g, 4.77 mmol) in CPME (5 mL) and (ACN 5 mL), under nitrogen, was treated with compound tert-butyl (4-aminobutyl)-carbamate (404 mg, 2.15 mmol) and followed by the addition of $K_2CO_3$ (2.31 g, 16.69 mmol) and KI (2.37 g, 14.31 mmol). The reaction mixture was heated at 85° C. for 18 h. After cooling to room temperature, the reaction mixture was filtered through Celite, washed with ethyl acetate, and the solvent was removed under vacuum to give the crude (2.6 g, 100%) product which was used for the next step without further purification; $^1$H-NMR (300 MHz, $CDCl_3$) δ 5.05 (m, 1H), 4.05 (t, 4H), 3.19-3.03 (m, 2H), 2.48-2.25 (m, 6H), 1.66-1.17 (m, 79H), 0.89-0.84 (m, 12H); CIMS m/z 865.7 $[M+H]^+$.

Synthesis of ((4-aminobutyl)azanediyl)bis(hexane-6,1-diyl) bis(2-hexyldecanoate) (L12-5)

To a solution of L12-4 (2.06 g, 2.38 mmol) in dichloromethane (20 mL) was added TFA (5 mL) at 0° C. and allowed the reaction to room temperature and stirred for 4 h. The Solvent was removed on rotavapor, crude purified by flash column chromatography ($SiO_2$: 0 to 10% MeOH/DCM with 1% $NH_4OH$) to yield L12-5 as sticky oil (1.5 g, 82%); $^1$H-NMR (300 MHz, $CDCl_3$) δ 4.05 (t, 4H), 2.75-2.71 (m, 2H), 2.45-2.27 (m, 8H), 1.66-1.15 (m, 74H), 0.89-0.84 (m, 12H). CIMS m/z 765.7 $[M+H]^+$.

Synthesis of ((4-((2-(methylamino)-3,4-dioxocyclobut-1-en-1-yl)amino)butyl)azanediyl)bis(hexane-6,1-diyl) bis(2-hexyldecanoate) (Compound 6)

To a solution of L12-5 (500 mg, 0.653 mmol) in diethyl ether (50 mL) was added 3,4-dimethoxy cyclobutene-1,2-dione (139 mg, 0.980 mmol) at 0° C. and allowed the reaction to room temperature and stirred for 3 h. TLC showed all starting material was consumed. To the reaction mixture was added methyl amine (2.0 M) in methanol (300 mg, 6.53 mmol) and continued stirring the reaction overnight at room temperature. Solvent was removed on rotavapor, and the crude was purified by flash column chromatography ($SiO_2$: 0 to 10% MeOH/DCM with 1% $NH_4OH$) to yield Compound 6 as sticky gum (300 mg, 53%); $^1$H-NMR (300 MHz, $CDCl_3$) δ 8.20 (b, 1H), 7.45 (b, 1H), 4.06 (t, 4H), 3.72-3.68 (m, 2H), 3.31 (d, 3H), 3.20-2.94 (m, 6H), 2.33-2.27 (m, 2H), 1.95-1.80 (m, 2H), 1.73-1.56 (m, 18H), 1.53-1.41 (m, 12H), 1.40-1.24 (m, 42H), 0.89-0.84 (t, 12H). CIMS m/z 874.7 $[M+H]^+$. Analytical HPLC column: Agilent Zorbax SB-C18, 5 m, 4.6×150 mm, mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: ELSD, $t_R$=11.84 min, purity: >99%; UPLC column: Thermo Scientific Hypersil GOLD C4, mobile phase A: acetonitrile with 0.1% trifluoroacetic acid, mobile phase B: water with 0.1% trifluoroacetic acid, use gradient: A in B 60% to 100% in 15 min, flow rate: 0.5 mL/min, column temperature: 20±2° C., detector: CAD, $t_R$=14.05 min, purity: 96.59%.
Synthesis of bis(3-pentyloctyl) 9-((2-((3-(dimethylamino)propyl)amino)-3,4-dioxocyclobut-1-en-1-yl)amino)heptadecanedioate (Compound 37)
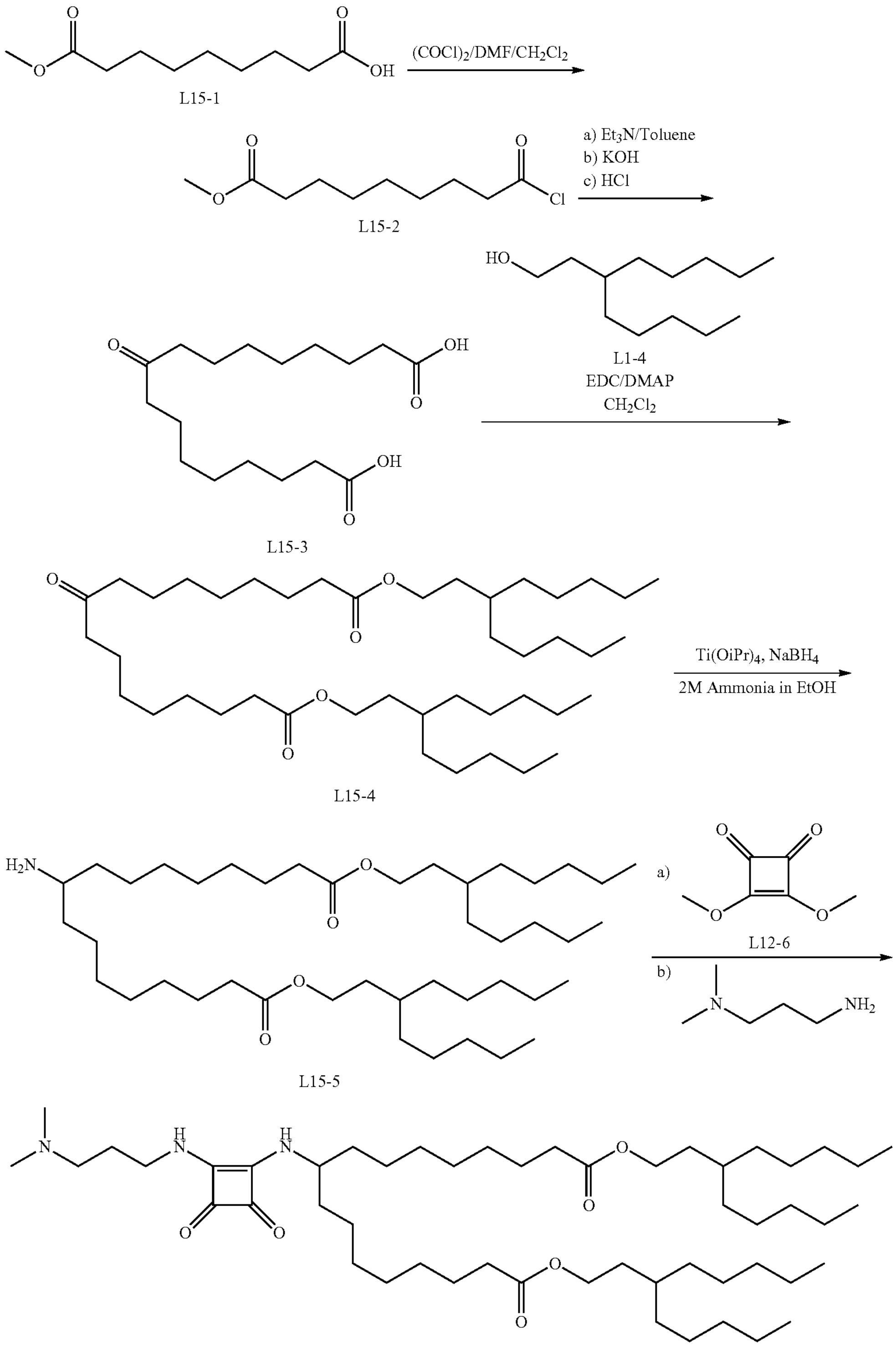
Compound 37

Synthesis of methyl 9-chloro-9-oxononanoate (L15-2)

To a solution of L15-1 (12 g, 59 mmol) in anhydrous DCM (40 mL) was added anhydrous DMF (1 mL). With ice bath cooling, a solution of oxalyl chloride (8.2 g, 65 mmol) in anhydrous DCM (10 mL) was dropped in under nitrogen with stirring. The resulting mixture was then stirred at room temperature under nitrogen overnight. The reaction mixture was concentrated and co-evaporated with anhydrous toluene to give L15-2 as colorless oil (11.6 g, 97%). $^1$H-NMR (300 MHz, $CDCl_3$) δ 3.63 (s, 3H), 2.85 (t, J=7.2 Hz, 2H), 2.27 (t, J=7.5 Hz, 2H), 1.77-1.48 (m, 4H), 1.41-1.19 (m, 6H).

Synthesis of 9-oxoheptadecanedioic acid (L15-3)

To an ice bath cooled solution of L15-2 (11 g, 50 mmol) in anhydrous toluene (85 mL) was added triethylamine (5 g, 50 mmol) in 10 min with stirring while keeping the reaction temperature below 25° C. After addition finished, the reaction mixture temperature was brought to 35-40° C. during 15-20 min with a warm water bath. After the temperature reached to 40° C., the water bath was removed, and the reaction mixture was stirred for 1 h. It was then filtered through a short pad of Celite and the Celite was rinsed with toluene (25 mL). The combined filtrates were evaporated to give an oil residue which was mixed with 2N aq. KOH (42 mL). The mixture was refluxed for 6 h and then cooled in ice-bath. The aqueous layer was washed with ether (35 mL×3) and acidified with concentrated HCl to pH 4. After cooling the mixture in ice bath for 1 h, the precipitates were filtered, washed with ice cold water and dried to yield L15-3 as an off-white solid (6.0 g, 71%). $^1$H-NMR (300 MHz, DMSO-$d_6$) δ 2.38 (t, J=7.1 Hz, 4H), 2.18 (t, J=7.4 Hz, 4H), 1.53-1.35 (m, 8H), 1.33-1.02 (m, 12H).

Synthesis of bis(3-pentyloctyl) 9-oxoheptadecanedioate (L15-4)

To a solution of L15-3 (1.8 g, 5.99 mmol) and L1-4 (2.52 g, 12.58 mmol) in DCM (20 mL) at room temperature was added DMAP (70 mg) and the reaction was stirred for 10 min followed by addition of EDC (2.45 g, 12.76 mmol). The reaction was stirred for 48 h at RT under nitrogen atmosphere. The reaction mixture was diluted with DCM (100 mL) and washed with saturated $NaHCO_3$ solution (2×25 mL), water (25 mL), and brine (25 mL). The organic layer was dried over anhydrous $Na_2SO_4$. Filtration and concentration yielded crude product which was purified by flash column chromatography ($SiO_2$: 5 to 8% ethyl acetate in hexane gradient) to yield L15-4 as colorless oil (2.1 g, 54%). $^1$H-NMR (300 MHz, $CDCl_3$) δ 4.09-4.04 (t, 4H), 2.39-2.34 (t, 4H), 2.29-2.24 (t, 4H), 1.59-1.52 (m, 12H), 1.29-1.25 (m, 46H), 0.89-0.85 (t, 12H). CIMS m/z 680.6 $[M+H]^+$.

Synthesis of bis(3-pentyloctyl) 9-aminoheptadecanedioate (L15-5)

To a solution of L15-4 (0.5 g, 0.736 mmol) in 2M ammonia in EtOH (2.0 mL) solution was added titanium (IV) isopropoxide (0.46 mL, 1.509 mmol) dropwise at ambient temperature. The reaction was stirred for 6 h, progress of imine formation was monitored by TLC/mass spec. After completion of the imine formation, sodium borohydride (56 mg, 1.472 mmol) was added to the reaction portion wise. Addition of borohydride was exothermic, therefore the reaction mixture was cooled over the course of the reaction. The reaction was further stirred overnight at RT. The reaction mixture was cooled in an ice bath and quenched by adding $NH_4OH$ solution (white precipitate formed). The reaction mixture was filtered through celite, and washed with EtOAc. Solvent was removed on in vacuo, and the crude material was purified by flash column chromatography ($SiO_2$: 5 to 7% MeOH/DCM (1% $NH_4OH$) to yield L15-5 as colorless oil (300 mg, 60%). $^1$H-NMR (300 MHz, $CDCl_3$) δ 4.07 (t, 4H), 2.68 (s, 1H), 2.27 (t, 4H), 1.60-1.55 (m, 8H), 1.53-1.25 (m, 54H), 0.90-0.85 (t, 12H). CIMS m/z 681.6 $[M+H]^+$.

Synthesis of bis(3-pentyloctyl) 9-((2-((3-(dimethylamino)propyl)amino)-3,4-dioxocyclobut-1-en-1-yl)amino)heptadecanedioate (Compound 37)

To a solution of L15-5 (200 mg, 0.294 mmol) in diethyl ether (20 mL) was added 3,4-dimethoxy cyclobutene-1,2-dione (63 mg, 0.441 mmol) at 0° C. and the reaction was allowed to warm room temperature and stirred for 3 h. Additional 3,4-dimethoxy cyclobutene-1,2-dione (63 mg, 0.441 mmol) was added to the reaction mixture and stirred for 2 h. To the reaction mixture was added N,N-dimethyl-1,3-propanediamine (300 mg, 2.94 mmol) and stirring was continued overnight at room temperature. Solvent was removed in vacuo, and crude material was purified by flash column chromatography ($SiO_2$: 6 to 8% MeOH/DCM (1% $NH_4OH$) to yield Compound 37 as sticky gum (132 mg, 52%). $^1$H-NMR (300 MHz, $CDCl_3$) δ 4.07 (t, 4H), 3.70 (s, 1H), 2.60 (s, 2H), 2.25-2.38 (s, 8H), 2.27 (t, 4H), 1.88-1.72 (m, 6H), 1.55 (m, 8H), 1.28-1.24 (m, 52H), 0.90-0.85 (t, 12H). CIMS m/z 860.7 $[M+H]^+$. Analytical HPLC column: Agilent Zorbax SB-C18, 5 m, 4.6×150 mm, mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: ELSD, $t_R$=11.85 min, purity: >99%; UPLC column: Thermo Scientific Hypersil GOLD C4, mobile phase A: acetonitrile with 0.1% trifluoroacetic acid, mobile phase B: water with 0.1% trifluoroacetic acid, use gradient: A in B 60% to 100% in 15 min, flow rate: 0.5 mL/min, column temperature: 20±2° C., detector: CAD, $t_R$=14.63 min, purity: 95.25%.

Synthesis of ((3-hydroxypropyl)azanediyl)bis(hexane-6,1-diyl) bis(4,4-bis(octyloxy)butanoate) Compound 50

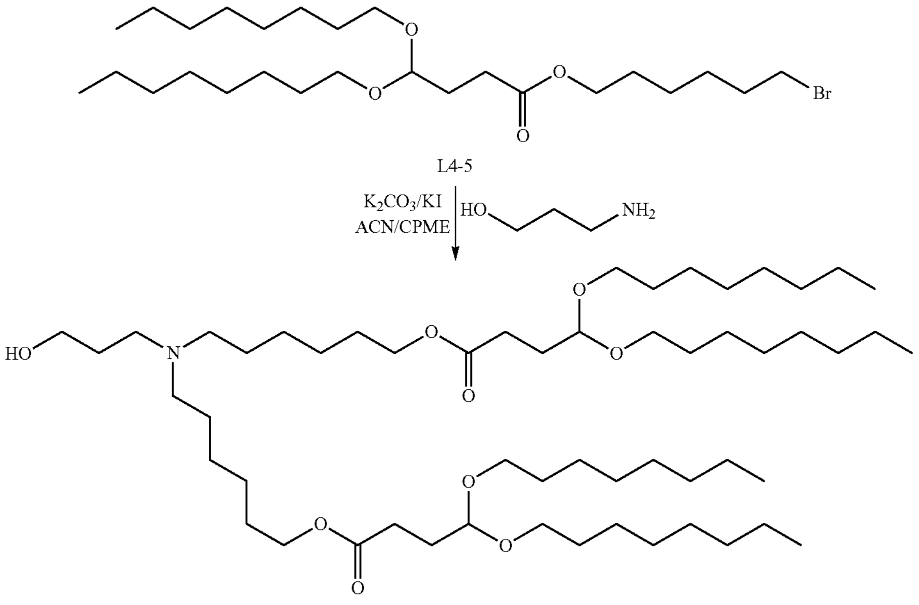

Compound 50

Synthesis of ((3-hydroxypropyl)azanediyl)bis(hexane-6,1-diyl) bis(4,4-bis(octyloxy)butanoate) (Compound 50)

To a solution of L4-5 (1.5 g, 2.96 mmol) and 3-amino-1-propanol (111 mg, 1.48 mmol) in $CH_3CN$ (5 mL) and CPME (5 mL) at room temperature under nitrogen was added $K_2CO_3$ (1.23 g, 8.87 mmol) and KI (1.47 g, 8.87 mmol). The reaction mixture was then heated at 85° C. for 18 h. After cooling to room temperature, the reaction mixture was filtered through Celite, and washed with ethyl acetate, and the solvent was removed under vacuum to give the crude product which was purified by flash chromatography (SiO2: MeOH in DCM 0-10% gradient) to yield Compound 50 as colorless oil (0.685 g, 50%). $^1$H-NMR (300 MHz, $CDCl_3$) δ; 4.49 (t, 2H), 4.05 (t, 4H), 3.78 (t, 2H), 3.60-3.52 (m, 4H), 3.43-3.36 (m, 4H), 2.67-2.60 (m, 2H), 2.42-2.32 (m, 8H), 1.92 (q, 4H), 1.67-1.39 (m, 20H), 1.38-1.10 (m, 47H), 0.87 (t, 12H); CIMS m/z $[M+H]^+$ 928.9; Analytical HPLC column: Agilent Zorbax SB-C18, 5 μm, 4.6×150 mm, mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: ELSD, $t_R$=11.60 min, purity: >99%; UPLC column: Thermo Scientific Hypersil GOLD C4, mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: CAD, $t_R$=14.23 min, purity: 97.97%.

Synthesis of ((3-(((benzyloxy)carbonyl)amino)propyl)azanediyl)bis(hexane-6,1-diyl) bis(4,4-bis(octyloxy)butanoate) (Compound 62) and ((3-(3,3-dimethylthioureido)propyl)-azanediyl)bis(hexane-6,1-diyl) bis(4,4-bis(octyloxy)butanoate) (Compound 54)

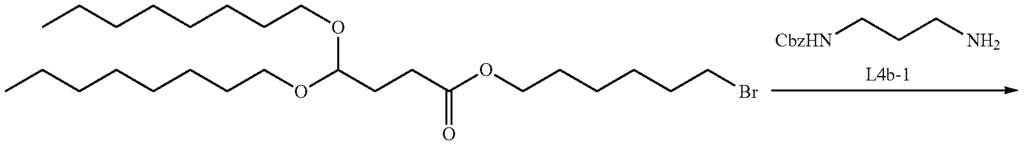

L4-5

-continued

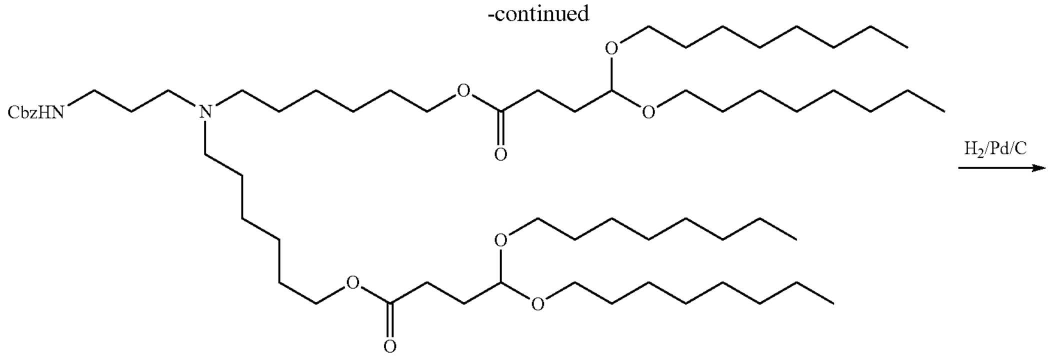

Compound 62

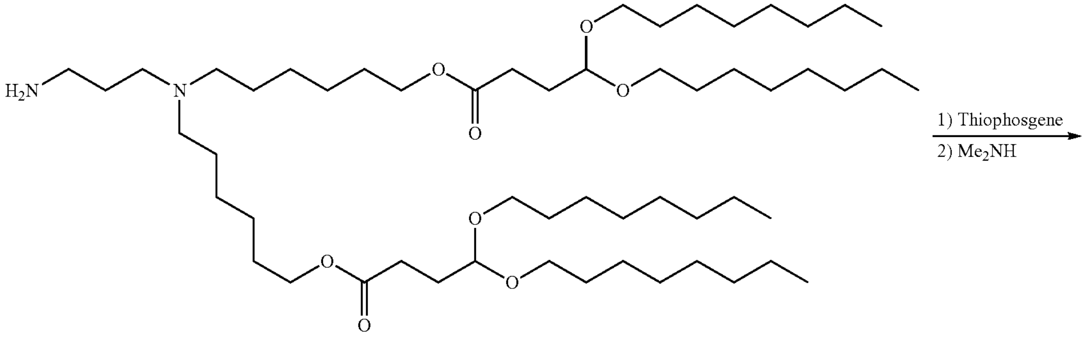

L4b-3

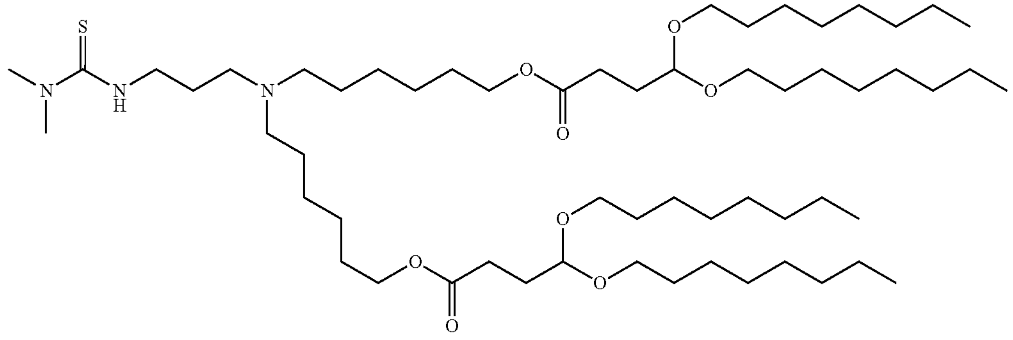

Compound 54

Synthesis of ((3-(((benzyloxy)carbonyl)amino)propyl)azanediyl)bis(hexane-6,1-diyl) bis(4,4-bis(octyloxy)butanoate) (Compound 62)

To a solution of compound L4-5 (4.5 g, 8.87 mmol) in $CH_3CN$ (10 mL) and CPME (10 mL) under nitrogen was added benzyl (3-aminopropyl)carbamate (994 mg, 4.43 mmol), followed by the addition of $K_2CO_3$ (3.68 g, 26.60 mmol) and KI (4.41 g, 26.60 mmol). The reaction mixture was heated at 85° C. for 18 h. After cooling to room temperature, the reaction mixture was filtered through Celite, washed with ethyl acetate, and the solvent was removed under vacuum to give the crude product which was purified by flash chromatography (SiO2: MeOH in DCM 0-5% gradient) to yield compound Compound 62 as colorless oil (1.2 g, 25%). $^1$H-NMR (300 MHz, $CDCl_3$) δ; 7.33-7.28 (m, 5H), 5.08 (s, 2H), 4.47 (t, 2H), 4.02 (t, 4H), 3.58-3.52 (m, 4H), 3.42-3.29 (m, 4H), 3.29-3.25 (m, 2H), 2.36 (t, 4H), 1.93-1.88 (m, 4H), 1.62-1.45 (m, 16H), 1.90-1.40 (m, 47H), 0.87 (t, 12H); CIMS m/z $[M+H]^+$ 1061.9; Analytical HPLC column: Agilent Zorbax SB-C18, 5 m, 4.6×150 mm, mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: ELSD, $t_R$=11.81 min, purity: >99%; UPLC column: Thermo Scientific Hypersil GOLD C4, mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: CAD, $t_R$=13.62 min, purity: 96.66%.

Synthesis of ((3-aminopropyl)azanediyl)bis(hexane-6,1-diyl) bis(4,4-bis(octyloxy)butanoate) (L4b-3)

A mixture of Compound 62 (0.85 g, 0.80 mmol), Pd/C (0.25 g) and acetic acid (0.144 g, 2.40 mmol) in ethyl acetate (15 mL) was stirred for 4 h under $H_2$ balloon. The reaction was filtered through a celite pad, and the solvent was removed in vacuo. Crude material was dissolved in DCM (25 mL) and washed with bicarbonate solution. The organic phase was separated, dried and evaporated to give L4b-3 as a sticky oil (330 mg, 45%) which was used for the next step without further purification.

Synthesis of ((3-(3,3-dimethylthioureido)propyl) azanediyl)bis(hexane-6,1-diyl) bis(4,4-bis(octyloxy) butanoate) (Compound 54)

To a solution of L4b-3 (400 mg, 0.431 mmol) in diethyl ether (30 mL) at 0° C. was added triethylamine (218 mg, 2.156 mmol) and thiophosgene (146 mg, 1.293 mmol). The reaction mixture was warmed to room temperature and stirred for 3 h. The volatile components were removed under reduced pressure and to the residue was added methyl amine (2.0 M) in THF (2.16 mL, 4.31 mmol). Stirring continued at room temperature for 16 h. Solvent was removed in vacuo, and crude material was purified by flash column chromatography ($SiO_2$: 0 to 10% MeOH/DCM with 1% $NH_4OH$) to yield Compound 54 as sticky gum (152 mg, 35%). $^1$H-NMR (300 MHz, $CDCl_3$) δ. 4.49 (t, 2H), 4.05 (t, 4H), 3.80 (b, 2H), 3.62-3.52 (m, 4H), 3.43-3.18 (m, 8H), 3.00 (b, 2H), 2.38 (t, 4H), 1.96-1.89 (m, 4H), 1.68-1.10 (m, 73H), 0.87 (t, 12H); CIMS m/z $[M+H]^+$ 1014.8. Analytical HPLC column: Agilent Zorbax SB-C18, 5 μm, 4.6×150 mm, mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: ELSD, $t_R$=7.96 min, purity: >99%; UPLC column: Thermo Scientific Hypersil GOLD C4, mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: CAD, $t_R$=13.77 min, purity: 98.33%.

Synthesis of ((3-((2-(methylamino)-3,4-dioxocyclobut-1-en-1-yl)amino)propyl)azanediyl) bis (hexane-6,1-diyl) bis(4,4-bis(octyloxy)butanoate) (Compound 56)

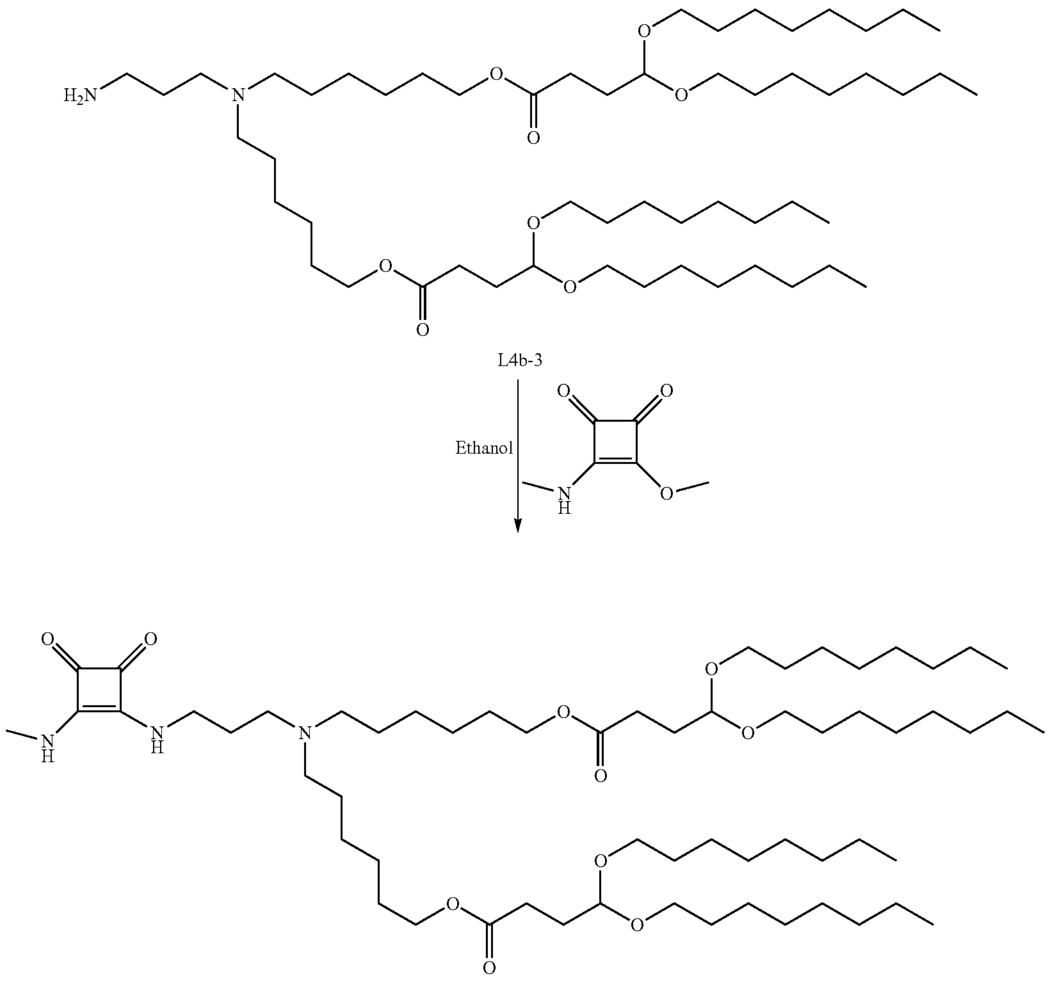

Compound 56

Synthesis of ((3-((2-(methylamino)-3,4-dioxocyclobut-1-en-1-yl)amino)propyl)azanediyl) bis(hexane-6,1-diyl) bis(4,4-bis(octyloxy)butanoate) (Compound 56)

To a solution of L4b-3 (750 mg, 0.809 mmol) in ethanol (5 mL) was added 3-methoxy-4-(methylamino)cyclobut-3-ene-1,2-dione (171 mg, 1.214 mmol) at 0° C. and the reaction was allowed to room temperature and stirred for 24 h. Solvent was removed in vacuo, and crude material was purified by flash column chromatography ($SiO_2$: 0 to 10% MeOH/DCM (1% $NH_4OH$)) to yield Compound 56 as light yellow color sticky oil (110 mg, 13%). $^1$H-NMR (300 MHz, $CDCl_3$) δ 4.48 (t, 2H), 4.05 (t, 4H), 3.72-3.68 (m, 1H), 3.60-3.52 (m, 4H), 3.43-3.36 (m, 4H), 3.29 (d, 3H), 2.92-2.60 (m, 3H), 2.38 (t, 4H), 1.95-1.86 (m, 6H), 1.68-1.46 (m, 18H), 1.40-1.24 (m, 53H), 0.89-0.85 (t, 12H). CIMS m/z 1036.9 $[M+H]^+$ 1036.9. Analytical HPLC column: Agilent Zorbax SB-C18, 5 m, 4.6×150 mm, mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: ELSD, $t_R$=8.52 min, purity: 95.32%; UPLC column: Thermo Scientific Hypersil GOLD C4, mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: CAD, $t_R$=3.26 min, purity: 87.12%.

Synthesis of ((3-((tert-butoxycarbonyl)amino)propyl)azanediyl)bis(hexane-6,1-diyl) bis(4,4-bis(octyloxy) butanoate) (Compound 60)

Synthesis of ((3-((tert-butoxycarbonyl)amino)propyl)azanediyl)bis(hexane-6,1-diyl) bis(4,4-bis(octyloxy) butanoate) (Compound 60)

To a solution of compound L4-5 (5.0 g, 9.88 mmol) in $CH_3CN$ (5 mL) and CPME (5 mL) under nitrogen was added tert-butyl (3-aminopropyl)carbamate (939 mg, 4.94 mmol) followed by the addition of $K_2CO_3$ (4.09 g, 29.63 mmol) and KI (4.92 g, 29.63 mmol). The reaction mixture was heated at 85° C. for 18 h. After cooling to room temperature, the reaction mixture was filtered through Celite, washed with ethyl acetate, and the solvent was removed under vacuum to give the crude product which was purified by flash chromatography (SiO2: MeOH in DCM 0-10% gradient) to yield Compound 60 as colorless oil (4.0 g, 79%). $^1$H-NMR (300 MHz, $CDCl_3$) δ; 4.49 (t, 2H), 4.05 (t, 4H), 3.60-3.52 (m, 4H), 3.43-3.36 (m, 4H), 3.15 (b, 2H), 2.50-2.25 (m, 10H), 1.95-1.88 (q, 4H), 1.67-1.16 (m, 76H), 0.87 (m, 12H); CIMS m/z $[M+H]^+$ 1027.9; Analytical HPLC column: Agilent Zorbax SB-C18, 5 μm, 4.6×150 mm, mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: ELSD, $t_R$=11.75 min, purity: >99%; UPLC column: Thermo Scientific Hypersil GOLD C4, mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: CAD, $t_R$=13.07 min, purity: >99%.

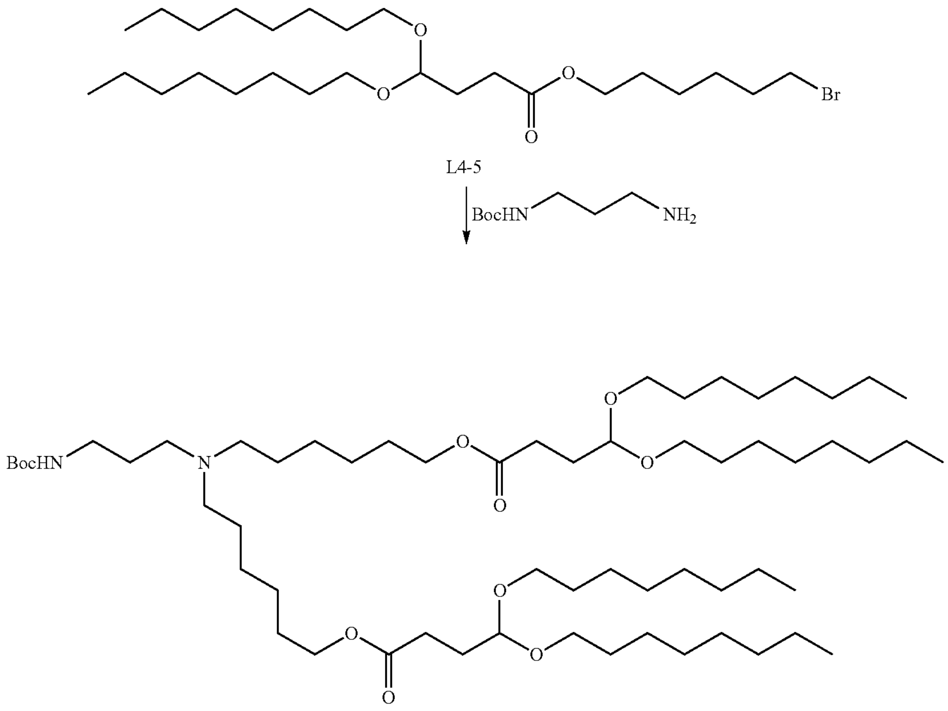

Compound 60

Synthesis of ((4-hydroxybutyl)azanediyl)bis(pentane-5,1-diyl) bis(4,4-bis(octyloxy)butanoate) (Compound 51)

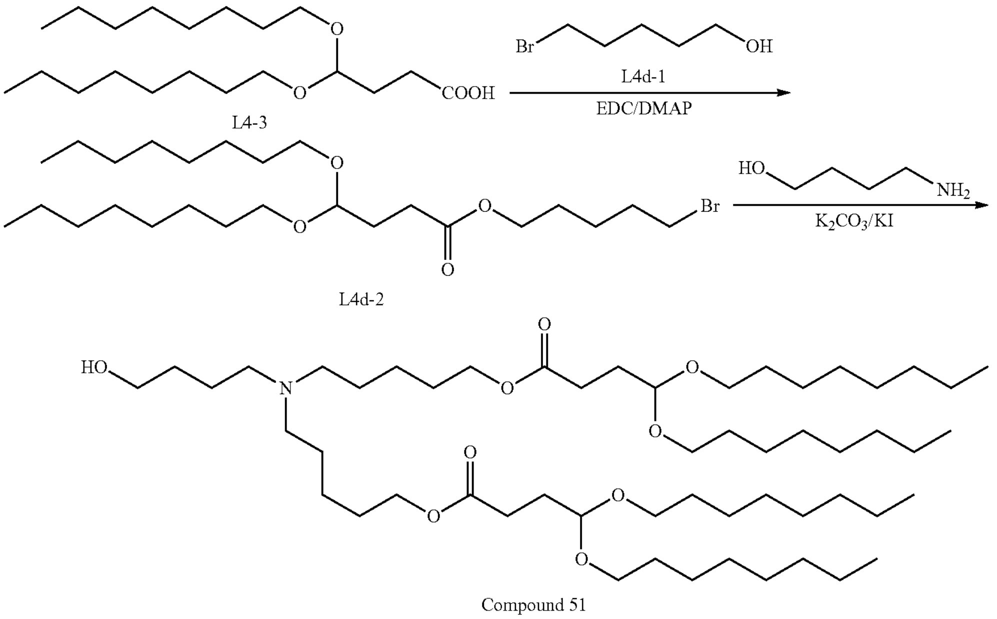

Compound 51

Synthesis of 5-bromopentyl 4,4-bis(octyloxy)butanoate (L4d-2)

To a solution of compound L4-3 (3.0 g, 8.70 mmol) in dichloromethane (60 mL) was added DMAP (1.06 mg, 8.70 mmol), EDC (6.67 g, 34.8 mmol) and L4d-1 (3.2 g, 19.1 mmol). The reaction mixture was stirred at room temperature for 12 h. The reaction mixture was evaporated under vacuum. The residue was dissolved in dichloromethane (100 mL) and washed with brine (80 mL×3). After drying over anhydrous $Na_2SO_4$, the solvent was evaporated, and the crude material was purified by column chromatography (330 g $SiO_2$: 0 to 30% Ethyl acetate in Hexane gradient) to obtain L4d-2 as colorless oil (2.6 g, 60%). $^1$H-NMR (300 MHz, $CDCl_3$) δ 4.48 (t, 1H), 4.06 (t, 2H), 3.59-3.31 (m, 6H), 2.37 (t, 2H), 1.95-1.85 (m, 4H), 1.67-1.47 (m, 8H), 1.38-1.18 (m, 20H), 0.86 (t, 6H).

Synthesis of ((4-hydroxybutyl)azanediyl)bis(pentane-5,1-diyl) bis(4,4-bis(octyloxy)butanoate) (Compound 51)

To a solution of compound L4d-2 (2.5 g, 5.1 mmol) in CPME (15 mL) and ACN (15 mL) under nitrogen was added 4-amino-1-butanol (200 mg, 2.24 mmol) followed by the addition of $K_2CO_3$ (1.2 g, 8.9 mmol) and KI (372 mg, 2.5 mmol). The reaction mixture was heated at 80° C. for 18 h. After cooling to room temperature, the reaction mixture was filtered through Celite, washed with ethyl acetate, and the solvent was removed under vacuum to give the crude product which was purified by flash chromatography. (80 g $SiO_2$: 0 to 30% Ethyl acetate in 5% triethylamine in hexane gradient) to obtain Compound 51 as colorless oil (0.8 g, 40%). $^1$H-NMR (300 MHz, $CDCl_3$) δ 4.48 (t, 2H), 4.04 (t, 4H), 3.59-3.35 (m, 10H), 2.44-2.34 (m, 10H), 1.94-1.87 (m, 4H), 1.67-1.44 (m, 20H), 1.38-1.13 (m, 45H), 0.86 (t, 12H)); CIMS m/z $[M+H]^+$ 914.7. Analytical HPLC column: Agilent Zorbax SB-C18, 5 μm, 4.6×150 mm, mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: ELSD, $t_R$=11.4 min, purity: >99%; UPLC column: Thermo Scientific Hypersil GOLD C4, mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: CAD, $t_R$=13.9 min, purity: >97%.

Synthesis of ((4-hydroxybutyl)azanediyl)bis(octane-8,1-diyl) bis(4,4-bis(octyloxy)butanoate) (Compound 52)

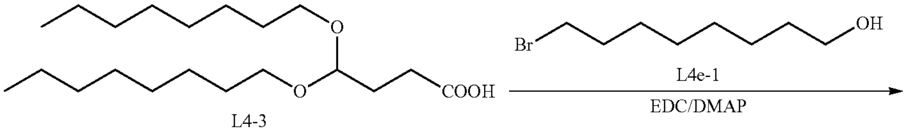

-continued

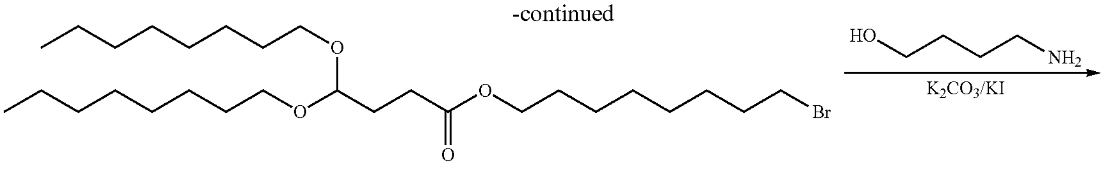

L4e-2

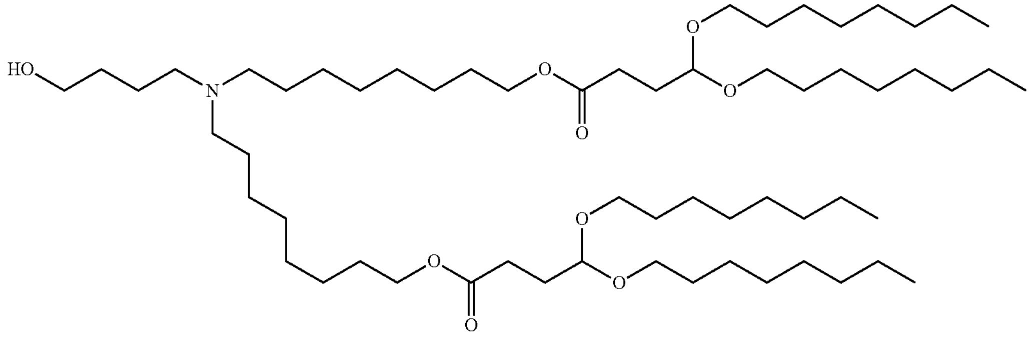

Compound 52

Synthesis of 8-bromooctyl 4,4-bis(octyloxy)butanoate (L4e-2)

To a solution of compound L4-3 (3.0 g, 8.70 mmol) in dichloromethane (60 mL) was added DMAP (1.06 mg, 8.70 mmol), EDCI (6.67 g, 34.8 mmol) and L4e-1 (4.0 g, 19.1 mmol). The reaction mixture was stirred at room temperature for 12 h. The reaction mixture was evaporated under vacuum. The residue was dissolved in dichloromethane (100 mL) and washed with brine (80 mL×3). After drying over anhydrous $Na_2SO_4$, the solvent was evaporated, and the crude was purified by column chromatography (330 g $SiO_2$: 0 to 30% Ethyl acetate in Hexane gradient) to obtain compound L4e-2 (3.3 g, 70%). $^1$H-NMR (300 MHz, $CDCl_3$) δ 4.48 (t, 1H), 4.04 (t, 2H), 3.59-3.35 (m, 6H), 2.37 (t, 2H), 1.95-1.86 (m, 3H), 1.67-1.08 (m, 35H), 0.86 (t, 6H). CIMS m/z $[M+H]^+$ 536.4.

Synthesis of ((4-hydroxybutyl)azanediyl)bis(octane-8,1-diyl) bis(4,4-bis(octyloxy)butanoate) (Compound 52)

To a solution of compound L4e-2 (3.17 g, 5.9 mmol) in CPME (15 mL) and ACN (15 mL) under nitrogen was added 4-amino-1-butanol (230 mg, 2.5 mmol) followed by the addition of $K_2CO_3$ (1.4 g, 10.3 mmol) and KI (428 mg, 2.5 mmol). The reaction mixture was heated at 80° C. for 18 h. After cooling to room temperature, the reaction mixture was filtered through Celite, washed with ethyl acetate, and the solvent was removed under vacuum to give the crude product which was purified by flash chromatography. (80 g $SiO_2$: 0 to 30% Ethyl acetate in 5% triethylamine in hexane gradient) to give Compound 52 (1.2 g, 47%) as colorless oil. $^1$H-NMR (300 MHz, $CDCl_3$) δ 4.49 (t, 2H), 4.03 (t, 4H), 3.59-3.35 (m, 10H), 2.43-2.34 (m, 10H), 1.94-1.87 (m, 4H), 1.63-1.42 (m, 18H), 1.37-1.18 (m, 58H), 0.86 (t, 12H); CIMS m/z $[M+H]^+$ 998.8. Analytical HPLC column: Agilent Zorbax SB-C18, 5 μm, 4.6×150 mm, mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: ELSD, $t_R$=11.8 min, purity: >99%; UPLC column: Thermo Scientific Hypersil GOLD C4, mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: CAD, $t_R$=14.8 min, purity: >87%.

Synthesis of ((4-hydroxybutyl) azanediyl)bis (hexane-6,1-diyl) bis(6,6-bis(octyloxy) hexanoate) (Compound 55)

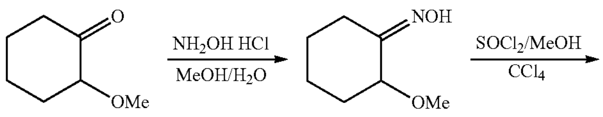

L4f-A1 L4f-A2

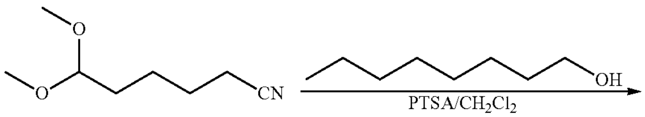

L4f-A3

-continued

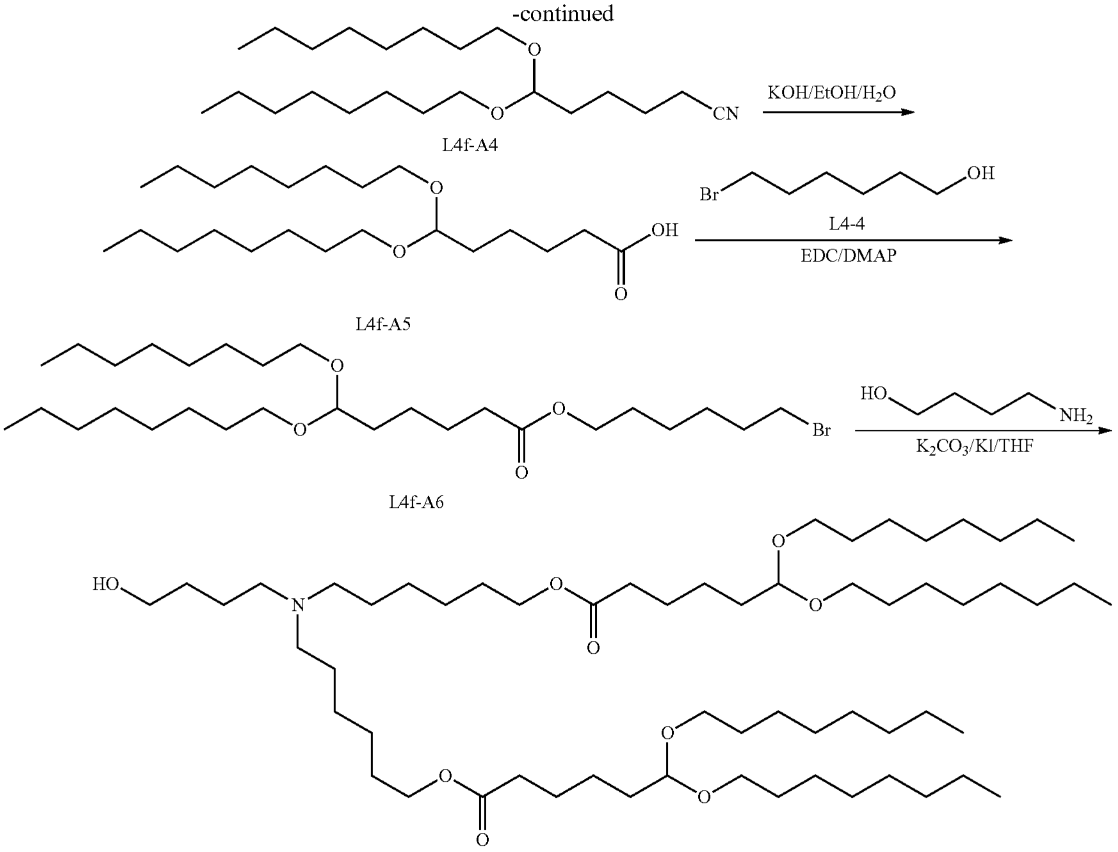

Compound 55

Synthesis of (E)-2-methoxycyclohexan-1-one oxime (L4f-A2)

To a 5 mL microwave reactor tube L4f-A1 (1.0 g, 7.80 mmol), hydroxylamine hydrochloride (1.139 g, 16.38 mmol), and sodium acetate (1.34 g, 16.38 mmol) were added. To this was added a mixture of MeOH and Water (2:1, 2 mL) and the reaction mixture was sealed with the vial cap and heated in a CEM microwave reactor at 100° C. for 5 min. After completion of the reaction the solvent was removed under vacuum. The residue was partitioned between ethyl acetate/brine (3 times). The ethyl acetate layers were combined and dried over anhydrous magnesium sulphate. The ethyl acetate was removed under vacuum to give 940 mg (84%) crude product L4f-A2. This crude product was used for the next step reaction without further purification. $^1$H NMR (300 MHz, $CDCl_3$): δ ppm 8.32 (bs, 1H), 3.72 (t, J=5.0 Hz, 1H), 3.27 (s, 3H), 3.10-3.25 (m, 1H), 2.10-2.01 (m, 2H), 1.81-1.30 (m, 6H) MS (CI): m/z $[M+H]^+$ 143.2.

Synthesis of 6,6-dimethoxyhexanenitrile (L4f-A3)

To a 100 mL of three neck flask L4f-A2 (5.7 g, 44.47 mmol) was added carbon tetrachloride (30 mL). The flask was flushed with nitrogen and cooled to 0° C. To this flask was added thionyl chloride (4.64 g, 2.89 ml, 66.70 mmol) dissolved in carbon tetrachloride (15 mL) dropwise over 10 min. The reaction was maintained at same temperature and stirred for 5 min. Anhydrous methanol (20 mL) was added dropwise to the reaction. The reaction was allowed to stir at 0-5° C. for 1 h. After completion of reaction, the reaction contents were poured into a 1000 mL round bottom flask containing 30 g of sodium bicarbonate and brine (5 mL). The reaction contents were allowed to neutralize for 5 min. Solvents were evaporated under vacuum. The residue was partitioned between ethyl acetate/brine (3 times), the ethyl acetate layers were combined, and passed through celite. The ethyl acetate layer was dried over anhydrous magnesium sulphate. The ethyl acetate was removed under vacuum and residue was kept in high vacuum to give crude product L4f-A3 (4.07 g, 58%). This crude was used for the next step without further purification. $^1$H NMR (300 MHz, $CDCl_3$): δ ppm 4.35 (t, J=5.0 Hz, 1H), 3.32 (s, 6H), 2.31 (t, J=6.0 Hz, 2H), 1.70-1.51 (m, 6H); MS (CI): m/z $[M+H]^+$ 157.3.

Synthesis of 6,6-bis(octyloxy)hexanenitrile (L4f-A4)

To a 100 mL round bottom flask was added L4f-A3 (2.0 g, 12.72 mmol) and octanol (9.94 g, 76.33 mmol). To this was added Pyridinium p-toluene sulfonate (480 mg, 1.91 mmol) and the reaction mixture was stirred at 120° C. for 2 h. After completion of the reaction the contents were loaded on to a 120 g flash silica column and purified by flash chromatography ($SiO_2$: ethyl acetate/hexane 0-20%) to get Compound L4f-A4 (2.99 g, 67%) as slightly yellow oil. $^1$H NMR (300 MHz, $CDCl_3$): δ ppm 4.45 (t, J=6.0 Hz, 1H), 3.57-3.53 (m, 2H), 3.42-3.37 (m, 2H), 2.33 (t, J=7.0 Hz, 2H), 1.62-1.50 (m, 6H), 1.41-1.16 (m, 24H), 0.89-0.84 (m, 6H); MS (CI): m/z $[M+H]^+$ 354.5.

Synthesis of 6,6-bis(octyloxy)hexanoic acid (L4f-A5)

To a 250 mL round bottom flask L4f-A4 (2.94 g, 8.31 mmol) and KOH (3.86 g, 68.815 mmol) were added. To this was added a mixture of ethanol and water (1:1, 80 mL) and the reaction mixture was refluxed at 110° C. for 30 h. After completion of the reaction the solvent was removed under vacuum. Residual paste was mixed with 100 g ice and acidified to pH 5 using 1M HCl. This mixture was partitioned in ethyl acetate: water. To this was added brine (100 mL). This mixture was filtered to remove any emulsion formed. The ethyl acetate layer separated well after filtration. The product was extracted with ethyl acetate three times. The combined ethyl acetate layers were dried over anhydrous sodium sulphate. The ethyl acetate was removed under vacuum to give crude compound L4f-A5 (2.45 g, 79%) as slightly yellow oil. $^1$H NMR (300 MHz, $CDCl_3$): δ ppm 4.44 (t, J=3.0 Hz, 1H), 3.55-3.50 (m, 2H), 3.42-3.36 (m, 2H), 2.33 (m, 2H), 1.59-1.16 (m, 30H), 0.89-0.84 (m, 6H); MS (CI): m/z $[M+H]^+$ 373.6.

Synthesis of 6-bromohexyl 6,6-bis(octyloxy)hexanoate (L4f-A6)

To a 250 mL round bottom flask L4f-A5 (2.0 g, 5.37 mmol), EDC (4.12 g, 21.47 mmol), DMAP (0.656 g, 5.37 mmol) were added. To this was added 6-bromohexanol (1.94 g, 10.73 mmol) along with dichloromethane (60 mL) and the reaction mixture was stirred at room temperature for 2 h. After completion of the reaction about 30 g of flash silica was added and the contents were stirred to yield a uniform mixture. Solvent was removed from this mixture under vacuum. The residue was loaded on to an empty flash cartridge, which was then attached to flash purification system loaded with 80 g flash silica column and was purified by flash chromatography ($SiO_2$: ethyl acetate/hexane 0-20%) to get Compound L4f-A6 (1.935 g, 67%) as slightly yellow oil. $^1$H NMR (300 MHz, $CDCl_3$): δ ppm 4.49 (t, J=6.0 Hz, 1H), 4.05 (t, J=6.0 Hz, 2H), 3.56-3.54 (m, 2H), 3.40-3.37 (m, 4H), 2.36 (t, J=7.0 Hz, 2H), 1.94-1.85 (m, 4H), 1.58-1.23 (m, 36H), 0.89-0.87 (m, 6H); MS (CI): m/z $[M+H]^+$ 535.4.

Synthesis of ((4-hydroxybutyl) azanediyl)bis (hexane-6,1-diyl) bis(6,6-bis(octyloxy) hexanoate) (Compound 55)

To a 40 mL microwave reactor tube L4f-A6 (1.56 g, 2.912 mmol), 4-amino-1-butanol (116.8 mg, 1.31 mmol), potassium carbonate (1.207 g, 8.74 mmol) and potassium iodide (725.1 mg, 4.368 mmol) were added. To this was added a mixture of CPME and ACN (1:1, 5 mL) and the reaction mixture was sealed and heated in a CEM microwave reactor at 100° C. for 6 h. After completion of the reaction, the contents were transferred to a 500 mL round bottom flask containing about 40 g of Flash silica (this silica was stirred in 300 mL 5% triethylamine in hexane for 10 min before use) and the contents were stirred well to get a uniform mixture. Solvent was removed from this mixture under vacuum. The residue was loaded on to an empty flash cartridge, which was then attached to flash purification system loaded with a 80 g size prepacked flash silica column (the flash column was equilibrated with 10% triethylamine in hexane for 15 min at a flow rate of 80 mL per min before use) and was purified by flash chromatography ($SiO_2$: ethyl acetate/hexane 0-50%) to get Compound 55 (520 mg, 18%). $^1$H NMR (300 MHz, $CDCl_3$): δ ppm 6.56 (bs, 1H), 4.44 (t, J=6.0 Hz, 2H), 4.03 (t, J=7.0 Hz, 4H), 3.56-3.36 (m, 10H), 2.42-2.28 (m, 10H), 1.95-1.88 (m, 4H), 1.64-1.20 (m, 70H), 0.89-0.86 (m, 12H); MS (CI): m/z $[M+H]^+$ 998.6. Analytical HPLC column: Agilent Zorbax SB-C18, 5 m, 4.6×150 mmol, mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: ELSD, $t_R$=10.7 min, purity: 96.78%; UPLC column: Thermo Scientific Hypersil GOLD C4, mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: CAD, $t_R$=13.1 min, purity: >99%.

Synthesis of ((4-hydroxybutyl) azanediyl)bis (hexane-6,1-diyl) bis(4,4-bis(hexyloxy) butanoate) (Compound 58)

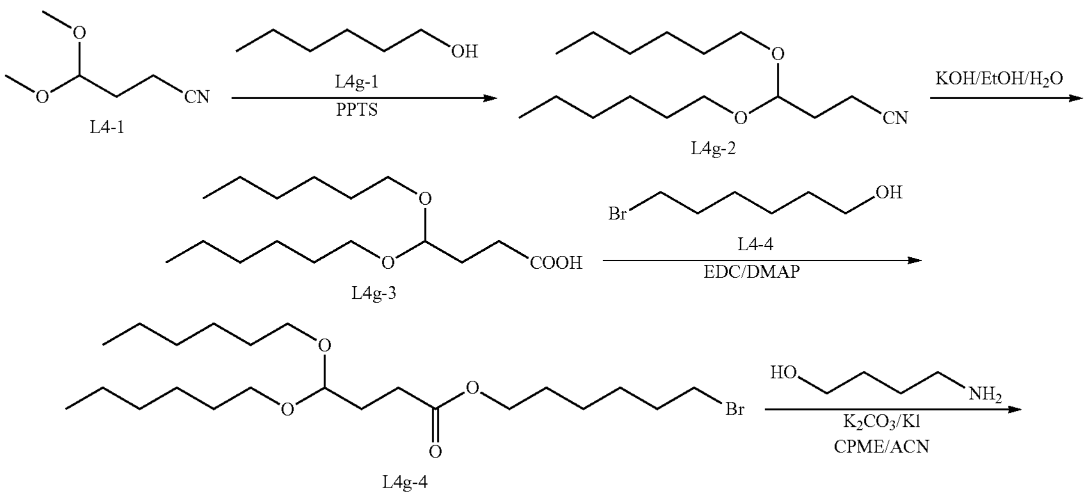

L4-1 L4g-2 L4g-3 L4g-4

-continued

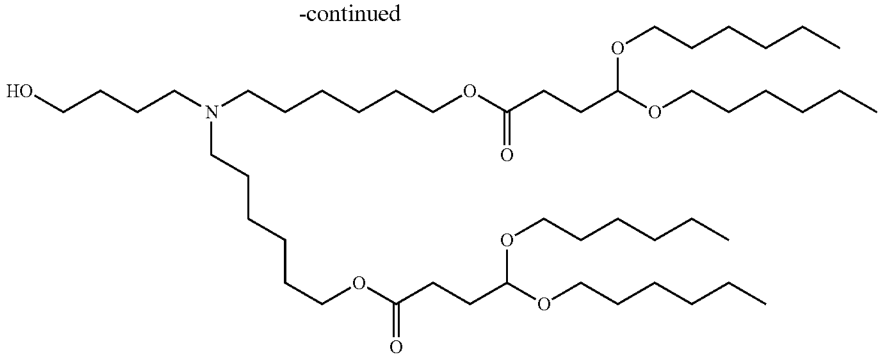

Compound 58

Synthesis of 4,4-bis(hexyloxy)butanenitrile (L4 g-2)

To a 250 mL round bottom flask L4-1 (10.0 g, 77.42 mmol) and L4 g-1 (30.11 g, 294.6 mmol) were added. To this was added Pyridinium p-toluenesulfonate (0.5 g, 1.989 mmol) and the reaction mixture was stirred at 125° C. for 26 h. After completion of the reaction the contents were loaded on to a 220 g flash silica column and was purified by flash chromatography ($SiO_2$: ethyl acetate/hexane 0-10%) to get Compound L4 g-2 (16.4 g, 79%) as slightly yellow oil. $^1H$ NMR (300 MHz, $CDCl_3$): δ ppm 4.54 (t, J=6.0 Hz, 1H), 3.63-3.55 (m, 2H), 3.46-3.38 (m, 2H), 2.43 (t, J=6.0 Hz, 2H), 1.95-1.92 (m, 2H), 1.56-1.32 (m, 4H), 1.32-1.29 (m, 12H), 0.87-0.85 (m, 6H); MS (CI): m/z $[M+H]^+$ 270.3.

Synthesis of 4,4-bis(hexyloxy)butanoic acid (L4 g-3)

To a 250 mL round bottom flask L4 g-2 (6.8 g, 25.24 mmol) and KOH (4.25 g, 75.71 mmol) were added. To this was added ethanol (50 mL) and water (50 mL) and the reaction mixture was refluxed at 110° C. for 18 h. After completion of the reaction the solvent was removed under vacuum. Residual paste was mixed with 100 g ice and acidified to pH 5 using 4M HCl. This mixture was partitioned in ethyl acetate and water. To this was added brine (100 mL). The ethyl acetate layer was separated. The product was extracted with ethyl acetate three times. The combined ethyl acetate layers were dried over anhydrous sodium sulphate. The ethyl acetate was removed under vacuum to give crude product. This crude was loaded on to a 220 g flash silica column and was purified by flash chromatography ($SiO_2$: ethyl acetate/hexane 0-10%) to get Compound L4 g-3 (6.9 g, 94%) as slightly yellow oil. $^1H$ NMR (300 MHz, $CDCl_3$): δ ppm 4.50 (t, J=6.0 Hz, 1H), 3.59-3.56 (m, 2H), 3.42-3.39 (m, 2H), 2.44-2.42 (m, 2H), 1.95-1.93 (m, 2H), 1.59-1.28 (m, 24H), 0.87-0.85 (m, 6H); MS (CI): m/z $[M+H]^+$ 289.4.

Synthesis of 6-bromohexyl 4,4-bis(hexyloxy)butanoate Compound (L4 g-4)

To a 250 mL round bottom flask L4 g-3 (3.0 g, 10.40 mmol), EDC (2.99 g, 15.60 mmol), DMAP (0.25 g, 2.08 mmol), and N, N-diisopropylethylamine (5.37 g, 41.65 mmol) were added in DCM (40 mL). To this was added 6-bromohexanol (2.45 g, 13.52 mmol) and the reaction mixture was stirred at room temperature for 3 days. After completion of the reaction the solvent was removed under vacuum. Residual paste was partitioned in ethyl acetate and water. It gave a milky emulsion. To this was added brine (100 mL). The milky emulsion was acidified to pH4 using 4M HCl. The ethyl acetate layer separated. The product was extracted with ethyl acetate three times. The combined ethyl acetate layers were washed with bicarbonate and dried over anhydrous sodium sulphate. The ethyl acetate was removed under vacuum and residue was loaded on to a 220 g flash silica column and was purified by flash chromatography ($SiO_2$: ethyl acetate/hexane 0-20%) to get Compound L4 g-4 (1.0 g, 22%) as slightly yellow oil. $^1H$ NMR (300 MHz, $CDCl_3$): δ ppm 4.50 (t, J=6.0 Hz, 1H), 4.05 (t, J=7.0 Hz, 2H), 3.58-3.35 (m, 6H), 2.37-2.34 (m, 2H), 1.93-1.90 (m, 2H), 1.59-1.28 (m, 24H), 0.87-0.85 (m, 6H); MS (CI): m/z $[M+H]^+$ 452.4.

Synthesis of ((4-hydroxybutyl) azanediyl)bis (hexane-6,1-diyl) bis(4,4-bis(hexyloxy) butanoate) (Compound 58)

To a 250 mL round bottom flask L4 g-4 (2.2 g, 4.87 mmol), 4-amino-1-butanol (0.195 g, 2.19 mmol), KI (1.213 g, 7.31 mmol) and potassium carbonate (2.02 g, 14.618 mmol) were added. To this was added anhydrous acetonitrile (10 mL) along with cyclopentylmethyl ether (CPME) (10 mL) and the reaction mixture was stirred under reflux at 90° C. for 36 h. After completion of the reaction about 40 g of Flash silica (this silica neutralized by stirring in 300 mL of 5% triethylamine in hexane for 10 min before use) was added and the contents were stirred well to get a uniform mixture. Solvent was removed from this mixture under vacuum. The residue was loaded on to an empty flash cartridge, which was then attached to flash purification system loaded with 80 g size prepacked flash silica column (The flash column was equilibrated with 10% triethylamine in hexane for 15 min at a flow rate of 80 mL per min before use) and was purified by flash chromatography ($SiO_2$: ethyl acetate/hexane 0-50%) to get Compound 58 (1.1 g, 28%). $^1H$ NMR (300 MHz, $CDCl_3$): δ ppm 4.50 (t, J=6.0 Hz, 2H), 4.05 (t, J=7.0 Hz, 4H), 3.58-3.34 (m, 10H), 2.42-2.34 (m, 10H), 1.95-1.88 (m, 4H), 1.64-1.28 (m, 54H), 0.89-0.85 (m, 12H); MS (CI): m/z $[M+H]^+$ 831.3. Analytical HPLC column: Agilent Zorbax SB-C18, 5 μm, 4.6×150 mmol, mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: ELSD, $t_R$=10.7 min, purity: >99%; UPLC column: Thermo Scientific Hypersil GOLD C4, mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: CAD, $t_R$=13.1 min, purity: >99%.

Synthesis of ((4-hydroxybutyl)azanediyl)bis (hexane-6,1-diyl) bis(4,4-bis(decyloxy) butanoate) (Compound 57)

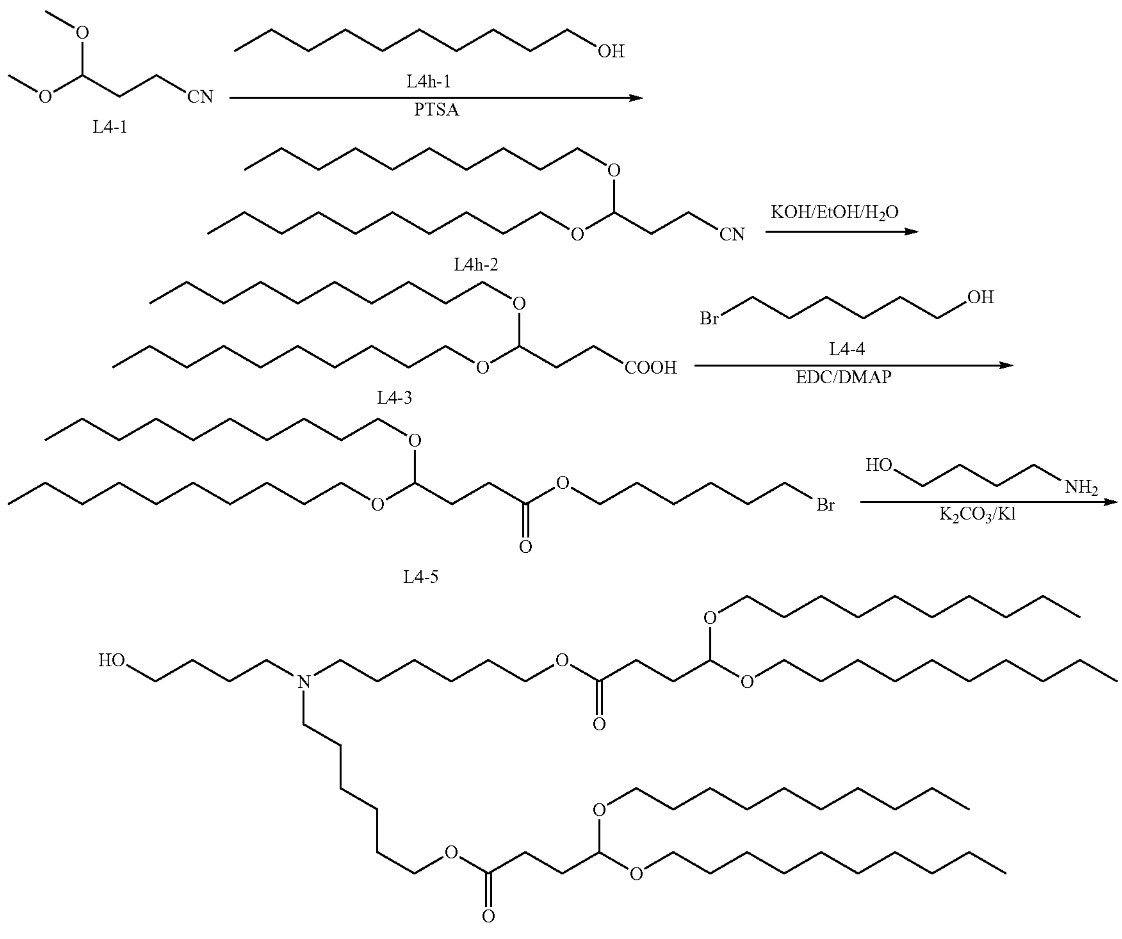

L4-1

L4h-2

L4-3

L4-5

Compound 57

Synthesis of 4,4-bis(decyloxy)butanenitrile (L4 h-2)

To a 100 mL round bottom flask L4-1 (5.0 g, 31.58 mmol) and L4 h-1 (15.05 g, 95.11 mmol) were added. To this was added Pyridinium p-toluenesulfonate (0.26 g, 1.015 mmol) and the reaction mixture was stirred at 125° C. for 26 h. After completion of the reaction the contents were loaded on to a 220 g flash silica column and purified by flash chromatography ($SiO_2$: ethyl acetate/hexane 0-10%) to get Compound L4 h-2 (8.96 g, 61%) as slightly yellow oil. $^1H$ NMR (300 MHz, $CDCl_3$): δ ppm 4.54 (t, J=6.0 Hz, 1H), 3.63-3.55 (m, 2H), 3.46-3.38 (m, 2H), 2.43 (t, J=6.0 Hz, 2H), 1.95-1.92 (m, 2H), 1.56-1.32 (m, 4H), 1.32-1.29 (m, 28H), 0.87-0.85 (m, 6H); MS (CI): m/z $[M+H]^+$ 381.4.

Synthesis of 4,4-bis(decyloxy)butanoic acid (L4-3)

To a 500 mL round bottom flask L4 h-2 (8.9 g, 23.47 mmol) and KOH (3.95 g, 70.43 mmol) were added. To this was added Ethanol (50 mL) and Water (50 mL). The reaction mixture was refluxed at 110° C. for 18 h. After completion of the reaction the solvent was removed under vacuum. Residual paste was mixed with 100 g ice and acidified to pH 5 using 4M HCl. This mixture was partitioned in ethyl acetate: water. To this was added brine (100 mL). The ethyl acetate layer was separated. The product was extracted with ethyl acetate three times. The combined ethyl acetate layers were dried over anhydrous sodium sulphate. The ethyl acetate was removed under vacuum to give crude product. This crude was loaded on to a 220 g flash silica column and was purified by flash chromatography ($SiO_2$: ethyl acetate/hexane 0-10%) to get Compound L4-3 (6.8 g, 73%) as slightly yellow oil. $^1H$ NMR (300 MHz, $CDCl_3$): δ ppm 4.52 (t, J=6.0 Hz, 1H), 3.59-3.53 (m, 2H), 3.42-3.38 (m, 2H), 2.46-2.42 (m, 2H), 1.95-1.93 (m, 2H), 1.59-1.28 (m, 28H), 0.89-0.84 (m, 6H); MS (CI): m/z $[M+H]^+$ 401.3.

Synthesis of 6-bromohexyl 4,4-bis(decyloxy)butanoate (L4-5)

To a 250 mL round bottom flask L4-3 (2.0 g, 4.992 mmol), EDC (3.83 g, 19.96 mmol), DMAP (0.61 g, 5.0 mmol) were added. To this was added 6-bromohexanol (1.81 g, 9.98 mmol) along with dichloromethane (80 mL) and the reaction mixture was stirred at room temperature for 2 h. After completion of the reaction about 40 g of Flash silica was added and the contents were stirred well to get a uniform mixture. Solvent was removed from this mixture under vacuum. The residue was loaded on to an empty flash cartridge, which was then attached to a flash purification system loaded with 80 g flash silica column and was purified by flash chromatography ($SiO_2$: ethyl acetate/hexane 0-10%) to get Compound L4-5 (2.18 g, 78%) as slightly yellow oil. $^1H$ NMR (300 MHz, $CDCl_3$): δ ppm 4.49 (t, J=6.0 Hz, 1H), 4.07 (t, J=6.0 Hz, 2H), 3.57-3.53 (m, 2H), 3.40-3.37 (m, 2H), 2.37 (t, J=7.0 Hz, 2H), 1.93-1.83 (m, 4H), 1.56-1.24 (m, 38H), 0.89-0.84 (m, 6H); MS (CI): m/z $[M+H]^+$ 563.7.

Synthesis of ((4-hydroxybutyl)azanediyl)bis (hexane-6,1-diyl) bis(4,4-bis(decyloxy) butanoate) (Compound 57)

To a 250 mL round bottom flask L4-5 (2.1 g, 3.725 mmol), 4-amino-1-butanol (0.149 g, 1.676 mmol), KI (0.93 g, 5.588 mmol) and potassium carbonate (1.54 g, 11.176 mmol) were added. To this was added anhydrous acetonitrile (15 mL) along with cyclopentylmethyl ether (CPME) (15 mL) and the reaction mixture was stirred under reflux at 90° C. for 36 h. After completion of the reaction about 40 g of Flash silica (this silica neutralized by stirring in 5% triethylamine in hexane (300 mL) for 10 min before use) was added and the contents were stirred well to get a uniform mixture. Solvent was removed from this mixture under vacuum. The residue was loaded on to an empty flash cartridge, which was then attached to flash purification system loaded with 80 g size prepacked flash silica column (The flash column was equilibrated with 10% triethylamine in hexane for 15 min at a flow rate of 80 mL per min before use) and was purified by flash chromatography ($SiO_2$: ethyl acetate/hexane 0-30%) to get Compound 57 (1.1 g, 28%). $^1H$ NMR (300 MHz, $CDCl_3$): δ ppm 4.48 (t, J=6.0 Hz, 2H), 4.05 (t, J=7.0 Hz, 4H), 3.58-3.36 (m, 10H), 2.44-2.34 (m, 10H), 1.92-1.90 (m, 2H), 1.64-1.20 (m, 86H), 0.89-0.84 (m, 12H); MS (CI): m/z $[M+H]^+$ 1054.7. Analytical HPLC column: Agilent Zorbax SB-C18, 5 μm, 4.6×150 mmol, mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: ELSD, $t_R$=10.7 min, purity: >99%; UPLC column: Thermo Scientific Hypersil GOLD C4, mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: CAD, $t_R$=13.1 min, purity: >99%.

Synthesis of ((4-hydroxybutyl)azanediyl)bis (hexane-6,1-diyl) bis(6,6-bis(hexyloxy) hexanoate) (Compound 59)

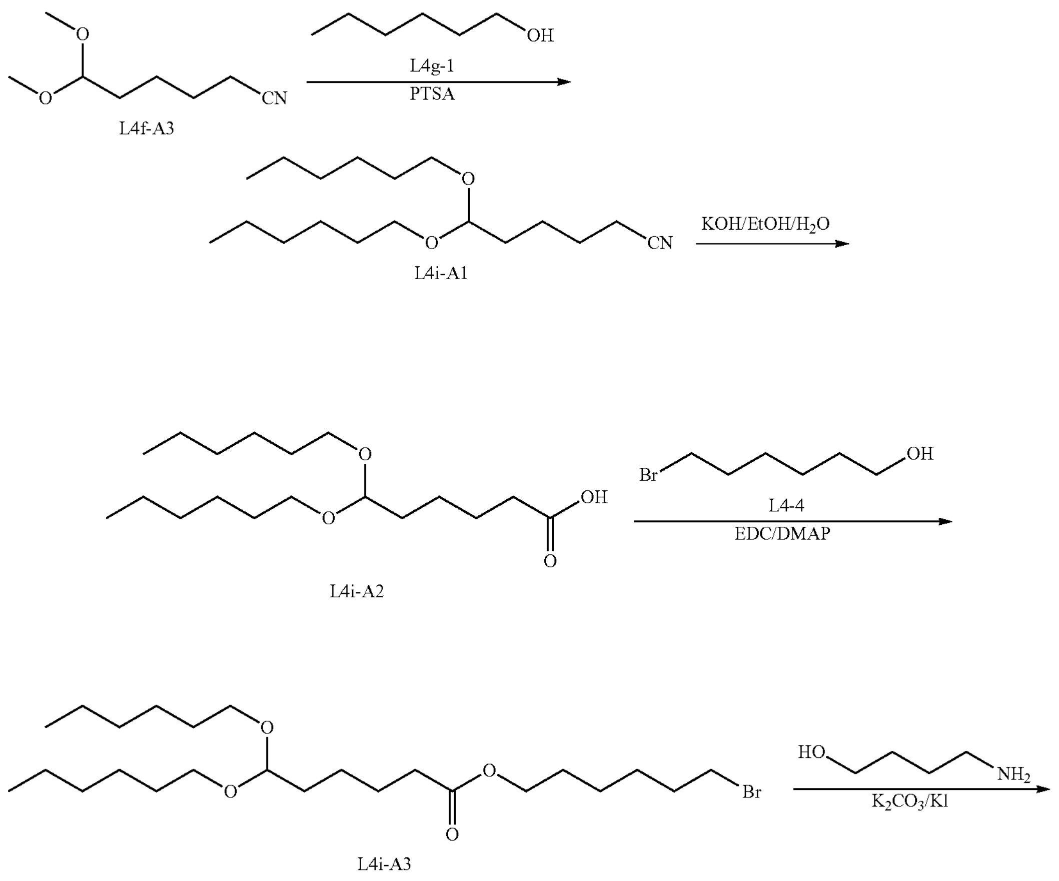

-continued

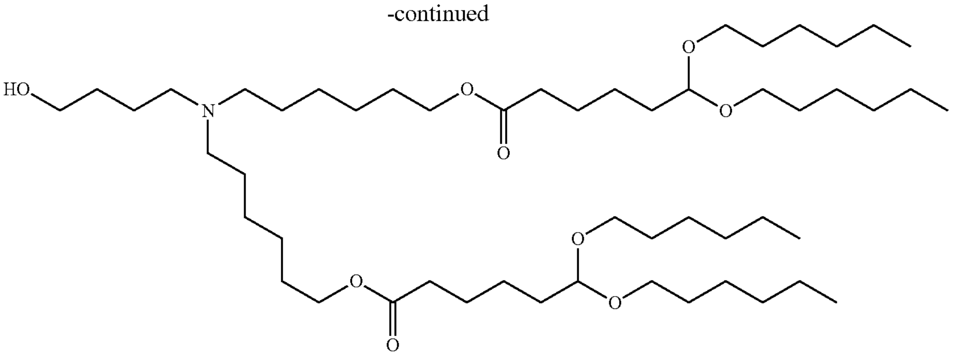

Compound 59

Synthesis of 6,6-bis(hexyloxy)hexanenitrile (L4i-A1)

To a 100 mL round bottom flask L4f-A3 (2.0 g, 12.72 mmol) and 1-hexanol (7.798 g, 76.33 mmol) were added. To this was added Pyridinium p-toluene sulfonate (480 mg, 1.91 mmol) and the reaction mixture was stirred at 120° C. for 2 h. After completion of the reaction the contents were loaded on to a 120 g flash silica column and was purified by flash chromatography ($SiO_2$: ethyl acetate/hexane 0-20%) to get Compound L4i-A1 (2.45 g, 65%) as slightly yellow oil. $^1H$ NMR (300 MHz, $CDCl_3$): δ ppm 4.45 (t, J=6.0 Hz, 1H), 3.57-3.53 (m, 2H), 3.42-3.37 (m, 2H), 2.33 (t, J=7.0 Hz, 2H), 1.62-1.50 (m, 6H), 1.41-1.16 (m, 16H), 0.89-0.84 (m, 6H); MS (CI): m/z $[M+H]^+$ 298.5.

Synthesis of 6,6-bis(hexyloxy)hexanoic acid (L4i-A2)

To a 250 mL round bottom flask L4i-A1 (2.45 g, 8.24 mmol) and KOH (1.386 g, 24.70 mmol) were added. To this was added mixture of 1:1 Ethanol: Water (80 mL) and the reaction mixture was refluxed at 110° C. for 30 h. After completion of the reaction the solvent was removed under vacuum. Residual paste was mixed with 100 g ice and acidified to pH 5 using 1M HCl. This mixture was partitioned in ethyl acetate: water. To this was added brine (100 mL). This mixture was filtered to remove any emulsion formed. The ethyl acetate layer separated well after filtration. The product was extracted with ethyl acetate three times. The combined ethyl acetate layers were dried over anhydrous sodium sulphate. The ethyl acetate was removed under vacuum to give L4i-A2 (2.07 g, 79%). as slightly yellow oil. $^1H$ NMR (300 MHz, $CDCl_3$): δ ppm 4.45 (t, J=7.0 Hz, 1H), 3.56-3.50 (m, 2H), 3.42-3.37 (m, 2H), 2.33 (t, J=7.0 Hz, 2H), 1.69-1.20 (m, 22H), 0.89-0.84 (m, 6H); MS (CI): m/z $[M+H]^+$ 316.4.

Synthesis of 6-bromohexyl 6,6-bis(hexyloxy)hexanoate (L4i-A3)

To a 250 mL round bottom flask L4i-A2 (2.07 g, 6.54 mmol), EDC (5.015 g, 26.16 mmol), DMAP (0.799 g, 6.54 mmol) were added. To this was added 6-bromohexanol (2.368 g, 13.08 mmol) along with dichloromethane (60 mL) and the reaction mixture was stirred at room temperature for 120 min. The reaction was monitored by TLC and using PMA staining. After completion of the reaction about 30 g of flash silica was added and the contents were stirred well to get a uniform mixture. Solvent was removed from this mixture under vacuum. The residue was loaded on to an empty flash cartridge, which was then attached to flash purification system loaded with 80 g flash silica column and was purified by flash chromatography ($SiO_2$: ethyl acetate/hexane 0-20%) to get Compound L4i-A3 (2.35 g, 75%) as slightly yellow oil. $^1H$ NMR (300 MHz, $CDCl_3$): δ ppm 4.44 (t, J=6.0 Hz, 1H), 4.05 (t, J=6.0 Hz, 2H), 3.56-3.52 (m, 2H), 3.42-3.36 (m, 4H), 2.29 (t, J=7.0 Hz, 2H), 1.88-1.80 (m, 4H), 1.62-1.27 (m, 28H), 0.89-0.85 (m, 6H); MS (CI): m/z $[M+H]^+$ 479.5.

Synthesis of ((4-hydroxybutyl)azanediyl)bis(hexane-6,1-diyl) bis(6,6-bis(hexyloxy) hexanoate) (Compound 59)

To a 40 mL microwave reactor tube L4f-A3 (2.3 g, 4.29 mmol), 4-amino-1-butanol (172.2 mg, 1.93 mmol), potassium carbonate (1.78 g, 12.88 mmol) and potassium iodide (1.07 g, 6.44 mmol) were added. To this was added a mixture of CPME and ACN (1:1, 5 mL) and the reaction mixture was sealed with cap and heated in CEM microwave reactor at 100° C. for 6 h. After completion of the reaction, the contents were transferred to a 500 mL round bottom flask containing about 40 g of Flash silica (this silica was stirred in of 10% triethylamine in hexane (300 mL) for 10 min before use) was added and the contents were stirred well to get a uniform mixture. Solvent was removed from this mixture under vacuum. The residue was loaded on to an empty flash cartridge, which was then attached to flash purification system loaded with 80 g size prepacked flash silica column (the flash column was equilibrated with 10% triethylamine in hexane for 15 min at a flow rate of 80 mL per min before use) and was purified by flash chromatography ($SiO_2$: ethyl acetate/hexane 0-50%) to get Compound 59 (1.1 g, 29%). $^1H$ NMR (300 MHz, $CDCl_3$): δ ppm 6.67 (bs, 1H), 4.44 (t, J=6.0 Hz, 2H), 4.03 (t, J=7.0 Hz, 4H), 3.56-3.36 (m, 10H), 2.44-2.28 (m, 10H), 1.63-1.28 (m, 64H), 0.89-0.84 (m, 12H); MS (CI): m/z $[M+H]^+$ 886.4. Analytical HPLC column: Agilent Zorbax SB-C18, 5 μm, 4.6×150 mmol, mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: ELSD, $t_R$=10.7 min, purity: >96.11%; UPLC column: Thermo Scientific Hypersil GOLD C4, mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: CAD, $t_R$=13.1 min, purity: >99%.

Synthesis of ((4-hydroxybutyl)azanediyl)bis(octane-8,1-diyl) bis(4,4-bis(hexyloxy) butanoate) (Compound 53)

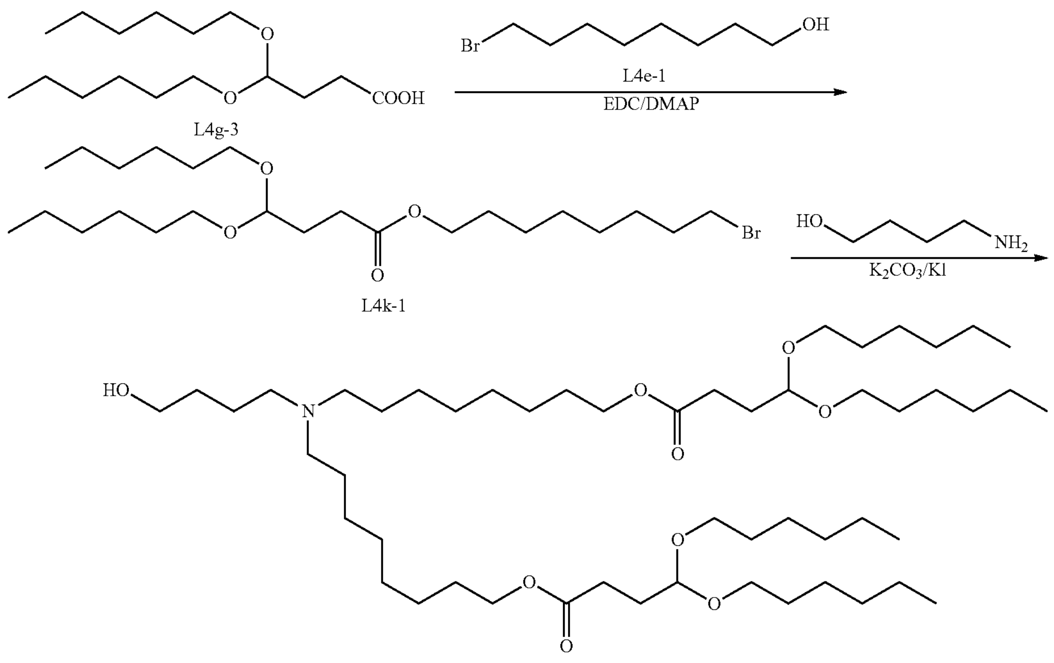

L4g-3

L4k-1

Compound 53

Synthesis of 8-bromooctyl 4,4-bis(hexyloxy)butanoate (L4k-1)

To a 250 mL round bottom flask L4 g-3 (1.6 g, 5.547 mmol), EDC (4.25 g, 22.189 mmol), DMAP (0.68 g, 5.547 mmol) were added. To this was added 6-bromooctanol (2.32 g, 11.095 mmol) along with dichloromethane (80 mL) and the reaction mixture was stirred at room temperature for 120 min. After completion of the reaction about 40 g of flash silica was added and the contents were stirred well to get a uniform mixture. Solvent was removed from this mixture under vacuum. The residue was loaded on to an empty flash cartridge, which was then attached to flash purification system loaded with 80 g flash silica column and was purified by flash chromatography ($SiO_2$: ethyl acetate/hexane 0-10%) to get Compound L4k-1 (2.0 g, 75%) as slightly yellow oil. $^1H$ NMR (300 MHz, $CDCl_3$): δ ppm 4.49 (t, J=6.0 Hz, 1H), 4.05 (t, J=6.0 Hz, 2H), 3.55-3.54 (m, 2H), 3.40-3.37 (m, 4H), 2.37 (t, J=7.0 Hz, 2H), 1.93-1.84 (m, 4H), 1.57-1.24 (m, 28H), 0.89-0.87 (m, 6H); MS (CI): m/z $[M+H]^+$ 479.5.

Synthesis of ((4-hydroxybutyl)azanediyl)bis(octane-8,1-diyl) bis(4,4-bis(hexyloxy) butanoate) (Compound 53)

To a 250 mL round bottom flask L4k-1 (2.0 g, 4.17 mmol), 4-amino-1-butanol (0.167 g, 1.87 mmol), KI (1.04 g, 6.25 mmol) and potassium carbonate (1.73 g, 12.51 mmol) were added. To this was added anhydrous ACN (10 mL) along with cyclopentylmethyl ether (CPME) (10 mL) and the reaction mixture was stirred under reflux at 90° C. for 36 h. After completion of the reaction about 40 g of Flash silica (this silica was stirred in of 5% triethylamine in hexane (300 mL) for 10 min before use) was added and the contents were stirred well to get a uniform mixture. Solvent was removed from this mixture under vacuum. The residue was loaded on to an empty flash cartridge, which was then attached to flash purification system loaded with 80 g size prepacked flash silica column (the flash column was equilibrated with 10% triethylamine in hexane for 15 min at a flow rate of 80 mL per min before use) and was purified by flash chromatography ($SiO_2$: ethyl acetate/hexane 0-50%) to get Compound 53 (1.0 g, 27%). $^1H$ NMR (300 MHz, $CDCl_3$): δ ppm 4.48 (t, J=6.0 Hz, 2H), 4.03 (t, J=7.0 Hz, 4H), 3.58-3.37 (m, 10H), 2.44-2.34 (m, 10H), 1.95-1.88 (m, 4H), 1.64-1.20 (m, 60H), 0.89-0.85 (m, 12H); MS (CI): m/z $[M+H]^+$ 886.3. Analytical HPLC column: Agilent Zorbax SB-C18, 5 μm, 4.6×150 mmol, mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: ELSD, $t_R$=10.7 min, purity: >99%; UPLC column: Thermo Scientific Hypersil GOLD C4, mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: CAD, $t_R$=13.1 min, purity: >99%.

Synthesis of 4-(bis(7-((dioctylamino)oxy)-7-oxo-heptyl)amino)butan-1-ol (Compound 19)

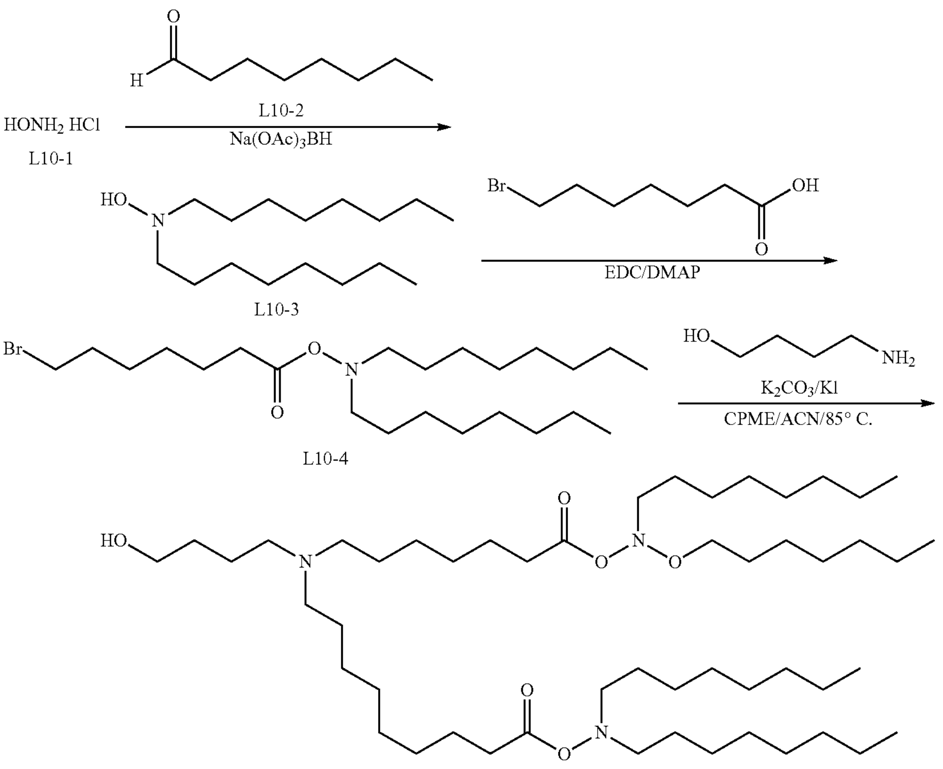

L10-1

L10-3

L10-4

Compound 19

Synthesis of N,N-dioctylhydroxylamine (L10-3)

A mixture of hydroxylamine hydrochloride L10-1 (1.75 g, 25 mmol), 1-octanal L10-2 (6.4 g, 50 mmol) and $Et_3N$ (3.5 mL, 25 mmol) in dichloroethane (75 mL) was stirred at room temperature under nitrogen atmosphere to form a clear solution. $NaBH(OAc)_3$ (15.5 g, 75 mmol) was added in portions and the resulting mixture was stirred for 20 h at room temperature. Sat. aq. sodium bicarbonate solution was slowly added to the reaction mixture until no bubbles were produced. The resulting phases were separated. The aqueous phase was extracted again with DCM (150 mL). Combined organic extracts were dried over anhydrous $Na_2SO_4$. Filtration and concentration provided crude material which was purified by flash column chromatography ($SiO_2$: 0 to 100% EtOAc/Hexanes) to yield L10-3 (2.9 g, 53%) as white solid; $^1$H-NMR (300 MHz, $CDCl_3$) δ 6.31 (s, bs, 1H), 2.63 (t, J=4.7 Hz, 4H), 1.70-1.49 (m, 4H), 1.43-1.15 (m, 20H), 0.87 (t, J=6.6 Hz, 6H). CIMS m/z $[M+H]^+$ 258.2.

Synthesis of O-(7-bromoheptanoyl)-N, N-dioctylhydroxylamine (L10-4)

To a solution of L10-3 (2.8 g, 11 mmol) in DCM (70 mL) was added 7-bromoheptanoic acid (2.8 g, 13 mmol) followed by DIPEA (4 mL, 22 mmol), DMAP (1.4 g, 11 mmol) and EDC (4.3 g, 22 mmol). The resulting mixture was stirred at room temperature under nitrogen atmosphere for 22 h. The reaction mixture was diluted with DCM (70 mL) and washed with saturated $NaHCO_3$ aqueous solution (50 mL), water (50 mL) and brine (50 mL). The organic phase was dried over anhydrous $Na_2SO_4$. Filtration and concentration provided crude material which was purified by flash column chromatography ($SiO_2$: 0 to 100% ethyl acetate in hexane gradient) to yield L10-4 as colorless oil (1.9 g, 38%). $^1$H-NMR (300 MHz, $CDCl_3$) δ 3.40 (t, J=7.0 Hz, 2H), 2.79 (t, J=7.7 Hz, 4H), 2.28 (t, J=7.7 Hz, 2H), 1.91-1.15 (m, 34H), 0.86 (t, J=6.9 Hz, 6H). CIMS m/z $[M+H]^+$ 448/450.

Synthesis of 4-(bis(7-((dioctylamino)oxy)-7-oxo-heptyl)amino)butan-1-ol (Compound 19)

A solution of L10-4 (650 mg, 1.4 mmol), 4-amino-1-butanol (56 mg, 0.6 mmol) in cyclopentyl methyl ether (1.5 mL) and acetonitrile (1.5 mL) containing potassium carbonate (386 mg, 2.8 mmol) and potassium iodide (232 mg, 1.4 mmol) was heated at 85° C. for 48 hours. After cooling to room temperature, the reaction mixture was filtered through Celite, washed with ethyl acetate, and then the solvent was removed under vacuum to give the crude product which was purified by flash chromatography ($SiO_2$: ethyl acetate/hexane 0-100% with 1% triethylamine in the eluent) to get Compound 19 (93 mg, 18%) as slightly yellow oil. $^1$H NMR (300 MHz, $CDCl_3$): δ ppm 3.54 (m, 2H), 2.78 (t, J=7.7 Hz, 8H), 2.42 (m, 6H), 2.27 (t, J=7.7 Hz, 4H), 1.70-1.16 (m, 68H), 0.86 (t, J=7.1 Hz, 12H); MS (CI): m/z $[M+H]^+$ 824; Analytical HPLC column: Agilent Zorbax SB-C18, 5 μm, 4.6×150 mm, mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: ELSD, $t_R$=11.1 min, purity: >99%; UPLC column: Thermo Scientific Hypersil GOLD C4, mobile phase A: acetonitrile with 0.1% trifluoroacetic acid, mobile phase B: water with 0.1% trifluoroacetic acid, use gradient: A in B 60% to 100% in 15 min, flow rate: 0.5 mL/min, column temperature: 20±2° C., detector: CAD, $t_R$=11.6 min, purity: 97.26%.

Synthesis of undecyl 6-((8-((dioctylamino)oxy)-8-oxooctyl)(2-hydroxyethyl)amino) hexanoate (Compound 21)

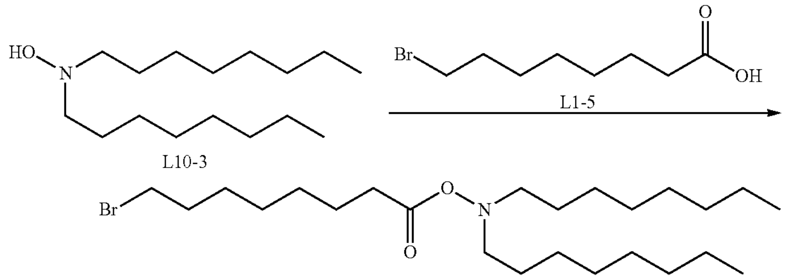

L10-3

L11-1

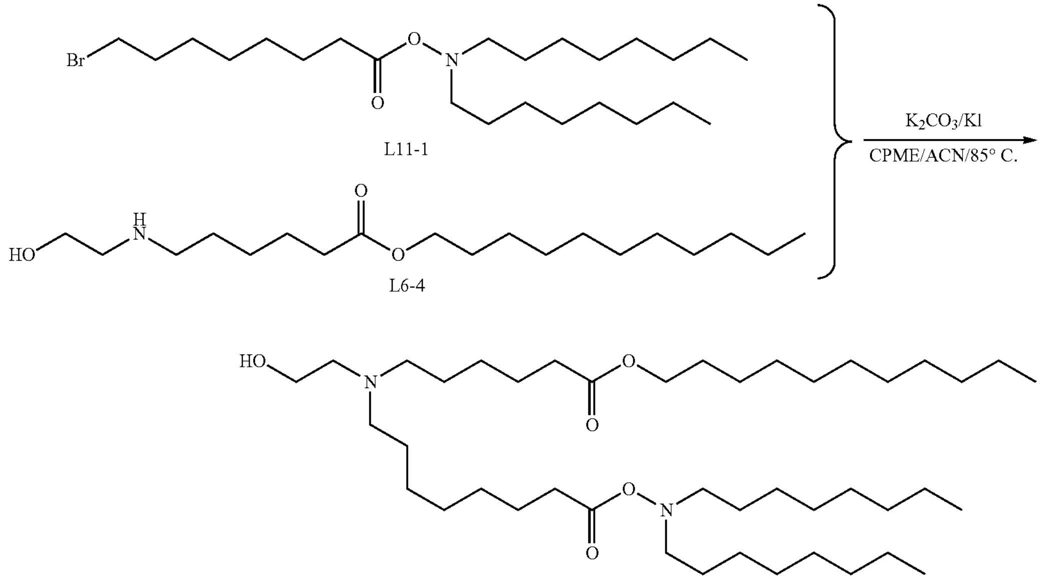

L11-1

L6-4

Compound 21

Synthesis of O-(8-bromooctanoyl)-N,N-dioctylhydroxylamine (L11-1)

To a solution of L10-3 (0.5 g, 1.9 mmol) in DCM (12 mL) was added 7-bromooctanoic acid (0.52 g, 2.3 mmol) followed by DIPEA (0.7 mL, 3.8 mmol), DMAP (0.25 g, 1.9 mmol) and EDC (0.78 g, 3.8 mmol). The resulting mixture was stirred at room temperature under nitrogen atmosphere for 22 h. The reaction mixture was diluted with DCM (10 mL) and washed with saturated $NaHCO_3$ aqueous solution (10 mL), water (10 mL) and brine (10 mL). The organic phase was dried over anhydrous $Na_2SO_4$. Filtration and concentration provided crude material which was purified by flash column chromatography ($SiO_2$: 0 to 100% ethyl acetate in hexane gradient) to yield L11-1 as colorless oil (0.4 g, 38%). $^1$H-NMR (300 MHz, $CDCl_3$) δ 3.39 (t, J=6.5 Hz, 2H), 2.79 (t, J=7.4 Hz, 4H), 2.28 (t, J=7.7 Hz, 2H), 1.90-1.15 (m, 36H), 0.86 (t, J=6.9 Hz, 6H). CIMS m/z $[M+H]^+$ 462/464.

Synthesis of undecyl 6-((8-((dioctylamino)oxy)-8-oxooctyl)(2-hydroxyethyl)amino) hexanoate (Compound 21)

A solution of L11-1 (460 mg, 0.86 mmol), L6-4 (234 mg, 0.72 mmol) in cyclopentyl methyl ether (5 mL) and acetonitrile (5 mL) containing potassium carbonate (300 mg, 2.2 mmol) and potassium iodide (143 mg, 0.86 mmol) was heated at 85° C. for 48 hours. After cooling to room temperature, the reaction mixture was filtered through Celite, washed with ethyl acetate, and then the solvent was removed under vacuum to give the crude product which was purified by flash chromatography ($SiO_2$: ethyl acetate/hexane 0-100% with 1% triethylamine in the eluent) to get Compound 21 (132 mg, 26%) as slightly yellow oil. $^1$H NMR (300 MHz, $CDCl_3$): δ ppm 4.05 (t, J=6.6 Hz, 2H), 3.53 (m, 2H), 2.79 (t, J=7.1 Hz, 4H), 2.40 (m, 6H), 2.58 (s, bs, 2H), 2.45 (s, bs, 4H), 2.29 (t, J=7.4 Hz, 2H), 2.27 (t, J=7.7 Hz, 2H), 1.70-1.15 (m, 68H), 0.87 (t, J=6.8 Hz, 3H), 0.86 (t, J=6.9 Hz, 6H); MS (CI): m/z $[M+H]^+$ 711.6; Analytical HPLC column: Agilent Zorbax SB-C18, 5 μm, 4.6×150 mm, mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: ELSD, $t_R$=10.3 min, purity: >99%; UPLC column: Thermo Scientific Hypersil GOLD C4, mobile phase A: acetonitrile with 0.1% trifluoroacetic acid, mobile phase B: water with 0.1% trifluoroacetic acid, use gradient: A in B 5% to 95% in 15 min, flow rate: 1 mL/min, A in B 60% to 100% in 15 min, flow rate: 0.5 mL/min, column temperature: 20±2° C., detector: CAD, $t_R$=10.2 min, purity: 97.65%.

Synthesis of ((4-(3-methylthioureido)butyl) azanediyl)bis(hexane-6,1-diyl) bis(2-hexyldecanoate) (Compound 5)

for 3 h. The volatile components were removed under reduced pressure and to the residue was added 2.0 M methyl amine in methanol (1.96 mL, 3.92 mmol). The resulting mixture was stirred at room temperature for 16 h. Solvent was removed under vacuum and the crude was purified by flash column chromatography ($SiO_2$: 0 to 10% MeOH/DCM with 1% $NH_4OH$) to yield Compound 5 as sticky gum (158 mg, 48%). $^1$H-NMR (300 MHz, $CDCl_3$) δ. 4.05 (t, 4H), 3.65 (b, 2H), 3.04 (d, 3H), 2.90 (b, 4H), 2.34-2.24 (m, 2H), 1.98-1.48 (m, 20H), 1.48-1.15 (m, 52H), 0.87 (t, 12H); CIMS m/z $[M+H]^+$ 838.8. Analytical HPLC column: Agilent Zorbax SB-C18, 5 μm, 4.6×150 mm, mobile phase A: acetonitrile with 0.1% trifluoroacetic acid, mobile phase B: water with 0.1% trifluoroacetic acid, use gradient: A in B 5%

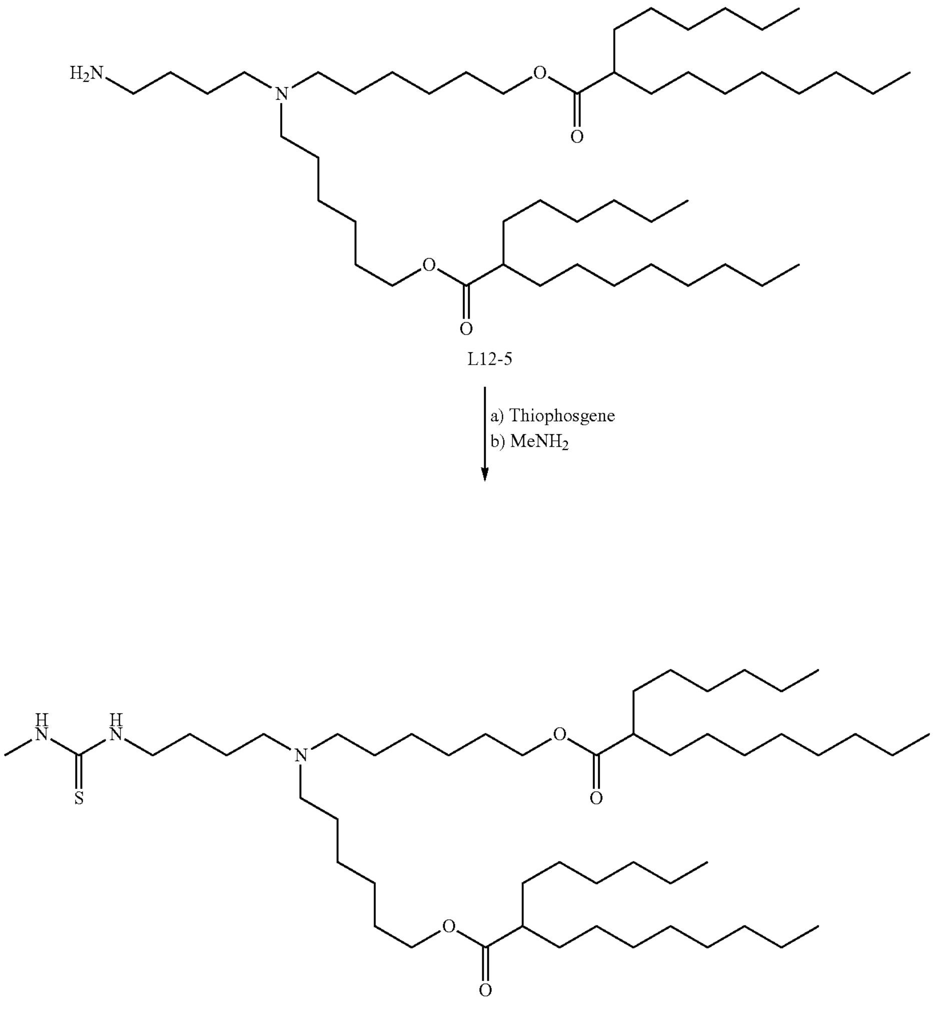

L12-5

Compound 5

Synthesis of ((4-(3-methylthioureido)butyl) azanediyl)bis(hexane-6,1-diyl) bis(2-hexyldecanoate) (Compound 5)

To a solution of L12-5 (300 mg, 0.392 mmol) in diethyl ether (30 mL) was added thiophosgene (136 mg, 1.176 mmol) at 0° C. under nitrogen atmosphere. The reaction mixture was then warmed to room temperature and stirred to 95% in 15 min, flow rate: 1 mL/min, column temperature: 20±2° C., detector: ELSD, $t_R$=11.27 min, purity: >99%; UPLC column: Thermo Scientific Hypersil GOLD C4, mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: CAD, $t_R$=13.83 min, purity: 92.71%.

Synthesis of ((2-((2-hydroxyethyl) (methyl)amino) ethyl)azanediyl)bis(hexane-6,1-diyl) bis(4,4-bis(octyloxy)butanoate) (Compound 61)

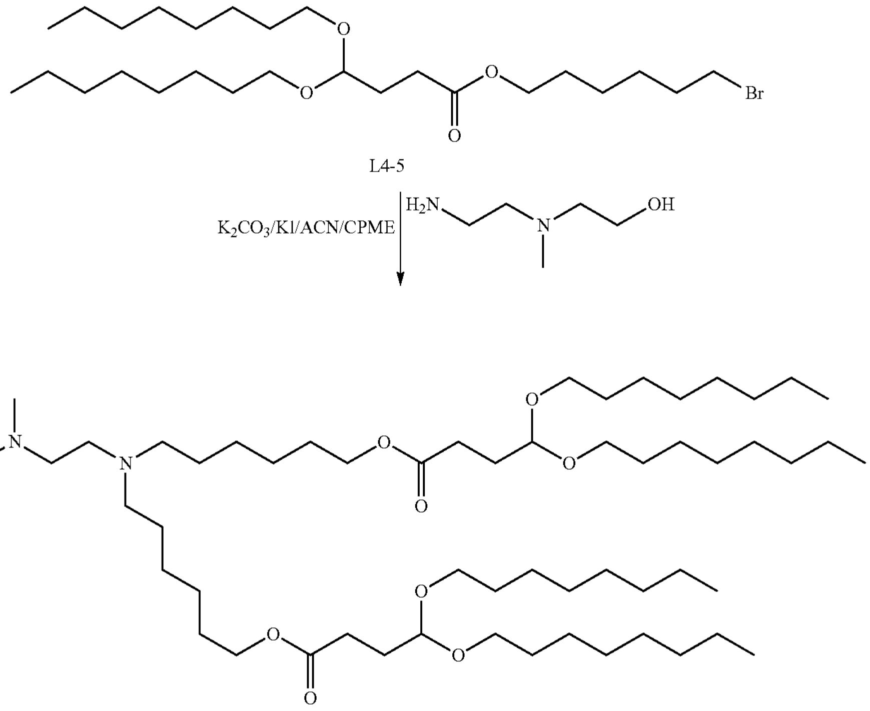

Compound 61

Synthesis of ((2-((2-hydroxyethyl) (methyl)amino) ethyl)azanediyl)bis(hexane-6,1-diyl) bis(4,4-bis(octyloxy)butanoate) (Compound 61)

To a solution of 6-bromohexyl 4,4-bis(octyloxy)butanoate L4-5 (2.13 g, 4.2 mmol) in acetonitrile (10 mL) and cyclopentylmethylether (10 mL) under nitrogen was added 2-((2-aminoethyl)-(methyl)amino)ethan-1-ol (224 mg, 1.9 mmol), $K_2CO_3$ (1.57 g, 11.4 mmol) and KI (315 mg, 1.9 mmol). The reaction mixture was heated at 80° C. overnight. After cooling to room temperature, the reaction mixture was filtered through Celite, and the filter cake was washed with ethyl acetate. The combined filtrates were concentrated to give crude product, which was purified by flash chromatography ($SiO_2$: 0 to 5% MeOH in DCM gradient) to yield Compound 61 as colorless oil (652 mg, 35%). $^1$H-NMR (300 MHz, $CDCl_3$) δ 4.48 (t, J=5.7, 2H), 4.04 (t, J=6.5, 4H), 3.56 (m, 6H), 3.38 (m, 4H), 2.6-2.8 (m, 6H), 2.37 (m, 7H), 1.9 (m, 4H), 1.52-1.6 (m, 16H), 1.26-1.35 (m, 52H), 0.87 (m, 12H); CIMS m/z $[M+H]^+$ 971.8; Analytical HPLC column: Agilent Zorbax SB-C18, 5 μm, 4.6×150 mm, mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: ELSD, $t_R$=8.45 min, purity: >99%; UPLC column: Thermo Scientific Hypersil GOLD C4, mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: CAD, $t_R$=11.19 min, purity: 98.46%.

Synthetic Scheme for Compound 77

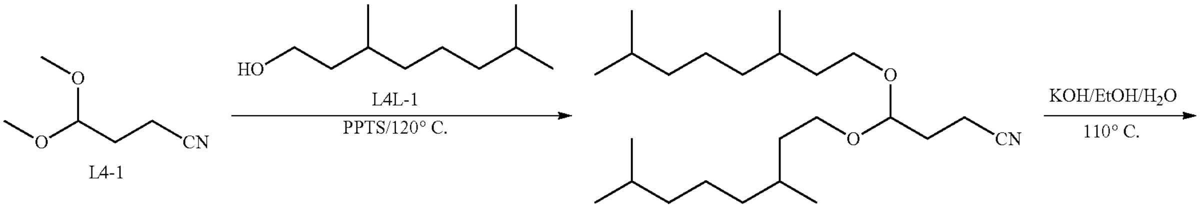

-continued

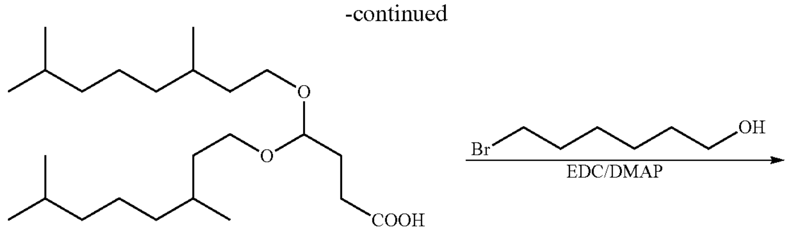

L4L-3

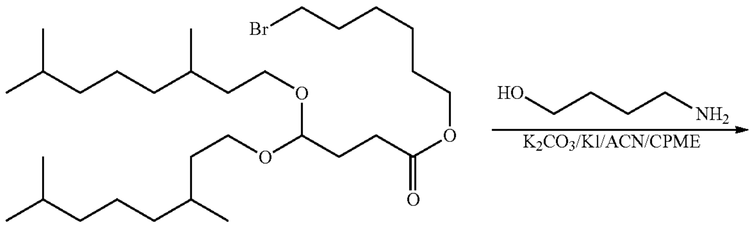

L4L-4

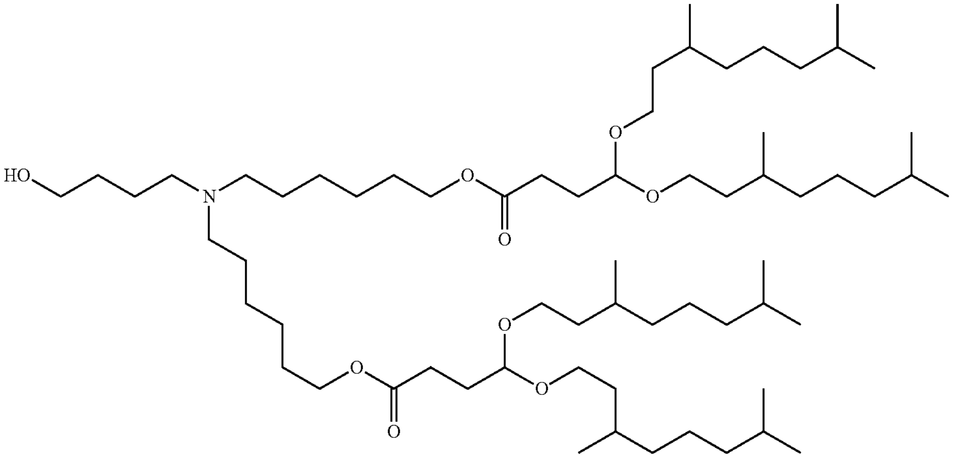

77

Synthesis of 4,4-bis(3,7-dimethyloctyl)oxy)butane nitrile (L4L-2) [Procedure A]

L4L-2

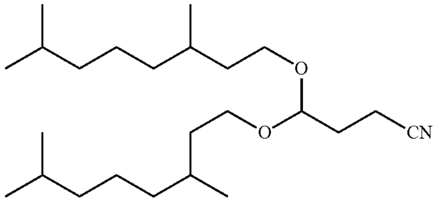

To a 100 mL round bottom flask, 4,4-dimethoxybutanenitrile (3.0 g, 23.2 mmol), alcohol (11.0 g, 69.7 mmol) and pyridinium p-toluenesulfonate (0.29 g 1.2 mmol) were added. The resulting mixture was stirred at 120° C. for 4 h and cooled to room temperature. EtOAc (50 mL) and $H_2O$ (20 mL) were added in, and the resulting phases were separated. The aqueous phase was extracted with EtOAc (50 mL). Combined organic extracts were washed with $H_2O$ (20 mL) and dried over anhydrous $MgSO_4$. Filtration and concentration provided crude material which was purified by flash column chromatography ($SiO_2$: 0 to 10% ethyl acetate in hexanes gradient) to yield L4L-2 as colorless oil (6.6 g, 74%); $^1$HNMR ($CDCl_3$) δ 4.50-4.53 (t, 1H), 3.58-3.60 (m, 2H), 3.41-3.49 (m, 2H), 2.39-2.44 (t, 2H), 1.92-1.94 (q, 2H), 1.50-1.55 (m, 6H), 1.38-1.42 (m, 2H), 1.11-1.14 (m, 14H) 0.88-0.84 (t, 18H); CIMS m/z $[M+H]^+$ 381.

Synthesis of 4,4-bis((3,7-dimethyloctyl) oxy) butanoic acid (L4L-3) [Procedure B]

L4L-3

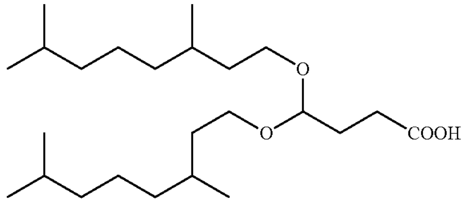

To a 100 mL round bottom flask containing a solution of L4L-2 (8.2 g, 21 mmol) in ethanol (50 mL) was added a solution of KOH (3.6 g, 64 mmol) in water (50 mL). The mixture was stirred at 120° C. for 20 h. The volatiles were removed, and the reaction pH was adjusted to 5. EtOAc (150 mL) and $H_2O$ (60 mL) were added, and the resulting phases were separated. The aqueous phase was extracted with EtOAc (50 mL). Combined organic extracts were washed with $H_2O$ (60 mL×2) and dried over anhydrous $MgSO_4$. Filtration and concentration provided L4L-3 (6.4 g, 74%) which was used for the next step without further purification. $^1$HNMR ($CDCl_3$) δ 4.54 (t, 1H), 3.60-3.65 (m, 2H), 3.45-3.49 (m, 2H), 2.39-2.44 (t, 2H), 1.92-1.94 (m, 2H), 1.50-1.95 (m, 6H), 1.26-1.55 (m, 8H), 1.11-1.14 (m, 6H). 0.84-0.88 (d, 18H); CIMS m/z $[M-H]^-$ 399.

Synthesis of 6-bromohexyl 4,4-bis((3,7-dimethyloctyl)oxy)butanoate (L4L-4) [Procedure C]

L4L-4

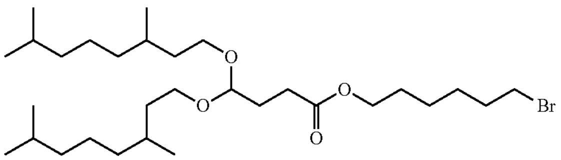

To an oven dried 100 mL round bottom flask containing a solution of acid L4L-3 (1.5 g, 3.8 mmol) in dichloromethane (10 mL) under nitrogen was added EDC (1.44 g, 7.6 mmol), DMAP (92 mg, 0.76 mmol). The mixture was stirred at room temperature for 15 min. The alcohol (0.61 g, 3.38 mmol) was then added and the reaction mixture was stirred for 20 h at room temperature. The reaction mixture was diluted with dichloromethane and water and the resulting phases were separated. The aqueous phase was extracted again with EtOAc (50 mL). Combined organic extracts were washed with $H_2O$ (60 mL×2) and dried over anhydrous $MgSO_4$. Filtration and concentration provided crude product which was purified by flash column chromatography ($SiO_2$: 0 to 10% ethyl acetate in hexanes gradient) to yield L4L-4 as colorless oil (1.1 g, 58%); $^1$H-NMR (300 MHz, $CDCl_3$) δ 4.49 (t, J=5.4 Hz, 1H), 4.05 (t, J=6.7 Hz, 2H), 3.70-3.33 (m, 6H), 2.36 (t, J=7.7 Hz, 2H), 1.99-1.77 (m, 2H), 1.70-1.00 (m, 28H), 0.87 (t, J=6.6 Hz, 18H).

Synthesis of ((4-hydroxybutyl)azanediyl)bis(hexane-6,1-diyl) bis(4,4-bis((3,7-dimethyloctyl)oxy)butanoate) (77) [Procedure D]

Compound 77

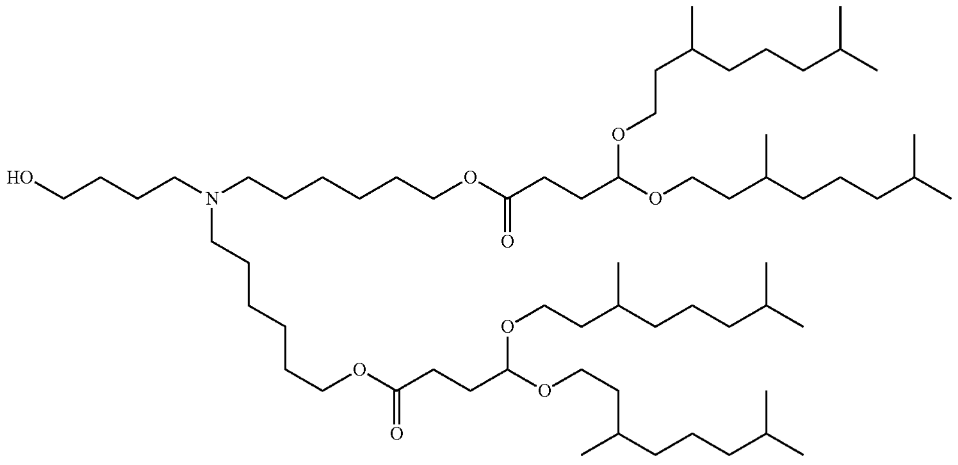

To a solution of compound L4L-4 (1.1 g, 1.9 mmol) in $CH_3CN$/CPME (1:1, 10 mL) under nitrogen was added 4-amino-1-butanol (79 mg, 0.88 mmol), followed by the addition of $K_2CO_3$ (0.37 g, 2.6 mmol) and KI (0.15 g, 0.88 mmol). The reaction mixture was heated at 80-90° C. for 18 h. After cooling to room temperature, the reaction mixture was filtered through Celite, washed with ethyl acetate, and the solvent was removed under vacuum to give the crude product which was purified by flash chromatography ($SiO_2$: DCM/MeOH 0-10%) to get final Compound 77 as slightly yellow oil (619 mg, 68%); $^1$H-NMR (300 MHz, $CDCl_3$) δ 4.48 (t, J=5.4 Hz, 2H), 4.04 (t, J=6.8 Hz, 4H), 3.70-3.35 (m, 10H), 2.51-2.32 (m, 10H), 1.96-1.87 (m, 4H), 1.72-1.03 (m, 60H), 0.91-0.83 (m, 36H); MS (CI): m/z $[M+H]^+$ 1054.9; Analytical HPLC column: Agilent Zorbax SB-C18, 5 m, 4.6×150 mm, mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: ELSD, $t_R$=8.8 min, purity: >99%; UPLC column: Waters Aquity UPLC® CSHTM, C18, 1.7 μm, 3.0×150 mm, (Part No. 186005302), mobile phase A: acetonitrile with 0.1% trifluoroacetic acid, mobile phase B: water with 0.1% trifluoroacetic acid, use gradient: A in B 60% to 100% in 15 min, flow rate: 0.5 mL/min, column temperature: 20±2° C., detector: CAD, $t_R$=15.4 min, purity: >99%.

Synthetic Scheme for Compound 78
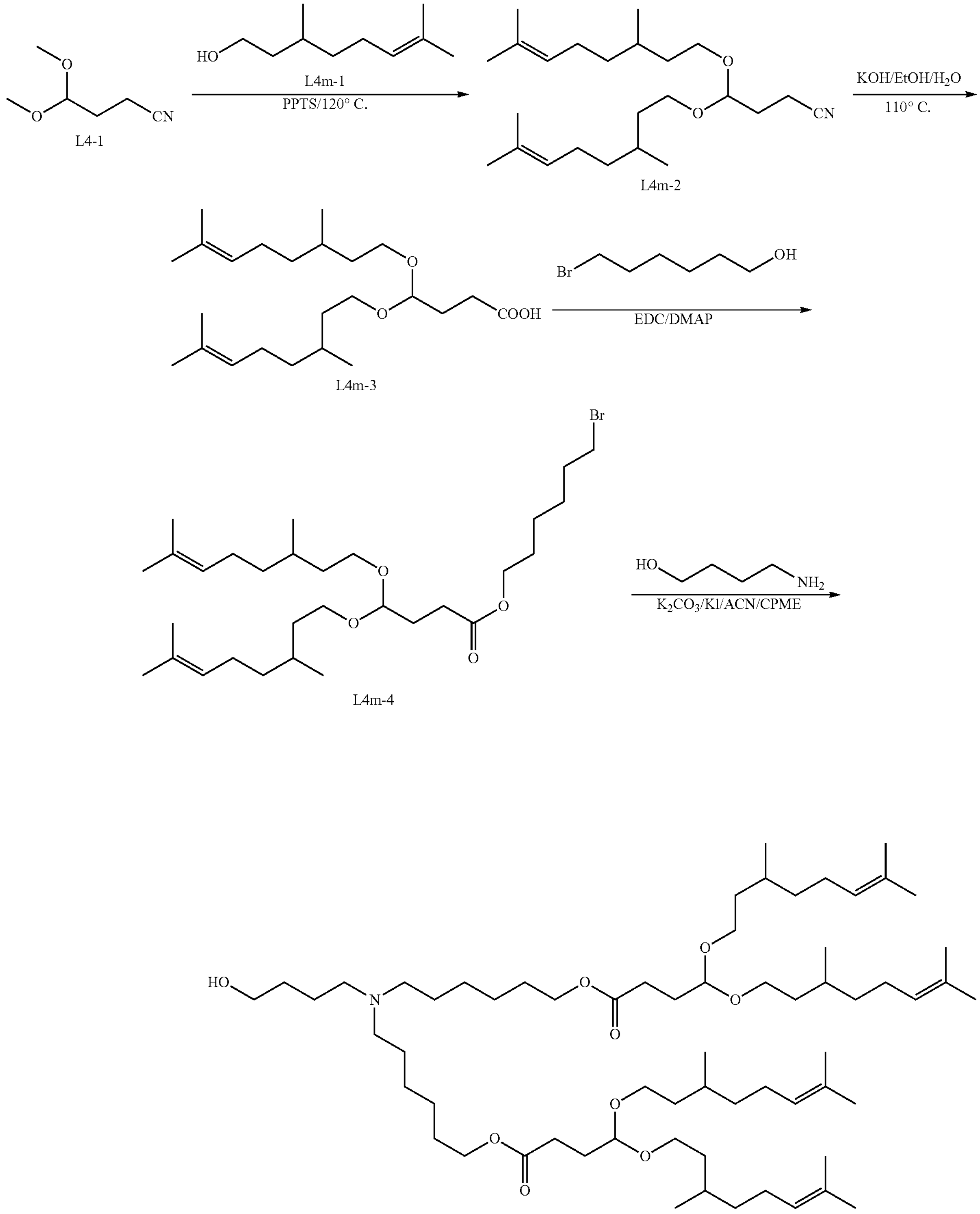
Compound 78

Synthesis of 4,4-bis((3,7-dimethyloct-6-en-1-yl)oxy) butanenitrile (L4m-2)

L4m-2

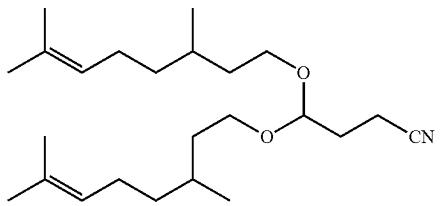

Prepared following Procedure A described in Compound 77 synthesis. Compound L4m-2 was isolated as colorless oil (6.2 g, 73%). $^1$H-NMR (300 MHz, $CDCl_3$) δ 5.08 (t, J=7.2 Hz, 2H), 4.54 (t, J=5.3 Hz, 1H), 3.72-3.36 (m, 4H), 2.41 (t, J=7.3 Hz, 2H), 2.10-1.84 (m, 6H), 1.80-1.05 (m, 22H), 0.89 (d, J=6.6 Hz, 6H).

Synthesis of 4,4-bis((3,7-dimethyloct-6-en-1-yl)oxy) butanoic acid (L4m-3)

L4m-3

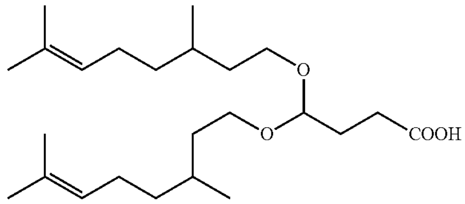

Prepared following Procedure B described in Compound 77 synthesis. Compound L4m-3 was isolated as colorless oil (6.2 g, 73%). $^1$H-NMR (300 MHz, $CDCl_3$) δ: 5.08 (t, J=6.84 Hz, 2H), 4.5 (t, J=5.22 Hz, 1H), 3.59 (m, 2H), 3.44 (m, 2H), 2.44 (t, J=7.44 Hz, 2H), 1.94 (m, 6H), 1.54-1.67 (m, 16H), 1.35 (m, 4H), 1.13 (m, 2H), 0.87 (d, J=6.33 Hz, 6H); CIMS m/z $[M+H]^+$ 396.2.

Synthesis of 6-bromohexyl 4,4-bis((3,7-dimethyl-oct-6-en-1-yl)oxy)butanoate (L4m-4)

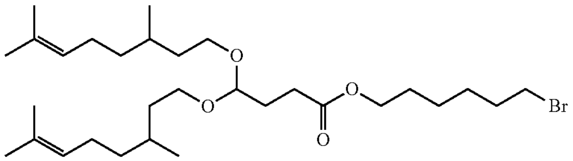 [SMILES: CC(C)=CCCC(C)CCOC(CCC(=O)OCCCCCCBr)OCCC(C)CCC=C(C)C]

Prepared following Procedure C described in Compound 77 synthesis. Compound L4m-4 was isolated as colorless oil (880 mg, 88%). $^1$H-NMR (300 MHz, $CDCl_3$) δ: 5.08 (t, J=7.14 Hz, 2H), 4.48 (t, J=5.49 Hz, 1H), 4.06 (t, J=6.57 Hz, 2H), 3.57 (m, 2H), 3.43 (m, 2H), 3.4 (t, J=6.87 Hz, 2H), 2.37 (t, J=7.41 Hz, 2H) 1.93 (m, 8H), 1.55-1.67 (m, 16H), 1.36 (m, 10H), 1.15 (m, 2H), 0.87 (d, J=6.33 Hz, 6H).

Synthesis of ((4-hydroxybutyl)azanediyl)bis (hexane-6,1-diyl) bis(4,4-bis((3,7-dimethyloct-6-en-1-yl)oxy)butanoate) (78)

Compound 78

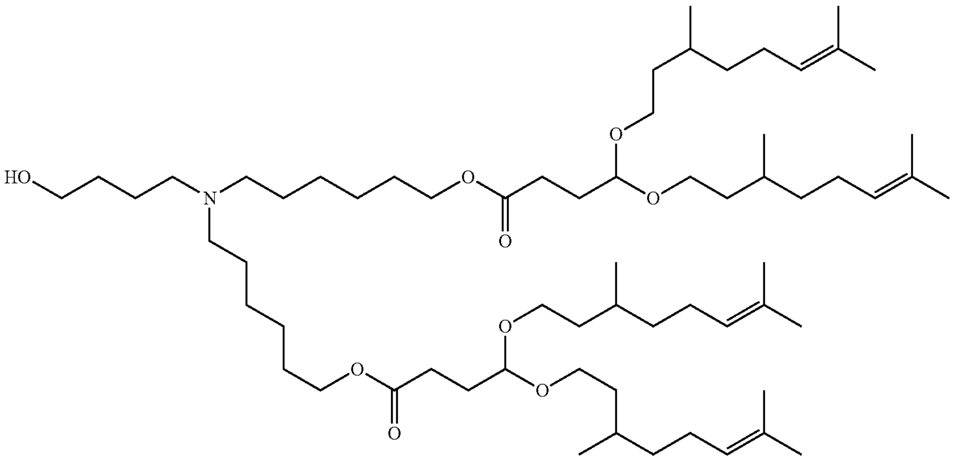

Prepared following Procedure D described in Compound 77 synthesis. Compound 78 was isolated as colorless oil (415 mg, 53%). $^1$H-NMR (300 MHz, $CDCl_3$) δ: 5.08 (t, J=7.14 Hz, 4H), 4.46 (t, J=5.4 Hz, 2H), 4.04 (t, J=6.5 Hz, 4H), 3.54-3.6 (m, 4H), 3.41-3.44 (m, 4H), 2.37 (m, 6H), 1.95 (m, 12H), 1.56-1.67 (m, 50H), 1.35 (m, 16H), 1.16 (m, 4H), 0.87 (m, 12H); CIMS m/z $[M+H]^+$ 1046.6. Analytical HPLC column: Agilent Zorbax SB-C18, 5 μm, 4.6×150 mm, mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: ELSD, $t_R$=8.4 min, purity: >99%; UPLC column: Waters Aquity UPLC® CSHTM, C18, 1.7 m, 3.0×150 mm, (Part No. 186005302), mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: CAD, $t_R$=14.1 min, purity: 96.7%.

Synthetic Scheme for Compound 79

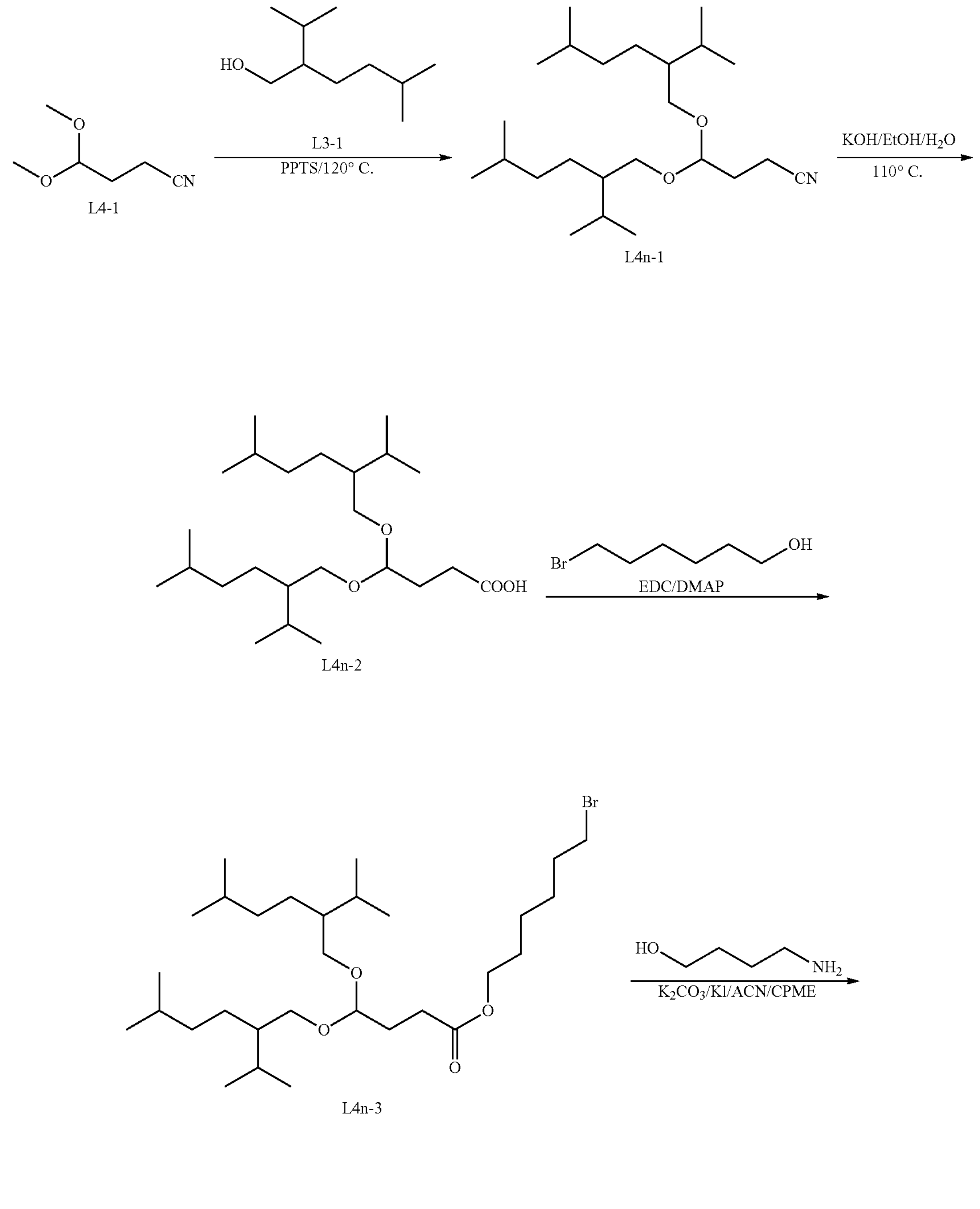

-continued

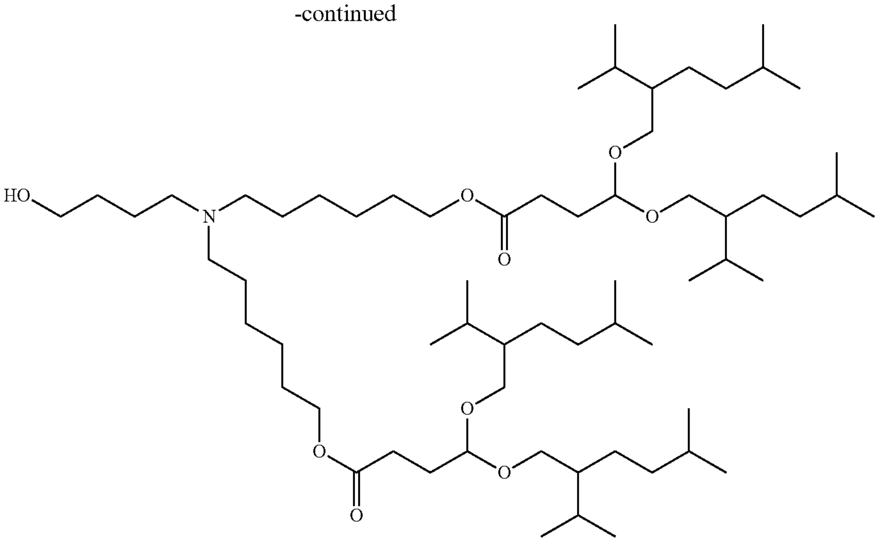

Compound 79

Synthesis of 4,4-bis((2-isopropyl-5-methylhexyl) oxy)butanenitrile (L4n-1)

L4n-1

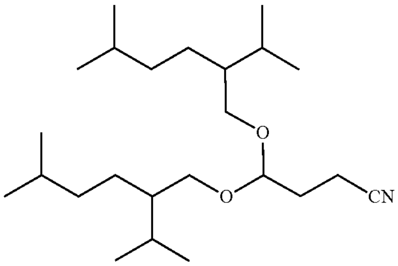

Prepared following Procedure A described in Compound 77 synthesis. Compound (L4n-1) was isolated as light-yellow oil in a yield of 3.66 g (92%). $^1$H-NMR (300 MHz, $CDCl_3$) δ 4.48 (dd, 1H), 3.62-3.49 (m, 2H), 3.42-3.31 (m, 2H), 2.42 (t, 2H), 1.97-1.78 (m, 2H), 1.58-1.42 (m, 2H), 1.41-1.08 (m, 10H), 0.87 (m, 24H).

Synthesis of 4,4-bis((2-isopropyl-5-methylhexyl) oxy)butanoic acid (L4n-2)

L4n-2

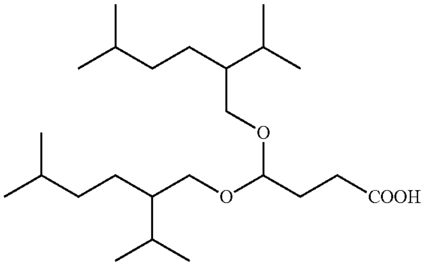

Prepared following Procedure B described in Compound 77 synthesis. Compound (L4n-2) was isolated as light-yellow oil in a yield of 3.7 g (98%). $^1$H-NMR (300 MHz, $CDCl_3$) δ 4.48 (dd, 1H), 3.62-3.49 (m, 2H), 3.42-3.31 (m, 4H), 2.38 (t, 2H), 1.94 (q, 2H), 1.83-1.67 (m, 2H), 1.54-1.39 (m, 2H), 1.38-1.01 (m, 10H), 0.87 (m, 24H).

Synthesis of 6-bromohexyl 4,4-bis((2-isopropyl-5-methylhexyl)oxy)butanoate (L4n-3)

L4n-3

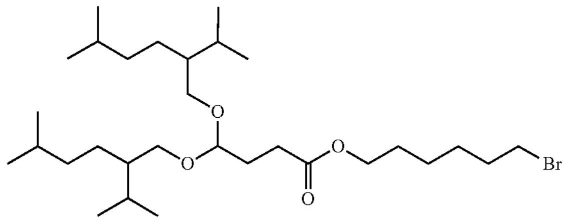

Prepared following Procedure C described in Compound 77 synthesis. Compound (L4n-3) was isolated as light-yellow oil in a yield of 1.8 g (85%). $^1$H-NMR (300 MHz, $CDCl_3$) δ 4.44 (dd, 1H), 4.06 (t, 2H), 3.55-3.43 (m, 2H), 3.40 (t, 2H), 3.31-3.18 (m, 2H), 2.38 (t, 2H), 1.94-1.71 (m, 6H), 1.68-1.54 (m, 2H), 1.54-1.01 (m, 16H), 0.87 (m, 24H).

Synthesis of ((4-hydroxybutyl)azanediyl)bis (hexane-6,1-diyl) bis(4,4-bis((2-isopropyl-5-methylhexyl)oxy)butanoate) (79)

Compound 79

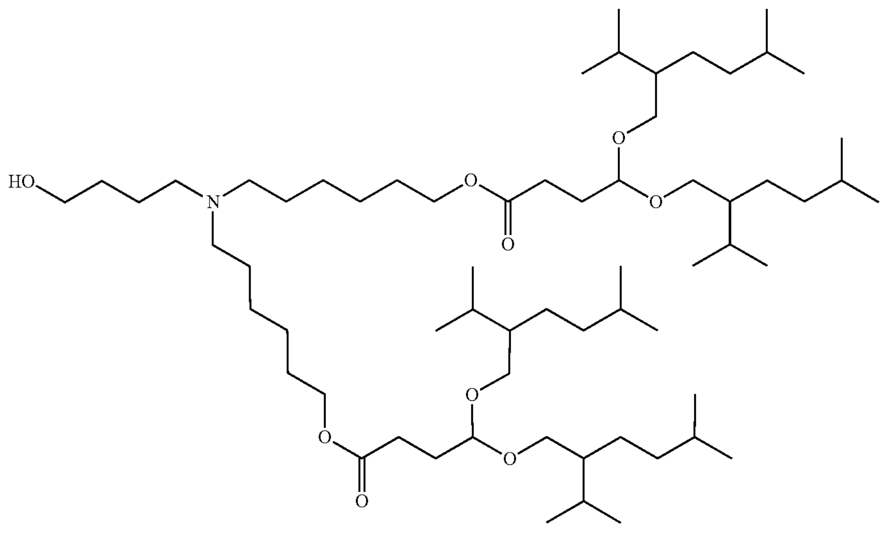

Prepared following Procedure D described in Compound 77 synthesis. Compound 79 was isolated as light yellow oil in a yield of 1.21 g (81%). $^1$H-NMR (300 MHz, $CDCl_3$) δ 4.43 (dd, 2H), 4.05 (t, 4H), 3.66-3.56 (m, 2H), 3.55-3.44 (m, 4H), 3.35-3.23 (m, 4H), 2.90-2.46 (bs, 6H), 2.37 (t, 4H), 1.92 (q, 4H), 1.86-1.72 (m, 6H), 1.70-1.53 (m, 12H), 1.54-1.43 (m, 6H), 1.42-1.24 (m, 16H), 1.24-1.04 (m, 14H), 0.87 (m, 48H); CIMS m/z $[M+H]^+$ 1055.1. Analytical HPLC column: Agilent Zorbax SB-C18, 5 μm, 4.6×150 mm, mobile phase A: acetonitrile with 0.1% trifluoroacetic acid, mobile phase B: water with 0.1% trifluoroacetic acid, use gradient: A in B 70% to 100% in 5 min, then 100% for 10 min. Flow rate: 1 mL/min, column temperature: 20±2° C., detector: ELSD, $t_R$=6.61 min, purity: >99.9%; UPLC column: Waters Aquity UPLC® CSHTM, C18, 1.7 m, 3.0×150 mm, (Part No. 186005302), mobile phase A: acetonitrile with 0.1% trifluoroacetic acid, mobile phase B: water with 0.1% trifluoroacetic acid, use gradient: A in B 70% to 100% in 5 min, then 100% for 15 min. Flow rate: 1 mL/min, column temperature: 20±2° C., detector: CAD, $t_R$=7.67 min, purity: 98.2%.

Synthetic Scheme for Compound 84

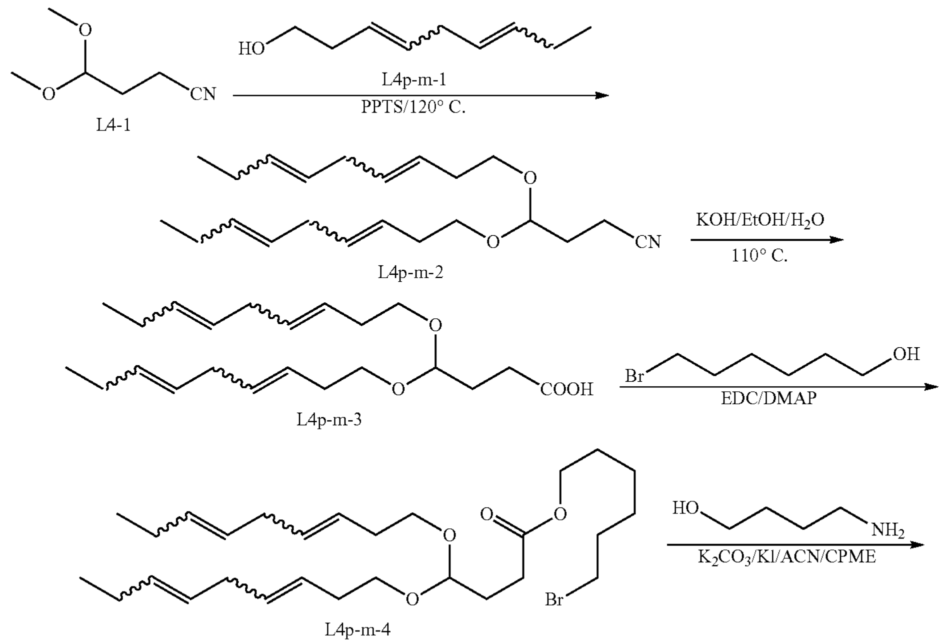

-continued

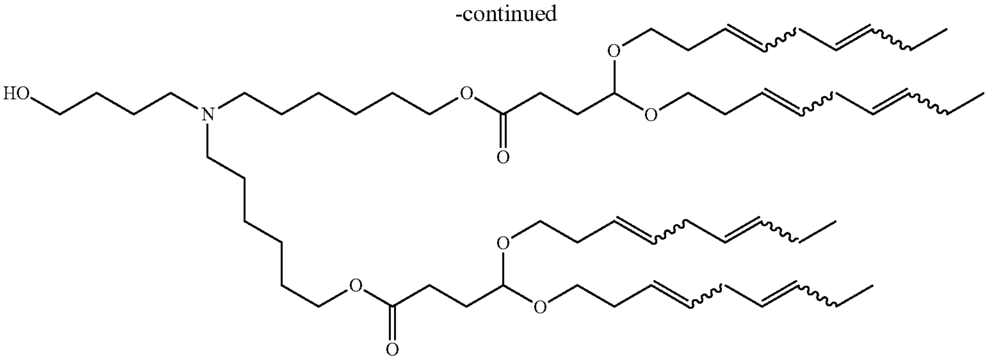

Compound 84

Synthesis of 4,4-bis(nona-3,6-dien-1-yloxy)butanenitrile L4p-m-2

L4p-m-2

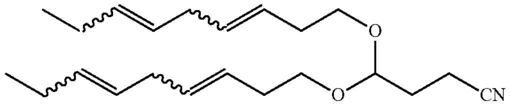

Prepared following Procedure A described in Compound 77 synthesis. L4p-m-2 was isolated as colorless oil (1.45 g, 54%). $^1$H-NMR (300 MHz, $CDCl_3$) δ 5.47-5.33 (m, 8H), 4.56 (t, 1H), 3.63-3.42 (m, 4H), 2.73 (t, 4H), 2.40 (t, 2H), 2.28-2.24 (m, 4H), 2.06-1.90 (m, 6H), 0.95 (t, 6H).

Synthesis of 4,4-bis(nona-3,6-dien-1-yloxy)butanoic acid L4p-m-3

L4p-m-3

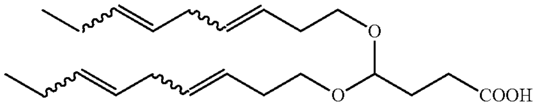

Prepared following Procedure B described in Compound 77 synthesis. Compound L4p-m-3 (1.35 g, 88%); $^1$H-NMR (300 MHz, $CDCl_3$) δ 5.46-5.28 (m, 8H), 4.53 (t, 1H), 3.61-3.41 (m, 4H), 2.73 (t, 4H), 2.44 (t, 2H), 2.29-2.23 (m, 4H), 2.06-1.90 (m, 6H), 0.95 (t, 6H).

Synthesis of 6-bromohexyl 4,4-bis(nona-3,6-dien-1-yloxy)butanoate L4p-m-4

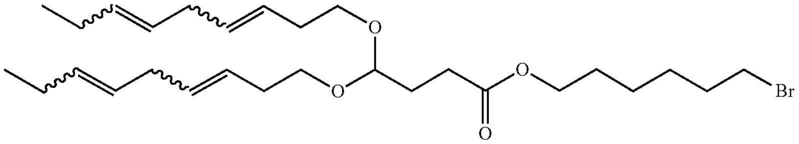

L4p-m-4

Prepared following Procedure C described in Compound 77 synthesis. Compound L4p-m-4 was isolated as colorless oil (1.08 g, 51%).

Synthesis of ((4-hydroxybutyl)azanediyl)bis (hexane-6,1-diyl) bis(4,4-bis(nona-3,6-dien-1-yloxy) butanoate) (Compound 84)

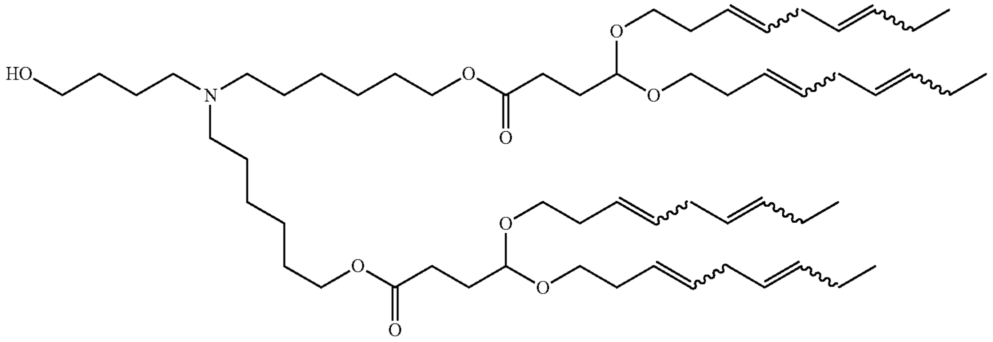

Compound 84

Prepared following Procedure D described in Compound 77 synthesis. Compound 84 was isolated as colorless oil (0.610 g, 61%); $^1$H-NMR (300 MHz, $CDCl_3$) δ 5.51-5.29 (m, 16H), 4.51 (t, 2H), 4.04 (t, 4H), 3.62-3.37 (m, 10H), 2.73 (t, 8H), 2.55 (bs, 5H), 2.36 (t, 4H), 2.25 (q, 8H), 2.08-1.88 (m, 12H), 1.74-1.18 (m, 28H), 0.95 (t, 12H); CIMS m/z $[M+H]^+$ 982.7; Analytical HPLC column: Agilent Zorbax SB-C18, 5 μm, 4.6×150 mm, mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: ELSD, $t_R$=7.44 min, purity: >99%; UPLC column: Waters Aquity UPLC® CSHTM, C18, 1.7 m, 3.0×150 mm, (Part No. 186005302), mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: CAD, $t_R$=11.39 min, purity: 98.3%.

Synthetic Scheme for Compound 81

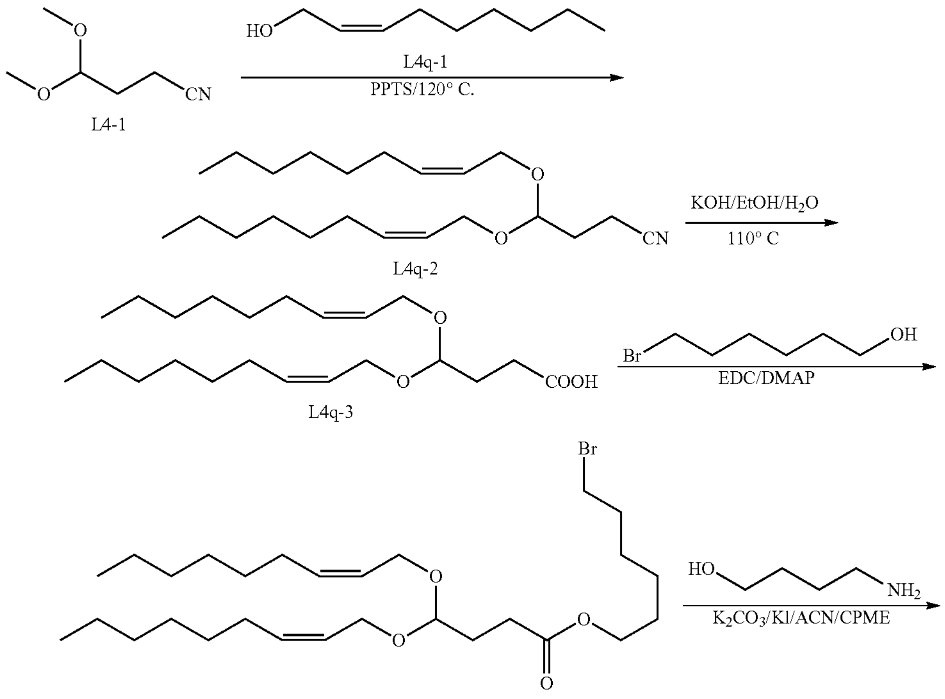

L4q-4

-continued

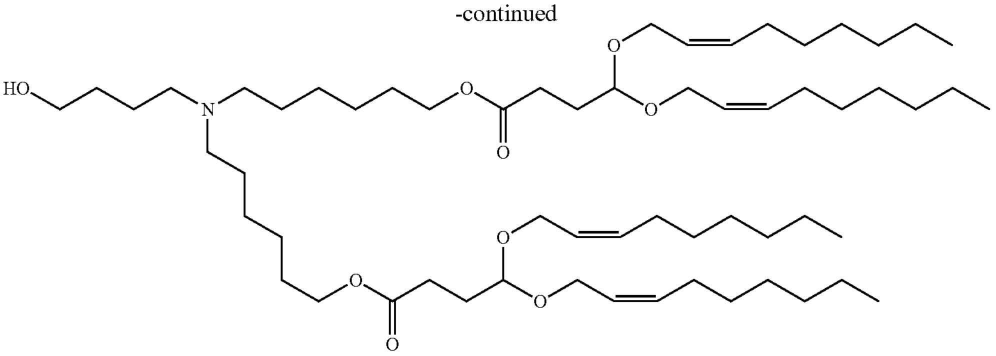

Compound 81

Synthesis of 4,4-bis(((Z)-non-2-en-1-yl)oxy)butanenitrile (L4q-2)

L4q-2

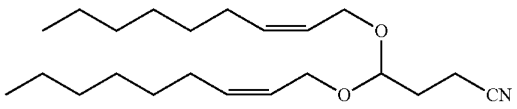

Prepared following Procedure A described in Compound 77 synthesis. Compound L4q-2 as pale Brown oil (2.0 g, 74%); $^{1}$H-NMR (300 MHz, $CDCl_3$) δ 5.58-5.47 (m, 4H), 4.65 (t, 1H), 4.19-4.06 (m, 4H), 2.43 (t, 2H), 2.07-1.92 (m, 6H), 1.37-1.18 (m, 16H), 0.88 (t, 6H).

Synthesis of 4,4-bis(((Z)-non-2-en-1-yl)oxy)butanoic acid (L4q-3)

L4q-3

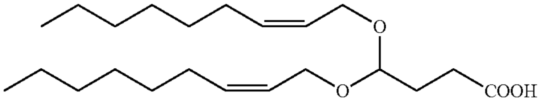

Prepared following Procedure B described in Compound 77 synthesis. Compound L4q-3 was isolated as light brown oil (1.93 g, 92%); $^{1}$H-NMR (300 MHz, $CDCl_3$) δ 5.60-5.47 (m, 4H), 4.62 (t, 1H), 4.18-4.04 (m, 4H), 2.48-2.43 (t, 2H), 2.08-1.93 (m, 6H), 1.40-1.18 (m, 16H), 0.87 (t, 6H).

Synthesis of 6-bromohexyl 4,4-bis(((Z)-non-2-en-1-yl)oxy)butanoate (L4q-4)

L4q-4

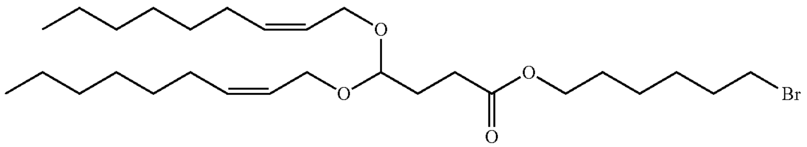

Prepared following Procedure C described in Compound 77 synthesis. Compound L4q-4 was isolated as light brown oil (1.08 g, 37%); $^{1}$H-NMR (300 MHz, $CDCl_3$) δ 5.58-5.46 (m, 4H), 4.59 (t, 1H), 4.13-4.02 (m, 6H), 3.40 (t, 2H), 2.39 (t, 2H), 2.08-1.81 (m, 8H), 1.68-1.58 (m, 2H), 1.50-1.18 (m, 20H), 0.87 (t, 6H).

Synthesis of ((4-hydroxybutyl)azanediyl)bis (hexane-6,1-diyl) bis(4,4-bis(((Z)-non-2-en-1-yl) oxy)butanoate) (81)

Compound 81

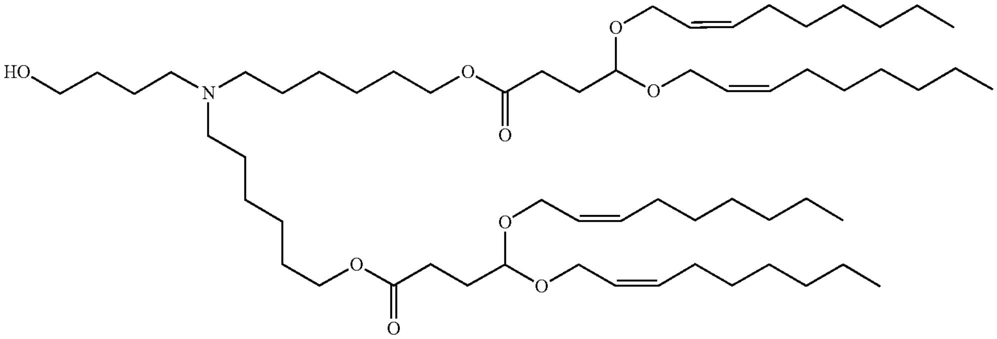

Prepared following Procedure D described in Compound 77 synthesis. Compound 81 was isolated as light brown oil (0.62 g, 62%). $^{1}$H-NMR (300 MHz, $CDCl_3$) δ 5.58-5.44 (m, 8H), 4.59 (t, 2H), 4.15-4.0 (m, 13H), 3.60 (bs, 2H), 2.70-2.48 (m, 4H), 2.39 (t, 4H), 2.08-1.92 (m, 12H), 1.78-1.44 (m, 14H), 1.42-1.18 (m, 43H), 0.87 (t, 12H); CIMS m/z $[M+H]^+$ 990.7; Analytical HPLC column: Agilent Zorbax SB-C18, 5 μm, 4.6×150 mm, mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: ELSD, $t_R$=11.19 min, purity: >99%; UPLC column: Waters Aquity UPLC® CSHTM, C18, 1.7 m, 3.0×150 mm, (Part No. 186005302), mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: CAD, $t_R$=13.94 min, purity: 94.66%.

Synthetic Scheme for Compound 82:

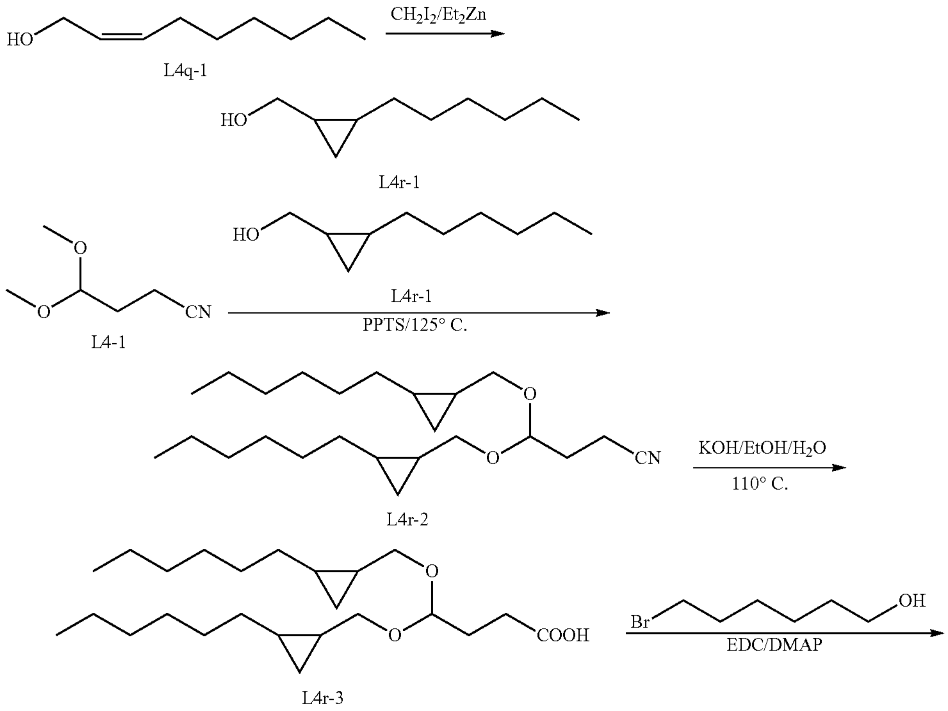

-continued

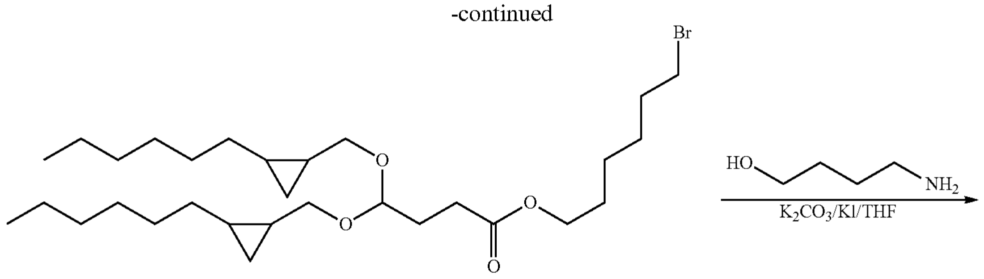

L4r-4

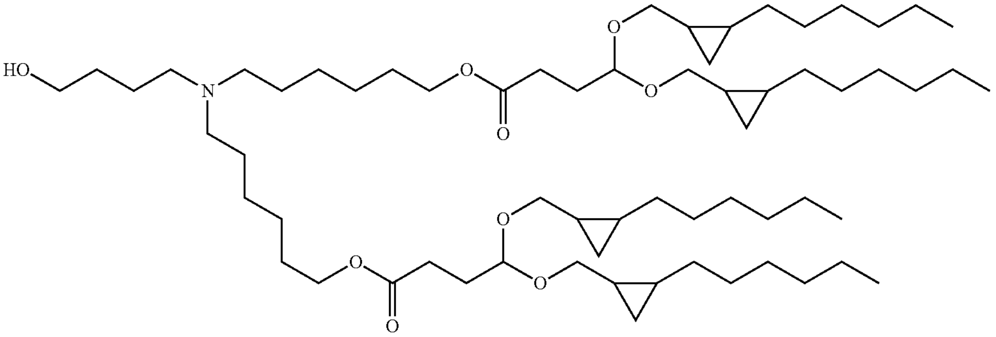

Compound 82

Synthesis of (2-hexylcyclopropyl)methanol (L4r-1)

L4r-1

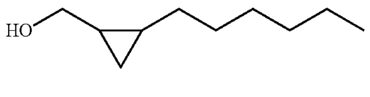

To an oven dry 500 mL three neck round bottom flask equipped with a 100 mL dropping funnel, a solution of diethyl zinc (1M in hexane, 50 mL) was added along with anhydrous dichloromethane (50 mL) and the contents were stirred at −40° C. under nitrogen atmosphere for 30 min. Diiodomethane (8.05 mL, 100 mmol) dissolved in anhydrous dichloromethane (30 mL) was added dropwise to the reaction. The resulting mixture was stirred at the same temperature for 60 min. To this mixture was added dropwise a solution of trichloroacetic acid (817.5 mg, 5 mmol) in anhydrous dichloromethane (20 mL) and anhydrous dimethoxy ethane (3 mL) and the reaction mixture was stirred for 1 h at −40° C. then allowed to warm to −15° C. in 1 h. A solution of L4q-1 in anhydrous dichloromethane (30 mL) was added dropwise to the reaction and the contents were stirred at −15° C. for 1 h then allowed to warm to room temperature and stirred overnight. After the completion of the reaction, the contents were added to a 2000 mL conical flask containing saturated $NH_4Cl$ (300 mL) and stirred for 15 min. The crude product was extracted with dichloromethane (100 mL×3). Combined organic phases were washed with brine and dried over anhydrous magnesium sulphate. The solvent was removed under vacuum to give crude product (4.0 g). This crude product was subjected to next step reaction without further purification. $^1$H NMR (300 MHz, $CDCl_3$): δ ppm 3.68-3.54 (m, 2H), 1.58-1.20 (m, 15H), 1.18-0.85 (m, 4H), 0.85-0.68 (m, 1H), 0.0-0.04 (m, 1H); CIMS m/z $[M+H]^+$ 157.32.

Synthesis of 4,4-bis((2-hexylcyclopropyl)methoxy)butanenitrile (Compound L4r-2)

L4r-2

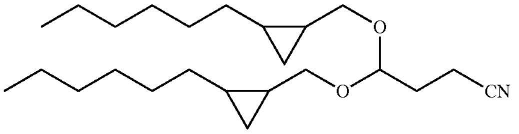

Prepared following Procedure A described in Compound 77 synthesis. Compound L4r-2 (2.55 g, 87%); $^1$H NMR (300 MHz, $CDCl_3$): δ 4.76-4.63 (m, 1H), 3.76-3.54 (m, 1H), 3.53-3.51 (m, 2H), 3.51 (t, J=6.0 Hz, 1H), 2.45 (t, J=6.0 Hz, 2H), 2.00 (t, J=6.0 Hz, 2H), 1.50-0.92 (m, 22H), 0.89-0.85 (m, 8H), 0.74-0.71 (m, 2H), 0.00-0.5 (m, 2H); CIMS m/z $[M+H]^+$ 378.71.

Synthesis of 4,4-bis((2-hexylcyclopropyl)methoxy)butanoic acid (L4r-3)

L4r-3

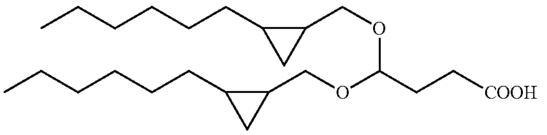

Prepared following Procedure B described in Compound 77 synthesis. Compound L4r-3 (2.0 g, 76%) was isolated as colorless oil. $^1$H NMR (300 MHz, $CDCl_3$): δ 4.68-4.57 (m, 1H), 3.68-3.59 (m, 1H), 3.58-3.49 (m, 2H), 3.39 (t, J=7.0 Hz, 1H), 2.49 (t, J=7.0 Hz, 2H), 1.98 (t, J=7.0 Hz, 2H), 1.53-0.85 (m, 30H), 0.72-0.70 (m, 2H), −0.009-0.06 (m, 2H); CIMS m/z $[M+H]^+$ 397.61.

Synthesis of 6-bromohexyl 4,4-bis((2-hexylcyclopropyl)methoxy)butanoate (L4r-4)

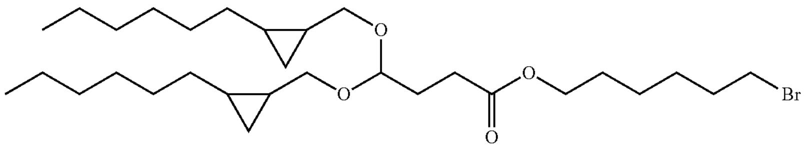

L4r-4

Prepared following Procedure C described in Compound 77 synthesis. Compound L4r-4 (1.33 g, 48%) as slightly yellow oil. $^1$H NMR (300 MHz, $CDCl_3$): δ 4.68-4.57 (m, 1H), 4.22-4.16 (m, 1H), 4.09 (t, J=6.0 Hz, 1H), 3.98-3.91 (m, 1H), 3.51-3.49 (m, 2H), 3.51-3.48 (m, 1H), 2.49 (t, J=7.0 Hz, 2H), 1.98 (t, J=7.0 Hz, 2H), 1.53-0.85 (m, 30H), 0.90-0.85 (m, 1OH), 0.72-0.69 (m, 2H), −0.008-0.073 (m, 2H); CIMS m/z $[M+H]^+$ 560.68.

Synthesis of ((4-hydroxybutyl)azanediyl)bis(hexane-6,1-diyl)bis(4,4-bis((2-hexylcyclopropyl)methoxy)butanoate) (82)

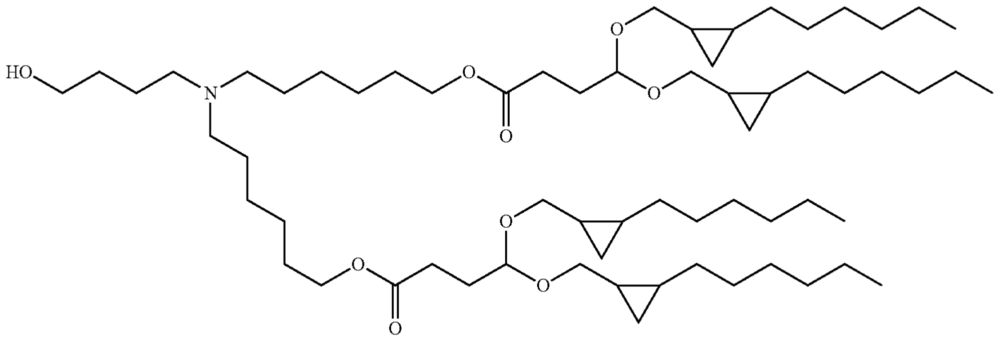

Compound 82

Prepared following Procedure D described in Compound 77 synthesis. Compound 82 (810 mg, 77%). $^1$H NMR (300 MHz, $CDCl_3$): δ 4.78-4.67 (m, 2H), 4.05 (t, J=6.0 Hz, 4H), 3.78-3.35 (m, 10H), 2.51-2.40 (m, 10H), 1.99-1.90 (m, 4H), 1.73-1.05 (m, 66H), 0.99-0.75 (m, 19H), −0.007-0.071 (m, 4H); CIMS m/z $[M+H]^+$ 1047.77. Analytical HPLC column: Agilent Zorbax SB-C18, 5 μm, 4.6×150 mm, mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: ELSD, $t_R$=10.7 min, purity: >99%; UPLC column: Waters Aquity UPLC® CSHTM, C18, 1.7 μm, 3.0×150 mm, (Part No. 186005302), mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: CAD, $t_R$=14.8 min, purity: >99%.

Synthetic Scheme for Compound 129:

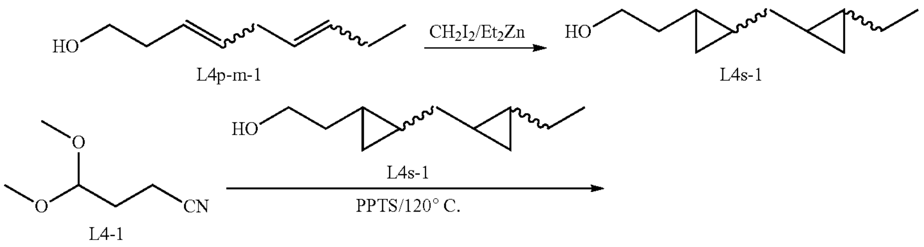

-continued

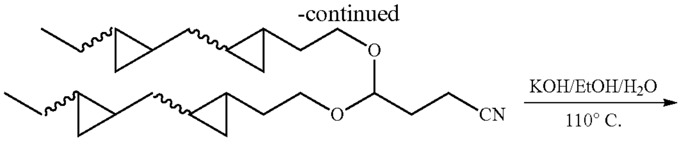

L4s-2

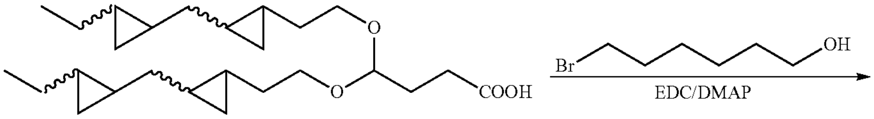

L4s-3

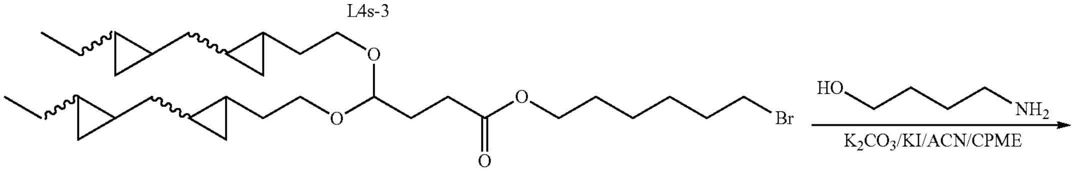

L4s-4

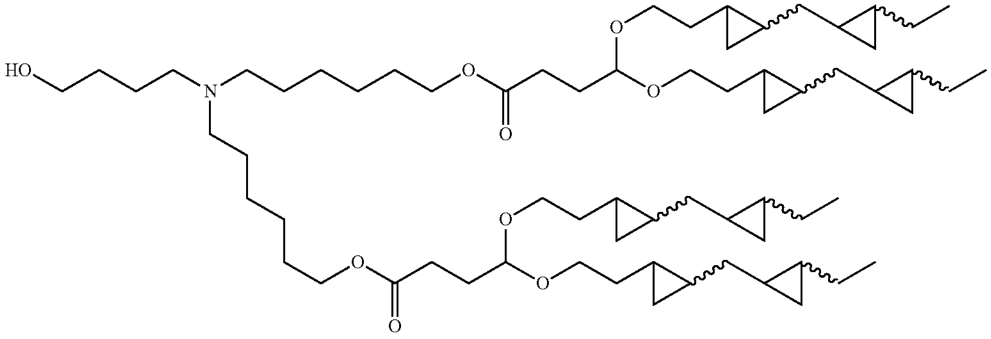

Compound 129

Synthesis of 2-(2-((2-ethylcyclopropyl)methyl)cyclopropyl)ethan-1-ol (L4s-1)

L4s-1

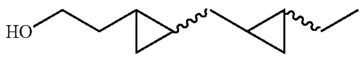

To an oven dry three neck 250 mL round bottom flask equipped with a 50 mL dropping funnel, a solution of diethyl zinc (0.9M in hexane, 72 mL) was added along with anhydrous dichloromethane (30 mL) and the contents were stirred at −40° C. under nitrogen atmosphere for 30 min. Diiodomethane (8.1 mL, 98.84 mmol) dissolved in anhydrous dichloromethane (20 mL) was added dropwise to the reaction. The resulting mixture was stirred at −40° C. for 60 min. To this mixture was added dropwise a solution of trichloroacetic acid (2.56 g, 15.68 mmol) in anhydrous dichloromethane (20 mL) and anhydrous dimethoxy ethane (6.7 mL) and the reaction mixture was stirred for 1 h at −40° C. then allowed to warm to −15° C. in 1 h. A solution of L4p-m-1 (2.2 g, 15.68 mmol) in anhydrous dichloromethane (10 mL) was added dropwise to the reaction and the contents were stirred at −15° C. for 1 h then allowed to warm to room temperature and stirred overnight. After the completion of the reaction, the contents were added to a 1000 mL conical flask containing saturated $NH_4Cl$ (400 mL) and stirred for 15 min. The crude product was extracted using dichloromethane (200 mL×3) from this mixture. Combined organic phases were washed with brine and dried over anhydrous magnesium sulphate. The solvent was removed under vacuum to give crude product. The crude material was adsorbed on 30 g flash silica and loaded on to an empty flash cartridge, which was then attached to flash purification system loaded with 40 g flash silica column and was purified by flash chromatography ($SiO_2$: ethyl acetate/hexane 0-10%) to get Compound L4s-1 (2.38 g, 90%). $^1H$ NMR (300 MHz, $CDCl_3$): δ ppm 3.78-3.72 (m, 2H), 3.00 (s, 2H), 1.62-1.14 (m, 6H), 0.99 (t, J=7.0 Hz, 3H), 0.68-0.56 (m, 4H), 0.28-0.25 (m, 2H), −0.25-0.29 (m, 1H); CIMS m/z $[M+H]^+$ 168.28.

Synthesis of 4,4-bis(2-(2-((2-ethylcyclopropyl)methyl)cyclopropyl)ethoxy)butanenitrile (L4s-2)

L4s-2

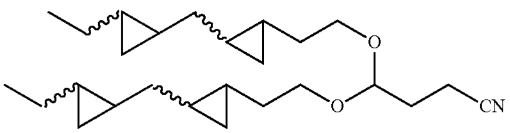

Prepared following Procedure A described in Compound 77 synthesis. Compound L4s-2 (1.88 g, 86%); $^1H$ NMR (300 MHz, $CDCl_3$): δ ppm 4.58 (t, J=5.0 Hz, 1H), 3.70-3.66 (m, 2H), 3.53-3.48 (m, 2H), 2.43 (t, J=7.0 Hz, 2H), 1.99-1.94 (m, 2H), 1.56-1.18 (m, 14H), 0.96 (t, J=7.0 Hz, 6H), 0.62-0.52 (m, 8H), 0.26-0.21 (m, 4H), −0.25-0.29 (m, 2H); CIMS m/z $[M+H]^+$ 402.75.

Synthesis of 4,4-bis(2-(2-((2-ethylcyclopropyl) methyl)cyclopropyl)ethoxy)butanoic acid (L4s-3)

L4s-3

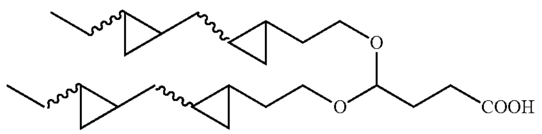

Prepared following Procedure B described in Compound 77 synthesis. Compound L4s-3 (1.71 g, 91%) was isolated as colorless oil. $^1$H NMR (300 MHz, $CDCl_3$): δ ppm ppm 4.56 (t, J=5.0 Hz, 1H), 3.70-3.66 (m, 2H), 3.52-3.48 (m, 2H), 2.47 (t, J=7.0 Hz, 2H), 1.99-1.94 (m, 2H), 1.50-1.17 (m, 14H), 0.96 (t, J=7.0 Hz, 6H), 0.62-0.52 (m, 8H), 0.25-0.20 (m, 4H), −0.28-0.31 (m, 2H); CIMS m/z $[M+H]^+$ 421.72.

Synthesis of 6-bromohexyl 4,4-bis(2-(2-((2-ethylcyclopropyl)methyl) cyclopropyl)ethoxy) butanoate (L4s-4)

L4s-4

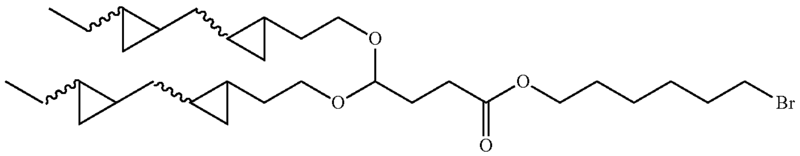

Prepared following Procedure C described in Compound 77 synthesis. Compound L4s-4 (1.7 g, 67%) was isolated as a clear oil. $^1$H NMR (300 MHz, $CDCl_3$): δ ppm 4.52 (t, J=5.0 Hz, 1H), 4.06 (t, J=7.0 Hz, 2H), 3.70-3.20 (m, 2H), 3.50-3.37 (m, 4H), 2.38 (t, J=7.0 Hz, 2H), 1.99-1.83 (m, 6H), 1.49-1.33 (m, 16H), 0.96 (t, J=7.0 Hz, 6H), 0.62-0.51 (m, 10H), 0.25-0.20 (m, 4H), −0.28-0.31 (m, 2H); CIMS m/z $[M+H]^+$ 584.71.

Synthesis of ((4-hydroxybutyl)azanediyl)bis (hexane-6,1-diyl) bis(4,4-bis(2-(2-((2-ethylcyclopropyl)methyl)cyclopropyl)ethoxy)butanoate) (129)

Compound 129

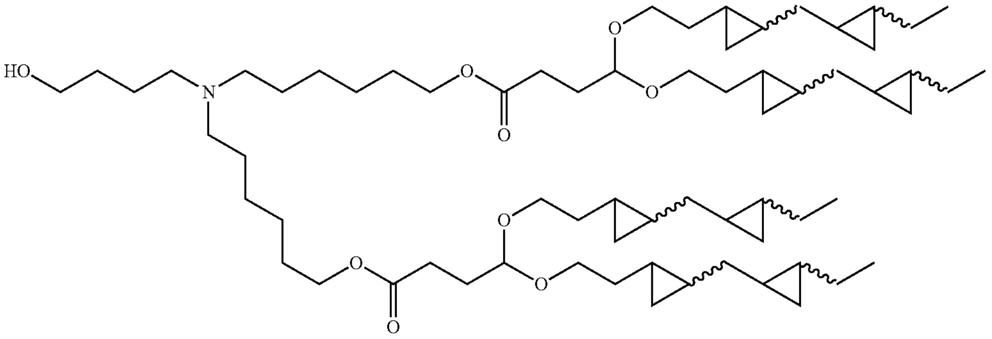

Prepared following Procedure D described in Compound 77 synthesis. Compound 129 (895 mg, 66%). $^1$H NMR (300 MHz, $CDCl_3$): δ ppm 4.5 (t, J=5.0 Hz, 2H), 4.06 (t, J=5.0 Hz, 4H), 3.78-3.61 (m, 4H), 3.60-3.51 (m, 6H), 2.39 (m, 1OH), 1.94 (m, 4H), 1.71-1.02 (m, 46H), 0.96 (t, J=7.0 Hz, 12H), 0.75-0.51 (m, 20H), 0.24-0.22 (m, 8H), −3.9-0.28 (m, 4H). CIMS m/z $[M+H]^+$ 1095.82. Analytical HPLC column: Agilent Zorbax SB-C18, 5 μm, 4.6×150 mm, mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: ELSD, $t_R$=10.7 min, purity: >99%; UPLC column: Waters Aquity UPLC® CSHTM, C18, 1.7 m, 3.0×150 mm, (Part No. 186005302), mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: CAD, $t_R$=14.3 min, purity: >99%.

Synthetic Scheme for Compound 66

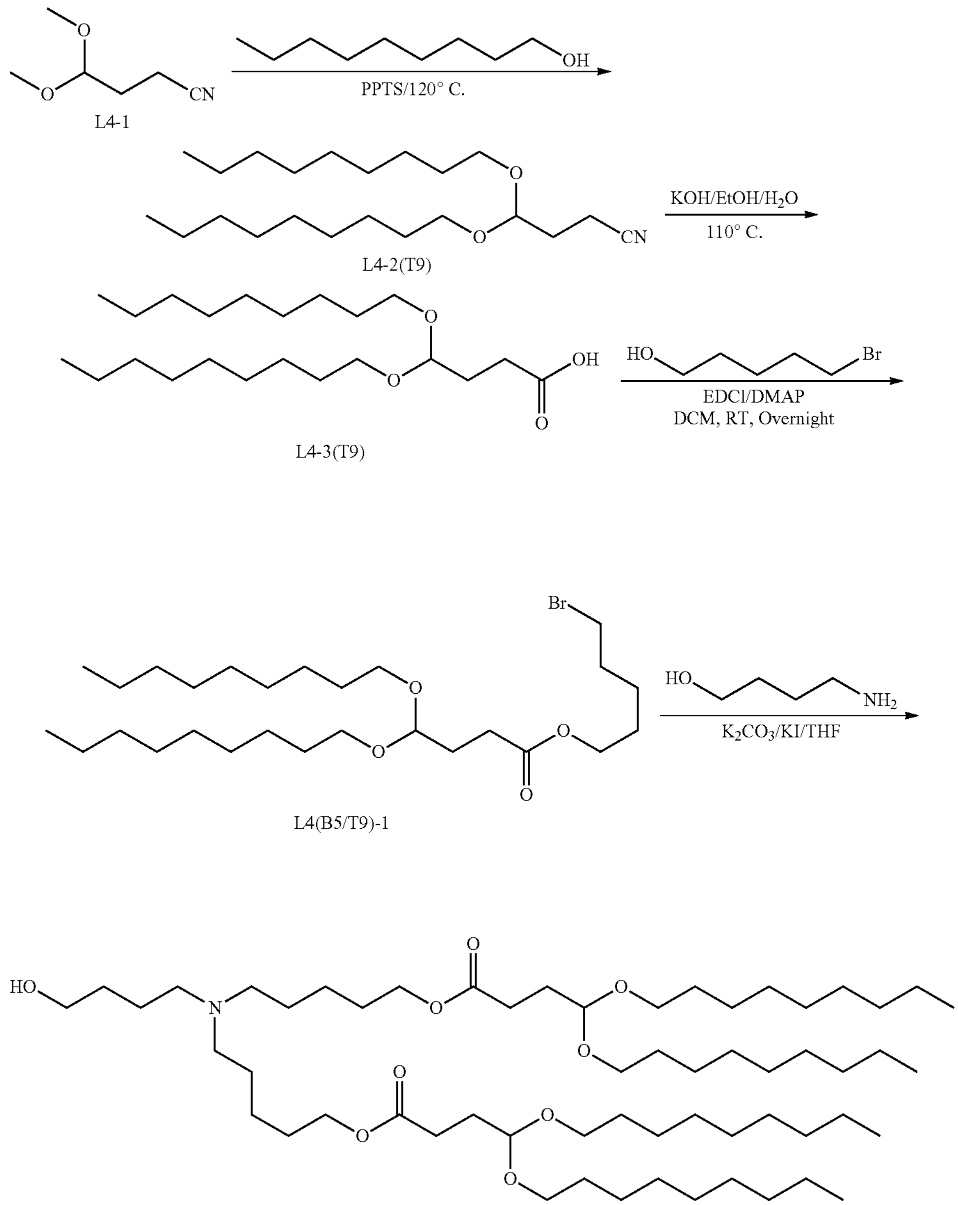

L4-1

L4-2(T9)

L4-3(T9)

L4(B5/T9)-1

Compound 66

Synthesis of 4,4-bis(nonyloxy)butanenitrile (L4-2(T9))

L4-2(T9)

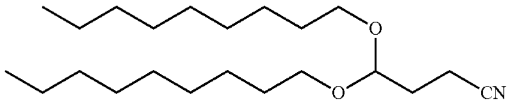

Prepared following Procedure A described in Compound 77 synthesis. Compound L4-2(T9) was isolated as light-yellow oil in a yield of 11.5 g (91%). $^1$HNMR ($CDCl_3$) δ: 4.5-4.56 (t, 1H), 3.57-3.56 (m, 2H), 3.40-3.43 (m, 2H), 2.39-2.41 (t, 2H), 1.92-1.95 (m, 2H), 1.54-1.56 (m, 2H), 1.26 (bs, 26H), 0.85-0.87 (t, 6H); CIMS m/z $[M+H]^+$ 354.

Synthesis of 4,4-bis(nonyloxy)butanoic acid (L4-3(T9))

L4-3(T9)

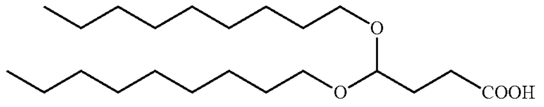

Prepared following Procedure B described in Compound 77 synthesis. Compound L4-3(T9) was isolated as light-yellow oil in a yield of 11.8 g (98%). $^1$HNMR ($CDCl_3$) δ: 4.53-4.56 (t, 1H), 3.57-3.60 (m, 2H), 3.40-3.43 (m, 2H), 2.39-2.41 (t, 2H), 1.90-1.95 (m, 2H), 1.54-1.56 (M, 4H), 1.26 (bs, 28H), 0.85-0.87 (t, 6H); CIMS m/z $[M-H]^-$ 371.

Synthesis of 5-bromopentyl 4,4-bis(nonyloxy)butanoate (L4(B5/T9)-1

L4(B5/T9)-1

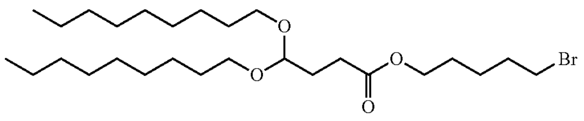

Prepared following Procedure C described in Compound 77 synthesis. Compound (L4(B5/T9)-1 was isolated as colorless oil (970 mg, 69%). $^1$H-NMR (300 MHz, $CDCl_3$) δ: 4.48 (t, J=5.52 Hz, 1H), 4.07 (t, J=6.6 Hz, 2H), 3.55 (m, 2H), 3.4 (m, 4H), 2.38 (t, J=7.44 Hz, 2H), 1.83-1.95 (m, 4H), 1.65 (m, 2H), 1.47-1.55 (m, 6H), 1.25 (m, 24H), 0.87 (m, 6H).

Synthesis of ((4-Hydroxybutyl)azanediyl)bis(pentane-5,1-diyl) bis(4,4-bis(nonyloxy) butanoate) (66)

Compound 66

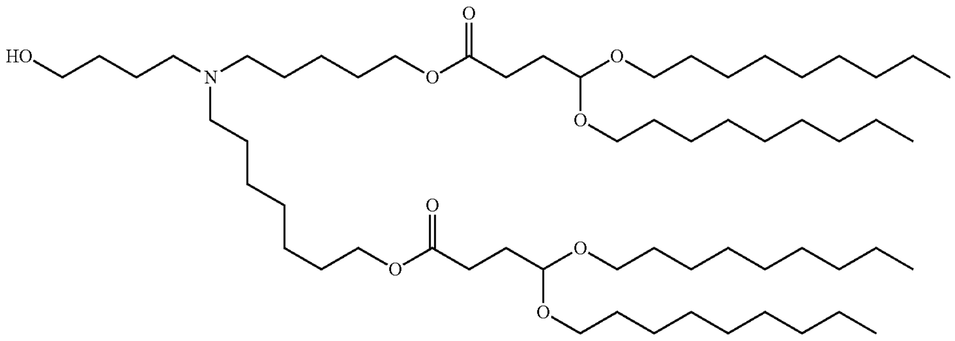

Prepared following Procedure D described in Compound 77 synthesis. Compound 66 was isolated as colorless oil (418 mg, 51%). $^1$H-NMR (300 MHz, $CDCl_3$) δ: 4.48 (t, J=5.49 Hz, 2H), 4.05 (t, J=6.6 Hz, 4H), 3.56 (m, 6H), 3.38 (m, 4H), 2.52 (brs, 2H), 2.37 (t, J=7.41 Hz, 4H), 1.9 (m, 4H), 1.52-1.66 (m, 20H), 1.25 (m, 56H), 0.87 (m, 12H); CIMS m/z $[M+H]^+$ 970.7. Analytical HPLC column: Agilent Zorbax SB-C18, 5 μm, 4.6×150 mm, mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: ELSD, $t_R$=9.4 min, purity: >99%; UPLC column: Waters Aquity UPLC® CSHTM, C18, 1.7 m, 3.0×150 mm, (Part No. 186005302), mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: CAD, $t_R$=15.2 min, purity: 98.6%.

Synthetic Scheme for Compound 71
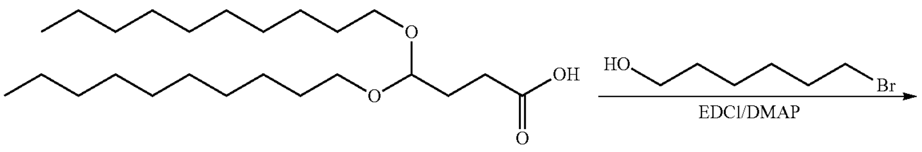
L4-3(T10)
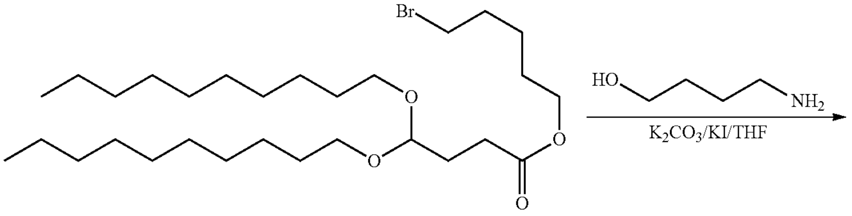
L4(B5/T10)-1
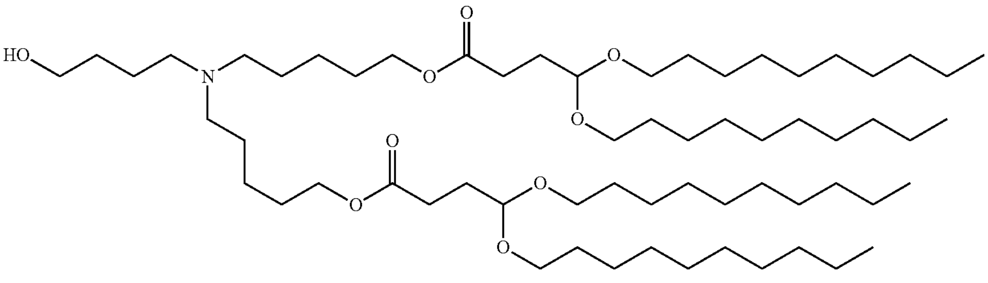
Compound 71
Synthesis of 5-bromopentyl 4,4-bis(decyloxy)butanoate L4(B5/T10)-1
L4(B5/T10)-1
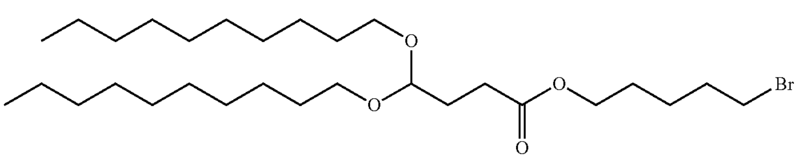
Prepared following Procedure C described in Compound 77 synthesis. Compound L4(B5/T10)-1 was isolated as colorless oil (1.0 g, 70%). $^1$H-NMR (300 MHz, $CDCl_3$) δ: 4.48 (t, J=5.49 Hz, 1H), 4.07 (t, J=6.57 Hz, 2H), 3.54 (m, 2H), 3.4 (m, 4H), 2.38 (t, J=7.41 Hz, 2H), 1.85-1.95 (m, 4H), 1.63 (m, 2H), 1.47-1.55 (m, 8H), 1.25 (m, 26H), 0.87 (m, 6H).

Synthesis of ((4-hydroxybutyl)azanediyl)bis(pentane-5,1-diyl) bis(4,4-bis(decyloxy) butanoate) (71)

Compound 71

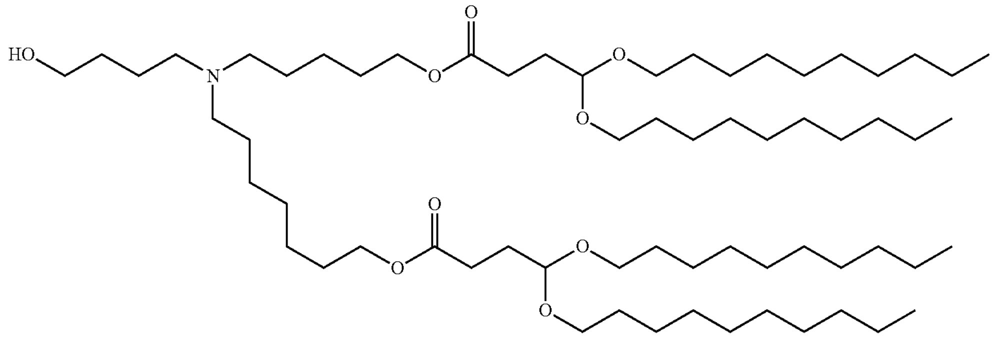

Prepared following Procedure D described in Compound 77 synthesis. Compound 71 was isolated as colorless oil (383 mg, 45%). $^{1}$H-NMR (300 MHz, $CDCl_3$) δ: 4.48 (t, J=5.49 Hz, 2H), 4.05 (t, J=6.6 Hz, 4H), 3.56 (m, 6H), 3.4 (m, 4H), 2.6 (br, 2H), 2.37 (t, J=7.9 Hz, 4H), 1.9 (m, 4H), 1.52-1.67 (m, 20H), 1.25 (m, 64H), 0.87 (m, 12H); CIMS m/z $[M+H]^+$ 1026.8. Analytical HPLC column: Agilent Zorbax SB-C18, 5 μm, 4.6×150 mm, mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: ELSD, $t_R$=9.6 min, purity: >99%; UPLC column: Waters Aquity UPLC® CSHTM, C18, 1.7 μm, 3.0×150 mm, (Part No. 186005302), mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: CAD, $t_R$=15.7 min, purity: >99%.

Synthetic Scheme for Compound 74

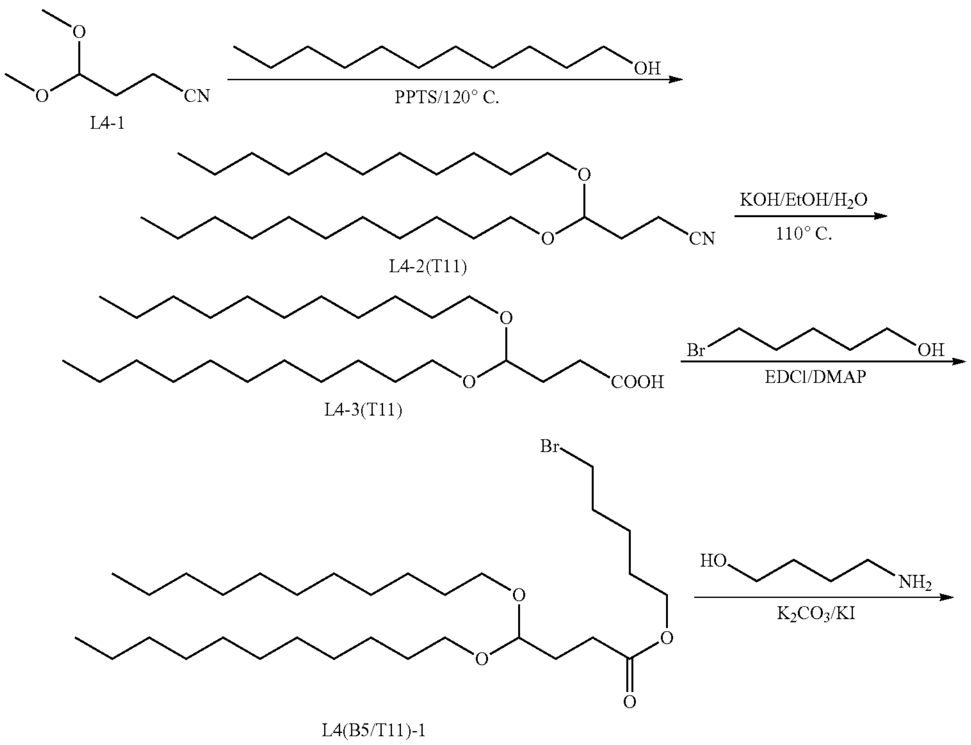

-continued

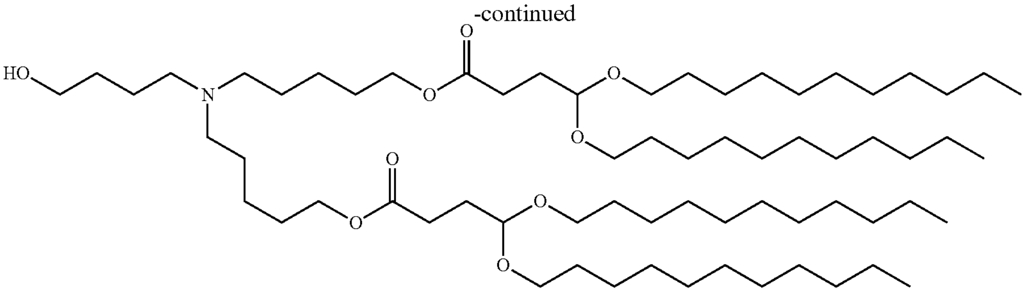

Compound 74

Synthesis of 4,4-bis(nonyloxy)butanenitrile (L4-2(T11))

L4-2(T11)

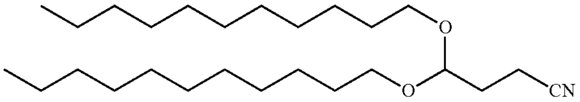

Prepared following Procedure A described in Compound 77 synthesis. Compound L4-2(T11) was isolated as colorless oil (4.5 g, 90%). $^1$H-NMR (300 MHz, $CDCl_3$) δ 4.54 (t, 1H), 3.60-3.55 (m, 2H), 3.45-3.40 (m, 2H), 2.41 (t, 2H), 1.96-1.90 (m, 2H), 1.58-1.53 (m, 4H), 1.39-1.15 (m, 32H), 0.87 (t, 6H); CIMS m/z $[M+H]^+$ 410.

Synthesis of 4,4-bis(nonyloxy)butanoic acid (L4-3(T11))

L4-3(T11)

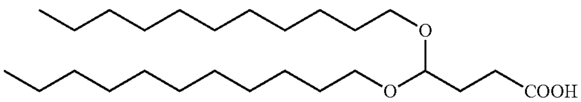

Prepared following Procedure B described in Compound 77 synthesis. Compound L4-3(T11) was isolated as white solid (11.8 g, 98%). $^1$H-NMR (300 MHz, $CDCl_3$) δ 4.50 (t, 1H), 3.82-3.52 (m, 2H), 3.41-3.38 (m, 2H), 2.41 (t, 2H), 1.95-1.88 (m, 2H), 1.57-1.50 (m, 4H), 1.39-1.18 (m, 32H), 0.87 (t, 6H); CIMS m/z $[M-H]^-$ 426.7.

Synthesis of (5-bromopentyl 4,4-bis(undecyloxy) butanoate) (L4(B5/T11)-1)

L4(B5/T11)-1

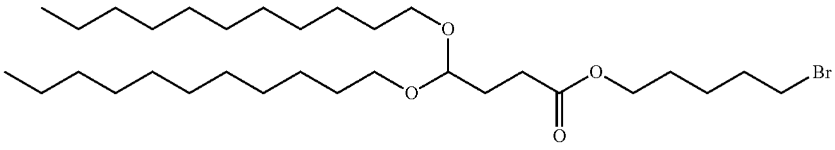

Prepared following Procedure C described in Compound 77 synthesis. L4-4(B5/T11)-1 was isolated as colorless oil (1.1 g, 82%). $^1$H-NMR (300 MHz, $CDCl_3$) δ 4.48 (t, 1H), 4.05 (t, 2H), 3.54-3.37 (m, 6H), 2.37 (t, 2H), 1.92-1.86 (m, 3H), 1.59-1.36 (m, 8H), 1.35-1.15 (m, 33H), 0.87 (t, 6H); CIMS m/z $[M+H]^+$ 578.6.

Synthesis of ((4-hydroxybutyl)azanediyl)bis(pentane-5,1-diyl) bis(4,4-bis(undecyloxy) butanoate)) (74)

Compound 74

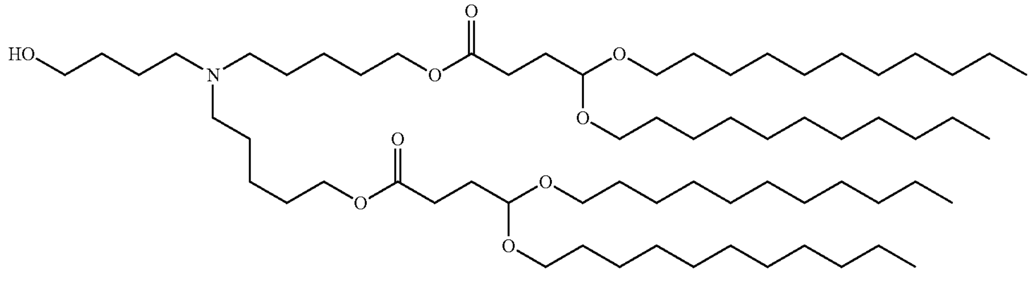

Prepared following Procedure D described in Compound 77 synthesis. Compound 74 was isolated as colorless oil (0.35 g, 41%). $^1$H-NMR (300 MHz, $CDCl_3$) δ 4.47 (t, 2H), 4.04 (t, 4H), 3.56-3.37 (m, 9H), 2.42-2.34 (m, 9H), 1.94-1.90 (m, 3H), 1.63-1.49 (m, 18H), 1.40-1.10 (m, 73H), 0.86 (t, 12H); CIMS m/z 1082.9 [M+H]. Analytical HPLC column: Agilent Zorbax SB-C18, 5 m, 4.6×150 mm, mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: ELSD, $t_R$=13.1 min, purity: >99%; UPLC column: Waters Aquity UPLC® CSHTM, C18, 1.7 μm, 3.0×150 mm, (Part No. 186005302), mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: CAD, $t_R$=16.5 min, purity: 92.2%.

Synthetic Scheme for Compound 67

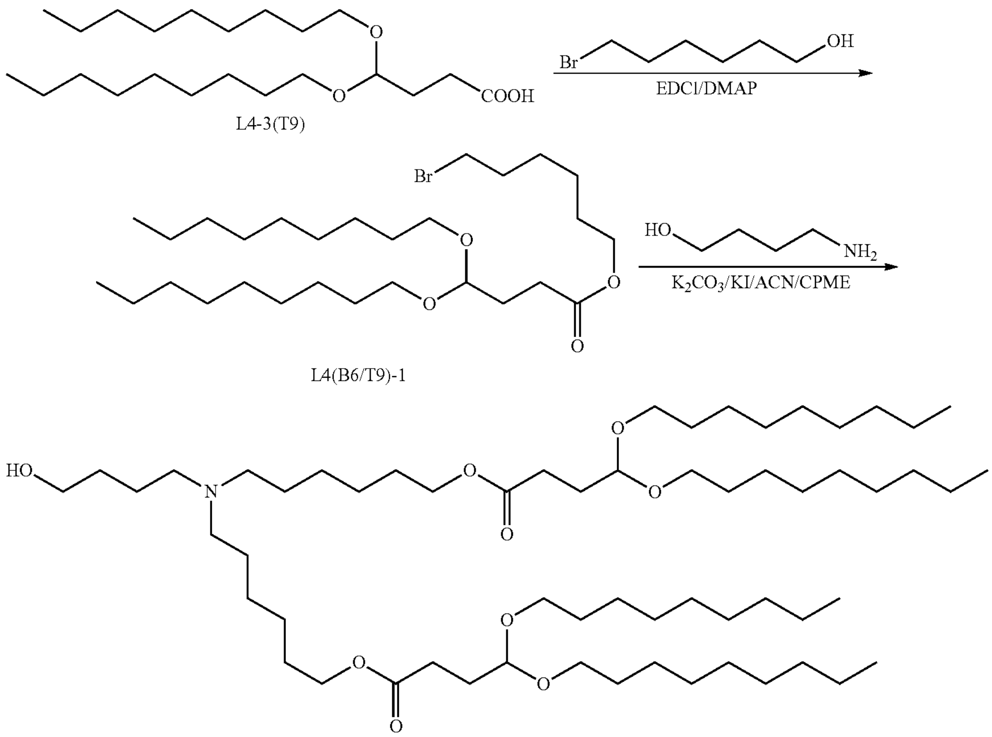

Compound 67

Synthesis of 6-bromohexyl 4,4-bis(nonyloxy)butanoate (L4(B6/T9)-1)

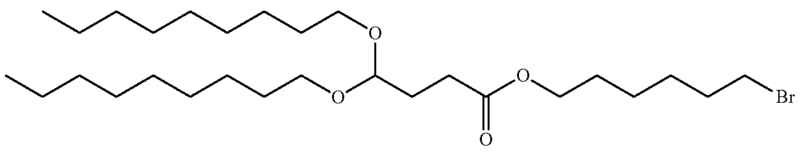

L4(B6/T9)-1

Prepared following Procedure C described in Compound 77 synthesis. L4(B6/T9)-1 was isolated as colorless oil (1.4 g, 49%). $^{1}$H-NMR (300 MHz, $CDCl_3$) δ 4.49 (t, 1H), 4.06 (t, 2H), 3.58-3.50 (m, 2H), 3.42-3.38 (m, 4H), 2.38 (t, 2H), 1.93-1.80 (m, 4H), 1.68-1.10 (m, 34H), 0.87 (t, 6H).

Synthesis of ((4-hydroxybutyl)azanediyl)bis(hexane-6,1-diyl) bis(4,4-bis(nonyloxy)butanoate) (67)

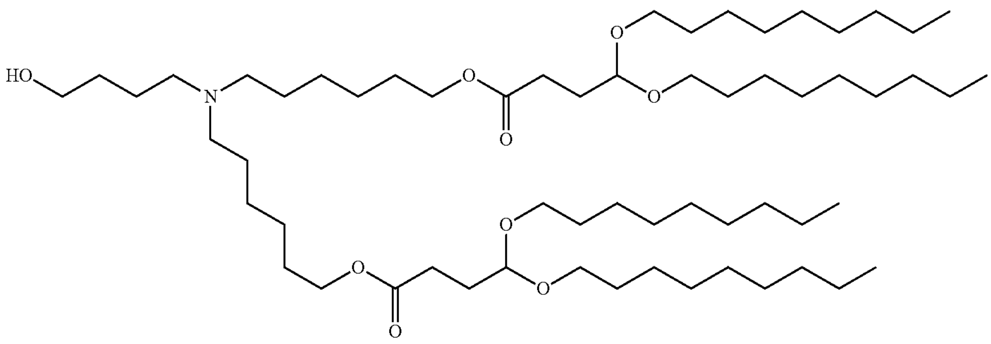

Compound 67

Prepared following Procedure D described in Compound 77 synthesis. Compound 67 was isolated as colorless oil (0.8 g, 61%). $^{1}$H-NMR (300 MHz, $CDCl_3$) δ 4.49 (t, 2H), 4.04 (t, 4H), 3.60-3.50 (m, 6H), 3.43-3.36 (m, 4H), 2.45-2.35 (m, 10H), 1.95-1.88 (m, 4H), 1.68-1.42 (m, 26H), 1.40-1.10 (m, 62H), 0.87 (t, 12H); CIMS m/z $[M+H]^+$ 999.2; Analytical HPLC column: Agilent Zorbax SB-C18, 5 m, 4.6×150 mm, mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: ELSD, $t_R$=11.95 min, purity: >99%; UPLC column: Waters Aquity UPLC® CSHTM, C18, 1.7 μm, 3.0×150 mm, (Part No. 186005302), mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: CAD, $t_R$=15.27 min, purity: 97.54%.

Synthetic Scheme for Compound 75

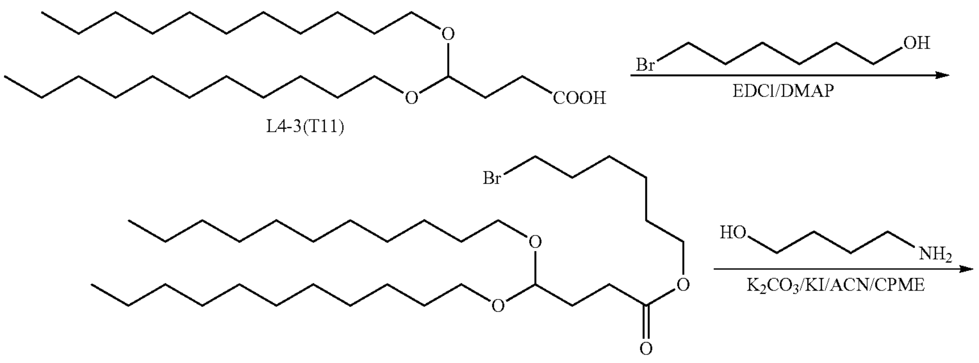

L4(B6/T11)-1

-continued

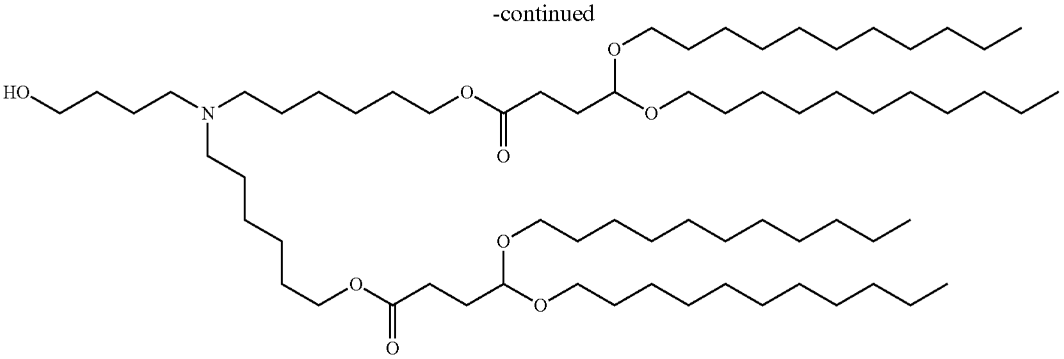

Compound 75

Synthesis of (6-bromohexyl 4,4-bis(undecyloxy)butanoate) (L4(B6/T11)-1

L4-4(B6/T11)-1

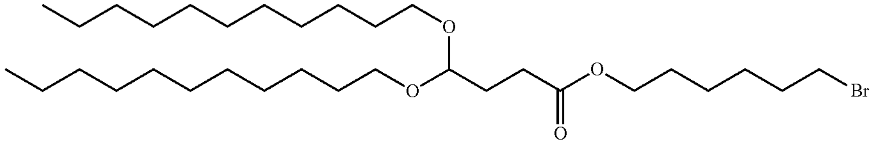

Prepared following Procedure C described in Compound 77 synthesis. L4-4(B6/T11)-1 was isolated as colorless oil (1.08 g, 78%). $^1$H-NMR (300 MHz, $CDCl_3$) δ 4.47 (t, 1H), 4.07 (t, 2H), 3.53-3.36 (m, 6H), 2.35 (t, 2H), 1.91-1.84 (m, 3H), 1.57-1.35 (m, 9H), 1.33-1.17 (m, 34H), 0.87 (t, 6H); CIMS m/z 591.6 [M+H].

Synthesis of ((4-hydroxybutyl)azanediyl)bis (hexane-6,1-diyl) bis(4,4-bis(undecyloxy)butanoate)) (75)

Compund 75

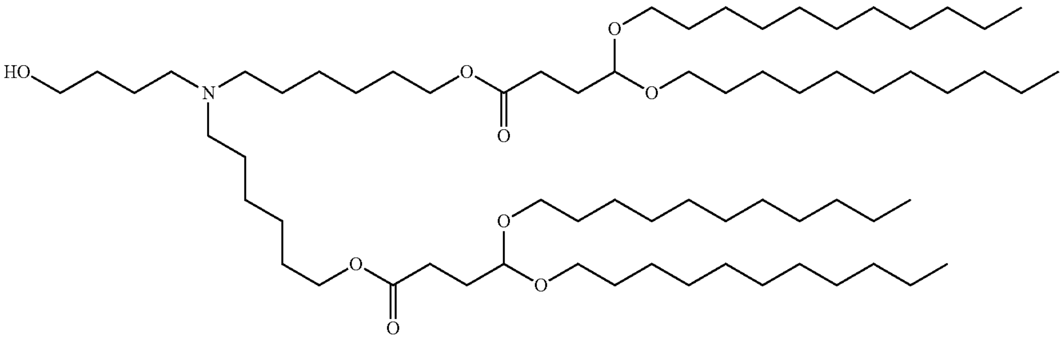

Prepared following Procedure D described in Compound 77 synthesis. Compound 75 was isolated as colorless oil (0.5 g, 57%). $^1$H-NMR (300 MHz, $CDCl_3$) δ 4.48 (t, 2H), 4.03 (t, 4H), 3.57-3.37 (m, 9H), 2.41-2.34 (m, 9H), 1.94-1.90 (m, 3H), 1.63-1.52 (m, 18H), 1.37-1.15 (m, 77H), 0.86 (t, 12H); CIMS m/z 1110.9 [M+H]. Analytical HPLC column: Agilent Zorbax SB-C18, 5 m, 4.6×150 mm, mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: ELSD, $t_R$=13.0 min, purity: >99%; UPLC column: Waters Aquity UPLC® CSHTM, C18, 1.7 μm, 3.0×150 mm, (Part No. 186005302), mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: CAD, $t_R$=16.7 min, purity: 93.5%.

Synthetic Scheme for Compound 64

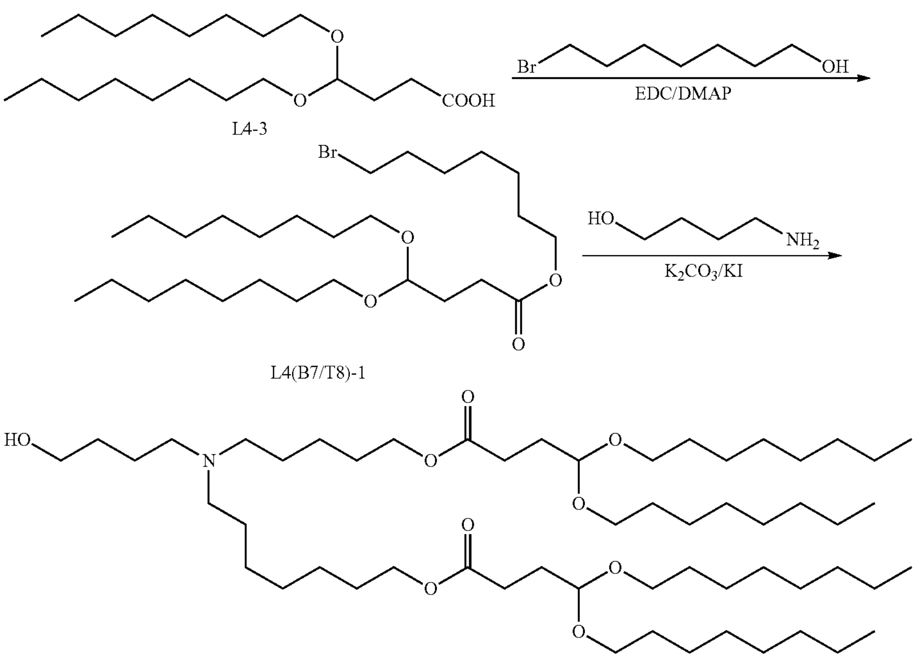

Compound 64

Synthesis of 7-bromoheptyl 4,4-bis(octyloxy)butanoate [L4(B7/T8)-1]

L4(B7/T8)-1

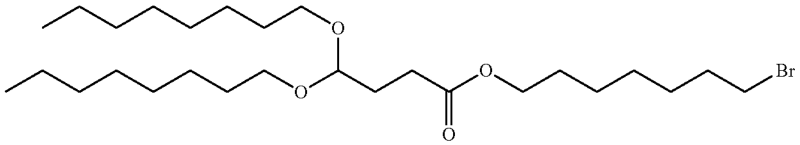

Prepared following Procedure C described in Compound 77 synthesis. Compound L4(B7/T8)-1 was isolated as light-yellow oil in a yield of 1.95 g (86%). $^1$H-NMR (300 MHz, $CDCl_3$) δ 4.49 (t, 1H), 4.05 (t, 2H), 3.62-3.49 (m, 2H), 3.42-3.31 (m, 4H), 2.38 (t, 2H), 1.97-1.78 (m, 4H), 1.69-1.49 (m, 8H), 1.44-1.18 (m, 24H), 0.87 (t, 6H).

Synthesis of ((4-hydroxybutyl)azanediyl)bis(heptane-7,1-diyl) bis(4,4-bis(octyloxy)butanoate) (64)

Compound 64

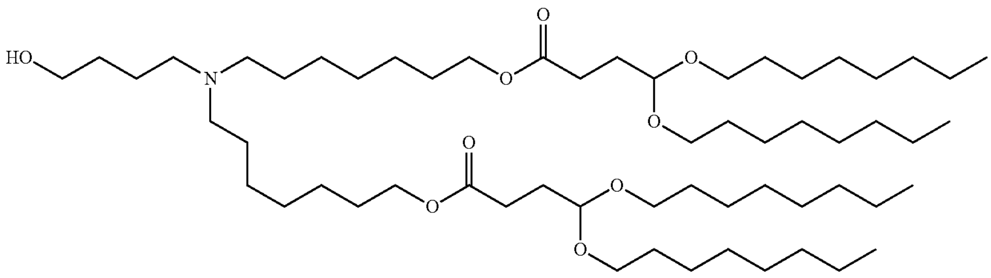

Prepared following Procedure D described in Compound 77 synthesis. Compound 64 was isolated as light-yellow oil in a yield of 940 mg (59%). $^{1}$H-NMR (300 MHz, $CDCl_3$) δ 4.49 (t, 2H), 4.05 (t, 4H), 3.66-3.49 (m, 6H), 3.45-3.34 (m, 4H), 2.92-2.46 (m, 6H), 2.38 (t, 4H), 1.97-1.86 (m, 4H), 1.79-1.42 (m, 22H), 1.40-1.12 (m, 51H), 0.87 (t, 12H); CIMS m/z $[M+H]^+$ 971.9. Analytical HPLC column: Agilent Zorbax SB-C18, 5 μm, 4.6×150 mm, mobile phase A: acetonitrile with 0.1% trifluoroacetic acid, mobile phase B: water with 0.1% trifluoroacetic acid, use gradient: A in B 70% to 100% in 5 min, then 100% for 10 min. Flow rate: 1 mL/min, column temperature: 20±2° C., detector: ELSD, $t_R$=6.70 min, purity: >99.9%; UPLC column: Waters Aquity UPLC® CSHTM, C18, 1.7 μm, 3.0×150 mm, (Part No. 186005302), mobile phase A: acetonitrile with 0.1% trifluoroacetic acid, mobile phase B: water with 0.1% trifluoroacetic acid, use gradient: A in B 70% to 100% in 5 min, then 100% for 15 min. Flow rate: 1 mL/min, column temperature: 20±2° C., detector: CAD, $t_R$=6.68 min, purity: 99.8%.

Synthetic Scheme for Compound 68

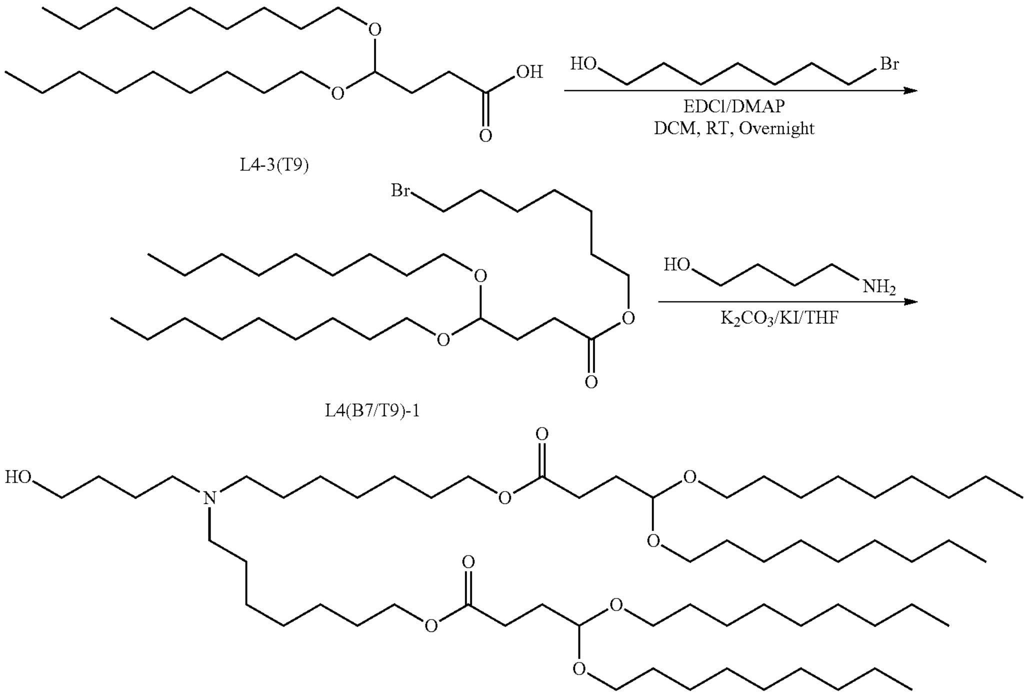

L4-3(T9)

L4(B7/T9)-1

Compound 68

Synthesis of 7-bromoheptyl 4,4-bis(nonyloxy)butanoate L4(B7/T9)-1

L4(B7/T9)-1

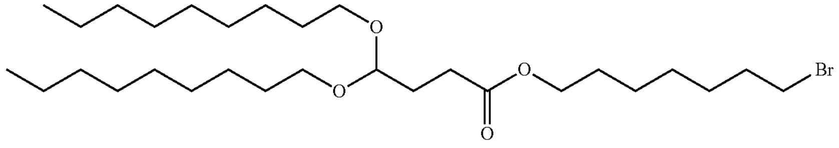

Prepared following Procedure C described in Compound 77 synthesis. L4(B7/T9)-1 was isolated as colorless oil (960 mg, 65%). $^{1}$H-NMR (300 MHz, $CDCl_3$) δ: 4.48 (t, J=5.49 Hz, 1H), 4.05 (t, J=6.6 Hz, 2H), 3.56 (m, 2H), 3.4 (m, 4H), 2.37 (t, J=7.41 Hz, 2H), 1.82-1.95 (m, 4H), 1.52-1.62 (m, 6H), 1.43 (m, 2H), 1.25-1.35 (m, 28H), 0.87 (m, 6H).

Synthesis of ((4-hydroxybutyl)azanediyl)bis(heptane-7,1-diyl) bis(4,4-bis(nonyloxy) butanoate) (68)

Compound 68

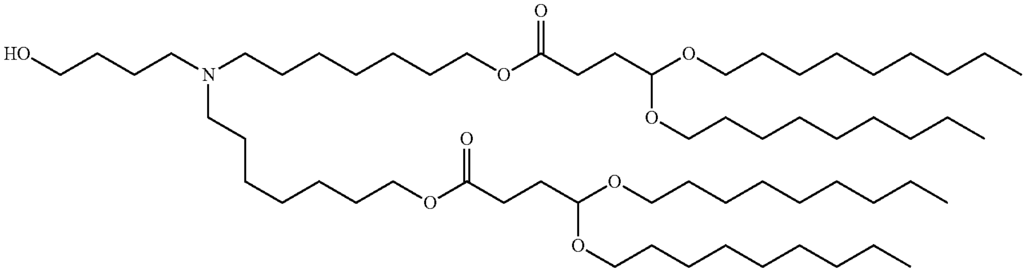

Prepared following Procedure D described in Compound 77 synthesis. Compound 68 was isolated as colorless oil (425 mg, 52%). $^1$H-NMR (300 MHz, $^1$H-NMR (300 MHz, $CDCl_3$) δ: 4.48 (t, J=5.76 Hz, 2H), 4.04 (t, J=6.5 Hz, 4H), 3.56 (m, 6H), 3.38 (m, 4H), 2.46 (br, 2H), 2.38 (t, J=7.4 Hz, 4H), 1.92 (m, 4H), 1.5-1.65 (m, 20H), 1.25 (m, 60H), 0.87 (m, 12H); CIMS m/z $[M+H]^+$ 1026.9. Analytical HPLC column: Agilent Zorbax SB-C18, 5 μm, 4.6×150 mm, mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: ELSD, $t_R$=8.7 min, purity: >99%; UPLC column: Waters Aquity UPLC® CSHTM, C18, 1.7 m, 3.0×150 mm, (Part No. 186005302), mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: CAD, $t_R$=15.5 min, purity: 97.9%.

Synthetic Scheme for Compound 72:

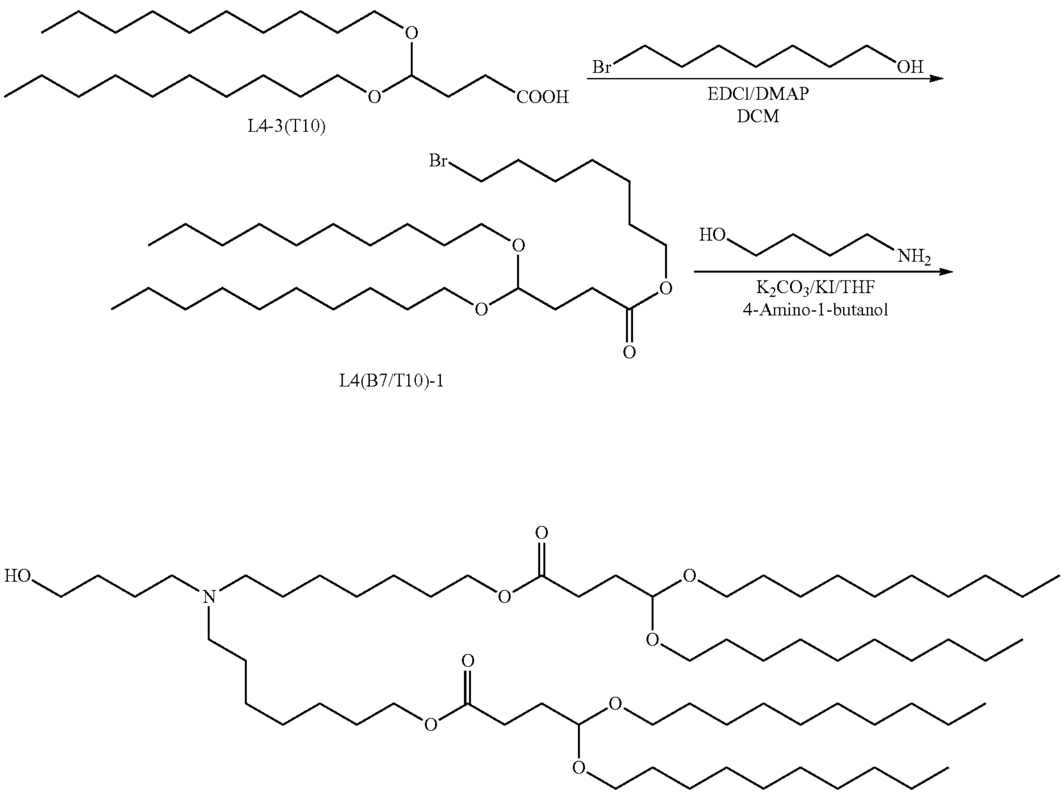

Compound 72

Synthesis of 7-bromoheptyl 4,4-bis(decyloxy)butanoate (L4(B7/T10)-1)

L4(B7/T10)-1

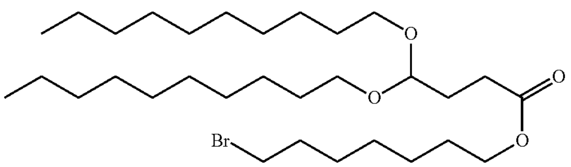

Prepared following Procedure C described in Compound 77 synthesis. Compound L4(B7/T10)-1 (1.37 g, 95%) was isolated as slightly yellow oil. $^1$H NMR (300 MHz, $CDCl_3$): δ ppm 4.49 (t, J=7.0 Hz, 1H), 4.05 (t, J=7.0 Hz, 1H), 3.65-3.50 (m, 2H), 3.42-3.37 (m, 4H), 2.35 (t, J=7.0 Hz, 2H), 1.95-1.82 (m, 4H), 1.61-1.19 (m, 40H), 0.87 (s, 6H). CIMS m/z $[M+H]^+$ 578.77.

Synthesis of ((4-hydroxybutyl)azanediyl)bis(heptane-7,1-diyl) bis(4,4-bis(decyloxy) butanoate) (72)

Compound 72

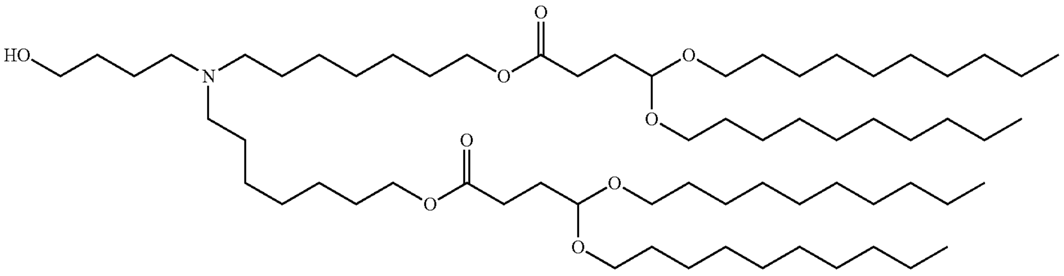

Prepared following Procedure D described in Compound 77 synthesis. Compound 72 (950 mg, 78%). $^1$H NMR (300 MHz, $CDCl_3$): δ ppm 4.49 (t, J=7.0 Hz, 2H), 4.04 (t, J=7.0 Hz, 4H), 3.75-3.350 (m, 10H), 2.42-2.30 (m, 10H), 1.95-1.82 (m, 4H), 1.61-1.35 (m, 20H), 1.26 (bs, 69H), 0.87 (t, J=6.0 Hz, 12H); CIMS m/z $[M+H]^+$ 1083.77. Analytical HPLC column: Agilent Zorbax SB-C18, 5 μm, 4.6×150 mm, mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: ELSD, $t_R$=10.7 min, purity: >99%; UPLC column: Waters Aquity UPLC® CSHTM, C18, 1.7 μm, 3.0×150 mm, (Part No. 186005302), mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: CAD, $t_R$ 16.1 min, purity: >99%.

Synthetic Scheme for Compound 69
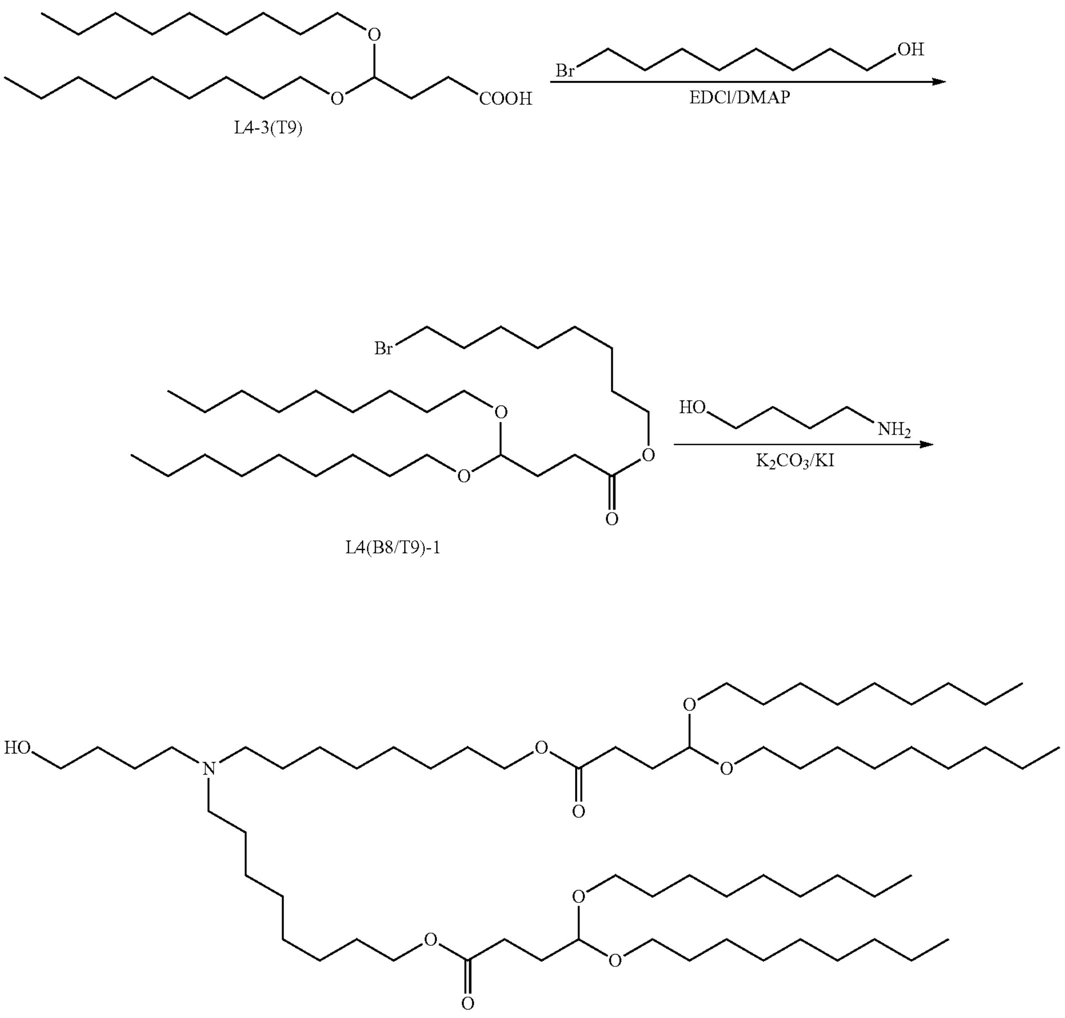
L4-3(T9)
L4(B8/T9)-1
Compound 69
Synthesis of (8-bromooctyl-4,4-bis(nonyloxy)butanoate) (L4(B8/T9-1)
L4(B8/T9)-1
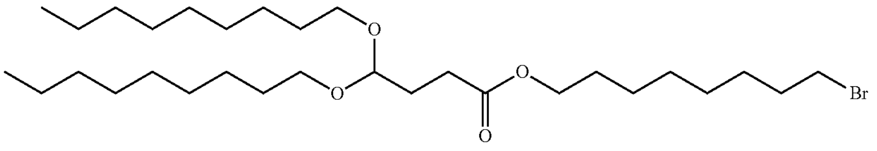
Prepared following Procedure C described in Compound 77 synthesis. L4-4(B8/T9)-1 was isolated as colorless oil (1.3 g, 86%). $^{1}$H-NMR (300 MHz, $CDCl_3$) δ 4.48 (t, 1H), 4.04 (t, 2H), 3.57-3.35 (m, 5H), 2.36 (t, 2H), 1.92-1.79 (m, 4H), 1.68-1.52 (m, 6H), 1.47-1.15 (m, 33H), 0.86 (t, 6H); CIMS m/z 563.56 [M+H].

Synthesis of ((4-hydroxybutyl)azanediyl)bis(octane-8,1-diyl) bis(4,4-bis(nonyloxy)butanoate) (69)

Compound 69

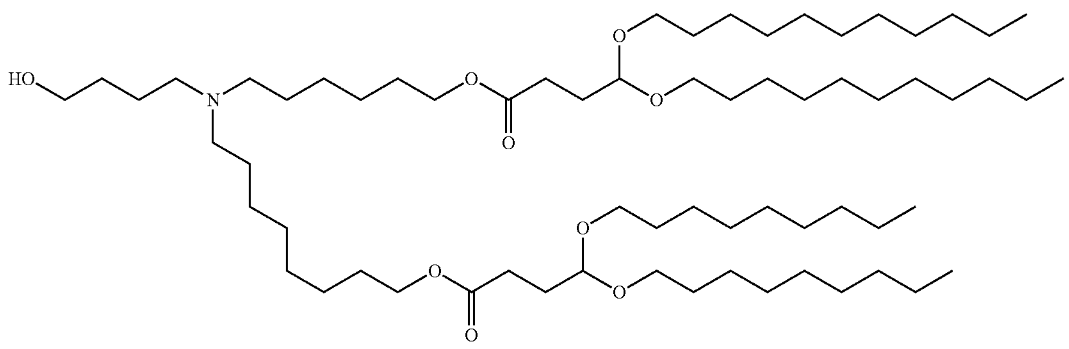

Prepared following Procedure D described in Compound 77 synthesis. Compound L4(B8/T9) was isolated as colorless oil (0.65 g, 73%). $^1$H-NMR (300 MHz, $CDCl_3$) δ 6.70 (s, 1H), 4.48 (t, 2H), 4.03 (t, 4H), 3.57-3.37 (m, 10H), 2.40-2.36 (m, 9H), 1.92-1.89 (m, 3H), 1.56-1.52 (m, 19H), 1.41-1.12 (m, 67H), 0.86 (t, 12H); CIMS m/z 1054.8 [M+H]. Analytical HPLC column: Agilent Zorbax SB-C18, 5 μm, 4.6×150 mm, mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: ELSD, $t_R$=8.8 min, purity: 94.9%; UPLC column: Waters Aquity UPLC® CSHTM, C18, 1.7 μm, 3.0×150 mm, (Part No. 186005302), mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: CAD, $t_R$=15.6 min, purity: 82.9%.

Synthetic Scheme for Compound 73

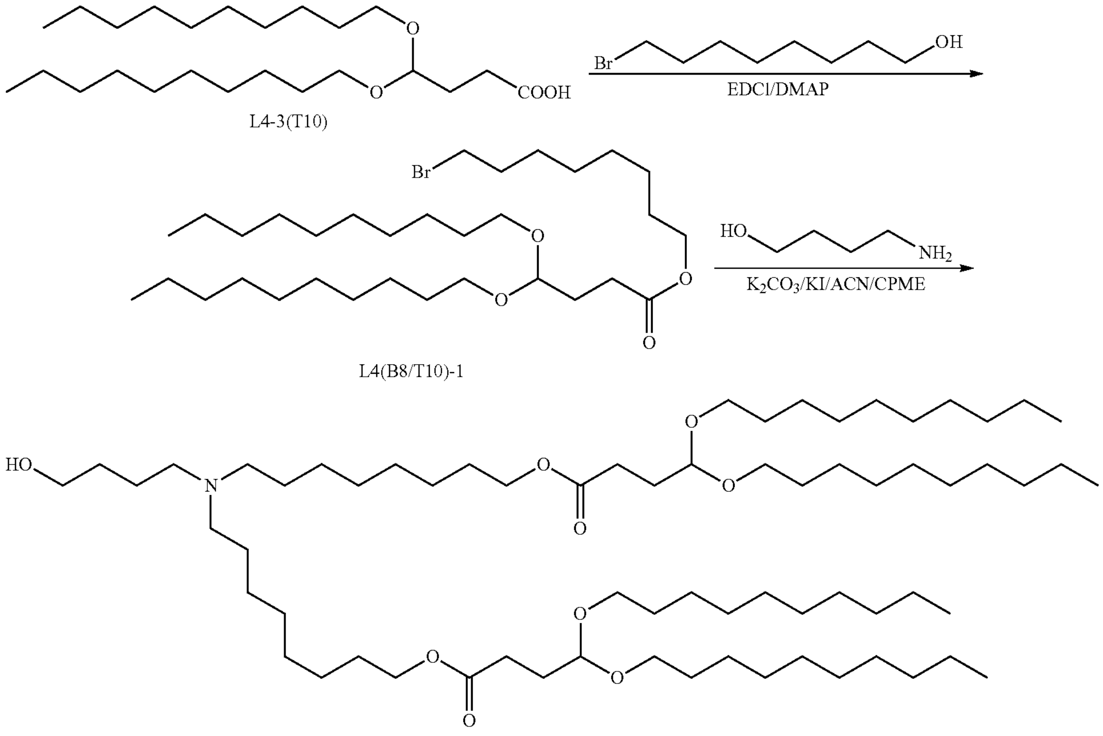

Compound 73

Synthesis of 8-bromooctyl 4,4-bis(decyloxy)butanoate (L4(B8/T10)-1)

L4(B8/T10)-1

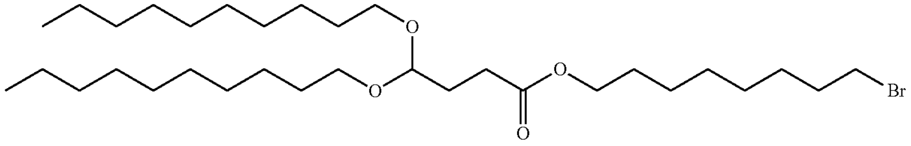

Prepared following Procedure C described in Compound 77 synthesis. Compound L4(B8/T10)-1 was isolated as colorless oil in a yield of 980 mg (67%). $^1$H-NMR (300 MHz, $CDCl_3$) δ 4.49 (t, 1H), 4.05 (t, 2H), 3.62-3.49 (m, 2H), 3.42-3.31 (m, 4H), 2.38 (t, 2H), 1.97-1.78 (m, 4H), 1.69-1.49 (m, 8H), 1.44–

Synthesis of ((4-hydroxybutyl)azanediyl)bis(octane-8,1-diyl) bis(4,4-bis(decyloxy)butanoate) (73)

Compound 73

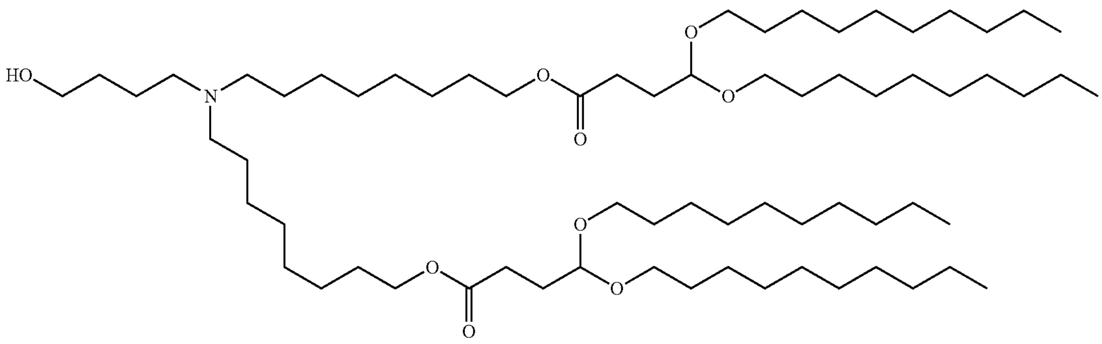

Prepared following Procedure D described in Compound 77 synthesis. Compound 73 was isolated as light-yellow oil in a yield of 442 mg (63%). $^1$H-NMR (300 MHz, $CDCl_3$) δ 4.49 (t, 2H), 4.05 (t, 4H), 3.67 (m, 2H), 3.59-3.49 (m, 4H), 3.44-3.31 (m, 4H), 3.18-2.51 (m, 6H), 2.36 (t, 4H), 1.97-1.78 (m, 6H), 1.74-1.44 (m, 24H), 1.38-1.12 (m, 78H), 0.87 (t, 12H); CIMS m/z $[M+H]^+$ 1111.9. Analytical HPLC column: Agilent Zorbax SB-C18, 5 μm, 4.6×150 mm, mobile phase A: acetonitrile with 0.1% trifluoroacetic acid, mobile phase B: water with 0.1% trifluoroacetic acid, use gradient: A in B 70% to 100% in 5 min, then 100% for 10 min. Flow rate: 1 mL/min, column temperature: 20±2° C., detector: ELSD, $t_R$=7.48 min, purity: >99.9%; UPLC column: Waters Aquity UPLC® CSHTM, C18, 1.7 μm, 3.0×150 mm, (Part No. 186005302), mobile phase A: acetonitrile with 0.1% trifluoroacetic acid, mobile phase B: water with 0.1% trifluoroacetic acid, use gradient: A in B 70% to 100% in 5 min, then 100% for 15 min. Flow rate: 1 mL/min, column temperature: 20±2° C., detector: CAD, $t_R$=7.72 min, purity: 99.6%.

Synthetic Scheme for Compound 65

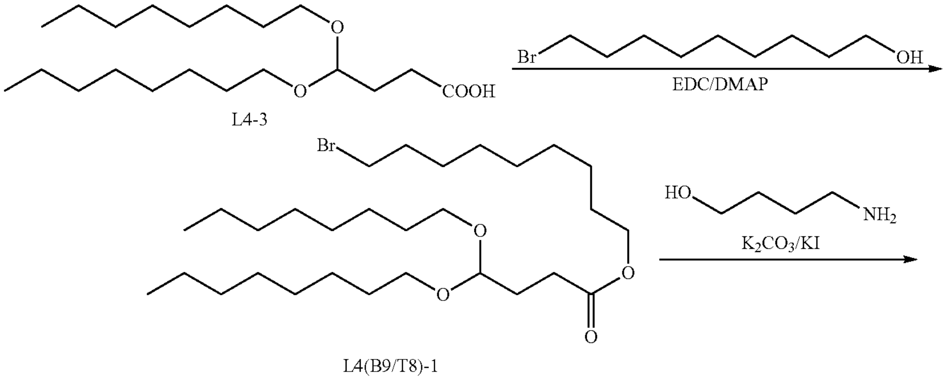

-continued

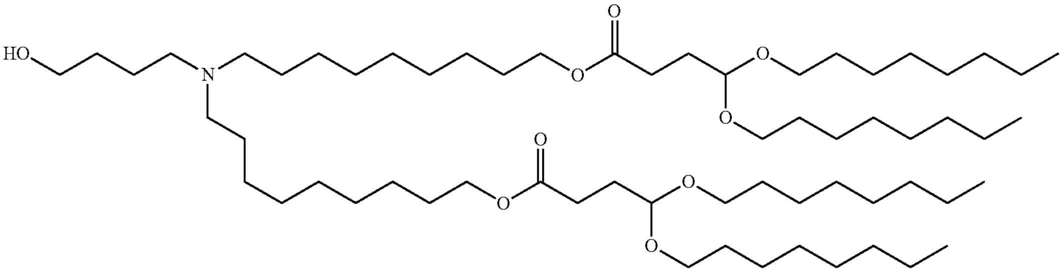

Compound 65

Synthesis of 9-bromononyl 4,4-bis(octyloxy)butanoate (L4(B9/T8)-1

L4(B9/T8)-1

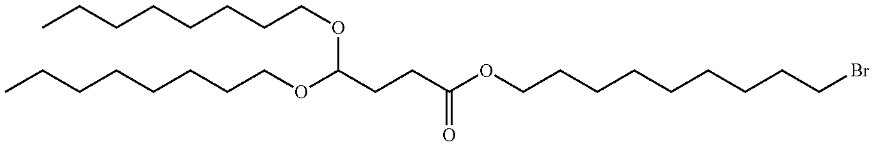

Prepared following Procedure C described in Compound 77 synthesis. Compound L4(B9/T8)-1 was isolated as light-yellow oil in a yield of 2.0 g (83%). $^1$H-NMR (300 MHz, $CDCl_3$) δ 4.49 (t, 1H), 4.05 (t, 2H), 3.62-3.49 (m, 2H), 3.42-3.31 (m, 4H), 2.38 (t, 2H), 1.97-1.78 (m, 4H), 1.69-1.49 (m, 6H), 1.44-1.18 (m, 30H), 0.87 (t, 6H).

Synthesis of ((4-hydroxybutyl)azanediyl)bis (nonane-9,1-diyl) bis(4,4-bis(octyloxy)butanoate) (65)

Compound 65

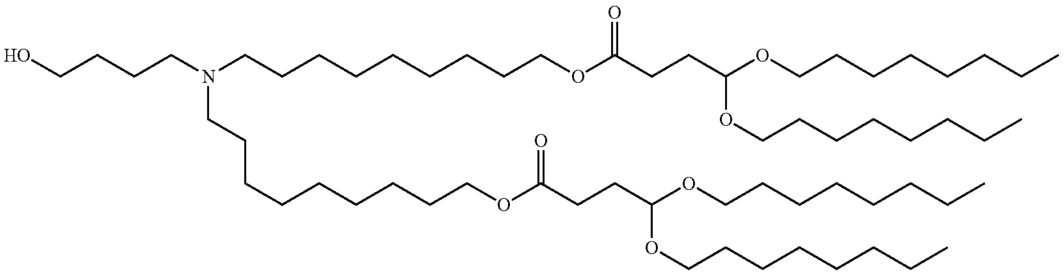

Prepared following Procedure D described in Compound 77 synthesis. Compound 65 was isolated as light-yellow oil in a yield of 880 mg (52%). $^1$H-NMR (300 MHz, $CDCl_3$) δ 4.49 (t, 2H), 4.05 (t, 4H), 3.68-3.49 (m, 6H), 3.45-3.34 (m, 4H), 2.96-2.46 (m, 6H), 2.37 (t, 4H), 1.97-1.86 (m, 4H), 1.84-1.42 (m, 24H), 1.40-1.12 (m, 57H), 0.87 (t, 12H); CIMS m/z $[M+H]^+$ 1027.9. Analytical HPLC column: Agilent Zorbax SB-C18, 5 μm, 4.6×150 mm, mobile phase A: acetonitrile with 0.1% trifluoroacetic acid, mobile phase B: water with 0.1% trifluoroacetic acid, use gradient: A in B 70% to 100% in 5 min, then 100% for 10 min. Flow rate: 1 mL/min, column temperature: 20±2° C., detector: ELSD, $t_R$=6.78 min, purity: >99.9%; UPLC column: Waters Aquity UPLC® CSHTM, C18, 1.7 μm, 3.0×150 mm, (Part No. 186005302), mobile phase A: acetonitrile with 0.1% trifluoroacetic acid, mobile phase B: water with 0.1% trifluoroacetic acid, use gradient: A in B 70% to 100% in 5 min, then 100% for 15 min. Flow rate: 1 mL/min, column temperature: 20±2° C., detector: CAD, $t_R$=7.17 min, purity: 99.1%.

Synthetic Scheme for Compound 70:

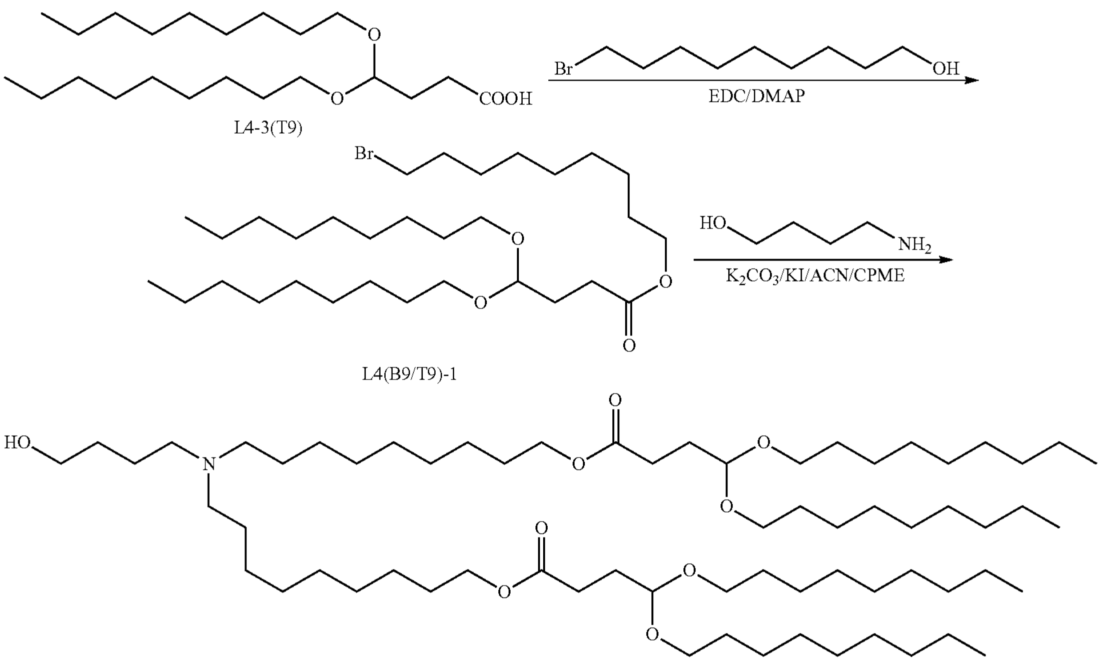

L4-3(T9)

L4(B9/T9)-1

Compound 70

Synthesis of 9-bromononyl 4,4-bis(nonyloxy)butanoate (L4(B9/T9)-1)

L4(B9/T9)-1

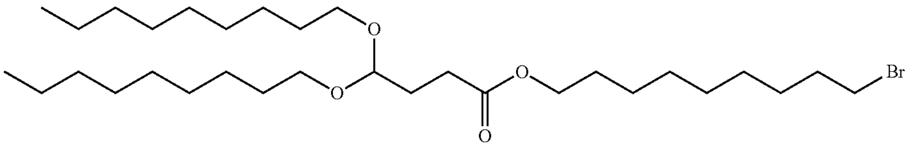

Prepared following Procedure C described in Compound 77 synthesis. Compound L4(B9/T9)-1 (810 mg, 52.25%) as a clear oil. $^1$H NMR (300 MHz, $CDCl_3$): δ 4.48 (t, J=7.0 Hz, 1H), 4.05 (t, J=7.0 Hz, 2H), 3.78-3.34 (m, 8H), 2.37 (t, J=7.0 Hz, 2H), 1.93-1.80 (m, 4H), 1.65-1.52 (m, 8H), 1.44-1.25 (m, 46H), 0.94-0.83 (m, 6H); CIMS m/z $[M+H]^+$ 578.87.

Synthesis of ((4-hydroxybutyl)azanediyl)bis(nonane-9,1-diyl) bis(4,4-bis(nonyloxy) butanoate) (70)

Compound 70

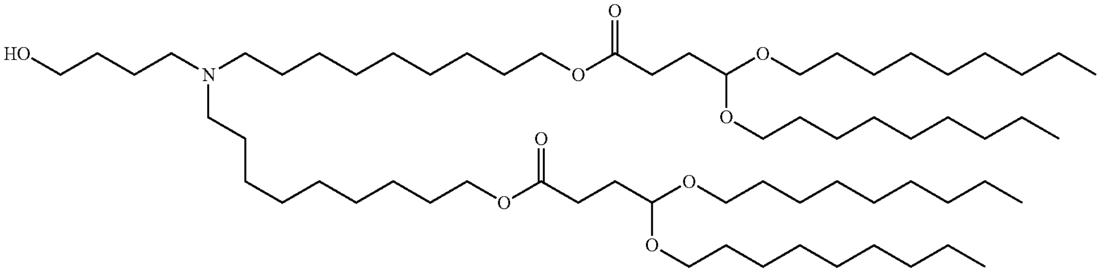

Prepared following Procedure D described in Compound 77 synthesis. Compound 70 (1.1 g, 89%). $^1$H NMR (300 MHz, $CDCl_3$): δ 4.48 (t, J=7.0 Hz, 2H), 4.05 (t, J=7.0 Hz, 4H), 3.70-3.34 (m, 10H), 2.42-2.34 (m, 10H), 1.93-1.80 (m, 4H), 1.65-1.52 (m, 20H), 1.42-1.23 (m, 71H), 0.90-0.83 (m, 12H); CIMS m/z $[M+H]^+$ 1083.77. Analytical HPLC column: Agilent Zorbax SB-C18, 5 μm, 4.6×150 mm, mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: ELSD, $t_R$=10.7 min, purity: >99%; UPLC column: Waters Aquity UPLC® CSHTM, C18, 1.7 μm, 3.0×150 mm, (Part No. 186005302), mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: CAD, $t_R$=15.9 min, purity: 98.08%.

Synthetic Scheme for Compound L4 (B10/T8)

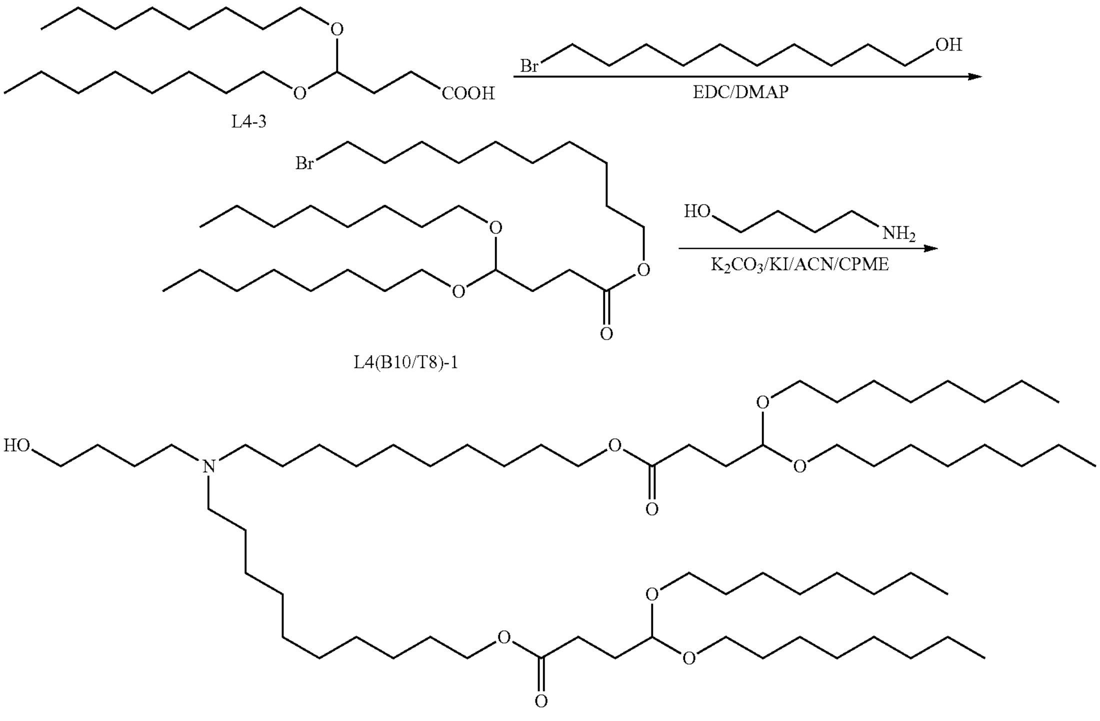

L4-3

L4(B10/T8)-1

Compound 76

Synthesis of 6-bromohexyl 4,4-bis(hexyloxy)butanoate Compound (L4(B10/T8)-1)

L4(B10/T8)-1

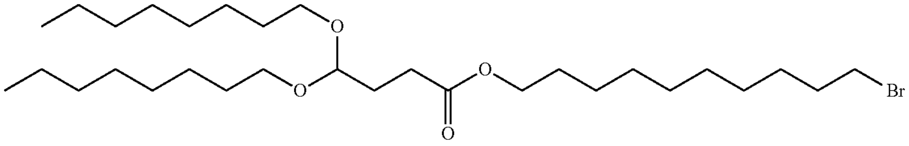

Prepared following Procedure C described in Compound 77 synthesis. Compound L4(B10/T8)-1 (1.6 g, 68%) was isolated as light-yellow oil. $^1$H NMR (300 MHz, $CDCl_3$): δ ppm 4.48 (t, 1H), 4.04 (t, 2H), 3.54-3.37 (m, 6H), 2.39-2.34 (m, 2H), 1.92-1.84 (m, 4H), 1.61-1.51 (m, 6H), 1.51-0.99 (m, 32H), 0.88-0.84 (m, 6H).

Synthesis of ((4-hydroxybutyl)azanediyl)bis(decane-10,1-diyl) bis(4,4-bis(octyloxy) butanoate) (76)

Compound 76

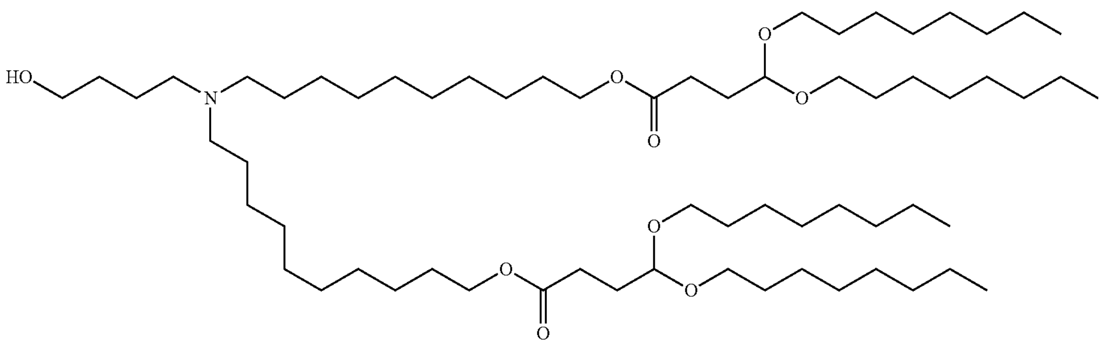

Prepared following Procedure D described in Compound 77 synthesis. Compound 76 (322 mg, 32%) was isolated as light-yellow oil. $^1$H-NMR (300 MHz, $CDCl_3$) δ 4.48 (t, 2H), 4.01-4.06 (m, 4H), 3.57-3.40 (m, 10H), 2.39-2.34 (m, 10H), 1.92-1.90 (m, 4H), 1.65-1.51 (m, 18H), 1.30-0.99 (m, 66H), 0.86 (t, 12H); APCI-MS: m/z $[M+H]^+$ 1055; Analytical HPLC column: Agilent Zorbax SB-C18, 5 μm, 4.6×150 mm, mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: ELSD, $t_R$=11.6 min, purity: >99%; UPLC column: Waters Aquity UPLC® CSHTM, C18, 1.7 μm, 3.0×150 mm, (Part No. 186005302), mobile phase A: acetonitrile with 0.1% trifluoroacetic acid, mobile phase B: water with 0.1% trifluoroacetic acid, use gradient: A in B 5% to 95% in 15 min, flow rate: 1 mL/min, column temperature: 20±2° C., detector: CAD, $t_R$=13.8 min, purity: >99%.

Synthetic Scheme for Compound 83

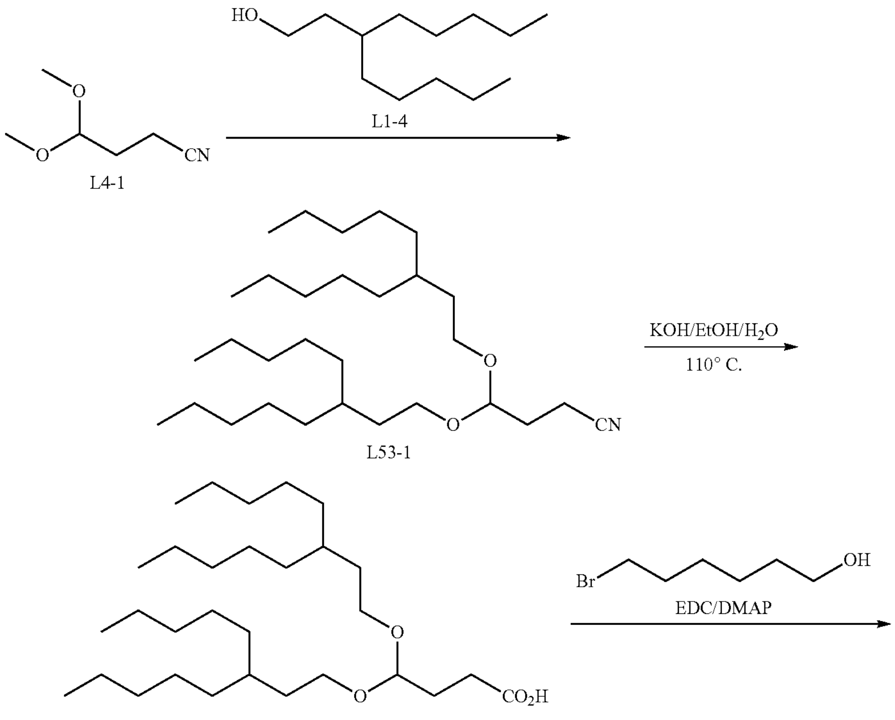

L53-2

-continued

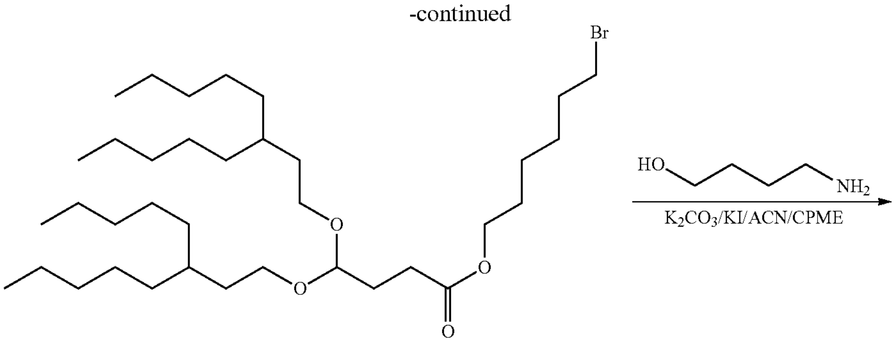

L53-3

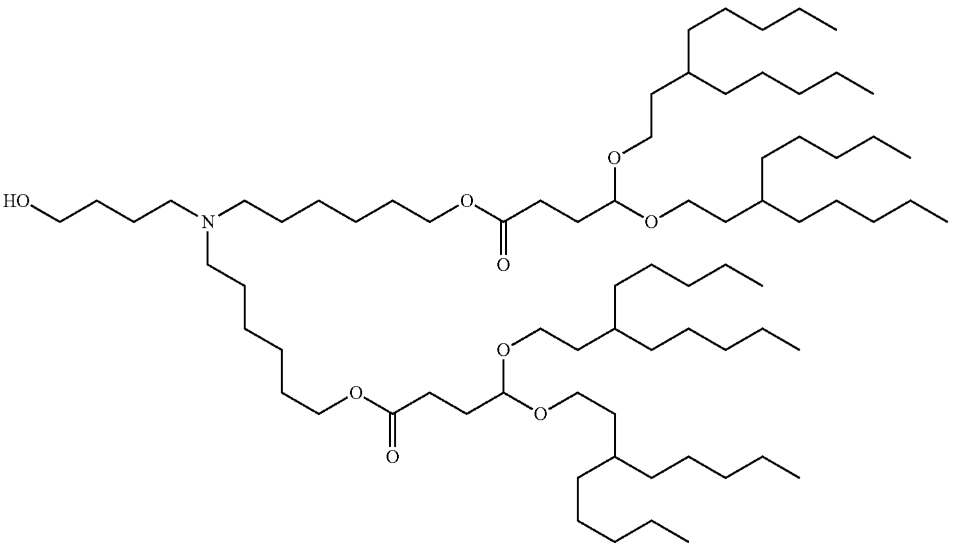

Compound 83

Synthesis of 8-bromooctyl 4,4-bis((3-pentyloctyl)oxy)butanenitrile (L53-1)

L53-1

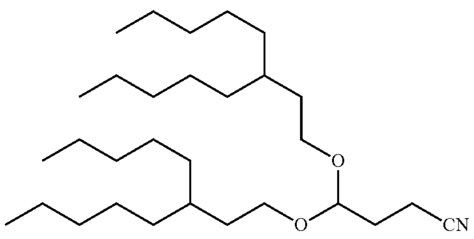

Prepared following Procedure A described in Compound 77 synthesis. L53-1 was isolated as light-yellow oil (3.66 g, 95%). $^{1}$H-NMR (300 MHz, $CDCl_3$) δ 4.54 (t, 1H), 3.64-3.52 (m, 2H), 3.48-3.37 (m, 2H), 2.42 (t, 2H), 1.97-1.84 (m, 2H), 1.61-1.44 (m, 4H), 1.44-1.08 (m, 28H), 0.87 (m, 12H).

Synthesis of 8-bromooctyl 4,4-bis((3-pentyloctyl)oxy)butanoic acid (L53-2)

L53-2

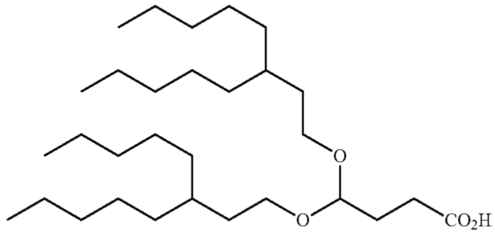

Prepared following Procedure B described in Compound 77 synthesis. L53-2 was isolated as light-yellow oil (3.2 g, 84%). CIMS m/z $[M-H]^-$ 683.

Synthesis of 6-bromohexyl 4,4-bis((3-pentyloctyl)oxy)butanoate (L53-3)

L53-3

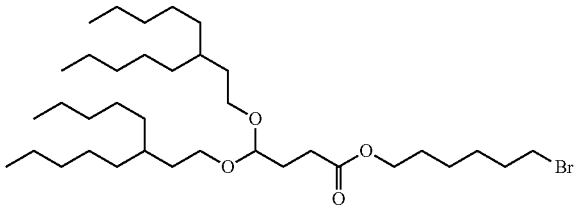

Prepared following Procedure C described in Compound 77 synthesis. L53-3 was isolated as light-yellow oil (400 mg, 32%). $^1$H-NMR (300 MHz, $CDCl_3$) δ 4.49 (t, 1H), 4.06 (t, 2H), 3.63-3.51 (m, 2H), 3.50-3.31 (m, 4H), 2.42 (t, 2H), 1.97-1.81 (m, 2H), 1.57-1.43 (m, 8H), 1.43-1.08 (m, 38H), 0.87 (m, 12H).

Synthesis of ((4-hydroxybutyl)azanediyl)bis(hexane-6,1-diyl) bis(4,4-bis((3-pentyloctyl)oxy)butanoate) (83)

Compound 83

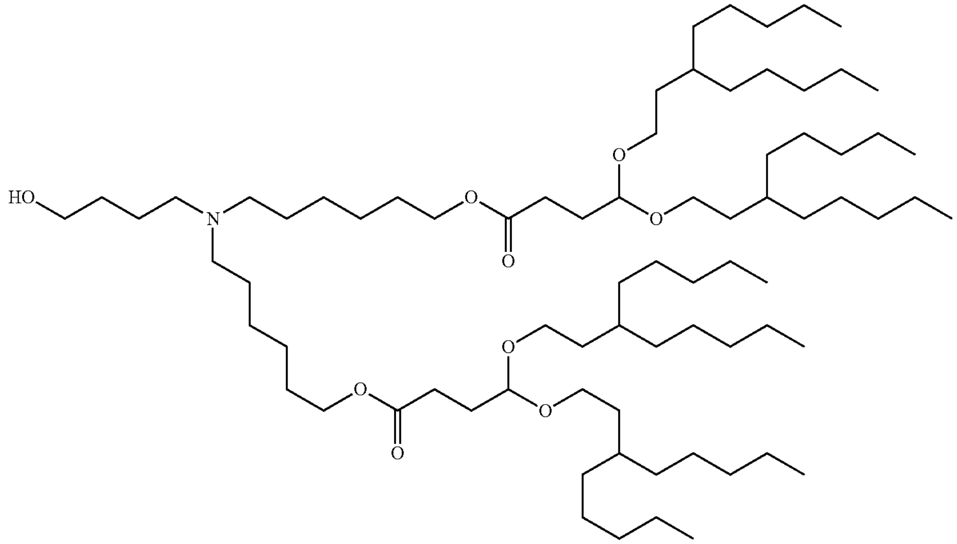

Prepared following Procedure D described in Compound 77 synthesis. Compound 83 was isolated as light-yellow oil (252 mg, 74%). $^1$H-NMR (300 MHz, $CDCl_3$) δ 4.48 (t, 2H), 4.05 (t, 4H), 3.71-3.62 (m, 2H), 3.62-3.51 (m, 4H), 3.47-3.3.36 (m, 4H), 3.08-2.58 (m, 6H), 2.37 (t, 4H), 1.97-1.86 (m, 4H), 1.74-1.56 (m, 10H), 1.55-1.46 (m, 8H), 1.44-1.06 (m, 80H), 0.87 (m, 24H); CIMS m/z $[M+H]^+$ 1223.2. Analytical HPLC column: Agilent Zorbax SB-C18, 5 μm, 4.6×150 mm, mobile phase A: acetonitrile with 0.1% trifluoroacetic acid, mobile phase B: water with 0.1% trifluoroacetic acid, use gradient: A in B 70% to 100% in 5 min, then 100% for 10 min. Flow rate: 1 mL/min, column temperature: 20±2° C., detector: ELSD, $t_R$=8.33 min, purity: >99.9%; UPLC column: Waters Aquity UPLC® CSHTM, C18, 1.7 μm, 3.0×150 mm, (Part No. 186005302), mobile phase A: acetonitrile with 0.1% trifluoroacetic acid, mobile phase B: water with 0.1% trifluoroacetic acid, use gradient: A in B 80% to 100% in 15 min, then 100% for 5 min. Flow rate: 1 mL/min, column temperature: 20±2° C., detector: CAD, $t_R$=16.4 min, purity: 99.7%.

Example 5

Preparation of Lipid Nanoparticles—General Procedure

Representative Lipids of the Disclosure, distearoylphosphatidylcholine (DSPC), cholesterol, and 1,2-dimyristoyl-rac-glycero-3-methoxypolyethylene glycol-2000 (DMG-PEG2000) were dissolved in pure ethanol at a molar ratio of 48.5:10:40:1.5 (IM administration) or 48.5:10:39:2.5 (IV administration) with a total lipid concentration of 10.8 mM. See, e.g., Qiu et al., *PNAS* 118:e2020401118 (2021). The lipid solution was then mixed with an acidic sodium acetate buffer (pH 4.0) or sodium citrate buffer (pH 4.0) containing mRNA (0.10 mg/mL0) by using the NanoAssemblr microfluidic system. The mRNA solution and the lipid solution were each injected into the NanoAssemblr microfluidic device at 12 mL/min total flow rate with mRNA solution to lipid solution at ratio of 3:1, and the device resulted in the rapid mixing of the two components and thus the self-assembly of LNPs. Formulations were further dialyzed against PBS (pH 7.4) or 20 mM Tris (pH 7.4) with 8% sucrose solution in dialysis cassettes overnight at 4° C. The particle size of formulations was measured by dynamic light scattering (DLS) using a Zetasizer Ultra (Malvern Panalytical). RNA encapsulation efficiency was characterized by Ribogreen assay.

Example 5-A

LNP Formulations A

Ionizable lipids, DSPC, cholesterol, and PEG2K-DMG were dissolved in pure ethanol at a 48.5:10:39:2.5 mol % ratio with a total lipid concentration of 10.8 mM. A 0.10 mg/mL mRNA solution was prepared using acidic buffer (pH 4.0-5.0) containing mRNAs encoding human erythropoietin (hEPO) and firefly luciferase (fLuc) (1:2 ratio). The nucleotide and lipid solutions were mixed at a 3:1 volume ratio using the NanoAssemblr microfluidic system at a 12 mL/min total flow rate resulting in rapid mixing and self-assembly of LNPs. Formulations were further dialyzed against PBS (pH 7.4) overnight at 4° C., concentrated using centrifugal filtration and filtered (0.2 μm pore size). The particle size and polydispersity index (PDI) of formulations was measured by dynamic light scattering (DLS) using a Zetasizer Ultra (Malverm Panalytical). RNA encapsulation efficiency (EE %) was determined by Ribogreen assay.

TABLE 5A

| ACYCLIC LNP Formulations | | | | | |
|---|---|---|---|---|---|
| Form. | Ionizable Lipid | Acidic Buffer | Size (nm) | PDI | EE % |
| F-1 | 14 | A | 74.4 | 0.13 | 91.4 |
| F-2* | 14 | A | 59.3 | 0.07 | 90.9 |
| F-3 | 14 | B | 86.0 | 0.03 | 98.0 |
| F-4 | 50 | A | 76.7 | 0.15 | 93.1 |
| F-5 | 51 | A | 76.7 | 0.13 | 94.6 |
| F-6 | 52 | A | 81.5 | 0.22 | 88.9 |
| F-7 | 53 | A | 102.3 | 0.08 | 80.7 |
| F-8 | 54 | B | 64.8 | 0.08 | 96.5 |
| F-9 | 55 | A | 76.7 | 0.12 | 93.2 |
| F-10 | 56 | B | 94.1 | 0.15 | 95.5 |
| F-11 | 57 | A | 76.0 | 0.09 | 94.2 |
| F-12 | 58 | A | 114.4 | 0.09 | 86.4 |
| F-13 | 59 | A | 109.7 | 0.08 | 87.0 |
| F-14 | 60 | A | 93.2 | 0.09 | 48.6 |
| F-15 | 61 | A | 70.1 | 0.24 | 94.7 |
| F-16 | 62 | B | 86.9 | 0.13 | 93.0 |
| F-19 | 64 | B | 85.9 | 0.05 | 98.0 |
| F-20 | 65 | B | 80.7 | 0.03 | 98.0 |
| F-21 | 66 | B | 83.2 | 0.05 | 89.0 |
| F-22 | 67 | B | 90.7 | 0.05 | 92.0 |
| F-23 | 68 | B | 88.0 | 0.03 | 90.0 |
| F-24 | 69 | B | 73.4 | 0.04 | 92.3 |
| F-25 | 70 | B | 90.1 | 0.03 | 86.0 |
| F-26 | 71 | B | 97.5 | 0.03 | 98.0 |
| F-27 | 72 | B | 86.8 | 0.00 | 99.0 |
| F-28 | 73 | B | 84.6 | 0.02 | 98.0 |
| F-29 | 74 | B | 91.3 | 0.02 | 98.0 |
| F-30 | 75 | B | 94.0 | 0.03 | 86.0 |
| F-31 | 76 | B | 93.4 | 0.04 | 83.0 |
| F-32 | 77 | B | 72.2 | 0.06 | 96.0 |
| F-33 | 78 | B | 72.1 | 0.05 | 97.5 |
| F-34 | 79 | B | 67.7 | 0.10 | 96.0 |
| F-35 | 81 | B | 79.7 | 0.07 | 91.0 |
| F-36 | 82 | B | 72.1 | 0.11 | 97.1 |
| F-37 | 83 | B | 81.5 | 0.11 | 93.9 |
| F-38 | 84 | B | 96.1 | 0.11 | 94.5 |
| F-39 | 85 | B | 69.9 | 0.07 | 94.8 |

Buffer A: 25 mM Sodium Acetate, pH 5.0; Buffer B: 50 mM Citrate, pH 4.0

Example 5-B

LNP Formulations B

Ionizable lipids, DSPC, cholesterol, and PEG2K-DSPE were dissolved in pure ethanol at a 48.5:10:40:1.5 mol % ratio with a total lipid concentration of 10.8 mM. A 0.10 mg/mL mRNA solution was prepared using acidic buffer (pH 4.0-5.0) containing mRNAs encoding firefly luciferase (fLuc). The nucleotide and lipid solutions were mixed at a 3:1 volume ratio using the NanoAssemblr microfluidic system at a 12 mL/min total flow rate resulting in rapid mixing and self-assembly of LNPs. Formulations were further dialyzed against PBS (pH 7.4) overnight at 4° C., concentrated using centrifugal filtration and filtered (0.2 μm pore size). The particle size and polydispersity index (PDI) of formulations was measured by dynamic light scattering (DLS) using a Zetasizer Ultra (Malvern Panalytical). RNA encapsulation efficiency (EE %) was determined by Ribogreen assay.

TABLE 5B

| ACYCLIC LNP Formulations | | | | | |
|---|---|---|---|---|---|
| Form. | Ionizable Lipid | Acidic Buffer | Size (nm) | PDI | EE % |
| F-40 | 68 | B | 91.4 | 0.032 | 86.0% |

Buffer A: 25 mM Sodium Acetate, pH 5.0; Buffer B: 50 mM Citrate, pH 4.0

Example 5-C

LNP Formulations C

Ionizable lipids, DSPC, cholesterol, and PEG2K-DMG were dissolved in pure ethanol at a 48.5:10:40:1.5 mol % ratio (formulations comprising ionizable lipids of the present disclosure) or 50:10:38.5:1.5 mol % ratio (SM102 formulations) with a total lipid concentration of 10.8 mM. A 0.10 mg/mL RNA solution was prepared using acidic buffer (pH 4.0-5.0) containing circular RNAs (oRNA) or linear mRNA encoding COVID spike protein, as indicated in Table 5C. The nucleotide and lipid solutions were mixed at a 3:1 volume ratio using the NanoAssemblr microfluidic system at a 12 mL/min total flow rate resulting in rapid mixing and self-assembly of LNPs. Formulations were further dialyzed against cryobuffer overnight at 4° C., concentrated using centrifugal filtration and filtered (0.2 μm pore size). The formulations were then stored at −80° C. until used. The particle size and polydispersity index (PDI) of formulations was measured by dynamic light scattering (DLS) using a Zetasizer Ultra (Malvern Panalytical). RNA encapsulation efficiency (EE %) was determined by Ribogreen assay.

TABLE 5C

| ACYCLIC LNP Formulations | | | | | | |
|---|---|---|---|---|---|---|
| Form. | Ionizable Lipid | Spike RNA | Buffer | Size (nm) | PDI | EE % |
| F-41 | 68 | oRNA | B | 89.29 | 0.28 | 97.7 |
| F-42 | 59 | oRNA | A | 90.37 | 0.082 | 96.7 |
| F-43 | Moderna SM102 | oRNA | A | 73.39 | 0.041 | 98.5 |
| F-44 | Moderna SM102 | Linear mRNA | A | 76.15 | 0.091 | 98.1 |

Buffer A: 25 mM Sodium Acetate, pH 5.0;
Buffer B: 50 mM Citrate, pH 4.0

Example 6 hEPO and fLUC In Vivo Reporter Assays

Balb/cAnNCrl (female, 6-8 weeks) were administrated with LNPs (formulated with 0.1 mg/kg EPO and 0.2 mg/kg Luc, see Example 5-A) by intravenous injection. Plasma samples were harvested at 5, 23 and 47 hours post dose for hEPO analysis. Bioluminescence imaging (BLI) of the mice was taken at 6, 24 and 48 hours post-dosing using an IVIS Lumina III LT system (PerkinElmer) after injection of D-luciferin solution (150 mg/kg, intraperitoneal injection (IP)) to determine. hEPO concentrations were measured using an ELISA kit (DEP00, R&D Systems). The maximal concentration or BLI signal (Cmax) and area under concentration vs time curve (AUC) of the individual mouse plasma hEPO or whole body BLI data was calculated using a non-compartment analysis (NCA) program (WinNonlin®, Version 8.3.4 [Pharsight Corp (Mountain View, CA, USA)]).

Table 6 reports the hEPO concentration at 5 hours and the AUC over the 48 hour period after dosing, both overall and vs an internal standard across experiments, for each formulation tested. Table 6 also reports the luciferase bioluminescence imaging measured at 6 hours and the AUC over the 48 hour period after dosing, for each formulation tested.

Data keys:

hEPO C5 hr (IU/μL): +=<10 IU/μL; 10 IU/μL≤++<100 IU/μL; 100≤+++<1,000 IU/μL hEPO AUC (hr*IU/μL): +=<10 hr*IU/μL; 10 hr*IU/μL≤++<100 hr*IU/μL; 100 hr*IU/μL≤+++<1,000 hr*IU/μL; 1,000 hr*IU/μL≤++++<10,000 hr*IU/μL

AUC ratio vs standard: * =<0.1; 0.1≤ <0.5; 0.5≤* <1.0; 1.0≤** <1.5; 1.5≤* <2.0; *** ≥2.0

Luciferase BLI C6 hr (photons/sec): #=<100 million p/s; 100 million p/s ≤##<1 billion p/s; 1 billion p/s ≤###<10 billion p/s; 10 billion p/s ≤####<100 billion p/s; 100 billion p/s ≤#####<1 trillion p/s Luciferase BLI AUC48 hr (hr*photons/sec): $ <10 billion hr*p/s; 10 billion hr*p/s ≤$$ <100 billion hr*p/s; 100 billion hr*p/s ≤$$$ <1 trillion hr*p/s; 1 trillion hr*p/s ≤$$$$ <10 trillion hr*p/s

TABLE 6

ACYCLIC In Vivo Assay Data

| | hEPO | | | Luciferase BLI Activity | |
|---|---|---|---|---|---|
| Form. | $C_{5\ hr}$ | $AUC_{0-48\ hr}$ | AUC ratio | $C_{6\ hr}$ | $AUC_{0-48\ hr}$ |
| F-1 | +++ | ++++ | **** | #### | $$$$ |
| F-2 | ++ | ++++ | ** | #### | $$$ |
| F-3 | ++ | ++++ | **** | #### | $$$ |
| F-4 | +++ | ++++ | *** | #### | $$$ |
| F-5 | +++ | ++++ | *** | #### | $$$$ |
| F-6 | +++ | ++++ | *** | #### | $$$$ |
| F-7 | +++ | ++++ | ***** | #### | $$$$ |
| F-8 | +++ | ++++ | **** | #### | $$$ |
| F-9 | +++ | ++++ | *** | #### | $$$ |
| F-10 | + | ++ | * | ## | $ |
| F-11 | +++ | ++++ | *** | #### | $$$$ |
| F-12 | ++ | ++++ | ** | #### | $$$ |
| F-13 | ++ | ++++ | ** | #### | $$$ |
| F-14 | + | +++ | * | ## | $$ |
| F-15 | + | ++ | * | # | $ |
| F-16 | + | +++ | * | ### | $$ |
| F-19 | +++ | ++++ | ***** | #### | $$$ |
| F-20 | ++ | ++++ | **** | #### | $$$ |
| F-21 | +++ | ++++ | ****** | #### | $$$$ |
| F-22 | +++ | ++++ | ****** | #### | $$$$ |
| F-23 | +++ | ++++ | ****** | #### | $$$$ |
| F-24 | +++ | ++++ | ***** | #### | $$$$ |
| F-25 | ++ | ++++ | *** | #### | $$$ |
| F-26 | ++ | ++++ | *** | #### | $$$ |
| F-27 | ++ | ++++ | *** | #### | $$$ |
| F-28 | ++ | +++ | *** | ### | $$$ |
| F-29 | ++ | +++ | ** | ### | $$$ |
| F-30 | +++ | ++++ | ***** | #### | $$$ |
| F-31 | ++ | ++++ | **** | #### | $$$ |
| F-32 | +++ | ++++ | **** | #### | $$$$ |
| F-33 | +++ | ++++ | ****** | #### | $$$$ |
| F-34 | ++ | +++ | ** | #### | $$$ |
| F-35 | +++ | ++++ | ***** | #### | $$$ |
| F-36 | +++ | ++++ | ***** | #### | $$$$ |
| F-37 | ++ | +++ | ** | #### | $$$ |
| F-38 | +++ | ++++ | ***** | ##### | $$$$ |
| F-39 | +++ | ++++ | **** | #### | $$$$ |

Example 7

In Vivo Organ Tropism assays

Balb/cAnNCrl (female, 6-8 weeks) were dosed LNP formulations (formulated with 0.2 mg/kg Luc mRNA, see Example 5B) by IV injection. At 6 hour post LNP dose, the mice were injected with D-luciferin solution (150 mg/kg, intraperitoneal (IP)). 10 minutes post D-luciferin dosing, Mice were sacrificed and organs (liver, spleen, lung, heart, kidney) were harvested. Bioluminescence imaging of the organs from each dosing groups were taken simultaneously using an IVIS Lumina III LT system (PerkinElmer).

The sum of the bioluminescence of all organs from each individual mouse were summed as the total flux (photons/second). The percentage of bioluminescence of each individual organ was calculated to determine the organ tropism of the LNP formulations.

Luciferase BLI C6 hr (photons/sec): #=<100 million p/s; 100 million p/s ≤##<1 billion p/s

TABLE 7

Total Flux of organs and percentage flux in each organ [ACYCLIC]

| | Total Flux | % of total flux at 6 hr post dose | | | | |
|---|---|---|---|---|---|---|
| Form. | (p/s) | liver | spleen | lung | kidney | heart |
| F-40 | # | 78.8 | 18.3 | 1.7 | 0.8 | 0.3 |

Example 8-A

In Vivo T Cell Responses to Spike Protein Encoding RNA—Murine

Dosing Protocol

LNP formulations were prepared as described in Example 5-C. Each formulation was injected in 5 BALB/c mice intramuscularly on day 0 and 21 with 0.02 mg/ml oRNA or linear mRNA encoding COVID spike protein in a total volume of 0.5 mL. Prior to dosing BALB/c mice were placed in a chamber prefilled with isoflurane at a flow rate of 0.4-0.8 liter/min until sedated so that no movement occurred during injection. The injection site was monitored for irritation after both doses. On day 35 all mice were humanely euthanized by $CO_2$ inhalation and spleens were collected and stored on wet ice until processing. All in vivo experiments in this study were performed under the approved animal care guidelines.

Analysis

Spleens were harvested and manually dissociated into single cell suspensions by filtration using a 70 μm filter (Miltenyi 130-098-462) and washed with 1×PBS (Fisher 10010049) containing 2 mM EDTA (ThermoFisher 15575-020) and 0.5% BSA (Miltenyi 130-091-376). Red blood cells were lysed using ACK Lysisg Buffer (ThermoFisher A1049201) and washed twice with 1×PBS+2 mM EDTA+0.5% BSA. Following final wash, cells were resuspended in 1×PBS and counted (ViCell XR, Beckman Coulter 731196). Cells were resuspended in CTL Test Plus Medium (C.T.L. CTLTP-005) containing 1×GlutaMAX (ThermoFisher TP-050122) and 1×Pen/Strep (ThermoFisher 15-140-122) at appropriate concentrations and plated for downstream functional assays.

ELISpot analysis was performed using the mouse IFN-γ ELISpotPLUS Kit (Mabtech 3321-4HST-10), according to the manufacturer's protocol. Briefly, plates were washed with 1×PBS and blocked with RPMI (ThermoFisher 72400-047) containing 10% FBS (ThermoFisher A38400-01) for 1 h at 37° C. Following blocking, cells were plated at 200,000 cells/well for DMSO and peptide-stimulated wells or 25,000 cells/well for PMA/Ionomycin treatment. Cells were incubated with either 1% DMSO (ThermoFisher D12345), 7.5 μg/mL of S1 or S2 peptide pools spanning the Spike protein of SARS-CoV-2 (JPT PM-WCPV-S-1), or 1×PMA/Ionomycin (ThermoFisher 00-4970-93) in triplicate. The plates were incubated overnight 37° C., 5% $CO_2$. Following incubation, plates were washed, and 1 μg/mL detection antibody added for 2 h at room temperature. Washes were repeated and 1×Streptavidin-HRP added and incubated for 1 hr at room temperature. Finally, plates were washed and TMB substrate added, incubated in the dark for spot development, then washed out using tap water. Plates were allowed to dry and counted by an ELISpot analyzer (ZellNet Consulting).

For intracellular staining (ICS) 5,000,000 cells per well were plated in a 96-well round bottom plate (Costar 3799) and stimulated using the same ELISpot conditions as described above and incubated at 37 C with 5% $CO_2$ for a total of 5.5 h. Golgi Plug (BD 555029) was added to all wells for the last 4.5 h of stimulation. Following incubation, cells were stained for flow cytometry using surface or intracellular antibodies listed in the table below. Briefly, cells were washed with 1×PBS and stained with Live/Dead Fixable Aqua (Invitrogen L34966) for 20 min at room temperature. Cells were then washed twice with Cell Staining Buffer (BioLegend 420201) and incubated with Fc Block (Biolegend 156604) for 5 min at 4° C., followed by surface antibody staining for 30 min at 4° C. Thereafter, cells were washed twice with Cell Staining Buffer, fixed at 4° C. for 30 min IC Fixation Buffer (ThermoFisher 88-8824-00) and permeabilized in 1× permeabilization buffer (ThermoFisher 88-8824-00) and intracellular staining performed overnight at 4° C. Thereafter, cells were washed twice with 1× permeabilization buffer, resuspended in 1×PBS, and acquired on cytometer (ThermoFisher Attune NXT with a laser configuration of Blue(3)/Red(3)/Violet(4)/Yellow(4)) equipped with a high-throughput autosampler (ThermoFisher CytKick). Compensation was performed using UltraComp eBeads (ThermoFisher 01-3333-41) and ArC Amine Reactive Compensation Bead Kit (ThermoFisher A10346).

Results Acyclic

Mice dosed with novel LNP formulations F-41 and F-42 demonstrated spike-specific polyfunctional CD4 T Cell responses comparable to the Moderna SM102 LNP formulations F-43 and F-44.

Example 8-B

In Vivo T Cell Responses to Spike Protein Encoding RNA—Non-Human Primate

Dosing Protocol

LNP formulations were prepared as described in Example 5-C. Each formulation was injected in 3 non-naïve Cynomolgus monkeys once on Day 1 and once on Day 22 via intramuscular injections at a dose level of 100 μg. All NHPs were temporarily restrained for dose administration and not sedated. Prior to dosing, the dosing site was shaved and marked as necessary for clinical observations. Each dose was administered using a syringe/needle within the demarcated area. Samples were collected throughout the study for clinical pathology parameters, pharmacokinetic analysis and immunogenicity analysis.

Analysis

Cryopreserved PBMCs were thawed in a 37° C. water bath and cells transferred to conical tube containing complete RPMI (RPMI [ThermoFisher 72400-047] containing 10% FBS [ThermoFisher A38400-01] and 1×Pen/Strep [ThermoFisher 15-140-122]. Cells were centrifuged, resuspended in complete RPMI containing 50 U/mL Benzonase (EMD 70664-10KUN), and incubated for 15 min at 37° C. Cells were centrifuged, resuspended in complete RPMI, and rested for 3 hr. Cells were centrifuged and resuspended in CTL Test Plus Medium (C.T.L. CTLTP-005) containing 1× GlutaMAX (ThermoFisher TP-050122) and 1×Pen/Strep and counted (ViCell XR, Beckman Coulter 731196). Concentrations were adjusted and cells plated for downstream functional assays.

ELISpot analysis was performed using the Monkey IFN-γ ELISpotPLUS Kit (Mabtech 3421M-4HST-10) according to the manufacturer's protocol. Briefly, plates were washed with 1×PBS and blocked with RPMI (ThermoFisher 72400-047) containing 10% FBS (ThermoFisher A38400-01) for 1 h at 37° C. Following blocking, cells were plated in triplicate and stimulated under the following conditions: no peptide (1% DMSO (ThermoFisher D12345)), 0.5 μg/mL of S1+S2 peptide pools spanning the Spike protein of SARS-CoV-2 (JPT PM-WCPV-S-1), and 1×PMA/Ionomycin (ThermoFisher 00-4970-93). 200,000 cells/well were plated for DMSO and peptide pool stimulations and 10,000/well from pooled samples from each group for PMA/Ionomycin stimulation.

The plates were incubated overnight 37° C., 5% $CO_2$. Following incubation plates were washed, and 1 μg/mL detection antibody added for 2 h at room temperature. Washes were repeated and 1× Streptavidin-HRP added and incubated for 1 h at room temperature. Finally, plates were washed and TMB substrate added, incubated in the dark for spot development, then washed out using tap water. Plates were allowed to dry and counted using an ELISpot analyzer (ZellNet Consulting).

For intracellular staining (ICS), approximately 2,000,000 cells per well from each animal were plated in a 96-well round bottom plate (Costar 3799) and stimulated using the same ELISpot conditions described above. After one hour of stimulation, Golgi Plug (BD 555029) was added to all wells and plates incubated overnight at 37° C. with 5% $CO_2$. Thereafter, cells were washed and stained for flow cytometry. Briefly, cells were washed with 1×PBS and stained with Live/Dead Fixable Aqua (Invitrogen L34966) for 20 min at room temperature. Cells were then washed twice with Cell Staining Buffer (BioLegend 420201) and incubated with Fc Block (Biolegend 156604) for 5 min at 4° C., followed by surface antibody staining for 30 min at 4° C. Following surface staining, cells were then washed twice with Cell Staining Buffer and fixed at 4° C. for 30 min in IC Fixation Buffer and permeabilized in (ThermoFisher 88-8824-00) 1× permeabilization buffer (ThermoFisher 88-8824-00). Intracellular staining was performed for 1 hr at 4° C. Thereafter, cells were washed twice with 1× permeabilization buffer, resuspended in 1×PBS, and acquired on cytometer (ThermoFisher Attune NXT with a laser configuration of Blue (3)/Red(3)/Violet(4)/Yellow(4)) equipped with a high-throughput autosampler (ThermoFisher CytKick). Compensation was performed using UltraComp eBeads (ThermoFisher 01-3333-41) and ArC Amine Reactive Compensation Bead Kit (ThermoFisher A10346).

Results Acyclic

NHPs dosed with novel LNP formulations F-41 and F-42 demonstrated spike-specific polyfunctional CD4 T Cell responses that were greater or comparable to the Moderna SM102 LNP formulations as assessed by ICS assay. Two weeks post-boost (day 36) LNP formulations F-41 demonstrated 30 and −2.6 fold greater spike-specific CD4 T Cell response as compared to formulation F-43 and F-44, respectively. Spike-specific CD4 T cell responses induced by F-42 formulation was 16-fold higher than F-43 and comparable to F-44 formulations. At Day 36, antigen-specific T cell responses in NHPs induced by novel LNP formulations F-41 and F-42 were greater than Moderna SM102 LNP formulations as determined by ELISpot assay. NHPs dosed with F-41 elicited Spike-specific IFNγ producing T cells that were 16 and 6-fold higher than T cell responses induced by F-43 and F-44 formulations, respectively. F-42 LNP formulations also induced increased spike-specific IFNγ producing T cells in NHPs that were 11 and 4-fold higher than those elicited by F-43 and F-44 formulations, respectively.

XIII. EQUIVALENTS AND SCOPE

Those skilled in the art will recognize, or be able to ascertain using no more than routine experimentation, many equivalents to the specific embodiments in accordance with the disclosure described herein. The scope of the present disclosure is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or the entire group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

The term "about" as used herein, means within 10% of a given value or range. Thus, "about 10" means 9 to 11.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the disclosure, to the tenth of the unit of the lower limit of the range, unless the context clearly dictates otherwise.

In addition, it is to be understood that any particular embodiment of the present disclosure that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the disclosure (e.g., any antibiotic, therapeutic or active ingredient; any method of production; any method of use; etc.) can be excluded from any one or more claims, for any reason, whether or not related to the existence of prior art.

It is to be understood that the words which have been used are words of description rather than limitation, and that changes may be made within the purview of the appended claims without departing from the true scope and spirit of the disclosure in its broader aspects.

While the present disclosure has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the disclosure.

The invention claimed is:

1. A compound selected from the group consisting of

| Structure | Cpd. |
| --- | --- |
| 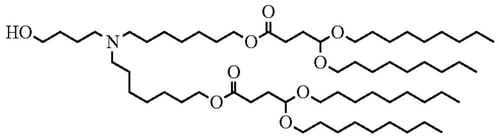 [SMILES: CCCCCCCCCOC(CCC(=O)OCCCCCCCN(CCCCO)CCCCCCCOC(=O)CCC(OCCCCCCCCC)OCCCCCCCCC)OCCCCCCCCC] | 68 |

or a pharmaceutically acceptable salt thereof.

2. A lipid nanoparticle (LNP) comprising an ionizable lipid selected from the group consisting of

| Structure | Cpd. |
| --- | --- |
| 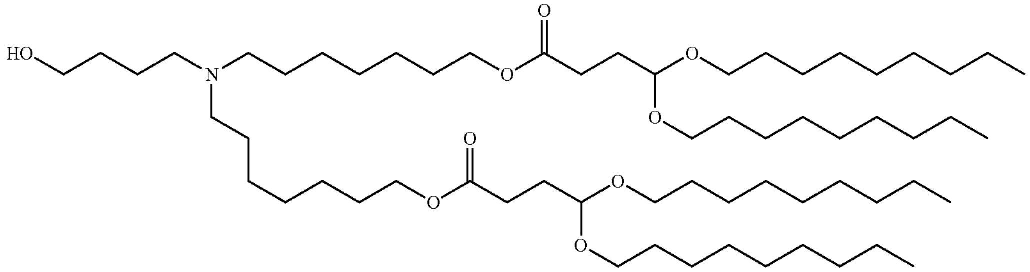 [SMILES: CCCCCCCCCOC(CCC(=O)OCCCCCCCN(CCCCO)CCCCCCCOC(=O)CCC(OCCCCCCCCC)OCCCCCCCCC)OCCCCCCCCC] | 68 |

or a pharmaceutically acceptable salt thereof.

3. The LNP of claim 2, further comprising:

(a) a PEG-lipid;

(b) a structural lipid; and (c) a non-ionizable lipid and/or a zwitterionic lipid.

4. The LNP of claim 3, wherein the PEG-lipid is selected from the group consisting of PEG-c-DOMG, PEG-DMG, PEG-DLPE, PEG-DMPE, PEG-DPPC, and PEG-DSPE.

5. The LNP of claim 3, wherein the structural lipid is selected from the group consisting of cholesterol, fecosterol, sitosterol, ergosterol, campesterol, stigmasterol, brassicasterol, tomatidine, ursolic acid, and alpha-tocopherol.

6. The LNP of claim 3, wherein the non-ionizable lipid is a phospholipid selected from the group consisting of 1,2-distearoyl-sn-glycero-3-phosphocholine (DSPC), 1,2-dioleoyl-sn-glycero-3-phosphoethanolamine (DOPE), 1,2-dilinoleoyl-sn-glycero-3-phosphocholine (DLPC), 1,2-dimyristoyl-sn-glycero-phosphocholine (DMPC), 1.2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 1-palmitoyl-2-oleoyl-sn-glycero-3-phosphocho line (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG-Na), sodium (S)-2-ammonio-3-((((R)-2-(oleoyloxy)-3-(stearoyloxy)propoxy)oxidophosphoryl)oxy)propanoate (L-α-phosphatidylserine; Brain PS), dimyristoyl phosphoethanolamine (DMPE), dimyristoylphosphatidylglycerol (DMPG), dioleoyl-phosphatidylethanolamine4-(N-maleimidomethyl)-cyclohexane-1-carboxylate (DOPE-mal), 1,2-dioleoyl-sn-glycero-3-phospho-rac-(1-glycerol) (DOPG), 1,2-dioleoyl-sn-glycero-3-(phospho-L-serine) (DOPS), a cell-fusogenicphospholipid (DPhPE), dipalmitoylphosphatidylethanolamine (DPPE), dipalmitoylphosphatidylglycerol (DPPG), dipalmitoylphosphatidylserine (DPPS), distearoyl-phosphatidyl-ethanolamine (DSPE), distearoyl phosphoethanolamineimidazole (DSPEI), egg phosphatidylcholine (EPC), 1,2-dioleoyl-sn-glycero-3-phosphate (18:1 PA; DOPA), ammonium bis((S)-2-hydroxy-3-(oleoyloxy)propyl) phosphate (18:1 DMP; LBPA), 1,2-dioleoyl-sn-glycero-3-phospho-(1'-myo-inositol) (DOPI; 18:1 PI), 1,2-distearoyl-sn-glycero-3-phospho-L-serine (18:0 PS), 1,2-dilinoleoyl-sn-glycero-3-phospho-L-serine (18:2 PS), 1-palmitoyl-2-oleoyl-sn-glycero-3-phospho-L-serine (16:0-18:1 PS; POPS), 1-stearoyl-2-oleoyl-sn-glycero-3-phospho-L-serine (18:0-18:1 PS), 1-stearoyl-2-linoleoyl-sn-glycero-3-phospho-L-serine (18:0-18:2 PS), 1-oleoyl-2-hydroxy-sn-glycero-3-phospho-L-serine (18:1 Lyso PS), 1-stearoyl-2-hydroxy-sn-glycero-3-phospho-L-serine (18:0 Lyso PS), and sphingomyelin.

7. The LNP of claim 3, comprising about 48.5 mol % ionizable lipid, about 10 mol % phospholipid, about 39 mol % structural lipid, and about 2.5 mol % PEG-lipid.

8. The LNP of claim 3, comprising about 48.5 mol % ionizable lipid, about 10 mol % phospholipid, about 40 mol % structural lipid, and about 1.5 mol % PEG-lipid.

9. A lipid nanoparticle (LNP) comprising:

(A) an ionizable lipid selected from the group consisting of:

| Structure | Cpd. |
|---|---|
| 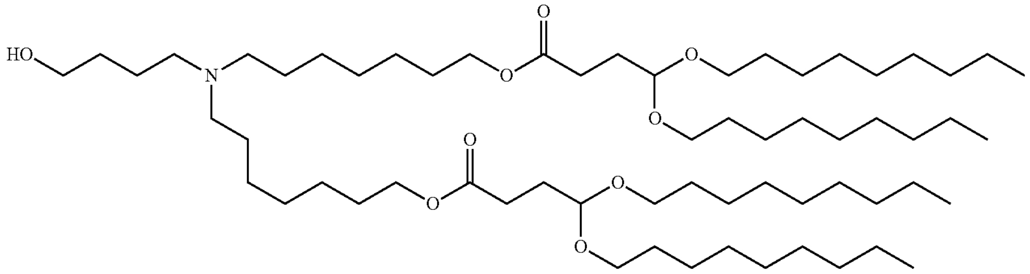 [SMILES: CCCCCCCCCOC(CCC(=O)OCCCCCCCN(CCCCO)CCCCCCCOC(=O)CCC(OCCCCCCCCC)OCCCCCCCCC)OCCCCCCCCC] | 68 |

or a pharmaceutically acceptable salt thereof; an (B) a coding RNA.

10. The LNP of claim 9, further comprising:

(a) a PEG-lipid;

(b) a structural lipid; and (c) a non-ionizable lipid and/or a zwitterionic lipid.

11. The LNP of claim 10, wherein the PEG-lipid is selected from the group consisting of PEG-c-DOMG, PEG-DMG, PEG-DLPE, PEG-DMPE, PEG-DPPC, and PEG-DSPE.

12. The LNP of claim 10, wherein the structural lipid is selected from the group consisting of cholesterol, fecosterol, sitosterol, ergosterol, campesterol, stigmasterol, brassicasterol, tomatidine, ursolic acid, and alpha-tocopherol.

13. The LNP of claim 10, wherein the non-ionizable lipid is a phospholipid selected from the group consisting of 1,2-distearoyl-sn-glycero-3-phosphocholine (DSPC), 1,2-dioleoyl-sn-glycero-3-phosphoethanolamine (DOPE), 1,2-dilinoleoyl-sn-glycero-3-phosphocholine (DLPC), 1,2-dimyristoyl-sn-glycero-phosphocholine (DMPC), 1.2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 1-palmitoyl-2-oleoyl-sn-glycero-3-phosphocho line (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG-Na), sodium (S)-2-ammonio-3-((((R)-2-(oleoyloxy)-3-(stearoyloxy)propoxy)oxidophosphoryl)oxy)propanoate (L-α-phosphatidylserine; Brain PS), dimyristoyl phosphoethanolamine (DMPE), dimyristoylphosphatidylglycerol (DMPG), dioleoyl-phosphatidylethanolamine4-(N-maleimidomethyl)-cyclohexane-1-carboxylate (DOPE-mal), 1,2-dioleoyl-sn-glycero-3-phospho-rac-(1-glycerol) (DOPG), 1,2-dioleoyl-sn-glycero-3-(phospho-L-serine) (DOPS), a cell-fusogenicphospholipid (DPhPE), dipalmitoylphosphatidylethanolamine (DPPE), dipalmitoylphosphatidylglycerol (DPPG), dipalmitoylphosphatidylserine (DPPS), distearoyl-phosphatidyl-ethanolamine (DSPE), distearoyl phosphoethanolamineimidazole (DSPEI), egg phosphatidylcholine (EPC), 1,2-dioleoyl-sn-glycero-3-phosphate (18:1 PA; DOPA), ammonium bis((S)-2-hydroxy-3-(oleoyloxy)propyl) phosphate (18:1 DMP; LBPA), 1,2-dioleoyl-sn-glycero-3-phospho-(1'-myo-inositol) (DOPI; 18:1 PI), 1,2-distearoyl-sn-glycero-3-phospho-L-serine (18:0 PS), 1,2-dilinoleoyl-sn-glycero-3-phospho-L-serine (18:2 PS), 1-palmitoyl-2-oleoyl-sn-glycero-3-phospho-L-serine (16:0-18:1 PS; POPS), 1-stearoyl-2-oleoyl-sn-glycero-3-phospho-L-serine (18:0-18:1 PS), 1-stearoyl-2-linoleoyl-sn-glycero-3-phospho-L-serine (18:0-18:2 PS), 1-oleoyl-2-hydroxy-sn-glycero-3-phospho-L-serine (18:1 Lyso PS), 1-stearoyl-2-hydroxy-sn-glycero-3-phospho-L-serine (18:0 Lyso PS), and sphingomyelin.

14. The LNP of claim 9, wherein the coding RNA is mRNA.

15. The LNP of claim 9, wherein the coding RNA is circRNA.

16. The LNP of claim 2, comprising about 48.5 mol % ionizable lipid, about 10 mol % phospholipid, about 39 mol % structural lipid, and about 2.5 mol % PEG-lipid.

17. The LNP of claim 2, comprising about 48.5 mol % ionizable lipid, about 10 mol % phospholipid, about 40 mol % structural lipid, and about 1.5 mol % PEG-lipid.

* * * * *

SEQUENCE LISTING

```
Sequence total quantity: 54
SEQ ID NO: 1            moltype = AA  length = 575
FEATURE                 Location/Qualifiers
source                  1..575
                        mol_type = protein
                        organism = Campylobacter jejuni
SEQUENCE: 1
MGFRINTNVA ALNAKANADL NSKSLDASLS RLSSGLRINS AADDASGMAI KDSLRSQANT  60
LGQAISNGND ALGILQTADK AMDEQLKILD TIKTKATQAA QDGQSLKTRT MLQADINRLM  120
EELDNIANTT SFNGKQLLSG NFINQEFQIG ASSNQTVKAS IGATQSSKIG LTRFETGSRI  180
SVGGEVQFTL KNYNGIDDFK FQKVVISTSV GTGLGALADE INKNADKTGV RATFTVETRG  240
MGAVRAGATS DDFAINGVKI GKVDYKDGDA NGALVSAINS VKDTTGVEAS IDENGKLLLT  300
SREGRGIKIE GNIGRGAFIN PNMLENYGRL SLVKNDGKDI LISGTNLSAI GFGTGNMISQ  360
ASVSLRESKG QIDANVADAM GFNSANKGNI LGGYSSVSAY MSSTGSGFSS GSGFSVGSGK  420
NYSTGFANTI AISAASQLSA VYNVSAGSGF SSGSNLSQFA TMKTSAGNTL GVKDETAGVT  480
TLKGAMAVMD IAETAITNLD QIRADIGSVQ NQVTSTINNI TVTQVNVKAA ESQIRDVDFA  540
AESANYSKAN ILAQSGSYAM AQANSVQQNV LRLLQ                             575

SEQ ID NO: 2            moltype = AA  length = 2710
FEATURE                 Location/Qualifiers
source                  1..2710
                        mol_type = protein
                        organism = Clostridioides difficile
SEQUENCE: 2
MSLISKEELI KLAYSIRPRE NEYKTILTNL DEYNKLTTNN NENKYLQLKK LNESIDVFMN  60
KYKTSSRNRA LSNLKKDILK EVILIKNSNT SPVEKNLHFV WIGGEVSDIA LEYIKQWADI  120
NAEYNIKLWY DSEAFLVNTL KKAIVESSTT EALQLLEEEI QNPQFDNMKF YKKRMEFIYD  180
RQKRFINYYK SQINKPTVPT IDDIIKSHLV SEYNRDETVL ESYRTNSLRK INSNHGIDIR  240
```

-continued

```
ANSLFTEQEL LNIYSQELLN RGNLAAASDI VRLLALKNFG GVYLDVDMLP GIHSDLFKTI  300
SRPSSIGLDR WEMIKLEAIM KYKKYINNYT SENFDKLDQQ LKDNFKLIIE SKSEKSEIFS  360
KLENLNVSDL EIKIAFALGS VINQALISKQ GSYLTNLVIE QVKNRYQFLN QHLNPAIESD  420
NNFTDTTKIF HDSLFNSATA ENSMFLTKIA PYLQVGFMPE ARSTISLSGP GAYASAYYDF  480
INLQENTIEK TLKASDLIEF KFPENNLSQL TEQEINSLWS FDQASAKYQF EKYVRDYTGG  540
SLSEDNGVDF NKNTALDKNY LLNNKIPSNN VEEAGSKNYV HYIIQLQGDD ISYEATCNLF  600
SKNPKNSIII QRNMNESAKS YFLSDDGESI LELNKYRIPE RLKNKEKVKV TFIGHGKDEF  660
NTSEFARLSV DSLSNEISSF LDTIKLDISP KNVEVNLLGC NMFSYDFNVE ETYPGKLLLS  720
IMDKITSTLP DVNKNSITIG ANQYEVRINS EGRKELLAHS GKWINKEEAI MSDLSSKEYI  780
FFDSIDNKLK AKSKNIPGLA SISEDIKTLL LDASVSPDTK FILNNLKLNI ESSIGDYIYY  840
EKLEPVKNII HNSIDDLIDE FNLLENVSDE LYELKKLNNL DEKYLISFED ISKNNSTYSV  900
RFINKSNGES VYVETEKEIF SKYSEHITKE ISTIKNSIIT DVNGNLLDNI QLDHTSQVNT  960
LNAAFFIQSL IDYSSNKDVL NDLSTSVKVQ LYAQLFSTGL NTIYDSIQLV NLISNAVNDT  1020
INVLPTITEG IPIVSTILDG INLGAAIKEL LDEHDPLLKK ELEAKVGVLA INMSLSIAAT  1080
VASIVGIGAE VTIFLLPIAG ISAGIPSLVN NELILHDKAT SVVNYFNHLS ESKKYGPLKT  1140
EDDKILVPID DLVISEIDFN NNSIKLGTCN ILAMEGGSGH TVTGNIDHFF SSPSISSHIP  1200
SLSIYSAIGI ETENLDFSKK IMMLPNAPSR VFWWETGAVP GLRSLENDGT RLLDSIRDLY  1260
PGKFYWRFYA FFDYAITTLK PVYEDTNIKI KLDKDTRNFI MPTITTNEIR NKLSYSFDGA  1320
GGTYSLLLSS YPISTNINLS KDDLWIFNID NEVREISIEN GTIKKGKLIK DVLSKIDINK  1380
NKLIIGNQTI DFSGDIDNKD RYIFLTCELD DKISLIIEIN LVAKSYSLLL SGDKNYLISN  1440
LSNTIEKINT LGLDSKNIAY NYTDESNNKY FGAISKTSQK SIIHYKKDSK NILEFYNDST  1500
LEFNSKDFIA EDINVFMKDD INTITGKYYV DNNTDKSIDF SISLVSKNQV KVNGLYLNES  1560
VYSSYLDFVK NSDGHHNTSN FMNLFLDNIS FWKLFGFENI NFVIDKYFTL VGKTNLGYVE  1620
FICDNNKNID IYFGEWKTSS SKSTIFSGNG RNVVVEPIYN PDTGEDISTS LDFSYEPLYG  1680
IDRYINKVLI APDLYTSLIN INTNYYSNEY YPEIIVLNPN TFHKKVNINL DSSSFEYKWS  1740
TEGSDFILVR YLEESNKKIL QKIRIKGILS NTQSFNKMSI DFKDIKKLSL GYIMSNFKSF  1800
NSENELDRDH LGFKIIDNKT YYYDEDSKLV KGLININNSL FYFDPIEFNL VTGWQTINGK  1860
KYYFDINTGA ALTSYKIING KHFYFNNDGV MQLGVFKGPD GFEYFAPANT QNNNIEGQAI  1920
VYQSKFLTLN GKKYYFDNNS KAVTGWRIIN NEKYYFNPNN AIAAVGLQVI DNNKYYFNPD  1980
TAIISKGWQT VNGSRYYFDT DTAIAFNGYK TIDGKHFYFD SDCVVKIGVF STSNGFEYFA  2040
PANTYNNNIE GQAIVYQSKF LTLNGKKYYF DNNSKAVTGL QTIDSKKYYF NTNTAEAATG  2100
WQTIDGKKYY FNTNTAEAAT GWQTIDGKKY YFNTNTAIAS TGYTIINGKH FYFNTDGIMQ  2160
IGVFKGPNGF EYFAPANTDA NNIEGQAILY QNEFLTLNGK KYYFGSDSKA VTGWRIINNK  2220
KYYFNPNNAI AAIHLCTINN DKYYFSYDGI LQNGYITIER NNFYFDANNE SKMVTGVFKG  2280
PNGFEYFAPA NTHNNNIEGQ AIVYQNKFLT LNGKKYYFDN DSKAVTGWQT IDGKKYYFNL  2340
NTAEAATGWQ TIDGKKYYFN LNTAEAATGW QTIDGKKYYF NTNTFIASTG YTSINGKHFY  2400
FNTDGIMQIG VFKGPNGFEY FAPANTDANN IEGQAILYQN KFLTLNGKKY YFGSDSKAVT  2460
GLRTIDGKKY YFNTNTAVAV TGWQTINGKK YYFNTNTSIA STGYTIISGK HFYFNTDGIM  2520
QIGVFKGPDG FEYFAPANTD ANNIEGQAIR YQNRFLYLHD NIYYFGNNSK AATGWVTIDG  2580
NRYYFEPNTA MGANGYKTID NKNFYFRNGL PQIGVFKGSN GFEYFAPANT DANNIEGQAI  2640
RYQNRFLHLL GKIYYFGNNS KAVTGWQTIN GKVYYFMPDT AMAAAGGLFE IDGVIYFFGV  2700
DGVKAPGIYG                                                        2710

SEQ ID NO: 3           moltype = AA  length = 2366
FEATURE                Location/Qualifiers
source                 1..2366
                       mol_type = protein
                       organism = Clostridioides difficile
SEQUENCE: 3
MSLVNRKQLE KMANVRFRTQ EDEYVAILDA LEEYHNMSEN TVVEKYLKLK DINSLTDIYI  60
DTYKKSGRNK ALKKFKEYLV TEVLELKNNN LTPVEKNLHF VWIGGQINDT AINYINQWKD  120
VNSDYNVNVF YDSNAFLINT LKKTVVESAI NDTLESFREN LNDPRFDYNK FFRKRMEIIY  180
DKQKNFINYY KAQREENPEL IIDDIVKTYL SNEYSKEIDE LNTYIEESLN KITQNSGNDV  240
RNFEEFKNGE SFNLYEQELV ERWNLAAASD ILRISALKEI GGMYLDVDML PGIQPDLFES  300
IEKPSSVTVD FWEMTKLEAI MKYKEYIPEY TSEHFDMLDE EVQSSFESVL ASKSDKSEIF  360
SSLGDMEASP LEVKIAFNSK GIINQGLISV KDSYCSNLIV KQIENRYKIL NNSLNPAISE  420
DNDFNTTTNT FIDSIMAEAN ADNGRFMMEL GKYLRVGFFP DVKTTINLSG PEAYAAAYQD  480
LLMFKEGSMN IHLIEADLRN FEISKTNISQ STEQEMASLW SFDDARAKAQ FEEYKRNYFE  540
GSLGEDDNLD FSQNIVVDKE YLLEKISSLA RSSERGYIHY IVQLQGDKIS YEAACNLFAK  600
TPYDSVLFQK NIEDSEIAYY YNPGDGEIQE IDKYKIPSII SDRPKIKLTF IGHGKDEFNT  660
DIFAGFDVDS LSTEIEAAID LAKEDISPKS IEINLLGCNM FSYSINVEET YPGKLLLKVK  720
DKISELMPSI SQDSIIVSAN QYEVRINSEG RRELLDHSGE WINKEESIIK DISSKEYISF  780
NPKENKITVK SKNLPELSTL LQEIRNNSNS SDIELEEKVM LTECEINVIS NIDTQIVEER  840
IEEAKNLTSD SINYIKDEFK LIESISDALC DLKQQNELED SHFISFEDIS ETDEGFSIRF  900
INKETGESIF VETEKTIFSE YANHITEEIS KIKGTIFDTV NGKLVKKVNL DTTHEVNTLN  960
AAFFIQSLIE YNSSKESLSN LSVAMKVQVY AQLFSTGLNT ITDAAKVVEL VSTALDETID  1020
LLPTLSEGLP IIATIIDGVS LGAAIKELSE TSDPLLRQEI EAKIGIMAVN LTTATTAIIT  1080
SSLGIASGFS ILLVPLAGIS AGIPSLVNNE LVLRDKATKV VDYFKHVSLV ETEGVFTLLD  1140
DKIMMPQDDL VISEIDFNNN SIVLGKCEIW RMEGGSGHTV TDDIDHFFSA PSITYREPHL  1200
SIYDVLEVQK EELDLSKDLM VLPNAPNRVF AWETGWTPGL RSLENDGTKL LDRIRDNYEG  1260
EFYWRYFAFI ADALITTLKP RYEDTNIRIN LDSNTRSFIV PIITTEYIRE KLSYSFYGSG  1320
GTYALSLSQY NMGINIELSE SDVWIIDVDN VVRDVTIESD KIKKGDLIEG ILSTLSIEEN  1380
KIILNSHEIN FSGEVNGSNG FVSLTFSILE GINAIIEVDL LSKSYKLLIS GELKILMLNS  1440
NHIQQKIDYI GFNSELQKNI PYSFVDSEGK ENGFINGSTK EGLFVSELPD VVLISKVYMD  1500
DSKPSFGYYS NNLKDVKVIT KDNVNILTGY YLKDDIKISL SLTLQDEKTI KLNSVHLDES  1560
GVAEILKFMN RKGNTNTSDS LMSFLESMNI KSIFVNFLQS NIKFILDANF IISGTTSIGQ  1620
FEFICDENDN IQPYFIKFNT LETNYTLYVG NRQNMIVEPN YDLDDSGDIS STVINFSQKY  1680
LYGIDSCVNK VVISPNIYTD EINITPVYET NNTYPEVIVL DANYINEKIN VNINDLSIRY  1740
VWSNDGNDFI LMSTSEENKV SQVKIRFVNV FKDKTLANKL SFNFSDKQDV PVSEIILSFT  1800
```

-continued

```
PSYYEDGLIG YDLGLVSLYN EKFYINNFGM MVSGLIYIND SLYYFKPPVN NLITGFVTVG  1860
DDKYYFNPIN GGAASIGETI IDDKNYYFNQ SGVLQTGVFS TEDGFKYFAP ANTLDENLEG  1920
EAIDFTGKLI IDENIYYFDD NYRGAVEWKE LDGEMHYFSP ETGKAFKGLN QIGDYKYYFN  1980
SDGVMQKGFV SINDNKHYFD DSGVMKVGYT EIDGKHFYFA ENGEMQIGVF NTEDGFKYFA  2040
HHNEDLGNEE GEEISYSGIL NFNNKIYYFD DSFTAVVGWK DLEDGSKYYF DEDTAEAYIG  2100
LSLINDGQYY FNDDGIMQVG FVTINDKVFY FSDSGIIESG VQNIDDNYFY IDDNGIVQIG  2160
VFDTSDGYKY FAPANTVNDN IYGQAVEYSG LVRVGEDVYY FGETYTIETG WIYDMENESD  2220
KYYFNPETKK ACKGINLIDD IKYYFDEKGI MRTGLISFEN NNYYFNENGE MQFGYINIED  2280
KMFYFGEDGV MQIGVFNTPD GFKYFAHQNT LDENFEGESI NYTGWLDLDE KRYYFTDEYI  2340
AATGSVIIDG EEYYFDPDTA QLVISE                                      2366

SEQ ID NO: 4           moltype = AA  length = 233
FEATURE                Location/Qualifiers
source                 1..233
                       mol_type = protein
                       organism = Entamoeba histolytica
SEQUENCE: 4
MFAFLLFIAF TSATNIILDL DQEVKDTNIY GVFLKNEASP EKLEEAEEKE KSSSAKPESS  60
SNEDNEDDED EKASSSDNSE SSSSDKPDNK PEASSSDKPE ASSSDKPDNK PEASSSDKPD  120
NKPEASSSDK PDNKPEASSS DKPDNKPEAS SSDKPDNKPE ASSTNKPEAS STNKPEASST  180
NKPEASSTNK PEASSTSNSN DKSGSSSDND NNNLDAASSP FIVFCAIIIA IIF         233

SEQ ID NO: 5           moltype = AA  length = 233
FEATURE                Location/Qualifiers
source                 1..233
                       mol_type = protein
                       organism = Entamoeba histolytica
SEQUENCE: 5
MSCNQQKECC KKECQEKECC KECCCPRIKA FKKFINTFEK AQIGKEAPEF KAPAYCPCGS  60
IKEIDINEYR GKYVVLLFYP LDWTFVCPTE MIGYSELAGQ LKEINCEVIG VSVDSVYCHQ  120
AWCEADKSKG GVGKLTFPLV SDIKRCISIK YGMLNVEAGI ARRGYVIIDD KGKVRYIQMN  180
DDGIGRSTEE TIRIVKAIQF SDEHGAVCPL NWKPGKDTIE PTPDGIKKYL TAH         233

SEQ ID NO: 6           moltype = AA  length = 266
FEATURE                Location/Qualifiers
source                 1..266
                       mol_type = protein
                       organism = Staphylococcus aureus
SEQUENCE: 6
MYKRLFISHV ILIFALILVI STPNVLAESQ PDPKPDELHK SSKFTGLMEN MKVLYDDNHV  60
SAINVKSIDQ FLYFDLIYSI KDTKLGNYDN VRVEFKNKDL ADKYKDKYVD VFGANYYYQC  120
YFSKKTNDIN SHQTDKRKTC MYGGVTEHNG NQLDKYRSIT VRVFEDGKNL LSFDVQTNKK  180
KVTAQELDYL TRHYLVKNKK LYEFNNSPYE TGYIKFIENE NSFWYDMMPA PGDKFDQSKY  240
LMMYNDNKMV DSKDVKIEVY LTTKKK                                      266

SEQ ID NO: 7           moltype = AA  length = 530
FEATURE                Location/Qualifiers
source                 1..530
                       mol_type = protein
                       note = Caliciviridae
                       organism = unidentified
SEQUENCE: 7
MMMASKDATS SVDGASGAGQ LVPEVNASDP LAMDPVAGSS TAVATAGQVN PIDPWIINNF  60
VQAPQGEFTI SPNNTPGDVL FDLSLGPHLN PFLLHLSQMY NGWVGNMRVR IMLAGNAFTA  120
GKIIVSCIPP GFGSHNLTIA QATLFPHVIA DVRTLDPIEV PLEDVRNVLF HNNDRNQQTM  180
RLVCMLYTPL RTGGGTGDSF VVAGRVMTCP SPDFNFLFLV PPTVEQKTRP FTLPNLPLSS  240
LSNSRAPLPI SSMGISPDNV QSVQFQNGRC TLDGRLVGTT PVSLSHVAKI RGTSNGTVIN  300
LTELDGTPFH PFEGPAPIGF PDLGGCDWHI NMTQFGHSSQ TQYDVDTTPD TFVPHLGSIQ  360
ANGIGSGNYV GVLSWISPPS HPSGSQVDLW KIPNYGSSIT EATHLAPSVY PPGFGEVLVF  420
FMSKMPGPGA YNLPCLLPQE YISHLASEQA PTVGEAALLH YVDPDTGRNL GEFKAYPDGF  480
LTCVPNGASS GPQQLPINGV FVFVSWVSRF YQLKPVGTAS SARGRLGLRR             530

SEQ ID NO: 8           moltype = AA  length = 569
FEATURE                Location/Qualifiers
source                 1..569
                       mol_type = protein
                       organism = Helicobacter pylori
SEQUENCE: 8
MKKISRKEYV SMYGPTTGDK VRLGDTDLIA EVEHDYTIYG EELKFGGGKT LREGMSQSNN  60
PSKEELDLII TNALIVDYTG IYKADIGIKD GKIAGIGKGG NKDMQDGVKN NLSVGPATEA  120
LAGEGLIVTA GGIDTHIHFI SPQQIPTAFA SGVTTMIGGG TGPADGTNAT TITPGRRNLK  180
WMLRAAEEYS MNLGFLAKGN ASNDASLADQ IEAGAIGFKI HEDWGTTPSA INHALDVADK  240
YDVQVAIHTD TLNEAGCVED TMAAIAGRTM HTFHTEGAGG GHAPDIIKVA GEHNILPAST  300
NPTIPFTVNT EAEHMDMLMV CHHLDKSIKE DVQFADSRIR PQTIAAEDTL HDMGIFSITS  360
SDSQAMGRVG EVITRTWQTA DKNKKEFGRL KEEKGDNDNF RIKRYLSKYT INPAIAHGIS  420
EYVGSVEVGK VADLVLWSPA FFGVKPNMII KGGFIALSQM GDANASIPTP QPVYYREMFA  480
HHGKAKYDAN ITFVSQAAYD KGIKEELGLE RQVLPVKNCR NITKKDMQFN DTTAHIEVNP  540
ETYHVFVDGK EVTSKPANKV SLAQLFSIF                                   569
```

-continued

```
SEQ ID NO: 9           moltype = AA  length = 247
FEATURE                Location/Qualifiers
source                 1..247
                       mol_type = protein
                       note = Reoviridae
                       organism = unidentified
SEQUENCE: 9
MASPFYRQLL SNSYVTNISD EVSEIGTRKA TNVTVNPGPF AQTRYAPVNW GHGELSDSTL  60
VQPTIDGPYQ PTTFNLPIDY WMLIAPTQIG RVAEGTNTTD RWFASVLVEP NVSNTQREYV  120
LDGQTVQLQV SNDSSTLWKF ILFIKLEKNG TYSQYSTLST SNKLCAWMKR EGRVYWYAGT  180
TPNASESYYL TINNDNSNVS CDAEFYLIPR SQTDLCAQYI NNGLPPIQNT RNVVPVSIAS  240
REIRHTR                                                            247

SEQ ID NO: 10          moltype = AA  length = 710
FEATURE                Location/Qualifiers
source                 1..710
                       mol_type = protein
                       organism = Candida albicans
SEQUENCE: 10
MTKRDRTIYS CDACRSRKIK CNRQTPCASC HKSKRDCVYT VSRQRDAQIT NRKLDKKTYH  60
QISAIEKKIS ALEGKKGLLQ VETINFNKSF TDQTPLVELQ SLFPYLLLSK QDPGCVLVRH  120
HCHHLLEKDP RYFEYSQLLA DLSLTKRHHL TARAKALLGE AYIPSPQEGH TIDQLKHVLS  180
LNPNFRFAGN FADPLTSFFS LIPPAWANKQ LVDTFFQHIY PVIPIIDETD FNTSINRVLG  240
PQIDGHYINS FPSIGSADDL PFLALFLLVL RISYMYTPGA CPVSYDTLRA AETIMKEFDI  300
TKTHSLTALQ AEIMLRFYKI VAPESYTQSN YVQVSVGVLI QNCYSLALHR DPEYIGEHNP  360
KQQHLRRKIW HLLLRMEVID SAIFQTILSS NPDASDTKLP QLIDQAPPME QSIVKHIWRS  420
TDLFVSLRKL VEINSKTSED TPLETVLELL VEVETKLQAF LATIDSEAST VFYNDLVIFS  480
VNFLLVYMYY SLYLFKGPTP LGNKYLLKSA QILFVDLART RSTSLFLAYF NLNYIHLVLM  540
ITNFLRMRVD CIIHRHLRAQ DSSVQDLQCC RYFLKIIFFS HVKELGNYSS SHKYAWQMRK  600
VYLTLAKIME RSSDVLISND PELVKSAAVD IPVKEINKLL EQYINFKGFT PTTLFDPTDN  660
ELIDEMQHEN LWNAMENIEY SEKVYSGWID AIKNVPSNWD WDYWDFLKIS             710

SEQ ID NO: 11          moltype = AA  length = 1255
FEATURE                Location/Qualifiers
source                 1..1255
                       mol_type = protein
                       organism = Severe acute respiratory syndrome related
                        coronavirus
SEQUENCE: 11
MFIFLLFLTL TSGSDLDRCT TFDDVQAPNY TQHTSSMRGV YYPDEIFRSD TLYLTQDLFL  60
PFYSNVTGFH TINHTFGNPV IPFKDGIYFA ATEKSNVVRG WVFGSTMNNK SQSVIIINNS  120
TNVVIRACNF ELCDNPFFAV SKPMGTQTHT MIFDNAFNCT FEYISDAFSL DVSEKSGNFK  180
HLREFVFKNK DGFLYVYKGY QPIDVVRDLP SGFNTLKPIF KLPLGINITN FRAILTAFSP  240
AQDIWGTSAA AYFVGYLKPT TFMLKYDENG TITDAVDCSQ NPLAELKCSV KSFEIDKGIY  300
QTSNFRVVPS GDVVRFPNIT NLCPFGEVFN ATKFPSVYAW ERKKISNCVA DYSVLYNSTF  360
FSTFKCYGVS ATKLNDLCFS NVYADSFVVK GDDVRQIAPG QTGVIADYNY KLPDDFMGCV  420
LAWNTRNIDA TSTGNYNYKY RYLRHGKLRP FERDISNVPF SPDGKPCTPP ALNCYWPLND  480
YGFYTTTGIG YQPYRVVVLS FELLNAPATV CGPKLSTDLI KNQCVNFNFN GLTGTGVLTP  540
SSKRFQPFQQ FGRDVSDFTD SVRDPKTSEI LDISPCSFGG VSVITPGTNA SSEVAVLYQD  600
VNCTDVSTAI HADQLTPAWR IYSTGNNVFQ TQAGCLIGAE HVDTSYECDI PIGAGICASY  660
HTVSLLRSTS QKSIVAYTMS LGADSSIAYS NNTIAIPTNF SISITTEVMP VSMAKTSVDC  720
NMYICGDSTE CANLLLQYGS FCTQLNRALS GIAAEQDRNT REVFAQVKQM YKTPTLKYFG  780
GFNFSQILPD PLKPTKRSFI EDLLFNKVTL ADAGFMKQYG ECLGDINARD LICAQKFNGL  840
TVLPPLLTDD MIAAYTAALV SGTATAGWTF GAGAALQIPF AMQMAYRFNG IGVTQNVLYE  900
NQKQIANQFN KAISQIQESL TTTSTALGKL QDVVNQNAQA LNTLVKQLSS NFGAISSVLN  960
DILSRLDKVE AEVQIDRLIT GRLQSLQTYV TQQLIRAAEI RASANLAATK MSECVLGQSK  1020
RVDFCGKGYH LMSFPQAAPH GVVFLHVTYV PSQERNFTTA PAICHEGKAY FPREGVFVFN  1080
GTSWFITQRN FFSPQIITTD NTFVSGNCDV VIGIINNTVY DPLQPELDSF KEELDKYFKN  1140
HTSPDVDLGD ISGINASVVN IQKEIDRLNE VAKNLNESLI DLQELGKYEQ YIKWPWYVWL  1200
GFIAGLIAIV MVTILLCCMT SCCSCLKGAC SCGSCCKFDE DDSEPVLKGV KLHYT       1255

SEQ ID NO: 12          moltype = AA  length = 1273
FEATURE                Location/Qualifiers
source                 1..1273
                       mol_type = protein
                       organism = Severe acute respiratory syndrome related
                        coronavirus
SEQUENCE: 12
MFVFLVLLPL VSSQCVNLTT RTQLPPAYTN SFTRGVYYPD KVFRSSVLHS TQDLFLPFFS  60
NVTWFHAIHV SGTNGTKRFD NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300
CTLKSFTVEK GIYQTSNFRV QPTESIVRFP NITNLCPFGE VFNATRFASV YAWNRKRISN  360
CVADYSVLYN SASFSTFKCY GVSPTKLNDL CFTNVYADSF VIRGDEVRQI APGQTGKIAD  420
YNYKLPDDFT GCVIAWNSNN LDSKVGGNYN YLYRLFRKSN LKPFERDIST EIYQAGSTPC  480
NGVEGFNCYF PLQSYGFQPT NGVGYQPYRV VVLSFELLHA PATVCGPKKS TNLVKNKCVN  540
FNFNGLTGTG VLTESNKKFL PFQQFGRDIA DTTDAVRDPQ TLEILDITPC SFGGVSVITP  600
GTNTSNQVAV LYQDVNCTEV PVAIHADQLT PTWRVYSTGS NVFQTRAGCL IGAEHVNNSY  660
```

-continued

```
ECDIPIGAGI CASYQTQTNS PRRARSVASQ SIIAYTMSLG AENSVAYSNN SIAIPTNFTI  720
SVTTEILPVS MTKTSVDCTM YICGDSTECS NLLLQYGSFC TQLNRALTGI AVEQDKNTQE  780
VFAQVKQIYK TPPIKDFGGF NFSQILPDPS KPSKRSFIED LLFNKVTLAD AGFIKQYGDC  840
LGDIAARDLI CAQKFNGLTV LPPLLTDEMI AQYTSALLAG TITSGWTFGA GAALQIPFAM  900
QMAYRFNGIG VTQNVLYENQ KLIANQFNSA IGKIQDSLSS TASALGKLQD VVNQNAQALN  960
TLVKQLSSNF GAISSVLNDI LSRLDKVEAE VQIDRLITGR LQSLQTYVTQ QLIRAAEIRA  1020
SANLAATKMS ECVLGQSKRV DFCGKGYHLM SFPQSAPHGV VFLHVTYVPA QEKNFTTAPA  1080
ICHDGKAHFP REGVFVSNGT HWFVTQRNFY EPQIITTDNT FVSGNCDVVI GIVNNTVYDP  1140
LQPELDSFKE ELDKYFKNHT SPDVDLGDIS GINASVVNIQ KEIDRLNEVA KNLNESLIDL  1200
QELGKYEQYI KWPWYIWLGF IAGLIAIVMV TIMLCCMTSC CSCLKGCCSC GSCCKFDEDD  1260
SEPVLKGVKL HYT                                                     1273

SEQ ID NO: 13          moltype = AA  length = 1353
FEATURE                Location/Qualifiers
source                 1..1353
                       mol_type = protein
                       organism = Middle East respiratory syndrome-related
                        coronavirus
SEQUENCE: 13
MIHSVFLLMF LLTPTESYVD VGPDSVKSAC IEVDIQQTFF DKTWPRPIDV SKADGIIYPQ  60
GRTYSNITIT YQGLFPYQGD HGDMYVYSAG HATGTTPQKL FVANYSQDVK QFANGFVVRI  120
GAAANSTGTV IISPSTSATI RKIYPAFMLG SSVGNFSDGK MGRFFNHTLV LLPDGCGTLL  180
RAFYCILEPR SGNHCPAGNS YTSFATYHTP ATDCSDGNYN RNASLNSFKE YFNLRNCTFM  240
YTYNITEDEI LEWFGITQTA QGVHLFSSRY VDLYGGNMFQ FATLPVYDTI KYYSIIPHSI  300
RSIQSDRKAW AAFYVYKLQP LTFLLDFSVD GYIRRAIDCG FNDLSQLHCS YESFDVESGV  360
YSVSSFEAKP SGSVVEQAEG VECDFSPLLS GTPPQVYNFK RLVFTNCNYN LTKLLSLFSV  420
NDFTCSQISP AAIASNCYSS LILDYFSYPL SMKSDLSVSS AGPISQFNYK QSFSNPTCLI  480
LATVPHNLTT ITKPLKYSYI NKCSRFLSDD RTEVPQLVNA NQYSPCVSIV PSTVWEDGDY  540
YRKQLSPLEG GGWLVASGST VAMTEQLQMG FGITVQYGTD TNSVCPKLEF ANDTKIASQL  600
GNCVEYSLYG VSGRGVFQNC TAVGVRQQRF VYDAYQNLVG YYSDDGNYYC LRACVSVPVS  660
VIYDKETKTH ATLFGSVACE HISSTMSQYS RSTRSMLKRR DSTYGPLQTP VGCVLGLVNS  720
SLFVEDCKLP LGQSLCALPD TPSTLTPRSV RSVPGEMRLA SIAFNHPIQV DQLNSSYFKL  780
SIPTNFSFGV TQEYIQTTIQ KVTVDCKQYV CNGFQKCEQL LREYGQFCSK INQALHGANL  840
RQDDSVRNLF ASVKSSQSSP IIPGFGGDFN LTLLEPVSIS TGSRSARSAI EDLLFDKVTI  900
ADPGYMQGYD DCMQQGPASA RDLICAQYVA GYKVLPPLMD VNMEAAYTSS LLGSIAGVGW  960
TAGLSSFAAI PFAQSIFYRL NGVGITQQVL SENQKLIANK FNQALGAMQT GFTTTNEAFH  1020
KVQDAVNNNA QALSKLASEL SNTFGAISAS IGDIIQRLDV LEQDAQIDRL INGRLTTLNA  1080
FVAQQLVRSE SAALSAQLAK DKVNECVKAQ SKRSGFCGQG THIVSFVVNA PNGLYFMHVG  1140
YYPSNHIEVV SAYGLCDAAN PTNCIAPVNG YFIKTNNTRI VDEWSYTGSS FYAPEPITSL  1200
NTKYVAPQVT YQNISTNLPP PLLGNSTGID FQDELDEFFK NVSTSIPNFG SLTQINTTLL  1260
DLTYEMLSLQ QVVKALNESY IDLKELGNYT YYNKWPWYIW LGFIAGLVAL ALCVFFILCC  1320
TGCGTNCMGK LKCNRCCDRY EEYDLEPHKV HVH                               1353

SEQ ID NO: 14          moltype = AA  length = 2193
FEATURE                Location/Qualifiers
source                 1..2193
                       mol_type = protein
                       organism = Enterovirus A
SEQUENCE: 14
MGSQVSTQRS GSHENSNSAT EGSTINYTTI NYYKDSYAAT AGKQSLKQDP DKFANPVKDI  60
FTEMAAPLKS PSAEACGYSD RVAQLTIGNS TITTQEAANI IVGYGEWPSY CSDDDATAVD  120
KPTRPDVSVN RFYTLDTKLW EKSSKGWYWK FPDVLTETGV FGQNAQFHYL YRSGFCIHVQ  180
CNASKFHQEA LLVAILPEYV IGTVAGGTGT EDSHPPYKQT QPGADGFELQ HPYVLDAGIP  240
ISQLTVCPHQ WINLRTNNCA TIIVPYMNTL PFDSALNHCN FGLLVVPISP LDFDQGATPV  300
IPITITLAPM CSEFAGLRQA VTQGFPTEPK PGTNQFLTTD DGVSAPILPN FHPTPCIHIP  360
GEVRNLLELC QVETILEVNN VPTNATSLME RLRFPVSAQA GKGELCAVFR ADPGRDGPWQ  420
STMLGQLCGY YTQWSGSLEV TFMFTGSFMA TGKMLIAYTP PGGPLPKDRA TAMLGTHVIW  480
DFGLQSSVTL VIPWISNTHY RAHARDGVFD YYTTGLVSIW YQTNYVVPIG APNTAYIIAL  540
AAAQKNFTTK LCKDTSHILQ TASIQGDRVA DVIESSIGDS VSRALTQALP APTGQNTQVS  600
SHRLDTGEVP ALQAAEIGAS SNTSDESMIE TRCVLNSHST AETTLDSFFS RAGLVGEIDL  660
PLKGTTNPNG YANWDIDITG YAQMRRKVEL FTYMRFDAEF TFAACTPTGE VVPQLLQYMF  720
VPPGAPKPES RESLAWQTAT NPSVFVKLTD PPAQVSVPFM SPASAYQWFY DGYPTFGEHK  780
QEKDLEYGAC PNNMMGTFSV RTVGSSKSKY PLVVRIYMRM KHVRAWIPRP MRNQNYLFKA  840
NPNYAGNSIK PTGTSRTAIT TLGKFGQQSG AIYVGNFRVV NRHLATHNDW ANLVWEDSSR  900
DLLVSSTTAQ GCDTIARCDC QTGVYYCNSK RKHYPVSFSK PSLIYVEASE YYPARYQSHL  960
MLAAGHSEPG DCGGILRCQH GVVGIVSTGG NGLVGFADVR DLLWLDEEAM EQGVSDYIKG  1020
LGDAFGTGFT DAVSREVEAL KNHLIGSEGA VEKILKNLIK LISALVIVIR SDYDMVTLTA  1080
TLALIGCHGS PWAWIKAKTA SILGIPIAQK QSASWLKKFN DMANAAKGLE WISSKISKFI  1140
DWLKEKIIPA AREKVEFLNN LKQLPLLESQ ISNLEQSAAS QEDLEAMFGN VSYLAHFCRK  1200
FQPLYATEAK RVYALEKRMN NYMQFKSKHR IEPVCLIIRG SPGTGKSLAT GIIARAIADK  1260
YHSSVYSLPP DPDHFDGYKQ QVVTVMDDLC QNPDGKDMSL FCQMVSTVDF IPPMASLEEK  1320
GVSFTSKFVI ASTNSSNIIV PTVSDSDAIR RRFYMDCDIE VTDSYKTDLG RLDAGRAAKL  1380
CSENNTANFK RCSPLVCGKA IQLRDRKSKV RYSVDTVVSE LIREYNNRSA IGNTIEALFQ  1440
GPPKFRPIRI SLEEKPAPDA ISDLLASVDS EEVRQYCRDQ GWIIPETPTN VERHLNRAVL  1500
VMQSIATVVA VVSLVYVIYK LFAGFQGAYS GAPKQILKKP VLRTATVQGP SLDFALSLLR  1560
RNIRQVQTDQ GHFTMLGVRD RLAVLPRHSQ PGKTIWVEHK LVNILDAVEL VDEQGVNLEL  1620
TLITLDTNEK FRDITKFIPE SISAASDATL VINTEHMPSM FVPVGDVVQY GFLNLSGKPT  1680
HRTMMYNFPT KAGQCGGVVT SVGKVIGIHI GGNGRQGFCA GLKRSYFASE QGEIQWVKPN  1740
KETGRLNING PTRTKLEPSV FHDVFEGNKE PAVLHSKDPR LEVDFEQALF SKYVGNTLYE  1800
```

```
PDEYIKEAAL HYANQLKQLD IDTSQMSMEE ACYGTENLEA IDLHTSAGYP YSALGIKKRV  1860
ILDSTTRDVS KMKFYMDKYG LDLPYSTYVK DELRSIDKIK KGKSRLIEAS SLNDSVYLRM  1920
TFGHLYETFH ANPGTVTGSA VGCNPDTFWS KLPILLPGSL FAFDYSGYDA SLSPVWFRAL  1980
ELVLREIGYS EEAVSLVEGI NHTHHVYRNK TYCVLGGMPS GCSGTSIFNS MINNIIIRAL  2040
LIKTFKGIDL DELNMVAYGD DVLASYPFPI DCLELARTGK EYGLTMTPAD KSPCFNEVNW  2100
DNATFLKRGF LPDEQFPFLI HPTMLMKEIH ESIRWTKDAR NTQDHVRSLC LLAWHNGKQE  2160
YEKFVSAIRS VPVGKALAIP NYENLRRNWL ELF                              2193

SEQ ID NO: 15          moltype = AA  length = 907
FEATURE                Location/Qualifiers
source                 1..907
                       mol_type = protein
                       organism = Human gammaherpesvirus 4
SEQUENCE: 15
MEAALLVCQY TIQSLIHLTG EDPGFFNVEI PEFPFYPTCN VCTADVNVTI NFDVGGKKHQ  60
LDLDFGQLTP HTKAVYQPRG AFGGSENATN LFLLELLGAG ELALTMRSKK LPINVTTGEE  120
QQVSLESVDV YFQDVFGTMW CHHAEMQNPV YLIPETVPYI KWDNCNSTNI TAVVRAQGLD  180
VTLPLSLPTS AQDSNFSVKT EMLGNEIDIE CIMEDGEISQ VLPGDNKFNI TCSGYESHVP  240
SGGILTSTSP VATPIPGTGY AYSLRLTPRP VSRFLGNNSI LYVFYSGNGP KASGGDYCIQ  300
SNIVFSDEIP ASQDMPTNTT DITYVGDNAT YSVPMVTSED ANSPNVTVTA FWAWPNNTET  360
DFKCKWTLTS GTPSGCENIS GAFASNRTFD ITVSGLGTAP KTLIITRTAT NATTTTHKVI  420
FSKAPESTTT SPTLNTTGFA DPNTTTGLPS STHVPTNLTA PASTGPTVST ADVTSPTPAG  480
TTSGASPVTP SPSPWDNGTE SKAPDMTSST SPVTTPTPNA TSPTPAVTTP TPNATSPTPA  540
VTTPTPNATS PTLGKTSPTS AVTTPTPNAT SPTLGKTSPT SAVTTPTPNA TSPTLGKTSP  600
TSAVTTPTPN ATGPTVGETS PQANATNHTL GGTSPTPVVT SQPKNATSAV TTGQHNITSS  660
STSSMSLRPS SNPETLSPST SDNSTSHMPL LTSAHPTGGE NITQVTPASI STHHVSTSSP  720
APRPGTTSQA SGPGNSSTST KPGEVNVTKG TPPQNATSPQ APSGQKTAVP TVTSTGGKAN  780
STTGGKHTTG HGARTSTEPT TDYGGDSTTP RPRYNATTYL PPSTSSKLRP RWTFTSPPVT  840
TAQATVPVPP TSQPRFSNLS MLVLQWASLA VLTLLLLLVM ADCAFRRNLS TSHTYTTPPY  900
DDAETYV                                                           907

SEQ ID NO: 16          moltype = AA  length = 269
FEATURE                Location/Qualifiers
source                 1..269
                       mol_type = protein
                       organism = Bordetella pertussis
SEQUENCE: 16
MRCTRAIRQT ARTGWLTWLA ILAVTAPVTS PAWADDPPAT VYRYDSRPPE DVFQNGFTAW  60
GNNDNVLDHL TGRSCQVGSS NSAFVSTSSS RRYTEVYLEH RMQEAVEAER AGRGTGHFIG  120
YIYEVRADNN FYGAASSYFE YVDTYGDNAG RILAGALATY QSEYLAHRRI PPENIRRVTR  180
VYHNGITGET TTEYSNARY VSQQTRANPN PYTSRRSVAS IVGTLVRMAP VIGACMARQA  240
ESSEAMAAWS ERAGEAMVLV YYESIAYSF                                   269

SEQ ID NO: 17          moltype = AA  length = 1315
FEATURE                Location/Qualifiers
source                 1..1315
                       mol_type = protein
                       organism = Clostridium tetani
SEQUENCE: 17
MPITINNFRY SDPVNNDTII MMEPPYCKGL DIYYKAFKIT DRIWIVPERY EFGTKPEDFN  60
PPSSLIEGAS EYYDPNYLRT DSDKDRFLQT MVKLFNRIKN NVAGEALLDK IINAIPYLGN  120
SYSLLDKFDT NSNSVSFNLL EQDPSGATTK SAMLTNLIIF GPGPVLNKNE VRGIVLRVDN  180
KNYFPCRDGF GSIMQMAFCP EYVPTFDNVI ENITSLTIGK SKYFQDPALL LMHELIHVLH  240
GLYGMQVSSH EIIPSKQEIY MQHTYPISAE ELFTFGGQDA NLISIDIKND LYEKTLNDYK  300
AIANKLSQVT SCNDPNIDID SYKQIYQQKY QFDKDSNGQY IVNEDKFQIL YNSIMYGFTE  360
IELGKKFNIK TRLSYFSMNH DPVKIPNLLD DTIYNDTEGF NIESKDLKSE YKGQNMRVNT  420
NAFRNVDGSG LVSKLIGLCK KIIPPTNIRE NLYNRTASLT DLGGELCIKI KNEDLTFIAE  480
KNSFSEEPFQ DEIVSYNTKN KPLNFNYSLD KIIVDYNLQS KITLPNDRTT PVTKGIPYAP  540
EYKSNAASTI EIHNIDDNTI YQYLYAQKSP TTLQRITMTN SVDDALINST KIYSYFPSVI  600
SKVNQGAQGI LFLQWVRDII DDFTNESSQK TTIDKISDVS TIVPYIGPAL NIVKQGYEGN  660
FIGALETTGV VLLLEYIPEI TLPVIAALSI AESSTQKEKI IKTIDNFLEK RYEKWIEVYK  720
LVKAKWLGTV NTQFQKRSYQ MYRSLEYQVD AIKKIIDYEY KIYSGPDKEQ IADEINNLKN  780
KLEEKANKAM ININIFMRES SRSFLVNQMI NEAKKQLLEF DTQSKNILMQ YIKANSKFIG  840
ITELKKLESK INKVFSTPIP FSYSKNLDCW VDNEEDIDVI LKKSTILNLD INNDIISDIS  900
GFNSSVITYP DAQLVPGING KAIHLVNNES SEVIVHKAMD IEYNDMFNNF TVSFWLRVPK  960
VSASHLEQYG TNEYSIISSM KKHSLSIGSG WSVSLKGNNL IWTLKDSAGE VRQITFRDLP  1020
DKFNAYLANK WVFITITNDR LSSANLYING VLMGSAEITG LGAIREDNNI TLKLDRCNNN  1080
NQYVSIDKFR IFCKALNPKE IEKLYTSYLS ITFLRDFWGN PLRYDTEYYL IPVASSSKDV  1140
QLKNITDYMY LTNAPSYTNG KLNIYYRRLY NGLKFIIKRY TPNNEIDSFV KSGDFIKLYV  1200
SYNNNEHIVG YPKDGNAFNN LDRILRVGYN APGIPLYKKM EAVKLRDLKT YSVQLKLYDD  1260
KNASLGLVGT HNGQIGNDPN RDILIASNWY FNHLKDKILG CDWYFVPTDE GWTND       1315

SEQ ID NO: 18          moltype = AA  length = 438
FEATURE                Location/Qualifiers
source                 1..438
                       mol_type = protein
                       organism = Francisella tularensis
SEQUENCE: 18
MLKSISRVLV AGFALAKVSP VFSMEIYTVK SNDYLYKIAK NHAVTGVSIS ELTDAIKGIN  60
```

```
KSEIPGIIDN RIRIGDKLAI PTTKAEVEDG LTLMRNQIIQ SSYQQPSSDT TSQQPSTPAA  120
NLGDNTAAAN DADDSSTPSV VSQDKIPVLI PTDDNSTPET YKSNLDTQIN SDNIQETASY  180
EQQPTQSSST WGSLFRFIIY VIILAVVVVV GKRFWETRNS KKEQELELIS KKKRDHLMSR  240
ISPVVSDNEF YRSDKVNNSP QEEFDFFGAA KSSRSEVTTV DEKIQSQQES EDTFEQPAQN  300
EEDLFAQRDK NIIVKTEKGV VFETNTDDTL VNSTADETKV EEIDSQQQAE QELQYINELI  360
EQFLDSEKYV EASITIQDSL EKDPNNIDLR YKLLEVYARA GDEIAFEGEV HFIKSKNIVS  420
MFDPLHQKIA KLRDKYFE                                                438

SEQ ID NO: 19          moltype = AA  length = 398
FEATURE                Location/Qualifiers
source                 1..398
                       mol_type = protein
                       organism = Streptococcus pneumoniae
SEQUENCE: 19
MNKKKLGIRL LSLLALGGFV LANPVFADQN FARNEKEAKD SAITFIQKSA AIKAGARSAE  60
DIKLDKVNLG GELSGSNMYV YNISTGGFVI VSGDKRSPEI LGYSTSGSFD ANGKENIASF  120
MESYVEQIKE NKKLDTTYAG TAEIKQPVVK SLLDSKGIHY NQGNPYNLLT PVIEKVKPGE  180
QSFVGQHAAT GCVATATAQI MKYHNYPNKG LKDYTYTLSS NNPYFNHPKN LFAAISTRQY  240
NWNNILPTYS GRESNVQKMA ISELMADVGI SVDMDYGPSS GSAGSSRVQR ALKENFGYNQ  300
SVHQINRSDF SKQDWEAQID KELSQNQPVY YQGVGKVGGH AFVIDGADGR NFYHVNWGWG  360
GVSDGFFRLD ALNPSALGTG GGAGGFNGYQ SAVVGIKP                          398

SEQ ID NO: 20          moltype = AA  length = 350
FEATURE                Location/Qualifiers
source                 1..350
                       mol_type = protein
                       organism = Staphylococcus aureus
SEQUENCE: 20
MTKHYLNSKY QSEQRSSAMK KITMGTASII LGSLVYIGAD SQQVNAATEA TNATNNQSTQ  60
VSQATSQPIN FQVQKDGSSE KSHMDDYMQH PGKVIKQNNK YYFQTVLNNA SFWKEYKFYN  120
ANNQELATTV VNDNKKADTR TINVAVEPGY KSLTTKVHIV VPQINYNHRY TTHLEFEKAI  180
PTLADAAKPN NVKPVQPKPA QPKTPTEQTK PVQPKVEKVK PTVTTTSKVE DNHSTKVVST  240
DTTKDQTKTQ TAHTVKTAQT AQEQNKVQTP VKDVATAKSE SNNQAVSDNK SQQTNKVTKH  300
NETPKQASKA KELPKTGLTS VDNFISTVAF ATLALLGSLS LLLFKRKESK              350

SEQ ID NO: 21          moltype = AA  length = 645
FEATURE                Location/Qualifiers
source                 1..645
                       mol_type = protein
                       organism = Staphylococcus aureus
SEQUENCE: 21
MNKQQKEFKS FYSIRKSSLG VASVAISTLL LLMSNGEAQA AAEETGGTNT EAQPKTEAVA  60
SPTTTSEKAP ETKPVANAVS VSNKEVEAPT SETKEAKEVK EVKAPKETKA VKPAAKATNN  120
TYPILNQELR EAIKNPAIKD KDHSAPNSRP IDFEMKKENG EQQFYHYASS VKPARVIFTD  180
SKPEIELGLQ SGQFWRKFEV YEGDKKLPIK LVSYDTVKDY AYIRFSVSNG TKAVKIVSST  240
HFNNKEEKYD YTLMEFAQPI YNSADKFKTE EDYKAEKLLA PYKKAKTLER QVYELNKIQD  300
KLPEKLKAEY KKKLEDTKKA LDEQVKSAIT EFQNVQPTNE KMTDLQDTKY VVYESVENNE  360
SMMDTFVKHP IKTGMLNGKK YMVMETTNDD YWKDFMVEGQ RVRTISKDAK NNTRTIIFPY  420
VEGKTLYDAI VKVHVKTIDY DGQYHVRIVD KEAFTKANTD KSNKKEQQDN SAKKEATPAT  480
PSKPTPSPVE KESQKQDSQK DDNKQLPSVE KENDASSESG KDKTPATKPT KGEVESSSTT  540
PTKVVSTTQN VAKPTTASSK TTKDVVQTSA GSSEAKDSAP LQKANIKNTN DGHTQSQNNK  600
NTQENKAKSL PQTGEESNKD MTLPLMALLA LSSIVAFVLP RKRKN                   645

SEQ ID NO: 22          moltype = AA  length = 1349
FEATURE                Location/Qualifiers
source                 1..1349
                       mol_type = protein
                       organism = Staphylococcus aureus
SEQUENCE: 22
MLNRENKTAI TRKGMVSNRL NKFSIRKYTV GTASILVGTT LIFGLGNQEA KAAESTNKEL  60
NEATTSASDN QSSDKVDMQQ LNQEDNTKND NQKEMVSSQG NETTSNGNKL IEKESVQSTT  120
GNKVEVSTAK SDEQASPKST NEDLNTKQTI SNQEALQPDL QENKSVVNVQ PTNEENKKVD  180
AKTESTTLNV KSDAIKSNDE TLVDNNSNSN NENNADIILP KSTAPKRLNT RMRIAAVQPS  240
STEAKNVNDL ITSNTTLTVV DADKNNKIVP AQDYLSLKSQ ITVDDKVKSG DYFTIKYSDT  300
VQVYGLNPED IKNIGDIKDP NNGETIATAK HDTANNLITY TFTDYVDRFN SVQMGINYSI  360
YMDADTIPVS KNDVEFNVTI GNTTTKTTAN IQYPDYVVNE KNSIGSAFTE TVSHVGNKEN  420
PGYYKQTIYV NPSENSLTNA KLKVQAYHSS YPNNIGQINK DVTDIKIYQV PKGYTLNKGY  480
DVNTKELTDV TNQYLQKITY GDNNSAVIDF GNADSAYVVM VNTKFQYTNS ESPTLVQMAT  540
LSSTGNKSVS TGNALGFTNN QSGGAGQEVY KIGNYVWEDT NKNGVQELGE KGVGNVTVTV  600
FDNNTNTKVG EAVTKEDGSY LIPNLPNGDY RVEFSNLPKG YEVTPSKQGN NEELDSNGLS  660
SVITVNGKDN LSADLGIYKP KYNLGDYVWE DTNKNGIQDQ DEKGISGVTV TLKDENGNVL  720
KTVTTDADGK YKFTDLDNGN YKVEFTTPEG YTPTTVTSGS DIEKDSNGLT TTGVINGADN  780
MTLDSGFYKT PKYNLGNYVW EDTNKDGKQD STEKGISGVT VTLKNENGEV LQTTKTDKDG  840
KYQFTGLENG TYKVEFETPS GYTPTQVGSG TDEGIDSNGT STTGVIKDKD NDTIDSGFYK  900
PTYNLGDYVW EDTNKNGVQD KDEKGISGVT VTLKDENDKV LKTVTTDENG KYQFTDLNNG  960
TYKVEFETPS GYTPTSVTSG NDTEKDSNGL TTTGVIKDAD NMTLDSGFYK TPKYSLGDYV  1020
WYDSNKDGKQ DSTEKGIKDV KVTLLNEKGE VIGTTKTDEN GKYCFDNLDS GKYKVIFEKP  1080
AGLTQTVTNT TEDDKDADGG EVDVTITDHD DFTLDNGYFE EDTSDSDSDS DSDSDSDSDS  1140
DSDSDSDSDS DSDSDSDSDS DSDSDSDSDS DSDSDSDSDS DSDSDSDSDS DSDSDSDSDS  1200
```

-continued

```
DSDSDSDSDS DSDSDSDSDS DSDSDSDSDS DSDSDSDSDS DSDSDSDSDS DSDSDSDSDS  1260
DSDSDSDSDS DSDSDSDSDS DSDSDSDSDA GKHTPVKPMS TTKDHHNKAK ALPETGSENN  1320
GSNNATLFGG LFAALGSLLL FGRRKKQNK                                    1349

SEQ ID NO: 23          moltype = AA  length = 1166
FEATURE                Location/Qualifiers
source                 1..1166
                       mol_type = protein
                       organism = Staphylococcus aureus
SEQUENCE: 23
MINRDNKKAI TKKGMISNRL NKFSIRKYTV GTASILVGTT LIFGLGNQEA KAAENTSTEN  60
AKQDDATTSD NKEVVSETEN NSTTENNSTN PIKKETNTDS QPEAKKESTS SSTQKQQNNV  120
TATTETKPQN IEKENVKPST DKTATEDTSV ILEEKKAPNN TNNDVTTKPS TSEPSTSEIQ  180
TKPTTPQEST NIENSQPQPT PSKVDNQVTD ATNPKEPVNV SKEELKNNPE KLKELVRNDS  240
NTDHSTKPVA TAPTSVAPKR VNAKMRFAVA QPAAVASNNV NDLIKVTKQT IKVGDGKDNV  300
AAAHDGKDIE YDTEFTIDNK VKKGDTMTIN YDKNVIPSDL TDKNDPIDIT DPSGEVIAKG  360
TFDKATKQIT YTFTDYVDKY EDIKSRLTLY SYIDKKTVPN ETSLNLTFAT AGKETSQNVT  420
VDYQDPMVHG DSNIQSIFTK LDEDKQTIEQ QIYVNPLKKS ATNTKVDIAG SQVDDYGNIK  480
LGNGSTIIDQ NTEIKVYKVN SDQQLPQSNR IYDFSQYEDV TSQFDNKKSF SNNVATLDFG  540
DINSAYIIKV VSKYTPTSDG ELDIAQGTSM RTTDKYGYYN YAGYSNFIVT SNDTGGGDGT  600
VKPEEKLYKI GDYVWEDVDK DGVQGTDSKE KPMANVLVTL TYPDGTTKSV RTDANGHYEF  660
GGLKDGETYT VKFETPTGYL PTKVNGTTDG EKDSNGSSVT VKINGKDDMS LDTGFYKEPK  720
YNLGDYVWED TNKDGIQDAN EPGIKDVKVT LKDSTGKVIG TTTTDASGKY KFTDLDNGNY  780
TVEFETPAGY TPTVKNTTAD DKDSNGLTTT GVIKDADNMT LDRGFYKTPK YSLGDYVWYD  840
SNKDGKQDST EKGIKDVTVT LQNEKGEVIG TTKTDENGKY RFDNLDSGKY KVIFEKPAGL  900
TQTVTNTTED DKDADGGEVD VTITDHDDFT LDNGYFEEDT SDSDSDSDSD SDSDSDSDSD  960
SDSDSDSDSD SDSDSDSDSD SDSDSDSDSD SDSDSDSDSD SDSDSDSDSD SDSDSDSDSD  1020
SDSDSDSDSD SDSDSDSDSD SDSDSDSDSD SDSDSDSDSD SDSDSDSDSD SDSDSDSDSD  1080
SDSDSDSDSD SDSDSDSDSD SDSDSDAGKH TPVKPMSTTK DHHNKAKALP ETGSENNGSN  1140
NATLFGGLFA ALGSLLLFGR RKKQNK                                       1166

SEQ ID NO: 24          moltype = AA  length = 338
FEATURE                Location/Qualifiers
source                 1..338
                       mol_type = protein
                       organism = Human alphaherpesvirus 1
SEQUENCE: 24
MLAVRSLQHL STVVLITAYG LVLVWYTVFG ASPLHRCIYA VRPTGTNNDT ALVWMKMNQT  60
LLFLGAPTHP PNGGWRNHAH ICYANLIAGR VVPFQVPPDA MNRRIMNVHE AVNCLETLWY  120
TRVRLVVVGW FLYLAFVALH QRRCMFGVVS PAHKMVAPAT YLLNYAGRIV SSVFLQYPYT  180
KITRLLCELS VQRQNLVQLF ETDPVTFLYH RPAIGVIVGC ELMLRFVAVG LIVGTAFISR  240
GACAITYPLF LTITTWCFVS TIGLTELYCI LRRGPAPKNA DKAAAPGRSK GLSGVCGRCC  300
SIILSGIAVR LCYIAVVAGV VLVALHYEQE IQRRLFDV                          338

SEQ ID NO: 25          moltype = AA  length = 448
FEATURE                Location/Qualifiers
source                 1..448
                       mol_type = protein
                       organism = Human alphaherpesvirus 2
SEQUENCE: 25
MDVRRPIREA VNNRRKPKFL SVSFNQDDSC FSVALENGFR IFNTDPLTSK LSKTFKESAT  60
NQSRGTGIGY TRMLYRTNYI ALVGGGKRPR HALNKLIIWD DLLQKETITL KFMSSIKDVF  120
LSRIHIVVVL ENTIEIFQFQ TNPQRICPIL DIPPNGSVDY VVCSSKHLQS QASQSQSKIL  180
EIIAFPSNKC VGQIQVADLS QIKYNSQNPK ESALLPTSII KAHKNPIKLV RLNRQGTMVA  240
TCSVQGTLIR IFSTHNGTLI KEFRRGVDKA DIYEMSFSPN GSKLAVLSNK QTLHIFQIFE  300
TTNTETNTPD HSRANGSSHP LKNYIPKGLW RPKYLDSVWS ICNAHLKNPI FDAHRNDNSG  360
DVTHDNEFYK DRCRIGWCQD SNNREQDDSL VLVWQNSGIW EKFVILEKEQ QDSSKTHYSL  420
NESLRNEDTK SAGEPTRWEL VRESWREL                                     448

SEQ ID NO: 26          moltype = AA  length = 361
FEATURE                Location/Qualifiers
source                 1..361
                       mol_type = protein
                       organism = Human Cytomegalovirus
SEQUENCE: 26
MWVLTPAAFA GKLLSVFRQP LSSLWRSLVP LFCWLRATFW LLATKRRKQQ LVLRGPDETK  60
EEEEDPPLPT TPTSVNYHFT RQCNYKCGFC FHTAKTSFVL PLEEAKRGLL LLKEAGMEKI  120
NFSGGEPFLQ DRGEYLGKLV RFCKVELRLP SVSIVSNGSL IRERWFQNYG EYLDILAISC  180
DSFDEEVNVL IGRGQGKKNH VENLQKLRRW CRDYRVAFKI NSVINRFNVE EDMTEQIKAL  240
NPVRWKVFQC LLIEGENCGE DALREAERFV IGDEEFERFL ERHKEVSCLV PESNQKMKDS  300
YLILDEYMRF LNCRKGRKDP SKSILDVGVE EAIKFSGFDE KMFLKRGGKY IWSKADLKLD  360
W                                                                  361

SEQ ID NO: 27          moltype = AA  length = 242
FEATURE                Location/Qualifiers
source                 1..242
                       mol_type = protein
                       organism = Human immunodeficiency virus 1
SEQUENCE: 27
```

-continued

```
MAETEALSKL REDFRMQNKS VFILGASGET GRVLLKEILE QGLFSKVTLI GRRKLTFDEE  60
AYKNVNQEVV DFEKLDDYAS AFQGHDVGFC CLGTTRGKAG AEGFVRVDRD YVLKSAELAK  120
AGGCKHFNLL SSKGADKSSN FLYLQVKGEV EAKVEELKFD RYSVFRPGVL LCDRQESRPG  180
EWLVRKFFGS LPDSWASGHS VPVVTVVRAM LNNVVRPRDK QMELLENKAI HDLGKAHGSL  240
KP                                                                242

SEQ ID NO: 28          moltype = AA  length = 505
FEATURE                Location/Qualifiers
source                 1..505
                       mol_type = protein
                       note = Papillomaviridae
                       organism = unidentified
SEQUENCE: 28
MSLWLPSEAT VYLPPVPVSK VVSTDEYVAR TNIYYHAGTS RLLAVGHPYF PIKKPNNNKI  60
LVPKVSGLQY RVFRIHLPDP NKFGFPDTSF YNPDTQRLVW ACVGVEVGRG QPLGVGISGH  120
PLLNKLDDTE NASAYAANAG VDNRECISMD YKQTQLCLIG CKPPIGEHWG KGSPCTNVAV  180
NPGDCPPLEL INTVIQDGDM VDTGFGAMDF TTLQANKSEV PLDICTSICK YPDYIKMVSE  240
PYGDSLFFYL RREQMFVRHL FNRAGAVGEN VPDDLYIKGS GSTANLASSN YFPTPSGSMV  300
TSDAQIFNKP YWLQRAQGHN NGICWGNQLF VTVVDTTRST NMSLCAAIST SETTYKNTNF  360
KEYLRHGEEY DLQFIFQLCK ITLTADVMTY IHSMNSTILE DWNFGLQPPP GGTLEDTYRF  420
VTSQAIACQK HTPPAPKEDP LKKYTFWEVN LKEKFSADLD QFPLGRKFLL QAGLKAKPKF  480
TLGKRKATPT TSSTSTTAKR KKRKL                                       505

SEQ ID NO: 29          moltype = AA  length = 498
FEATURE                Location/Qualifiers
source                 1..498
                       mol_type = protein
                       note = Influenza virus
                       organism = unidentified
SEQUENCE: 29
MASQGTKRSY EQMETDGERQ NATEIRASVG KMIGGIGRFY IQMCTELKLS DYEGRLIQNS  60
LTIERMVLSA FDERRNKYLE EHPSAGKDPK KTGGPIYRRV NGKWMRELIL YDKEEIRRIW  120
RQANNGDDAT AGLTHMMIWH SNLNDATYQR TRALVRTGMD PRMCSLMQGS TLPRRSGAAG  180
AAVKGVGTMV MELVRMIKRG INDRNFWRGE NGRKTRIAYE RMCNILKGKF QTAAQKAMMD  240
QVRESRNPGN AEFEDLTFLA RSALILRGSV AHKSCLPACV YGPAVASGYD FEREGYSLVG  300
IDPFRLLQNS QVYSLIRPNE NPAHKSQLVW MACHSAAFED LRVLSFIKGT KVLPRGKLST  360
RGVQIASNEN METMESSTLE LRSRYWAIRT RSGGNTNQQR ASAGQISIQP TFSVQRNLPF  420
DRTTIMAAFN GNTEGRTSDM RTEIIRMMES ARPEDVSFQG RGVFELSDEK AASPIVPSFD  480
MSNEGSYFFG DNAEEYDN                                               498

SEQ ID NO: 30          moltype = AA  length = 252
FEATURE                Location/Qualifiers
source                 1..252
                       mol_type = protein
                       note = Influenza virus
                       organism = unidentified
SEQUENCE: 30
MSLLTEVETY VLSIVPSGPL KAEIAQRLED VFAGKNTDLE VLMEWLKTRP ILSPLTKGIL  60
GFVFTLTVPS ERGLQRRRFV QNALNGNGDP NNMDKAVKLY RKLKREITFH GAKEIALSYS  120
AGALASCMGL IYNRMGAVTT EVAFGLVCAT CEQIADSQHR SHRQMVTTTN PLIRHENRMV  180
LASTTAKAME QMAGSSEQAA EAMDIASQAR QMVQAMRTIG THPSSSAGLK DDLLENLQAY  240
QKRMGVQMQR FK                                                     252

SEQ ID NO: 31          moltype = AA  length = 565
FEATURE                Location/Qualifiers
source                 1..565
                       mol_type = protein
                       note = Influenza virus
                       organism = unidentified
SEQUENCE: 31
MKANLLVLLC ALAAADADTI CIGYHANNST DTVDTVLEKN VTVTHSVNLL EDSHNGKLCR  60
LKGIAPLQLG KCNIAGWLLG NPECDPLLPV RSWSYIVETP NSENGICYPG DFIDYEELRE  120
QLSSVSSFER FEIFPKESSW PNHNTNGVTA ACSHEGKSSF YRNLLWLTEK EGSYPKLKNS  180
YVNKKGKEVL VLWGIHHPPN SKEQQNLYQN ENAYVSVVTS NYNRRFTPEI AERPKVRDQA  240
GRMNYYWTLL KPGDTIIFEA NGNLIAPMYA FALSRGFGSG IITSNASMHE CNTKCQTPLG  300
AINSSLPYQN IHPVTIGECP KYVRSAKLRM VTGLRNIPSI QSRGLFGAIA GFIEGGWTGM  360
IDGWYGYHHQ NEQGSGYAAD QKSTQNAING ITNKVNTVIE KMNIQFTAVG KEFNKLEKRM  420
ENLNKKVDDG FLDIWTYNAE LLVLLENERT LDFHDSNVKN LYEKVKSQLK NNAKEIGNGC  480
FEFYHKCDNE CMESVRNGTY DYPKYSEESK LNREKVDGVK LESMGIYQIL AIYSTVASSL  540
VLLVSLGAIS FWMCSNGSLQ CRICI                                       565

SEQ ID NO: 32          moltype = AA  length = 354
FEATURE                Location/Qualifiers
source                 1..354
                       mol_type = protein
                       organism = human polyomavirus
SEQUENCE: 32
MAPTKRKGER KDPVQVPKLL IRGGVEVLEV KTGVDSITEV ECFLTPEMGD PDEHLRGFSK  60
SISISDTFES DSPNRDMLPC YSVARIPLPN LNEDLTCGNI LMWEAVTLKT EVIGVTSLMN  120
```

-continued

```
VHSNGQATHD NGAGKPVQGT SFHFFSVGGE ALELQGVLFN YRTKYPDGTI FPKNATVQSQ  180
VMNTEHKAYL DKNKAYPVEC WVPDPTRNEN TRYFGTLTGG ENVPPVLHIT NTATTVLLDE  240
FGVGPLCKGD NLYLSAVDVC GMFTNRSGSQ QWRGLSRYFK VQLRKRRVKN PYPISFLLTD  300
LINRRTPRVD GQPMYGMDAQ VEEVRVFEGT EELPGDPDMM RYVDKYGQLQ TKML        354

SEQ ID NO: 33          moltype = AA  length = 95
FEATURE                Location/Qualifiers
source                 1..95
                       mol_type = protein
                       organism = Mycobacterium tuberculosis
SEQUENCE: 33
MTEQQWNFAG IEAAASAIQG NVTSIHSLLD EGKQSLTKLA AAWGGSGSEA YQGVQQKWDA  60
TATELNNALQ NLARTISEAG QAMASTEGNV TGMFA                             95

SEQ ID NO: 34          moltype = AA  length = 317
FEATURE                Location/Qualifiers
source                 1..317
                       mol_type = protein
                       organism = Variola virus
SEQUENCE: 34
MTEQMTLRGT LKGHNGWVTQ IATTPQFPDM ILSASRDKTI IMWKLTRDET NYGIPQRALR  60
GHSHFVSDVV ISSDGQFALS GSWDGTLRLW DLTTGTTTRR FVGHTKDVLS VAFSSDNRQI  120
VSGSRDKTIK LWNTLGVCKY TVQDESHSEW VSCVRFSPNS SNPIIVSCGW DKLVKVWNLA  180
NCKLKTNHIG HTGYLNTVTV SPDGSLCASG GKDGQAMLWD LNEGKHLYTL DGGDIINALC  240
FSPNRYWLCA ATGPSIKIWD LEGKIIVDEL KQEVISTSSK AEPPQCTSLA WSADGQTLFA  300
GYTDNLVRVW QVTIGTR                                                 317

SEQ ID NO: 35          moltype = AA  length = 83
FEATURE                Location/Qualifiers
source                 1..83
                       mol_type = protein
                       organism = Pseudomonas aeruginosa
SEQUENCE: 35
MNNVLKFSAL ALAAVLATGC SSHSKETEAR LTATEDAAAR AQARADEAYR KADEALGAAQ  60
KAQQTADEAN ERALRMLEKA SRK                                          83

SEQ ID NO: 36          moltype = AA  length = 574
FEATURE                Location/Qualifiers
source                 1..574
                       mol_type = protein
                       organism = Human orthopneumovirus
SEQUENCE: 36
MELLILKANA ITTILTAVTF CFASGQNITE EFYQSTCSAV SKGYLSALRT GWYTSVITIE  60
LSNIKENKCN GTDAKVKLIK QELDKYKNAV TELQLLMQST PPTNNRARRE LPRFMNYTLN  120
NAKKTNVTLS KKRKRRFLGF LLGVGSAIAS GVAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEIN LCNVDIFNPK YDCKIMTSKT DVSSSVITSL GAIVSCYGKT  420
KCTASNKNRG IIKTFSNGCD YVSNKGMDTV SVGNTLYYVN KQEGKSLYVK GEPIINFYDP  480
LVFPSDEFDA SISQVNEKIN QSLAFIRKSD ELLHNVNAGK STTNIMITTI IVIIVILLS   540
LIAVGLLLYC KARSTPVTLS KDQLSGINNI AFSN                              574

SEQ ID NO: 37          moltype = AA  length = 246
FEATURE                Location/Qualifiers
source                 1..246
                       mol_type = protein
                       organism = Rubivirus rubellae
SEQUENCE: 37
FHTETRTVWQ LSVAGVSCNV TTEHPFCNTP HGQLEVQVPP DPGDLVEYIM NYTGNQQSRW  60
GLGSPNCHGP DWASPVCQRH SPDCSRLVGA TPERPRLRLV DADDPLLRTA PGPGEVWVTP  120
VIGSQARKCG LHIRAGPYGH ATVEMPEWIH AHTTSDPWHP PGPLGLKFKT VRPVTLPRAL  180
APPRNVRVTG CYQCGTPALV EGLAPGGGNC HLTVNGEDVG AFPPGKFVTA ALLNTPPPYQ  240
VSCGGE                                                             246

SEQ ID NO: 38          moltype = AA  length = 230
FEATURE                Location/Qualifiers
source                 1..230
                       mol_type = protein
                       organism = Toxoplasma gondii
SEQUENCE: 38
MAHGGIHLRQ KRNFCPVTVS TVAVVFVVFM GVLVNSLGGV AVAADSGGVK QTPSETGSSG  60
GQQEAVGTTE DYVNSSAMGG GQGDSLAEDD TTSEAAEGDV DPFPVLANEG KSEARGPSLE  120
ERIEEQGTRR RYSSVQEPQA KVPSKRTQKR HRLIGAVVLA VSVAMLTAFF LRRTGRRSPQ  180
EPSGDGGGND AGNNAGNGGN EGRGYGGRGE GGAEDDRRPL HPERVNVFDY             230

SEQ ID NO: 39          moltype = AA  length = 623
FEATURE                Location/Qualifiers
source                 1..623
```

```
                        mol_type = protein
                        organism = Human alphaherpesvirus 3
SEQUENCE: 39
MGTVNKPVVG VLMGFGIITG TLRITNPVRA SVLRYDDFHI DEDKLDTNSV YEPYYHSDHA  60
ESSWVNRGES SRKAYDHNSP YIWPRNDYDG FLENAHEHHG VYNQGRGIDS GERLMQPTQM  120
SAQEDLGDDT GIHVIPTLNG DDRHKIVNVD QRQYGDVFKG DLNPKPQGQR LIEVSVEENH  180
PFTLRAPIQR IYGVRYTETW SFLPSLTCTG DAAPAIQHIC LKHTTCFQDV VVDVDCAENT  240
KEDQLAEISY RFQGKKEADQ PWIVVNTSTL FDELELDPPE IEPGVLKVLR TEKQYLGVYI  300
WNMRGSDGTS TYATFLVTWK GDEKTRNPTP AVTPQPRGAE FHMWNYHSHV FSVGDTFSLA  360
MHLQYKIHEA PFDLLLEWLY VPIDPTCQPM RLYSTCLYHP NAPQCLSHMN SGCTFTSPHL  420
AQRVASTVYQ NCEHADNYTA YCLGISHMEP SFGLILHDGG TTLKFVDTPE SLSGLYVFVV  480
YFNGHVEAVA YTVVSTVDHF VNAIEERGFP PTAGQPPATT KPKEITPVNP GTSPLLRYAA  540
WTGGLAAVVL LCLVIFLICT AKRMRVKAYR VDKSPYNQSM YYAGLPVDDF EDSESTDTEE  600
EFGNAIGGSH GGSSYTVYID KTR                                          623

SEQ ID NO: 40           moltype = AA  length = 2474
FEATURE                 Location/Qualifiers
source                  1..2474
                        mol_type = protein
                        organism = Chikungunya virus
SEQUENCE: 40
MDPVYVDIDA DSAFLKALQR AYPMFEVEPR QVTPNDHANA RAFSHLAIKL IEQEIDPDST  60
ILDIGSAPAR RMMSDRKYHC VCPMRSAEDP ERLANYARKL ASAAGKVLDR NISGKIGDLQ  120
AVMAVPDTET PTFCLHTDVS CRQRADVAIY QDVYAVHAPT SLYHQAIKGV RLAYWVGFDT  180
TPFMYNAMAG AYPSYSTNWA DEQVLKAKNI GLCSTDLTEG RRGKLSIMRG KKLEPCDRVL  240
FSVGSTLYPE SRKLLKSWHL PSVFHLKGKL SFTCRCDTVV SCEGYVVKRI TMSPGLYGKT  300
TGYAVTHHAD GFLMCKTTDT VDGERVSFSV CTYVPATICD QMTGILATEV TPEDAQKLLV  360
GLNQRIVVNG RTQRNTNTMK NYMIPVVAQA FSKWAKECRK DMEDEKLLGV RERTLTCCCL  420
WAFKKQKTHT VYKRPDTQSI QKVQAEFDSF VVPSLWSSGL SIPLRTRIKW LLSKVPKTDL  480
TPYSGDAQEA RDAEKEAEEE REAELTLEAL PPLQAAQEDV QVEIDVEQLE DRAGAGIIET  540
PRGAIKVTAQ PTDHVVGEYL VLSPQTVLRS QKLSLIHALA EQVKTCTHSG RAGRYAVEAY  600
DGRVLVPSGY AISPEDFQSL SESATMVYNE REFVNRKLHH IAMHGPALNT DEESYELVRA  660
ERTEHEYVYD VDQRRCCKKE EAAGLVLVGD LTNPPYHEFA YEGLKIRPAC PYKIAVIGVF  720
GVPGSGKSAI IKNLVTRQDL VTSGKKENCQ EITTDVMRQR GLEISARTVD SLLLNGCNRP  780
VDVLYVDEAF ACHSGTLLAL IALVRPRQKV VLCGDPKQCG FFNMMQMKVN YNHNICTQVY  840
HKSISRRCTL PVTAIVSSLH YEGKMRTTNE YNKPIVVDTT GSTKPDPGDL VLTCFRGWVK  900
QLQIDYRGHE VMTAAASQGL TRKGVYAVRQ KVNENPLYAS TSEHVNVLLT RTEGKLVWKT  960
LSGDPWIKTL QNPPKGNFKA TIKEWEVEHA SIMAGICSHQ MTFDTFQNKA NVCWAKSLVP  1020
ILETAGIKLN DRQWSQIIQA FKEDKAYSPE VALNEICTRM YGVDLDSGLF SKPLVSVYYA  1080
DNHWDNRPGG KMFGFNPEAA SILERKYPFT KGKWNINKQI CVTTRRIEDF NPTTNIIPAN  1140
RRLPHSLVAE HRPVKGERME WLVNKINGHH VLLVSGCSLA LPTKRVTWVA PLGVRGADYT  1200
YNLELGLPAT LGRYDLVVIN IHTPFRIHHY QQCVDHAMKL QMLGGDSLRL LKPGGSLLIR  1260
AYGYADRTSE RVICVLGRKF RSSRALKPPC VTSNTEMFFL FSNFDNGRRN FTTHVMNNQL  1320
NAAFVGQATR AGCAPSYRVK RMDIAKNDEE CVVNAANPRG LPGDGVCKAV YKKWPESFKN  1380
SATPVGTAKT VMCGTYPVIH AVGPNFSNYS ESEGDRELAA AYREVAKEVT RLGVNSVAIP  1440
LLSTGVYSGG KDRLTQSLNH LFTAMDSTDA DVVIYCRDKE WEKKISEAIQ MRTQVELLDE  1500
HISIDCDVVR VHPDSSLAGR KGYSTTEGAL YSYLEGTRFH QTAVDMAEIY TMWPKQTEAN  1560
EQVCLYALGE SIESIRQKCP VDDADASSPP KTVPCLCRYA MTPERVTRLR MNHVTSIIVC  1620
SSFPLPKYKI EGVQKVKCSK VMLFDHNVPS RVSPREYRPS QESVQEASTT TSLTHSQFDL  1680
SVDGKILPVP SDLDADAPAL EPALDDGAIH TLPSATGNLA AVSDWVMSTV PVAPPRRRRG  1740
RNLTVTCDER EGNITPMASV RFFRAELCPV VQETAETRDT AMSLQAPPST ATELSHPPIS  1800
FGAPSETFPI TFGDFNEGEI ESLSSELLTF GDFLPGEVDD LTDSDWSTCS DTDDELRLDR  1860
AGGYIFSSDT GPGHLQQKSV RQSVLPVNTL EEVHEEKCYP PKLDEAKEQL LLKKLQESAS  1920
MANRSRYQSR KVENMKATII QRLKRGCRLY LMSETPKVPT YRTTYPAPVY SPPINVRLSN  1980
PESAVAACNE FLARNYPTVS SYQITDEYDA YLDMVDGSES CLDRATFNPS KLRSYPKQHA  2040
YHAPSIRSAV PSPFQNTLQN VLAAATKRNC NVTQMRELPT LDSAVFNVEC FKKFACNQEY  2100
WEEFAASPIR ITTENLTTYV TKLKGPKAAA LFAKTHNLLP LQEVPMDRFT VDMKRDVKVT  2160
PGTKHTEERP KVQVIQAAEP LATAYLCGIH RELVRRLNAV LLPNVHTLFD MSAEDFDAII  2220
AAHFKPGDTV LETDIASFDK SQDDSLALTA LMLLEDLGVD HSLLDLIEAA FGEISSCHLP  2280
TGTRFKFGAM MKSGMFLTLF VNTLLNITIA SRVLEDRLTK SACAAFIGDD NIIHGVVSDE  2340
LMAARCATWM NMEVKIIDAV VSQKAPYFCG GFILHDIVTG TACRVADPLK RLFKLGKPLA  2400
AGDEQDEDRR RALADEVVRW QRTGLIDELE KAVYSRYEVQ GISVVVMSMA TFASSRSNFE  2460
KLRGPVVTLY GGPK                                                    2474

SEQ ID NO: 41           moltype = AA  length = 3391
FEATURE                 Location/Qualifiers
source                  1..3391
                        mol_type = protein
                        organism = Dengue virus
SEQUENCE: 41
MNNQRKKARN TPFNMLKRER NRVSTVQQLT KRFSLGMLQG RGTLKLFMAL VAFLRFLTIP  60
PTAGILKRWG TIKKSKAINV LRGFRKEIGR MLNILNRRRR TAGIIIMMIP TVMAFHLTTR  120
NGEPHMIVSR QEKGKSLLFK TENGVNMCTL MAMDLGELCE DTITYNCPLL RQNEPEDIDC  180
WCNSTSTWVT YGTCTATGEH RREKRSVALV PHVGMGLETR TETWMSSEGA WKHAQRIETW  240
ILRHPGFTIM AAILAYTIGT TYFQRVLIFI LLTAVTPSMA MRCIGISNRD FVEGVSGGSW  300
VDIVLEHGSC VTTMAKNKPT LDFELIKTEA KHLATLRKYC VEAKLTNTTT ASRCPTQGEP  360
SLNEEQDKRF VCKHSMVDRG WGNGCGLFGK GGIVTCAMFT CKKNMEGKVV QPENLEYTIV  420
ITPHSGEENA VGNDTGKHGK EIKVTPQSSI TEAELTGYGT VTMECSPRTG LDFNEMVLLQ  480
MENKAWLVHR QWFLDLPLPW LPGADTQGSN WIQKETLVTF KNPHAKKQDV VLGSQEGAM   540
```

-continued

```
HTALTGATEI QMSSGNLLFT GHLKCRLRMD KLQLKGMSYS MCTGKFKVVK EIAETQHGTI  600
VIRVQYEGDG SPCKIPFEIM DLEKRHVLGR LITVNPIVTE KDSPVNIEAE PPFGDSYIII  660
GVEPGQLKLS WFKKGSSIGQ MFETTMRGAK RMAILGDTAW DFGSLGGVFT SIGKALHQVF  720
GAIYGAAFSG VSWTMKILIG VVITWIGMNS RSTSLSVSLV LVGVVTLYLG VMVQADSGCV  780
VSWKNKELKC GSGIFITDNV HTWTEQYKFQ PESPSKLASA IQKAHEEGIC GIRSVTRLEN  840
LMWKQITPEL NHILTENEVK LTIMTGDIKG IMQAGKRTLR PQPTELKYSW KAWGKAKMLS  900
TELHNHTFLI DGPETAECPN TNRAWNSLEV EDYGFGVFTT NIWLKLKERQ DVFCDSKLMS  960
AAIKDNRAVH ADMGYWIESA LNDTWKIEKA SFIEVKSCHW PKSHTLWSNG VLESEMIIPK  1020
NFAGPVSQHN YRPGYHTQTA GPWHLGRLEM DFDFCEGTTV VVTEDCGNRG PSLRTTTASG  1080
KLITEWCCRS CTLPPLRYRG EDGCWYGMEI RPLKEKEENL VNSLVTAGHG QIDNFSLGVL  1140
GMALFLEEML RTRVGTKHAI LLVAVSFVTL ITGNMSFRDL GRVMVMVGAT MTDDIGMGVT  1200
YLALLAAFKI RPTFAAGLLL RKLTSKELMM TTIGIVLLSQ STIPESILEL TDALALGMMV  1260
LKIVRNMEKY QLAVTIMAIL CVPNAVILQN AWKVSCTTLA VVSVSPLLLT SSQQKADWIP  1320
LALTIKGLNP TAIFLTTLSR TSKKRSWPLN EAIMAVGMVS ILASSLLKND IPMTGPLVAG  1380
GLLTVCYVLT GRSADLELER AADVRWEEQA EISGSSPILS ITISEDGSMS IKNEEEEQTL  1440
TILIRTGLLV ISGLFPVSIP ITAAAWYLWE VKKQRAGVLW DVPSPPPVGK AELEDGAYRI  1500
KQKGILGYSQ IGAGVYKEGT FHTMWHVTRG AVLMHKGKRI EPSWADVKKD LISYGGGWKL  1560
EGEWKEGEEV QVLALEPGKN PRAVQTKPGL FKTNTGTIGA VSLDFSPGTS GSPIVDKKGK  1620
VVGLYGNGVV TRSGTYVSAI AQTEKSIEDN PEIEDDIFRK KRLTIMDLHP GAGKTKRYLP  1680
AIVREAIKRG LRTLILAPTR VVAAEMEEAL RGLPIRYQTP AIRAEHTGRE IVDLMCHATF  1740
TMRLLSPIRV PNYNLIIMDE AHFTDPASIA ARGYISTRVE MGEAAGIFMT ATPPGSRDPF  1800
PQSNAPIMDE EKEIPERSWN SGHEWVTDFK GKTVWFVPSI KAGNDIAACL RKNGKKVIQL  1860
SRKTFDSEYI KTRTNDWDFV VTTDISEMGA NFKAERVIDP RRCMKPVILT DGEERVILAG  1920
PMPVTHSSAA QRRGRVGRNP KNENDQYIYM GEPLENDEDC AHWKEAKMLL DNINTPEGII  1980
PSMFEPEREK VDAIDGEYRL RGEARKTFVD LMRRGDLPVW LAYRVAAEGI NYADRRWCFD  2040
GVKNNQILEE NVEVEIWTKE GERKKLKPRW LDARIYSDPL ALKEFKEFAA GRKSLTLNLI  2100
TEMGRLPTFM TQKAKNALDN LAVLHTAEAG GRAYNHALSE LPETLETLLL LTLLATVTGG  2160
IFLFLMSGKG IGKMTLGMCC IITASILLWY AQIQPHWIAA SIILEFFLIV LLIPEPEKQR  2220
TPQDNQLTYV VIAILTVVAA TMANEMGFLE KTKKDFGLGS ITTQQPESNI LDIDLRPASA  2280
WTLYAVATTF ITPMLRHSIE NSSVNVSLTA IANQATVLMG LGKGWPLSKM DIGVPLLAIG  2340
CYSQVNPITL TAALLLLVAH YAIIGPGLQA KATREAQKRA AAGIMKNPTV DGMTVIDLDP  2400
IPYDPKFEKQ LGQVMLLVLC VTQVLMMRTT WALCEALTLA TGPISTLWEG NPGRFWNTTI  2460
AVSMANIFRG SYLAGAGLLF SIMKNTANTR RGTGNTGETL GEKWKNRLNA LGKSEFQIYK  2520
KSGIQEVDRT LAKEGIKRGE TDHHAVSRGS AKLRWFVERN LVTPEGKVVD LGCGRGGWSY  2580
YCGGLKNVKE VKGLTKGGPG HEEPIPMSTY GWNLVRLQSG VDVFFTPPEK CDTLLCDIGE  2640
SSPNPTVEAG RTLRVLNLVE NWLNNNTQFC IKVLNPYMPS VIEKMEALQR KYGGALVRNP  2700
LSRNSTHEMY WVSNASGNIV SSVNMISRML INRFTMRHKK ATYEPDVDLG SGTRNIGIES  2760
ETPNLDIIGK RIEKIKQEHE TSWHYDQDHP YKTWAYHGSY ETKQTGSASS MVNGVVRLLT  2820
KPWDVIPMVT QMAMTDTTPF GQQRVFKEKV DTRTQEPKEG TKKLMKITAE WLWKELGKKK  2880
TPRMCTREEF TRKVRSNAAL GAIFTDENKW KSAREAVEDS GFWELVDKER NLHLEGKCET  2940
CVYNMMGKRE KKLGEFGKAK GSRAIWYMWL GARFLEFEAL GFLNEDHWFS RENSLSGVEG  3000
EGLHKLGYIL RDVSKKEGGA MYADDTAGWD TRITLEDLKN EEMVTNHMEG EHKKLAEAIF  3060
KLTYQNKVVR VQRPTPRGTV MDIISRRDQR GSGQVVTYGL NTFTNMEAQL IRQMEGEGVF  3120
KSIQQLTVKE EIAVKNWLIR VGRERLSRMA ISGDDCVVKP LDDRFASALT ALNDMGKVRK  3180
DIQQWEPSRG WNDWTQVPFC SHHFHELIMK DGRVLVVPCR NQDELIGRAR ISQGAGWSLR  3240
ETACLGKSYA QMWSLMYFHR RDLRLAANAI CSAVPSHWIP TSRTTWSIHA THEWMTTEDM  3300
LTVWNRVWIQ ENPWMEDKTP VESWEEIPYL GKREDQWCGS LIGLTSRATW AKNIQTAINQ  3360
VRSLIGNEEY TDYMPSMKRF RREEEEAGVL W                                3391
```

```
SEQ ID NO: 42          moltype = AA  length = 524
FEATURE                Location/Qualifiers
source                 1..524
                       mol_type = protein
                       organism = Rabies lyssavirus
SEQUENCE: 42
MVPQALLFVP LLVFPLCFGK FPIYTILDKL GPWSPIDIHH LSCPNNLVVE DEGCTNLSGF  60
SYMELKVGYI LAIKMNGFTC TGVVTEAETY TNFVGYVTTT FKRKHFRPTP DACRAAYNWK  120
MAGDPRYEES LHNPYPDYRW LRTVKTTKES LVIISPSVAD LDPYDRSLHS RVFPSGKCSG  180
VAVSSTYCST NHDYTIWMPE NPRLGMSCDI FTNSRGKRAS KGSETCGFVD ERGLYKSLKG  240
ACKLKLCGVL GLRLMDGTWV AMQTSNETKW CPPDQLVNLH DFRSDEIEHL VVEELVRKRE  300
ECLDALESIM TTKSVSFRRL SHLRKLVPGF GKAYTIFNKT LMEADAHYKS VRTWNEILPS  360
KGCLRVGGRC HPHVNGVFFN GIILGPDGNV LIPEMQSSLL QQHMELLESS VIPLVHPLAD  420
PSTVFKDGDE AEDFVEVHLP DVHNQVSGVD LGLPNWGKYV LLSAGALTAL MLIIFLMTCC  480
RRVNRSEPTQ HNLRGTGREV SVTPQSGKII SSWESHKSGG ETRL                  524
```

```
SEQ ID NO: 43          moltype = AA  length = 835
FEATURE                Location/Qualifiers
source                 1..835
                       mol_type = protein
                       organism = Trypanosoma cruzi
SEQUENCE: 43
MSRRHFYSAV LLLLLVVMVC GGSGAAHAVE RNSGDLQLPQ EIAMLVPNKT QVVPKSGGEG  60
KVKDIFASPA LVRAGGVMIA FVEGRTKNKL FPEVIDLSSS DIVAGYIKAP ETWQSLVAEV  120
TKEYWQAHTV LESANNSNHR VGVARLPTGI TRGNKVFLLV GSYEERREID DYIWKAEAWN  180
IKVIEGEATQ STEVQPTQPI NWSEPKPLFQ TDSPNNKGDL KEFLGGGGSG IVMGNGTLVF  240
PLTAKDESNK VFSLITYSTD DGQKWEIPGG VSSVACRSPR VTEWEEGTLL MVTYCEDGRK  300
VFESRDMGKT WTEAFGTLPG VWLKSGPELP EVSLRVDALI TATIEGRKVM LYTQKVRHFL  360
EVDEPNALHL WVTDNNRTFH LGPFSVDCAE NKTFANTLLY SDDALHLLQA KGDHESTAVS  420
LARLTEELNT INSVLSTWVQ LDASFSESSI PTAGLVGFLS NTTSSGDTWI DGYRCMNATV  480
```

```
TKAAKVENGF KFTGPGSRAT WPVNSRWDIK QYGFVDYNFT IVAMATIHQV PSESTPLLGA  540
SLRGNKRTKL IGLSYGAGGK WETVYDGTKT VQGGTWEPGR EYQVALMLQD GNKGFVYVDG  600
VLVGNPAMLP TPEERWTEFS HFYFGGDEGD SGSDATLTDV FLYNRPLSVG ELKMIKEVED  660
KKEKGSGDSE DKKESGDSED KKESGDSEDK KGSGDSEDKK ESGDSEDKKE SGDSEDKKGS  720
GDGAFTPAVS NATTHTAEEE TVNQSASGTF SITDSTEGDV SSDENGETTG GADGQEEDIQ  780
PQDGEANAAA LGLALKSSLG TSSQWDGSVA GTMRESRVLL PSLFLLLGLW GFAAL       835

SEQ ID NO: 44          moltype = AA  length = 676
FEATURE                Location/Qualifiers
source                 1..676
                       mol_type = protein
                       organism = Zaire ebolavirus
SEQUENCE: 44
MGVTGILQLP RDRFKRTSFF LWVIILFQRT FSIPLGVIHN STLQVSDVDK LVCRDKLSST  60
NQLRSVGLNL EGNGVATDVP SATKRWGFRS GVPPKVVNYE AGEWAENCYN LEIKKPDGSE  120
CLPAAPDGIR GFPRCRYVHK VSGTGPCAGD FAFHKEGAFF LYDRLASTVI YRGTTFAEGV  180
VAFLILPQAK KDFFSSHPLR EPVNATEDPS SGYYSTTIRY QATGFGTNET EYLFEVDNLT  240
YVQLESRFTP QFLLQLNETI YTSGKRSNTT GKLIWKVNPE IDTTIGEWAF WETKKNLTRK  300
IRSEELSFTV VSNGAKNISG QSPARTSSDP GTNTTTEDHK IMASENSSAM VQVHSQGREA  360
AVSHLTTLAT ISTSPQSLTT KPGPDNSTHN TPVYKLDISE ATQVEQHHRR TDNDSTASDT  420
PSATTAAGPP KAENTNTSKS TDFLDPATTT SPQNHSETAG NNNTHHQDTG EESASSGKLG  480
LITNTIAGVA GLITGGRRTR REAIVNAQPK CNPNLHYWTT QDEGAAIGLA WIPYFGPAAE  540
GIYIEGLMHN QDGLICGLRQ LANETTQALQ LFLRATTELR TFSILNRKAI DFLLQRWGGT  600
CHILGPDCCI EPHDWTKNIT DKIDQIIHDF VDKTLPDQGD NDNWWTGWRQ WIPAGIGVTG  660
VIIAVIALFC ICKFVF                                                 676

SEQ ID NO: 45          moltype = AA  length = 1639
FEATURE                Location/Qualifiers
source                 1..1639
                       mol_type = protein
                       note = Plasmodium falciparum
                       organism = unidentified
SEQUENCE: 45
MKIIFFLCSF LFFIINTQCV THESYQELVK KLEALEDAVL TGYSLFQKEK MVLNEGTSGT  60
AVTTSTPGSK GSVASGGSGG SVASGGSVAS GGSVASGGSV ASGGSGNSRR TNPSDNSSDS  120
DAKSYADLKH RVRNYLLTIK ELKYPQLFDL TNHMLTLCDN IHGFKYLIDG YEEINELLYK  180
LNFYFDLLRA KLNDVCANDY CQIPFNLKIR ANELDVLKKL VFGYRKPLDN IKDNVGKMED  240
YIKKNKKTIE NINELIEESK KTIDKNKNAT KEEEKKKLYQ AQYDLSIYNK QLEEAHNLIS  300
VLEKRIDTLK KNENIKELLD KINEIKNPPP ANSGNTPNTL LDKNKKIEEH EKEIKEIAKT  360
IKFNIDSLFT DPLELEYYLR EKNKNIDISA KVETKESTEP NEYPNGVTYP LSYNDINNAL  420
NELNSFGDLI NPFDYTKEPS KNIYTDNERK KFINEIKEKI KIEKKKIESD KKSYEDRSKS  480
LNDITKEYEK LLNEIYDSKF NNNIDLTNFE KMMGKRYSYK VEKLTHHNTF ASYENSKHNL  540
EKLTKALKYM EDYSLRNIVV EKELKYYKNL ISKIENEIET LVENIKKDEE QLFEKKITKD  600
ENKPDEKILE VSDIVKVQVQ KVLLMNKIDE LKKTQLILKN VELKHNIHVP NSYKQENKQE  660
PYYLIVLKKE IDKLKVFMPK VESLINEEKK NIKTEGQSDN SEPSTEGEIT GQATTKPGQQ  720
AGSALEGDSV QAQAQEQKQA QPPVPVPVPE AKAQVPTPPA PVNNKTENVS KLDYLEKLYE  780
FLNTSYICHK YILVSHSTMN EKILKQYKIT KEEESKLSSC DPLDLLFNIQ NNIPVMYSMF  840
DSLNNSLSQL FMEIYEKEMV CNLYKLKDND KIKNLLEEAK KVSTSVKTLS SSSMQPLSLT  900
PQDKPEVSAN DDTSHSTNLN NSLKLFENIL SLGKNKNIYQ ELIGQKSSEN FYEKILKDSD  960
TFYNESFTNF VKSKADDINS LNDESKRKKL EEDINKLKKT LQLSFDLYNK YKLKLERLFD  1020
KKKTVGKYKM QIKKLTLLKE QLESKLNSLN NPKHVLQNFS VFFNKKKEAE IAETENTLEN  1080
TKILLKHYKG LVKYYNGESS PLKTLSEESI QTEDNYASLE NFKVLSKLEG KLKDNLNLEK  1140
KKLSYLSSGL HHLIAELKEV IKNKNYTGNS PSENNTDVNN ALESYKKFLP EGTDVATVVS  1200
ESGSDTLEQS QPKKPASTHV GAESNTITTS QNVDDEVDDV IIVPIFGESE EDYDDLGQVV  1260
TGEAVTPSVI DNILSKIENE YEVLYLKPLA GVYRSLKKQL ENNVMTFNVN VKDILNSRFN  1320
KRENFKNVLE SDLIPYKDLT SSNYVVKDPY KFLNKEKRDK FLSSYNYIKD SIDTDINFAN  1380
DVLGYYKILS EKYKSDLDSI KKYINDKQGE NEKYLPFLNN IETLYKTVND KIDLFVIHLE  1440
AKVLNYTYEK SNVEVKIKEL NYLKTIQDKL ADFKKNNNFV GIADLSTDYN HNNLLTKFLS  1500
TGMVFENLAK TVLSNLLDGN LQGMLNISQH QCVKKQCPQN SGCFRHLDER EECKCLLNYK  1560
QEGDKCVENP NPTCNENNGG CDADAKCTEE DSGSNGKKIT CECTKPDSYP LFDGIFCSSS  1620
NFLGISFLLI LMLILYSFI                                              1639

SEQ ID NO: 46          moltype = AA  length = 303
FEATURE                Location/Qualifiers
source                 1..303
                       mol_type = protein
                       organism = Marburg marburgvirus
SEQUENCE: 46
MASSSNYNTY MQYLNPPPYA DHGANQLIPA DQLSNQQGIT PNYVGDLNLD DQFKGNVCHA  60
FTLEAIIDIS AYNERTVKGV PAWLPLGIMS NFEYPLAHTV AALLTGSYTI TQFTHNGQKF  120
VRVNRLGTGI PAHPLRMLRE GNQAFIQNMV IPRNFSTNQF TYNLTNLVLS VQKLPDDAWR  180
PSKDKLIGNT MHPAVSIHPN LPPIVLPTVK KQAYRQHKNP NNGPLLAISG ILHQLRVEKV  240
PEKTSLFRIS LPADMFSVKE GMMKKRGENS PVVYFQAPEN FPLNGFNNRQ VVLAYANPTL  300
SAV                                                               303

SEQ ID NO: 47          moltype = AA  length = 3432
FEATURE                Location/Qualifiers
source                 1..3432
                       mol_type = protein
```

-continued

```
                         organism = Japanese encephalitis virus
SEQUENCE: 47
MTKKPGGPGK NRAINMLKRG LPRVFPLVGV KRVVMSLLDG RGPVRFVLAL ITFFKFTALA  60
PTKALLGRWK AVEKSVAMKH LTSFKRELGT LIDAVNKRGR KQNKRGGNEG SIMWLASLAV  120
VIACAGAMKL SNFQGKLLMT INNTDIADVI VIPTSKGENR CWVRAIDVGY MCEDTITYEC  180
PKLTMGNDPE DVDCWCDNQE VYVQYGRCTR TRHSKRSRRS VSVQTHGESS LVNKKEAWLD  240
STKATRYLMK TENWIIRNPG YAFLAAVLGW MLGSNNGQRV VFTILLLLVA PAYSFNCLGM  300
GNRDFIEGAS GATWVDLVLE GDSCLTIMAN DKPTLDVRMI NIEASQLAEV RSYCYHASVT  360
DISTVARCPT TGEAHNEKRA DSSYVCKQGF TDRGWGNGCG LFGKGSIDTC AKFSCTSKAI  420
GRTIQPENIK YEVGIFVHGT TTSENHGNYS AQVGASQAAK FTVTPNAPSI TLKLGDYGEV  480
TLDCEPRSGL NTEAFYVMTV GSKSFLVHRE WFHDLALPWT SPSSTAWRNR ELLMEFEGAH  540
ATKQSVVALG SQEGGLHQAL AGAIVVEYSS SVKLTSGHLK CRLKMDKLAL KGTTYGMCTE  600
KFSFAKNPVD TGHGTVVIEL SYSGSDGPCK IPIVSVASLN DMTPVGRLVT VNPFVATSSA  660
NSKVLVEMEP PFGDSYIVVG RGDKQINHHW HKAGSTLGKA FSTTLKGAQR LAALGDTAWD  720
FGSIGGVFNS IGRAVHQVFG GAFRTLFGGM SWITQGLMGA LLLWMGVNAR DRSIALAFLA  780
TGGVLVFLAT NVHADTGCAI DITRKEMRCG SGIFVHNDVE AWVDRYKYLP ETPRSLAKIV  840
HKAHKEGVCG VRSVTRLEHQ MWEAVRDELN VLLKENAVDL SVVVNKPVGR YRSAPKRLSM  900
TQEKFEMGWK AWGKSILFAP ELANSTFVVD GPETKECPDE HRAWNSMQIE DFGFGITSTR  960
VWLKIREEST DECDGAIIGT AVKGHVAVHS DLSYWIESRY NDTWKLERAV FGEVKSCTWP  1020
ETHTLWGDDV EESELIIPHT IAGPKSKHNR REGYKTQNQG PWDENGIVLD FDYCPGTKVT  1080
ITEDCSKRGP SVRTTTDSGK LITDWCCRSC SLPPLRFRTE NGCWYGMEIR PVMHDETTLV  1140
RSQVDAFKGE MVDPFQLGLL VMFLATQEVL RKRWTARLTI PAVLGVLLVL MLGGITYTDL  1200
ARYVVLVAAA FAEANSGGDV LHLALIAVFK IQPAFLVMNM LSTRWTNQEN VILVLGAAFF  1260
QLASVDLQIG VHGILNAAAI AWMIVRAITF PTTSSVTMPV LALLTPGMRA LYLDTYRIIL  1320
LVIGICSLLH ERKKTMAKKK GAVLLGLALT STGWFSPTTI AAGLMVCNPN KKRGWPATEF  1380
LSAVGLMFAI VGGLAELDIE SMSIPFMLAG LMAVSYVVSG KATDMWLERA ADISWEMDAA  1440
ITGSSRRLDV KLDDDGDFHL IDDPGVPWKV WVLRMSCIGL AALTPWAIVP AAFGYWLTLK  1500
TTKRGGVFWD TPSPKPCSKG DTTTGVYRIM ARGILGTYQA GVGVMYENVF HTLWHTTRGA  1560
AIMSGEGKLT PYWGSVREDR IAYGGPWRFD RKWNGTDDVQ VIVVEPGKAA VNIQTKPGVF  1620
RTPFGEVGAV SLDYPRGTSG SPILDSNGDI IGLYGNGVEL GDGSYVSAIV QGDRQEEPVP  1680
EAYTPNMLRK RQMTVLDLHP GSGKTRKILP QIIKDAIQQR LRTAVLAPTR VVAAEMAEAL  1740
RGLPVRYQTS AVQREHQGNE IVDVMCHATL THRLMSPNRV PNYNLFVMDE AHFTDPASIA  1800
ARGYIATKVE LGEAAAIFMT ATPPGTTDPF PDSNAPIHDL QDEIPDRAWS SGYEWITEYA  1860
GKTVWFVASV KMGNEIAMCL QRAGKKVIQL NRKSYDTEYP KCKNGDWDFV ITTDISEMGA  1920
NFGASRVIDC RKSVKPTILE EGEGRVILGN PSPITSASAA QRRGRVGRNP NQVGDEYHYG  1980
GATSEDDSNL AHWTEAKIML DNIHMPNGLV AQLYGPEREK AFTMDGEYRL RGEEKKNFLE  2040
LLRTADLPVW LAYKVASNGI QYTDRKWCFD GPRTNAILED NTEVEIVTRM GERKILKPRW  2100
LDARVYADHQ ALKWFKDFAA GKRSAVSFIE VLGRMPEHFM GKTREALDTM YLVATAEKGG  2160
KAHRMALEEL PDALETITLI VAITVMTGGF FLLMMQRKGI GKMGLGALVL TLATFFLWAA  2220
EVPGTKIAGT LLIALLLMVV LIPEPEKQRS QTDNQLAVFL ICVLTVVGVV AANEYGMLEK  2280
TKADLKSMFG GKTQASGLTG LPSMALDLRP ATAWALYGGS TVVLTPLLKH LITSEYVTTS  2340
LASINSQAGS LFVLPRGVPF TDLDLTVGLV FLGCWGQITL TTFLTAMVLA TLHYGYMLPG  2400
WQAEALRAAQ RRTAAGIMKN AVVDGMVATD VPELERTTPL MQKKVGQVLL IGVSVAAFLV  2460
NPNVTTVREA GVLVTAATLT LWDNGASAVW NSTTATGLCH VMRGSYLAGG SIAWTLIKNA  2520
DKPSLKRGRP GGRTLGEQWK EKLNAMSREE FFKYRREAII EVDRTEARRA RRENNIVGGH  2580
PVSRGSAKLR WLVEKGFVSP IGKVIDLGCG RGGWSYYAAT LKKVQEVRGY TKGGAGHEEP  2640
MLMQSYGWNL VSLKSGVDVF YKPSEPSDTL FCDIGESSPS PEVEEQRTLR VLEMTSDWLH  2700
RGPREFCIKV LCPYMPKVIE KMEVLQRRFG GGLVRLPLSR NSNHEMYWVS GAAGNVVHAV  2760
NMTSQVLLGR MDRTVWRGPK YEEDVNLGSG TRAVGKGEVH SNQEKIKKRI QKLKEEFATT  2820
WHKDPEHPYR TWTYHGSYEV KATGSASSLV NGVVELMSKP WDAIANVTTM AMTDTTPFGQ  2880
QRVFKEKVDT KAPEPPAGAK EVLNETTNWL WAHLSREKRP RLCTKEEFIK KVNSNAALGA  2940
VFAEQNQWST AREAVDDPRF WEMVDEEREN HLRGECHTCI YNMMGKREKK PGEFGKAKGS  3000
RAIWFMWLGA RYLEFEALGF LNEDHWLSRE NSGGGVEGSG VQKLGYILRD IAGKQGGKMY  3060
ADDTAGWDTR ITRTDLENEA KVLELLDGEH RMLARAIIEL TYRHKVVKVM RPAAEGKTVM  3120
DVISREDQRG SGQVVTYALN TFTNIAVQLV RLMEAEGVIG PQHLEQLPRK TKIAVRTWLF  3180
ENGEERVTRM AISGDDCVVK PLDDRFATAL HFLNAMSKVR KDIQEWKPSH GWHDWQQVPF  3240
CSNHFQEIVM KDGRSIVVPC RGQDELIGRA RISPGAGWNV KDTACLAKAY AQMWLLLYFH  3300
RRDLRLMANA ICSAVPVDWV PTGRTSWSIH SKGEWMTTED MLQVWNRVWI EENEWMMDKT  3360
PITSWTDVPY VGKREDIWCG SLIGTRSRAT WAENIYAAIN QVRAVIGKEN YVDYMTSLRR  3420
YEDVLIQEDR VI                                                3432

SEQ ID NO: 48            moltype = AA  length = 767
FEATURE                  Location/Qualifiers
source                   1..767
                         mol_type = protein
                         organism = Saint Louis encephalitis virus
SEQUENCE: 48
AVDKRTALKH LNGFKRDLGS MLDTINRRPS KKRGGTGSLL GLAMLIGLAS SLQLSTHQGK  60
VLISINKTDA QSAINIPSAN GVNTCIVRAL DVGVMCKDDI TYLCPVLSAG NDPEDIDCWC  120
DAEEVWVHYG RCTRMGHSRR SRRSISVQHH GDSTLATKNT PWLDTIKTTK YLTKVENWVL  180
RNPGYALVAL AIGWMLGSNN TQKVVFVIML MLIAPAYSFN CLGTSNRDFV EGASGATWID  240
LVLEGGGCVT VMAPEKPTLD FKVMKMEATE LATVREYCYE ATLNTLSTVA RCPTTGEAHN  300
TKRSDPTFVC KRDVVDRGWG NGCGLFGKGS IDTCAKFTCK NKATGKTILR ENIKYEVAIF  360
VHGSTDSTSH GNYAEQIGKN QAARFTISPQ APSFTANMGE YGTVTIDCEA RSGINTEDYY  420
VFTAKEKSWL VNRDWFHDLN LPWTSPATTD WRNRETLVEF EEPHATKQTV VALGSQEGAL  480
HTALAGAIPA TVSSSTLTLQ SGHLKCRAKL DKVKIKGTTY GMCDSAFIFS KNPTDTGHGT  540
VIVELQYTGS NGPCRVPISV TANLMDLTPV GRLVTVNPFI STGGANNKVM IEVEPPFGDS  600
YVVVGRGTTQ INYHWHKEGS SIGKALATTW KGAQRLAVLG DTAWDFGSIG GVFNSIGKAV  660
HQVFGGAFRT LFGGMSWITQ GLLGALLLWM GLQARDRSIS LTLLATGGIL IFLATSVQAD  720
```

```
SGCAIDLQRR ELKCGGGIFV YNDVEKWKSG YKYFPLTPTG LARVIKG            767

SEQ ID NO: 49           moltype = AA  length = 3433
FEATURE                 Location/Qualifiers
source                  1..3433
                        mol_type = protein
                        organism = West Nile virus
SEQUENCE: 49
MSKKPGGPGK SRAVNMLKRG MPRVLSLIGL KRAMLSLIDG KGPIRFVLAL LAFFRFTAIA  60
PTRAVLDRWR GVNKQTAMKH LLSFKKELGT LTSAINRRSS KQKKRGGKTG IAVMIGLIAS  120
VGAVTLSNFQ GKVMMTVNAT DVTDVITIPT AAGKNLCIVR AMDVGYMCDD TITYECPVLS  180
AGNDPEDIDC WCTKSAVYVR YGRCTKTRHS RRSRRSLTVQ THGESTLANK KGAWMDSTKA  240
TRYLVKTESW ILRNPGYALV AAVIGWMLGS NTMQRVVFVV LLLLVAPAYS FNCLGMSNRD  300
FLEGVSGATW VDLVLEGDSC VTIMSKDKPT IDVKMMNMEA ANLAEVRSYC YLATVSDLST  360
KAACPTMGEA HNDKRADPAF VCRQGVVDRG WGNGCGLFGK GSIDTCAKFA CSTKAIGRTI  420
LKENIKYEVA IFVHGPTTVE SHGNYSTQVG ATQAGRFSIT PAAPSYTLKL GEYGEVTVDC  480
EPRSGIDTNA YYVMTVGTKT FLVHREWFMD LNLPWSSAGS TVWRNRETLM EFEEPHATKQ  540
SVIALGSQEG ALHQALAGAI PVEFSSNTVK LTSGHLKCRV KMEKLQLKGT TYGVCSKAFK  600
FLGTPADTGH GTVVLELQYT GTDGPCKVPI SSVASLNDLT PVGRLVTVNP FVSVATANAK  660
VLIELEPPFG DSYIVVGRGE QQINHHWHKS GSSIGKAFTT TLKGAQRLAA LGDTAWDFGS  720
VGGVFTSVGK AVHQVFGGAF RSLFGGMSWI TQGLLGALLL WMGINARDRS IALTFLAVGG  780
VLLFLSVNVH ADTGCAIDIS RQELRCGSGV FIHNDVEAWM DRYKYYPETP QGLAKIIQKA  840
HKEGVCGLRS VSRLEHQMWE AVKDELNTLL KENGVDLSVV VEKQEGMYKS APKRLTATTE  900
KLEIGWKAWG KSILFAPELA NNTFVVDGPE TKECPTQNRA WNSLEVEDFG FGLTSTRMFL  960
KVRESNTTEC DSKIIGTAVK NNLAIHSDLS YWIESRLNDT WKLERAVLGE VKSCTWPETH  1020
TLWGDGILES DLIIPVTLAG PRSNHNRRPG YKTQNQGPWD EGRVEIDFDY CPGTTVTLSE  1080
SCGHRGPATR TTTESGKLIT DWCCRSCTLP PLRYQTDSGC WYGMEIRPQR HDEKTLVQSQ  1140
VNAYNADMID PFQLGLLVVF LATQEVLRKR WTAKISMPAI LIALLVLVFG GITYTDVLRY  1200
VILVGAAFAE SNSGGDVVHL ALMATFKIQP VFMVASFLKA RWTNQENILL MLAAVFFQMA  1260
YHDARQILLW EIPDVLNSLA VAWMILRAIT FTTTSNVVVP LLALLTPGLR CLNLDVYRIL  1320
LLMVGIGSLI REKRSAAAKK KGASLLCLAL ASTGLFNPMI LAAGLIACDP NRKRGWPATE  1380
VMTAVGLMFA IVGGLAELDI DSMAIPMTIA GLMFAAFVIS GKSTDMWIER TADISWESDA  1440
EITGSSERVD VRLDDDGNFQ LMNDPGAPWK IWMLRMVCLA ISAYTPWAIL PSVVGFWITL  1500
QYTKRGGVLW DTPSPKEYKK GDTTTGVYRI MTRGLLGSYQ AGAGVMVEGV FHTLWHTTKG  1560
AALMSGEGRL DPYWGSVKED RLCYGGPWKL QHKWNGQDEV QMIVVEPGKN VKNVQTKPGV  1620
FKTPEGEIGA VTLDFPTGTS GSPIVDKNGD VIGLYGNGVI MPNGSYISAI VQGERMDEPI  1680
PAGFEPEMLR KKQITVLDLH PGAGKTRRIL PQIIKEAINR RLRTAVLAPT RVVAAEMAEA  1740
LRGLPIRYQT SAVPREHNGN EIVDVMCHAT LTHRLMSPHR VPNYNLFVMD EAHFTDPASI  1800
AARGYISTKV ELGEAAAIFM TATPPGTSDP FPESNSPISD LQTEIPDRAW NSGYEWITEY  1860
TGKTVWFVPS VKMGNEIALC LQRAGKKVVQ LNRKSYETEY PKCKNDDWDF VITTDISEMG  1920
ANFKASRVID SRKSVKPTII TEGEGRVILG EPSAVTAASA AQRRGRIGRN PSQVGDEYCY  1980
GGHTNEDDSN FAHWTEARIM LDNINMPNGL IAQFYQPERE KVYTMDGEYR LRGEERKNFL  2040
ELLRTADLPV WLAYKVAAAG VSYHDRRWCF DGPRTNTILE DNNEVEVITK LGERKILRPR  2100
WIDARVYSDH QALKAFKDFA SGKRSQIGLI EVLGKMPEHF MGKTWEALDT MYVVATAEKG  2160
GRAHRMALEE LPDALQTIAL IALLSVMTMG VFFLLMQRKG IGKIGLGGAV LGVATFFCWM  2220
AEVPGTKIAG MLLLSLLLMI VLIPEPEKQR SQTDNQLAVF LICVMTLVSA VAANEMGWLD  2280
KTKSDISSLF GQRIEVKENF SMGEFLLDLR PATAWSLYAV TTAVLTPLLK HLITSDYINT  2340
SLTSINVQAS ALFTLARGFP FVDVGVSALL LAAGCWGQVT LTVTVTAATL LFCHYAYMVP  2400
GWQAEAMRSA QRRTAAGIMK NAVVDGIVAT DVPELERTTP IMQKKVGQIM LILVSLAAVV  2460
VNPSVKTVRE AGILITAAAV TLWENGASSV WNATTAIGLC HIMRGGWLSC LSITWTLIKN  2520
MEKPGLKRGG AKGRTLGEVW KERLNQMTKE EFTRYRKEAI IEVDRSAAKH ARKEGNVTGG  2580
HPVSRGTAKL RWLVERRFLE PVGKVIDLGC GRGGWCYYMA TQKRVQEVRG YTKGGPGHEE  2640
PQLVQSYGWN IVTMKSGVDV FYRPSECCDT LLCDIGESSS SAEVEEHRTI RVLEMVEDWL  2700
HRGPREFCVK VLCPYMPKVI EKMELLQRRY GGGLVRNPLS RNSTHEMYWV SRASGNVVHS  2760
VNMTSQVLLG RMEKRTWKGP QYEEDVNLGS GTRAVGKPLL NSDTSKIKNR IERLRREYSS  2820
TWHHDENHPY RTWNYHGSYD VKPTGSASSL VNGVVRLLSK PWDTITNVTT MAMTDTTPFG  2880
QQRVFKEKVD TKAPEPPEGV KYVLNETTNW LWAFLAREKR PRMCSREEFI RKVNSNAALG  2940
AMFEEQNQWR SAREAVEDPK FWEMVDEERE AHLRGECHTC IYNMMGKREK KPGEFGKAKG  3000
SRAIWFMWLG ARFLEFEALG FLNEDHWLGR KNSGGGVEGL GLQKLGYILR EVGTRPGGKI  3060
YADDTAGWDT RITRADLENE AKVLELLDGE HRRLARAIIE LTYRHKVVKV MRPAADGRTV  3120
MDVISREDQR GSGQVVTYAL NTFTNLAVQL VRMMEGEGVI GPDDVEKLTK GKGPKVRTWL  3180
FENGEERLSR MAVSGDDCVV KPLDDRFATS LHFLNAMSKV RKDIQEWKPS TGWYDWQQVP  3240
FCSNHFTELI MKDGRTLVVP CRGQDELVGR ARISPGAGWN VRDTACLAKS YAQMWLLLYF  3300
HRRDLRLMAN AICSAVPVNW VPTGRTTWSI HAGGEWMTTE DMLEVWNRVW IEENEWMEDK  3360
TPVEKWSDVP YSGKREDIWC GSLIGTRARA TWAENIQVAI NQVRAIIGDE KYVDYMSSLK  3420
RYEDTTLVED TVL                                                  3433

SEQ ID NO: 50           moltype = AA  length = 3173
FEATURE                 Location/Qualifiers
source                  1..3173
                        mol_type = protein
                        organism = Yellow fever virus
SEQUENCE: 50
SEDLGKTFSV GTGNCTTNIL EAKYWCPDSM EYNCPNLSPR EEPDDIDCWC YGVENVRVAY  60
GKCDSAGRSR RSRRAIDLPT HENHGLKTRQ EKWMTGRMGE RQLQKIERWL VRNPFFAATA  120
LAIAYLVGSN MTQRVVIALL VLAVGPAYSA HCIGITDRDF IEGVXXXXXX XXXXXXXXXX  180
XXXXXXXXXX XXXXXXXXXX XXXXXXXXXX XXXXXXXXXX XXXXXXXXXX XXXXXXXXXX  240
XXXXXXXXXX XXXXXXXXXX XXXXXAKFTC AKSMSLFEVD QTKIQYVIRA QLHVGAKQEN  300
WNTDIKTLKF DALSGSQEAE FTGYGRATLE CQVQTAVDFS NSYIAEMEKE SWIVDKQWAQ  360
```

-continued

```
DLTLPWQSGS GGVWREMHHL VEFEPPHAAT IKVLALGNQE GSLKTALTGA MRVTKXXXXX  420
XXXXXXXXXX XXXXXXXXXX XXXXXXXXXX XXXXXXXXXX XXXXXXXXXX XXXXXXXXXX  480
XXXXXXXXXX XXXXXXXXXX XXXXASTNDD EVLIEVNPPF GDSYIIVGTG DSRLTYQWHK  540
EGSSIGKLFT QTMKGAERLA VMGDAAWDFG SAGGFFTSVG KGIHTVFGSA FQGLFGGLSW  600
ITKVIMGVVL IWVGINTRNM TMSMSMILVG VIMMFLSLGV GADQGCAINF GKRELKCXXX  660
XXXXXXXXXX XXXXXXXXXX XXXXXXXXXX XXXXXXXXXX XXXXXXXXXX XXXXXXXXXX  720
XXXXXXXXXX XXXXXXXXXX XXXQYGWKTW GKNLVFSPGR KNGSFIIDGK  780
SRKECPFSNR VWNSFQIEEF GTGVFTTRVY MDAVFEYTMD CDGSILGAAV NGKKSAHGSP  840
TFWMGSHEVN GTWMIHTLET LDYKECEWPL THTIGTSVEE SDMFMPRSIG GPVSSHNHIP  900
GYKVQTNGPW MQVPLEVKRE ACXXXXXXXX XXXXXXXXXX XXXXXXXXXX XXXXXXXXXX  960
XXXXXXXXXX XXXXXXXXXX XXXXXXXXXX XXXXXXXXXX XXXXXXXXXX XXXXXXXXXX  1020
XXXXXVGGMV LLGAMLVGQV TILDLLKLTV AVGLHFHEMN NGGDAMYMAL IAAFSIRPGL  1080
LIGFGLRTLW SPRERLVLTL GAAMVEIALG GMMGGLWKYL NAVSLCILTI NAVASRKASN  1140
VILPLMALLT PVTMAEVRLA TMLFCTVVII GVLHQNSKDT SMQKTIPXXX XXXXXXXXXX  1200
XXXXXXXXXX XXXXXXXXXX XXXXXXXXXX XXXXXXXXXX XXXXXXXXXX XXXXXXXXXX  1260
XXXXXXXXXX XXXXXXXXWE EEAEISGSSA RYDVTLSEQG EFKLLSEEKV PWDQVVMTSL  1320
ALVGAAIHPF ALLLVLAGWL FHVKGARRSG DVLWDIPTPK IIEECEYLED GIYGIFQSTF  1380
LGASQRGVGV AQGGVFHTMW HVTRGAFLVR NGKKLVPSWA SVKEDLVAYG GSWKLEGRWD  1440
GXXXXXXXXX XXXXXXXXXX XXXXXXXXXX XXXXXXXXXX XXXXXXXXXX XXXXXXXXXX  1500
XXXXXXXXXX XXXXXXXXTE VKEEGKEELQ EIPTMLKKGM TTILDFHPGA GKTRRFLPQI  1560
LAECARRRLR TLVLAPTRVV LSEMKEAFHG LDVKFHTQAF SAHGSGKEVI DAMCHATLTY  1620
RMLEPTRVVN WEVIIMDEAH FLDPASIAAR GWAAHRARAN ESATILMTAT PXXXXXXXXX  1680
XXXXXXXXXX XXXXXXXXXX XXXXXXXXXX XXXXXXXXXX XXXXXXXXXX XXXXXXXXXX  1740
XXXXXXXXXX XXXXXXXXLA TDIAEMGANL CVERVLDCRT AFKPVLVDEG RKVAIKGPLR  1800
ISASSAAQRR GRIGRNPNRD GDSYYYSEPT SEDNAHHVCW LEASMLLDNM EVRGGMVAPL  1860
YGIEGTKTPV SPGEMRLRDD QRRVFRELVR NCDLPVWLSW QVAKAGLKTN DRKWCFEXXX  1920
XXXXXXXXXX XXXXXXXXXX XXXXXXXXXX XXXXXXXXXX XXXXXXXXXX XXXXXXXXXX  1980
XXXXXXXXXX XXXXXXXXXX LLHSEEGSRA YRNALSMMPE AMTTVMLFVL AGLLTSGMVI  2040
FFMSPKGISR MSMAMGTMAG CGYLMFLGGV KPTHISYIML IFFVLMVVVV PEPGQQRTIQ  2100
DNQVAYLIIG ILTLISVVAA NELGMLEKTK EDLFGKKNLI PSSAAPWSWP DFDLKPGAXX  2160
XXXXXXXXXX XXXXXXXXXX XXXXXXXXXX XXXXXXXXXX XXXXXXXXXX XXXXXXXXXX  2220
XXXXXXXXXX XXXXXXXXXX XXXXXXXXXX XXXLAQRRVF HGVAKNPVVD GNPTVDIEEA  2280
PEMPALYEKK LALYLLLALS LASVAMCRTP FSLAEGIVLA SAALGPLIEG NTSLLWNGPM  2340
AVSMTGVMRG NYYAFVGVMY NLWKMKTGRR GRANGKTLGE VWKRELNLLD KQQFELYKRT  2400
DIVEVDXXXX XXXXXXXXXX XXXXXXXXXX XXXXXXXXXX XXXXXXXXXX XXXXXXXXXX  2460
XXXXXXXXXX XXXXXXXXXX XXXXXXXXLG WNIITFKDKT DVHRLEPIKC DTLLCDIGES  2520
SPSSVTEGER TMRVLDTVEK WLSCGVESFC VKVLAPYMPD VLEKLELLQR RFGGTVIRNP  2580
LSRNSTHEMY YVSGARSNIT FTVNQTSRLL MRRMRRPTGK VTLEADVILP IGTRSVETXX  2640
XXXXXXXXXX XXXXXXXXXX XXXXXXXXXX XXXXXXXXXX XXXXXXXXXX XXXXXXXXXX  2700
XXXXXXXXXX XXXXXXXXXX XXXXXXXXXV DTRAKDPPAG TRKIMKVVNR WLFRHLAREK  2760
NPRLCTKEEF IAKVRSHAAI GAFLEEQEQW KTANEAVQDP KFWELVDEER RLHQQGRCRT  2820
CVYNMMGKRE KKLSEFGKAK GSRAIWYMWL GARYLEFEAL GFLNEDHWAS RENSGGGVEG  2880
IGLQYLGYVI RDLAALEGGG FYXXXXXXXX XXXXXXXXXX XXXXXXXXXX XXXXXXXXXX  2940
XXXXXXXXXX XXXXXXXXXX XXXXXXXXXX XXXXXXXXXX XXXXXXXXXX XXXXXXXXXV  3000
IHHQHVQDCD DTALTKLEAW LAEHGCDRLK RMAVSGDDCV VRPIDDRFGL ALSHLNAMSK  3060
VRKDISEWQP SKGWDDWESV PFCSHHFHEL QLKDGRRIVV PCRDQDELVG RGRVSPGNGW  3120
MIKETACLSK AYANMWSLMY FHKRDMRLLS LAVSSAVPTS WVPQGRTTWS VHG         3173
```

```
SEQ ID NO: 51           moltype = AA  length = 809
FEATURE                 Location/Qualifiers
source                  1..809
                        mol_type = protein
                        organism = Bacillicus anthracis
SEQUENCE: 51
MNIKKEFIKV ISMSCLVTAI TLSGPVFIPL VQGAGGHGDV GMHVKEKEKN KDENKRKDEE  60
RNKTQEEHLK EIMKHIVKIE VKGEEAVKKE AAEKLLEKVP SDVLEMYKAI GGKIYIVDGD  120
ITKHISLEAL SEDKKKIKDI YGKDALLHEH YVYAKEGYEP VLVIQSSEDY VENTEKALNV  180
YYEIGKILSR DILSKINQPY QKFLDVLNTI KNASDSDGQD LLFTNQLKEH PTDFSVEFLE  240
QNSNEVQEVF AKAFAYYIEP QHRDVLQLYA PEAFNYMDKF NEQEINLSLE ELKDQRMLAR  300
YEKWEKIKQH YQHWSDSLSE EGRGLLKKLQ IPIEPKKDDI IHSLSQEEKE LLKRIQIDSS  360
DFLSTEEKEF LKKLQIDIRD SLSEEEKELL NRIQVDSSNP LSEKEKEFLK KLKLDIQPYD  420
INQRLQDTGG LIDSPSINLD VRKQYKRDIQ NIDALLHQSI GSTLYNKIYL YENMNINNLT  480
ATLGADLVDS TDNTKINRGI FNEFKKNFKY SISSNYMIVD INERPALDNE RLKWRIQLSP  540
DTRAGYLENG KLILQRNIGL EIKDVQIIKQ SEKEYIRIDA KVVPKSKIDT KIQEAQLNIN  600
QEWNKALGLP KYTKLITFNV HNRYASNIVE SAYLILNEWK NNIQSDLIKK VTNYLVDGNG  660
RFVFTDITLP NIAEQYTHQD EIYEQVHSKG LYVPESRSIL LHGPSKGVEL RNDSEGFIHE  720
FGHAVDDYAG YLLDKNQSDL VTNSKKFIDI FKEEGSNLTS YGRTNEAEFF AEAFRLMHST  780
DHAERLKVQK NAPKTFQFIN DQIKFIINS                                    809
```

```
SEQ ID NO: 52           moltype = AA  length = 576
FEATURE                 Location/Qualifiers
source                  1..576
                        mol_type = protein
                        organism = Clostridium botulinum
SEQUENCE: 52
MKPGGNTIVI WMYAVATWLC FGSTSGWSFT LEDNNIFPKQ YPIINFTTAG ATVQSYTNFI  60
RAVRGRLTTG ADVRHEIPVL PNRVGLPINQ RFILVELSNH AELSVTLALD VTNAYVVGYR  120
```

-continued

```
AGNSAYFFHP DNQEDAEAIT HLFTDVQNRY TFAFGGNYDR LEQLAGNLRE NIELGNGPLE  180
EAISALYYYS TGGTQLPTLA RSFIICIQMI SEAARFQYIE GEMRTRIRYN RRSAPDPSVI  240
TLENSWGRLS TAIQESNQGA FASPIQLQRR NGSKFSVYDV SILIPIIALM VYRCAPPPSS  300
QFSLLIRPVV PNFNADVCMD PEPIVRIVGR NGLCVDVRDG RFHNGNAIQL WPCKSNTDAN  360
QLWTLKRDNT IRSNGKCLTT YGYSPGVYVM IYDCNTAATD ATRWQIWDNG TIINPRSSLV  420
LAATSGNSGT TLTVQTNIYA VSQGWLPTNN TQPFVTTIVG LYGLCLQANS GQVWIEDCSS  480
EKAEQQWALY ADGSIRPQQN RDNCLTSDSN IRETVVKILS CGPASSGQRW MFKNDGTILN  540
LYSGLVLDVR ASDPSLKQII LYPLHGDPNQ IWLPLF                            576

SEQ ID NO: 53          moltype = AA  length = 576
FEATURE                Location/Qualifiers
source                 1..576
                       mol_type = protein
                       organism = Ricinus communis
SEQUENCE: 53
MKPGGNTIVI WMYAVATWLC FGSTSGWSFT LEDNNIFPKQ YPIINFTTAG ATVQSYTNFI  60
RAVRGRLTTG ADVRHEIPVL PNRVGLPINQ RFILVELSNH AELSVTLALD VTNAYVVGYR  120
AGNSAYFFHP DNQEDAEAIT HLFTDVQNRY TFAFGGNYDR LEQLAGNLRE NIELGNGPLE  180
EAISALYYYS TGGTQLPTLA RSFIICIQMI SEAARFQYIE GEMRTRIRYN RRSAPDPSVI  240
TLENSWGRLS TAIQESNQGA FASPIQLQRR NGSKFSVYDV SILIPIIALM VYRCAPPPSS  300
QFSLLIRPVV PNFNADVCMD PEPIVRIVGR NGLCVDVRDG RFHNGNAIQL WPCKSNTDAN  360
QLWTLKRDNT IRSNGKCLTT YGYSPGVYVM IYDCNTAATD ATRWQIWDNG TIINPRSSLV  420
LAATSGNSGT TLTVQTNIYA VSQGWLPTNN TQPFVTTIVG LYGLCLQANS GQVWIEDCSS  480
EKAEQQWALY ADGSIRPQQN RDNCLTSDSN IRETVVKILS CGPASSGQRW MFKNDGTILN  540
LYSGLVLDVR ASDPSLKQII LYPLHGDPNQ IWLPLF                            576

SEQ ID NO: 54          moltype = AA  length = 315
FEATURE                Location/Qualifiers
source                 1..315
                       mol_type = protein
                       organism = Shigella dysenteriae
SEQUENCE: 54
MKIIIFRVLT FFFVIFSVNV VAKEFTLDFS TAKTYVDSLN VIRSAIGTPL QTISSGGTSL  60
LMIDSGTGDN LFAVDVRGID PEEGRFNNLR LIVERNNLYV TGFVNRTNNV FYRFADFSHV  120
TFPGTTAVTL SGDSSYTTLQ RVAGISRTGM QINRHSLTTS YLDLMSHSGT SLTQSVARAM  180
LRFVTVTAEA LRFRQIQRGF RTTLDDLSGR SYVMTAEDVD LTLNWGRLSS VLPDYHGQDS  240
VRVGRISFGS INAILGSVAL ILNCHHHASR VARMASDEFP SMCPADGRVR GITHNKILWD  300
SSTLGAILMR RTISS                                                   315
```